US012733981B2

(12) United States Patent
Pavlovskaia et al.

(10) Patent No.: US 12,733,981 B2

(45) Date of Patent: Sep. 15, 2026

(54) SYSTEMS AND METHODS FOR SURGICAL PLANNING OF ARTHROPLASTY PROCEDURES

(71) Applicant: HOWMEDICA OSTEONICS CORPORATION, Mahwah, NJ (US)

(72) Inventors: Elena I. Pavlovskaia, San Francisco, CA (US); Oleg Mishin, Foster City, CA (US); Boris E. Shpungin, Pleasanton, CA (US); Ilwhan Park, Walnut Creek, CA (US); Venkata Surya Sarva, Fremont, CA (US); Irene Min Choi, Emeryville, CA (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 377 days.

(21) Appl. No.: 18/379,806

(22) Filed: Oct. 13, 2023

(65) Prior Publication Data

US 2024/0050155 A1 Feb. 15, 2024

Related U.S. Application Data

(63) Continuation of application No. 17/246,604, filed on May 1, 2021, now Pat. No. 11,819,282, which is a
(Continued)

(51) Int. Cl.

*A61B 34/10* (2016.01)
*A61B 5/055* (2006.01)
(Continued)

(52) U.S. Cl.

CPC .............. *A61B 34/10* (2016.02); *A61B 5/055* (2013.01); *A61B 6/032* (2013.01); *A61B 17/1675* (2013.01); *A61B 17/1703* (2013.01); *A61B 17/7013* (2013.01); *A61B 90/37* (2016.02); *B33Y 10/00* (2014.12); *B33Y 50/00* (2014.12); *B33Y 50/02* (2014.12); *B33Y 80/00* (2014.12); *G06F 30/00* (2020.01); *G06F 30/20* (2020.01); *G06T 7/0012* (2013.01); *G06T 7/12* (2017.01); *G06T 7/13* (2017.01); *G06T 17/00* (2013.01);
(Continued)

(58) Field of Classification Search

None
See application file for complete search history.

(56) References Cited

U.S. PATENT DOCUMENTS 8,617,171 B2 * 12/2013 Park .................. A61B 17/1675 606/88
8,737,700 B2 * 5/2014 Park ...................... B33Y 80/00 382/128

(Continued)

*Primary Examiner* — Rodney E Fuller

(74) *Attorney, Agent, or Firm* — Howard & Howard Attorneys PLLC

(57) ABSTRACT

A method for planning an arthroplasty procedure on a patient bone. The method may include accessing generic bone data stored in a memory of a computer, using the computer to generate modified bone data by modifying the generic bone data according to medical imaging data of the patient bone, using the computer to derive a location of non-bone tissue data relative to the modified bone data, and superimposing implant data and the modified bone data in defining a resection of an arthroplasty target region of the patient bone.

20 Claims, 223 Drawing Sheets

Related U.S. Application Data continuation of application No. 17/018,777, filed on Sep. 11, 2020, now Pat. No. 10,993,744, which is a continuation-in-part of application No. 16/923,548, filed on Jul. 8, 2020, now Pat. No. 11,045,228, which is a continuation of application No. 16/803,664, filed on Feb. 27, 2020, now Pat. No. 11,033,300, which is a continuation of application No. 16/522,281, filed on Jul. 25, 2019, now Pat. No. 10,575,875, which is a continuation-in-part of application No. 16/229,997, filed on Dec. 21, 2018, now Pat. No. 10,675,063, which is a continuation of application No. 15/581,974, filed on Apr. 28, 2017, now Pat. No. 10,159,513, which is a continuation of application No. 14/946,106, filed on Nov. 19, 2015, now Pat. No. 9,687,259, which is a continuation of application No. 13/731,697, filed on Dec. 31, 2012, now Pat. No. 9,208,263, which is a continuation of application No. 13/374,960, filed on Jan. 25, 2012, now Pat. No. 8,532,361, which is a continuation of application No. 13/066,568, filed on Apr. 18, 2011, now Pat. No. 8,160,345, which is a continuation-in-part of application No. 12/386,105, filed on Apr. 14, 2009, now Pat. No. 8,311,306, said application No. 16/522,281 is a continuation-in-part of application No. 16/017,320, filed on Jun. 25, 2018, now Pat. No. 10,617,475, which is a continuation of application No. 15/802,137, filed on Nov. 2, 2017, now Pat. No. 10,034,714, which is a continuation of application No. 15/469,171, filed on Mar. 24, 2017, now Pat. No. 9,839,485, which is a continuation of application No. 15/242,312, filed on Aug. 19, 2016, now Pat. No. 9,636,120, which is a continuation of application No. 14/476,500, filed on Sep. 3, 2014, now Pat. No. 9,451,970, which is a continuation of application No. 13/731,850, filed on Dec. 31, 2012, now Pat. No. 8,961,527, which is a continuation of application No. 12/505,056, filed on Jul. 17, 2009, now Pat. No. 8,777,875, said application No. 16/522,281 is a continuation-in-part of application No. 16/211,735, filed on Dec. 6, 2018, now Pat. No. 11,033,334, which is a continuation of application No. 15/167,710, filed on May 27, 2016, now Pat. No. 10,182,870, which is a continuation-in-part of application No. 14/084,255, filed on Nov. 19, 2013, now Pat. No. 9,782,226, which is a continuation of application No. 13/086,275, filed on Apr. 13, 2011, now Pat. No. 8,617,171, which is a continuation-in-part of application No. 12/760,388, filed on Apr. 14, 2010, now Pat. No. 8,737,700, which is a continuation-in-part of application No. 12/563,809, filed on Sep. 21, 2009, now Pat. No. 8,545,509, said application No. 12/760,388 is a continuation-in-part of application No. 12/546,545, filed on Aug. 24, 2009, now Pat. No. 8,715,291, said application No. 12/563,809 is a continuation-in-part of application No. 12/111,924, filed on Apr. 29, 2008, now Pat. No. 8,480,679, said application No. 12/546,545 is a continuation-in-part of application No. 11/959,344, filed on Dec. 18, 2007, now Pat. No. 8,221,430, said application No. 12/563,809 is a continuation-in-part of application No. 12/505,056, filed on Jul. 17, 2009, now Pat. No. 8,777,875, said application No. 12/563,809 is a continuation-in-part of application No. 11/959,344, filed on Dec. 18, 2007, now Pat. No. 8,221,430, said application No. 12/760,388 is a continuation-in-part of application No. 11/959,344, filed on Dec. 18, 2007, now Pat. No. 8,221,430, and a continuation-in-part of application No. 12/111,924, filed on Apr. 29, 2008, now Pat. No. 8,480,679, and a continuation-in-part of application No. 12/505,056, filed on Jul. 17, 2009, now Pat. No. 8,777,875, said application No. 17/018,777 is a continuation-in-part of application No. 14/776,660, filed as application No. PCT/US2014/030496 on Mar. 17, 2014, now Pat. No. 10,912,571, which is a continuation-in-part of application No. 12/546,545, filed on Aug. 24, 2009, now Pat. No. 8,715,291, which is a continuation-in-part of application No. 11/959,344, filed on Dec. 18, 2007, now Pat. No. 8,221,430, said application No. PCT/US2014/030496 is a continuation-in-part of application No. 12/505,056, filed on Jul. 17, 2009, now Pat. No. 8,777,875.

(60) Provisional application No. 61/126,102, filed on Apr. 30, 2008, provisional application No. 61/083,053, filed on Jul. 23, 2008, provisional application No. 61/102,692, filed on Oct. 3, 2008, provisional application No. 61/794,514, filed on Mar. 15, 2013.

(51) Int. Cl.

| | |
|---|---|
| ***A61B 6/03*** | (2006.01) |
| ***A61B 17/16*** | (2006.01) |
| ***A61B 17/17*** | (2006.01) |
| ***A61B 17/70*** | (2006.01) |
| ***A61B 90/00*** | (2016.01) |
| ***B33Y 10/00*** | (2015.01) |
| ***B33Y 50/00*** | (2015.01) |
| ***B33Y 50/02*** | (2015.01) |
| ***B33Y 80/00*** | (2015.01) |
| ***G06F 30/00*** | (2020.01) |
| ***G06F 30/20*** | (2020.01) |
| ***G06T 7/00*** | (2017.01) |
| ***G06T 7/12*** | (2017.01) |
| ***G06T 7/13*** | (2017.01) |
| ***G06T 17/00*** | (2006.01) |
| ***G06T 17/20*** | (2006.01) |
| ***G06V 10/44*** | (2022.01) |
| ***G16H 50/50*** | (2018.01) |
| *A61B 17/15* | (2006.01) |
| *G06T 7/70* | (2017.01) |

(52) U.S. Cl.

CPC ............ *G06T 17/20* (2013.01); *G06V 10/454* (2022.01); *G16H 50/50* (2018.01); *A61B 17/155* (2013.01); *A61B 17/157* (2013.01); *A61B 2017/1602* (2013.01); *A61B 2034/105* (2016.02); *A61B 2034/107* (2016.02); *A61B 2034/108* (2016.02); *A61B 2090/374* (2016.02); *A61B 2090/3762* (2016.02); *G06T 7/70* (2017.01); *G06T 2200/08* (2013.01); *G06T 2207/30008* (2013.01); *G06V 2201/033* (2022.01); *Y10T 29/49826* (2015.01)

(56) References Cited

U.S. PATENT DOCUMENTS

| | | | | |
|---|---|---|---|---|
| 9,131,945 | B2 * | 9/2015 | Aram | A61B 17/157 |
| 9,532,845 | B1 * | 1/2017 | Dossett | A61B 34/10 |
| 10,342,621 | B2 | 7/2019 | Dossett et al. | |
| 11,819,282 | B2 | 11/2023 | Pavlovskaia et al. | |
| 2009/0204222 | A1 * | 8/2009 | Burstein | A61F 2/4657 623/20.34 |

(56) References Cited

U.S. PATENT DOCUMENTS

| | | | | |
|---|---|---|---|---|
| 2013/0211531 | A1 | 8/2013 | Steines et al. | |
| 2015/0105698 | A1 | 4/2015 | Park | |
| 2018/0235641 | A1* | 8/2018 | McAuliffe | A61B 17/155 |
| 2022/0087827 | A1 | 3/2022 | Bojarski et al. | |

* cited by examiner

GENERATE 2D IMAGES 16 OF PATIENT'S JOINT 14 VIA MEDICAL IMAGING.
[BLOCK 100]

IDENTIFY A POINT P IN THE IMAGES 16 THAT IS AT THE APPROXIMATE MEDIAL-LATERAL AND ANTERIOR-POSTERIOR CENTER OF THE PATIENT'S KNEE JOINT 14.
[BLOCK 105]

CONTINUED IN [BLOCK 130] IN FIG.1D

CONTINUED IN [BLOCK 110] IN FIG.1C

FROM [BLOCK 105] IN FIG.1B

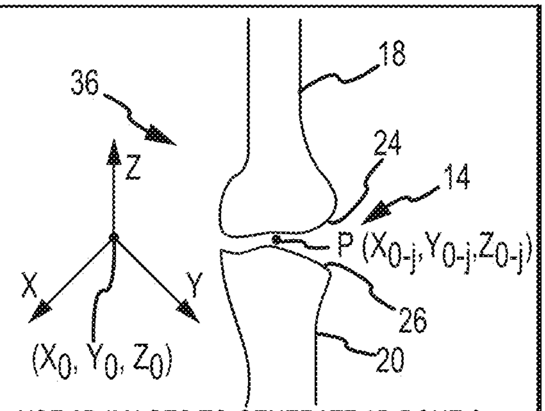

USE 2D IMAGES TO GENERATE 3D BONE & CARTILAGE MODELS (I.E., "ARTHRITIC MODELS") 36 OF BONES 18, 20 FORMING PATIENT'S JOINT 14, AND LOCATE "ARTHRITIC MODELS" 36 SUCH THAT POINT P IS AT COORDINATES ($X_{0-j}$, $Y_{0-j}$, $Z_{0-j}$) RELATIVE TO ORIGIN ($X_0$, $Y_0$, $Z_0$). THUS "ARTHRITIC MODELS" 36 AND "BONE MODELS" 22 SHARE SAME LOCATION AND ORIENTATION RELATIVE TO THE ORIGIN. [BLOCK 130]

FOR ANY MOVEMENT OF "RESTORED BONE MODELS" 28 IN POP [BLOCK 120] OR ANY OTHER PROCESS INVOLVING "BONE MODELS" 22 OR "RESTORED BONE MODELS" 28 FROM POINT P AT COORDINATES ($X_{0-j}$, $Y_{0-j}$, $Z_{0-j}$) TO POINT P' AT COORDINATES ($X_{0-k}$, $Y_{0-k}$, $Z_{0-k}$), CAUSE IDENTICAL MOVEMENT IN 3D "ARTHRITIC MODELS" 36 SUCH THAT LOCATION AND ORIENTATION OF "ARTHRITIC MODELS" 36 MATCH THOSE OF THE "BONE MODELS" 22 AND "RESTORED BONE MODELS" 28. [BLOCK 135]

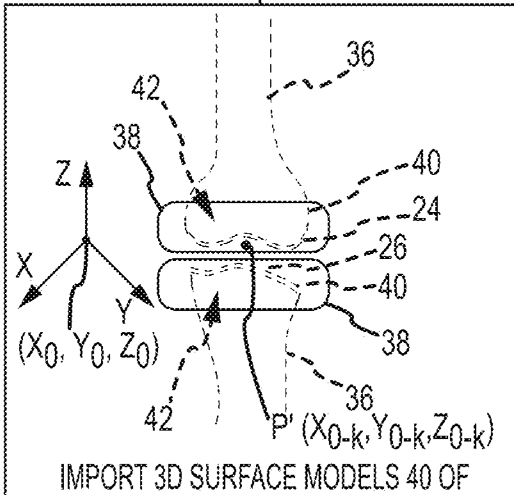

IMPORT 3D SURFACE MODELS 40 OF ARTHROPLASTY TARGET AREAS 42 OF "ARTHRITIC MODELS" 36 INTO 3D MODELS OF ARTHROPLASTY CUTTING JIGS 38. [BLOCK 140]

TO [BLOCK 145] IN FIG.1E

FIG.1D

FROM [BLOCK 105] IN FIG.1B

CORONAL 2D IMAGE SAGITTAL 2D RELATIONSHIP AXIAL 2D IMAGE

18 TROCHLEAR GROOVE LINE $(X_0, Y_0, Z_0)$ Z X $D_1$ $D_2$ JOINT LINE $W(X_{0-j}, Y_{0-j}, Z_{0-j})$

18 Z Y $(X_0, Y_0, Z_0)$ $D_1,D_2$ $P_1,P_2$ $W(X_{0-j}, Y_{0-j}, Z_{0-j})$

18 $(X_0, Y_0, Z_0)$ X Y $P_1$ $P_2$ JOINT LINE TROCHLEAR GROOVE LINE

DETERMINE FEMUR REFERENCE DATA: ANALYZE 2D CORONAL AND AXIAL FEMUR IMAGES TO IDENTIFY MOST DISTAL FEMUR POINTS $D_1$, $D_2$ AND MOST PROXIMAL FEMUR POINTS $P_1$ $P_2$ RESPECTIVELY, AND DEPICT THE POINTS IN A SAGITTAL VIEW. [BLOCK 110]

EMPLOY FEMUR REFERENCE DATA $P_1$, $P_2$, $D_1$, $D_2$ TO SELECT APPROPRIATE FEMUR IMPLANT. [BLOCK 112]

SAGITTAL 2D RELATIONSHIP $(X_0, Y_0, Z_0)$ Z Y 34 32 30 $P_1',P_2'$ $P_1,P_2$ $D_1,D_2$, $D_1',D_2'$ $W(X_{0-j}, Y_{0-j}, Z_{0-j})$

CORRELATE FEMUR REFERENCE DATA $P_1$, $P_2$, $D_1$, $D_2$ TO SIMILAR REFERENCE DATA $P_1'$, $P_2'$, $D_1'$, $D_2'$ OF THE SELECTED FEMUR IMPLANT IN SAGITTAL VIEW. [BLOCK 114]

ADJUST POSITION OF CUT PLANE 30 WITH RESPECT TO FEMUR TO ACCOUNT FOR CARTILAGE THICKNESS. [BLOCK 118]

CONTINUED IN [BLOCK 120] IN FIG.1C2

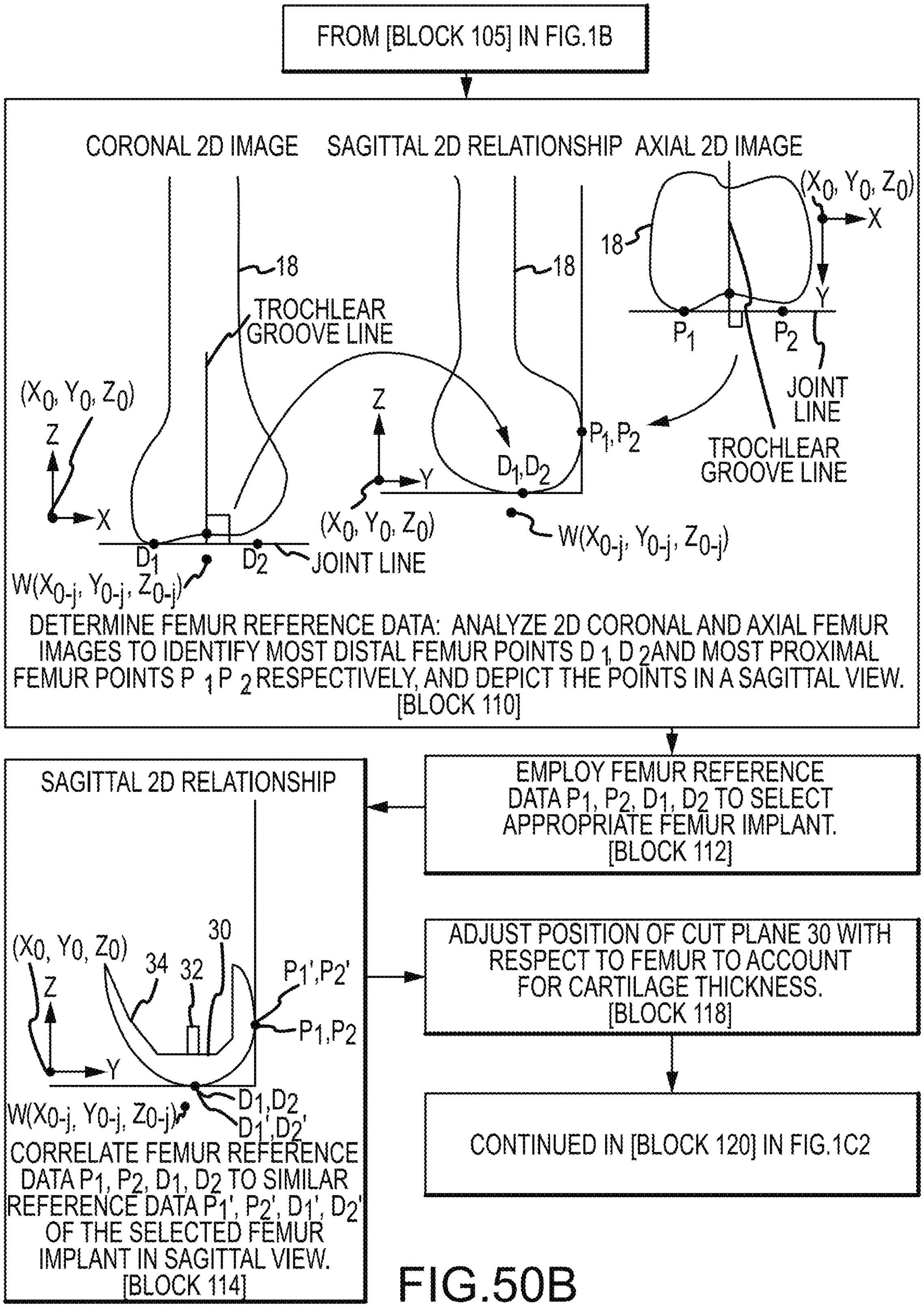

FIG.50B

FROM [BLOCK 118] IN FIG. 1C1

REPEAT PROCESS OF BLOCK 110 FOR TIBIA IN SIMILAR MANNER, EXCEPT SAGITTAL AND CORONAL IMAGE SLICES OF TIBIA ARE ANALYZED TO IDENTIFY THE LOWEST AND MOST ANTERIOR AND POSTERIOR POINTS OF THE TIBIA RECESSED CONDYLAR SURFACES, THIS TIBIA REFERENCE DATA THEN BEING PROJECTED ON TO AN AXIAL VIEW.
[BLOCK 120]

EMPLOY TIBIA REFERENCE DATA TO SELECT APPROPRIATE TIBIA IMPLANT.
[BLOCK 121]

REPEAT PROCESS OF BLOCK 114 FOR TIBIA IN SIMILAR MANNER, EXCEPT IN AN AXIAL VIEW CORRELATE TIBIA REFERENCE DATA TO SIMILAR REFERENCE DATA OF THE SELECTED TIBIA IMPLANT.
[BLOCK 122]

ADJUST POSITION OF CUT PLANE 30 WITH RESPECT TO TIBIA TO ACCOUNT FOR CARTILAGE THICKNESS.
[BLOCK 123]

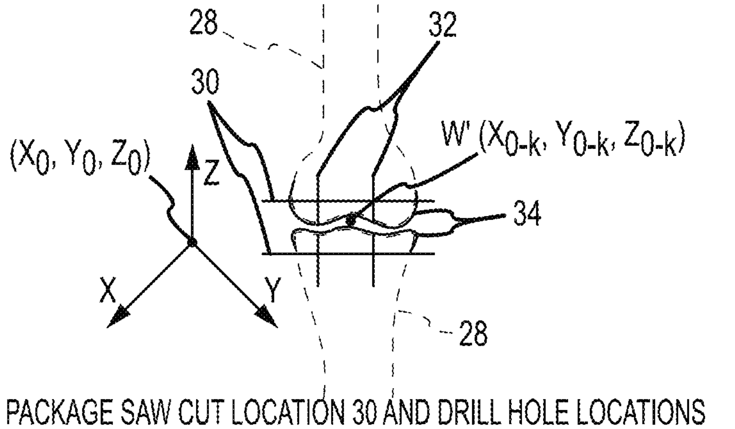

PACKAGE SAW CUT LOCATION 30 AND DRILL HOLE LOCATIONS 32 ASSOCIATED WITH PRE-OPERATIVE PLANNING ("POP") OF FEMUR AND TIBIA IMPLANTS 34 RELATIVE TO THE FEMUR AND TIBIA DATA 28 AND THE UPDATED POINT W'$(X_{0-k}, Y_{0-k}, Z_{0-k})$, WHICH MAY BE DIFFERENT FROM ORIGINAL POINT W$(X_{0-j}, Y_{0-j}, Z_{0-j})$ DUE TO ADJUSTMENTS TO DATA POSITIONS DURING ANY ONE OR MORE OF THE PROCESSES OF BLOCKS 110-124.
[BLOCK 124]

CONTINUED IN [BLOCK 125] IN FIG.1E

FIG.50C $\overrightarrow{EF} // \overrightarrow{AB} // \overrightarrow{CD}$ $\overrightarrow{CD} \perp \overrightarrow{OG}$ $\overrightarrow{EF} \perp \overrightarrow{OH}$

---

$\overrightarrow{OG} \perp \overrightarrow{EF}$ $\overrightarrow{OH} \perp \overrightarrow{CD}$ $\overrightarrow{AB} \perp \overrightarrow{OG}$ $OG \perp OH$ MEASURE THE MINIMUM CARTILAGE THICKNESS FOR THE UNDAMAGED AND DAMAGED FEMORAL CONDYLES. [BLOCK 1170]

USE THE CARTILAGE THICKNESS MEASURED FOR THE LEAST DAMAGED CONDYLE CARTILAGE AS THE CARTILAGE THICKNESS REFERENCE FOR POP. [BLOCK 1175]

SYSTEMS AND METHODS FOR SURGICAL PLANNING OF ARTHROPLASTY PROCEDURES

CROSS REFERENCE TO RELATED APPLICATION

The present application is a continuation of U.S. patent application Ser. No. 17/246,604, filed May 1, 2021, which application is a continuation of U.S. patent application Ser. No. 17/018,777, filed Sep. 11, 2020, now U.S. Pat. No. 10,993,744, which is a continuation-in-part application of U.S. patent application Ser. No. 16/923,548 filed Jul. 8, 2020, now U.S. Pat. No. 11,045,228, which application is a continuation application of U.S. patent application Ser. No. 16/803,664, filed Feb. 27, 2020, now U.S. Pat. No. 11,033,300, which application is a continuation of U.S. patent application Ser. No. 16/522,281, filed Jul. 25, 2019, now U.S. Pat. No. 10,575,875, which application is a continuation-in-part application of U.S. patent application Ser. No. 16/229,997, filed Dec. 21, 2018, now U.S. Pat. No. 10,675,063, which is a continuation application of U.S. patent application Ser. No. 15/581,974 filed Apr. 28, 2017, now U.S. Pat. No. 10,159,513, which application is a continuation of U.S. patent application Ser. No. 14/946,106 filed Nov. 19, 2015, now U.S. Pat. No. 9,687,259, which application is a continuation of U.S. patent application Ser. No. 13/731,697 filed Dec. 31, 2012, now U.S. Pat. No. 9,208,263, which application is a continuation of U.S. patent application Ser. No. 13/374,960 filed Jan. 25, 2012, now U.S. Pat. No. 8,532,361, which application is a continuation of U.S. patent application Ser. No. 13/066,568, filed Apr. 18, 2011, now U.S. Pat. No. 8,160,345, which application is a continuation-in-part application of U.S. patent application Ser. No. 12/386,105 filed Apr. 14, 2009, now U.S. Pat. No. 8,311,306. U.S. patent application Ser. No. 12/386,105 claims the benefit of U.S. Provisional Patent Application No. 61/126,102, filed on Apr. 30, 2008.

U.S. patent application Ser. No. 16/522,281, filed Jul. 25, 2019, is also a continuation-in-part of U.S. patent application Ser. No. 16/017,320, filed Jun. 25, 2018, now U.S. Pat. No. 10,617,475, which is a continuation application of U.S. patent application Ser. No. 15/802,137, filed Nov. 2, 2017, now U.S. Pat. No. 10,034,714, which is a continuation application of U.S. patent application Ser. No. 15/469,171, filed Mar. 24, 2017, now U.S. Pat. No. 9,839,485, which is a continuation application of U.S. patent application Ser. No. 15/242,312, filed Aug. 19, 2016, now U.S. Pat. No. 9,636,120, which is a divisional application of U.S. patent application Ser. No. 14/476,500, filed Sep. 3, 2014, now U.S. Pat. No. 9,451,970, which is a continuation application of U.S. patent application Ser. No. 13/731,850, filed Dec. 31, 2012, now U.S. Pat. No. 8,961,527, which is a continuation application of U.S. patent application Ser. No. 12/505,056, filed Jul. 17, 2009, now U.S. Pat. No. 8,777,875, which claims the benefit of U.S. Provisional Patent Application No. 61/083,053, filed Jul. 23, 2008.

U.S. patent application Ser. No. 16/522,281, filed Jul. 25, 2019, is also a continuation-in-part of U.S. patent application Ser. No. 16/211,735, filed Dec. 6, 2018, now U.S. Pat. No. 11,033,334, which is a continuation of U.S. patent application Ser. No. 15/167,710 filed May 27, 2016, now U.S. Pat. No. 10,182,870, which application is a continuation-in-part of U.S. patent application Ser. No. 14/084,255 filed Nov. 19, 2013, now U.S. Pat. No. 9,782,226, which application is a continuation of U.S. patent application Ser. No. 13/086,275 ("the '275 application"), filed Apr. 13, 2011, now U.S. Pat. No. 8,617,171. The '275 application is a continuation-in-part ("CIP") of U.S. patent application Ser. No. 12/760,388 ("the '388 application"), filed Apr. 14, 2010, now U.S. Pat. No. 8,737,700. The '388 application is a CIP application of U.S. patent application Ser. No. 12/563,809 ("the '809 application), filed Sep. 21, 2009, now U.S. Pat. No. 8,545,509, which claims the benefit of U.S. Provisional Patent Application 61/102,692 ("the '692 application"), filed Oct. 3, 2008. The '388 application is also a CIP application of U.S. patent application Ser. No. 12/546,545 ("the 545 application"), filed Aug. 24, 2009, now U.S. Pat. No. 8,715,291, which claims the benefit of the '692 application. The '809 application is also a CIP application of U.S. patent application Ser. No. 12/111,924 ("the '924 application"), filed Apr. 29, 2008, now U.S. Pat. No. 8,480,679. The '545 application is also a CIP application of U.S. patent application Ser. No. 11/959,344 ("the '344 application), filed Dec. 18, 2007, now U.S. Pat. No. 8,221,430. The '809 application is a CIP application of U.S. patent application Ser. No. 12/505,056 ("the '056 application"), filed Jul. 17, 2009, now U.S. Pat. No. 8,777,875. The '056 application claims the benefit of U.S. Provisional Patent Application 61/083,053, filed Jul. 23, 2008. The '809 application is also a CIP application of the '344 application. The '388 application is also a CIP of the '344 application. The '388 application is also a CIP of the '924 application. And the '388 application is also a CIP of the '056 application.

U.S. patent application Ser. No. 17/018,777 is also a continuation-in-part application of U.S. patent application Ser. No. 14/776,660, filed Sep. 14, 2015, now U.S. Pat. No. 10,912,571, which was the National Stage of International Application No. PCT/US2014/030496, filed Mar. 17, 2014, which claims the benefit of U.S. Provisional Patent Application No. 61/794,514, filed Mar. 15, 2013, and is also a continuation-in-part application of U.S. patent application Ser. No. 12/546,545, filed Aug. 24, 2009, now U.S. Pat. No. 8,715,291, which claims the benefit of U.S. Provisional Patent Application No. 61/102,692, filed Oct. 3, 2008. U.S. patent application Ser. No. 12/546,545 is a continuation-in-part application of Ser. No. 11/959,344, filed Dec. 18, 2007, now U.S. Pat. No. 8,221,430. PCT/US2014/030496 is also a continuation-in-part application of U.S. patent application Ser. No. 12/505,056, filed Jul. 17, 2009, now U.S. Pat. No. 8,777,875, which claims the benefit of U.S. Provisional Patent Application No. 61/083,053, filed Jul. 23, 2008.

Each of the aforementioned applications is hereby incorporated by reference in its entirety into the present application.

FIELD OF THE INVENTION

The present invention relates to image segmentation, morphing bone models to pre-degenerated states, and planning surgeries.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. Cartilage wearing down can result in fluid accumulating in the joint areas, pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA procedure. A one- to two-millimeter translational misalignment, or a one- to two-degree rotational misalignment, may result in imbalanced ligaments, and may thereby significantly affect the outcome of the TKA procedure. For example, implant misalignment may result in intolerable post-surgery pain, and also may prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots that are configured to accept such an instrument.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state. However, the system and method for generating the customized jigs often relies on a human to "eyeball" bone models on a computer screen to determine configurations needed for the generation of the customized jigs. This "eyeballing" or manual manipulation of the bone modes on the computer screen is inefficient and unnecessarily raises the time, manpower and costs associated with producing the customized arthroplasty jigs. Furthermore, a less manual approach may improve the accuracy of the resulting jigs.

There is a need in the art for a system and method for reducing the labor associated with generating customized arthroplasty jigs. There is also a need in the art for a system and method for increasing the accuracy of customized arthroplasty jigs.

SUMMARY

Aspects of the present disclosure may involve a method for planning an arthroplasty procedure on a patient bone. The method may include accessing generic bone data stored in a memory of a computer, using the computer to generate modified bone data by modifying the generic bone data according to medical imaging data of the patient bone, using the computer to derive a location of non-bone tissue data relative to the modified bone data, and superimposing implant data and the modified bone data in defining a resection of an arthroplasty target region of the patient bone.

In certain instances, the non-bone tissue data may include a contour of the non-bone tissue data.

In certain instances, the non-bone tissue data pertains to cartilage.

In certain instances, the non-bone tissue data may include modified non-bone tissue data that may be computer generated by accessing generic non-bone tissue data stored in the memory and using the computer to modify the generic non-bone tissue data according to the medical imaging data of the patient bone.

In certain instances, the modified non-bone tissue data may include a contour of the non-bone tissue data.

In certain instances, the modified non-bone tissue data pertains to cartilage.

In certain instances, the contour of the non-bone tissue data may be used in registering the resection with the patient bone.

Aspects of the present disclosure may involve a surgical method and further may include resecting the resection into the patient bone.

In certain instances, the contour of the non-bone tissue data may be used in defining a registration surface of an arthroplasty jig, the registration surface registering the arthroplasty jig with the patient bone when the arthroplasty jig may be used to guide the resection in the arthroplasty target region of the patient bone.

Aspects of the present disclosure may involve a manufacturing method and further may include manufacturing the arthroplasty jig to may include the registration surface and a resection guide capable of guiding the resection when the registration surface interdigitates with the patient bone.

In certain instances, the method further may include comparing the modified bone data to candidate implant models stored in the memory of the computer.

In certain instances, the method further may include recommending an implant model based on the comparison of the modified bone data to the candidate implant models.

In certain instances, the method further may include presenting the defined resection to a surgeon for review.

Aspects of the present disclosure may involve a method for planning an arthroplasty procedure on a joint region of a patient bone. The method may include constructing a virtual bone model of the joint region of the patient bone, the virtual bone model may include a contour of soft tissue and a bone surface, determining a location and configuration of the soft tissue relative to the bone surface of the virtual bone model, identifying a registration surface including at least part of the location and configuration of the soft tissue, superimposing a virtual implant model over the bone surface of the virtual bone model, determining a resection relative to the bone surface of the virtual bone model based on the superimposing, the resection being adapted to facilitate an implant being implanted on the patient bone as part of the arthroplasty procedure, the implant corresponding to the virtual implant model, and referencing the resection to the registration surface.

In certain instances, the soft tissue may include cartilage.

In certain instances, the virtual bone model may be computer generated by accessing a generic bone model stored in a memory and using a computer to modify the generic bone model according to medical imaging data of the joint region of the patient bone.

In certain instances, the method further may include comparing the virtual bone model to candidate implant models stored in a memory of a computer.

In certain instances, the method further may include recommending an implant model based on the comparison of the virtual bone model to the candidate implant models.

In certain instances, the method further may include presenting the resection to a surgeon for review.

In certain instances, the virtual bone model may include a bone and cartilage model and a bone-only model.

Aspects of the present disclosure may involve a surgical method which further may include resecting the resection into the patient bone.

Aspects of the present disclosure may involve a manufacturing method and further may include manufacturing an arthroplasty jig to include a mating surface and a resection guide, the mating surface adapted to interdigitate with the registration surface, and the resection guide capable of guiding the resection when the mating surface interdigitates with the patient bone.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 1B-1E are flow chart diagrams outlining the jig production method disclosed herein.

FIG. 45J is similar to FIG. 45I, except depicting a tool with a larger diameter.

FIG. 45K is similar to FIG. 45J, except depicting a tool with a larger diameter.

FIG. 45L depicts the irregular region 2402D from FIG. 45D including a proposed area of overestimation indicated by the dashed line.

FIG. 45M shows an analysis of the regular region 2402A from FIG. 45D.

FIG. 45N is a diagrammatic sagittal-coronal-distal isometric view of three contour lines of three adjacent image slices depicting angular relationships that may be used to determine whether portions of the one or more contour lines may be employed to generate 3D computer models.

Figure 45A:
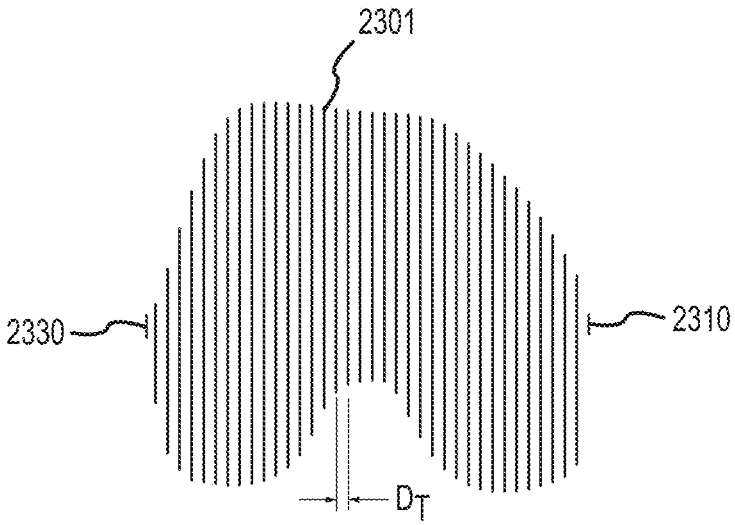
FIG. 45A illustrates the distal axial view of the 3D model of the patient's femur shown in FIG. 42A with the contour lines of the image slices shown and spaced apart by the thickness DT of the slices.
Figure 45B:
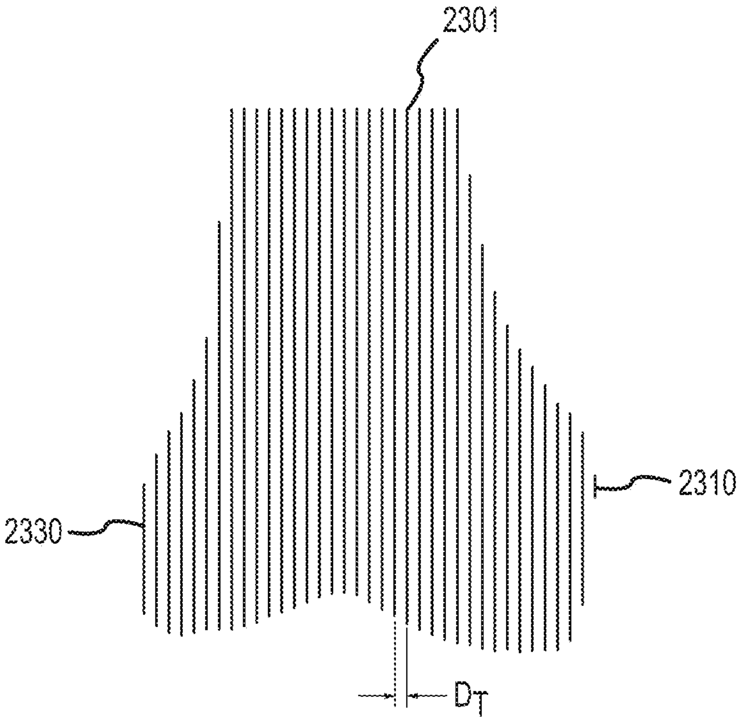
FIG. 45B represents a coronal view of a 3D model of the patient's femur with the contour lines of the image slices shown and spaced apart by the thickness DT of the slices.
Figure 45C:
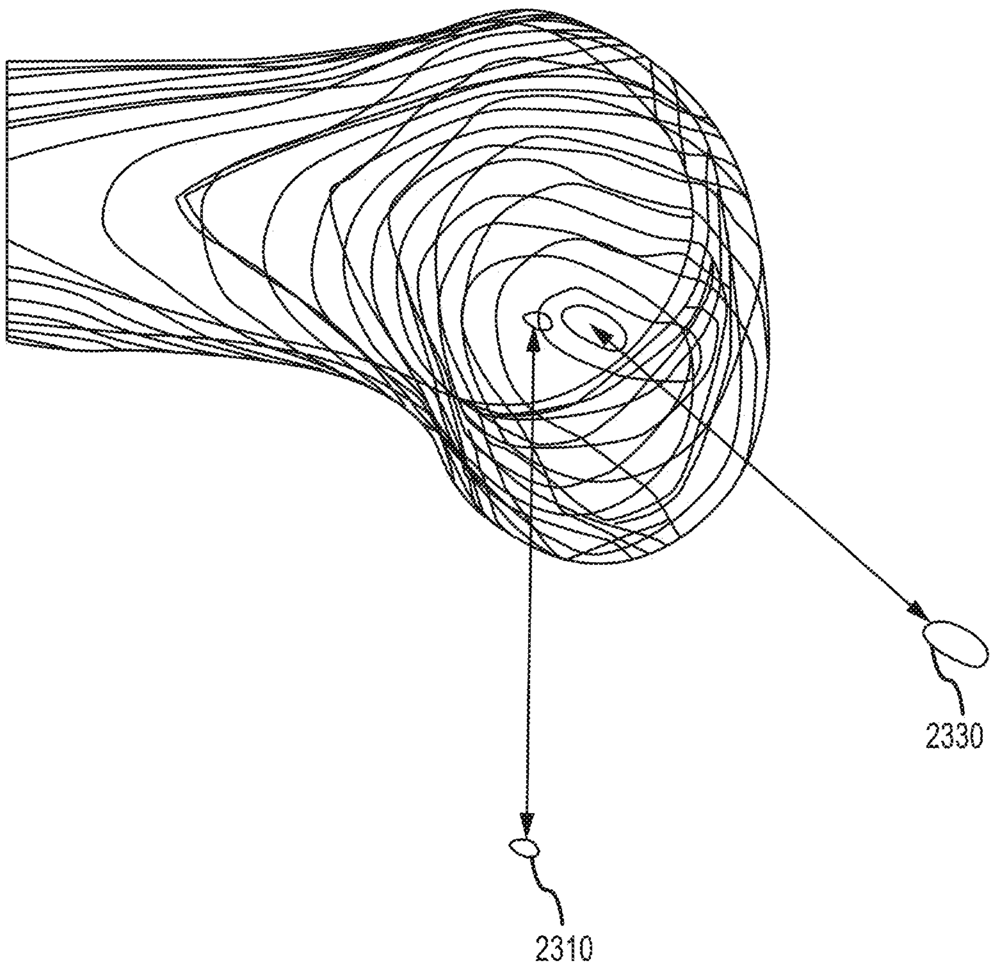
FIG. 45C illustrates an example sagittal view of compiled contour lines of successive sagittal 2D MRI images based on the slices shown in FIGS. 45A-B with a slice thickness DT of 2 mm.
Figure 45D:
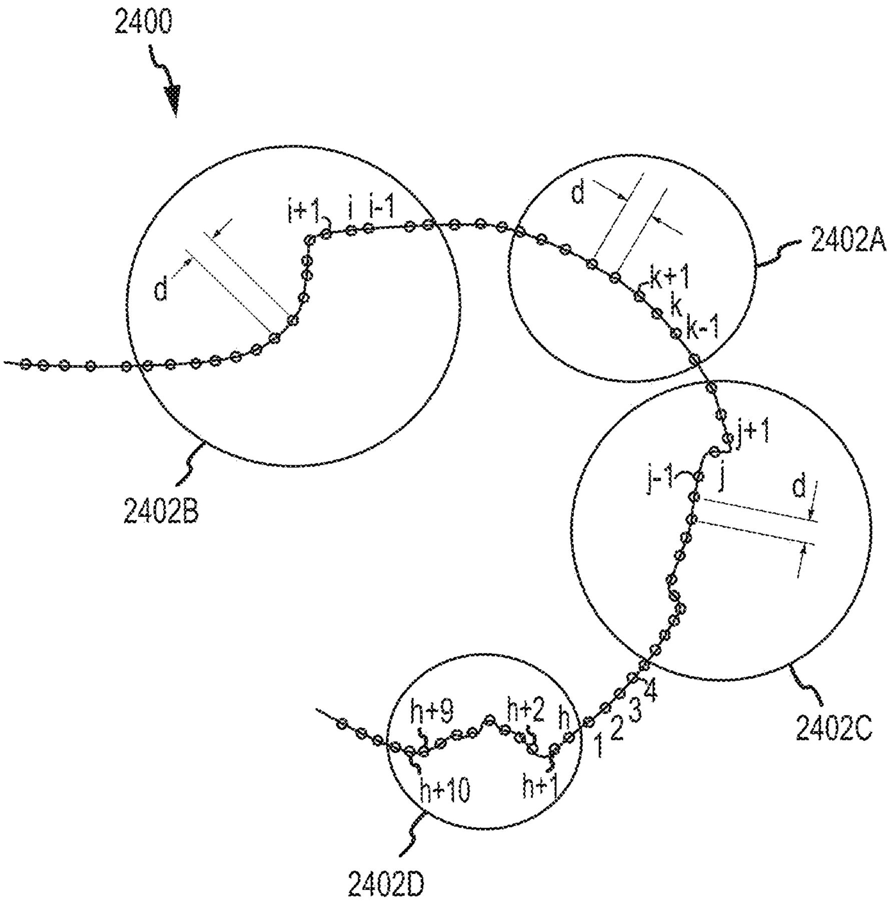
FIG. 45D illustrates an example contour line of one of the contour lines depicted in FIGS. 45A-45C, wherein the contour line is depicted in a sagittal view and is associated with an image slice of the femoral condyle.
Figure 45E:
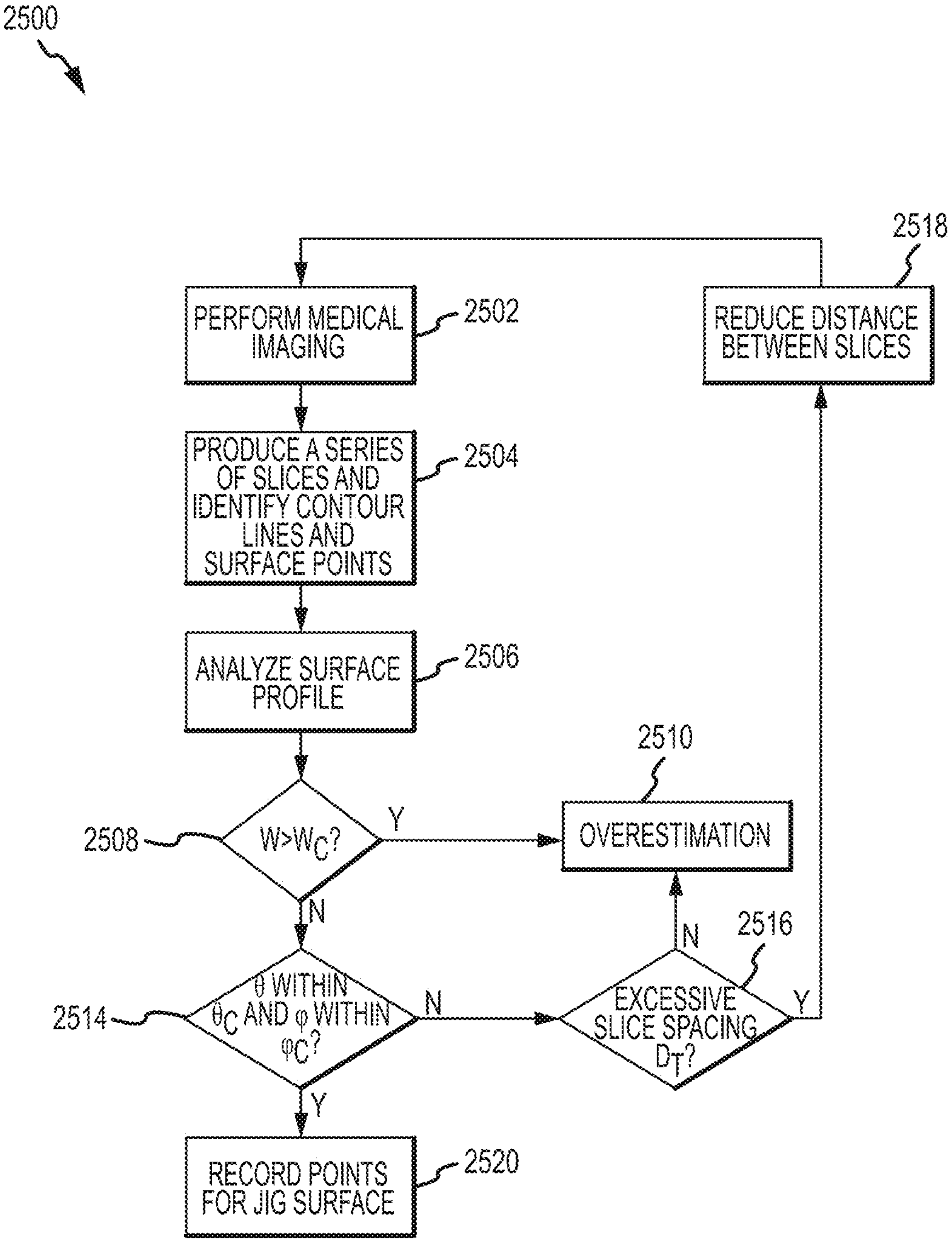
FIG. 45E represents an example overestimation algorithm that may be used to identify and adjust for irregular contour line regions when forming the 3D model.

FIGS. 45O-T are example right triangles that may be used for determining the angular deviation θ between corresponding coordinate points of contour lines of adjacent image slices per block 2514 of FIG. 45E.

Figures 46A, 46B:
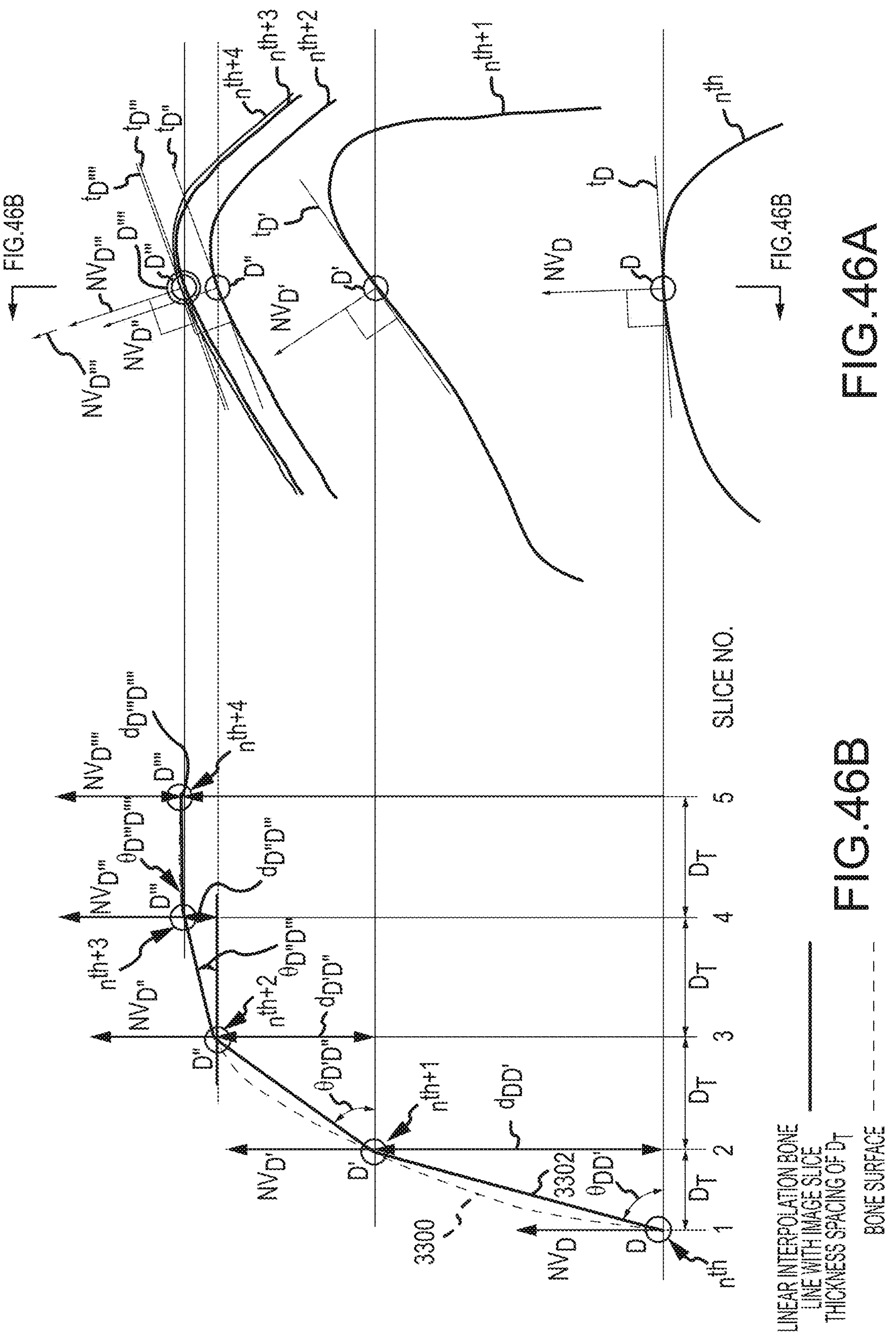

FIG. 46A depicts portions of contour lines $n^{th}$, $n^{th+1}$, $n^{th+2}$, $n^{th+3}$ and $n^{th+4}$ in a sagittal view similar to that of FIG. 45C.

FIG. 46B is a bone surface contour line and a linear interpolation bone surface contour line as viewed along a section line 33B-33B transverse to image slices containing the contour lines $n^{th}$, $n^{th+1}$, $n^{th+2}$, $n^{th+3}$ and $n^{th+4}$ of FIG. 46A.

Figures 46C, 46D:
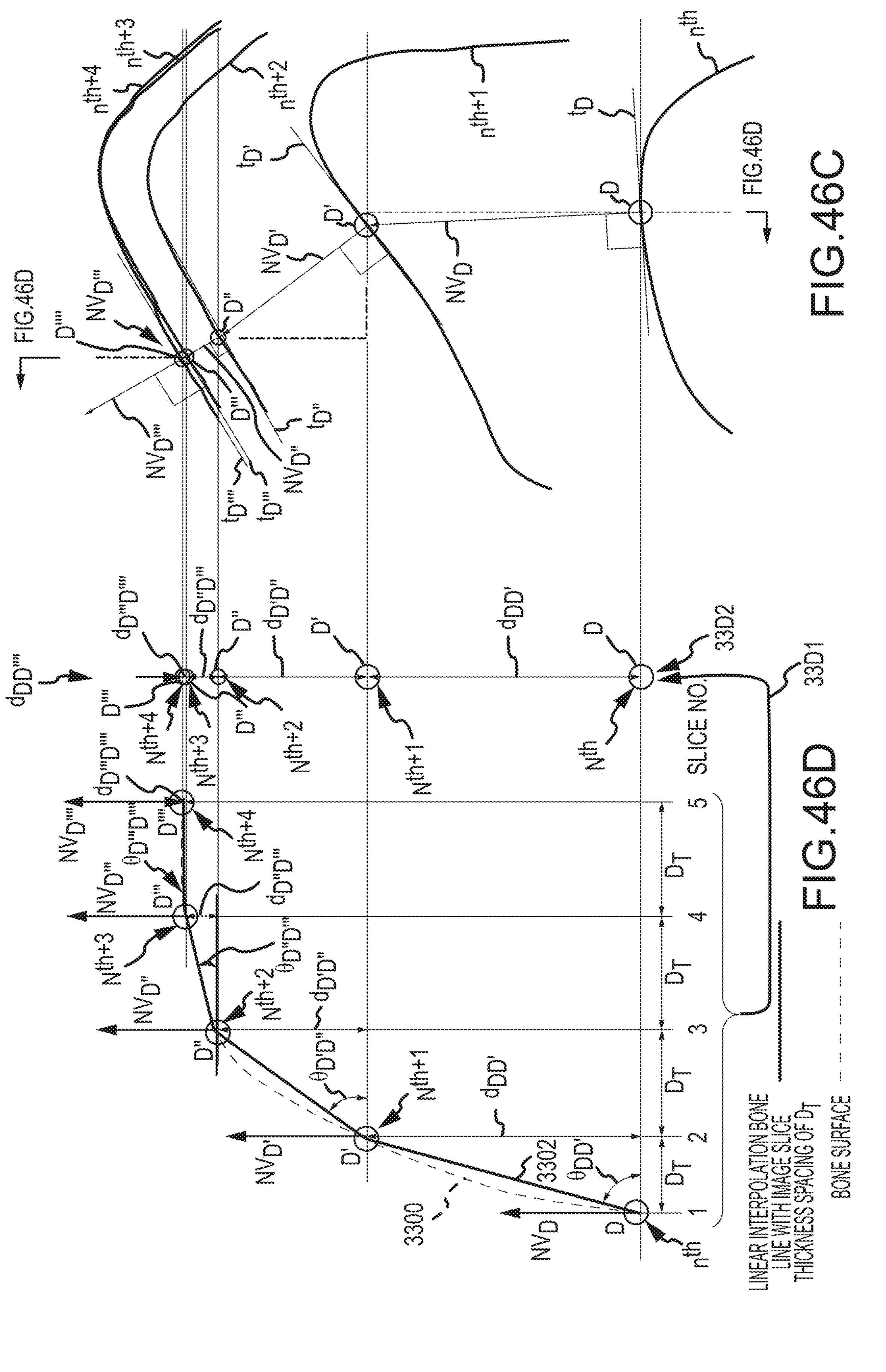

FIG. 46C depicts portions of contour lines $n^{th}$, $n^{th+1}$, $n^{th+2}$, $n^{th+3}$ and $n^{th+4}$ in a sagittal view similar to that of FIG. 45C.

FIG. 46D is a bone surface contour line and a linear interpolation bone surface contour line as viewed along a section line 46D-46D transverse to image slices containing the contour lines $n^{th}$, $n^{th+1}$, $n^{th+2}$, $n^{th+3}$ and $n^{th+4}$ of FIG. 46C.

Figure 46E:
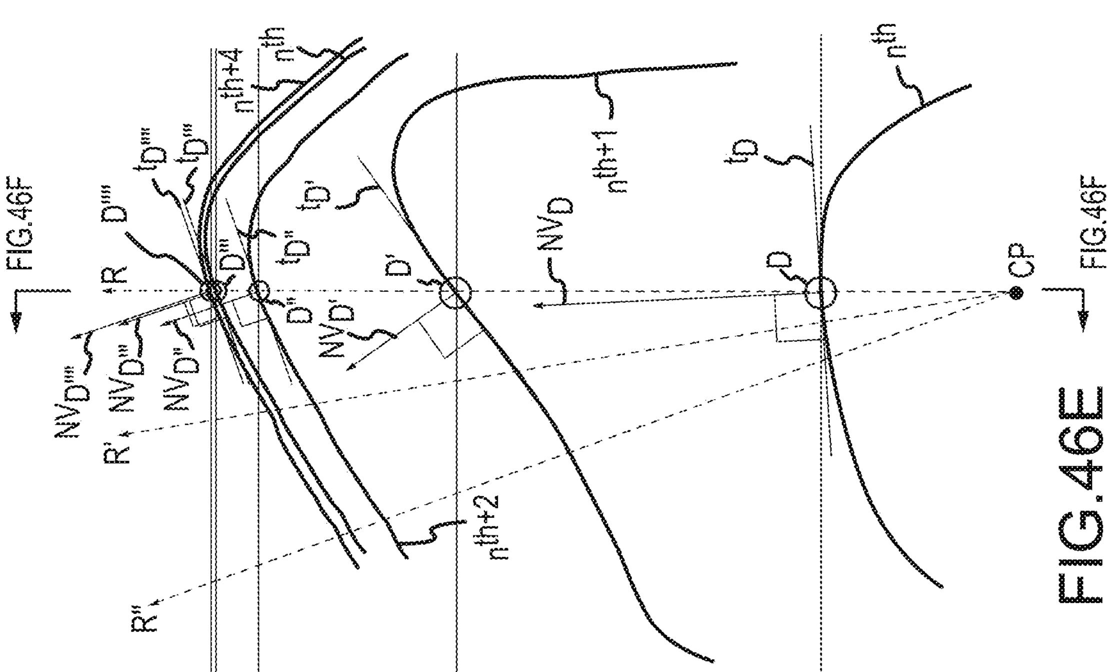

FIG. 46E depicts portions of contour lines $n^{th}$, $n^{th+1}$, $n^{th+2}$, $n^{th+3}$ and $n^{th+4}$ in a sagittal view similar to that of FIG. 45C.

Figure 46F:
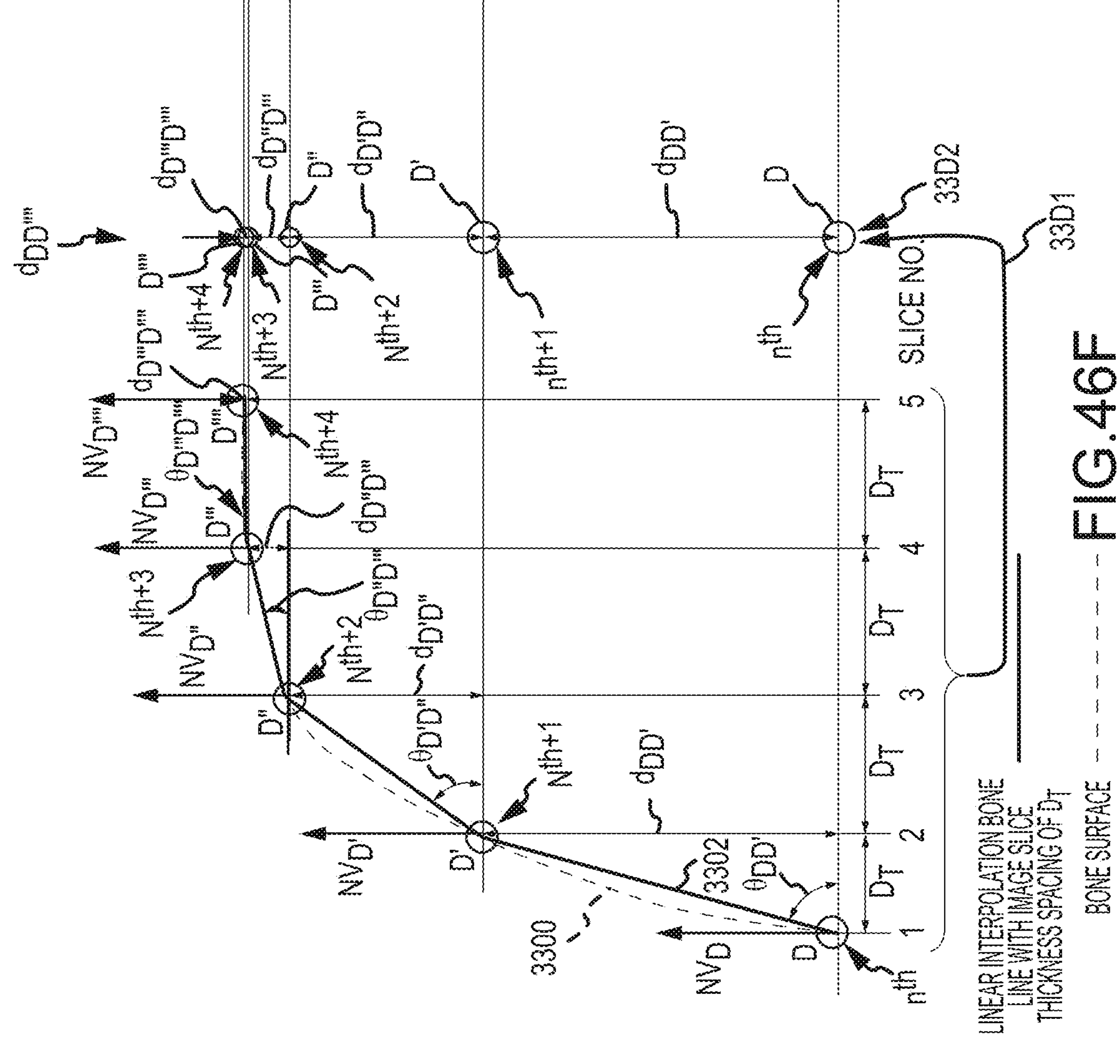

FIG. 46F is a bone surface contour line and a linear interpolation bone surface contour line as viewed along a section line 46F-46F transverse to image slices containing the contour lines $n^{th}$, $n^{th+1}$, $n^{th+2}$, $n^{th+3}$ and $n^{th+4}$ of FIG. 46E.

Figure 42A:
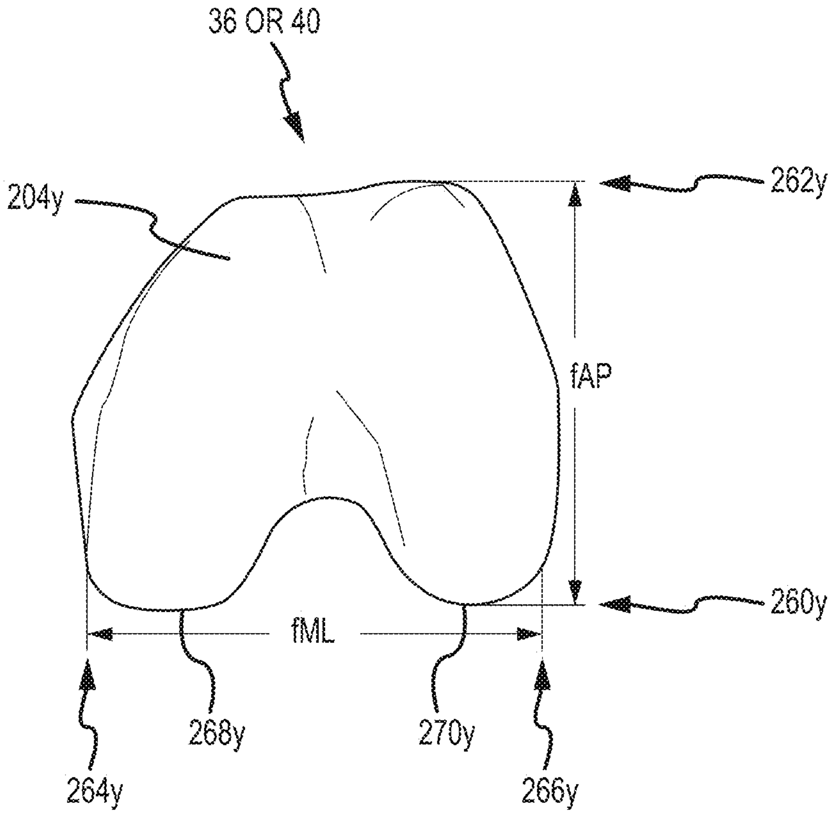
FIG. 42A is an axial view of the 3D surface model or arthritic model of the patient's left femur as viewed in a direction extending distal to proximal.
Figure 46G:
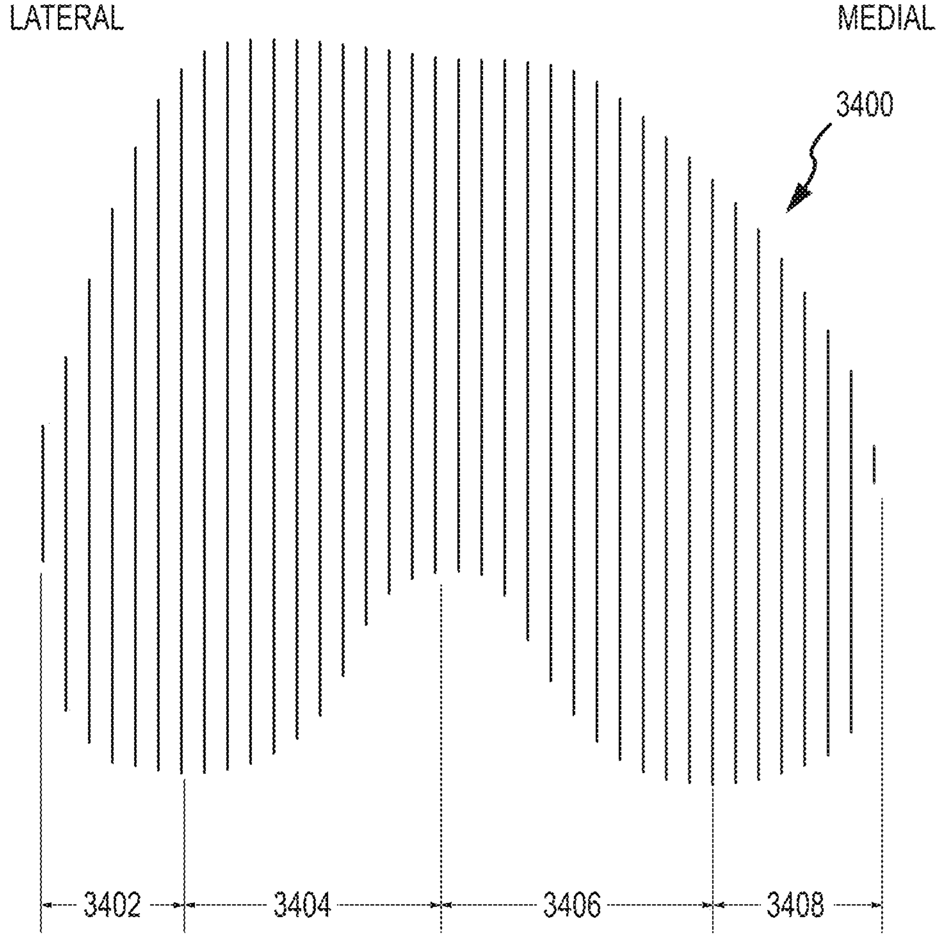

FIG. 46G is a distal view similar to that of FIG. 42A depicting contour lines produced by imaging the right femur at an image spacing DT of, for example, 2 mm.

FIGS. 46H-46K are sagittal views of the contour lines of respective regions of FIG. 46G.

Figure 47A:
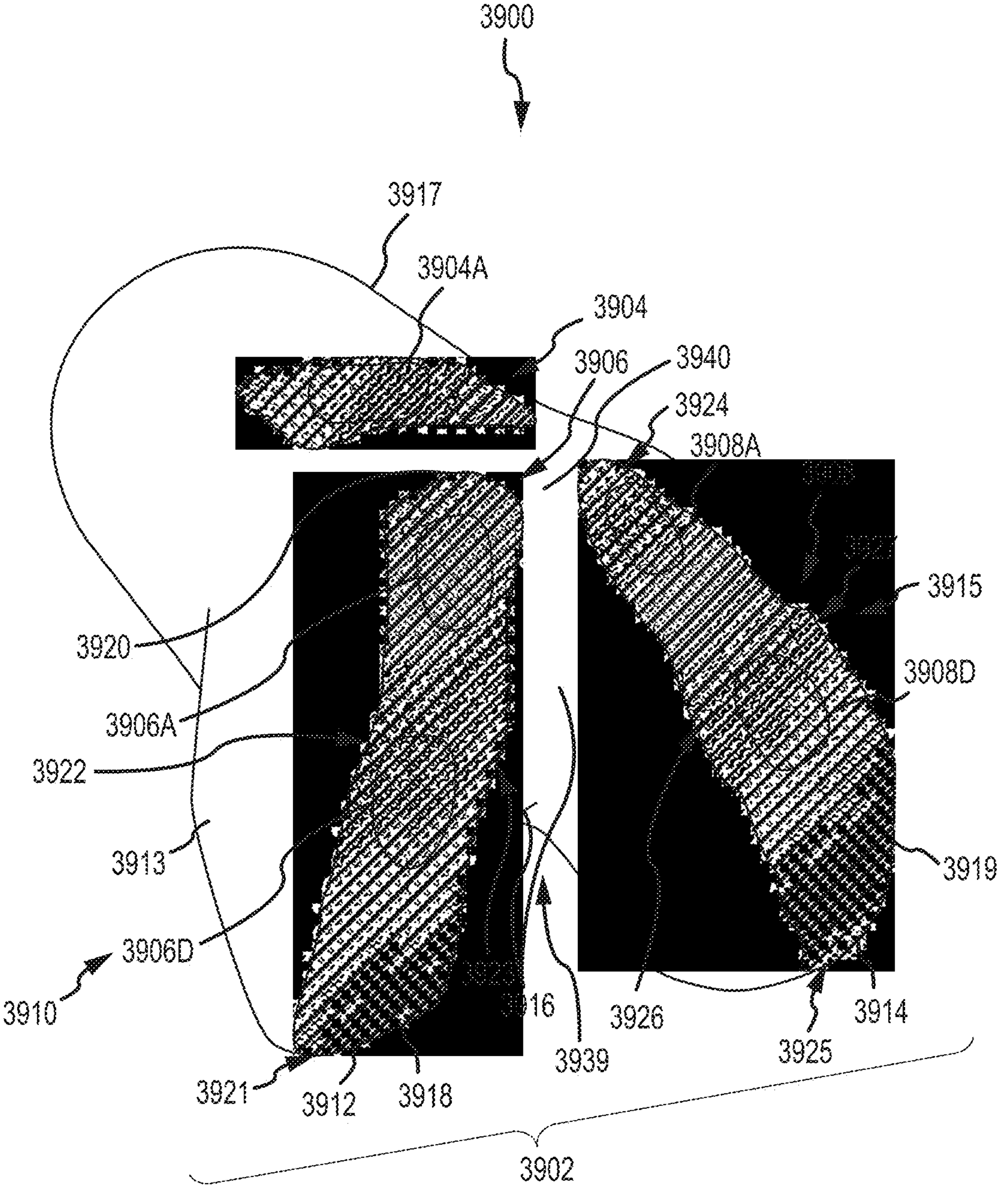

FIG. 47A is distal-sagittal isometric view of a femoral distal end.

Figure 47B:
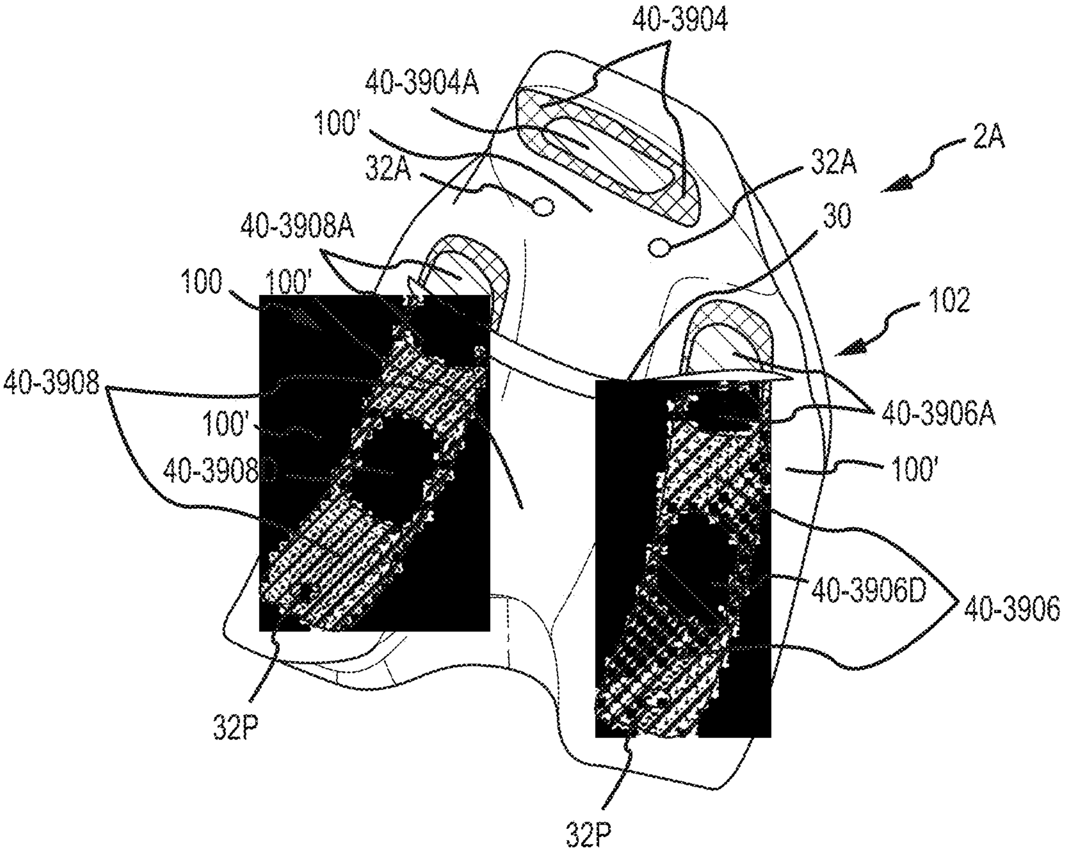

FIG. 47B is a bottom perspective view of an example customized arthroplasty femur jig that has been generated via the overestimation process disclosed herein.

Figure 47C:
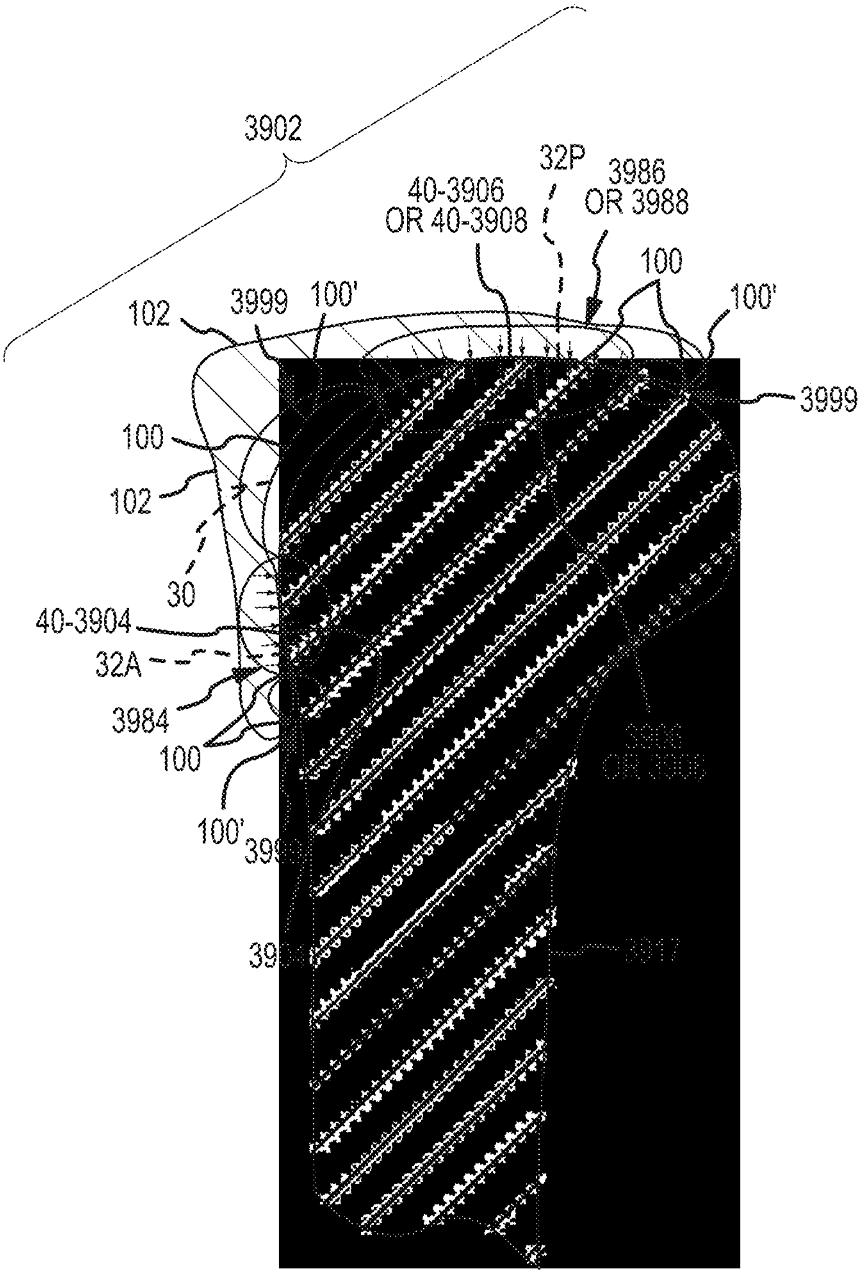

FIG. 47C is an anterior-posterior cross-section of the femur jig of FIG. 47B mounted on the femur distal end of FIG. 47A.

Figure 47D:
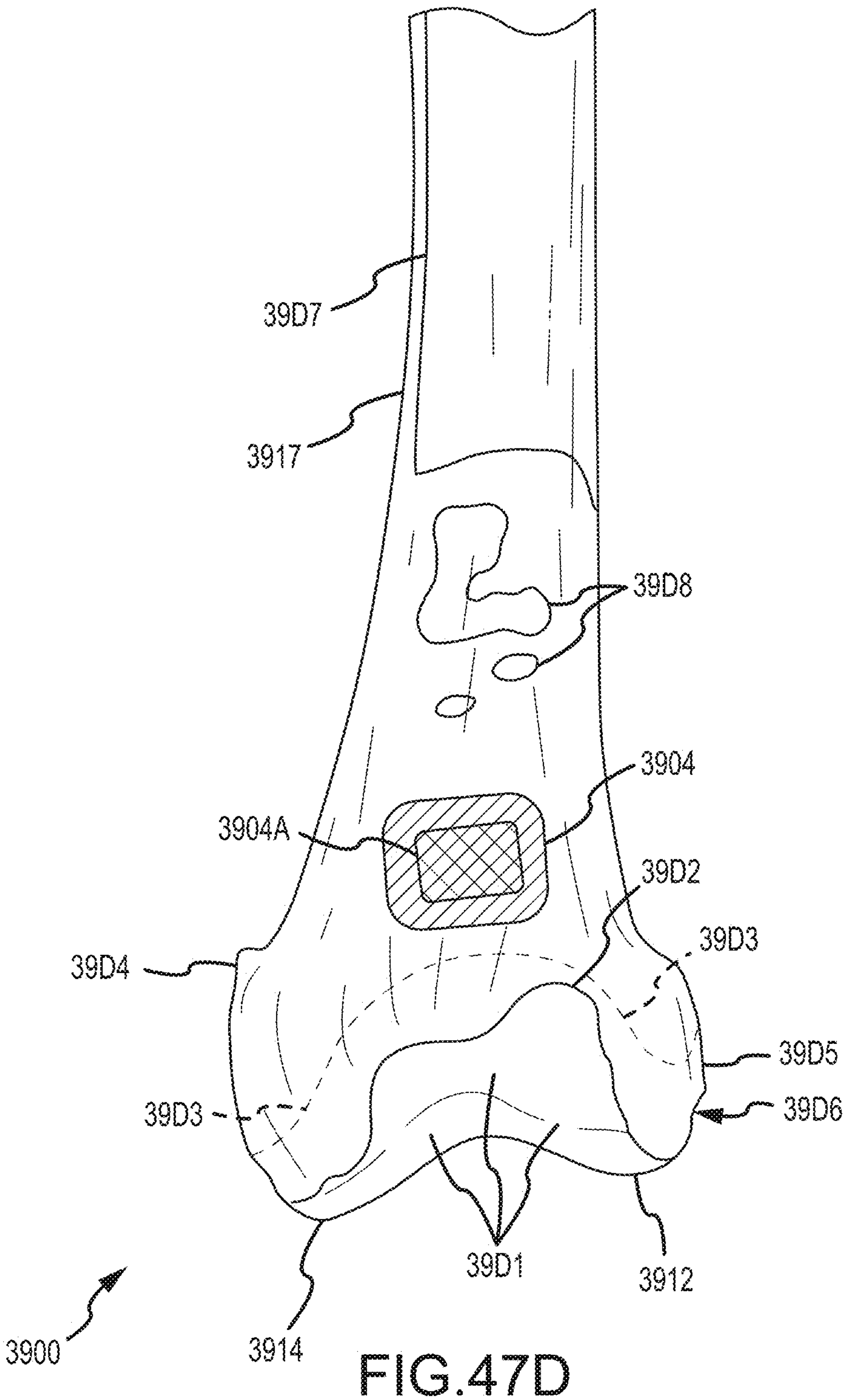

FIG. 47D is a coronal view of the anterior side of the femoral distal end.

Figure 47E:
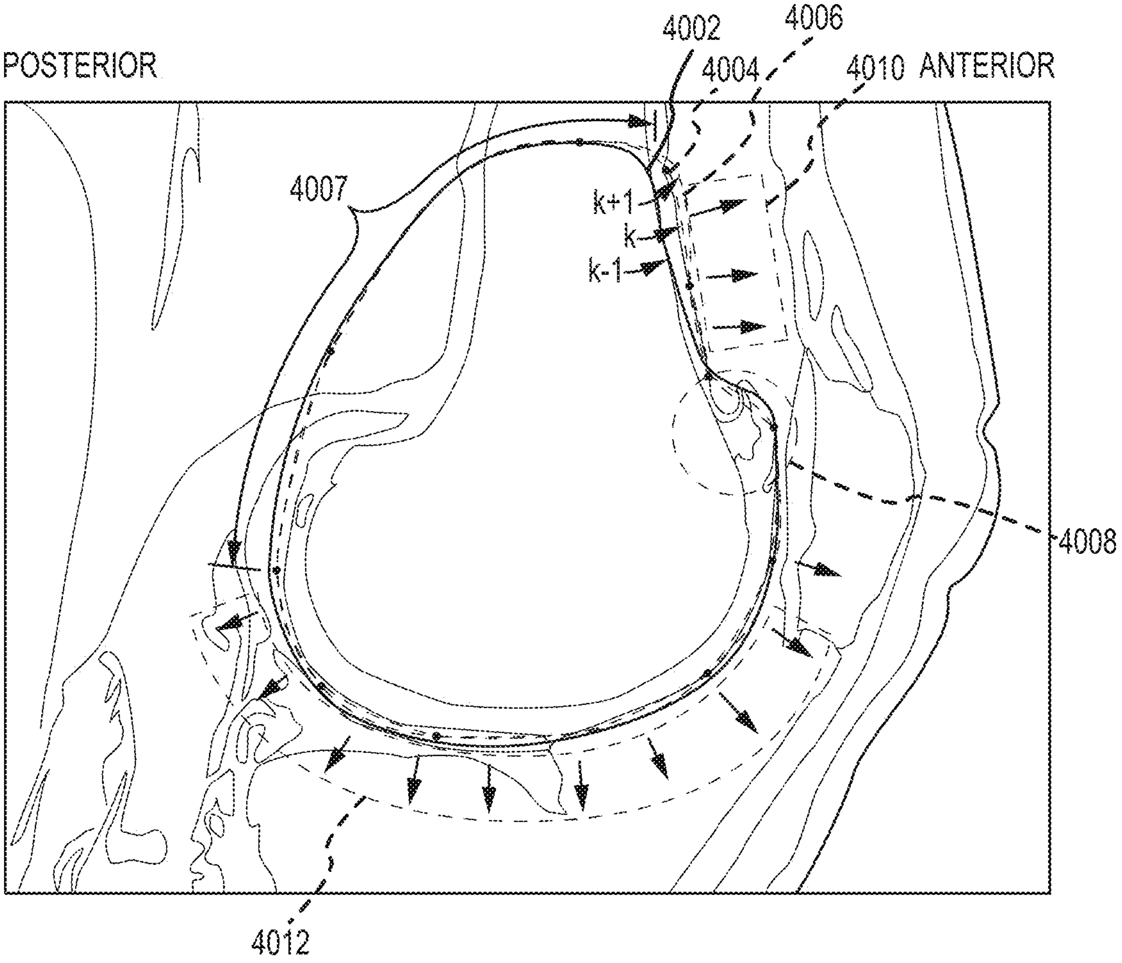

FIG. 47E depicts closed-loop contour lines that are image segmented from image slices, wherein the contour lines outline the cortical bone surface of the lower end of the femur.

Figure 48B:
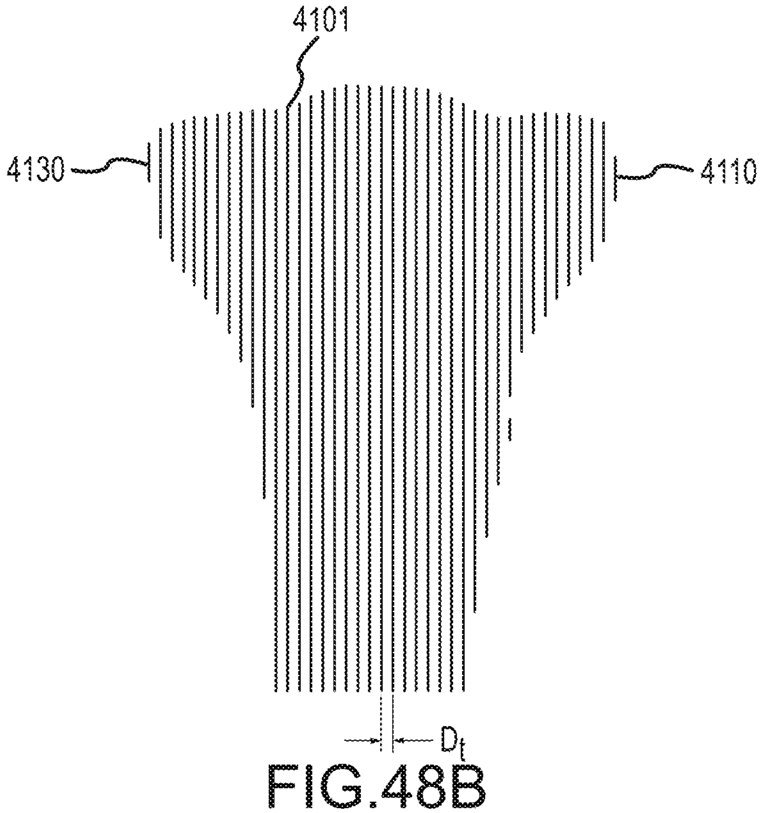
Figure 48A:
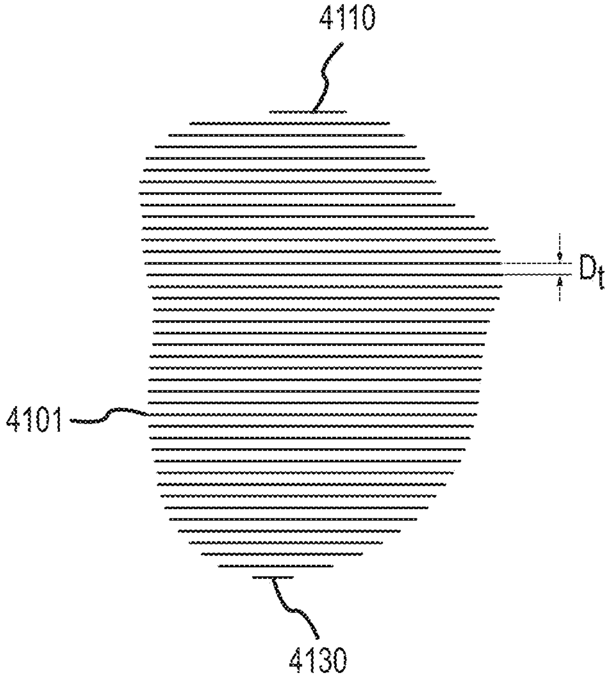

FIG. 48A illustrates the proximal axial view of the 3D model of the patient's tibia shown in FIG. 15 with the contour lines of the image slices shown and spaced apart by the thickness DT of the slices.

FIG. 48B represents a coronal view of a 3D model of the patient's tibia with the contour lines of the image slices shown and spaced apart by the thickness DT of the slices.

Figure 41A:
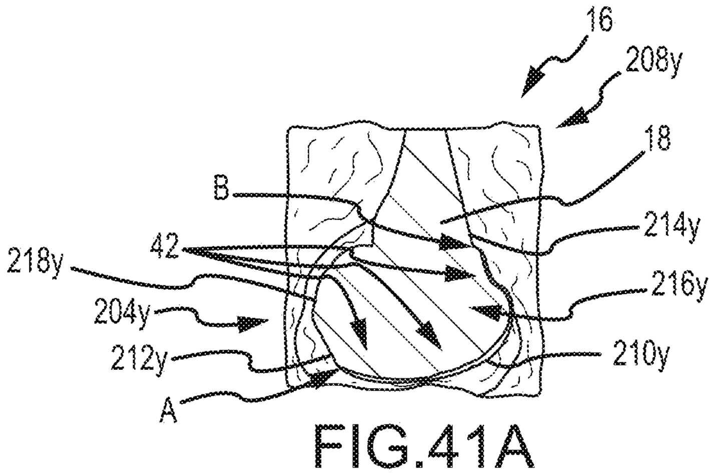
FIG. 41A is an anterior-posterior image slice of the damaged lower or knee joint end of the patient's femur, wherein the image slice includes an open-loop contour line segment corresponding to the targeted region of the damaged lower end.
Figure 41B:
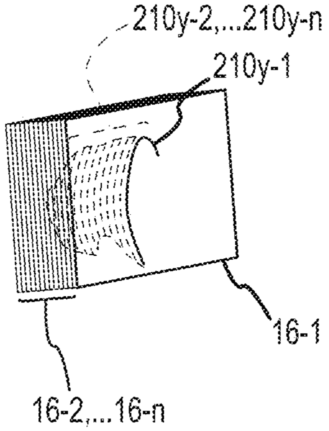
FIG. 41B is a plurality of image slices with their respective open-loop contour line segments, the open-loop contour line segments being accumulated to generate the 3D model of the targeted region.
Figure 48C:
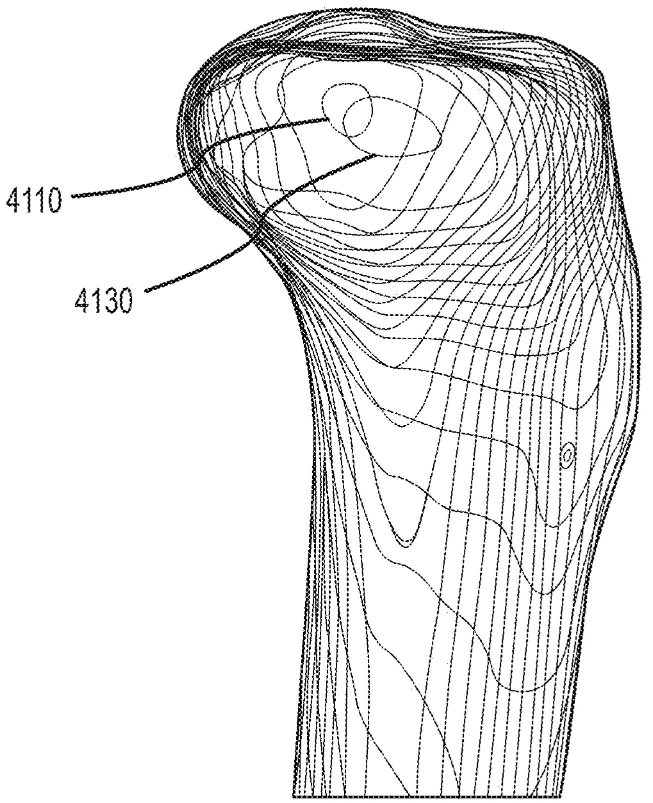

FIG. 48C illustrates an example sagittal view of compiled contour lines of successive sagittal 2D MRI images based on the slices shown in FIGS. 41A-B with a slice thickness DT of 2 mm.

Figure 48D:
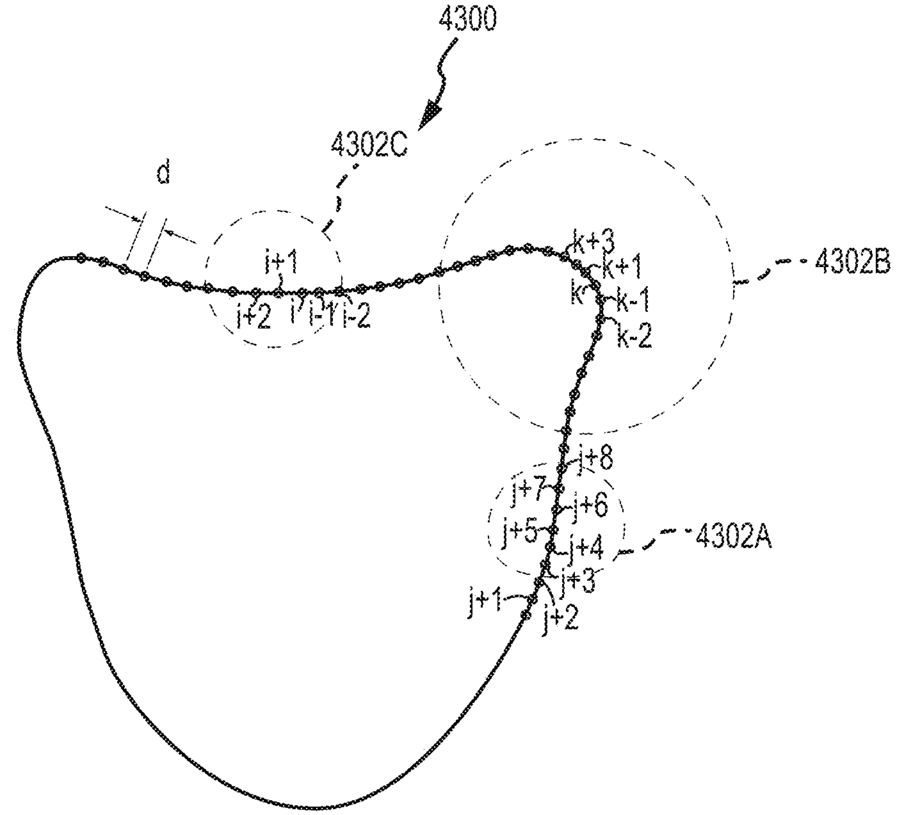

FIG. 48D illustrates an example contour line of one of the contour lines depicted in FIGS. 48A-48C, wherein the contour line is depicted in a sagittal view and is associated with an image slice of the tibia plateau.

Figure 48E:
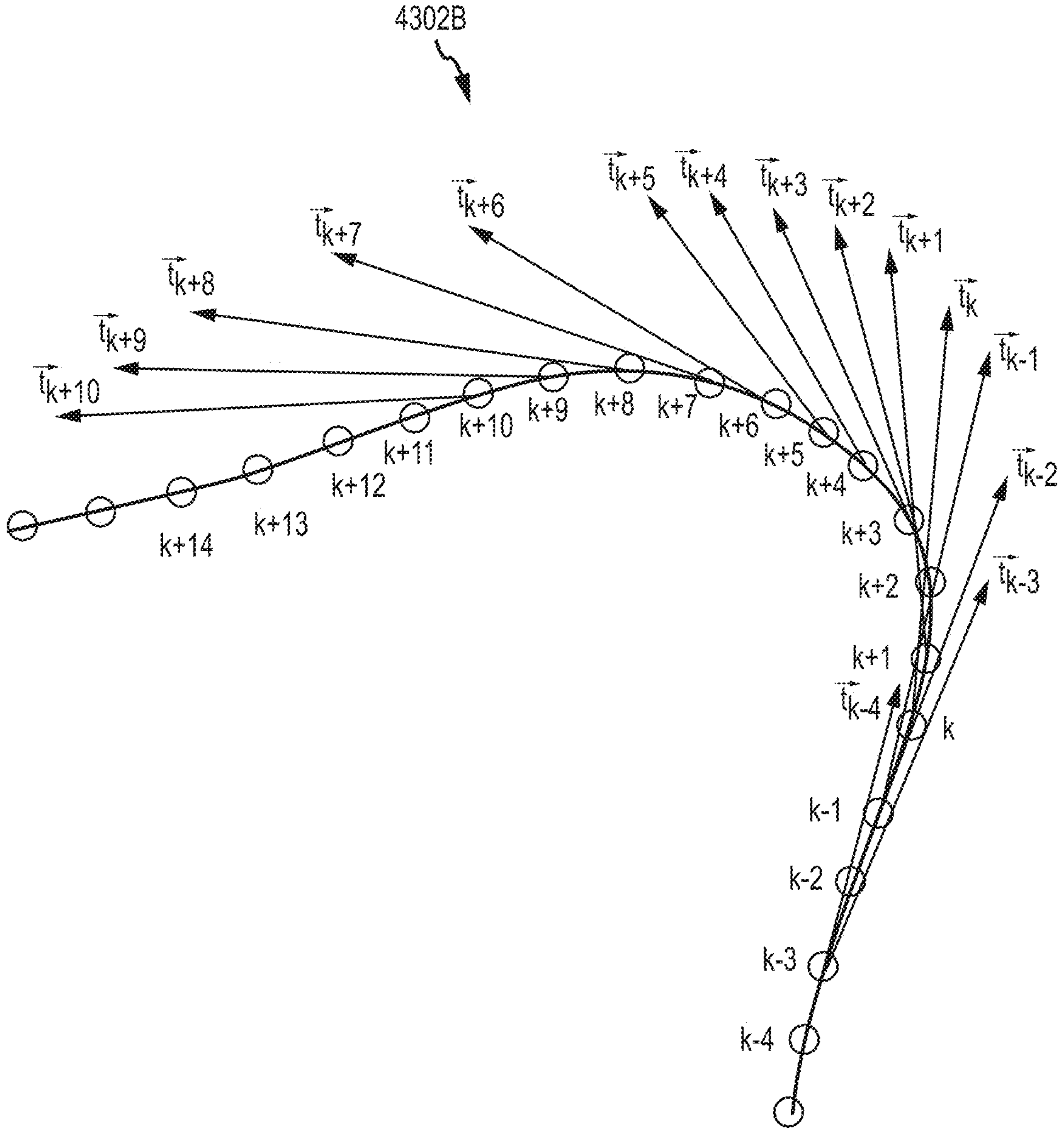

FIG. 48E depicts implementing an example analysis scheme (according to block 2506) on the irregular contour line region 4302B of FIG. 48D.

Figure 48F:
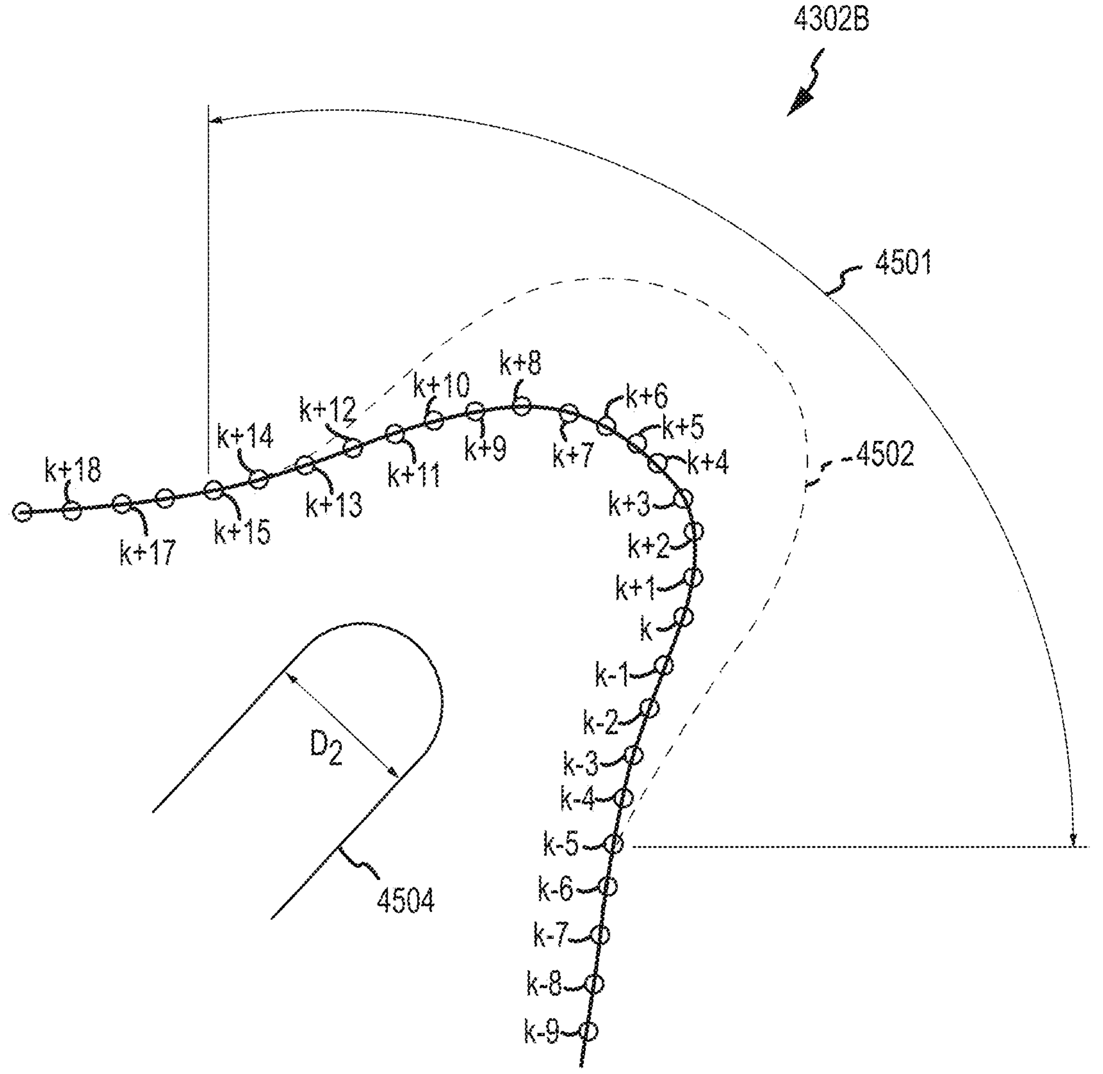

FIG. 48F depicts the irregular region 4302B from FIG. 48E including a proposed area of overestimation, wherein an overestimation procedure creates an adjusted contour line and positionally deviates the adjusted contour line from the original surface profile contour line.

Figure 48G:
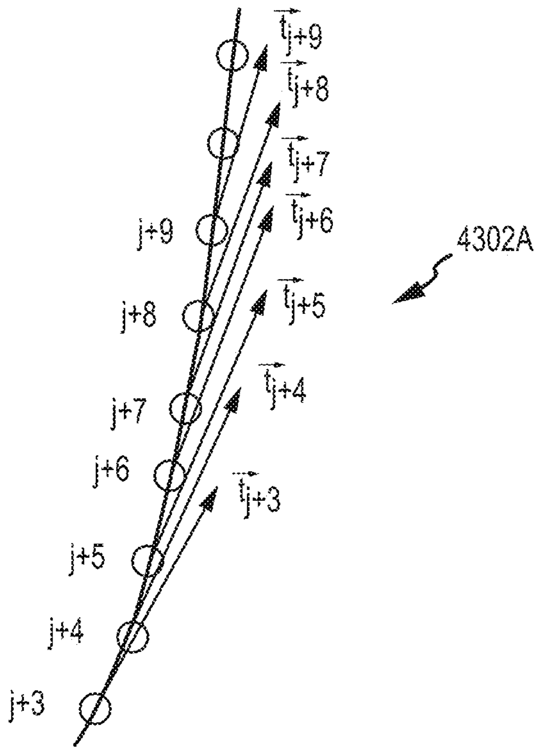
Figure 48H:
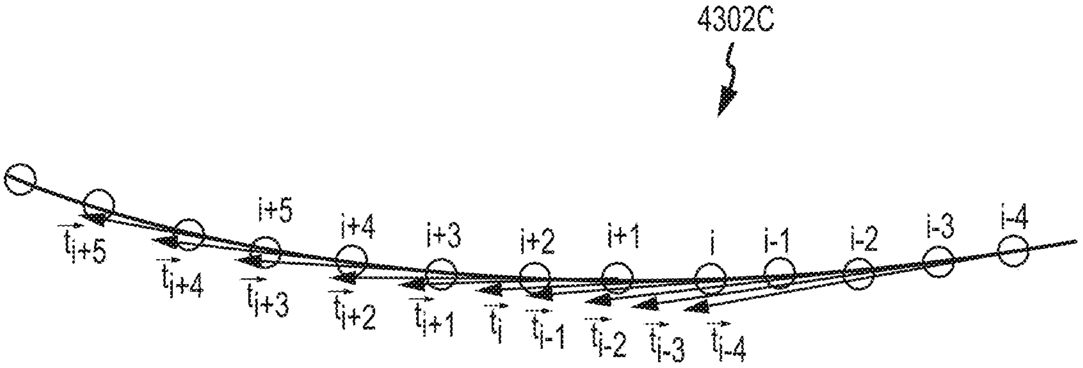

FIGS. 48G and 48H show an analysis of the regular regions 4302A and 4302C from FIG. 48D.

Figure 43A:
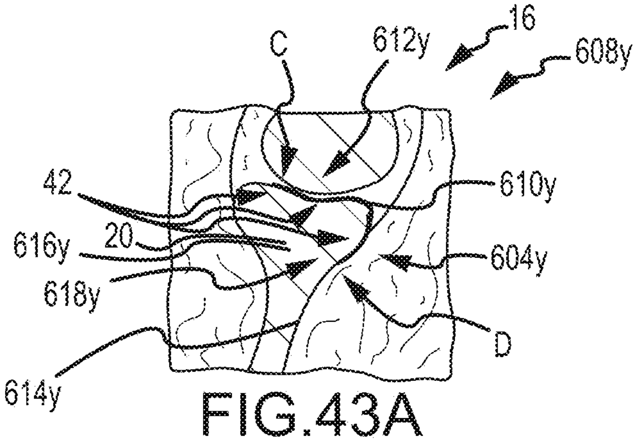
FIG. 43A is an anterior-posterior image slice of the damaged upper or knee joint end of the patient's tibia, wherein the image slice includes an open-loop contour line segment corresponding to the target area of the damaged upper end.
Figure 43B:
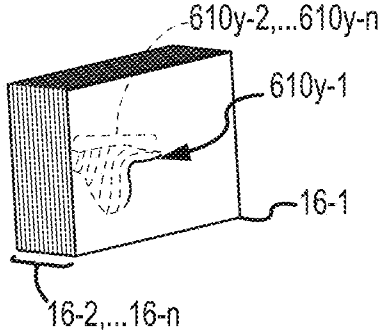
FIG. 43B is a plurality of image slices with their respective open-loop contour line segments, the open-loop contour line segments being accumulated to generate the 3D model of the target area.
Figure 43C:
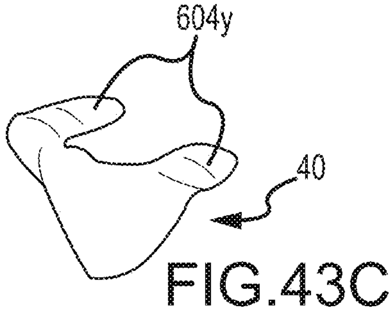
FIG. 43C is a 3D model of the target area of the damaged upper end as generated using the open-loop contour line segments depicted in FIG. 43B.
Figure 43D:
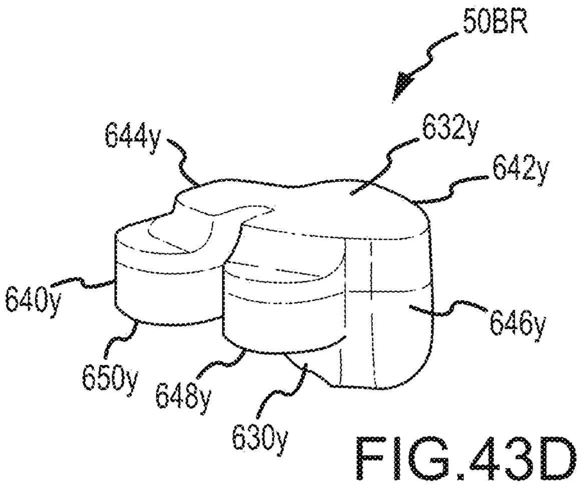
FIG. 43D is a top perspective view of a right tibia cutting jig blank having predetermined dimensions.
Figure 43E:
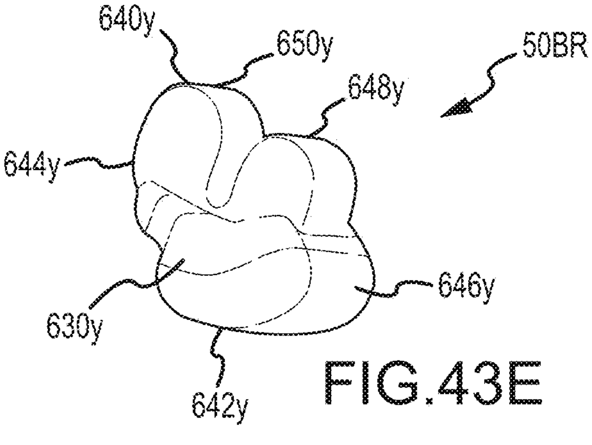
FIG. 43E is a bottom perspective view of the jig blank depicted in FIG. 43D.
Figure 43F:
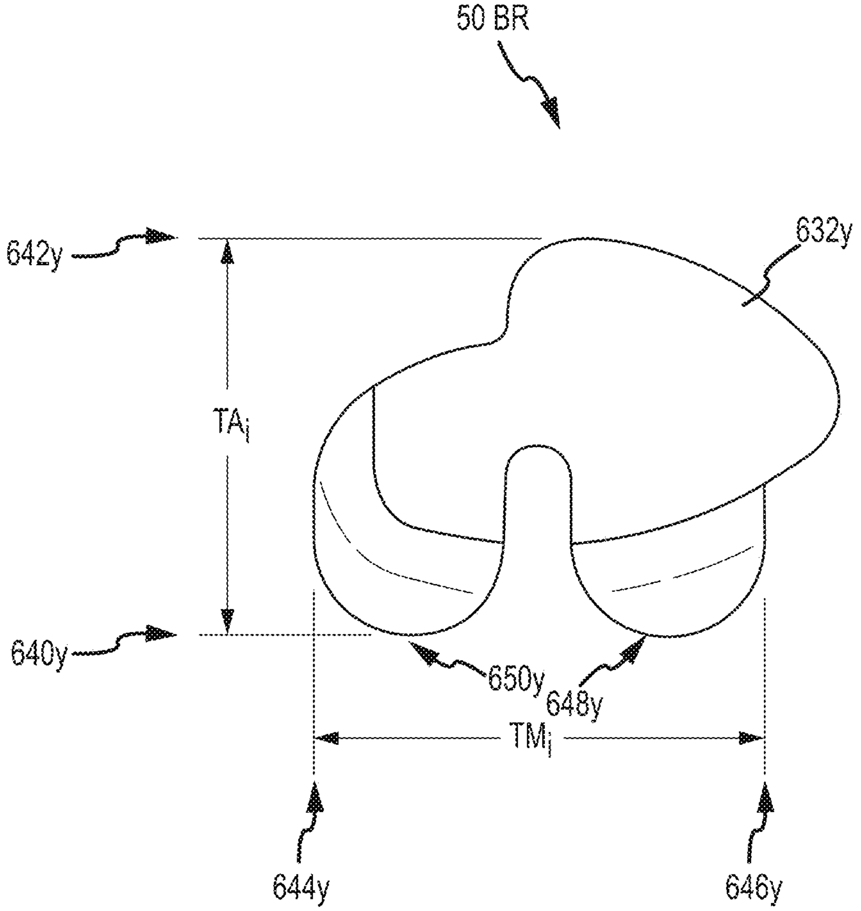
FIG. 43F is plan view of an exterior side or portion of the jig blank depicted in FIG. 43D.
Figure 43G:
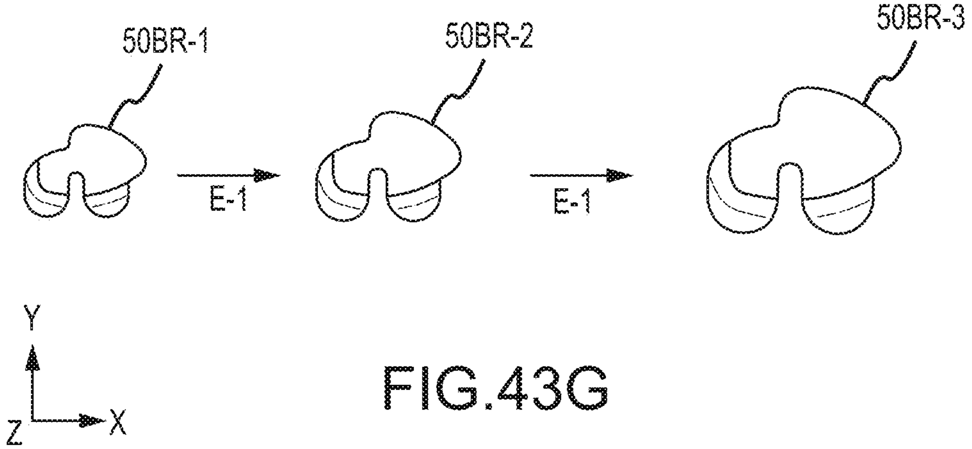
FIG. 43G is a plurality of available sizes of right tibia jig blanks, each depicted in the same view as shown in FIG. 43F.
Figure 43H:
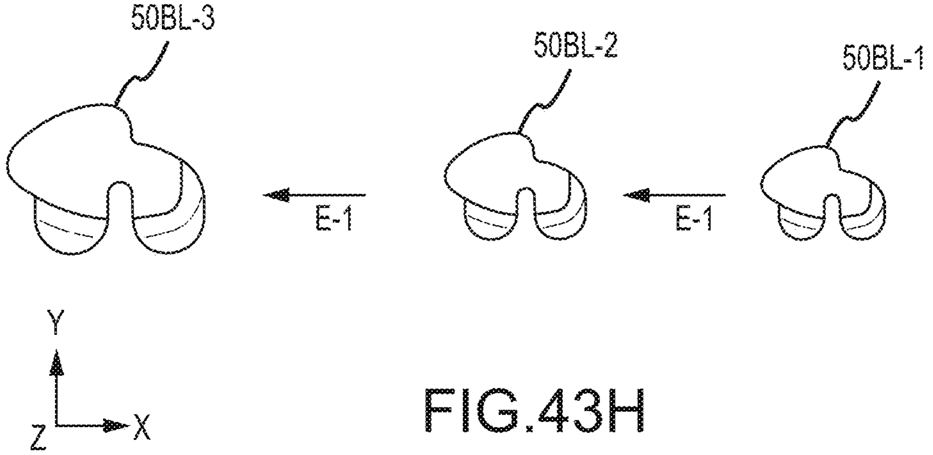
FIG. 43H is a plurality of available sizes of left tibia jig blanks, each depicted in the same view as shown in FIG. 43F.
Figure 43I:
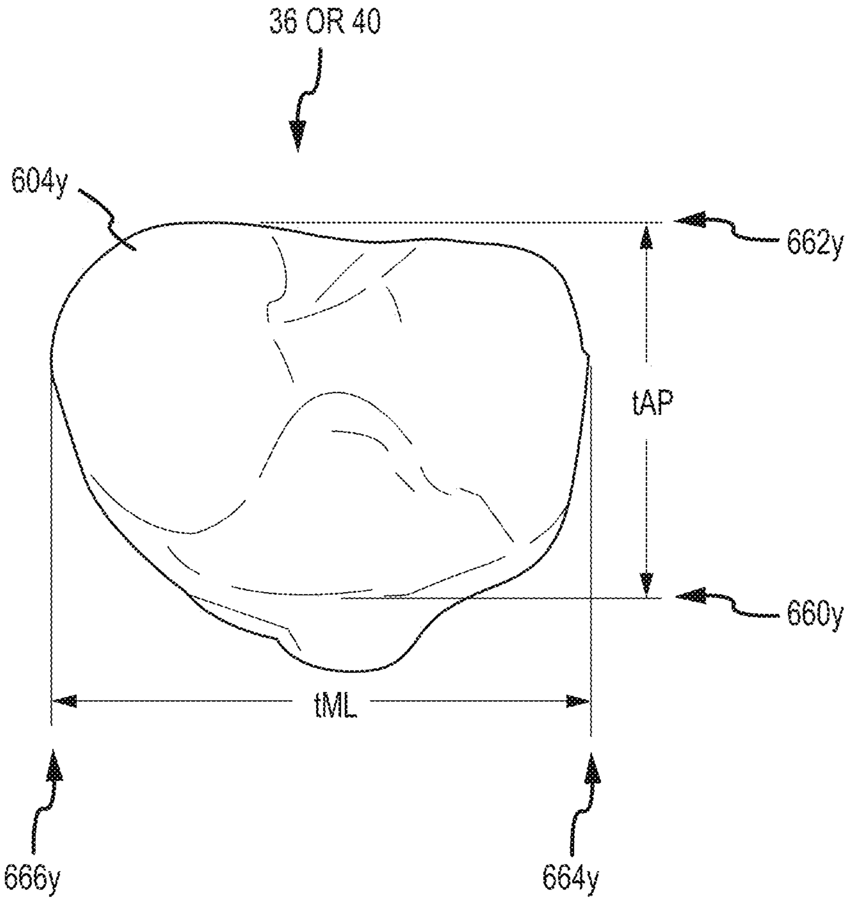
FIG. 43I is an axial view of the 3D surface model or arthritic model of the patient's right tibia as viewed in a direction extending proximal to distal.
Figure 48I:
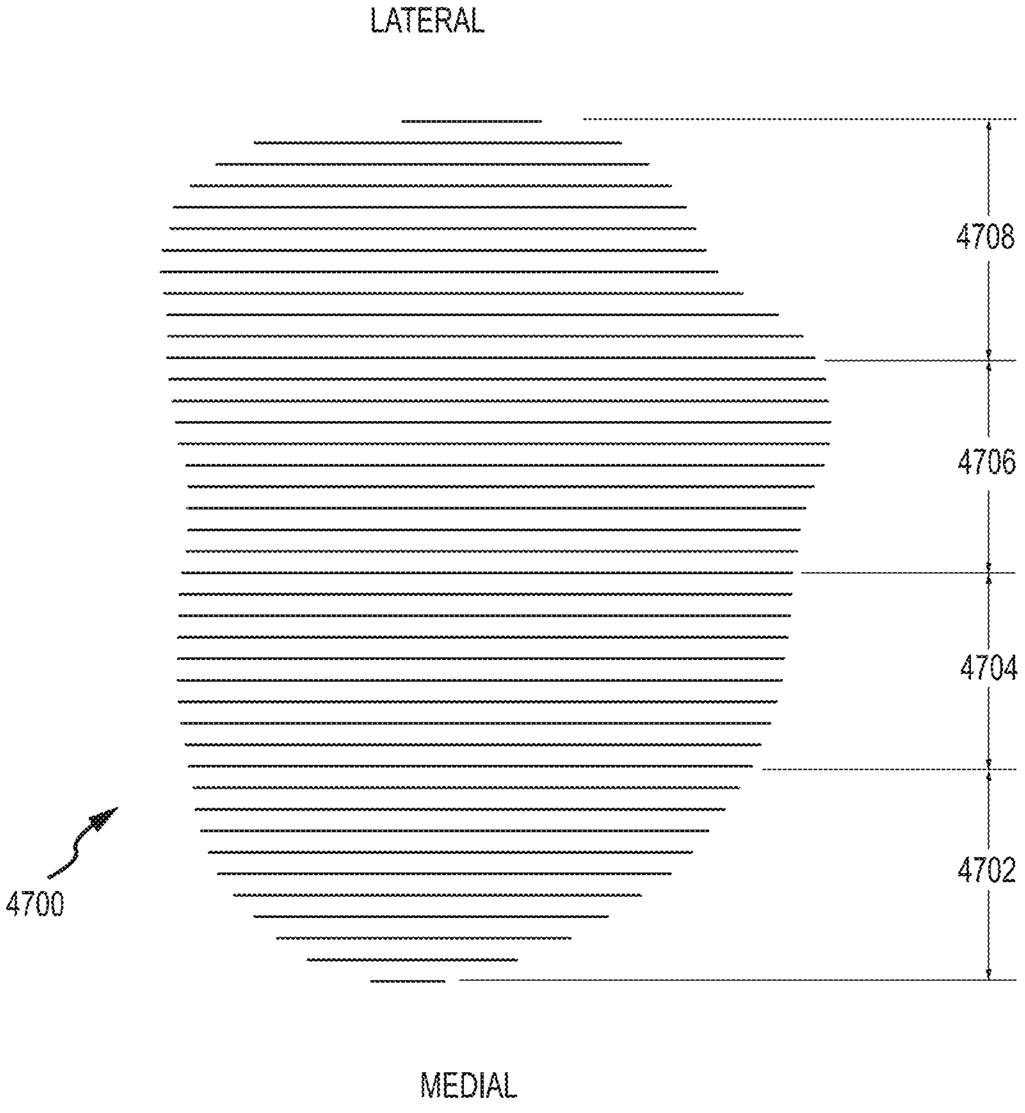

FIG. 48I is a distal view similar to that of FIG. 43I depicting contour lines produced by imaging the left tibia at an image spacing DT of, for example, 2 mm.

FIGS. 48J-48M are sagittal views of the contour lines of respective regions of FIG. 48I.

Figure 49A:
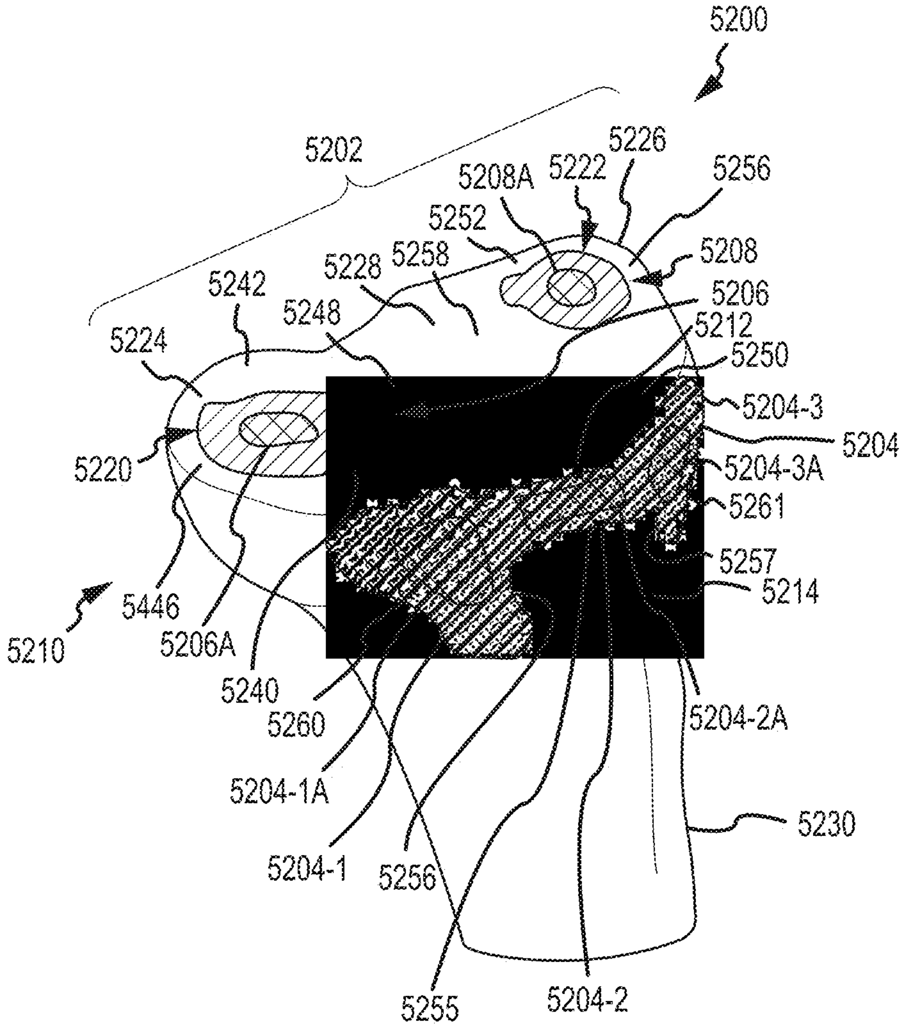

FIG. 49A is distal-sagittal isometric view of a tibial proximal end.

Figure 49B:
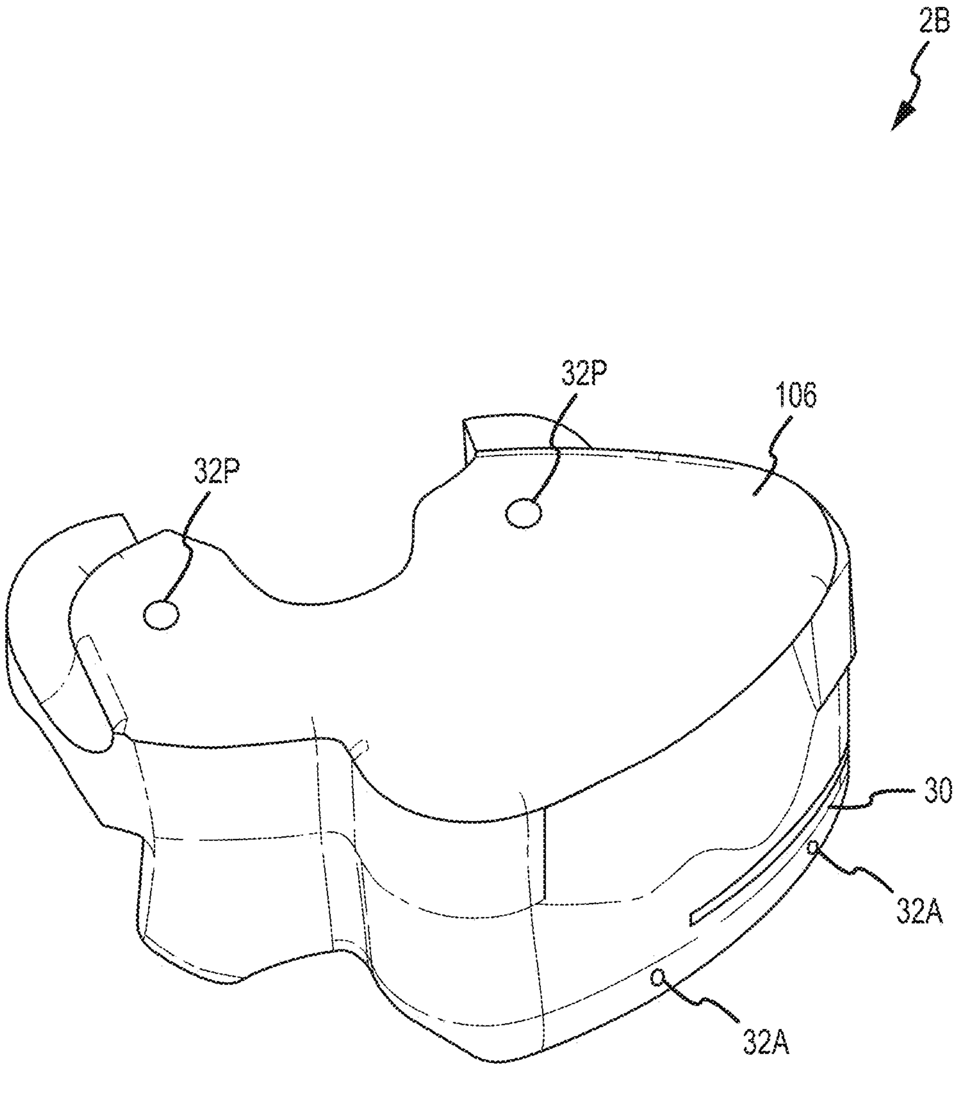
Figure 49C:
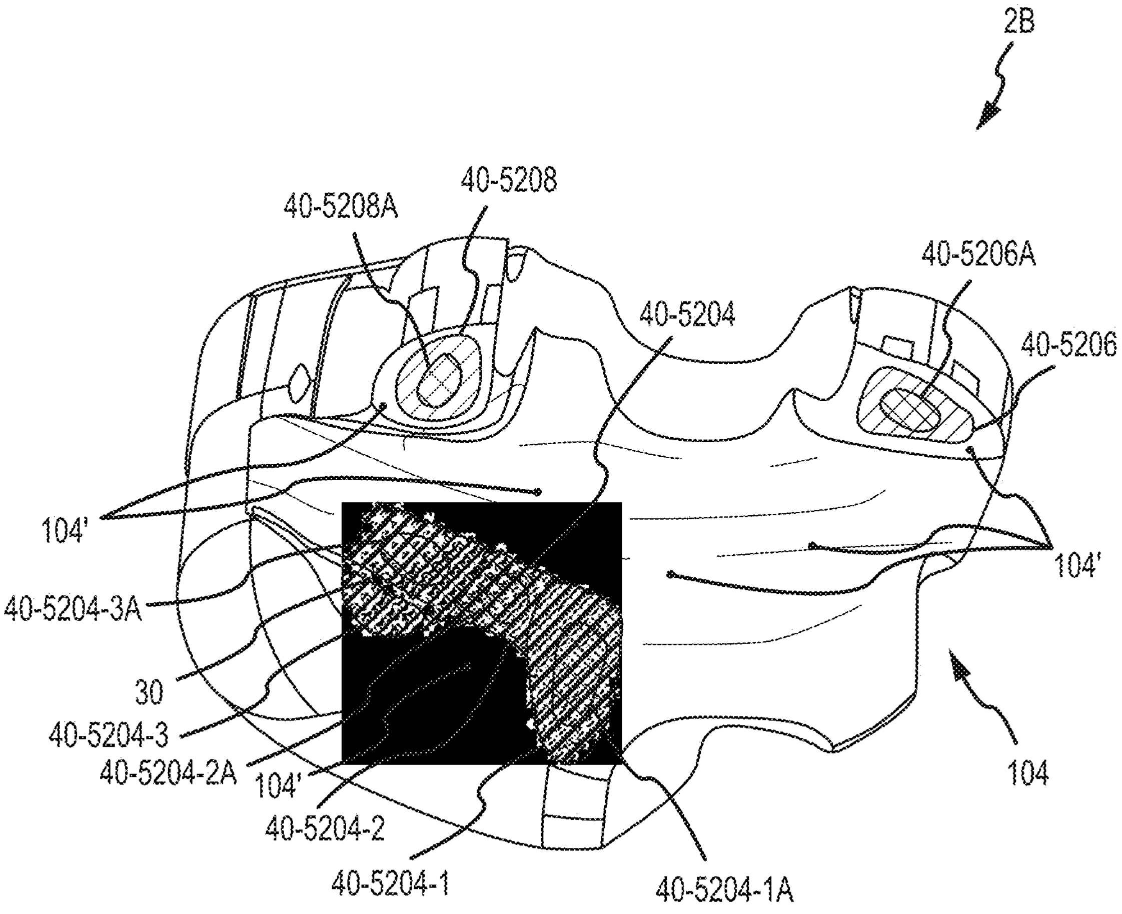

FIGS. 49B-49C are, respectively, top and bottom perspective views of an example customized arthroplasty tibia jig that has been generated via the overestimation process disclosed herein.

Figure 49D:
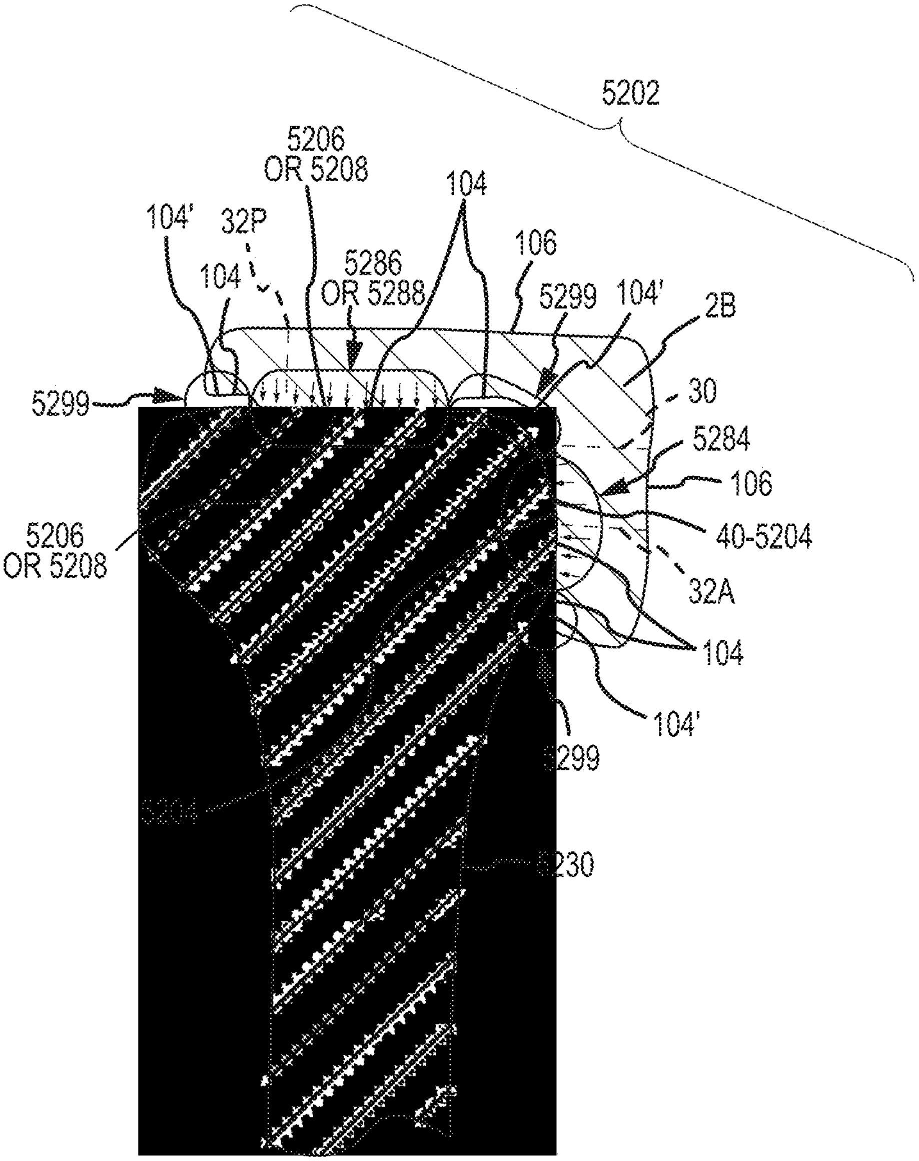

FIG. 49D is an anterior-posterior cross-section of the tibia jig of FIGS. 49B-C mounted on the tibia proximal end of FIG. 49A.

Figure 49E:
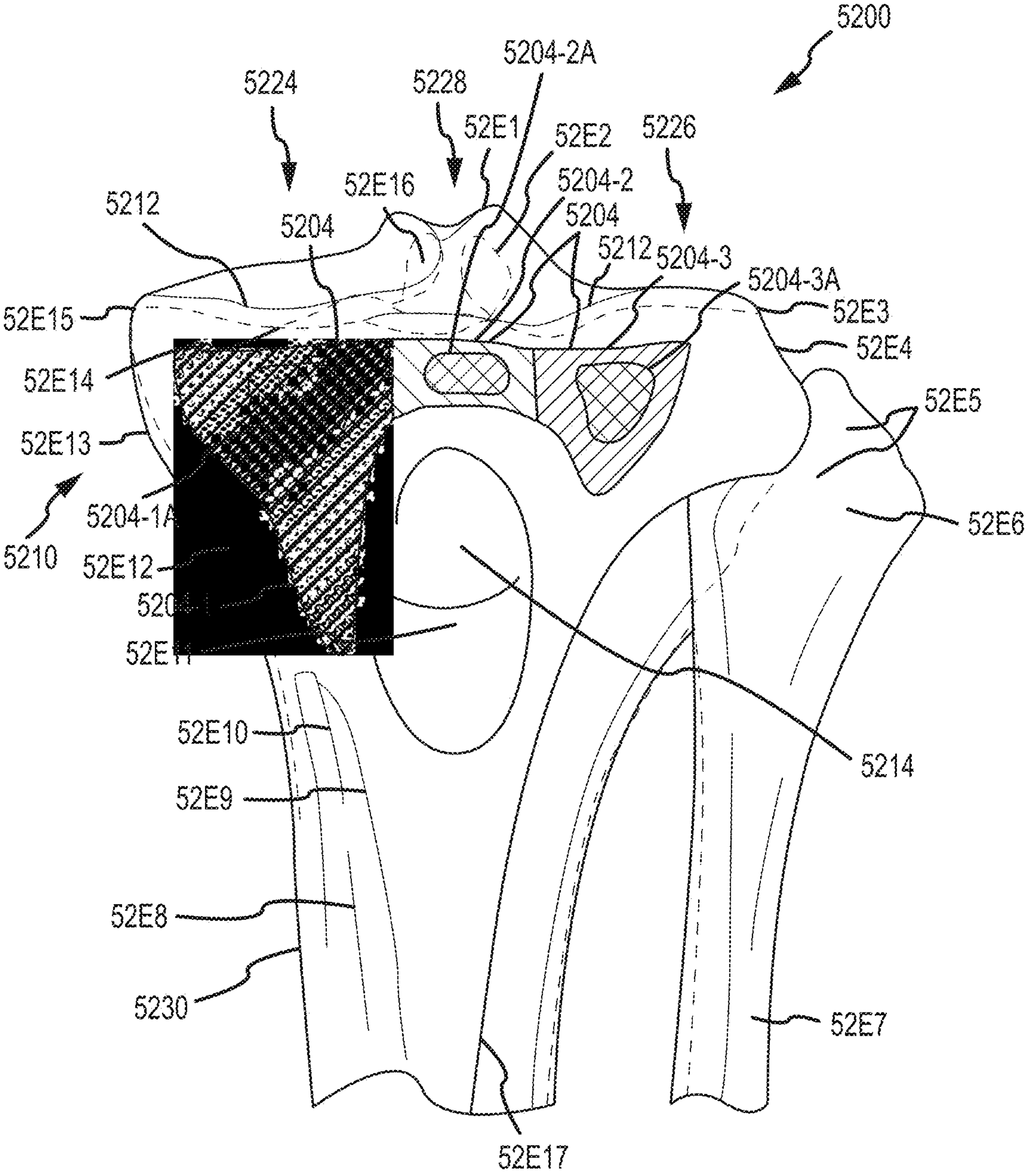

FIG. 49E is a coronal view of the anterior side of the tibial proximal end.

Figure 49F:
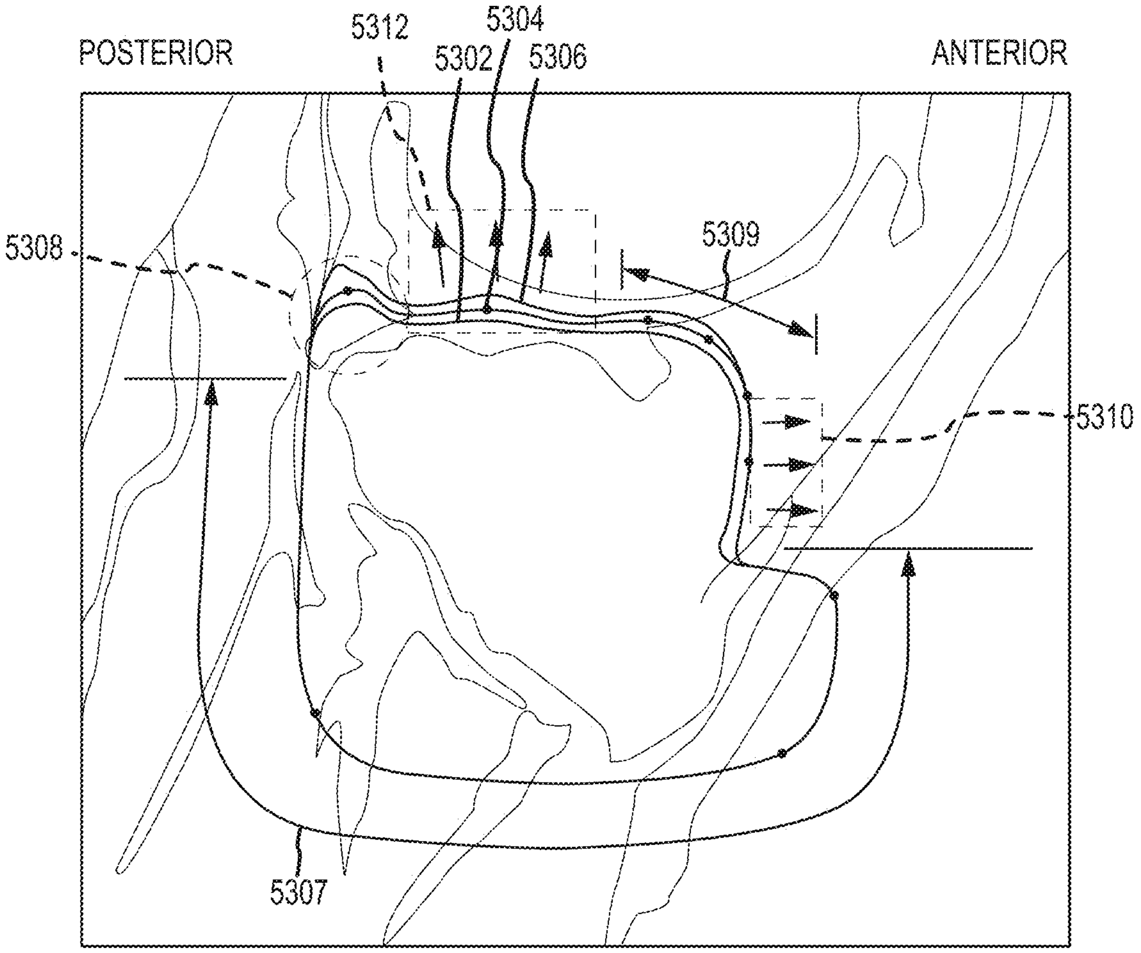

FIG. 49F depicts closed-loop contour lines that are image segmented from image slices, wherein the contour lines outline the cortical bone surface of the upper end of the tibia.

Figure 49G:
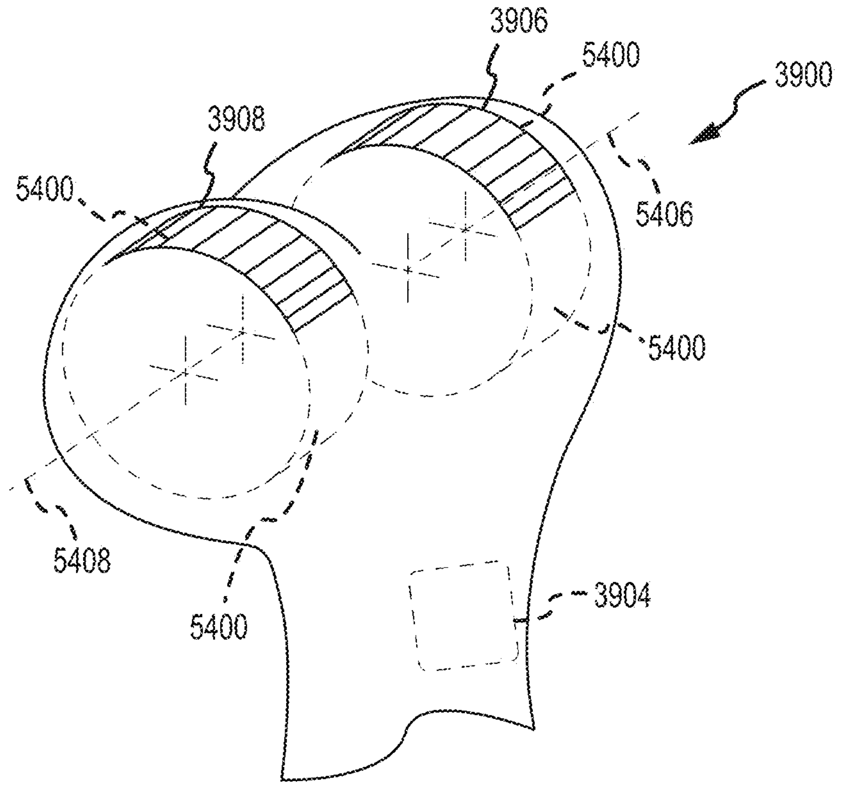

FIG. 49G is an anterior isometric view of the femur distal end.

Figure 49H:
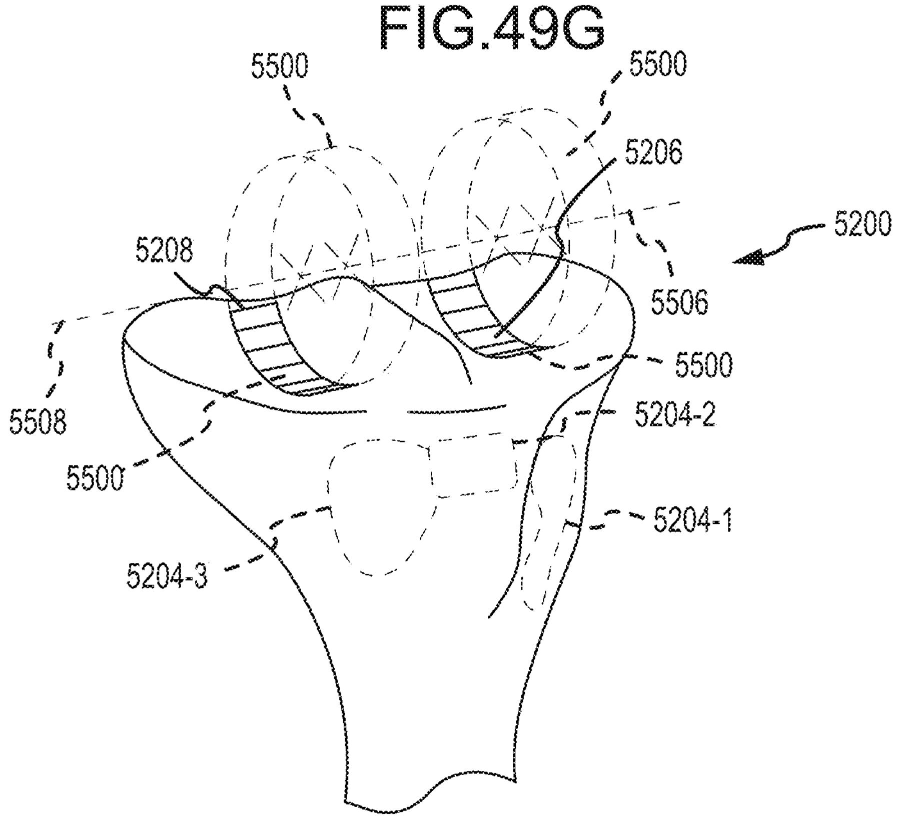

FIG. 49H is an anterior isometric view of the tibia proximal end.

FIGS. 50A-50E are flow chart diagrams outlining the jig production method disclosed herein.

Figure 51A:
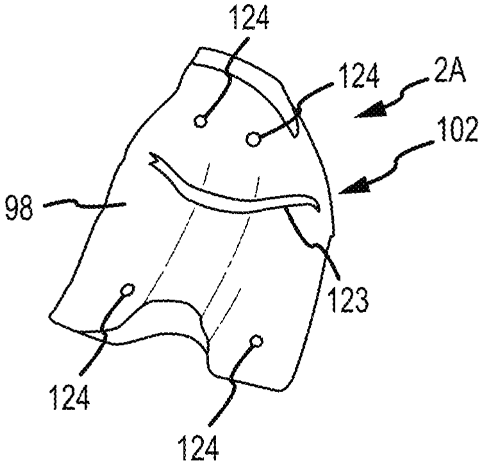
Figure 51B:
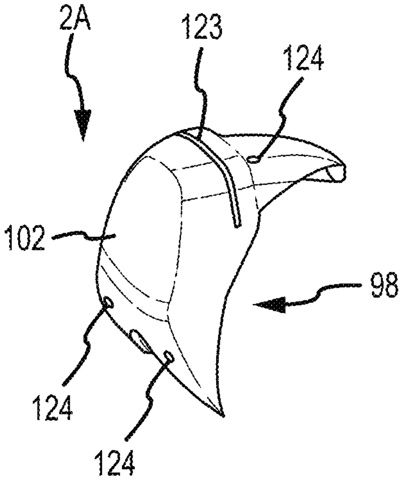

FIGS. 51A and 51B are, respectively, bottom and top perspective views of an example customized arthroplasty femur jig.

Figure 51C:
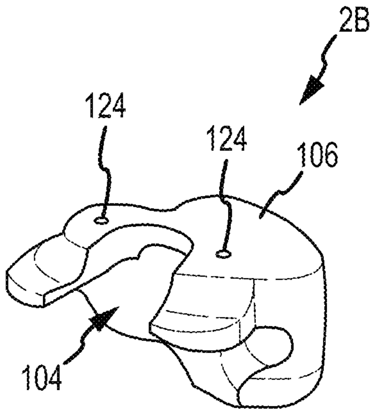
Figure 51D:
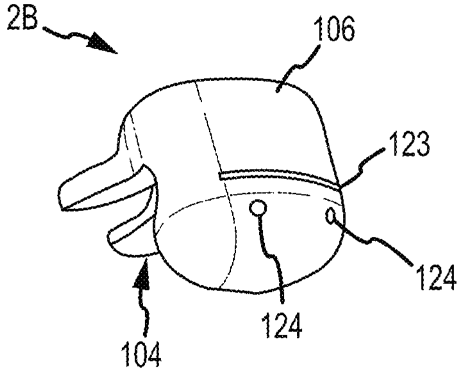

FIGS. 51C and 51D are, respectively, top/posterior and bottom/anterior perspective views of an example customized arthroplasty tibia jig.

Figure 52A:
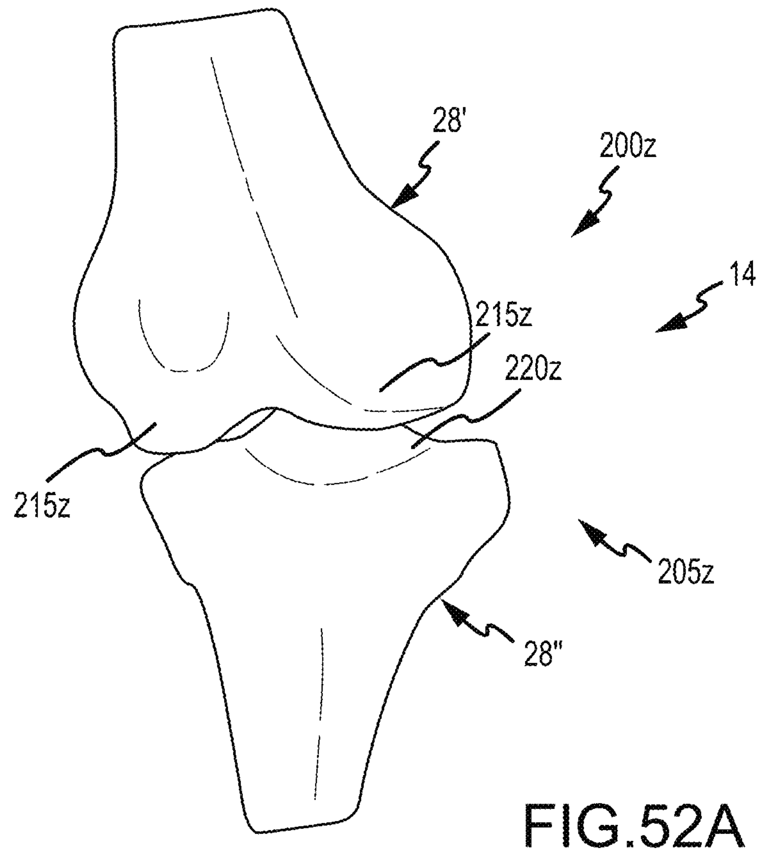

FIG. 52A is an isometric view of a 3D computer model of a femur lower end and a 3D computer model of a tibia upper end in position relative to each to form a knee joint and representative of the femur and tibia in a non-degenerated state.

Figure 52B:
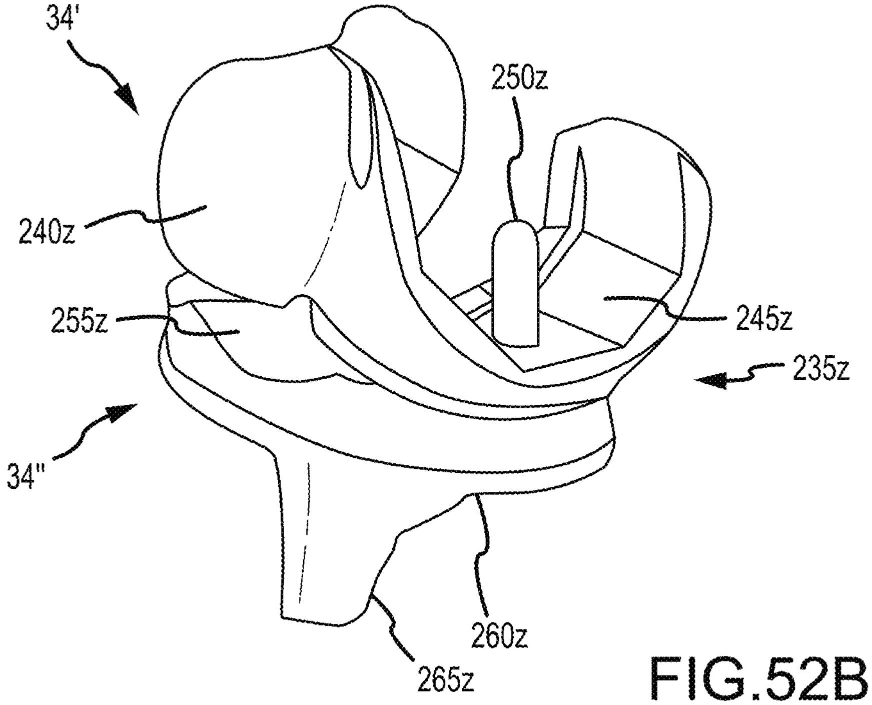

FIG. 52B is an isometric view of a 3D computer model of a femur implant and a 3D computer model of a tibia implant in position relative to each to form an artificial knee joint.

Figure 53:
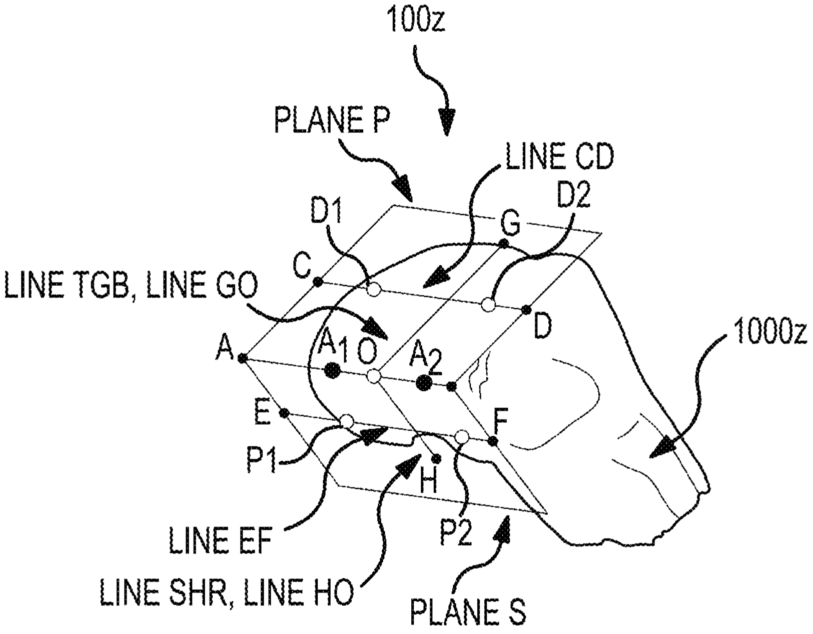

FIG. 53 is a perspective view of the distal end of 3D model of the femur wherein the femur reference data is shown.

Figure 54A:
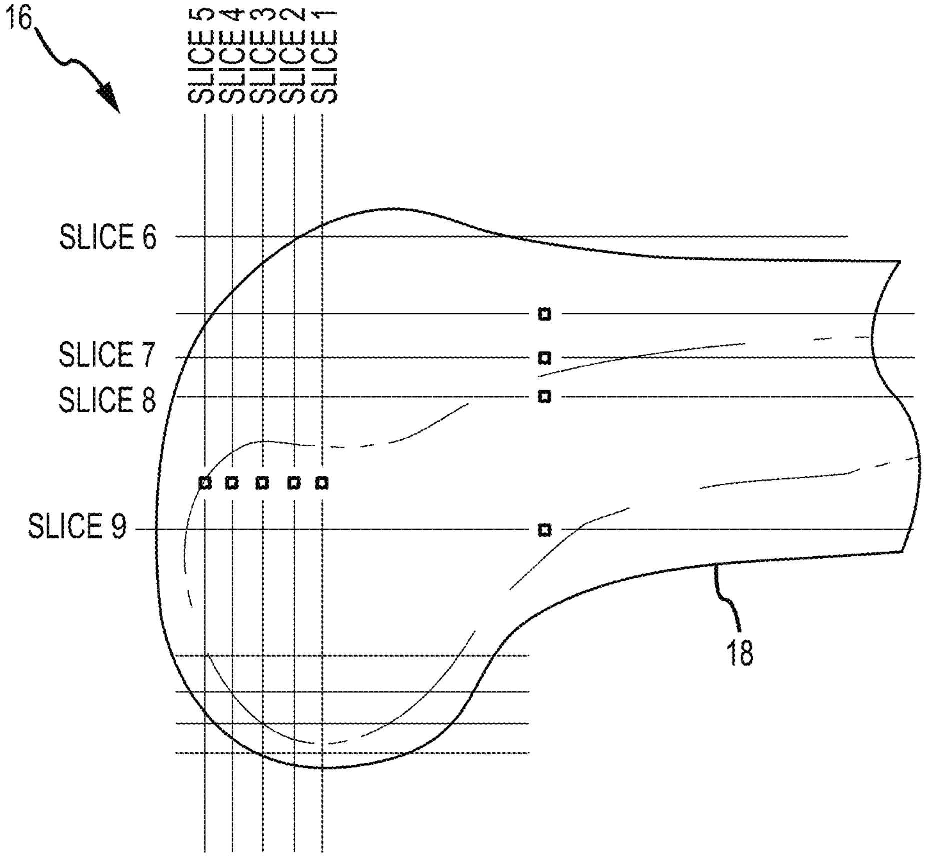

FIG. 54A is a sagittal view of a femur illustrating the orders and orientations of imaging slices utilized in the femur POP.

Figure 54B:
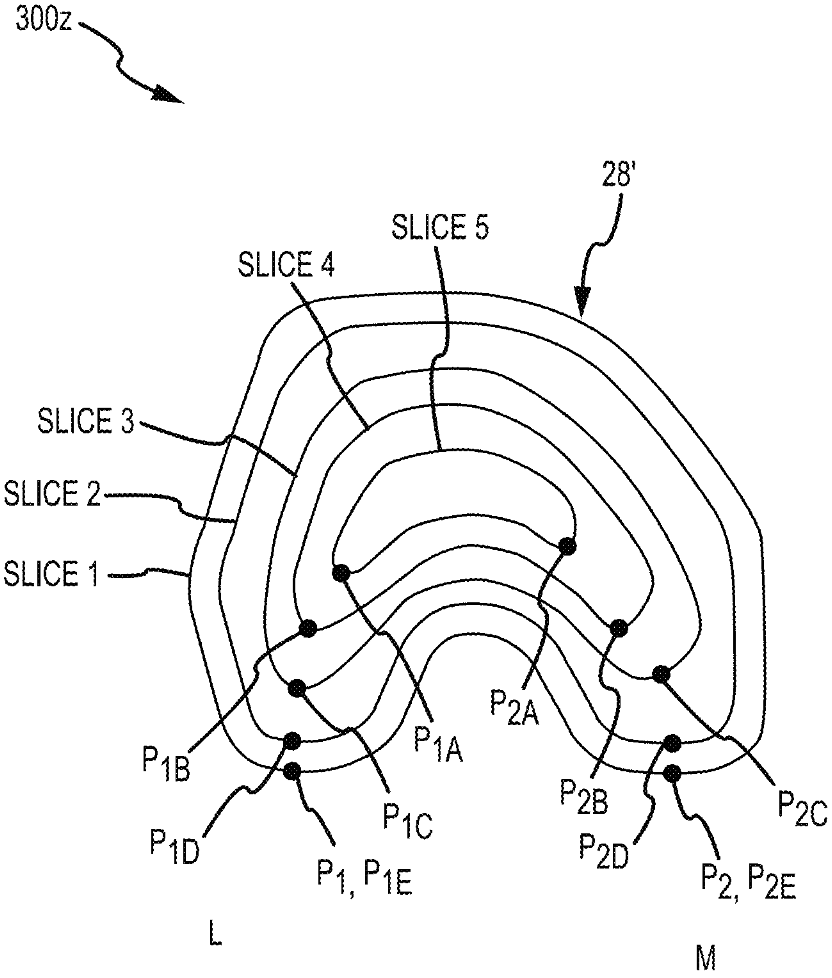

FIG. 54B depicts axial imaging slices taken along section lines of the femur of FIG. 54A.

Figure 54C:
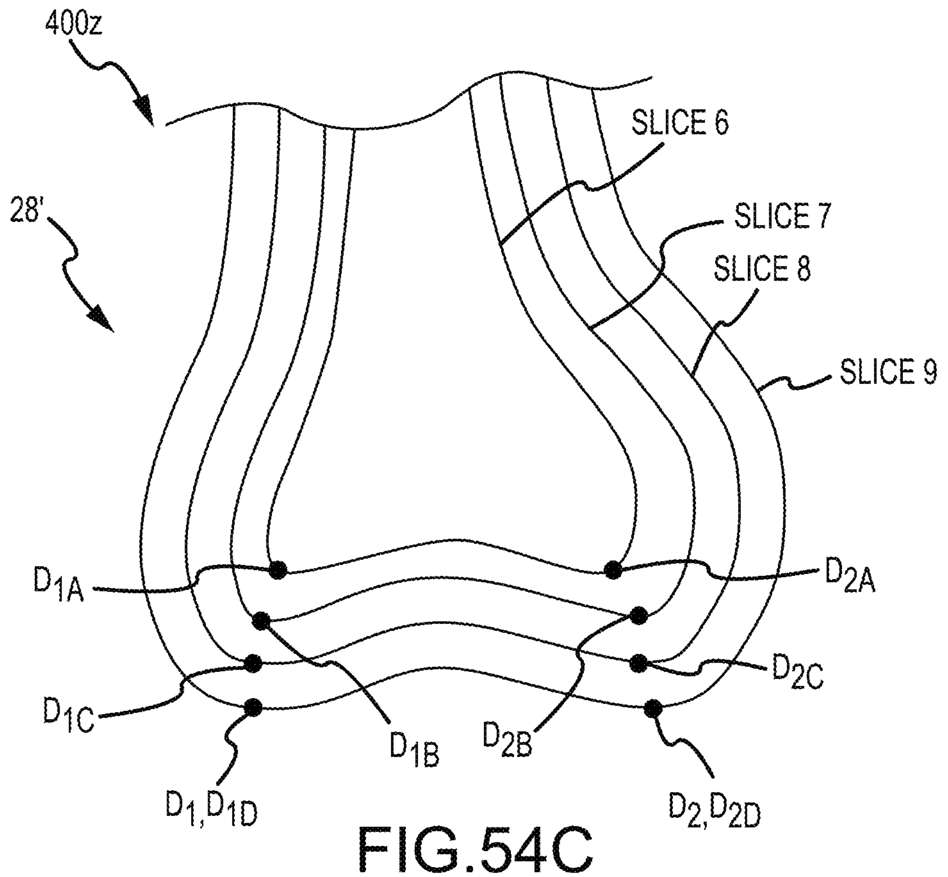

FIG. 54C depicts coronal imaging slices taken along section lines of the femur of FIG. 54A.

Figure 55A:
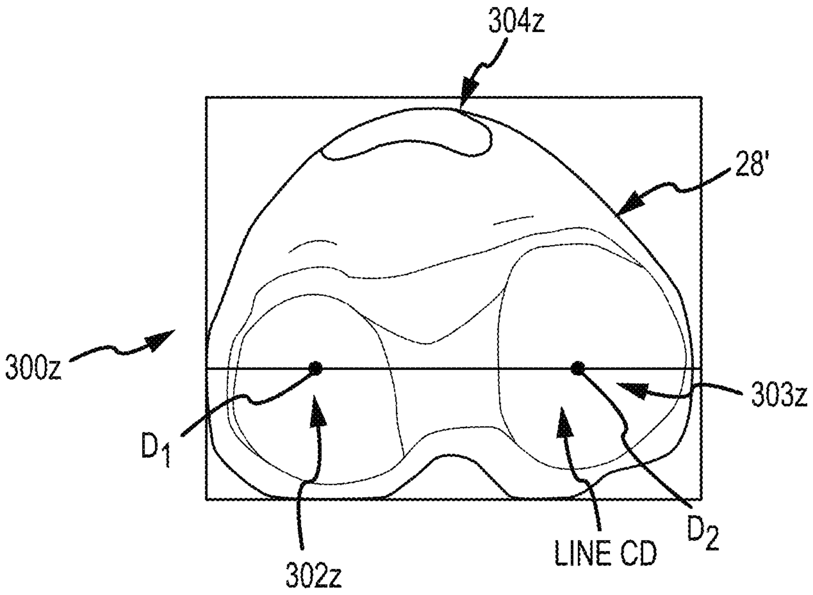

FIG. 55A is an axial imaging slice taken along section lines of the femur of FIG. 54A, wherein the distal reference points are shown.

Figure 55B:
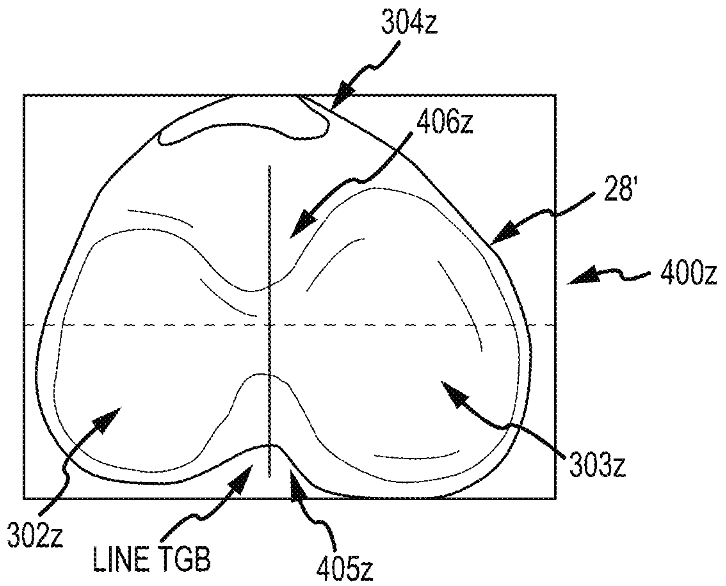

FIG. 55B is an axial imaging slice taken along section lines of the femur of FIG. 54A, wherein the trochlear groove bisector line is shown.

Figure 55C:
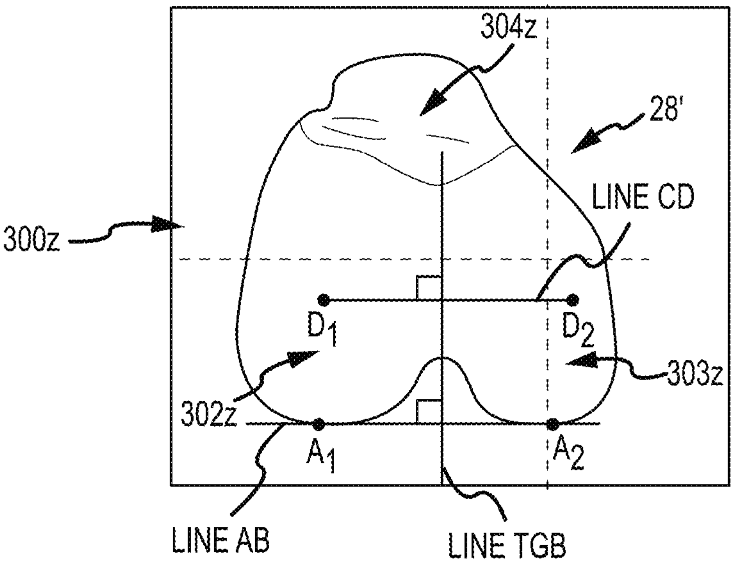

FIG. 55C is an axial imaging slice taken along section lines of the femur of FIG. 54A, wherein the femur reference data is shown.

Figure 55D:
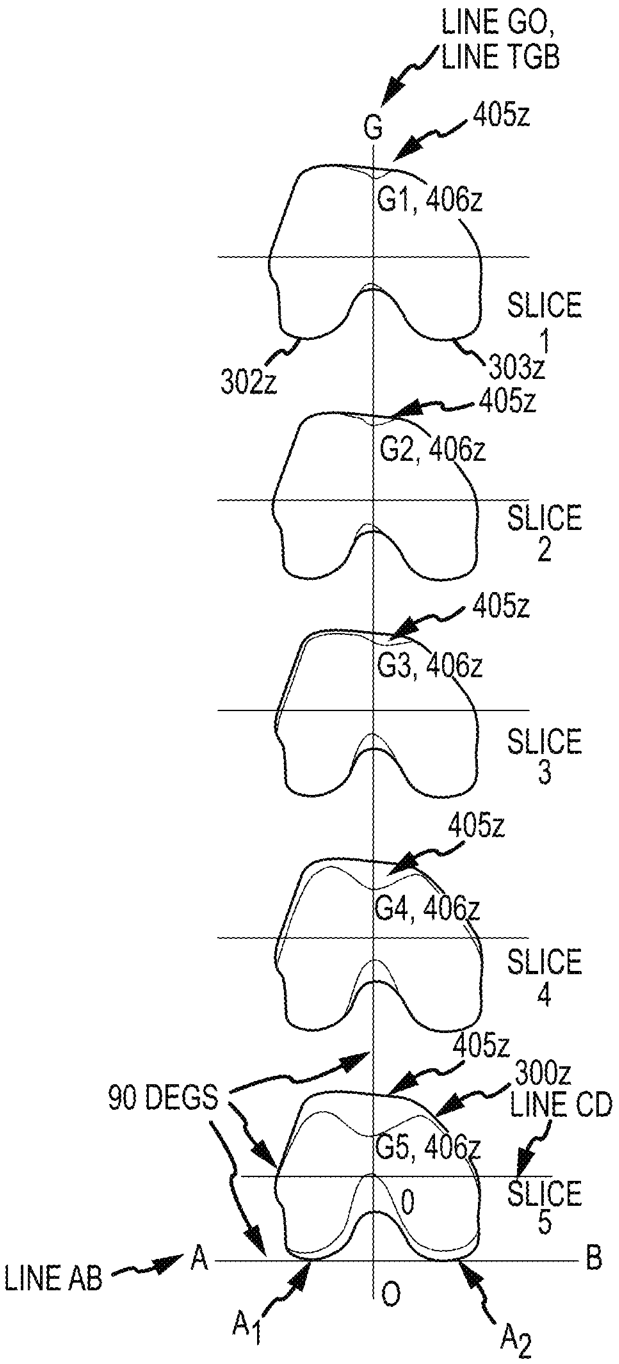

FIG. 55D is the axial imaging slices taken along section lines of the femur in FIG. 54A.

Figure 56A:
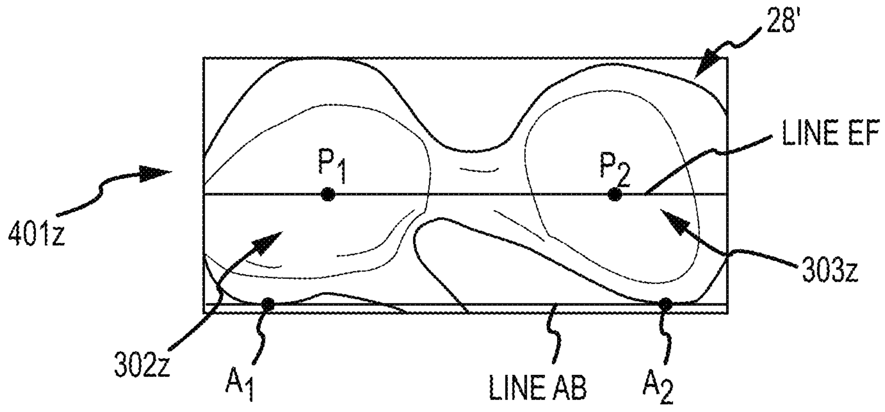
Figure 56B:
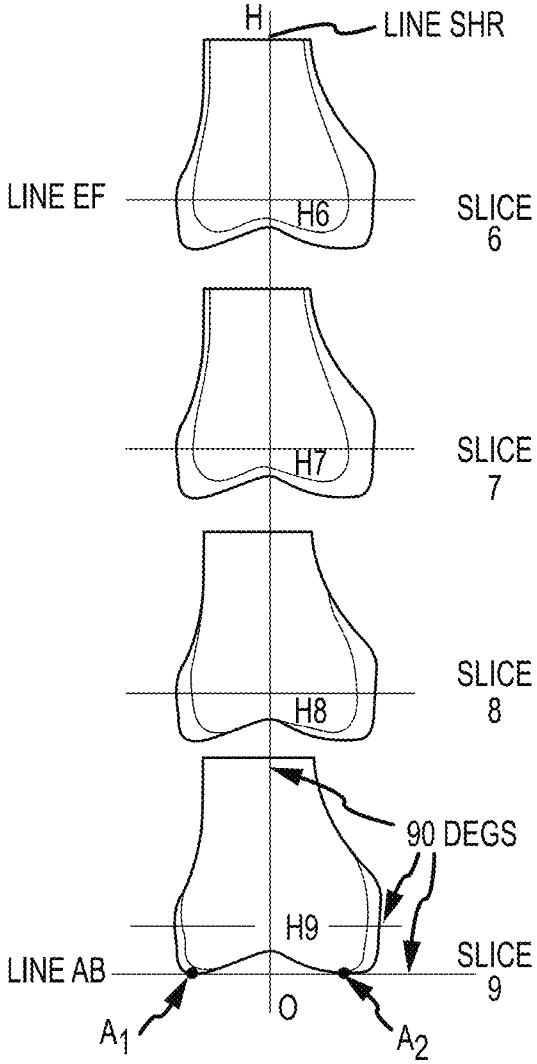

FIG. 56A is a coronal slice taken along section lines of the femur of FIG. 54A, wherein the femur reference data is shown FIG. 56B is the coronal imaging slices taken along section lines of the femur in FIG. 54A.

Figure 56C:
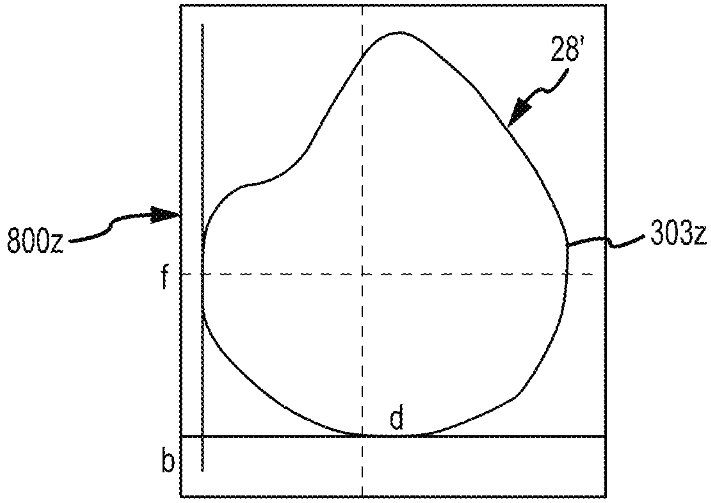

FIG. 56C is a sagittal imaging slice of the femur in FIG. 54A.

Figure 56D:
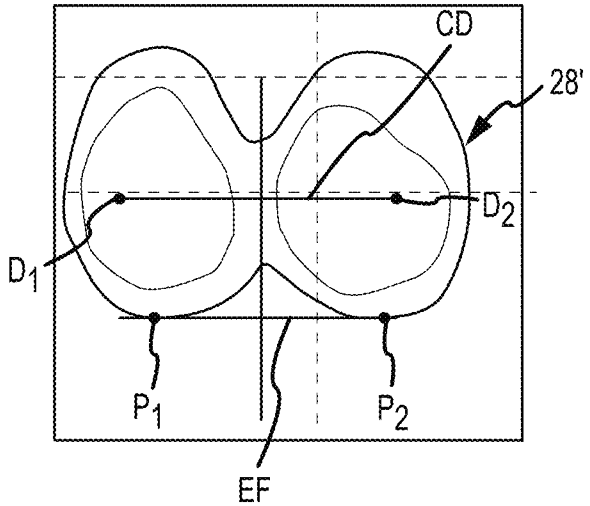

FIG. 56D is an axial imaging slice taken along section lines of the femur of FIG. 54A, wherein the femur reference data is shown.

Figure 56E:
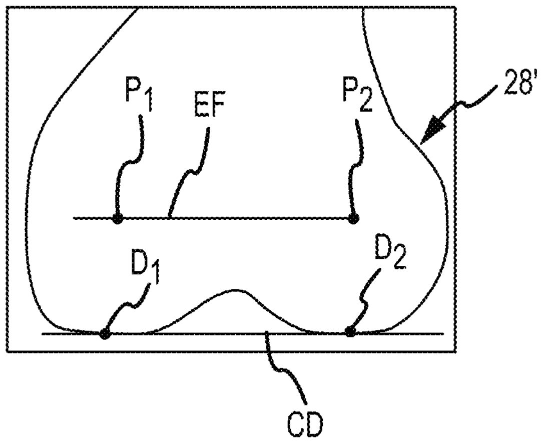

FIG. 56E is a coronal imaging slice taken along section lines of the femur of FIG. 54A, wherein the femur reference data is shown.

Figure 57:
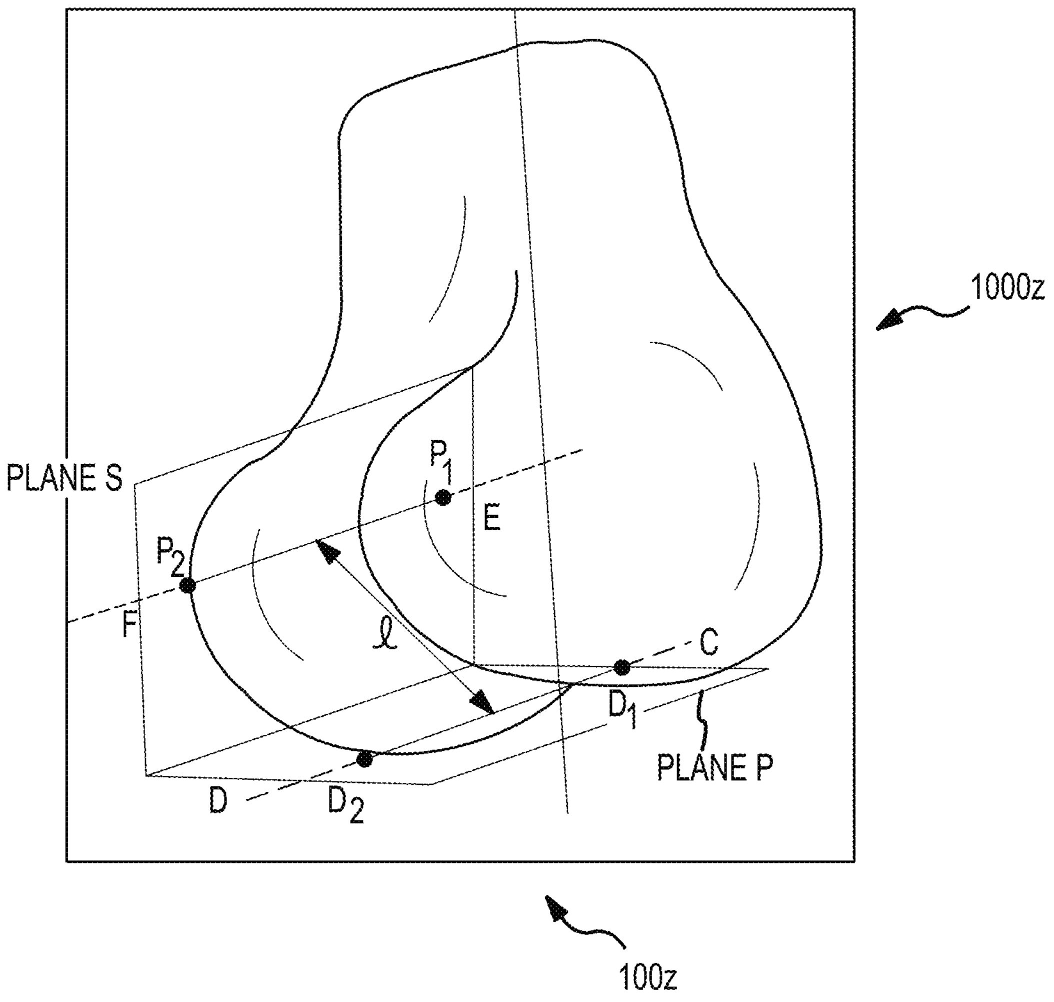

FIG. 57 is a posterior view of a 3D model of a distal femur.

Figure 58:
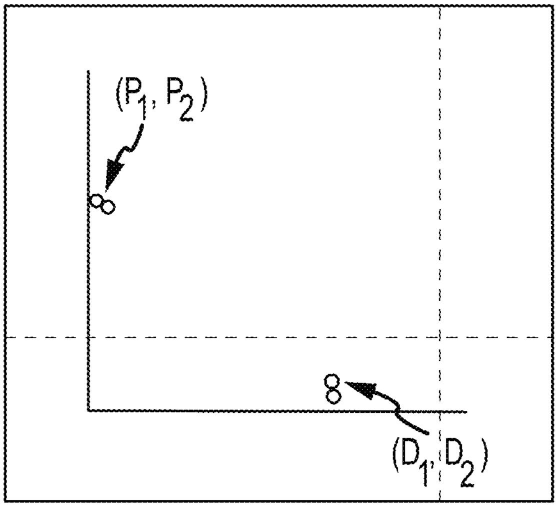

FIG. 58 depicts a y-z coordinate system wherein the femur reference data is shown.

Figure 59:
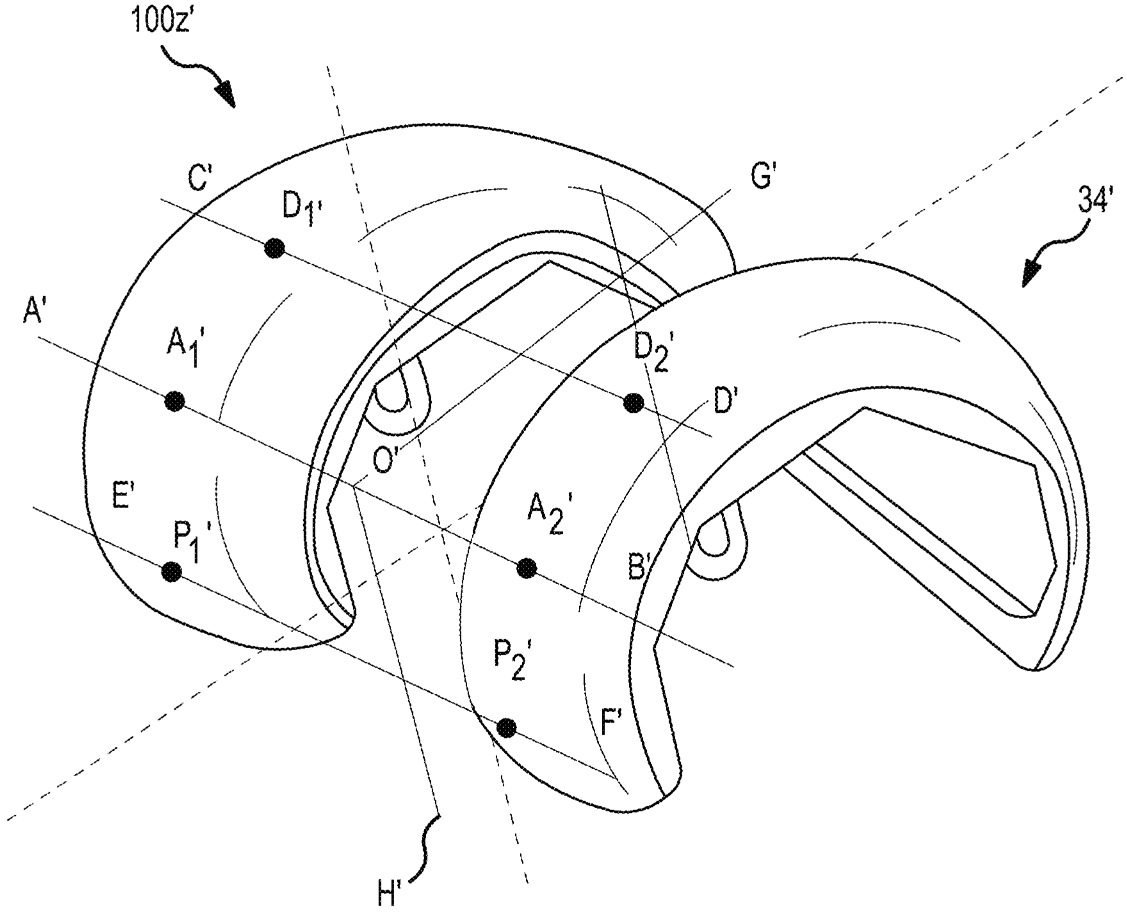

FIG. 59 is a perspective view of a femoral implant model, wherein the femur implant reference data is shown.

Figure 60:
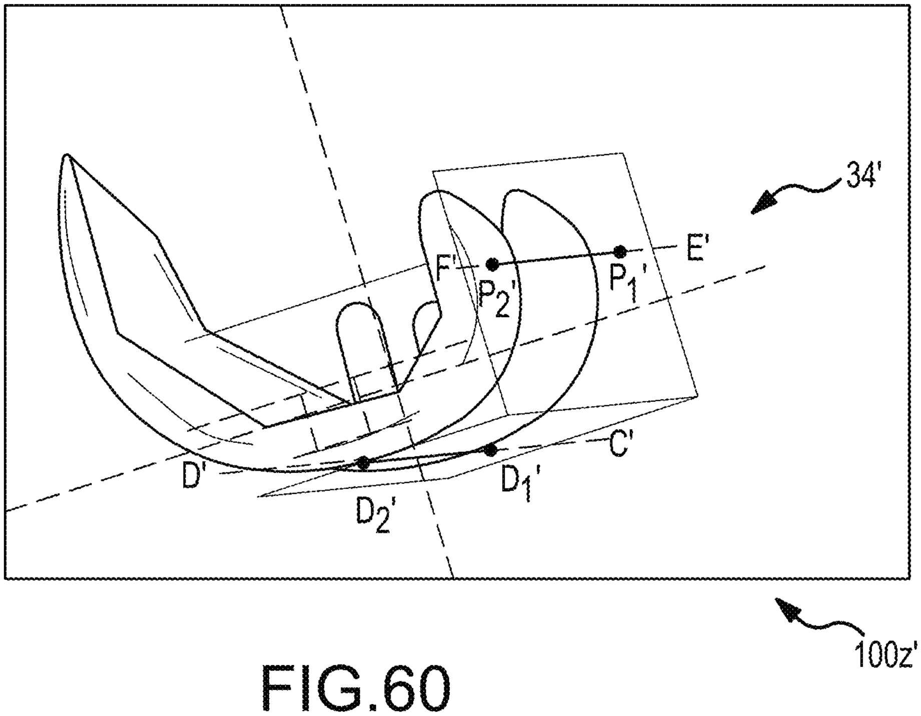

FIG. 60 is another perspective view of a femoral implant model, wherein the femur implant reference data is shown.

Figure 61:
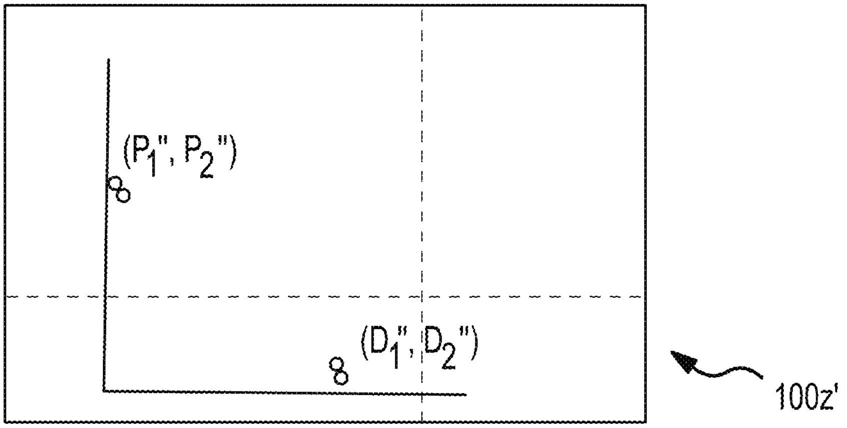

FIG. 61 is a y-z coordinate system wherein some of the femur implant reference data is shown.

Figure 62:
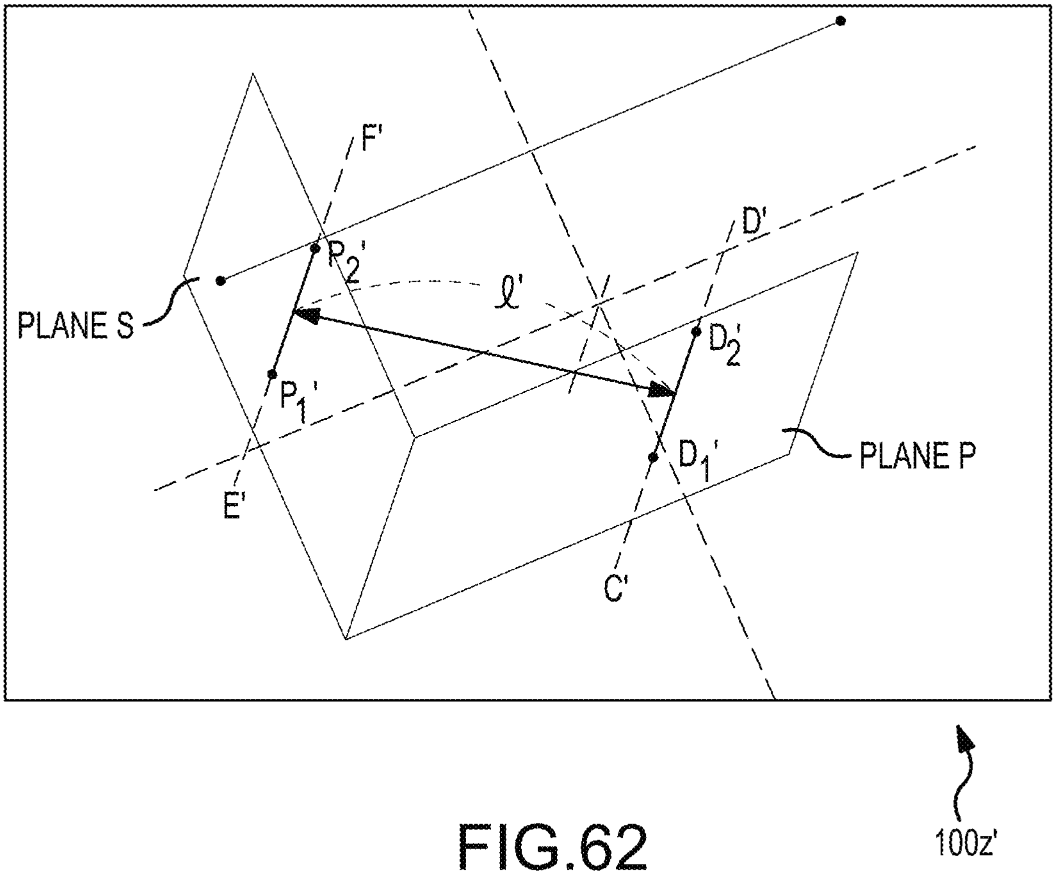

FIG. 62 is an x-y-z coordinate system wherein the femur implant reference data is shown.

Figure 63A:
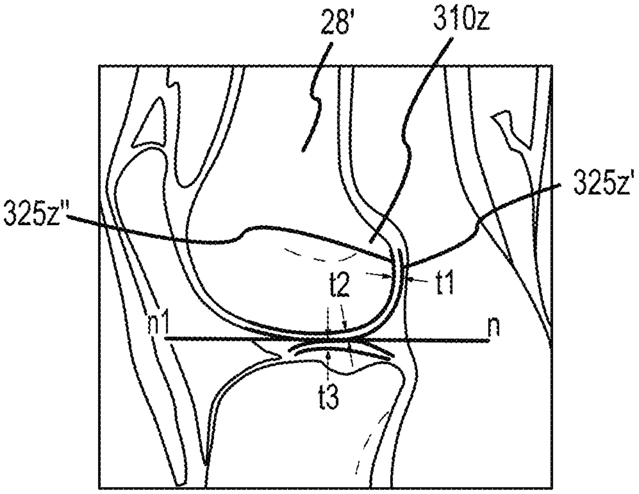

FIG. 63A shows the femoral condyle and the proximal tibia of the knee in a sagittal view MRI image slice.

Figure 63B:
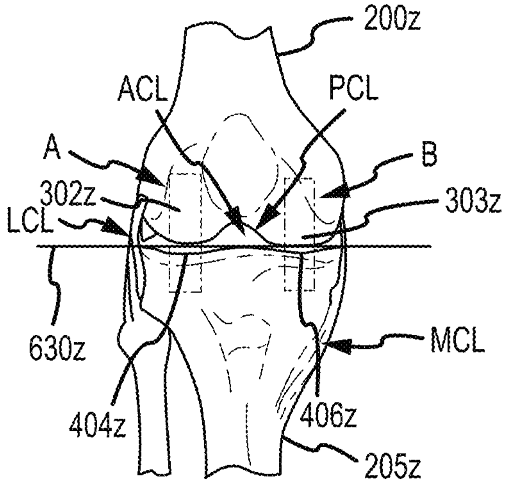

FIG. 63B is a coronal view of a knee model in extension.

Figure 63C:
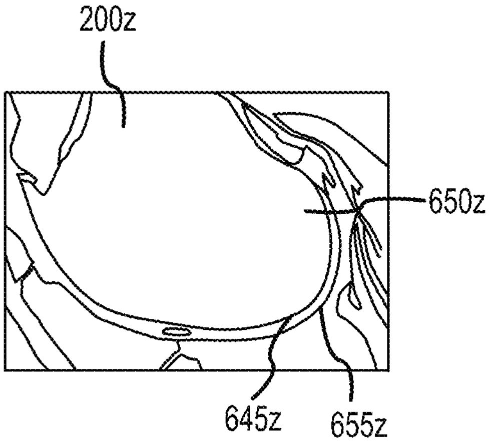
Figure 63D:
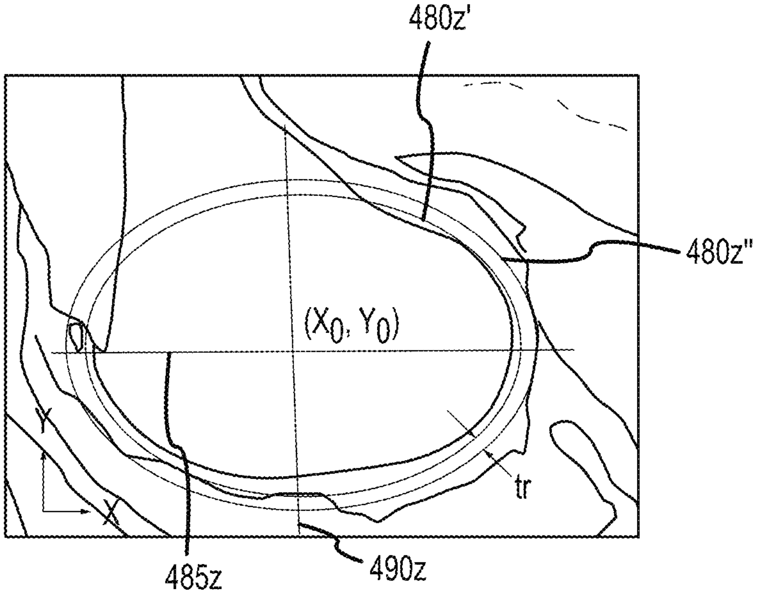

FIGS. 63C and 63D illustrate MRI segmentation slices for joint line assessment.

Figure 63E:
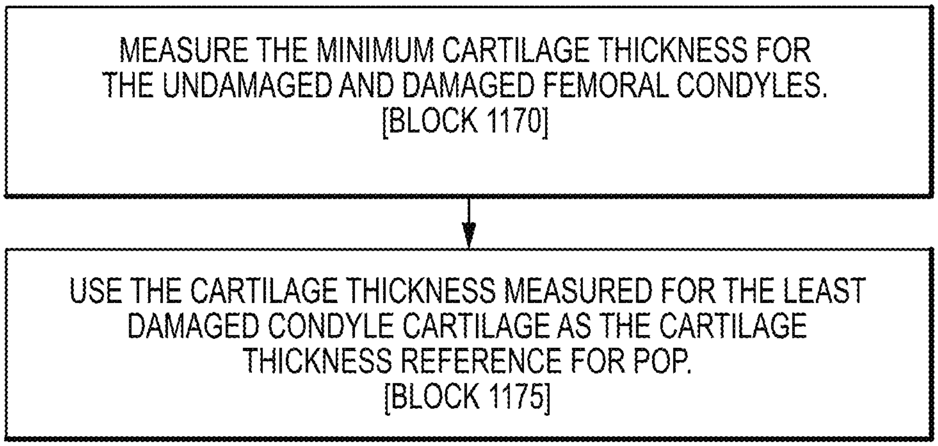

FIG. 63E is a flow chart illustrating the method for determining cartilage thickness used to determine proper joint line.

Figure 63F:
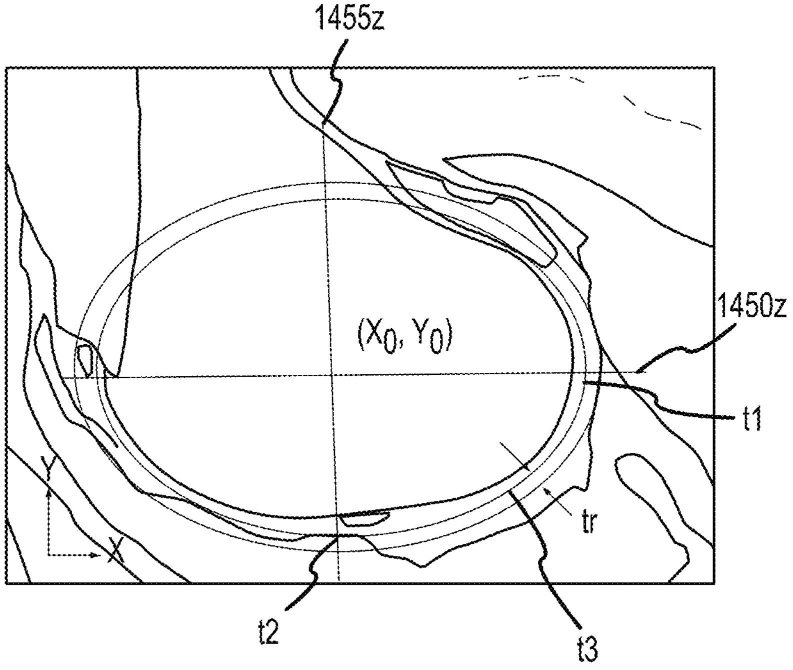

FIG. 63F illustrates a MRI segmentation slice for joint line assessment.

Figure 63G:
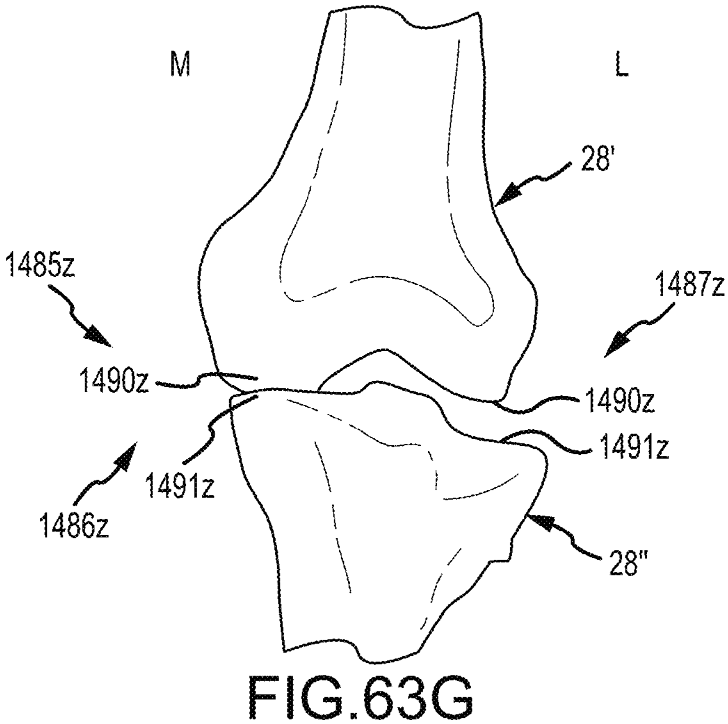
Figure 63H:
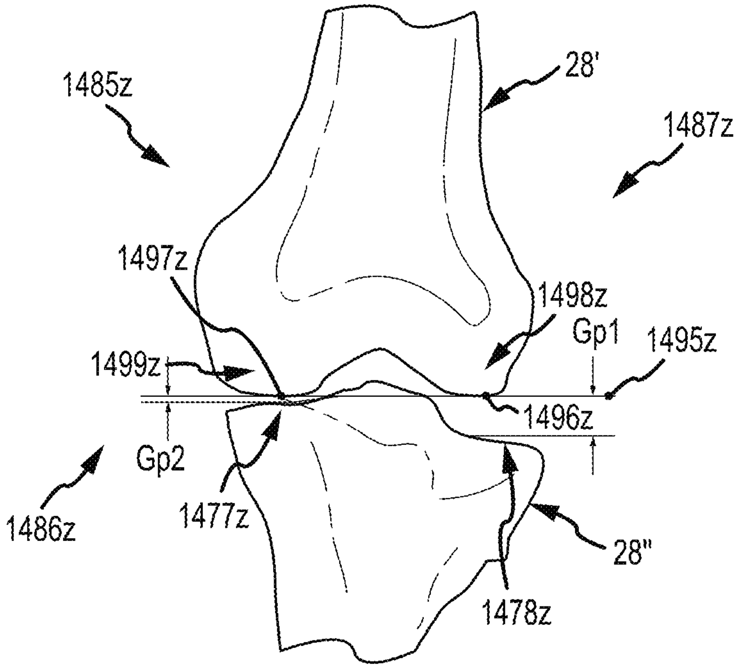

FIGS. 63G and 63H illustrate coronal views of the bone images in their alignment relative to each as a result of OA.

Figure 63I:
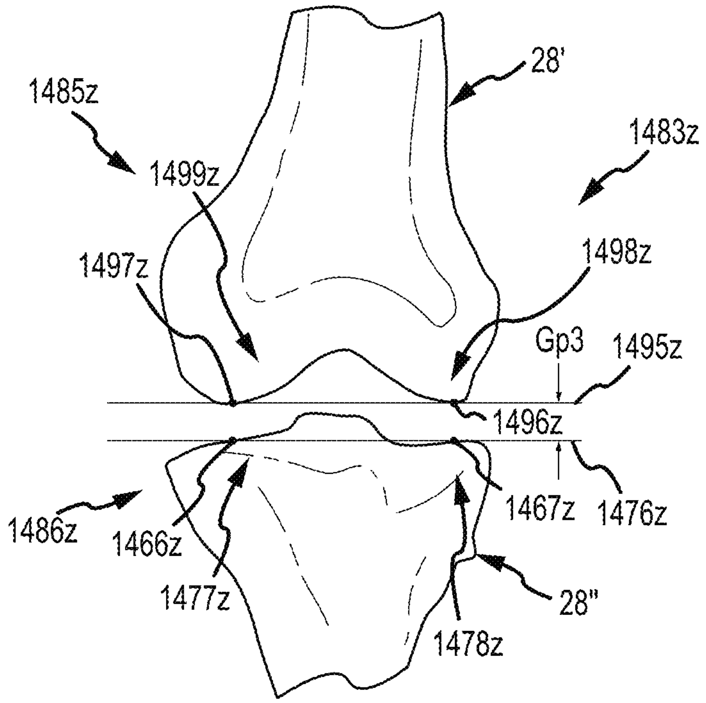

FIG. 63I illustrates a coronal view of the bone images with a restored gap Gp3.

Figure 63J:
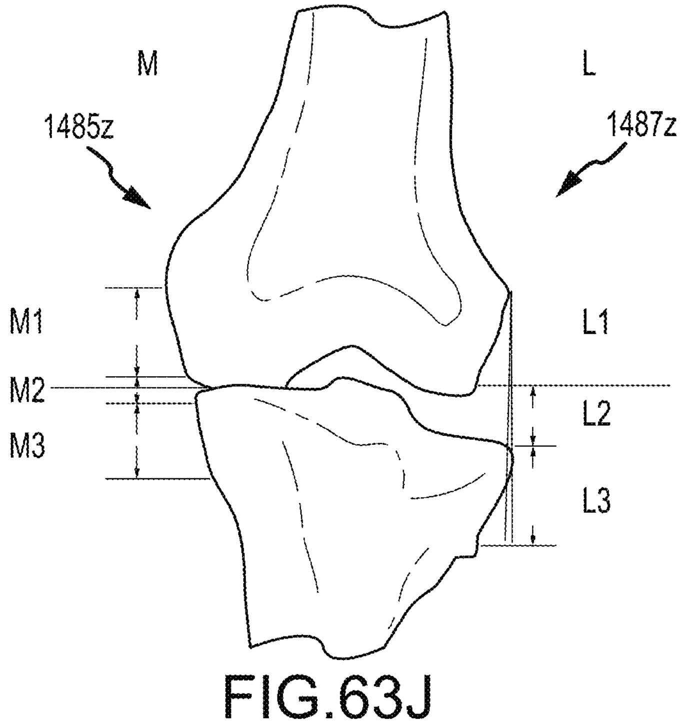

FIG. 63J is a coronal view of bone images oriented relative to each other in a deteriorated state orientation.

Figure 64:
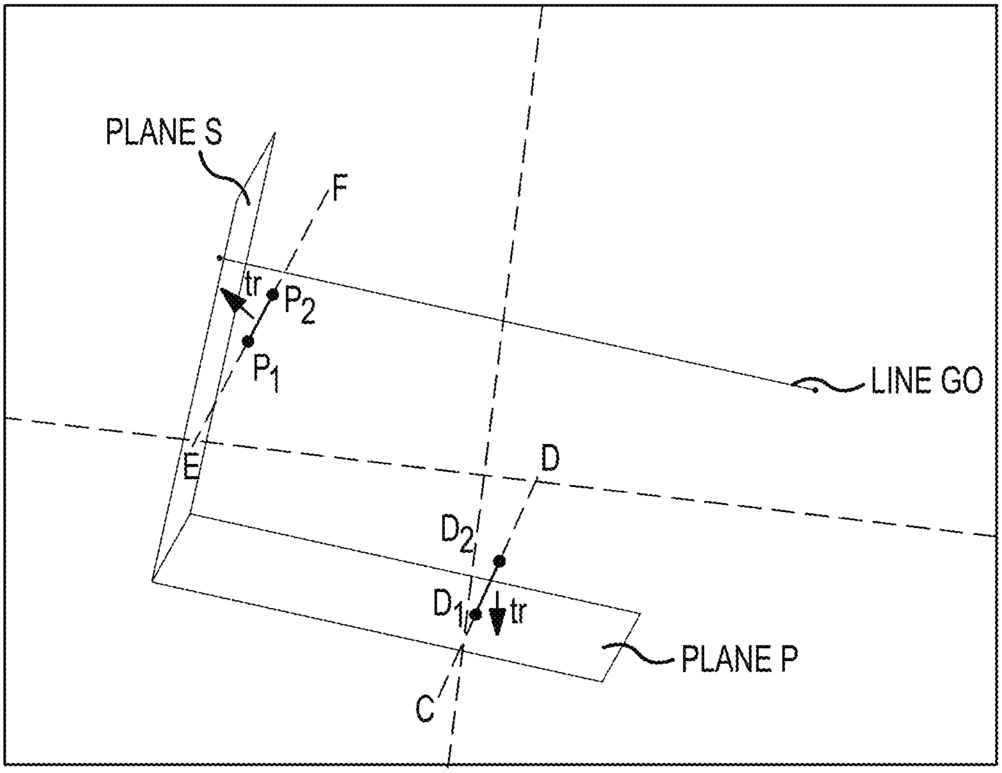

FIG. 64 is a 3D coordinate system wherein the femur reference data is shown.

Figure 65:
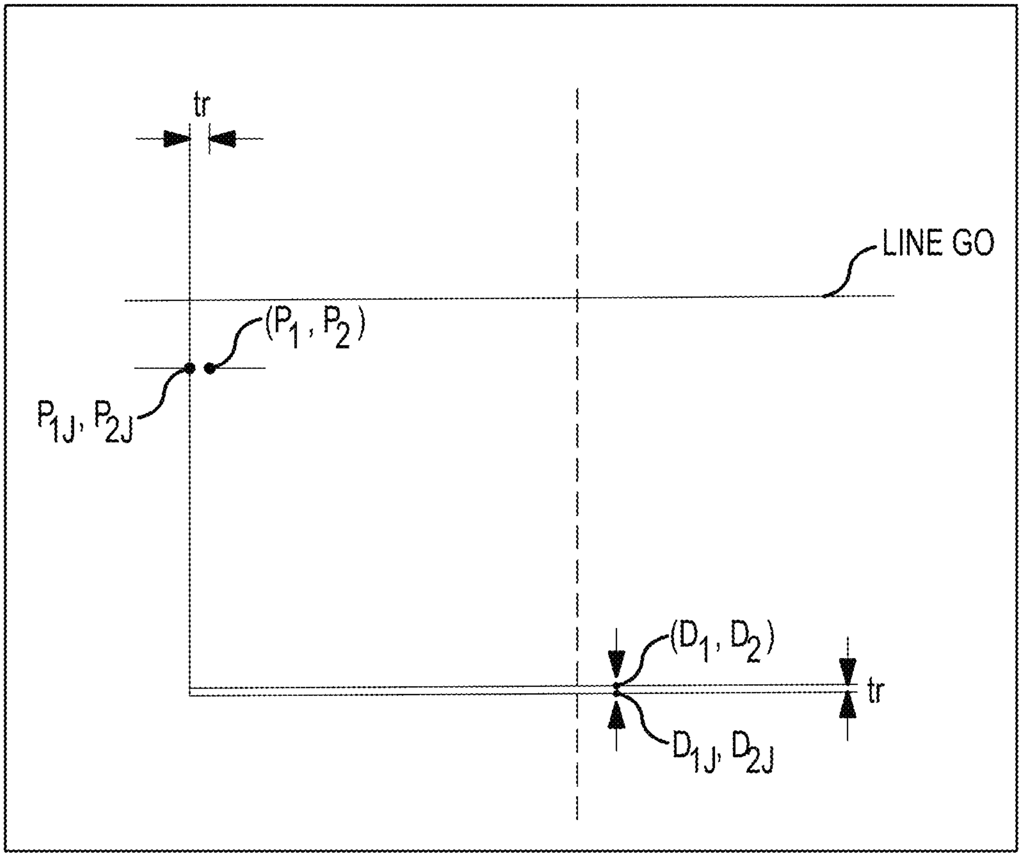

FIG. 65 is a y-z plane wherein the joint compensation points are shown.

Figure 66:
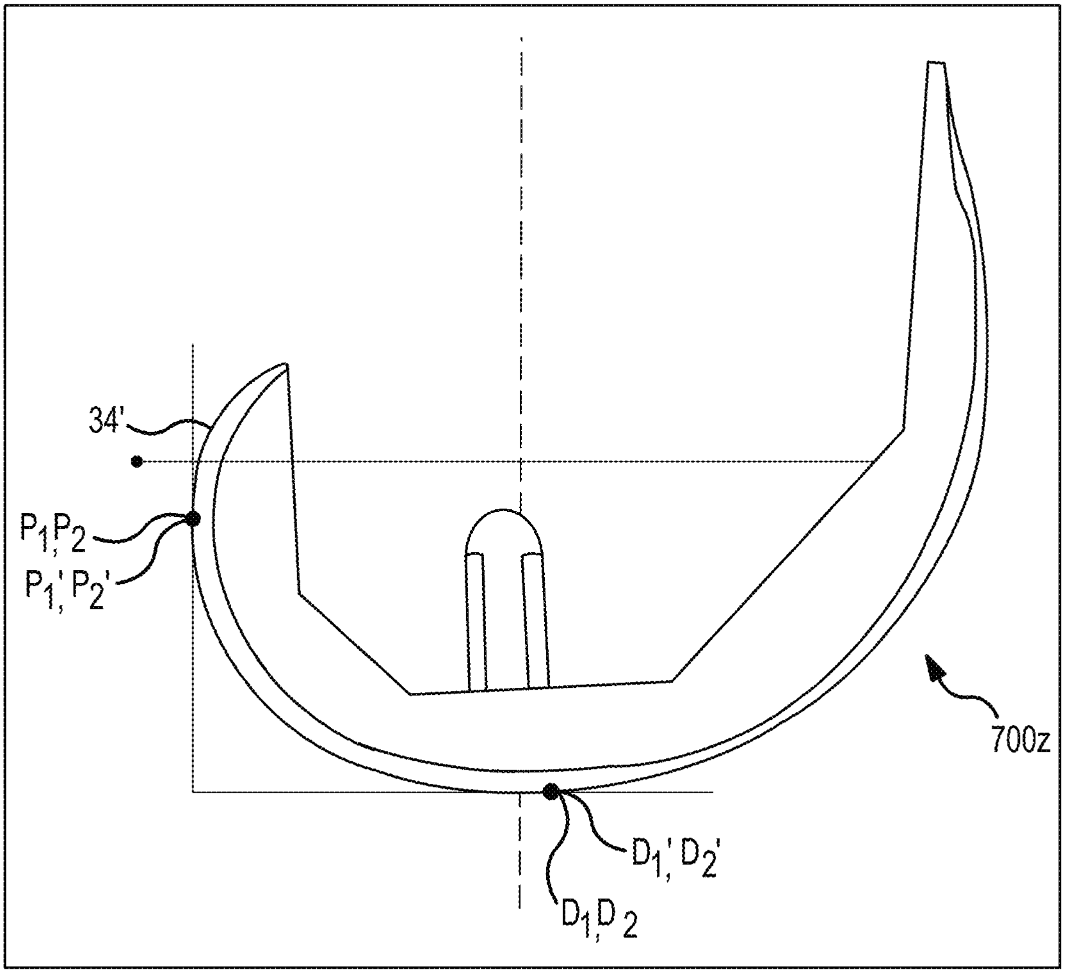

FIG. 66 illustrates the implant model 34' placed onto the same coordinate plane with the femur reference data.

Figure 67A:
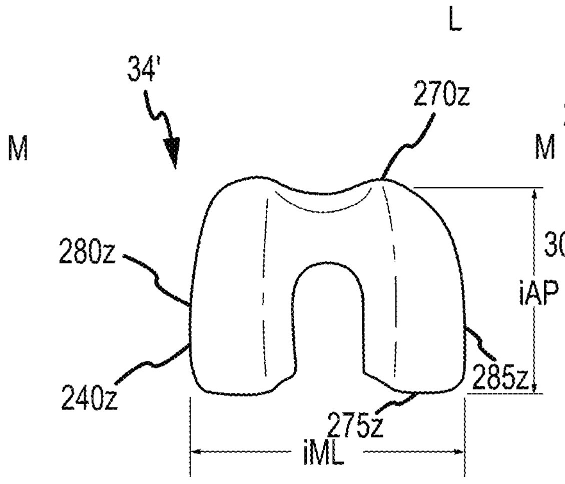

FIG. 67A is a plan view of the joint side of the femur implant model depicted in FIG. 52B.

Figure 67B:
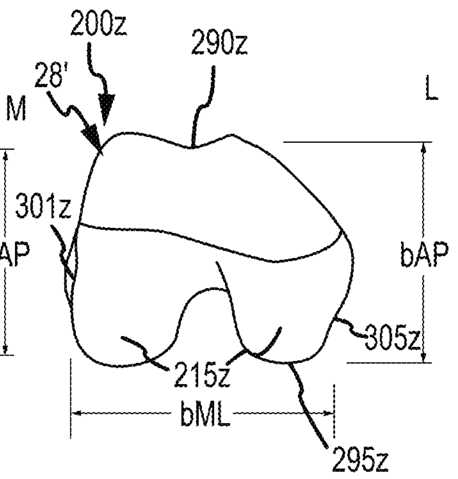

FIG. 67B is an axial end view of the femur lower end of the femur bone model depicted in FIG. 52A.

Figure 67C:
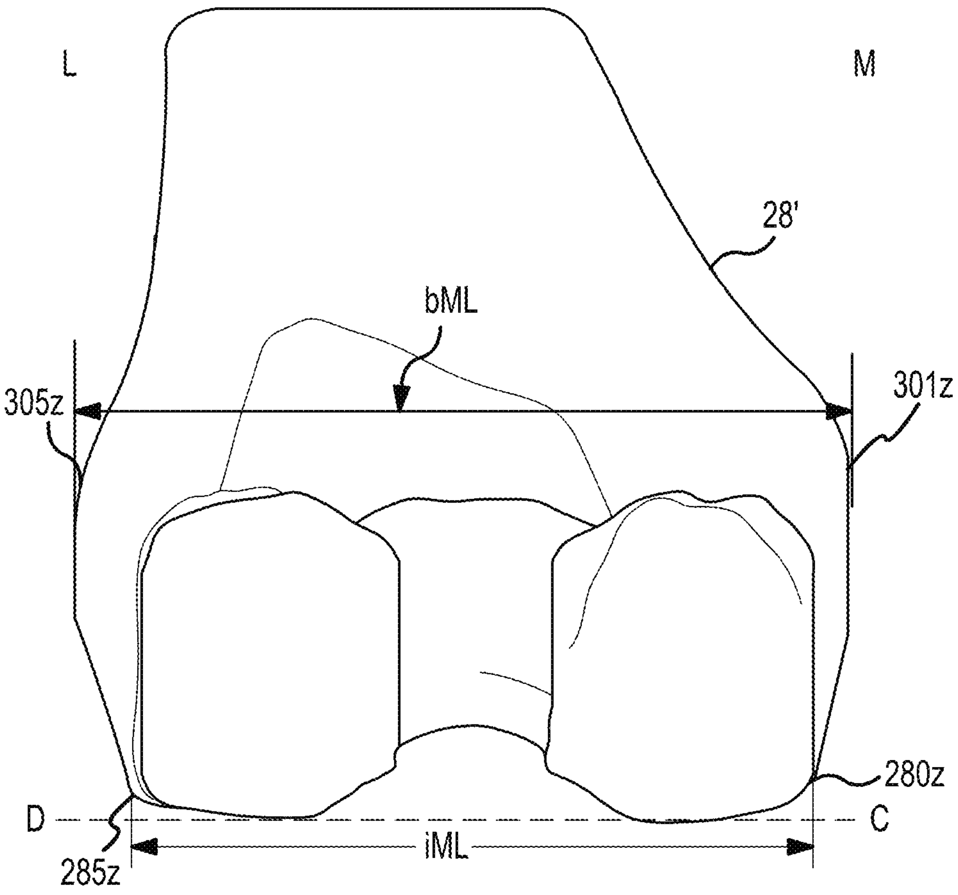

FIG. 67C illustrates the implant extents AP and iML and the femur extents bAP, bML as they may be aligned for proper implant placement.

Figure 68A:
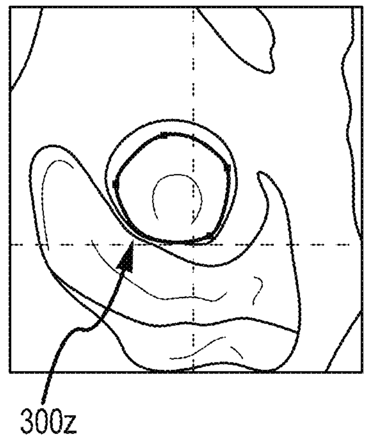

FIG. 68A shows the most medial edge of the femur in a 2D sagittal imaging slice.

Figure 68B:
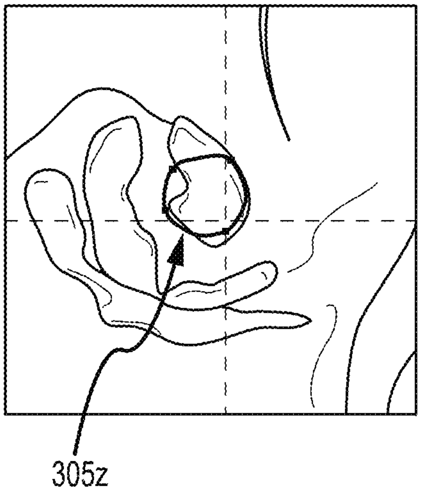

FIG. 68B, illustrates the most lateral edge of the femur in a 2D sagittal imaging slice.

Figure 68C:
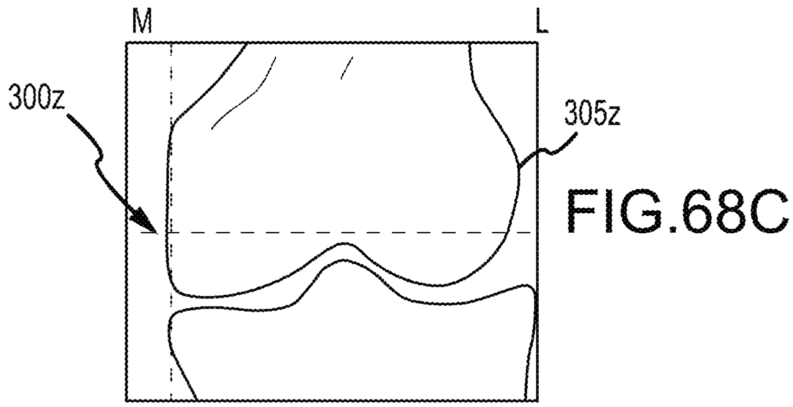

FIG. 68C is a 2D imaging slice in coronal view showing the medial and lateral edges.

Figure 69A:
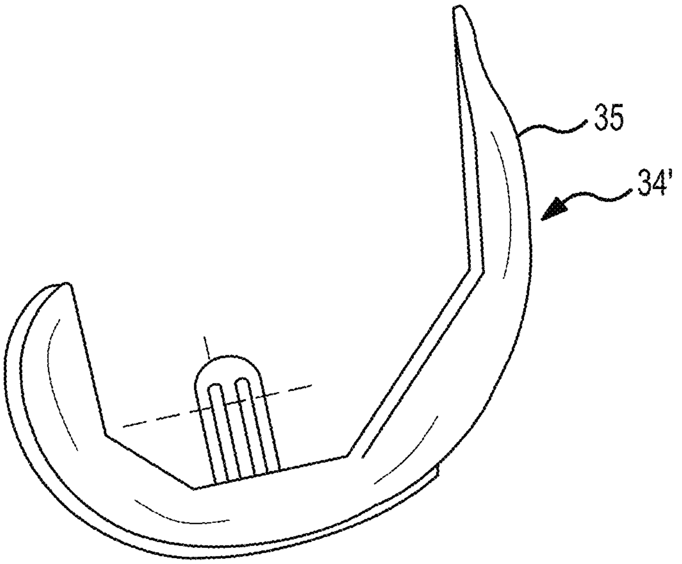

FIG. 69A is a candidate implant model mapped onto a y-z plane.

Figure 69B:
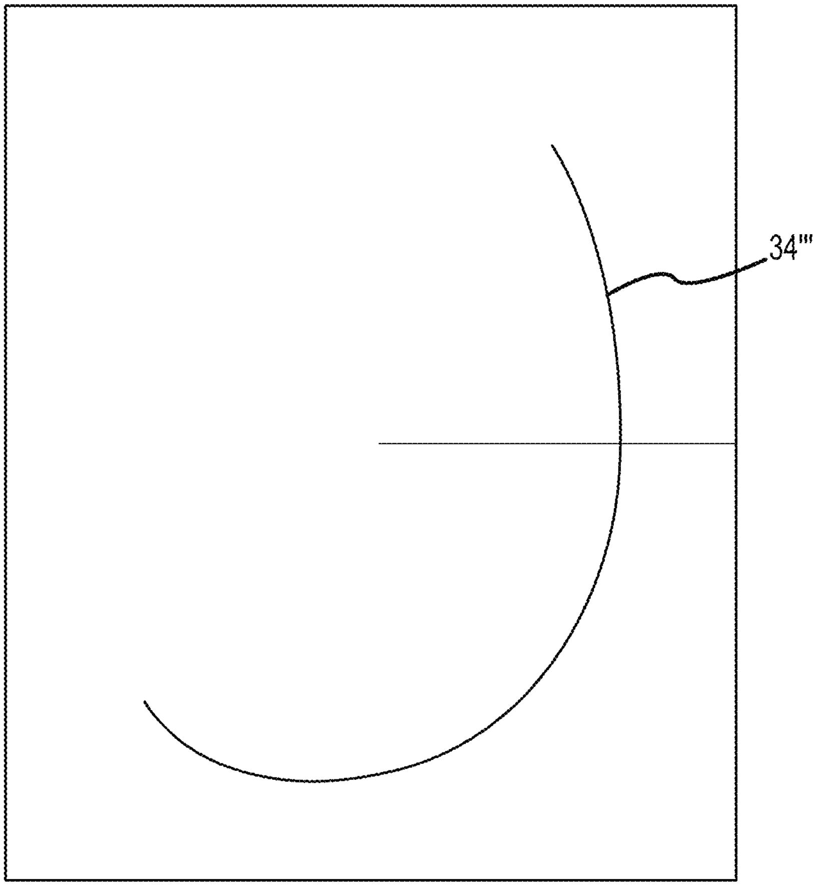

FIG. 69B is the silhouette curve of the articular surface of the candidate implant model.

Figure 69C:
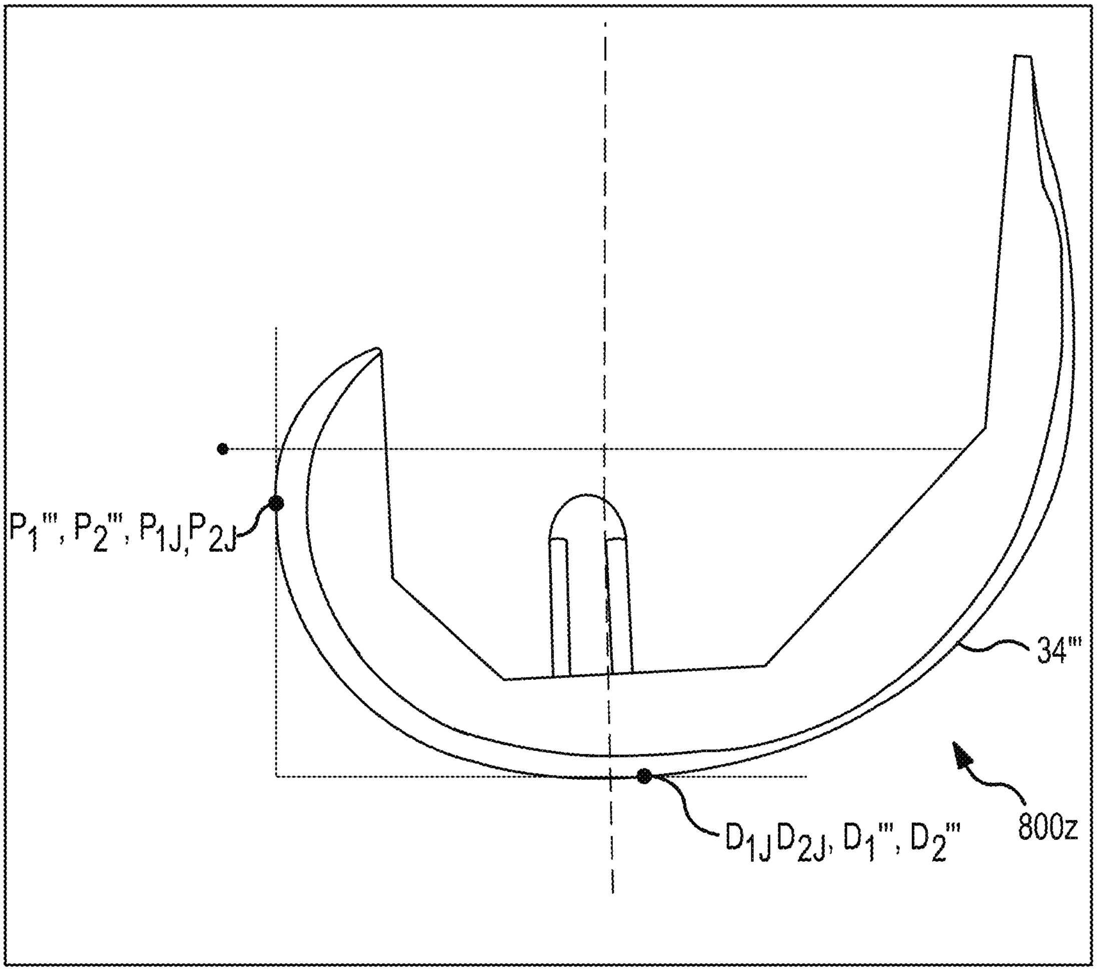

FIG. 69C is the silhouette curve of the candidate implant model aligned with the joint spacing compensation points $D_{1J}D_{2J}$ and $P_{1J}P_{2J}$.

Figure 70A:
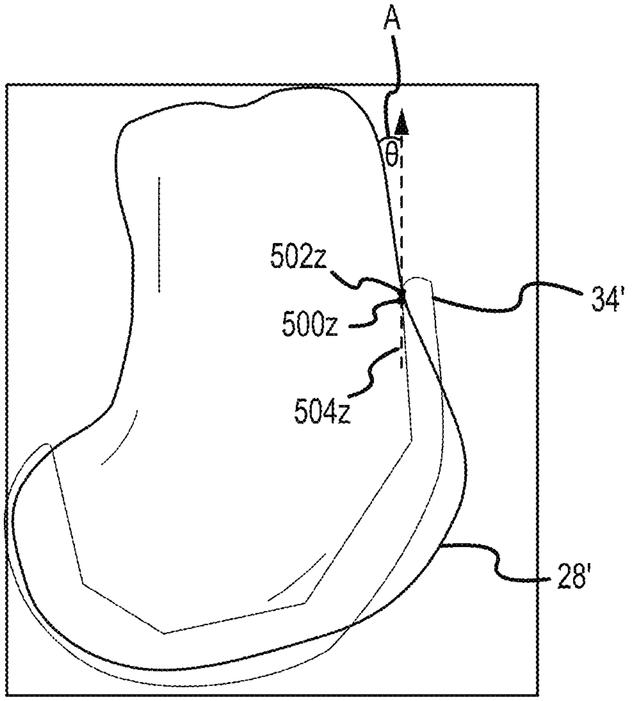

FIG. 70A illustrates a sagittal imaging slice of a distal femur with an implant model.

Figure 70B:
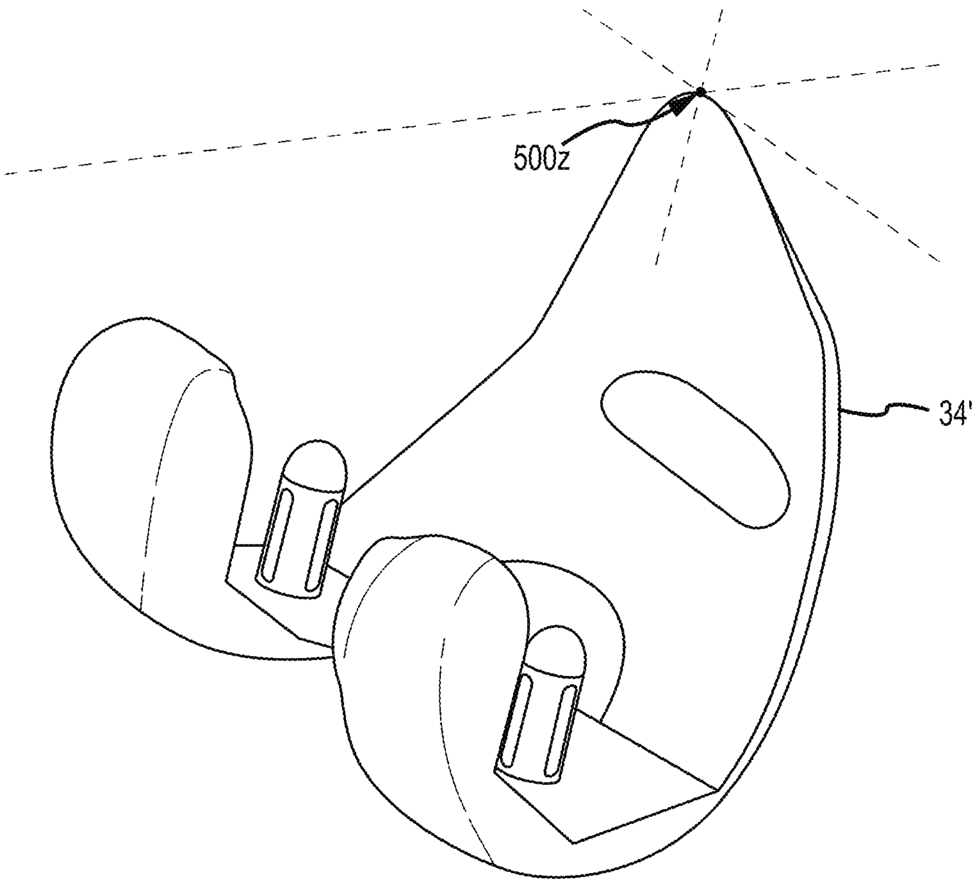

FIG. 70B depicts a femur implant model wherein the flange point on the implant is shown.

Figure 70C:
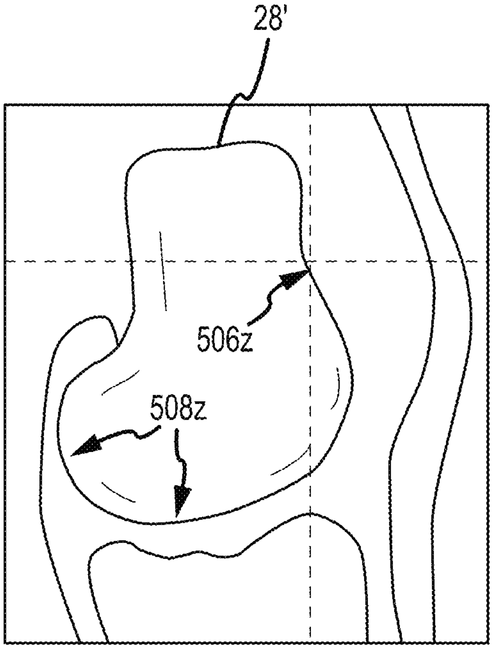

FIG. 70C shows an imaging slice of the distal femur in the sagittal view, wherein the inflection point located on the anterior shaft of the spline is shown.

Figure 70D:
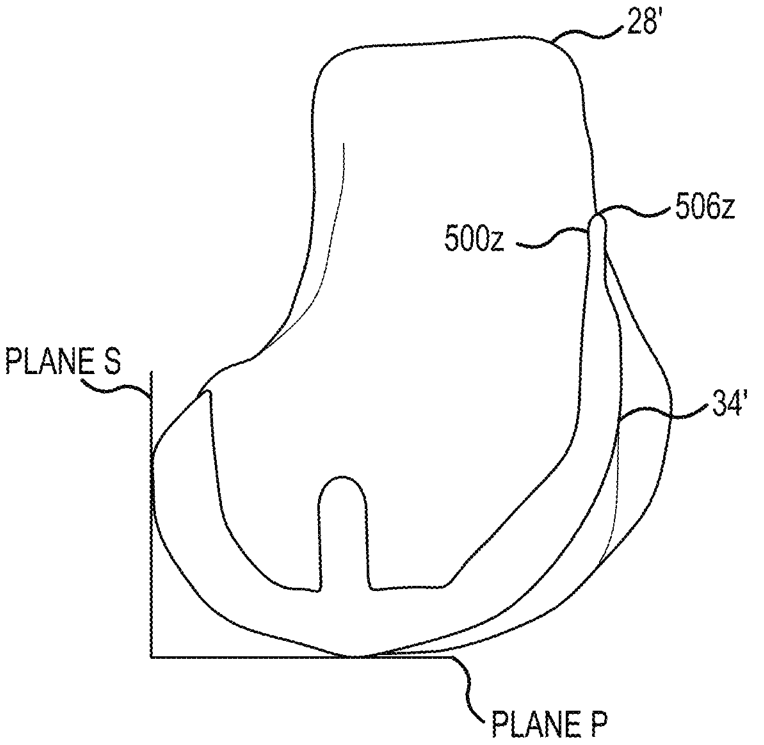

FIG. 70D illustrates the 2D implant model properly positioned on the 2D femur image, as depicted in a sagittal view.

Figure 7A:
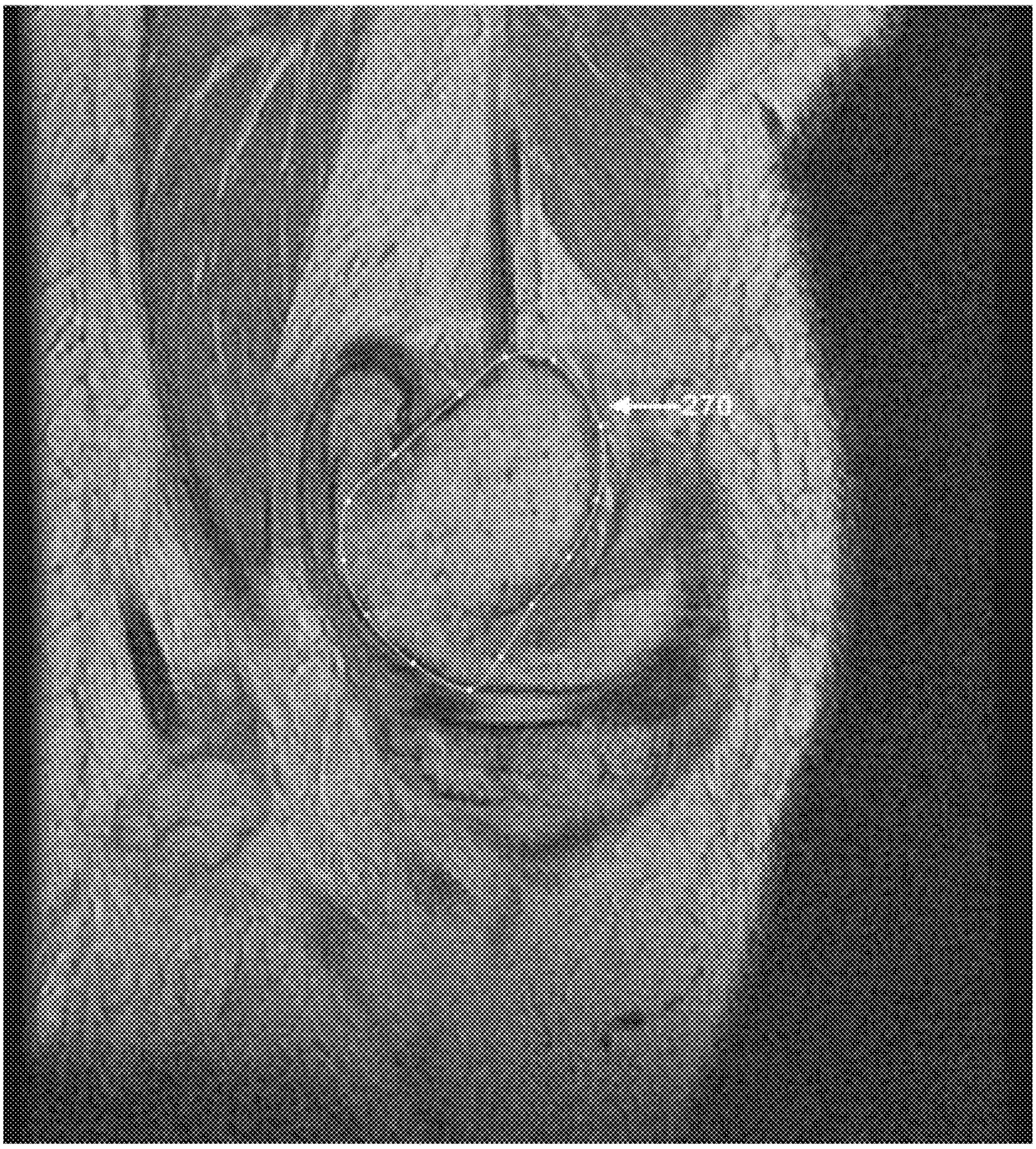
FIG. 7A is a sagittal plane image slice of a segmented femur.
Figure 7B:
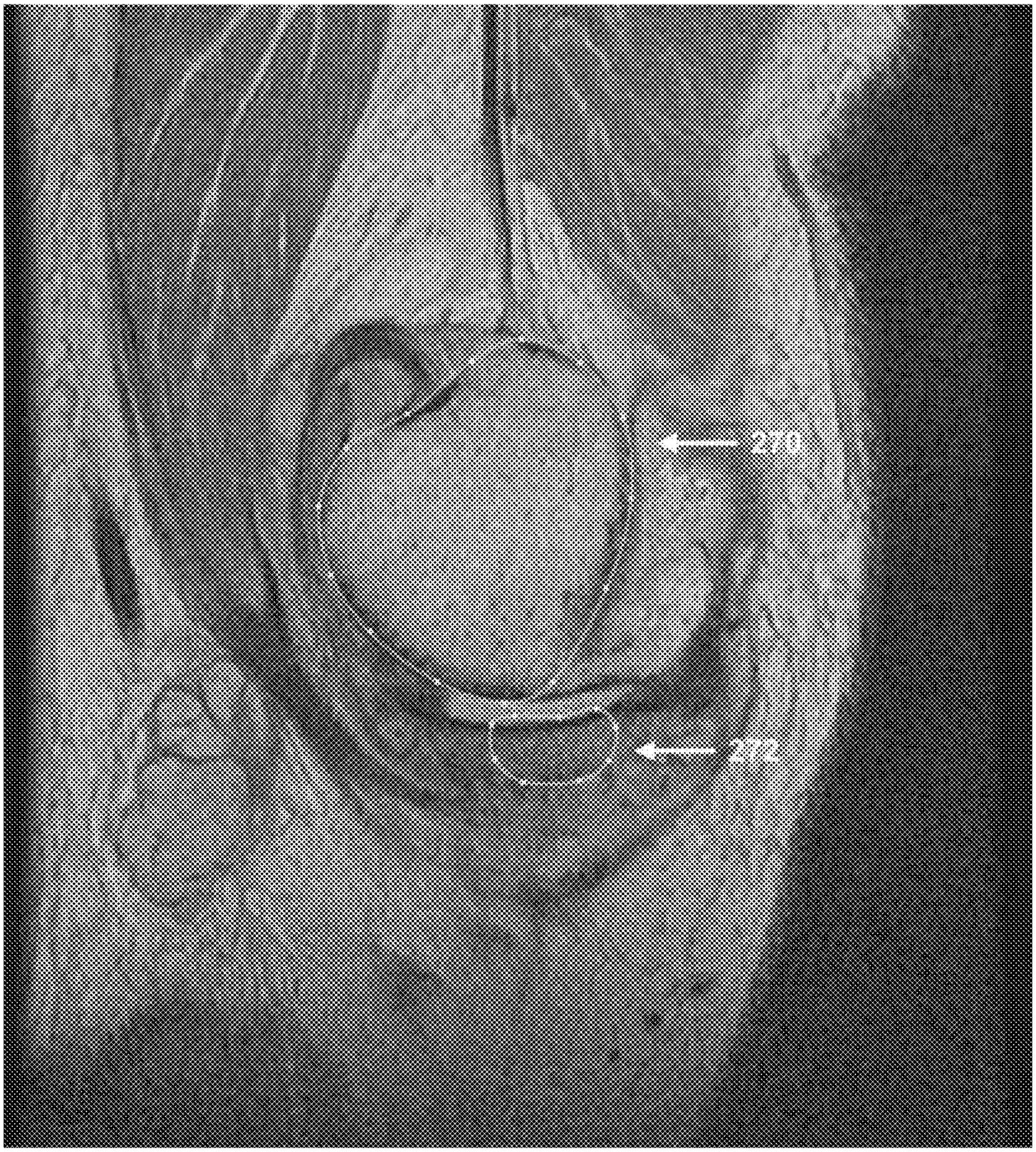
FIG. 7B is a sagittal plane image slice of a segmented femur and tibia.
Figure 7C:
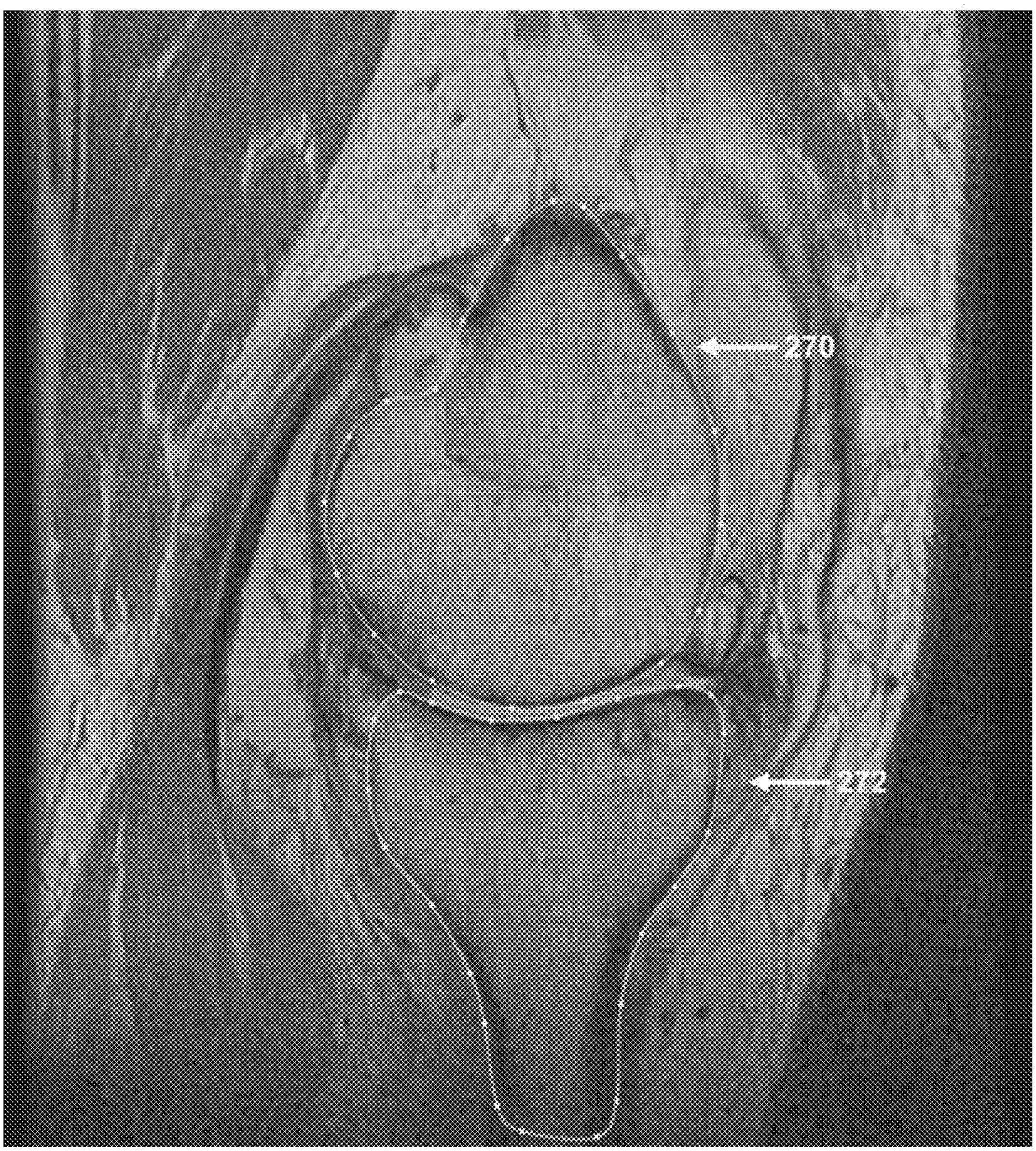
FIG. 7C is another sagittal plane image slice of a segmented femur and tibia.
Figure 7D:
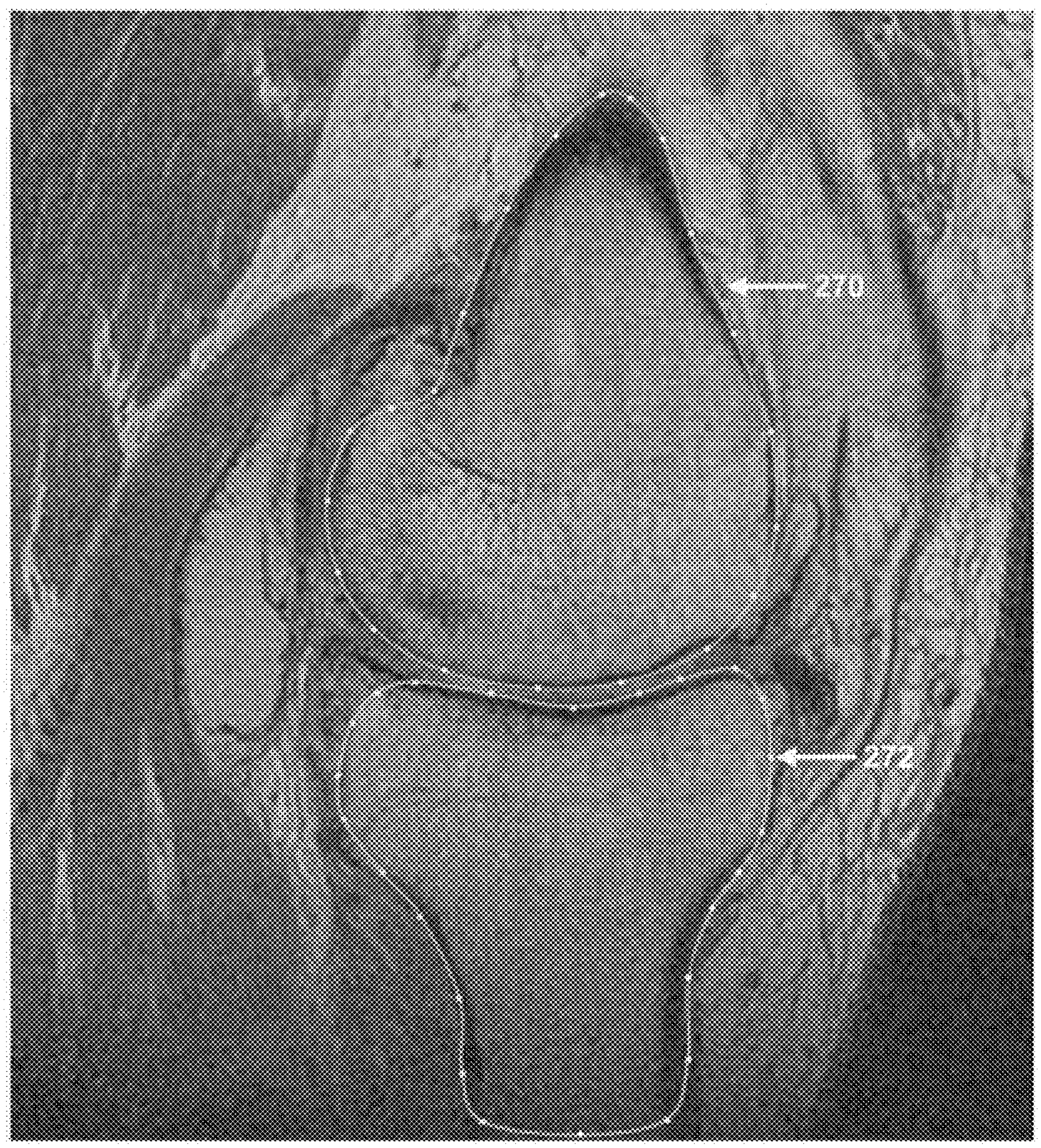
FIG. 7D is another sagittal plane image slice of a segmented femur and tibia.
Figure 7E:
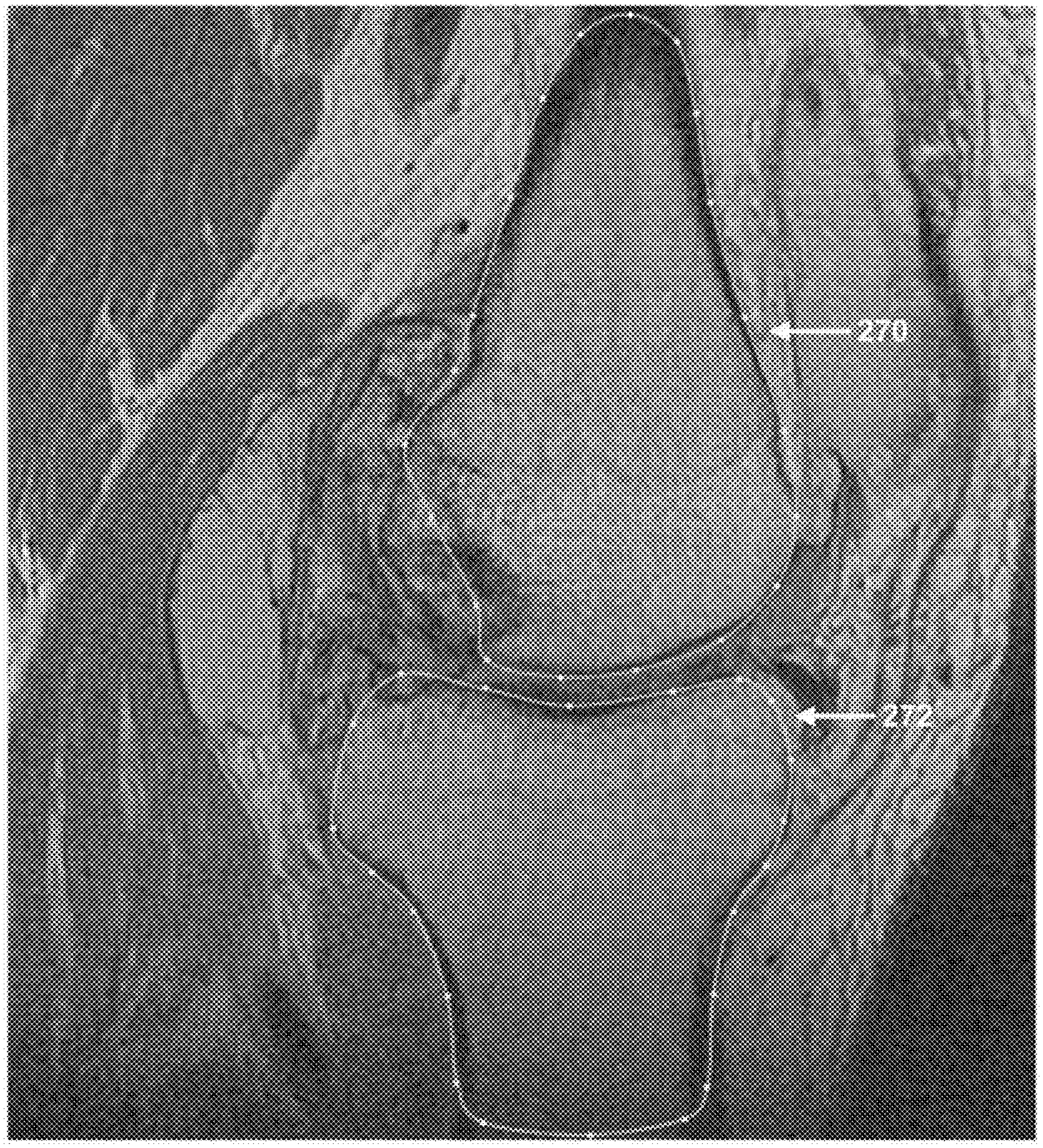
FIG. 7E is another sagittal plane image slice of a segmented femur and tibia.
Figure 7F:
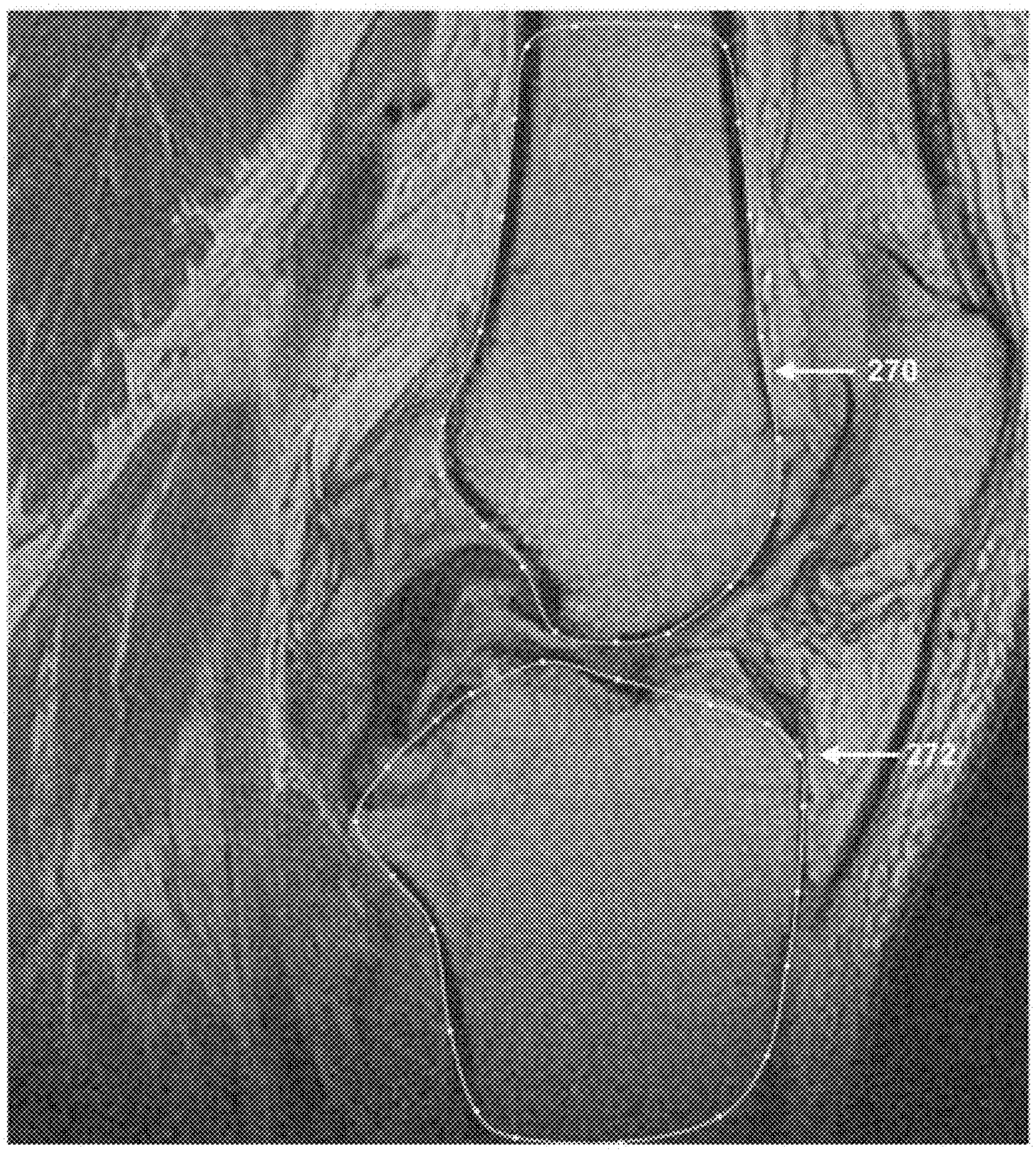
FIG. 7F is another sagittal plane image slice of a segmented femur and tibia.
Figure 7G:
FIG. 7G is another sagittal plane image slice of a segmented femur and tibia.
Figure 7H:
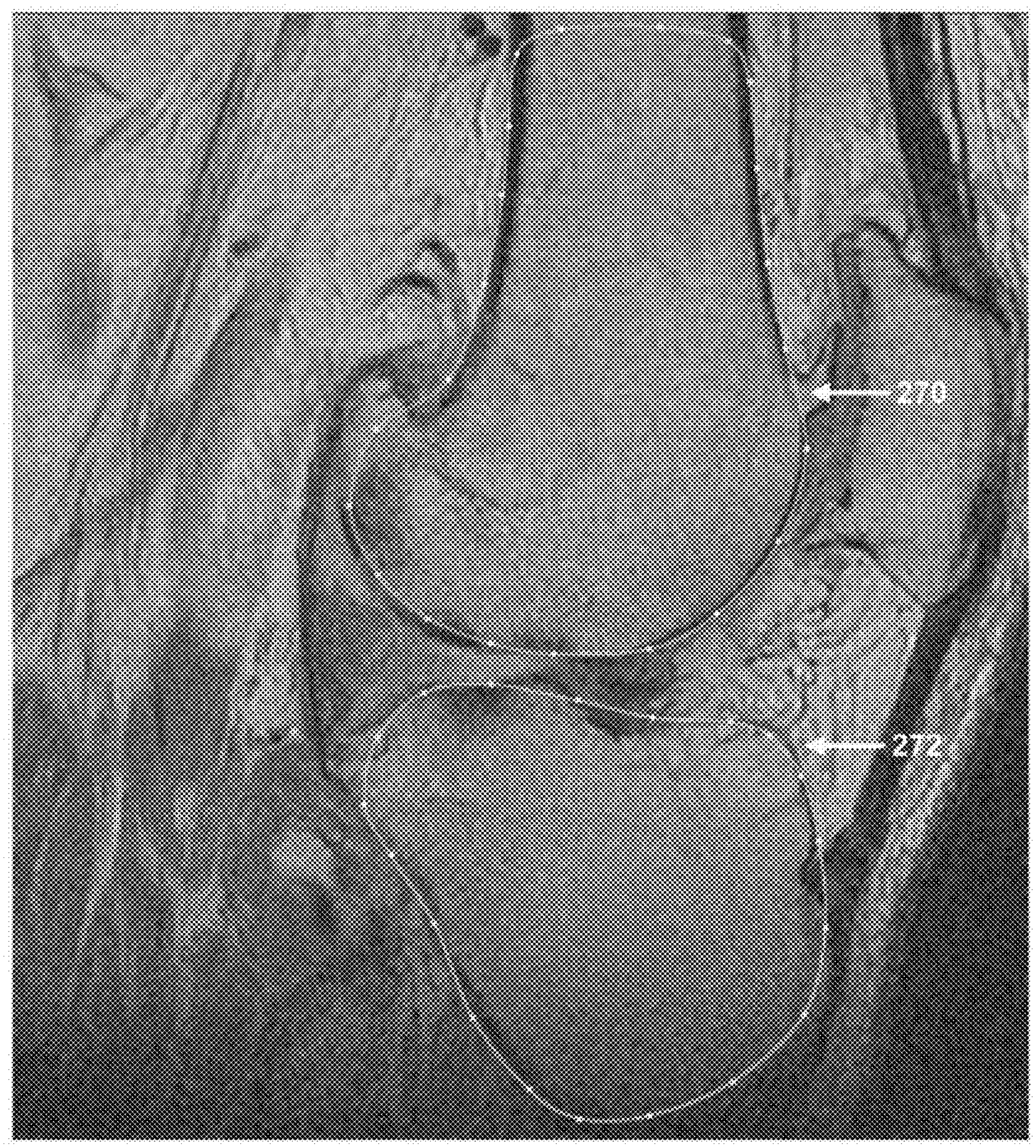
FIG. 7H is another sagittal plane image slice of a segmented femur and tibia.
Figure 7I:
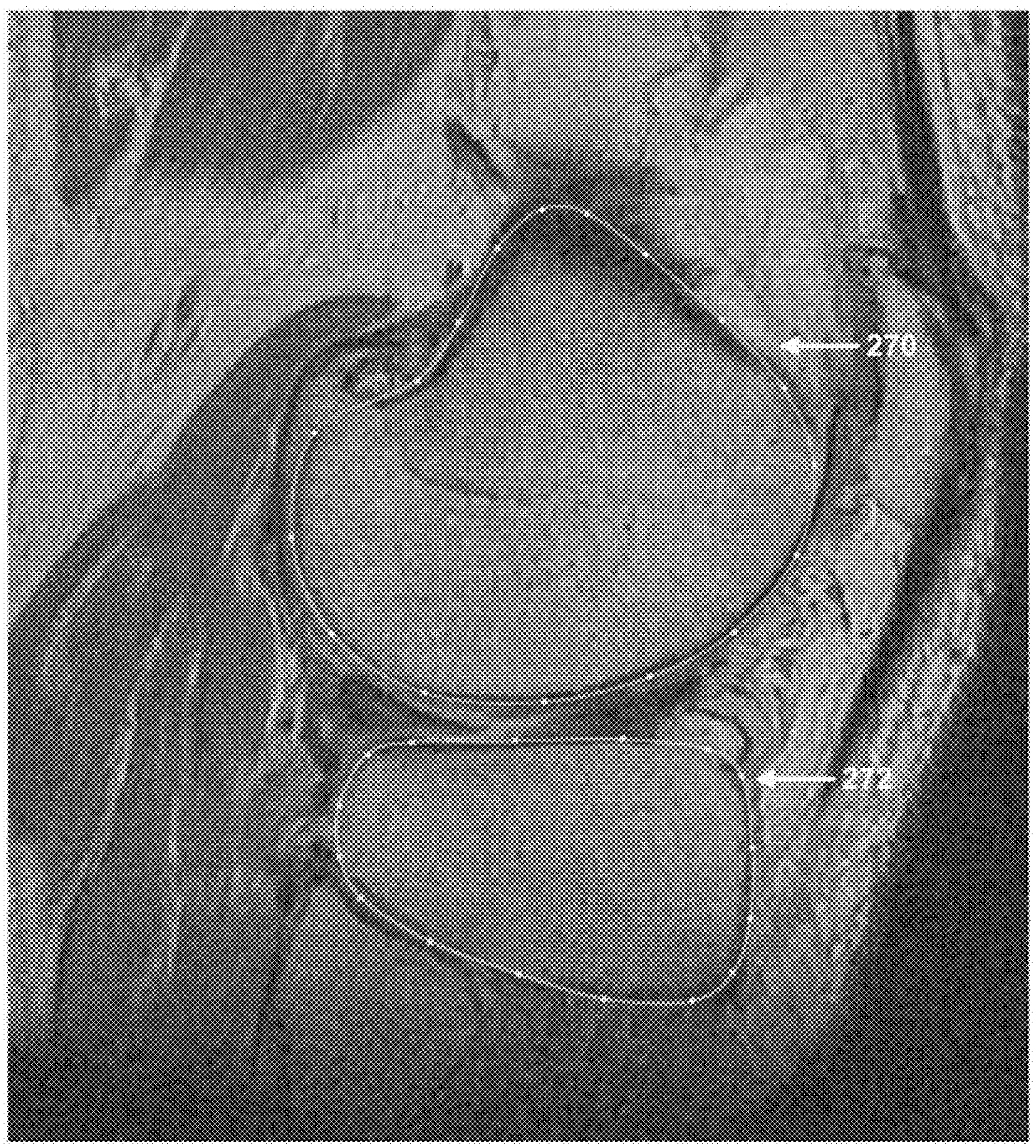
FIG. 7I is another sagittal plane image slice of a segmented femur and tibia.
Figure 7J:
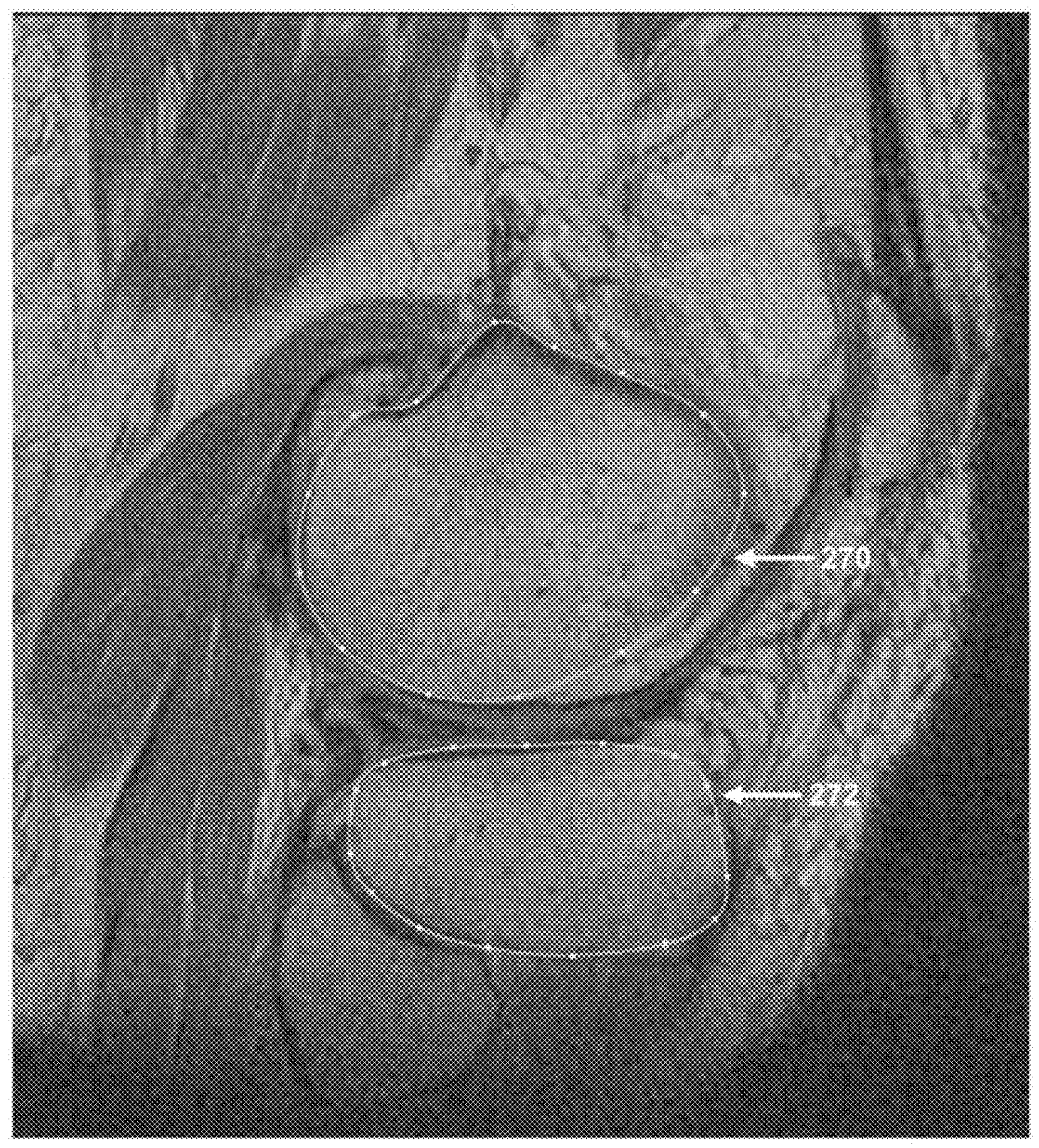
FIG. 7J is another sagittal plane image slice of a segmented femur and tibia.
Figure 7K:
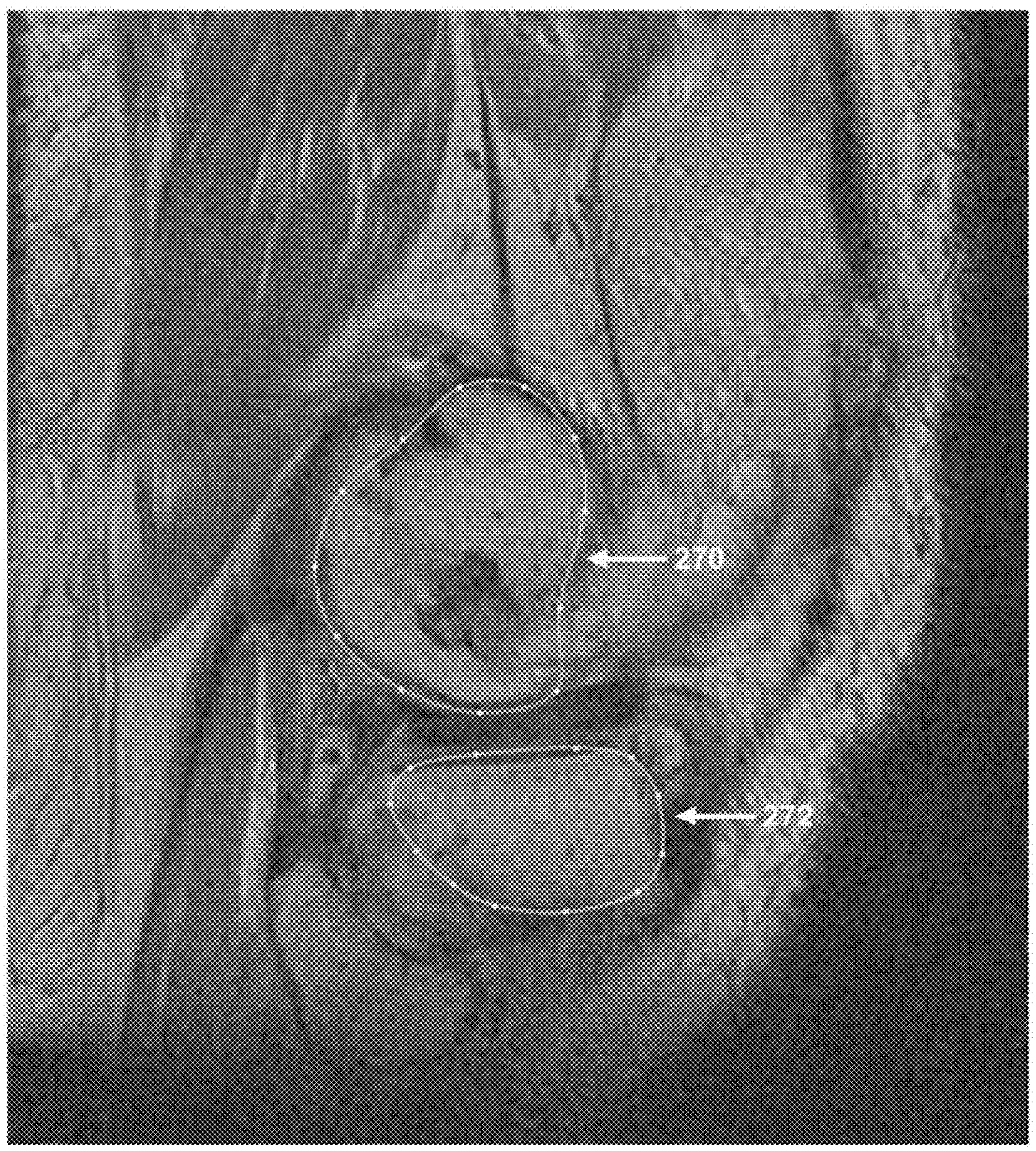
FIG. 7K is another sagittal plane image slice of a segmented femur and tibia.

FIG. 7IA depicts an implant model that is improperly aligned on a 2D femur image, as depicted in a sagittal view.

FIG. 7IB illustrates the implant positioned on a femur transform wherein a femur cut plane is shown, as depicted in a sagittal view.

Figure 72:
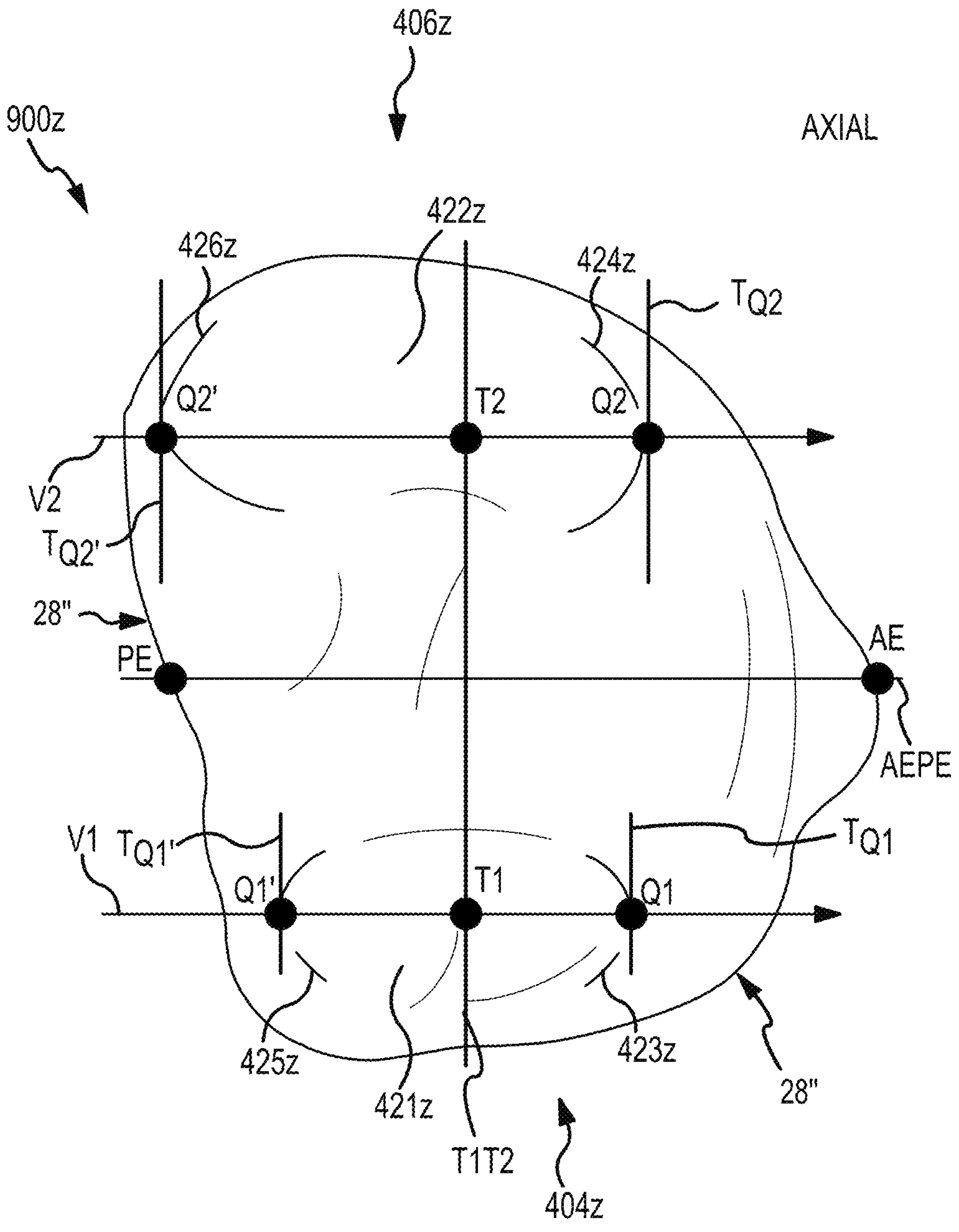

FIG. 72 is a top view of the tibia plateaus of a tibia bone image or model.

Figure 73A:
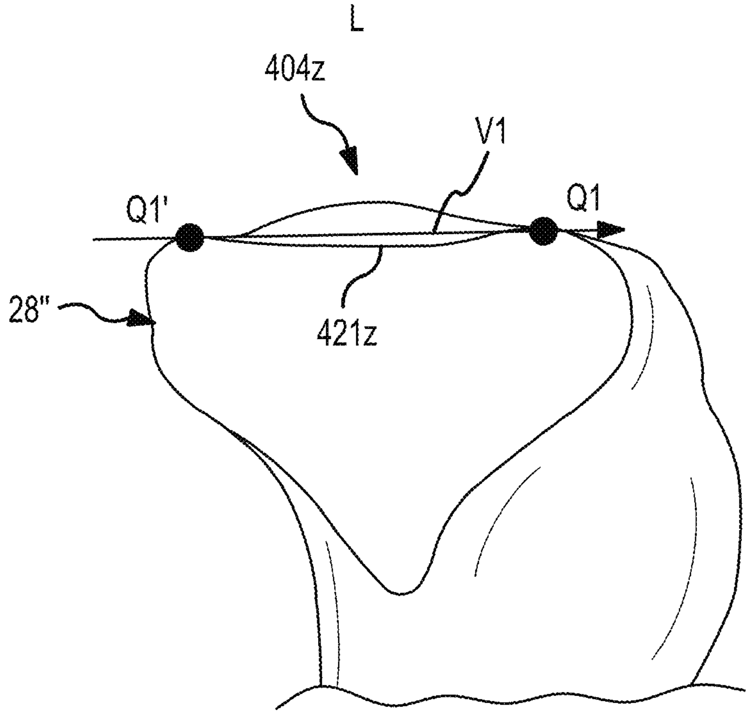

FIG. 73A is a sagittal cross section through a lateral tibia plateau of the 2D tibia bone model or image.

Figure 73B:
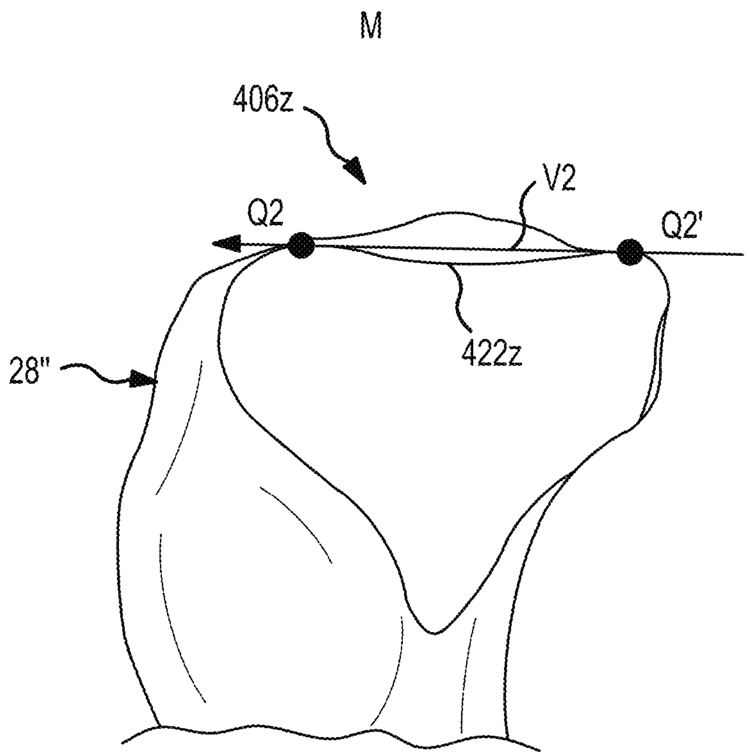

FIG. 73B is a sagittal cross section through a medial tibia plateau of the 2D tibia bone model or image.

Figure 73C:
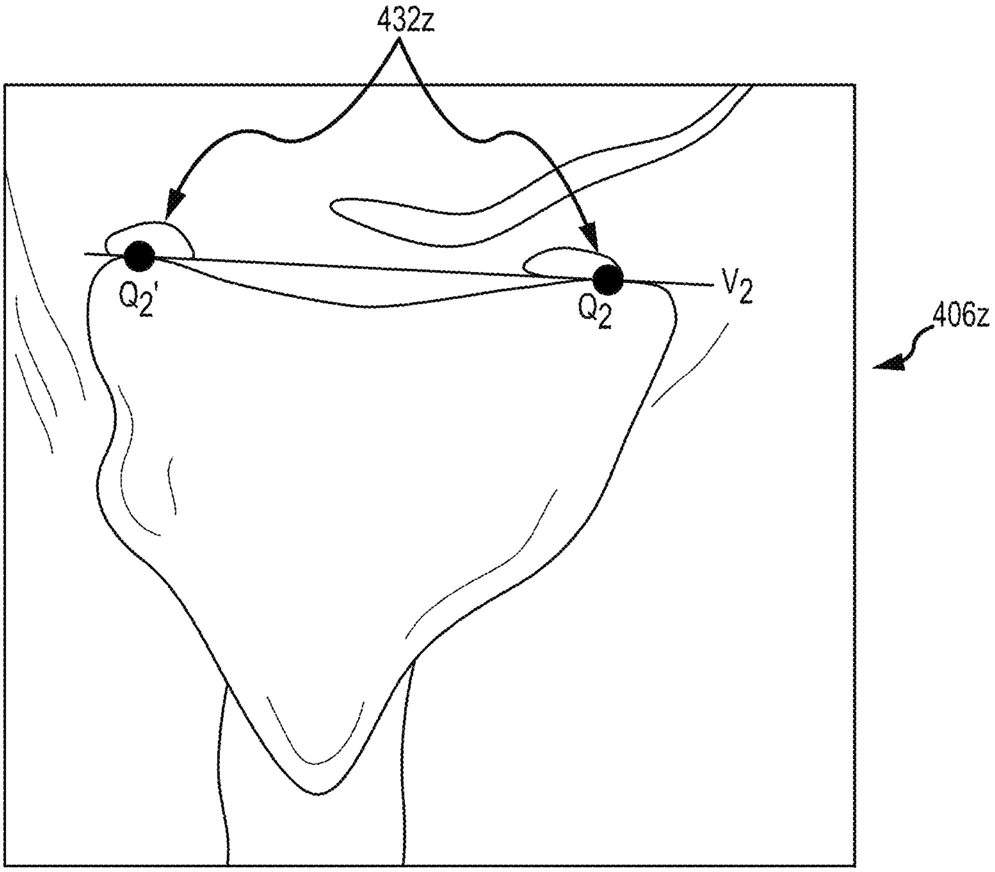

FIG. 73C depicts a sagittal cross section through an undamaged or little damaged medial tibia plateau of the 2D tibia model, wherein osteophytes are also shown.

Figure 73D:
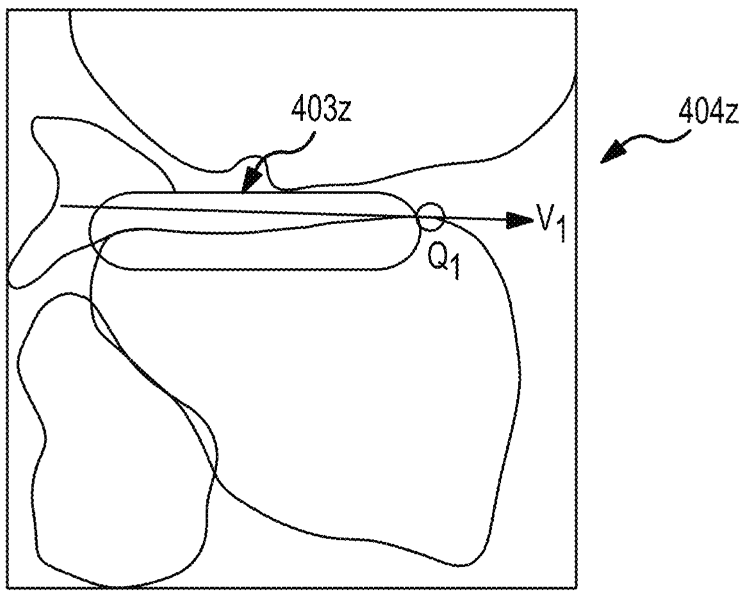

FIG. 73D is a sagittal cross section through a damaged lateral tibia plateau of the 2D tibia model.

Figure 74A:
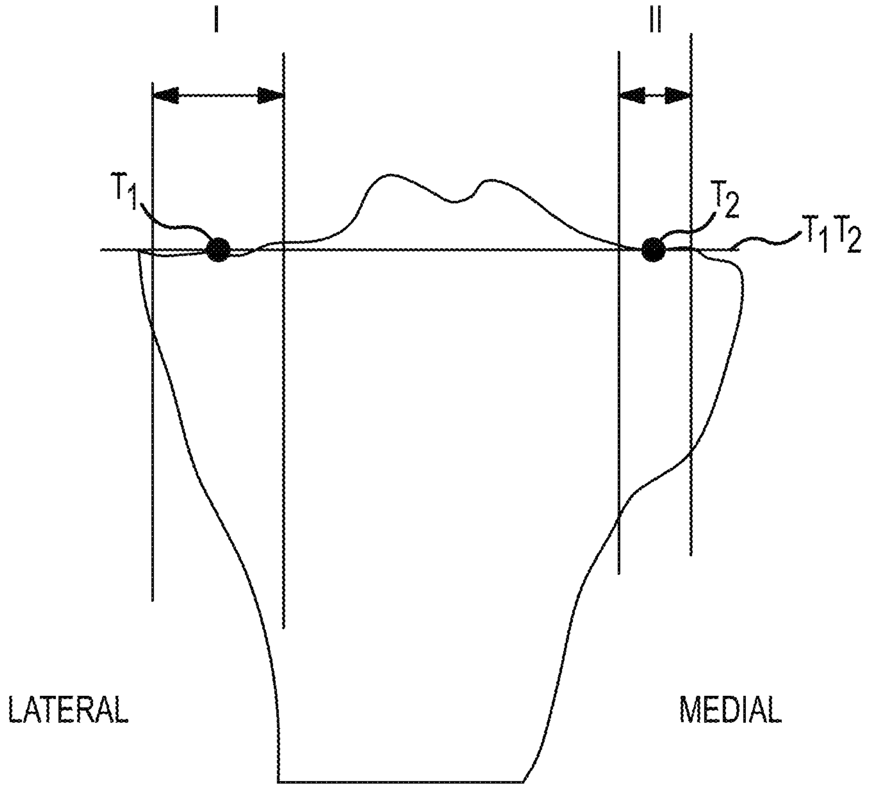

FIG. 74A is a coronal 2D imaging slice of the tibia.

Figure 74B:
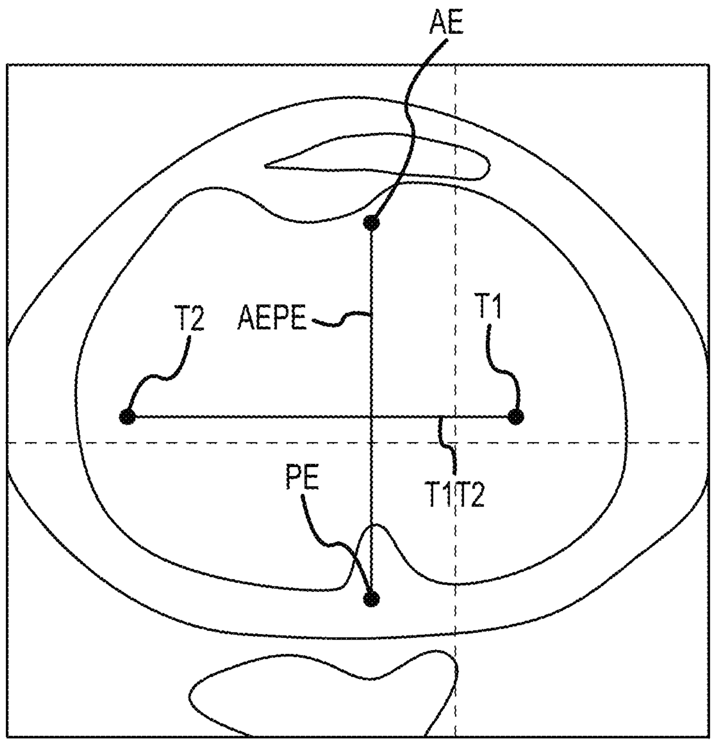

FIG. 74B is an axial 2D imaging slice of the tibia.

Figure 75A:
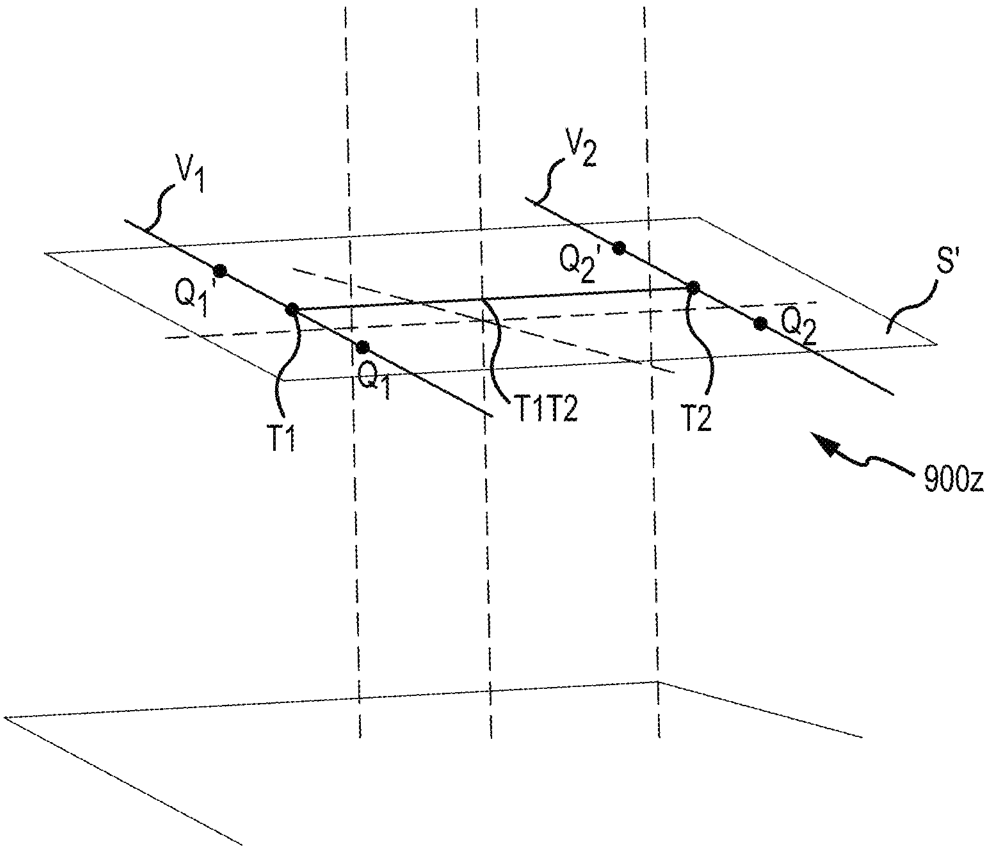

FIG. 75A depicts the tibia reference data on an x-y coordinate system.

Figure 75B:
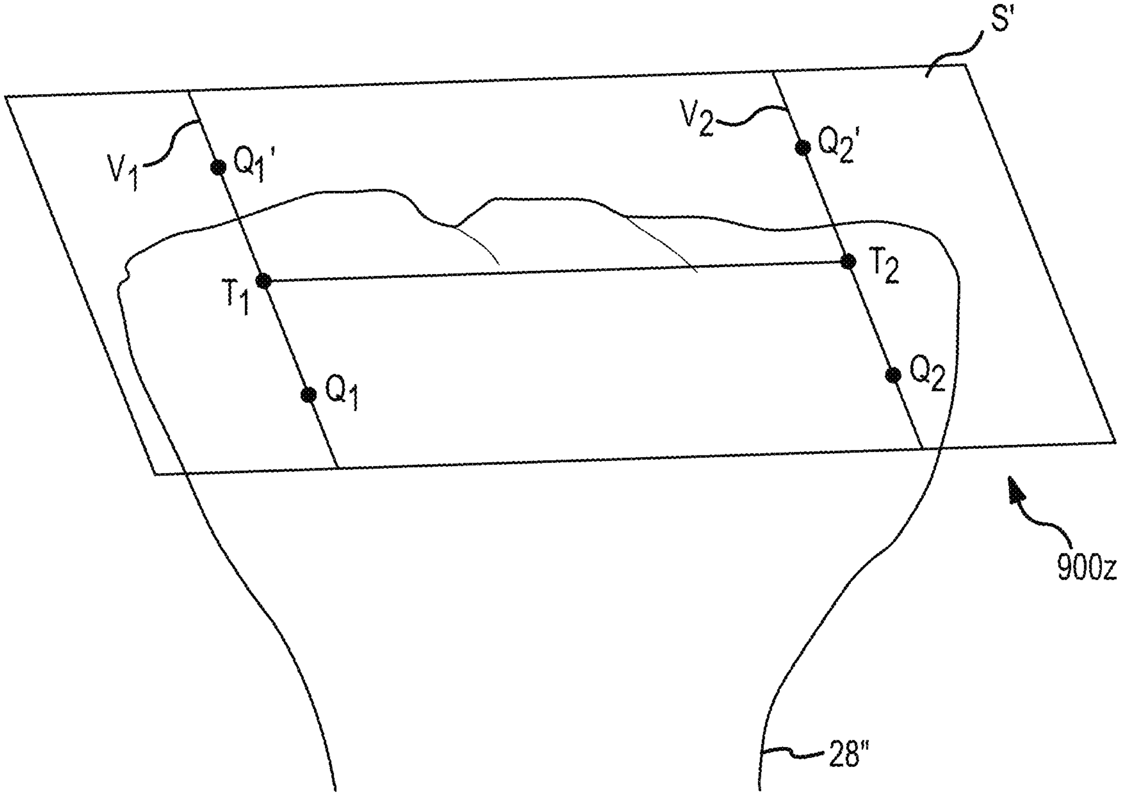

FIG. 75B depicts the tibia reference data on a proximal end of the tibia to aid in the selection of an appropriate tibia implant.

Figure 76A:
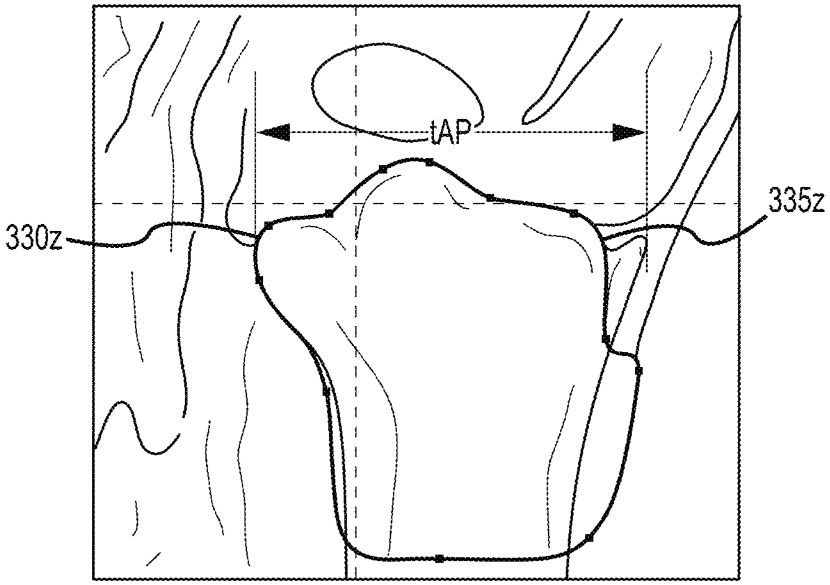

FIG. 76A is a 2D sagittal imaging slice of the tibia wherein a segmentation spline with an AP extant is shown.

Figure 76B:
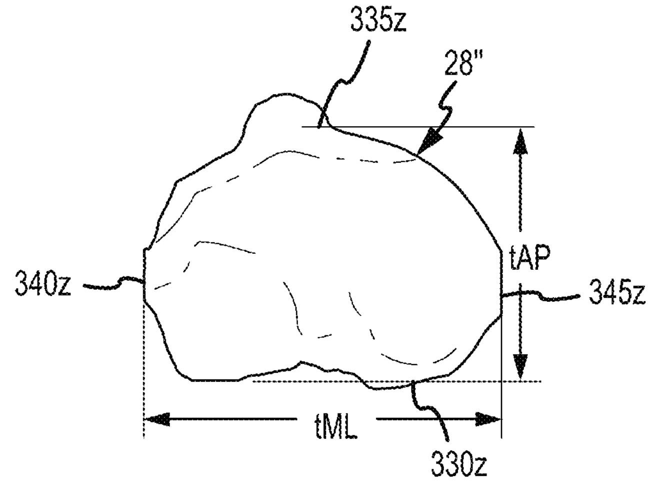

FIG. 76B is an axial end view of the tibia upper end of the tibia bone model depicted in FIG. 52A.

Figure 76C:
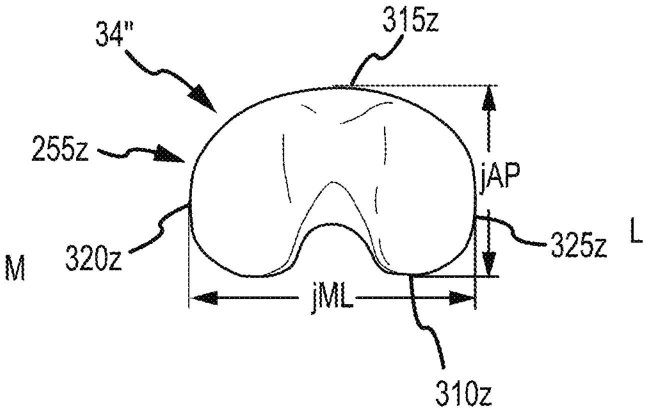

FIG. 76C is a plan view of the joint side of the tibia implant model depicted in FIG. 52B.

Figure 77:
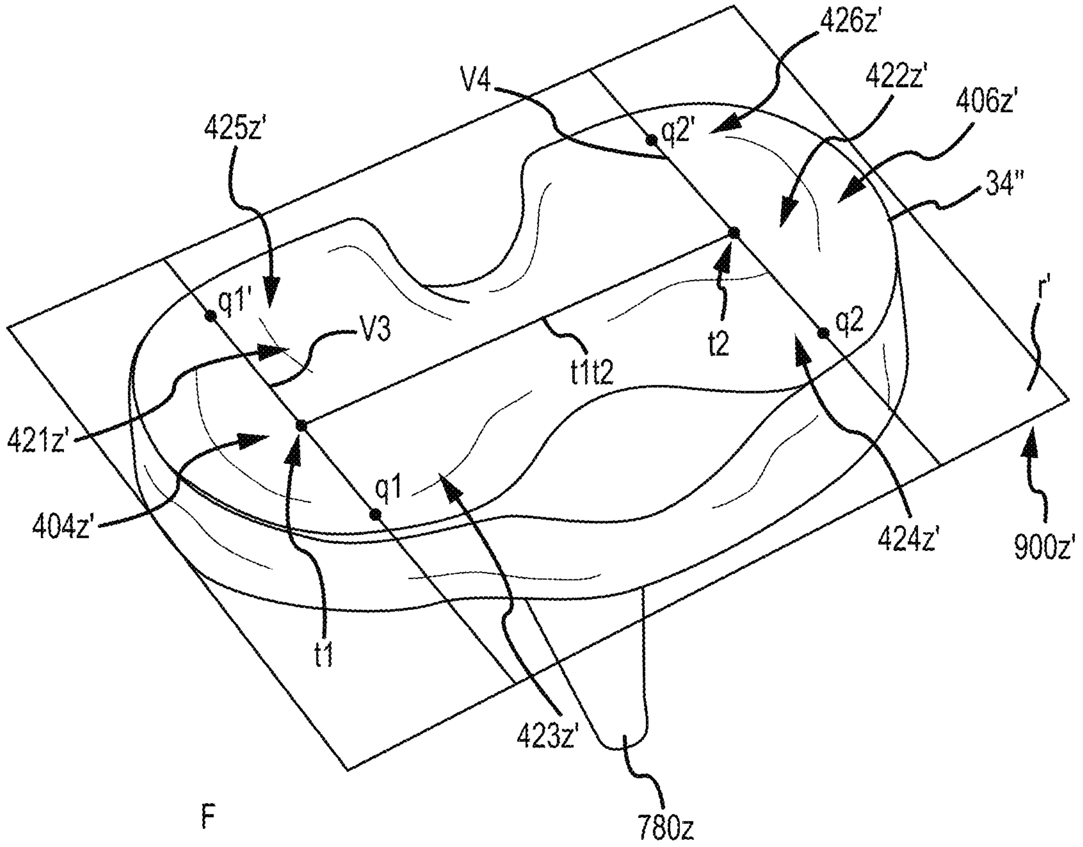

FIG. 77 is a top isometric view of the tibia plateaus of a tibia implant model.

Figure 78A:
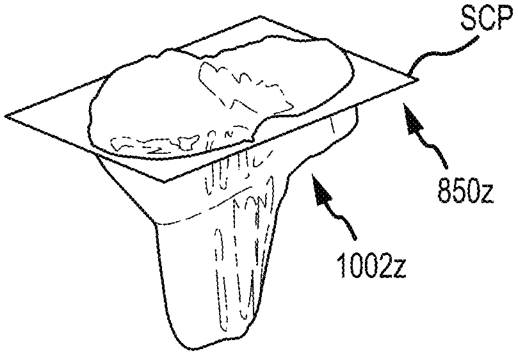

FIG. 78A is an isometric view of the 3D tibia bone model showing the surgical cut plane SCP design.

Figure 78B:
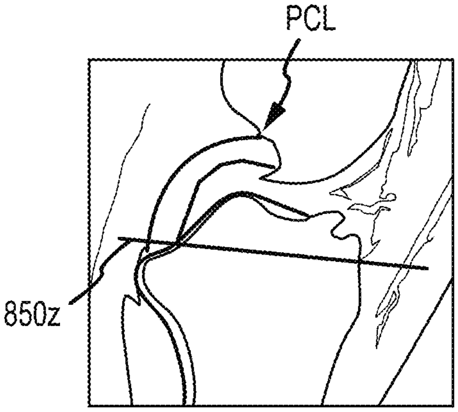
Figure 78C:
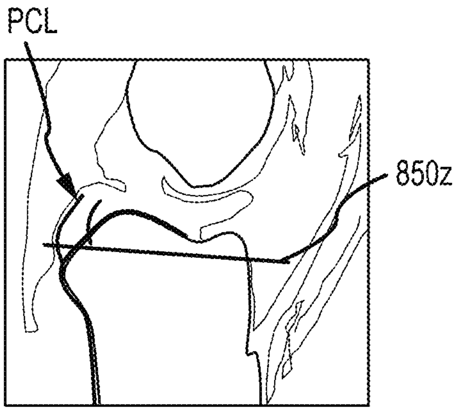

FIGS. 78B and 78C are sagittal MRI views of the surgical tibia cut plane SCP design with the posterior cruciate ligament PCL.

Figure 79A:
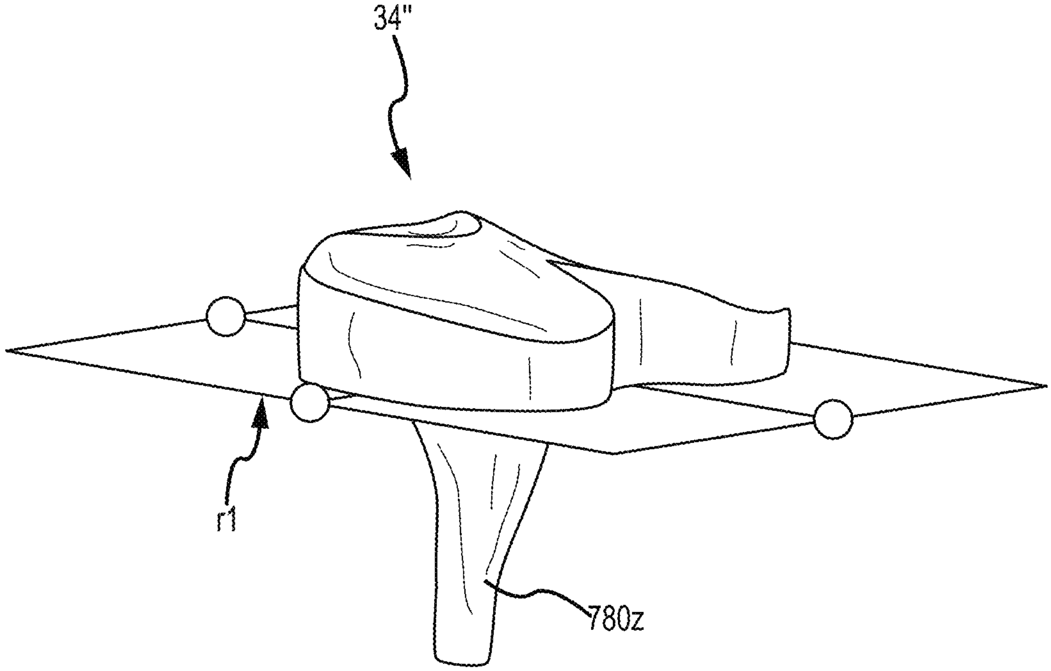

FIG. 79A is an isometric view of the tibia implant wherein a cut plane is shown.

Figure 79B:
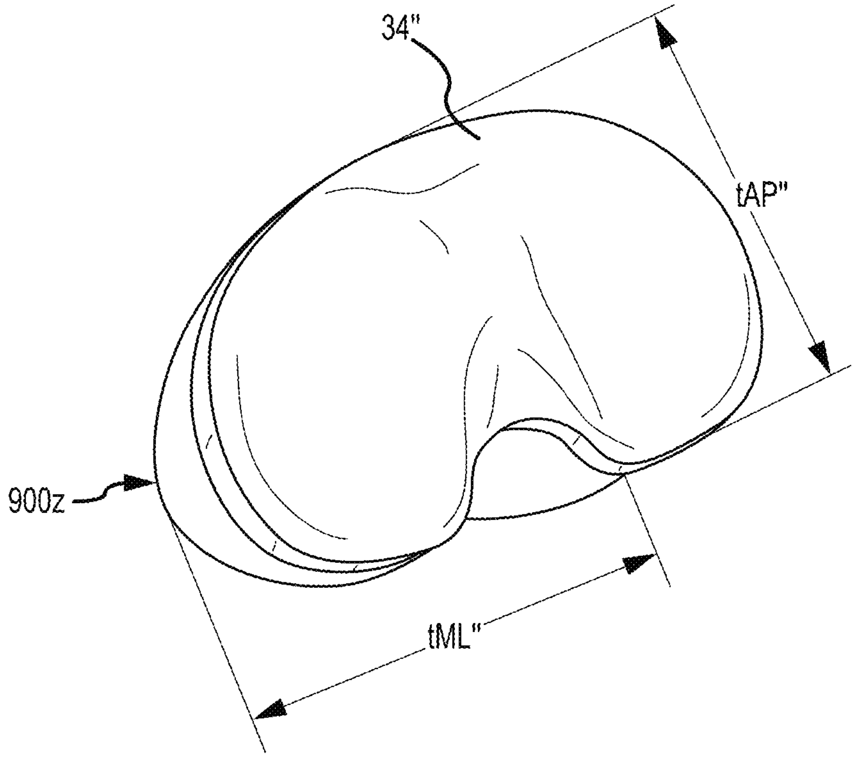

FIG. 79B is a top axial view of the implant superimposed on the tibia reference data.

Figure 79C:
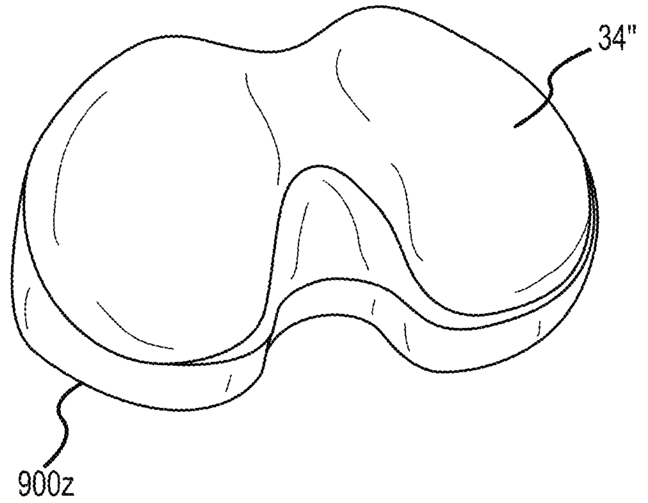

FIG. 79C is an axial view of the tibial implant aligned with the tibia reference data.

Figure 79D:
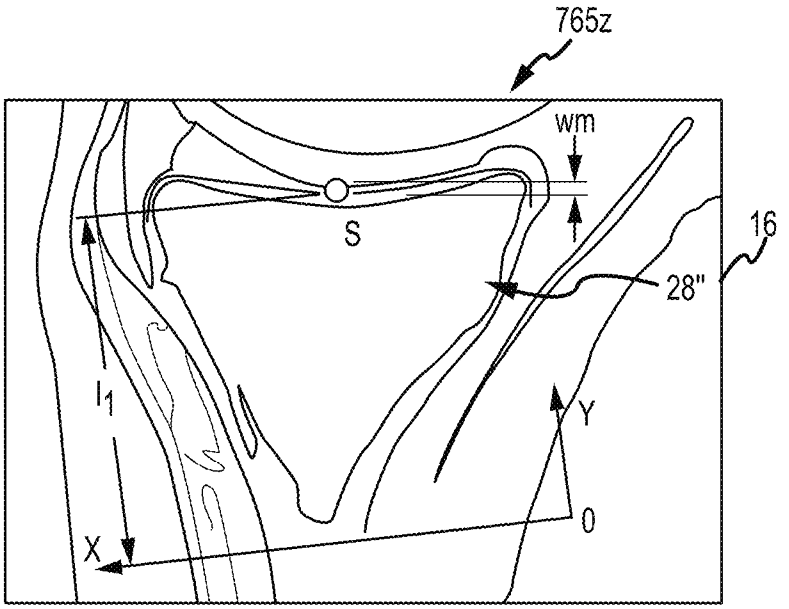

FIG. 79D is a MRI imaging slice of the medial portion of the proximal tibia and indicates the establishment of landmarks for the tibia POP design, as depicted in a sagittal view.

Figure 79E:
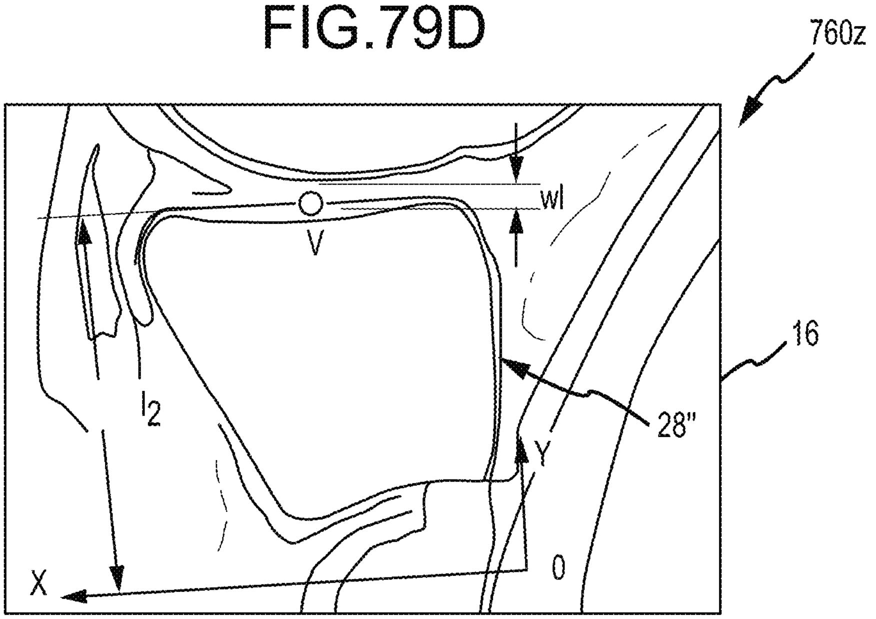

FIG. 79E is a MRI imaging slice of the lateral portion of the proximal tibia, as depicted in a sagittal view.

Figure 79F:
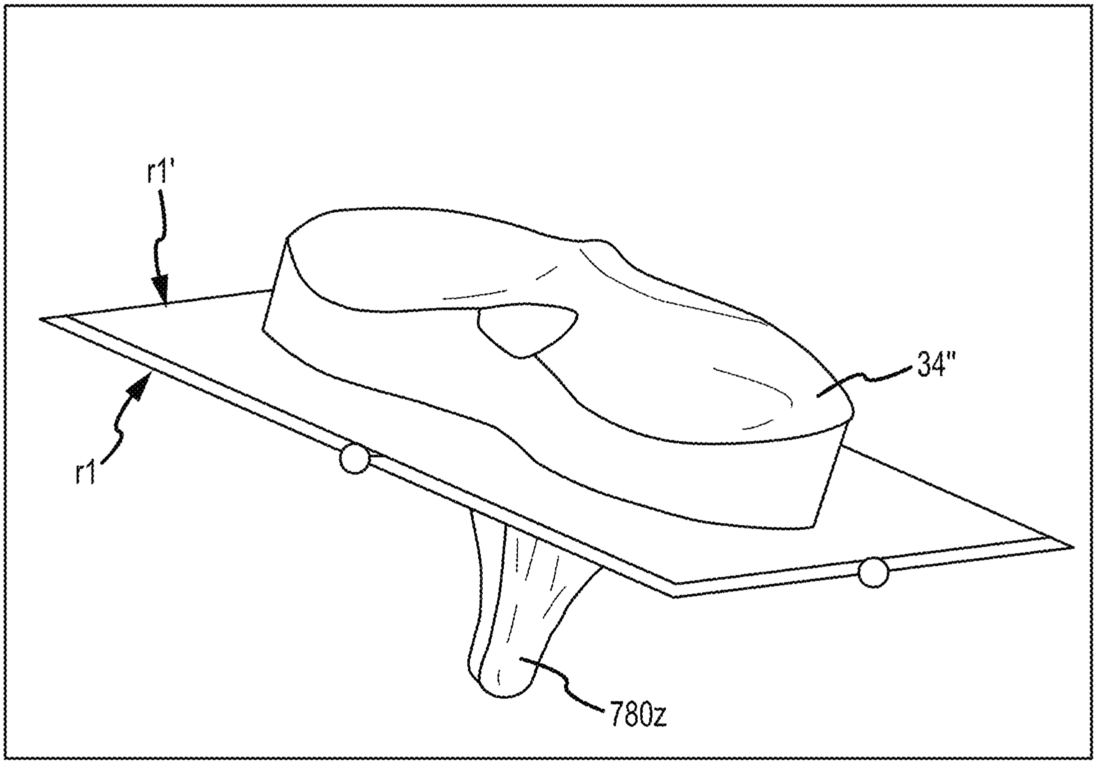

FIG. 79F is an isometric view of the 3D model of the tibia implant and the cut plane.

Figure 80A:
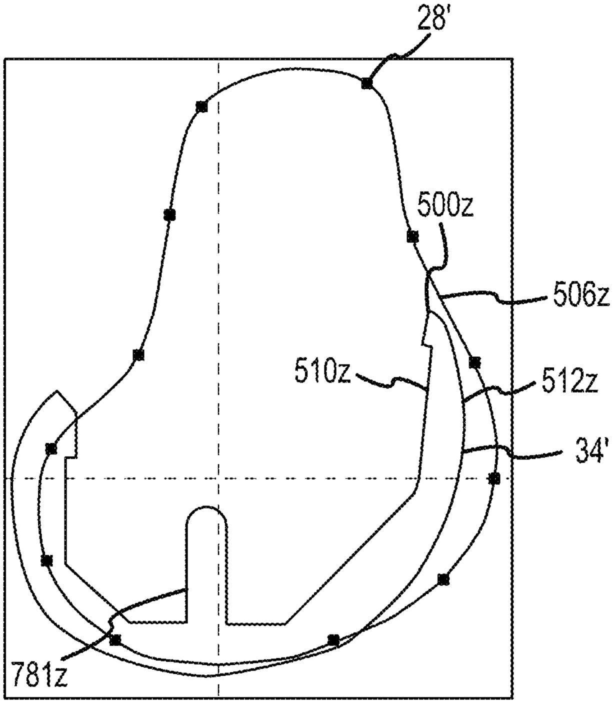
Figure 80B:
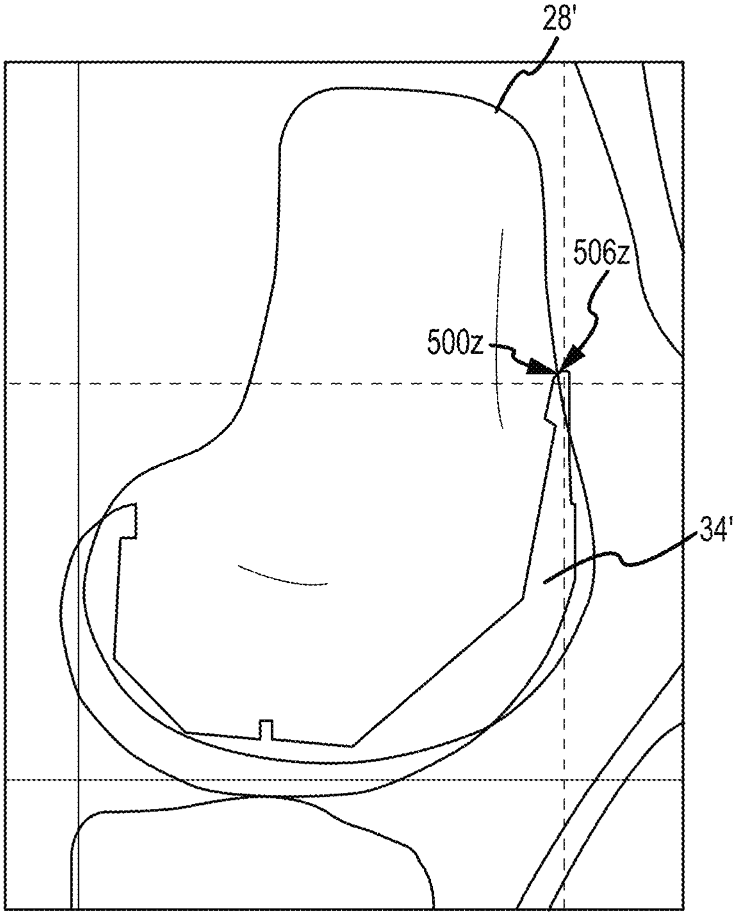

FIGS. 80A-80B are sagittal views of a 2D imaging slice of the femur wherein the 2D computer generated implant models are also shown.

Figure 80C:
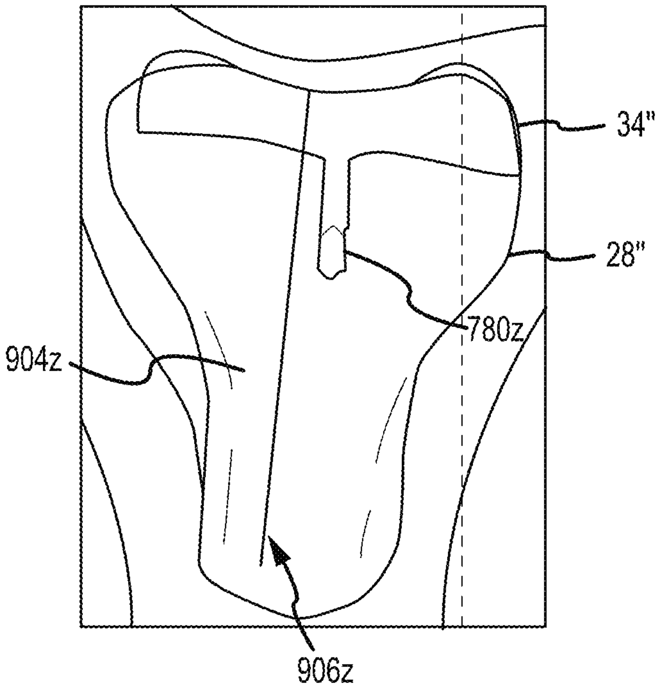

FIG. 80C is a sagittal view of a 2D imaging slice of the tibia wherein the 2D computer generated implant model is also shown.

Figures 81A, 81B, 81C:
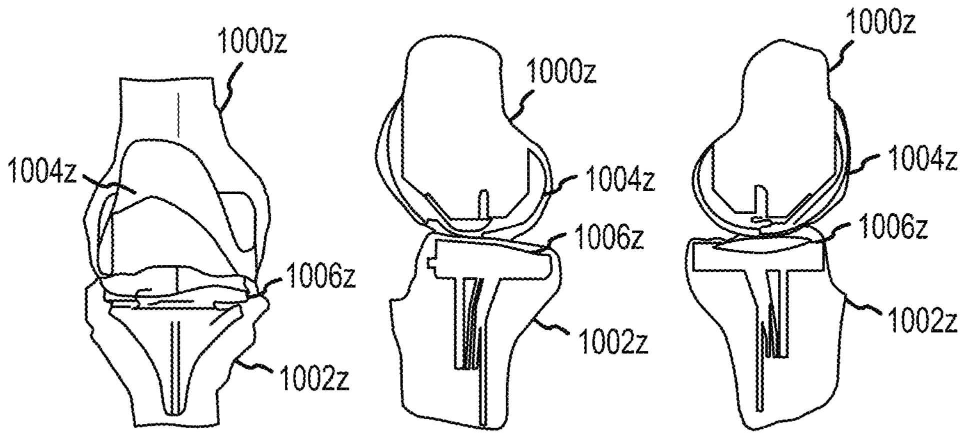

FIGS. 81A-81C are various views of the 2D implant models superimposed on the 2D bone models.

Figure 81D:
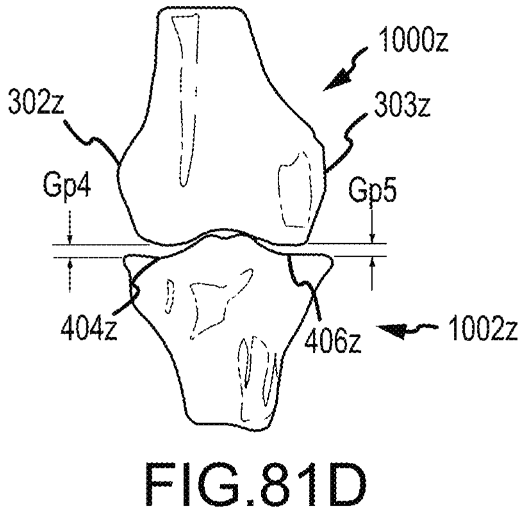

FIG. 81D is a coronal view of the 2D bone models.

Figure 81E:
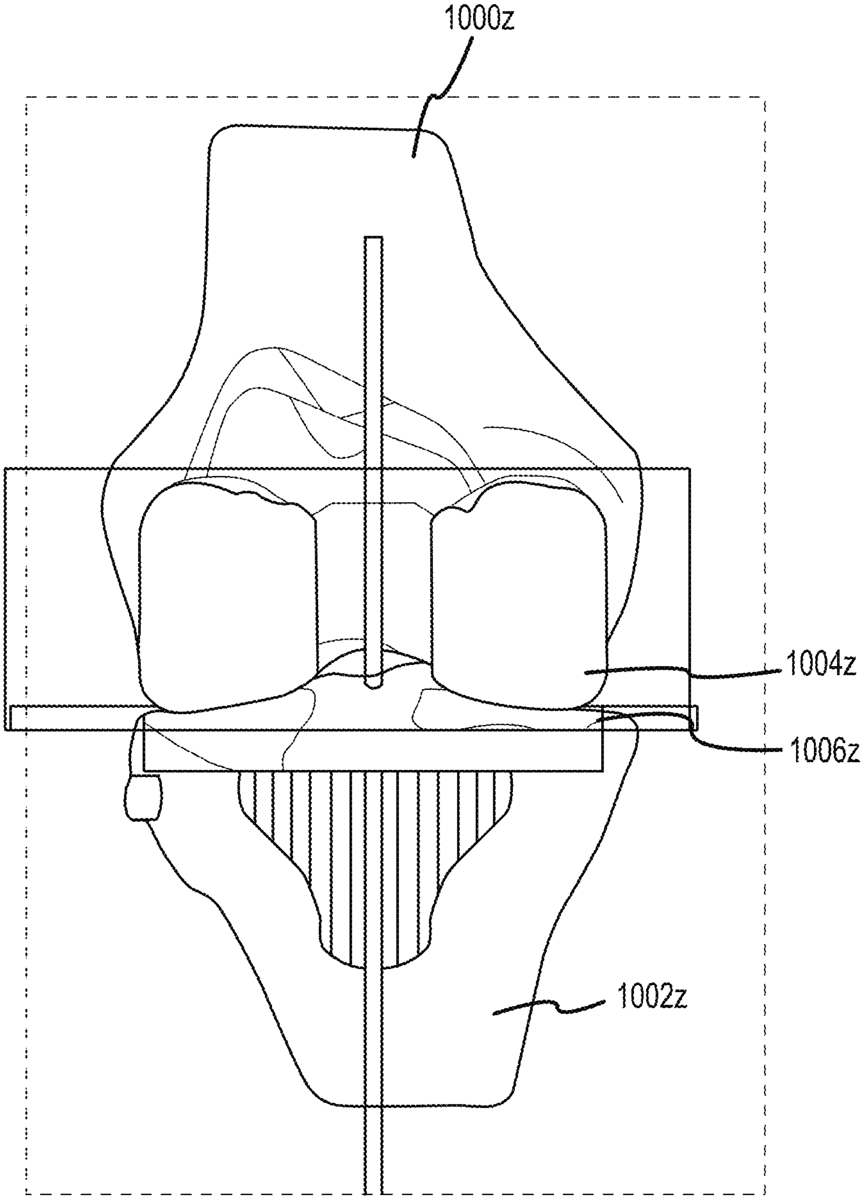
Figure 81F:
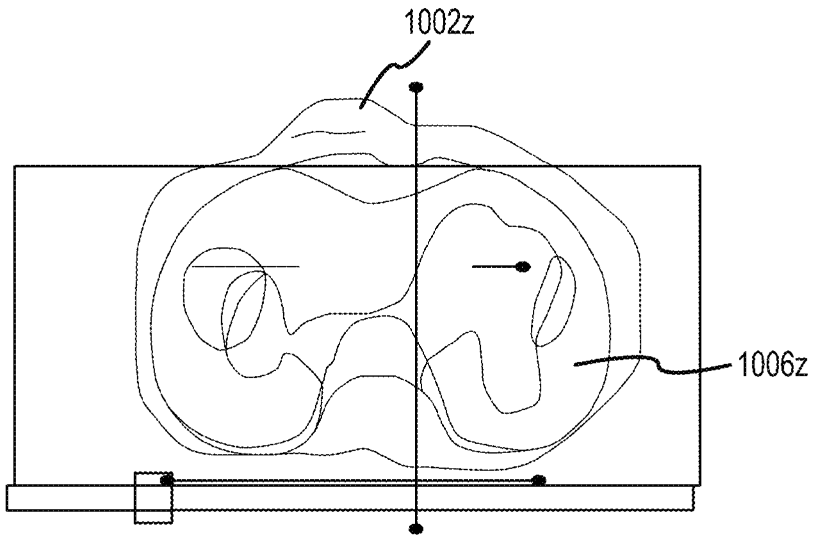
Figure 81G:
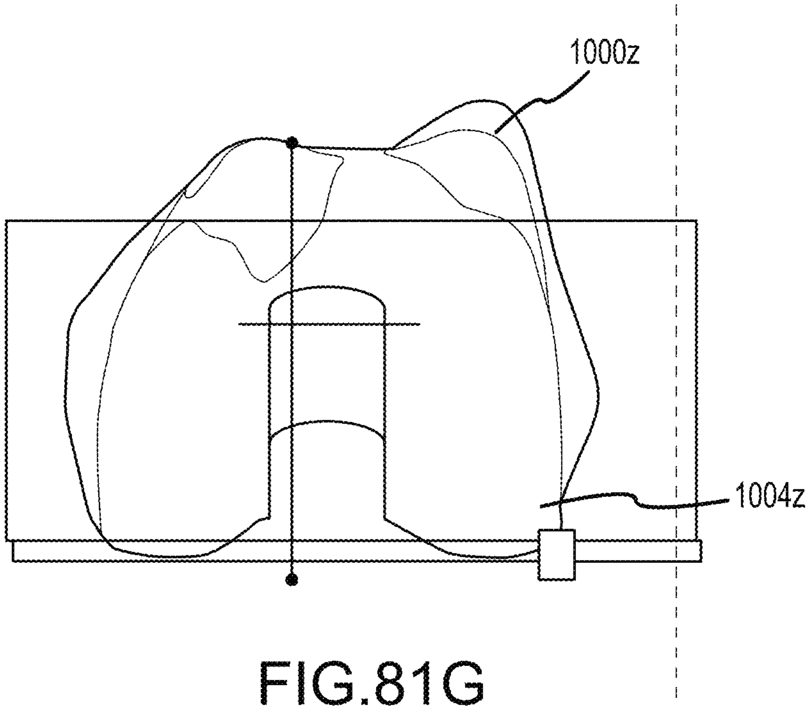

FIGS. 81E-81G are various views of the 2D implant models superimposed on the 2D bone models.

Figure 82A:
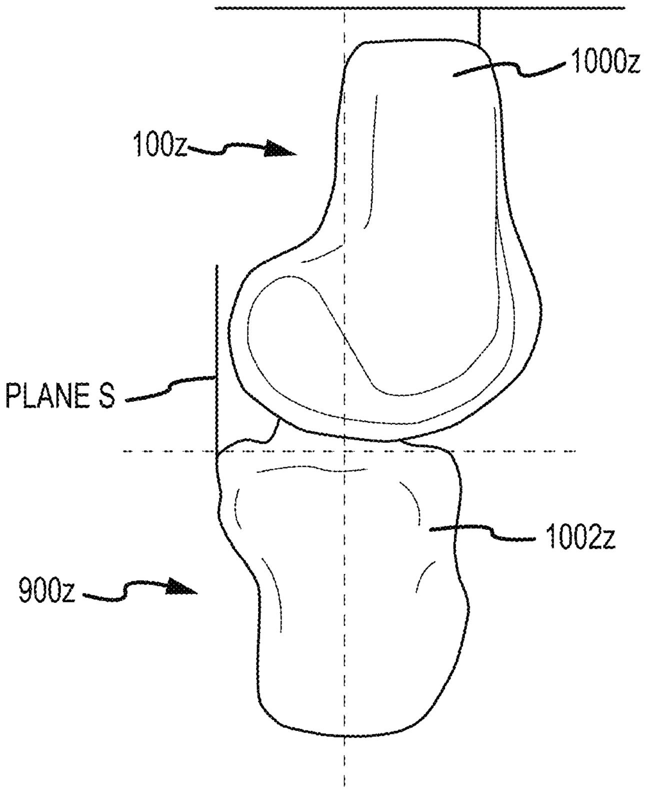

FIG. 82A is a medial view of the 3D bone models.

Figure 82B:
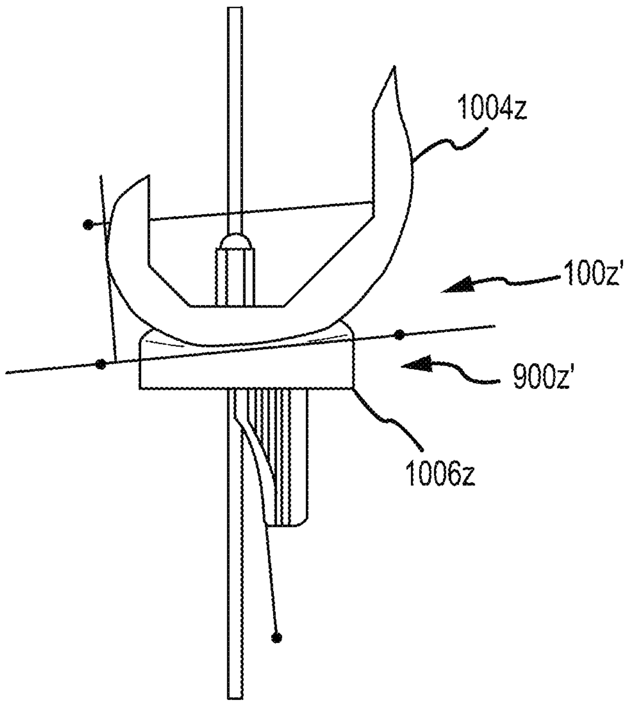

FIG. 82B is a medial view of the 3D implant models

Figure 82C:
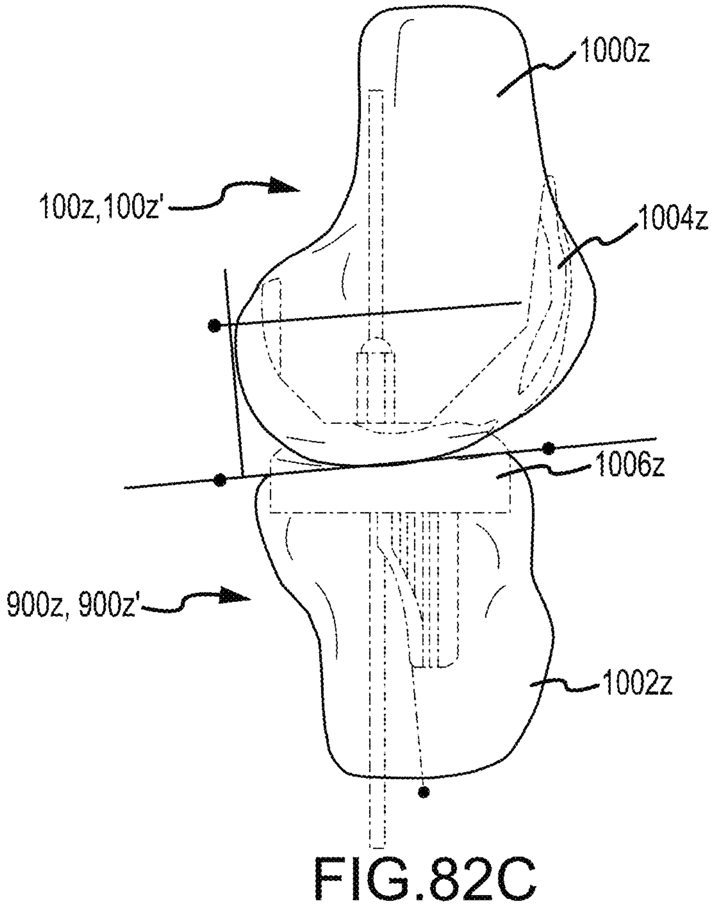

FIG. 82C is a medial view of the 3D implant models superimposed on the 3D bone models.

DETAILED DESCRIPTION

Disclosed herein are customized arthroplasty jigs 2 and systems 4 for, and methods of, producing such jigs 2. The jigs 2 are customized to fit specific bone surfaces of specific patients. Depending on the embodiment and to a greater or lesser extent, the jigs 2 are automatically planned and generated and may be similar to those disclosed in these three U.S. patent applications: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. patent applications are incorporated by reference in their entireties into this Detailed Description.

As an overview, Section I. of the present disclosure provides a description of systems and methods of manufacturing custom arthroplasty cutting guides. Section II. of the present disclosure provides an overview of exemplary segmentation processes performed on medical images, and the generation of bone models representing bones of a joint in a deteriorated state. Section III. of the present disclosure describes an overestimation process where certain areas of the bone in the medical images are identified for generating mating jig surfaces, and certain areas of the bone in the medical images are identified as non-mating areas between a jig and the bone surface. And Section IV. of the present disclosure provides an overview of the pre-operative surgical planning process that may take place on the patient's image data.

Figure 1A:
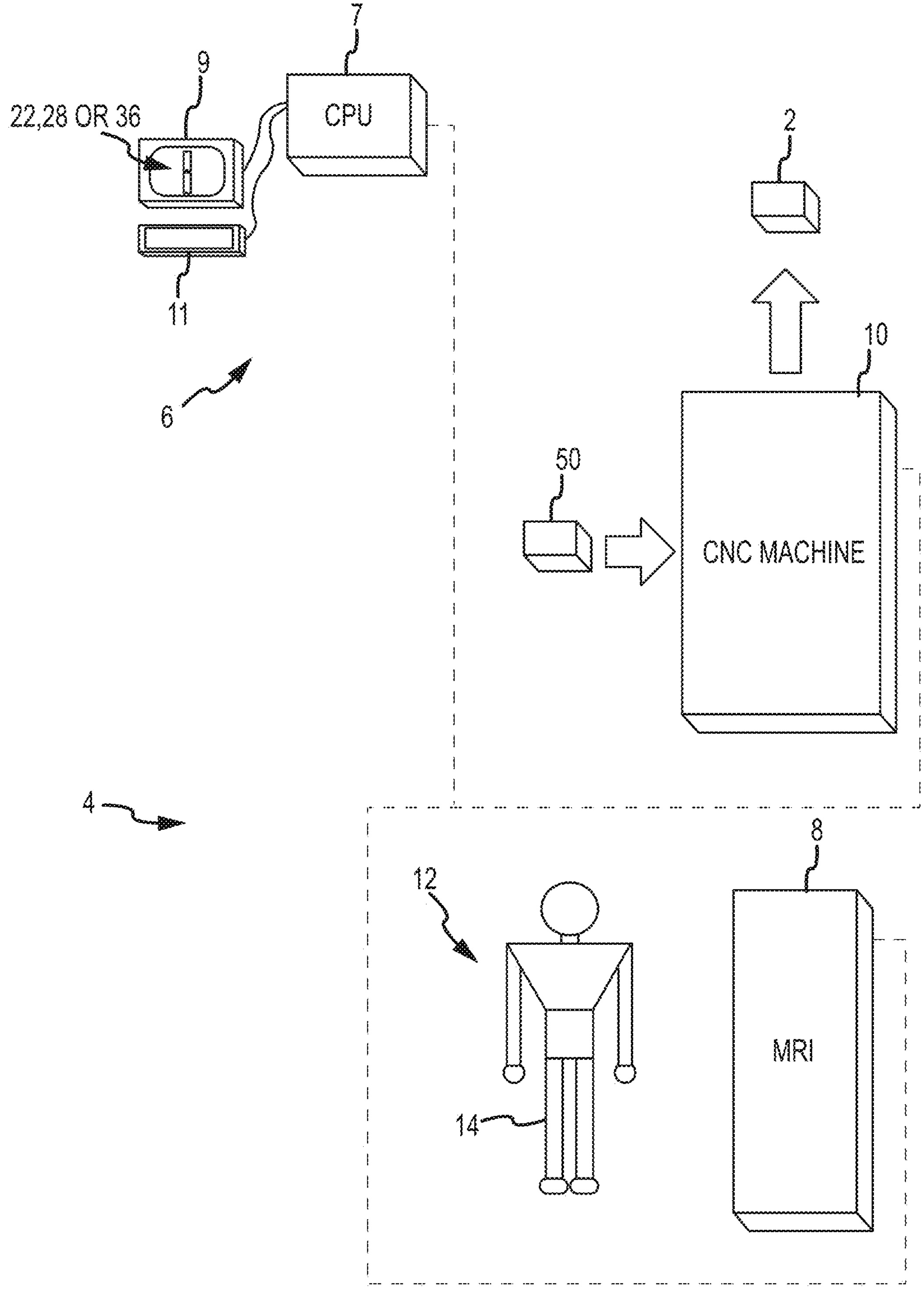
FIG. 1A is a schematic diagram of a system for employing the automated jig production method disclosed herein.

I. Overview of System and Method for Manufacturing Customized Arthroplasty Cutting Jigs For an overview discussion of the systems 4 for, and methods of, producing the customized arthroplasty jigs 2, reference is made to FIGS. 1A-1E. FIG. 1A is a schematic diagram of a system 4 for employing the automated jig production method disclosed herein. FIGS. 1B-1E are flow chart diagrams outlining the jig production method disclosed herein. The following overview discussion can be broken down into three sections.

The first section, which is discussed with respect to FIG. 1A and [blocks 100-125] of FIGS. 1B-1E, pertains to an example method of determining, in a three-dimensional ("3D") computer model environment, saw cut and drill hole locations 30, 32 relative to 3D computer models that are termed restored bone models 28 (also referenced as "planning models" throughout this submission.) In some embodiments, the resulting "saw cut and drill hole data" 44 is referenced to the restored bone models 28 to provide saw cuts and drill holes that will allow arthroplasty implants to restore the patient's joint to its pre-degenerated state. In other words, in some embodiments, the patient's joint may be restored to its natural alignment, whether valgus, varus or neutral.

While many of the embodiments disclosed herein are discussed with respect to allowing the arthroplasty implants to restore the patient's joint to its pre-degenerated or natural alignment state, many of the concepts disclosed herein may be applied to embodiments wherein the arthroplasty implants restore the patient's joint to a zero mechanical axis alignment such that the patient's knee joint ends up being neutral, regardless of whether the patient's predegenerated condition was varus, valgus or neutral. For example, as disclosed in U.S. patent application Ser. No. 12/760,388 to Park et al., titled "Preoperatively Planning An Arthroplasty Procedure And Generating A Corresponding Patient Specific Arthroplasty Resection Guide", filed Apr. 14, 2010, and incorporated by reference into this Detailed Description in its entirety, the system 4 for producing the customized arthroplasty jigs 2 may be such that the system initially generates the preoperative planning ("POP") associated with the jig in the context of the POP resulting in the patient's knee being restored to its natural alignment. Such a natural alignment POP is provided to the physician, and the physician determines if the POP should result in (1) natural alignment, (2) mechanical alignment, or (3) something between (1) and (2). The POP is then adjusted according to the physician's determination, the resulting jig 2 being configured such that the arthroplasty implants will restore the patient's joint to (1), (2) or (3), depending on whether the physician elected (1), (2) or (3), respectively. Accordingly, this disclosure should not be limited to methods resulting in natural alignment only, but should, where appropriate, be considered as applicable to methods resulting in natural alignment, zero mechanical axis alignment or an alignment somewhere between natural and zero mechanical axis alignment.

The second section, which is discussed with respect to FIG. 1A and [blocks 100-105 and 130-145] of FIGS. 1B-1E, pertains to an example method of importing into 3D computer generated jig models 38 3D computer generated surface models 40 of arthroplasty target areas 42 of 3D computer generated arthritic models 36 of the patient's joint bones. The resulting "jig data" 46 is used to produce a jig customized to matingly receive the arthroplasty target areas of the respective bones of the patient's joint.

Figure 1B:
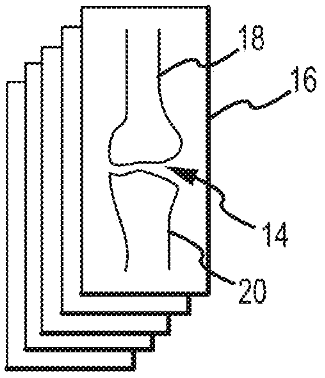
Figure 1B:
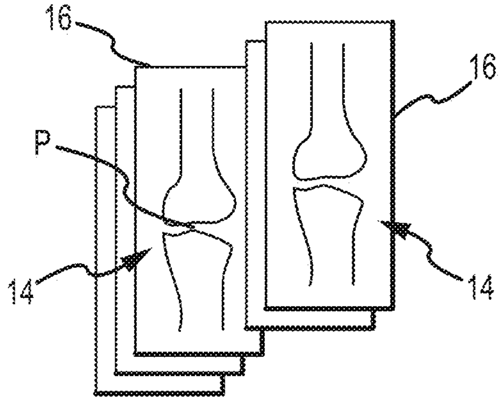
Figure 1C:
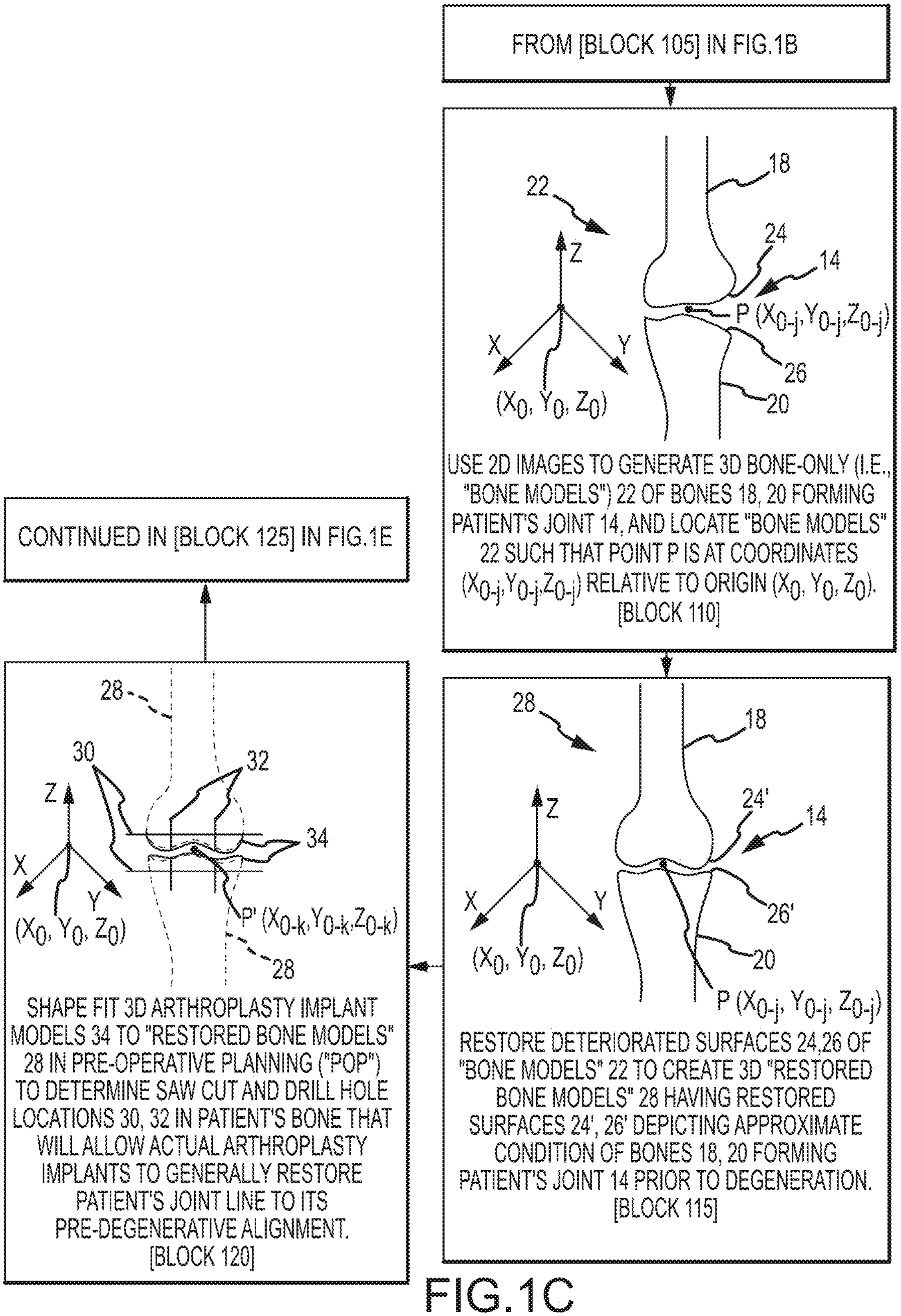
Figure 1E:
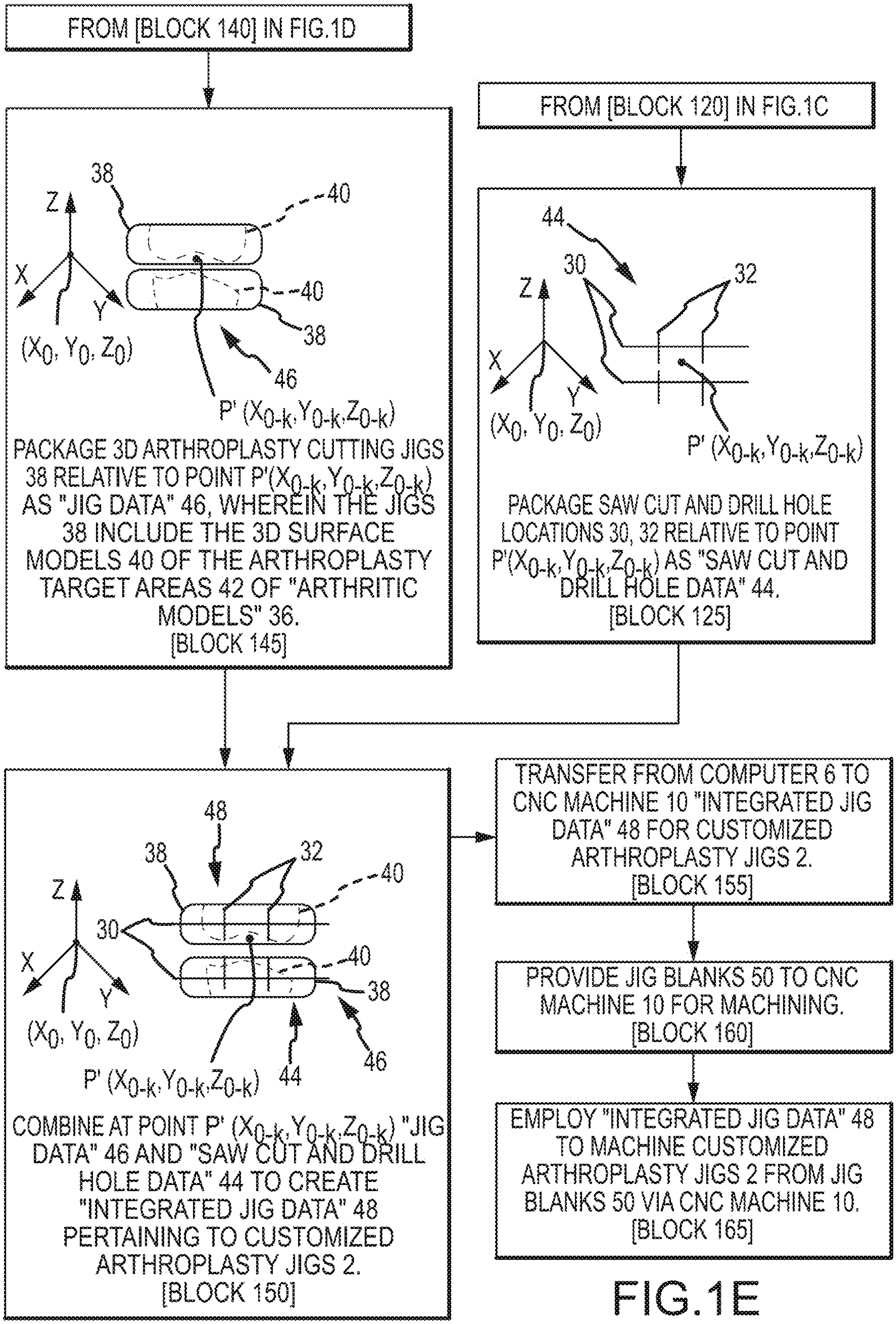

The third section, which is discussed with respect to FIG. 1A and [blocks 150-165] of FIG. 1E, pertains to a method of combining or integrating the "saw cut and drill hole data" 44 with the "jig data" 46 to result in "integrated jig data" 48. The "integrated jig data" 48 is provided to the CNC machine 10 for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to generally restore the patient's joint line to its pre-degenerated state.

As shown in FIG. 1A, the system 4 includes one or more computers 6 having a CPU 7, a monitor or screen 9 and an operator interface controls 11. The computer 6 is linked to a medical imaging system 8, such as a CT or MRI machine 8, and a computer controlled machining system 10, such as a CNC milling machine 10.

In another embodiment, rather than using a single computer for the whole process, multiple computers can perform separate steps of the overall process, with each respective step managed by a respective technician skilled in that particular aspect of the overall process. The data generated in one process step on one computer can be then transferred for the next process step to another computer, for instance via a network connection.

As indicated in FIG. 1A, a patient 12 has a joint 14 (e.g., a knee, elbow, ankle, wrist, hip, shoulder, skull/vertebrae or vertebrae/vertebrae interface, etc.) to be replaced. The patient 12 has the joint 14 scanned in the imaging machine 8. The imaging machine 8 makes a plurality of scans of the joint 14, wherein each scan pertains to a thin slice of the joint 14.

As can be understood from FIG. 1B, the plurality of scans is used to generate a plurality of two-dimensional ("2D") images 16 of the joint 14 [block 100]. Where, for example, the joint 14 is a knee 14, the 2D images will be of the femur 18 and tibia 20. The imaging may be performed via CT or MRI. In one embodiment employing MRI, the imaging process may be as disclosed in U.S. patent application Ser. No. 11/946,002 to Park, which is entitled "Generating MRI Images Usable For The Creation Of 3D Bone Models Employed To Make Customized Arthroplasty Jigs," was filed Nov. 27, 2007 and is incorporated by reference in its entirety into this Detailed Description.

As can be understood from FIG. 1A, the 2D images are sent to the computer 6 for creating computer generated 3D models. As indicated in FIG. 1B, in one embodiment, point P is identified in the 2D images 16 [block 105]. In one embodiment, as indicated in [block 105] of FIG. 1A, point P may be at the approximate medial-lateral and anterior-posterior center of the patient's joint 14. In other embodiments, point P may be at any other location in the 2D images 16, including anywhere on, near or away from the bones 18, 20 or the joint 14 formed by the bones 18, 20.

As described later in this overview, point P may be used to locate the computer generated 3D models 22, 28, 36 created from the 2D images 16 and to integrate information generated via the 3D models. Depending on the embodiment, point P, which serves as a position and/or orientation reference, may be a single point, two points, three points, a point plus a plane, a vector, etc., so long as the reference P can be used to position and/or orient the 3D models 22, 28, 36 generated via the 2D images 16.

As discussed in detail below, the 2D images 16 are segmented along bone boundaries to create bone contour lines. Also, the 2D images 16 are segmented along bone and cartilage boundaries to create bone and cartilage lines.

As shown in FIG. 1C, the segmented 2D images 16 (i.e., bone contour lines) are employed to create computer generated 3D bone-only (i.e., "bone models") 22 of the bones 18, 20 forming the patient's joint 14 [block 110]. The bone models 22 are located such that point P is at coordinates ($X_P$, $Y_P$, $Z_P$) relative to an origin ($X_0$, $Y_0$, $Z_0$) of an X-Y-Z coordinate system [block 110]. The bone models 22 depict the bones 18, 20 in the present deteriorated condition with their respective degenerated joint surfaces 24, 26, which may be a result of osteoarthritis, injury, a combination thereof, etc.

Computer programs for creating the 3D computer generated bone models 22 from the segmented 2D images 16 (i.e., bone contour lines) include: Analyze from AnalyzeDirect, Inc., Overland Park, KS; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, MI; and Paraview available at www.paraview.org. Further, some embodiments may use customized software such as OMSegmentation (renamed "PerForm" in later versions), developed by OtisMed, Inc. The OMSegmentation software may extensively use "ITK" and/or "VTK" (Visualization Toolkit from Kitware, Inc, available at www.vtk.org.) Some embodiments may include using a prototype of OMSegmentation, and as such may utilize InsightSNAP software.

As indicated in FIG. 1C, the 3D computer generated bone models 22 are utilized to create 3D computer generated "restored bone models" or "planning bone models" 28 wherein the degenerated surfaces 24, 26 are modified or restored to approximately their respective conditions prior to degeneration [block 115]. Thus, the bones 18, 20 of the restored bone models 28 are reflected in approximately their condition prior to degeneration. The restored bone models 28 are located such that point P is at coordinates ($X_P$, $Y_P$, $Z_P$) relative to the origin ($X_0$, $Y_0$, $Z_0$). Thus, the restored bone models 28 share the same orientation and positioning relative to the origin ($X_0$, $Y_0$, $Z_0$) as the bone models 22.

In one embodiment, the restored bone models 28 are manually created from the bone models 22 by a person sitting in front of a computer 6 and visually observing the bone models 22 and their degenerated surfaces 24, 26 as 3D computer models on a computer screen 9. The person visually observes the degenerated surfaces 24, 26 to determine how and to what extent the degenerated surfaces 24, 26 surfaces on the 3D computer bone models 22 need to be modified to restore them to their pre-degenerated condition. By interacting with the computer controls 11, the person then manually manipulates the 3D degenerated surfaces 24, 26 via the 3D modeling computer program to restore the surfaces 24, 26 to a state the person believes to represent the pre-degenerated condition. The result of this manual restoration process is the computer generated 3D restored bone models 28, wherein the surfaces 24', 26' are indicated in a non-degenerated state.

In one embodiment, the bone restoration process is generally or completely automated. In other words, a computer program may analyze the bone models 22 and their degenerated surfaces 24, 26 to determine how and to what extent the degenerated surfaces 24, 26 surfaces on the 3D computer bone models 22 need to be modified to restore them to their pre-degenerated condition. The computer program then manipulates the 3D degenerated surfaces 24, 26 to restore the surfaces 24, 26 to a state intended to represent the pre-degenerated condition. The result of this automated restoration process is the computer generated 3D restored bone models 28, wherein the surfaces 24', 26' are indicated in a non-degenerated state. For more detail regarding a generally or completely automated system for the bone restoration process, see U.S. patent application Ser. No. 12/111,924 to Park, which is titled "Generation of a Computerized Bone Model Representative of a Pre-Degenerated State and Usable in the Design and Manufacture of Arthroplasty Devices", was filed Apr. 29, 2008, and is incorporated by reference in its entirety into this Detailed Description.

As depicted in FIG. 1C, the restored bone models 28 are employed in a pre-operative planning ("POP") procedure to determine saw cut locations 30 and drill hole locations 32 in the patient's bones that will allow the arthroplasty joint implants to generally restore the patient's joint line to it pre-degenerative alignment [block 120].

In one embodiment, the POP procedure is a manual process, wherein computer generated 3D implant models 34 (e.g., femur and tibia implants in the context of the joint being a knee) and restored bone models 28 are manually manipulated relative to each other by a person sitting in front of a computer 6 and visually observing the implant models 34 and restored bone models 28 on the computer screen 9 and manipulating the models 28, 34 via the computer controls 11. By superimposing the implant models 34 over the restored bone models 28, or vice versa, the joint surfaces of the implant models 34 can be aligned or caused to correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28.

In one embodiment, the POP process is generally or completely automated. For example, a computer program may manipulate computer generated 3D implant models 34 (e.g., femur and tibia implants in the context of the joint being a knee) and restored bone models or planning bone models 28 relative to each other to determine the saw cut and drill hole locations 30, 32 relative to the restored bone models 28. The implant models 34 may be superimposed over the restored bone models 28, or vice versa. In one embodiment, the implant models 34 are located at point P' ($X_{P'}$, $Y_{P'}$, $Z_{P'}$) relative to the origin ($X_0$, $Y_0$, $Z_0$), and the restored bone models 28 are located at point P ($X_P$, $Y_P$, $Z_P$). To cause the joint surfaces of the models 28, 34 to correspond, the computer program may move the restored bone models 28 from point P ($X_P$, $Y_P$, $Z_P$) to point P' ($X_{P'}$, $Y_{P'}$, $Z_{P'}$), or vice versa. Once the joint surfaces of the models 28, 34 are in close proximity, the joint surfaces of the implant models 34 may be shape-matched to align or correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28. For more detail regarding a generally or completely automated system for the POP process, see U.S. patent application Ser. No. 12/563,809 to Park, which is titled Arthroplasty System and Related Methods, was filed Sep. 21, 2009, and is incorporated by reference in its entirety into this Detailed Description.

While the preceding discussion regarding the POP process is given in the context of the POP process employing the restored bone models as computer generated 3D bone models, in other embodiments, the POP process may take place without having to employ the 3D restored bone models, but instead taking placing as a series of 2D operations. For more detail regarding a generally or completely automated system for the POP process wherein the POP process does not employ the 3D restored bone models, but instead utilizes a series of 2D operations, see U.S. patent application Ser. No. 12/546,545 to Park, which is titled Arthroplasty System and Related Methods, was filed Aug. 24, 2009, and is incorporated by reference in its entirety into this Detailed Description.

As indicated in FIG. 1E, in one embodiment, the data 44 regarding the saw cut and drill hole locations 30, 32 relative to point P' ($X_{P'}$, $Y_{P'}$, $Z_{P'}$) is packaged or consolidated as the "saw cut and drill hole data" 44 [block 145]. The "saw cut and drill hole data" 44 is then used as discussed below with respect to [block 150] in FIG. 1E.

As can be understood from FIG. 1D, the 2D images 16 employed to generate the bone models 22 discussed above with respect to [block 110] of FIG. 1C are also segmented along bone and cartilage boundaries to form bone and cartilage contour lines that are used to create computer generated 3D bone and cartilage models (i.e., "arthritic models") 36 of the bones 18, 20 forming the patient's joint 14 [block 130]. Like the above-discussed bone models 22, the arthritic models 36 are located such that point P is at coordinates ($X_P$, $Y_P$, $Z_P$) relative to the origin ($X_0$, $Y_0$, $Z_0$) of the X-Y-Z axis [block 130]. Thus, the bone and arthritic models 22, 36 share the same location and orientation relative to the origin ($X_0$, $Y_0$, $Z_0$). This position/orientation relationship is generally maintained throughout the process discussed with respect to FIGS. 1B-1E. Accordingly, movements relative to the origin ($X_0$, $Y_0$, $Z_0$) of the bone models 22 and the various descendants thereof (i.e., the restored bone models 28, bone cut locations 30 and drill hole locations 32) are also applied to the arthritic models 36 and the various descendants thereof (i.e., the jig models 38). Maintaining the position/orientation relationship between the bone models 22 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2.

Computer programs for creating the 3D computer generated arthritic models 36 from the segmented 2D images 16 (i.e., bone and cartilage contour lines) include: Analyze from AnalyzeDirect, Inc., Overland Park, KS; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, MI; and Paraview available at www.paraview.org. Some embodiments may use customized software such as OMSegmentation (renamed "PerForm" in later versions), developed by OtisMed, Inc. The OMSegmentation software may extensively use "ITK" and/or "VTK" (Visualization Toolkit from Kitware, Inc, available at www.vtk.org.). Also, some embodiments may include using a prototype of OMSegmentation, and as such may utilize InsightSNAP software.

Similar to the bone models 22, the arthritic models 36 depict the bones 18, 20 in the present deteriorated condition with their respective degenerated joint surfaces 24, 26, which may be a result of osteoarthritis, injury, a combination thereof, etc. However, unlike the bone models 22, the arthritic models 36 are not bone-only models, but include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 1D and already mentioned above, to coordinate the positions/orientations of the bone and arthritic models 36, 36 and their respective descendants, any movement of the restored bone models 28 from point P to point P' is tracked to cause a generally identical displacement for the "arthritic models" 36 [block 135].

As depicted in FIG. 1D, computer generated 3D surface models 40 of the arthroplasty target areas 42 of the arthritic models 36 are imported into computer generated 3D arthroplasty jig models 38 [block 140]. Thus, the jig models 38 are configured or indexed to matingly receive the arthroplasty target areas 42 of the arthritic models 36. Jigs 2 manufactured to match such jig models 38 will then matingly receive the arthroplasty target areas of the actual joint bones during the arthroplasty surgical procedure.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly receive the arthroplasty target areas 42 of the arthritic models 36. Point P' ($X_{P'}$, $Y_{P'}$, $Z_{P'}$) can also be imported into the jig models 38, resulting in jig models 38 positioned and oriented relative to point P' ($X_{P'}$, $Y_{P'}$, $Z_{P'}$) to allow their integration with the bone cut and drill hole data 44 of [block 125].

In one embodiment, the procedure for indexing the jig models 38 to the arthroplasty target areas 42 is generally or completely automated, as disclosed in U.S. patent application Ser. No. 11/959,344 to Park, which is entitled System and Method for Manufacturing Arthroplasty Jigs, was filed Dec. 18, 2007 and is incorporated by reference in its entirety into this Detailed Description. For example, a computer program may create 3D computer generated surface models 40 of the arthroplasty target areas 42 of the arthritic models 36. The computer program may then import the surface models 40 and point P' ($X_{P'}$, $Y_{P'}$, $Z_{P'}$) into the jig models 38, resulting in the jig models 38 being indexed to matingly receive the arthroplasty target areas 42 of the arthritic models 36. The resulting jig models 38 are also positioned and oriented relative to point P' ($X_{P'}$, $Y_{P'}$, $Z_{P'}$) to allow their integration with the bone cut and drill hole data 44 of [block125].

In one embodiment, the arthritic models 36 may be 3D volumetric models as generated from a closed-loop process. In other embodiments, the arthritic models 36 may be 3D surface models as generated from an open-loop process.

As indicated in FIG. 1E, in one embodiment, the data regarding the jig models 38 and surface models 40 relative to point P' ($X_{P'}$, $Y_{P'}$, $Z_{P'}$) is packaged or consolidated as the "jig data" 46 [block 145]. The "jig data" 46 is then used as discussed below with respect to [block 150] in FIG. 1E.

As can be understood from FIG. 1E, the “saw cut and drill hole data” 44 is integrated with the “jig data” 46 to result in the “integrated jig data” 48 [block 150]. As explained above, since the “saw cut and drill hole data” 44, “jig data” 46 and their various ancestors (e.g., models 22, 28, 36, 38) are matched to each other for position and orientation relative to point P and P', the “saw cut and drill hole data” 44 is properly positioned and oriented relative to the “jig data” 46 for proper integration into the “jig data” 46. The resulting “integrated jig data” 48, when provided to the CNC machine 10, results in jigs 2: (1) configured to matingly receive the arthroplasty target areas of the patient’s bones; and (2) having cut slots and drill holes that facilitate preparing the arthroplasty target areas in a manner that allows the arthroplasty joint implants to generally restore the patient’s joint line to its pre-degenerated state.

As can be understood from FIGS. 1A and 1E, the “integrated jig data” 44 is transferred from the computer 6 to the CNC machine 10 [block 155]. Jig blanks 50 are provided to the CNC machine 10 [block 160], and the CNC machine 10 employs the “integrated jig data” to machine the arthroplasty jigs 2 from the jig blanks 50.

Figure 1F:
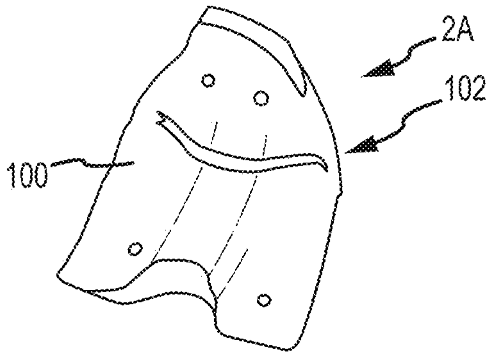
FIGS. 1F and 1G are, respectively, bottom and top perspective views of an example customized arthroplasty femur jig.
Figure 1G:
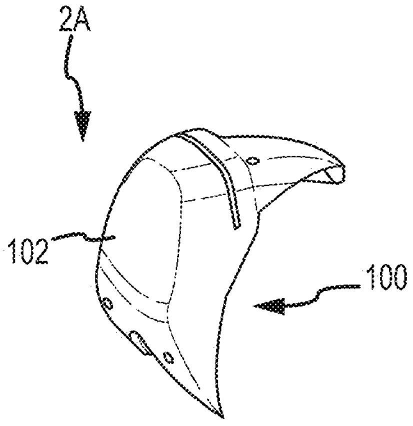
Figure 1H:
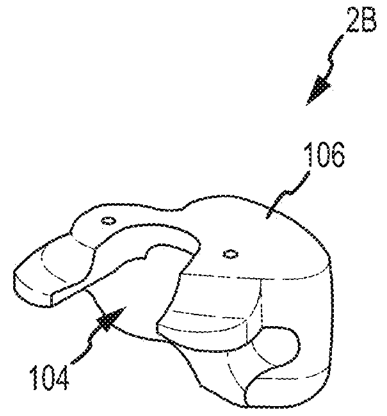
FIGS. 1H and 1I are, respectively, bottom and top perspective views of an example customized arthroplasty tibia jig.
Figure 1I:
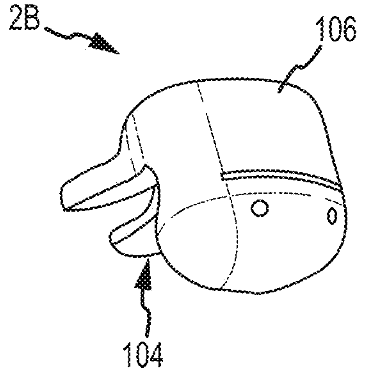

For a discussion of example customized arthroplasty cutting jigs 2 capable of being manufactured via the above-discussed process, reference is made to FIGS. 1F-1I. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 1F-1I are for total knee replacement (“TKR”) or partial knee replacement (“PKR”) procedures. Thus, FIGS. 1F and 1G are, respectively, bottom and top perspective views of an example customized arthroplasty femur jig 2A, and FIGS. 1H and 1I are, respectively, bottom and top perspective views of an example customized arthroplasty tibia jig 2B.

As indicated in FIGS. 1F and 1G, a femur arthroplasty jig 2A may include an interior side or portion 100 and an exterior side or portion 102. When the femur cutting jig 2A is used in a TKR or PKR procedure, the interior side or portion 100 faces and matingly receives the arthroplasty target area 42 of the femur lower end, and the exterior side or portion 102 is on the opposite side of the femur cutting jig 2A from the interior portion 100.

The interior portion 100 of the femur jig 2A is configured to match the surface features of the damaged lower end (i.e., the arthroplasty target area 42) of the patient’s femur 18. Thus, when the target area 42 is received in the interior portion 100 of the femur jig 2A during the TKR or PKR surgery, the surfaces of the target area 42 and the interior portion 100 match.

The surface of the interior portion 100 of the femur cutting jig 2A is machined or otherwise formed into a selected femur jig blank 50A and is based or defined off of a 3D surface model 40 of a target area 42 of the damaged lower end or target area 42 of the patient’s femur 18.

As indicated in FIGS. 1H and 1I, a tibia arthroplasty jig 2B may include an interior side or portion 104 and an exterior side or portion 106. When the tibia cutting jig 2B is used in a TKR or PKR procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient’s tibia 20. Thus, when the target area 42 is received in the interior portion 104 of the tibia jig 2B during the TKR or PKR surgery, the surfaces of the target area 42 and the interior portion 104 match.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient’s tibia 20.

II. Overview of Segmentation Process

A. Automatic Segmentation of Scanner Modality Image Data to Generate 3D Surface Model of a Patient’s Bone In one embodiment as mentioned above, the 2D images 16 of the patient’s joint 14 as generated via the imaging system 8 (see FIG. 1A and [block 100] of FIG. 1B) are segmented or, in other words, analyzed to identify the contour lines of the bones and/or cartilage surfaces that are of significance with respect to generating 3D models 22, 36, as discussed above with respect to [blocks 110 and 130] of FIGS. 1C and 1D. Specifically, a variety of image segmentation processes may occur with respect to the 2D images 16 and the data associated with such 2D images 16 to identify contour lines that are then compiled into 3D bone models, such as bone models 22 and arthritic models 36. A variety of processes and methods for performing image segmentation are disclosed in the remainder of this Detailed Description.

Figure 2A:
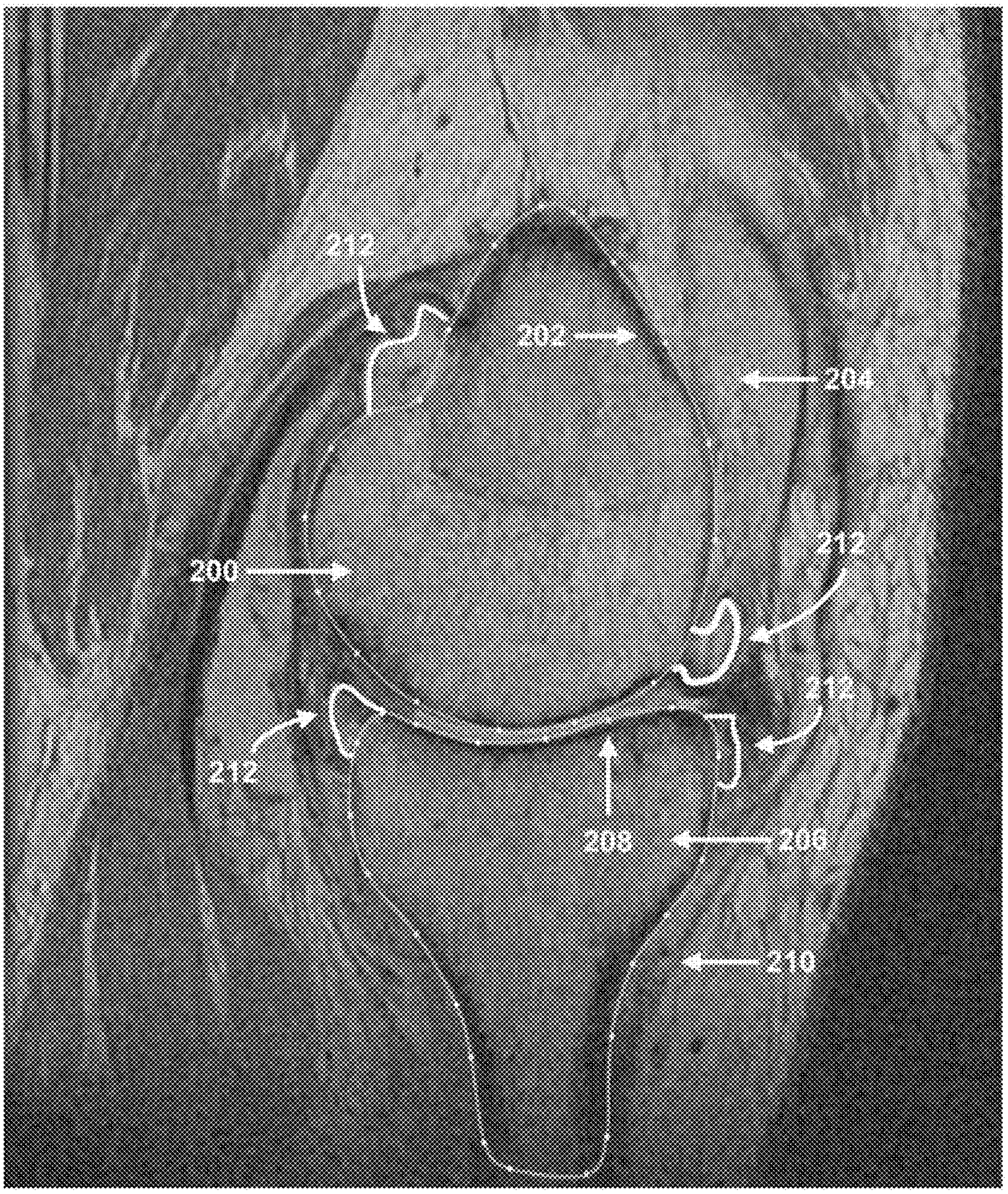
FIG. 2A is a sagittal plane image slice depicting a femur and tibia and neighboring tissue regions with similar image intensity.

The imager 8 typically generates a plurality of image slices 16 via repetitive imaging operations. Depending on whether the imager 8 is a MRI or CT imager, each image slice will be a MRI or CT slice. As shown in FIG. 2A, the image slice may depict the cancellous bone 200, the cortical bone 202 surrounding the cancellous bone, and the articular cartilage lining portions of the cortical bone 202 of an object of interest of a joint, e.g., a femur 204 in a patient’s knee joint 14. The image may further depict the cancellous bone 206, the cortical bone 208 of another object of interest in the joint, e.g., a tibia 210 of the knee joint 14. In one embodiment, each image slice 16 may be a two-millimeter 2D image slice.

One embodiment may automatically segment one or more features of interest (e.g., bones) present in MRI or CT scans of a patient joint, e.g., knee, hip, elbow, etc. A typical scan of a knee joint may represent approximately a 100-millimeter by 150-millimeter by 150-millimeter volume of the joint and may include about 40 to 80 slices taken in sagittal planes. A sagittal plane is an imaginary plane that travels from the top to the bottom of the object (e.g., the human body), dividing it into medial and lateral portions. It is to be appreciated that a large inter-slice spacing may result in voxels (volume elements) with aspect ratios of about one to seven between the resolution in the sagittal plane (e.g., the y z plane) and the resolution along the x axis (i.e., each scan slice lies in the yz plane with a fixed value of x). For example, a two-millimeter slice that is 150-millimeters by 150-millimeters may be comprised of voxels that are approximately 0.3-millimeter by 0.3-millimeter by 2-millimeters (for a 512 by 512 image resolution in the sagittal plane).

In one embodiment, each slice may be a gray scale image with a resolution of 512 by 512 voxels where the voxel value represents the brightness (intensity) of the voxel. The intensity may be stored as a 16-bit integer resulting in an intensity range from 0 to 65,535, where 0 may represent black and 65,535 may represent white. The intensity of each voxel typically represents the average intensity of the voxel volume. Other embodiments may employ scans having higher or lower resolutions in the sagittal plane, different inter-slice spacing, or images where the intensity may be represented by a 24 bit vector (e.g., eight bits each for a red component, green component and blue component). Additionally, other embodiments may store intensity values as 32-bit signed integers or floating point values.

Figure 2B:
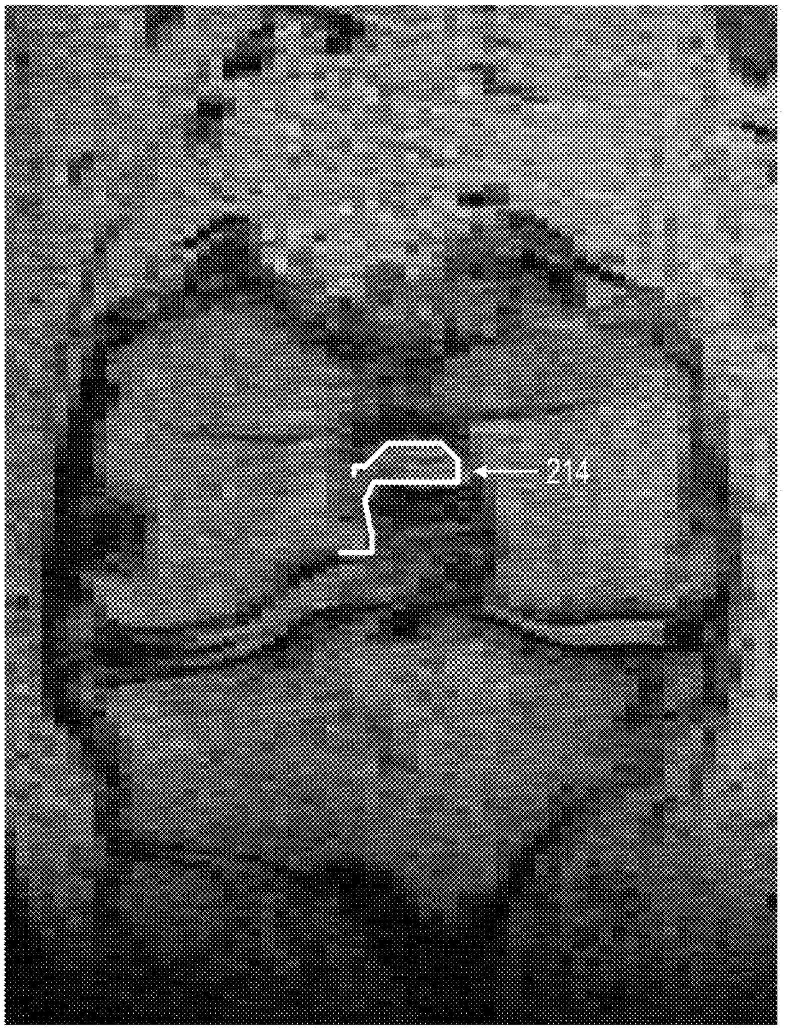
FIG. 2B is a sagittal plane image slice depicting a region extending into the slice from an adjacent image slice.
Figure 2C:
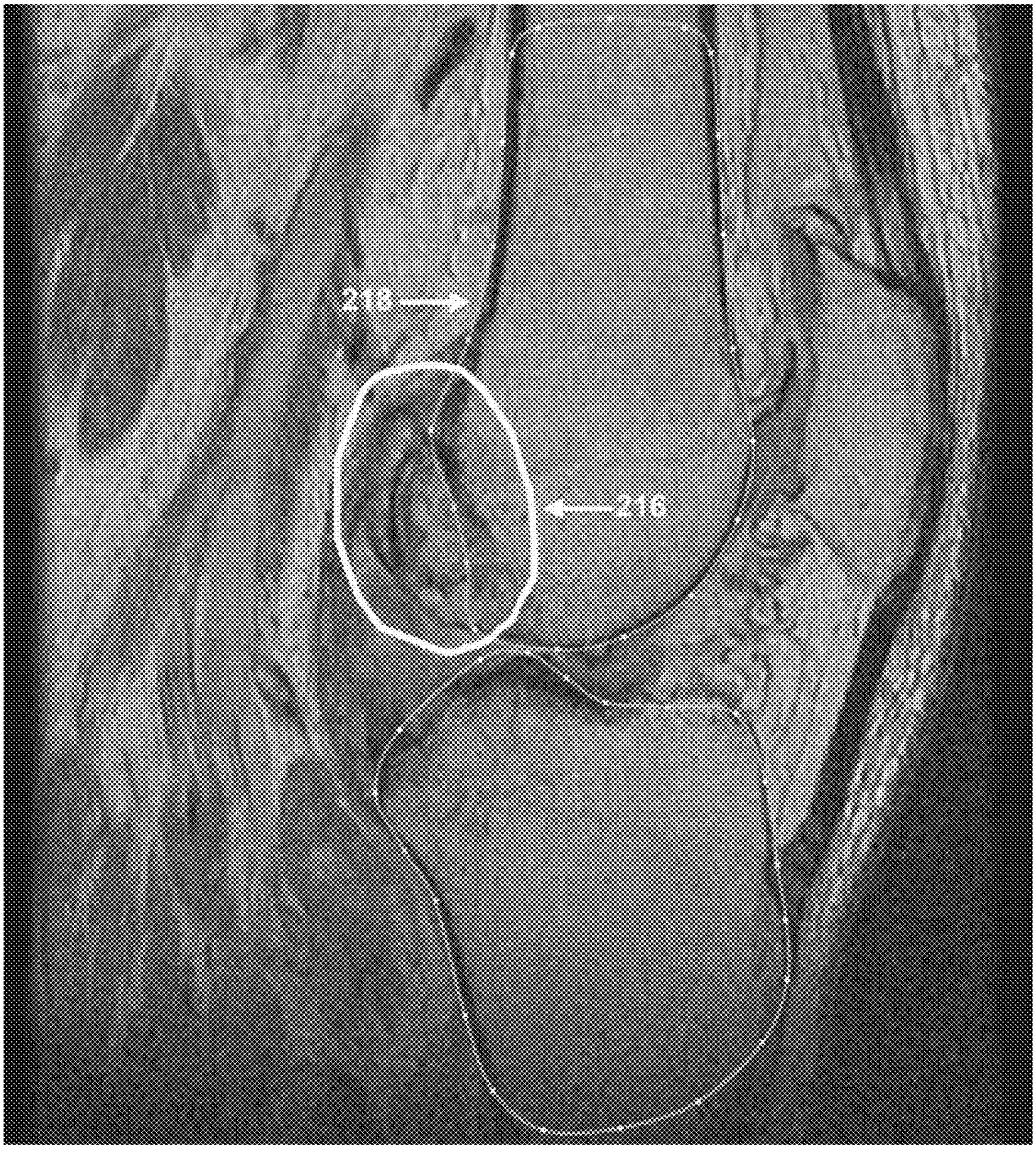
FIG. 2C is a sagittal plane image slice depicting a region of a femur that is approximately tangent to the image slice.

Typical MRI and CT scan data generally provide images where parts of a bone boundary of interest may be well defined while other parts of the bone boundary may be difficult to determine due to voxel volume averaging, the presence of osteophyte growth, the presence of tissue having similar image intensities in neighboring areas to the object to be segmented, amongst other things. Such poor definition of parts of the bone boundary in the images may cause traditional automated segmentation techniques to fail. For example, FIG. 2A depicts regions 212 within a slice where an object boundary may not be visible due to neighboring tissue having about the same intensity as the feature of interest. Depicted in FIG. 2B are regions 214 that may be extended into the slice from adjacent slices due to a high voxel aspect ratio. Depicted in FIG. 2C is a region 216 of the bone boundary 218 that may disappear or lose regularity when the bone boundary 218 is approximately tangent to the slice.

One embodiment may employ image segmentation techniques using a golden template to segment bone boundaries and provide improved segmentation results over traditional automated segmentation techniques. Such techniques may be used to segment an image when similarity between pixels within an object to be identified may not exist. That is, the pixels within a region to be segmented may not be similar with respect to some characteristic or computed property such as a color, intensity or texture that may be employed to associate similar pixels into regions. Instead, a spatial relationship of the object with respect to other objects may be used to identify the object of interest. In one embodiment, a 3D golden template of a feature of interest to be segmented may be used during the segmentation process to locate the target feature in a target scan. For example, when segmenting a scan of a knee joint, a typical 3D image of a known good femur (referred to as a golden femur template) may be used to locate and outline (i.e., segment) a femur in a target scan.

Generally, much of the tissues surrounding the cancellous and cortical matter of the bone to be segmented may vary from one MRI scan to another MRI scan. This may be due to disease and/or patient joint position (e.g., a patient may not be able to straighten the joint of interest because of pain). By using surrounding regions that have a stable connection with the bone (e.g., the grown golden and boundary golden regions of the template as described in more detail below), the registration may be improved. Additionally, use of these regions allows the bone geometry of interest to be captured during the segmentation rather than other features not of interest. Further, the segmentation takes advantage of the higher resolution of features of interest in certain directions of the scan data through the use of a combination of 2D and 3D techniques, that selectively increases the precision of the segmentation as described in more detail below with respect to refining the bone registration using an artificially generated image.

Figure 3A:
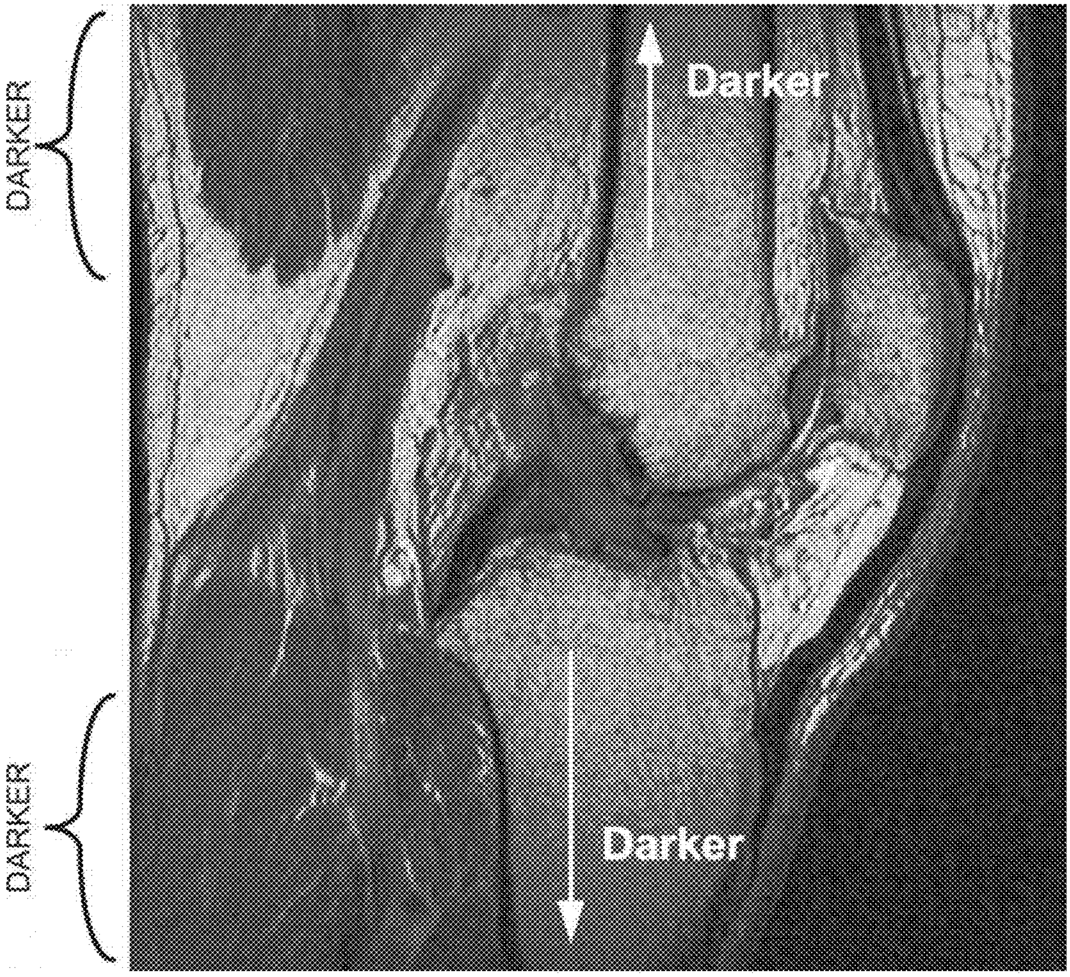
FIG. 3A is a sagittal plane image slice depicting an intensity gradient across the slice.
Figure 3B:
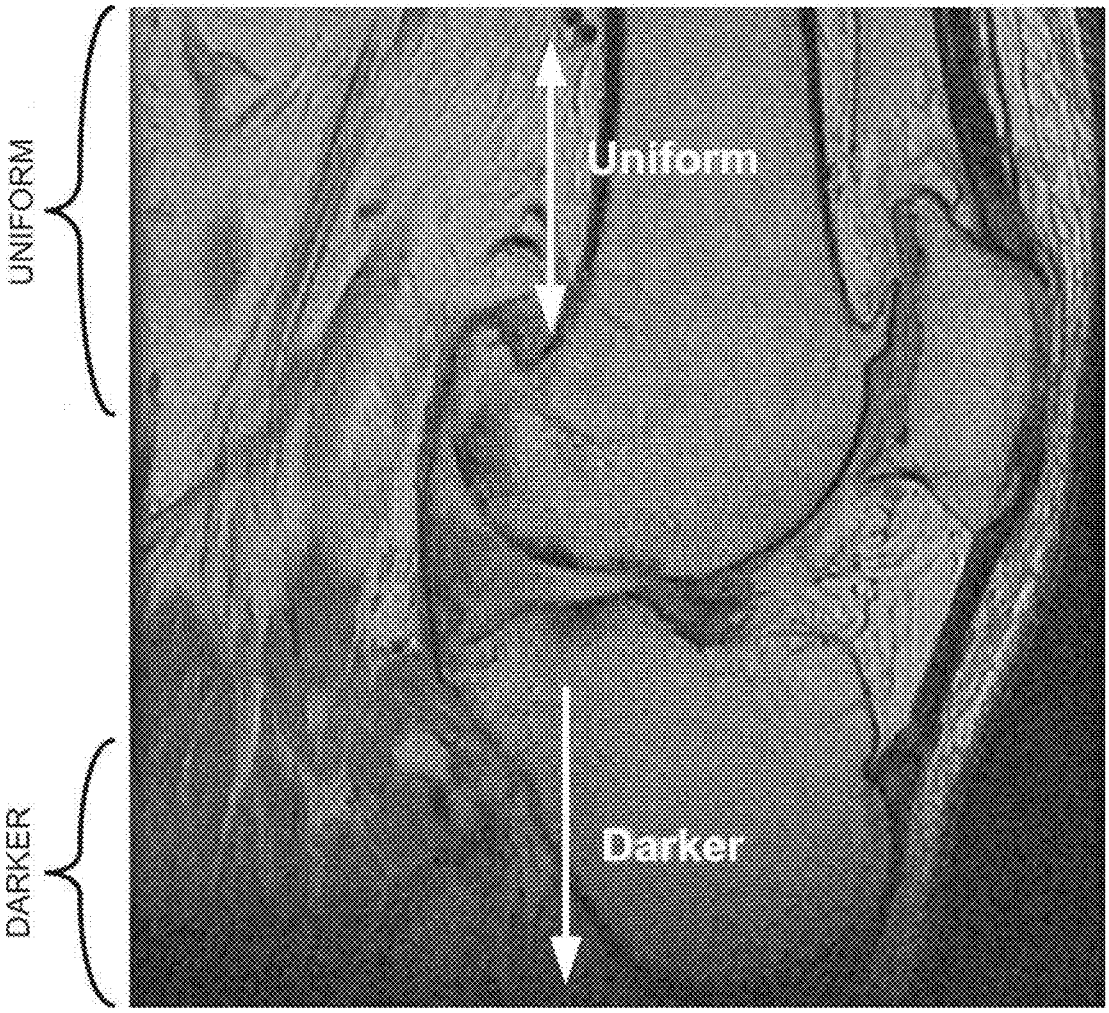
FIG. 3B is a sagittal plane image slice depicting another intensity gradient across the slice.
Figure 3C:
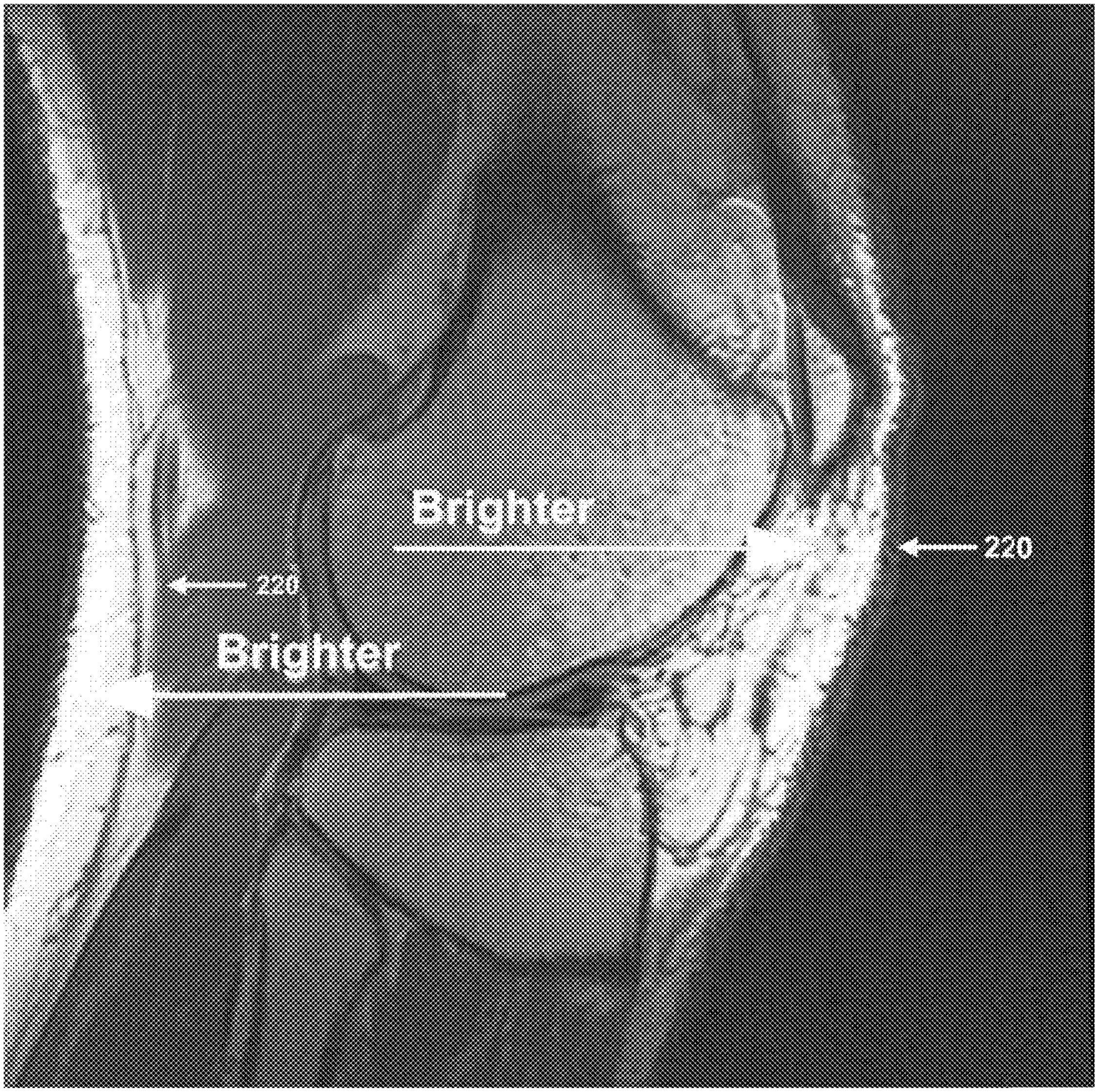
FIG. 3C is a sagittal plane image slice depicting another intensity gradient across the slice.
Figure 4A:
FIG. 4A depicts a sagittal plane image slice with a high noise level.
Figure 4B:
FIG. 4B depicts a sagittal plane image slice with a low noise level.

The segmentation method employed by one embodiment may accommodate a variety of intensity gradients across the scan data. FIGS. 3A-C depict intensity gradients (i.e., the intensity varies non-uniformly across the image) in slices (an intensity gradient that is darker on the top and bottom as depicted in FIG. 3A, an intensity gradient that is darker on the bottom as depicted in FIG. 3B, and an intensity gradient 220 that is brighter on the sides as depicted in FIG. 3C) that may be segmented by one embodiment. Further, the embodiment generally does not require approximately constant noise in the slices to be segmented. The embodiment may accommodate different noise levels, e.g., high noise levels as depicted in FIG. 4A as well as low noise levels as depicted in FIG. 4B. The decreased sensitivity to intensity gradients and noise level typically is due to image registration techniques using a golden template, allowing features of interest to be identified even though the feature may include voxels with differing intensities and noise levels.

Segmentation generally refers to the process of partitioning a digital image into multiple regions (e.g., sets of pixels for a 2D image or sets of voxels in a 3D image). Segmentation may be used to locate features of interest (bones, cartilage, ligaments, etc.) and boundaries (lines, curves, etc. that represent the bone boundary or surface) in an image. In one embodiment, the output of the automatic segmentation of the scan data may be a set of images (scan slices 16) where each image 16 includes a set of extracted closed contours representing bone outlines that identify respective bone location and shape for bones of interest (e.g., the shape and location of the tibia and femur in the scan data of a knee joint). The generation of a 3D model correspondent to the above closed contours may be additionally included into the segmentation process. The automatic or semi-automatic segmentation of a joint, using image slices 16 to create 3D models (e.g., bone models 22 and arthritic models 36) of the surface of the bones in the joint, may reduce the time required to manufacture customized arthroplasty cutting jigs 2. It is to be appreciated that certain embodiments may generate open contours of the bone shapes of interest to further reduce time associated with the process.

In one embodiment, scan protocols may be chosen to provide good definition in areas where precise geometry reconstruction is required and to provide lower definition in areas that are not as important for geometry reconstruction. The automatic or semi-automatic image segmentation of one embodiment employs components whose parameters may be tuned for the characteristics of the image modality used as input to the automatic segmentation and for the features of the anatomical structure to be segmented, as described in more detail below.

In one embodiment, a General Electric 3T MRI scanner may be used to obtain the scan data. The scanner settings may be set as follows: pulse sequence: FRFSE-XL Sagittal PD; 3 Pane Locator-Scout Scan Thickness: 4-millimeters; Imaging Options: TRF, Fast, FR; Gradient Mode: Whole; TE: approximately 31; TR: approximately 2100; Echo Train Length: 8; Bandwidth: 50 Hz; FOV: 16 centimeters, centered at the joint line; Phase FOV: 0.8 or 0.9; Slice Thickness: 2 millimeters; Spacing: Interleave; Matrix: 384×192; NEX: 2; Frequency: SI; and Phase Correct: On. It is to be appreciated that other scanners and settings may be used to generate the scan data.

Typically, the voxel aspect ratio of the scan data is a function of how many scan slices may be obtained while a patient remains immobile. In one embodiment, a two-millimeter inter-slice spacing may be used during a scan of a patient's knee joint. This inter-slice spacing provides sufficient resolution for constructing 3D bone models of the patient's knee joint, while allowing sufficiently rapid completion of scan before the patient moves.

Figure 5:
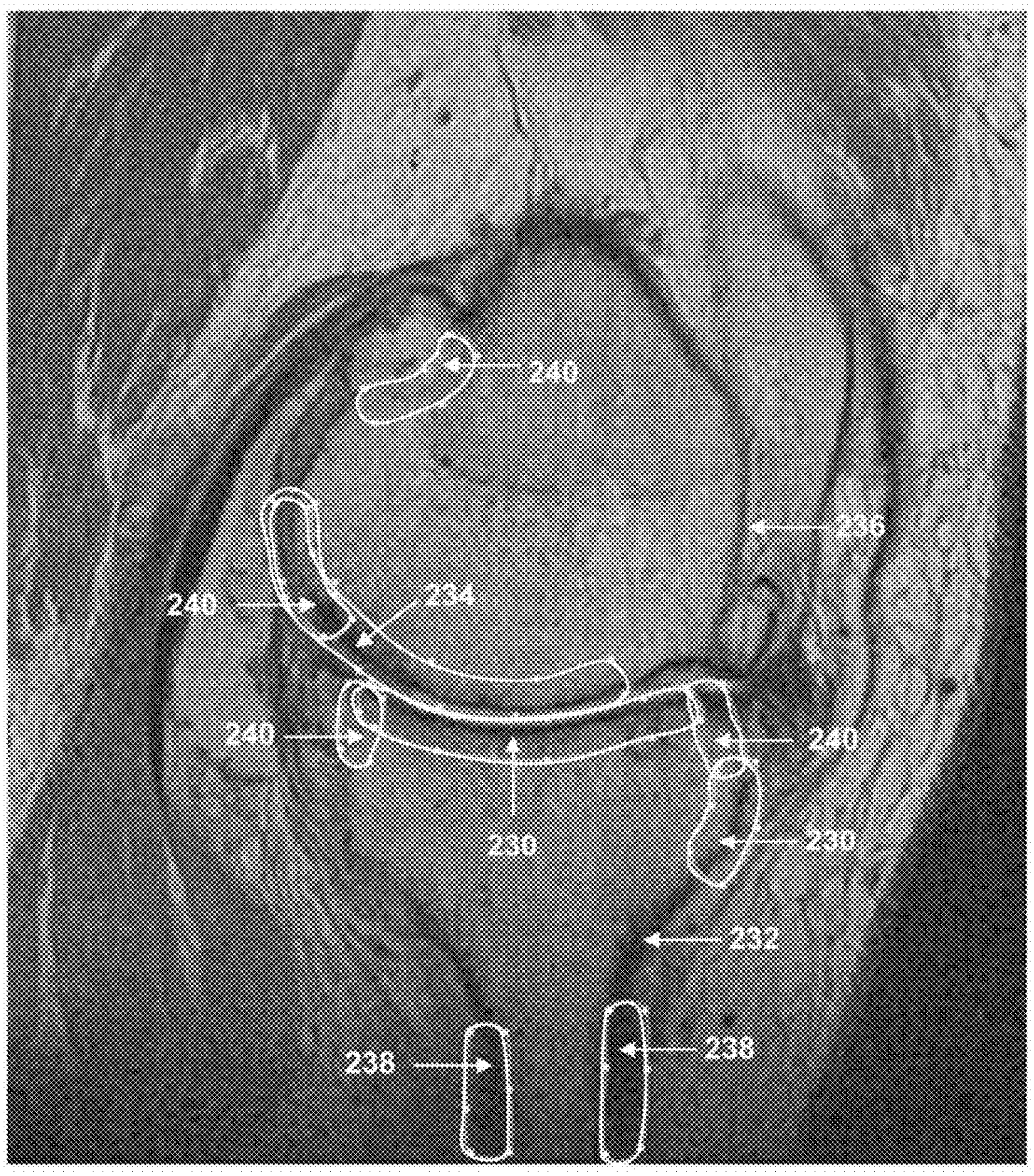
FIG. 5 is a sagittal plane image slice of a femur and tibia depicting regions where good definition may be needed during automatic segmentation of the femur and tibia.

FIG. 5 depicts a MRI scan slice that illustrates image regions where good definition may be needed during automatic segmentation of the image. Typically, this may be areas where the bones come in contact during knee motion, in the anterior shaft area next to the joint and areas located at about a 10- to 30-millimeter distance from the joint. Good definition may be needed in regions 230 of the tibia 232 and regions 234 of the femur 236. Regions 238 depict areas where the tibia is almost tangent to the slice and boundary information may be lost due to voxel volume averaging.

Voxel volume averaging may occur during the data acquisition process when the voxel size is larger than a feature detail to be distinguished. For example, the detail may have a black intensity while the surrounding region may have a white intensity. When the average of the contiguous data enclosed in the voxel is taken, the average voxel intensity value may be gray. Thus, it may not be possible to determine in what part of the voxel the detail belongs.

Regions 240 depict areas where the interface between the cortical bone and cartilage is not clear (because the intensities are similar), or where the bone is damaged and may need to be restored, or regions where the interface between the cancellous bone and surrounding region may be unclear due to the presence of a disease formation (e.g., an osteophyte growth which has an image intensity similar to the adjacent region).

Figure 6:
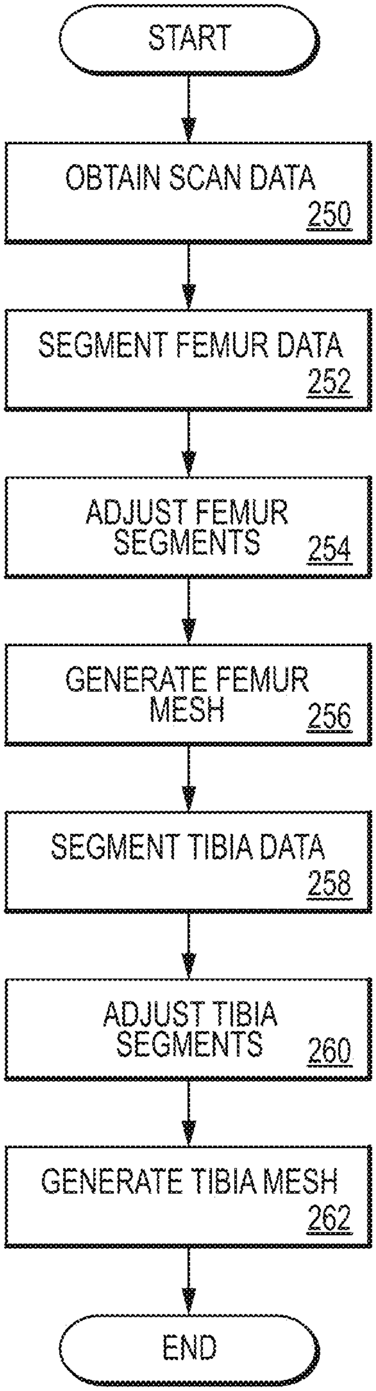
FIG. 6 depicts a flowchart illustrating one method for automatic segmentation of an image modality scan of a patient's knee joint.

FIG. 6 depicts a flowchart illustrating one method for automatic or semi-automatic segmentation of Femur and Tibia Planning models of an image modality scan (e.g., an MRI scan) of a patient's knee joint. Initially, operation 250 obtains a scan of the patient's knee joint. In one embodiment, the scan may include about 50 sagittal slices. Other embodiments may use more or fewer slices. Each slice may be a gray scale image having a resolution of 512 by 512 voxels. The scan may represent approximately a 100-millimeter by 150-millimeter by 150-millimeter volume of the patient's knee. While the invention will be described for an MRI scan of a knee joint, this is by way of illustration and not limitation. The invention may be used to segment other types of image modality scans such as computed tomography (CT) scans, ultrasound scans, positron emission tomography (PET) scans, etc., as well as other joints including, but not limited to, hip joints, elbow joints, etc. Further, the resolution of each slice may be higher or lower and the images may be in color rather than gray scale. It is to be appreciated that transversal or coronal slices may be used in other embodiments.

After operation 250 obtains scan data (e.g., scan images 16) generated by imager 8, operation 252 may be performed to segment the femur data of the scan data. During this operation, the femur may be located and spline curves 270 may be generated to outline the femur shape or contour lines in the scan slices, as depicted in FIGS. 7A-7K. It should be appreciated that one or more spline curves may be generated in each slice to outline the femur contour depending on the shape and curvature of the femur as well as the femur orientation relative to the slice direction.

Figure 8:
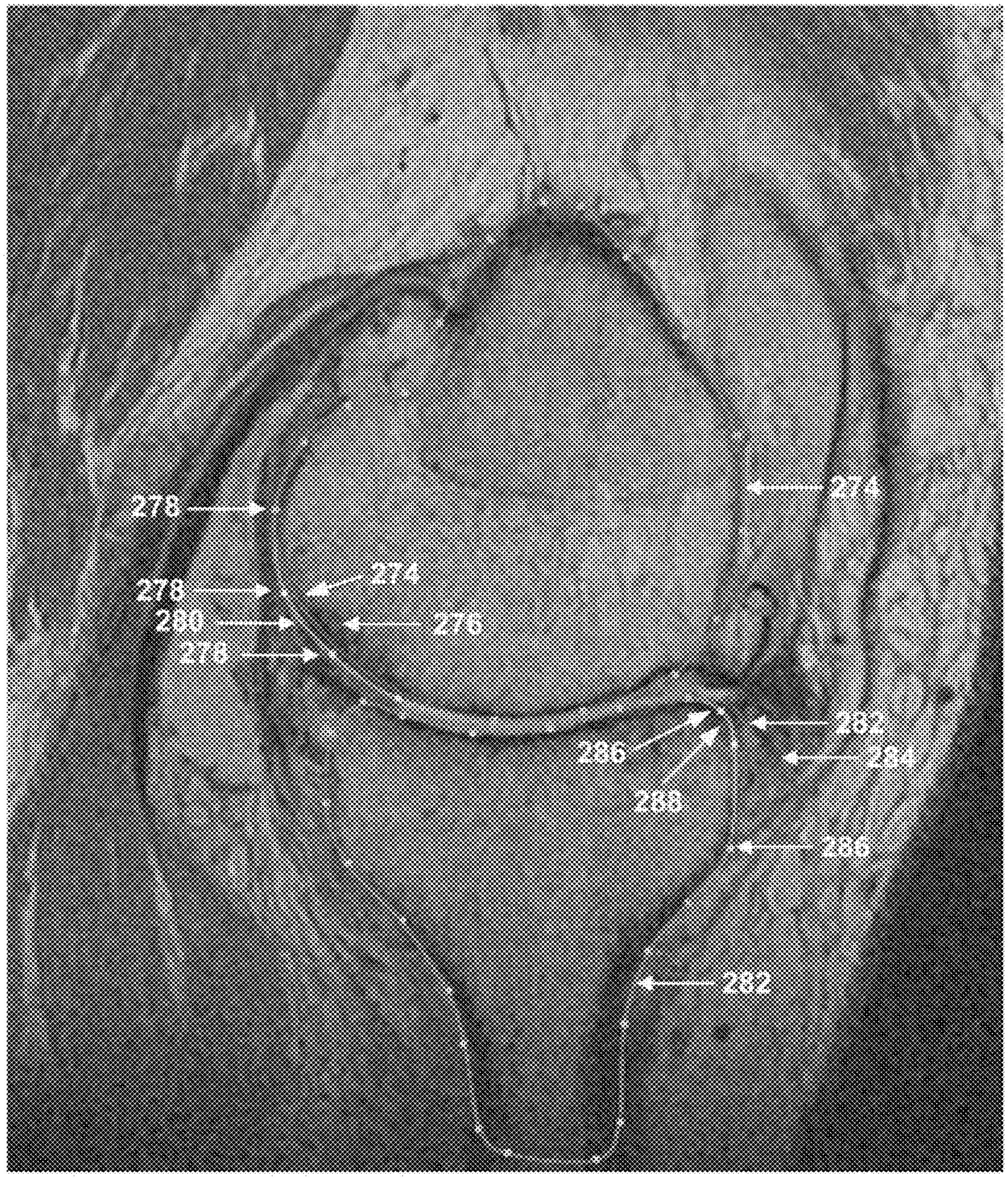
FIG. 8 is a sagittal plane image slice depicting automatically generated slice curves of a femur and a tibia.

Next, in operation 254, a trained technician may verify that the contours of the femur spline curves generated during operation 252 follow the surface of the femur bone. The technician may determine that a spline curve does not follow the bone shape in a particular slice. For example, FIG. 8 depicts an automatically generated femur spline curve 274. The technician may determine that the curve should be enlarged in the lower left part 276 of the femur. There may be various reasons why the technician may decide that the curve needs to be modified. For example, a technician may want to generate a pre-deteriorated bone shape, yet the bone may be worn out in this region and may need reconstruction. The technician may determine this by examining the overall 3D shape of the segmented femur and also by comparing lateral and medial parts of the scan data. The segmented region of the slice may be enlarged by dragging one or more control points 278 located on the spline curve 274 to adjust the curve to more closely follow the femur boundary as determined by the technician, as shown by adjusted curve 280. The number of control points on a spline curve may be dependent on the curve length and curvature variations. Typically, 10-25 control points may be associated with a spline curve for spline modification.

Figure 9:
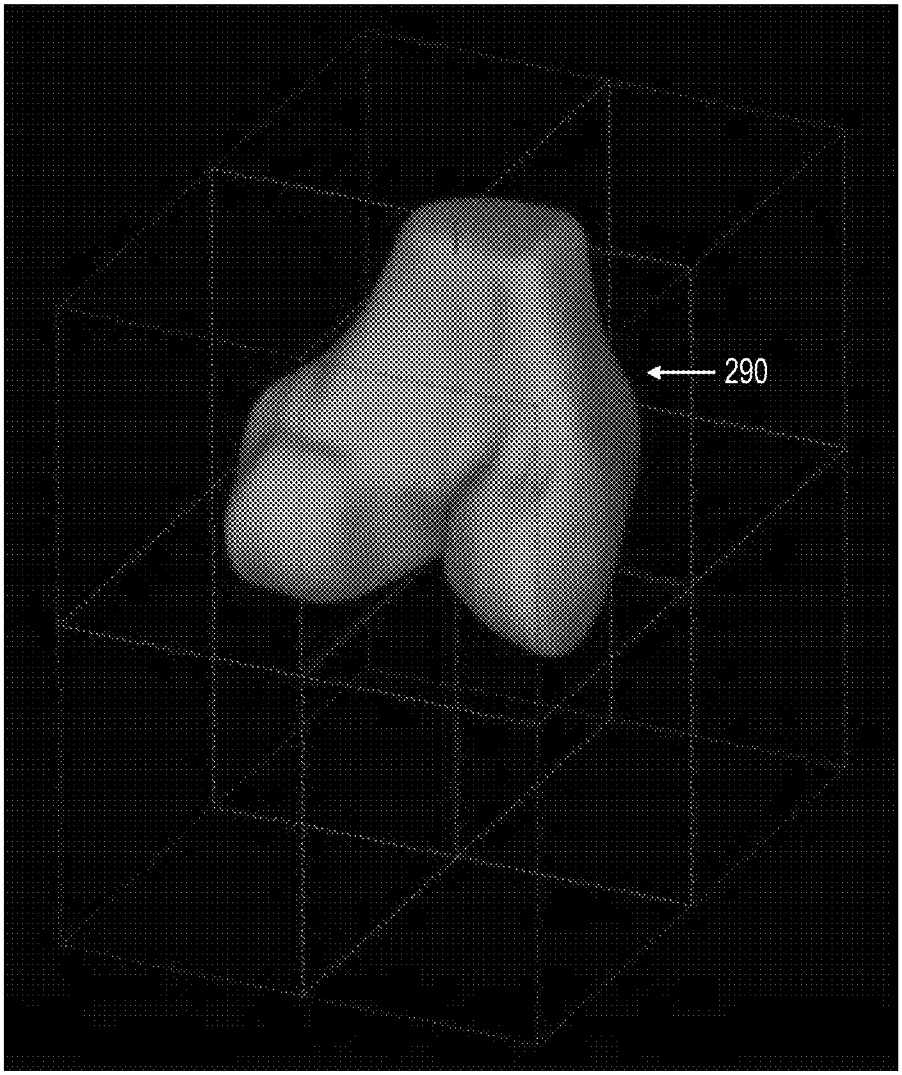
FIG. 9 depicts a 3D mesh geometry of a femur.

Once the technician is satisfied with all of the femur spline curves in the scan slices, operation 256 generates a watertight triangular mesh geometry from the femur segmentation that approximates the 3D surface of the femur. The mesh closely follows the femur spline curves 270 and smoothly interpolates between them to generate a 3D surface model of the femur. FIG. 9 depicts typical 3D mesh geometry 290 of a target femur generated by one embodiment. Such a 3D model may be a 3D surface model or 3D volume model resulting from open-loop contour lines or closed loop contour lines, respectively. In one embodiment, such a 3D model as depicted in FIG. 9 may be a bone model 22 or an arthritic model 36.

After operation 256, operation 258 may be performed to segment the tibia data in the scan data. During this operation, the tibia is located and spline curves may be generated to locate and outline the shape of the tibia found in the scan slices, as depicted by tibia spline curves 272 in FIGS. 7A-7K. It should be appreciated that one or more spline curves may be generated in each slice to outline the tibia depending on the shape and curvature of the tibia as well as the tibia orientation relative to the slice direction.

Next, in operation 260, the technician may verify the tibia spline curves generated during operation 258. The technician may determine that a spline curve does not follow the tibia in a particular slice. For example, referring back to FIG. 8, an automatically generated tibia spline curve 282 is depicted that may not follow the tibia in the right part of the tibia due to the presence of an osteophyte growth 284. The presence of the osteophyte growth 284 may be determined by examining neighboring slices. In this case, the segmented region may be reduced by dragging one or more control points 286 located on the spline curve to modify the tibia spline curve 282 to obtain the adjusted tibia spline curve 288. As previously discussed, each spline curve may have approximately 10-25 control points depending on the length and curvature variation of the spline curve.

When the purpose of the segmentation is generating bone models that will be shown to a surgeon in the images where they are overlapped by implants, a technician will not need to restore the segmentation model to its pre-deteriorated bone shape, and thus will not need to spend time on adjusting splines to follow the pre-deteriorated bone shape. Also there is no need to get highly precise segmentation in the bone areas that are to be replaced with implant. So there is no need to spend time on adjusting the non-perfect curves in the "to be replaced" areas.

Figure 10:
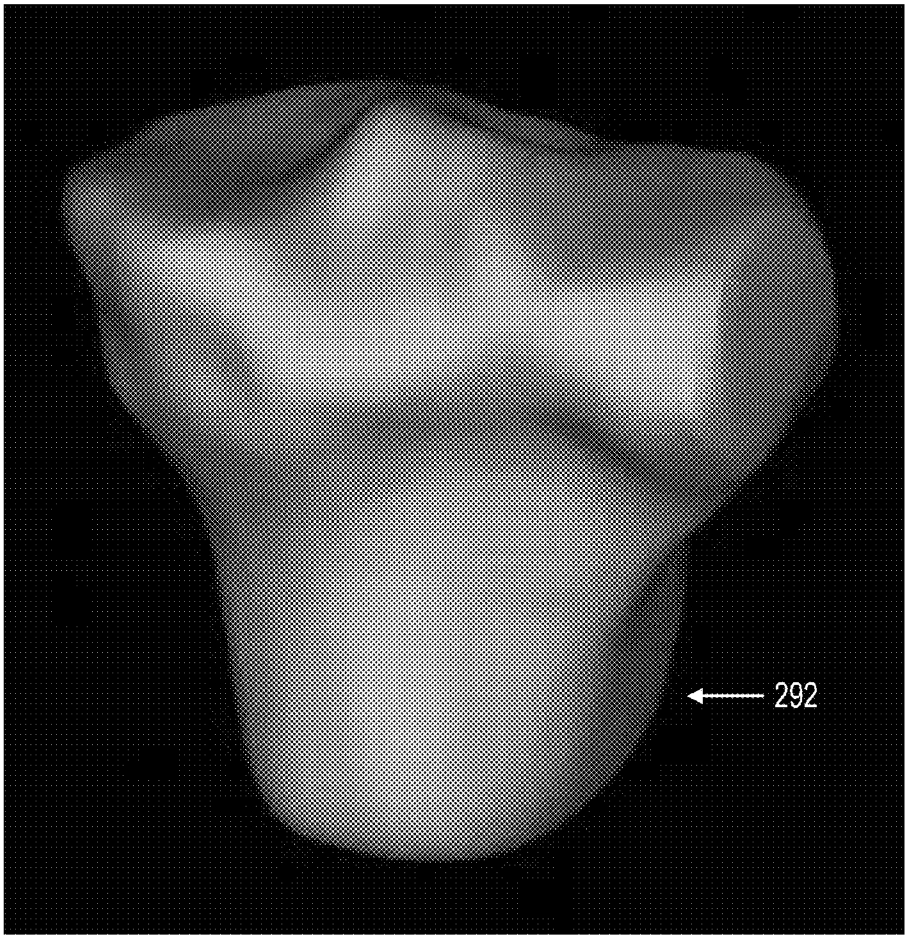
FIG. 10 depicts a 3D mesh geometry of a tibia.

Once the technician is satisfied with all of the tibia spline curves in the scan slices, operation 262 generates a watertight triangular mesh geometry from the tibia segmentation. The mesh closely follows the spline curves and smoothly interpolates between them to generate a 3D surface model of the tibia. FIG. 10 depicts a typical 3D mesh geometry 292 of a target tibia generated by one embodiment. Such a 3D model may be a 3D surface model or 3D volume model resulting from open-loop contour lines or closed loop contour lines, respectively. In one embodiment, such a 3D model as depicted in FIG. 10 may be a bone model 22 or an arthritic model 36.

Because the objects to be located in the scan data typically cannot be segmented by grouping similar voxels into regions, a golden template representative of a typical size and shape of the feature of interest may be employed during the segmentation process to locate the target feature of interest.

Figure 11:
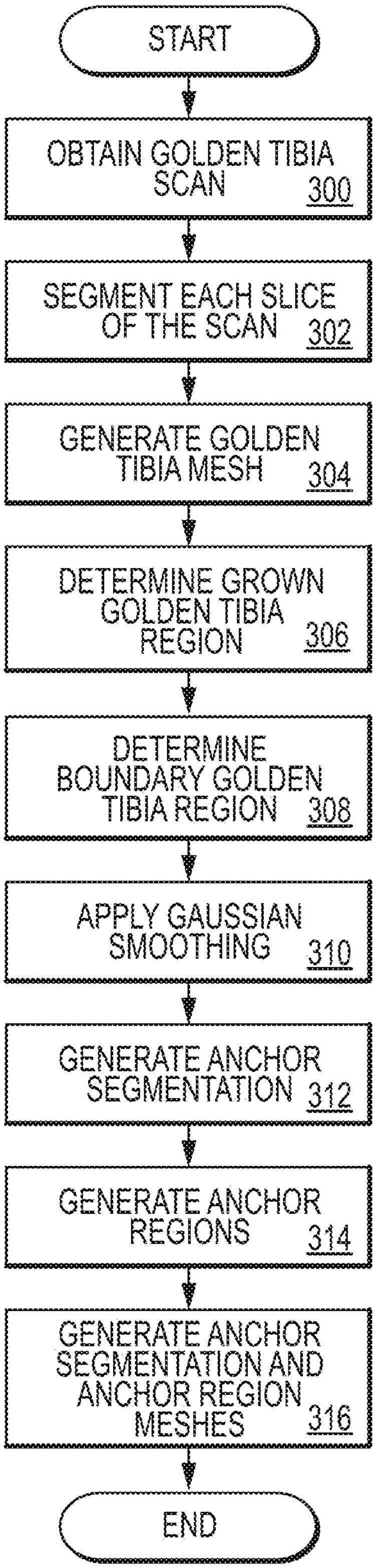
FIG. 11 depicts a flowchart illustrating one method for generating a golden template.

FIG. 11 depicts a flowchart illustrating one method for generating a golden template. The method will be described for generating a golden template of a tibia by way of illustration and not limitation. The method may be used to generate golden templates of other bones including, but not limited to a femur bone, a hip bone, etc.

Initially, operation 300 obtains a scan of a tibia that is not damaged or diseased. The appropriate tibia scan may be chosen by screening multiple MRI tibia scans to locate a MRI tibia scan having a tibia that does not have damaged cancellous and cortical matter (i.e., no damage in tibia regions that will be used as fixed images to locate a corresponding target tibia in a target scan during segmentation), which has good MRI image quality, and which has a relatively average shape, e.g., the shaft width relative to the largest part is not out of proportion (which may be estimated by eye-balling the images). This tibia scan data, referred to herein as a golden tibia scan, may be used to create a golden tibia template. It is to be appreciated that several MRI scans of a tibia (or other bone of interest) may be selected, a template generated for each scan, statistics gathered on the success rate when using each template to segment target MRI scans, and the one with the highest success rate selected as the golden tibia template.

In other embodiments, a catalog of golden models may be generated for any given feature, with distinct variants of the feature depending on various patient attributes, such as (but not limited to) weight, height, race, gender, age, and diagnosed disease condition. The appropriate golden mesh would then be selected for each feature based on a given patient's characteristics.

Figure 12A:
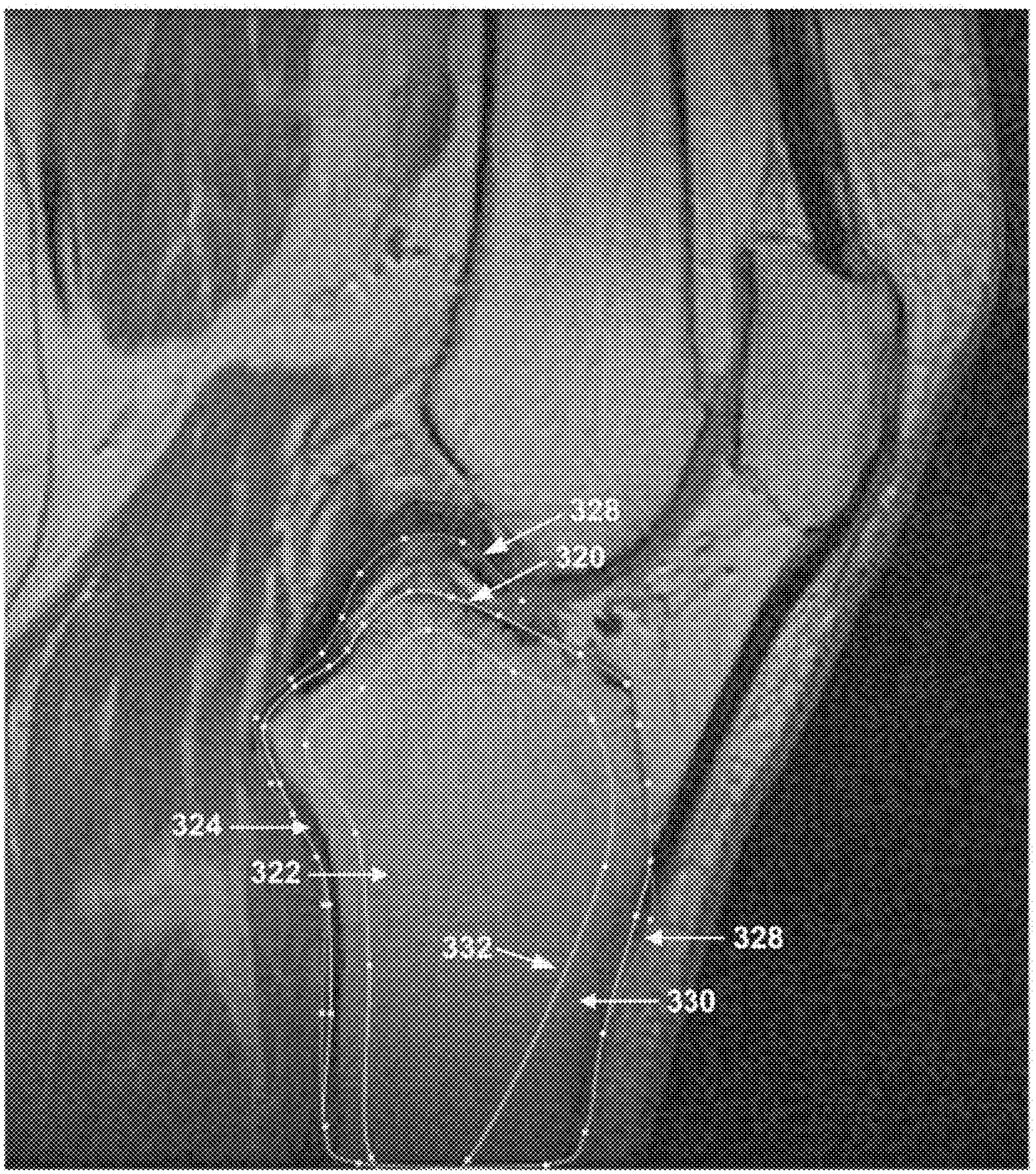
FIG. 12A is a sagittal plane image slice depicting a contour curve outlining a golden tibia region, a contour curve outlining a grown tibia region and a contour curve outlining a boundary golden tibia region.

Then, in operation 302 the tibia is segmented in each scan slice. Each segmentation region includes the cancellous matter 322 and cortical matter 324 of the tibia, but excludes any cartilage matter to form a golden tibia region, outlined by a contour curve 320, as depicted in FIG. 12A.

Figure 13A:
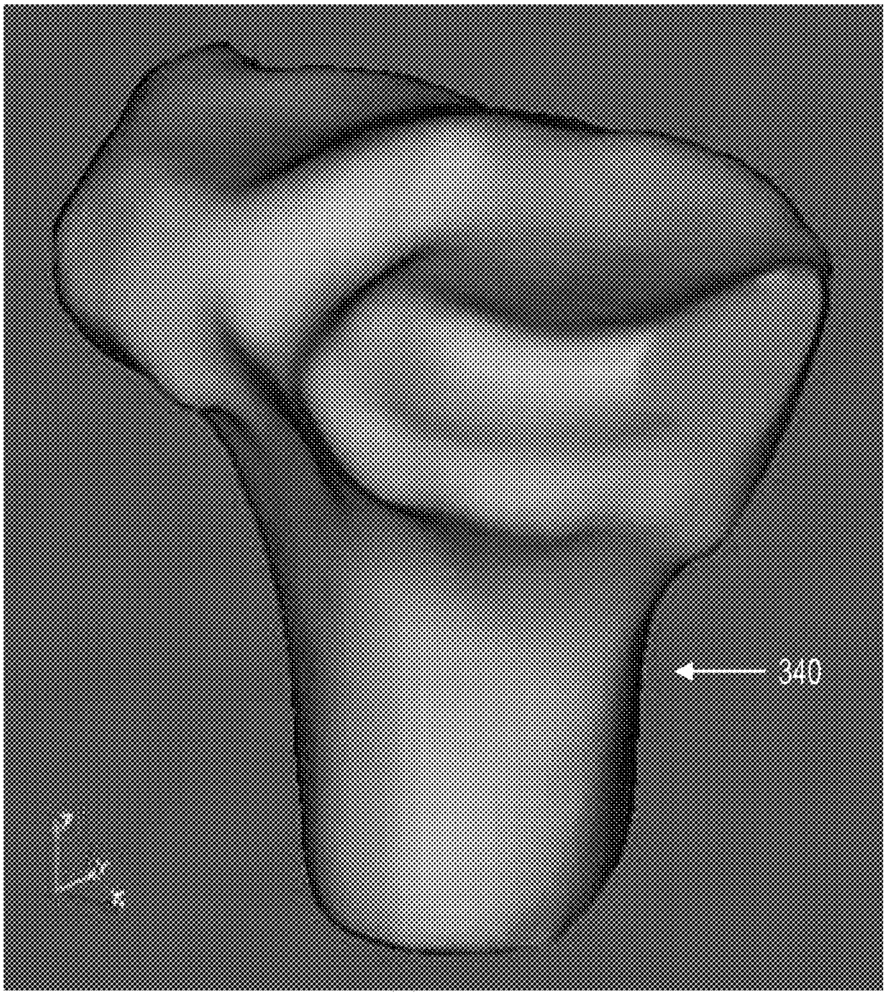
FIG. 13A depicts a golden tibia 3D mesh.

Next, operation 304 generates a golden tibia mesh 340 from the accumulated golden tibia contours of the image slices, as illustrated in FIG. 13A.

Next, operation 306 increases the segmented region in each slice by growing the region to include boundaries between the tibia and adjacent structures where the contact area is generally relatively stable from one MRI scan to another MRI scan. This grown region may be referred to herein as a grown golden tibia region, outlined by contour curve 328, as depicted in FIG. 12A.

The grown golden region may be used to find the surface that separates the hard bone (cancellous and cortical) from the outside matter (cartilage, tendons, water, etc.). The changes in voxel intensities when going from inside the surface to outside of the surface may be used to define the surface. The grown golden region may allow the registration process to find intensity changes in the target scan that are similar to the golden template intensity changes near the surface. Unfortunately, the golden segmentation region does not have stable intensity changes (e.g., near the articular surface) or may not have much of an intensity change. Thus, the grown region typically does not include such regions because they do not provide additional information and may slow down the registration due to an increased number of points to be registered.

Finally, use of a grown golden region may increase the distance where the metric function detects a feature during the registration process. When local optimization is used, the registration may be moved in a particular direction only when a small movement in that direction improves the metric function. When a golden template feature is farther away from the corresponding target bone feature (e.g., when there is a significant shape difference), the metric typically will not move toward that feature. Use of the larger grown region may allow the metric to detect the feature and move toward it.

Next, operation 308 cuts off most of the inner part of the grown golden tibia region to obtain a boundary golden tibia region 330 depicted in FIG. 12A. The boundary golden tibia region 330 is bounded on the inside by contour curve 332 and the outside by contour curve 328.

The boundary region may be used to obtain a more precise registration of the target bone by using the interface from the cancellous bone to the cortical bone. This may be done so that intensity variations in other areas (e.g., intensity variations deep inside the bone) that may move the registration toward wrong features and decrease the precision of locating the hard bone surface are not used during the registration.

Then, operation 310 applies Gaussian smoothing with a standard deviation of two pixels to every slice of the golden tibia scan. In one embodiment, a vtkImageGaussianSmooth filter (part of Visualization Toolkit, a free open source software package) may be used to perform the Gaussian smoothing by setting the parameter "Standard Deviation" to a value of two.

Then, operation 312 generates an anchor segmentation. The anchor segmentation typically follows the original segmentation where the tibia boundary is well defined in most MRI scans. In areas where the tibia boundary may be poorly defined, but where there is another well-defined feature close to the tibia boundary, the anchor segmentation may follow that feature instead. For example, in an area where a healthy bone normally has cartilage, a damaged bone may or may not have cartilage. If cartilage is present in this damaged bone region, the bone boundary separates the dark cortical bone from the gray cartilage matter. If cartilage is not present in this area of the damaged bone, there may be white liquid matter next to the dark cortical bone or there may be another dark cortical bone next to the damaged bone area. Thus, the interface from the cortical bone to the outside matter in this region of the damaged bone typically varies from MRI scan to MRI scan. In such areas, the interface between the cortical and the inner cancellous bone may be used. These curves may be smoothly connected together in the remaining tibia areas to obtain the tibia anchor segmentation curve 358, depicted in FIG. 14A.

Figure 14A:
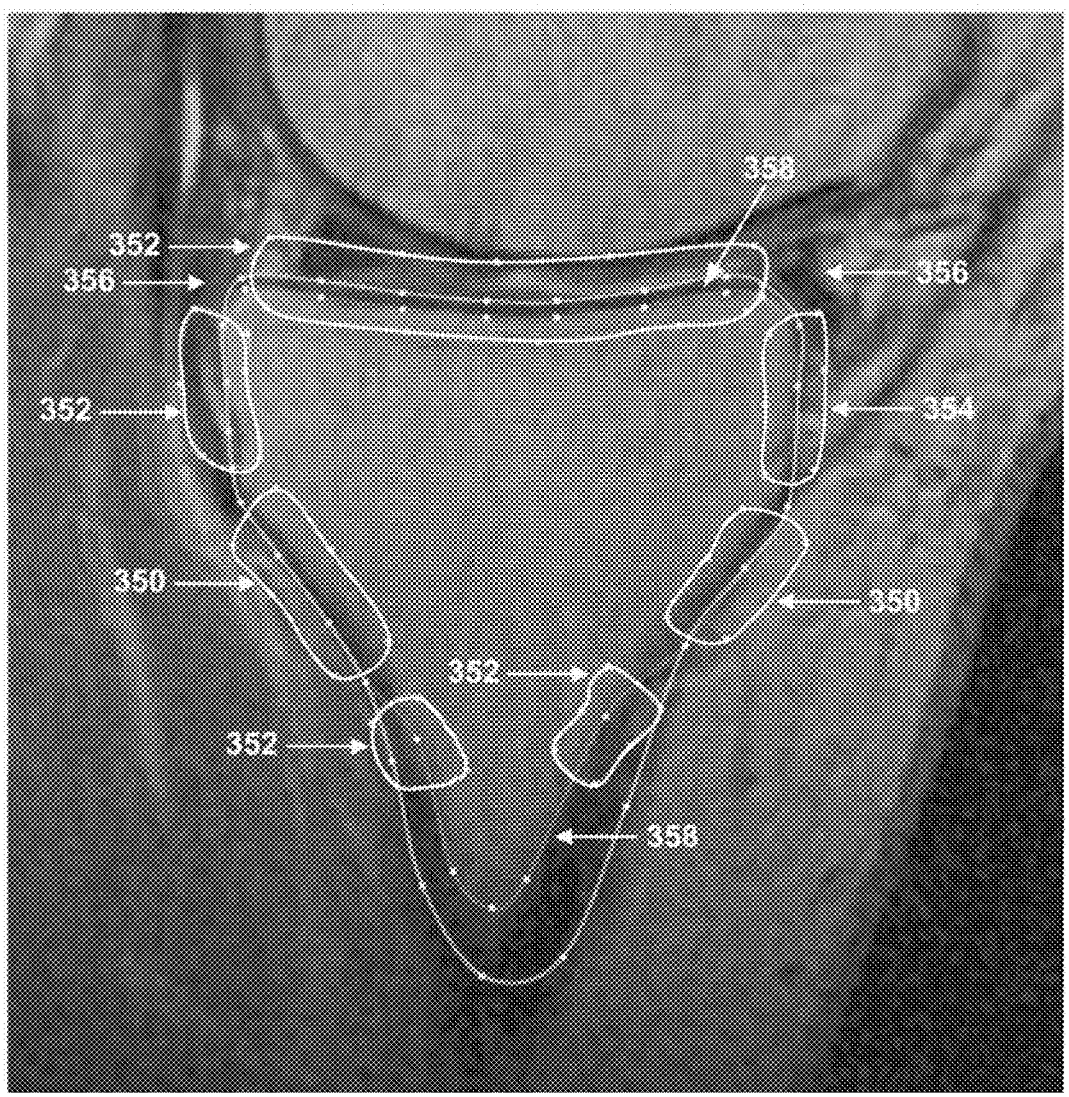
FIG. 14A is a sagittal plane image slice depicting anchor segmentation regions of a tibia.

Then, operation 314 may determine three disjoint regions along the anchor segmentation boundary. Each of these regions is generally well defined in most MRI scans. FIG. 14A depicts these three disjoint regions for a particular image slice. The first region 350, referred to herein as the tibia InDark-OutLight region, depicts a region where the anchor segmentation boundary separates the inside dark intensity cortical matter voxels from the outside light intensity voxels. The second region 352, referred to herein as the tibia InLight-OutDark region, depicts a region where the boundary separates the inside light intensity cancellous matter voxels from the outside dark intensity cortical matter voxels. Finally, region 354, referred to herein as the tibia Dark-in-Light region, depicts a region that has a very thin layer of dark intensity cortical matter voxels along the boundary, but which has light intensity matter voxels away from the boundary (i.e., on both sides of the boundary). Generally, the other regions along the anchor segmentation boundary vary from scan to scan or may not be clear in most of the scans, as depicted by regions 356. Such regions may be an osteophyte growth with an arbitrary shape but which has about the same intensity as the region next to it. Thus, such regions typically are not used as anchor regions in one embodiment of the invention.

Figure 15A:
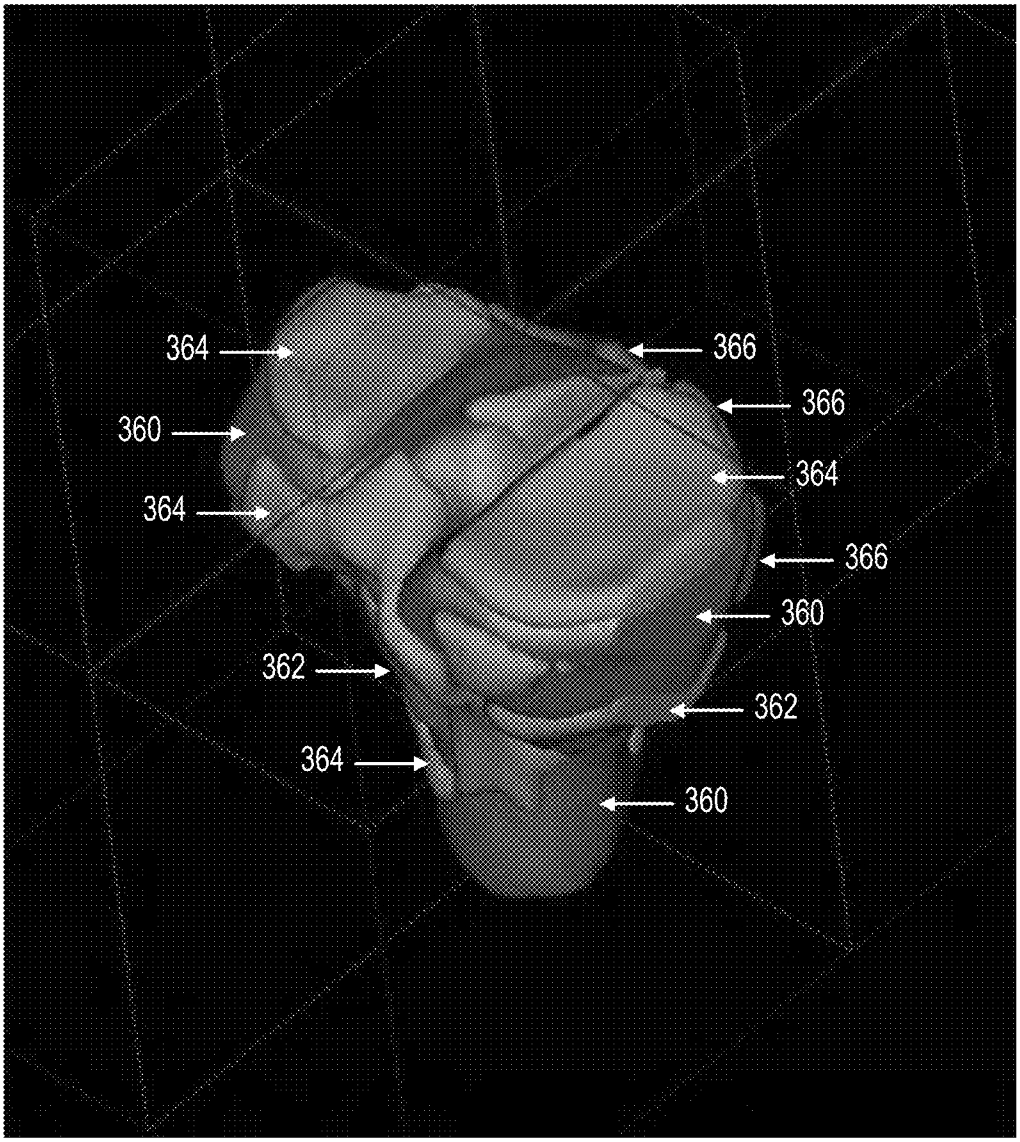
FIG. 15A is a 3D mesh geometry depicting the anchor segmentation mesh, the InDark-OutLight anchor mesh, the InLight-OutDark anchor mesh, and the Dark-In-Light anchor mesh of a tibia.

Finally, operation 316 generates a mesh corresponding to the anchor segmentation and also generates a mesh for each anchor region. FIG. 15A depicts the anchor segmentation mesh 360, the InDark-OutLight anchor region mesh 362, the InLight-OutDark anchor region mesh 364 and the Dark-in-Light anchor region mesh 366 for the tibia. These 3D meshes model the surface of the golden tibia in the specified regions. It is to be appreciated that the 3D meshes are distinct and generally are not combined to create a composite mesh. These meshes may be used to create an artificial fixed image that is used during the registration process as described in more detail below.

Figure 12B:
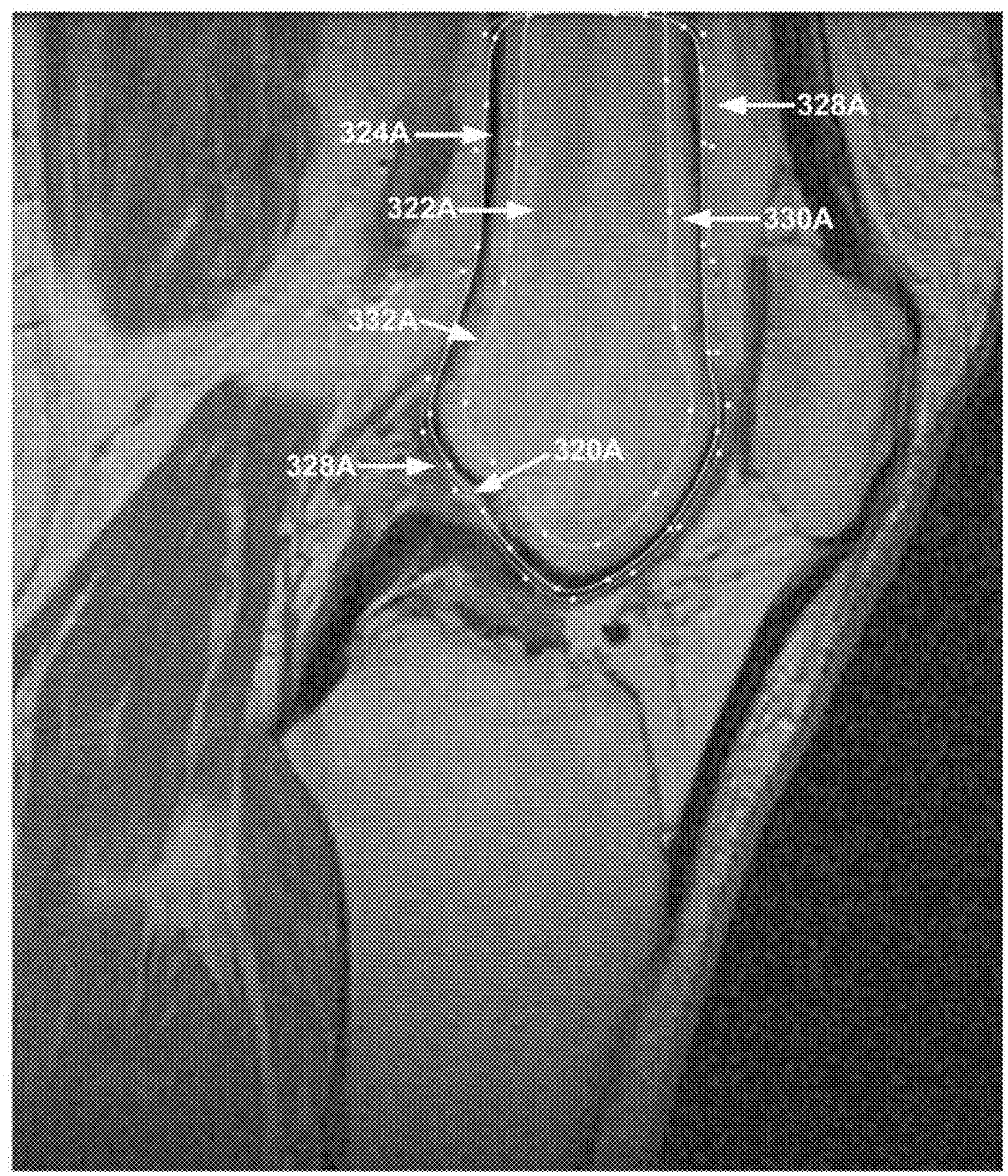
FIG. 12B is a sagittal plane image slice depicting a contour curve outlining a golden femur region, a contour curve outlining a grown femur region and a contour curve outlining a boundary golden femur region.
Figure 13B:
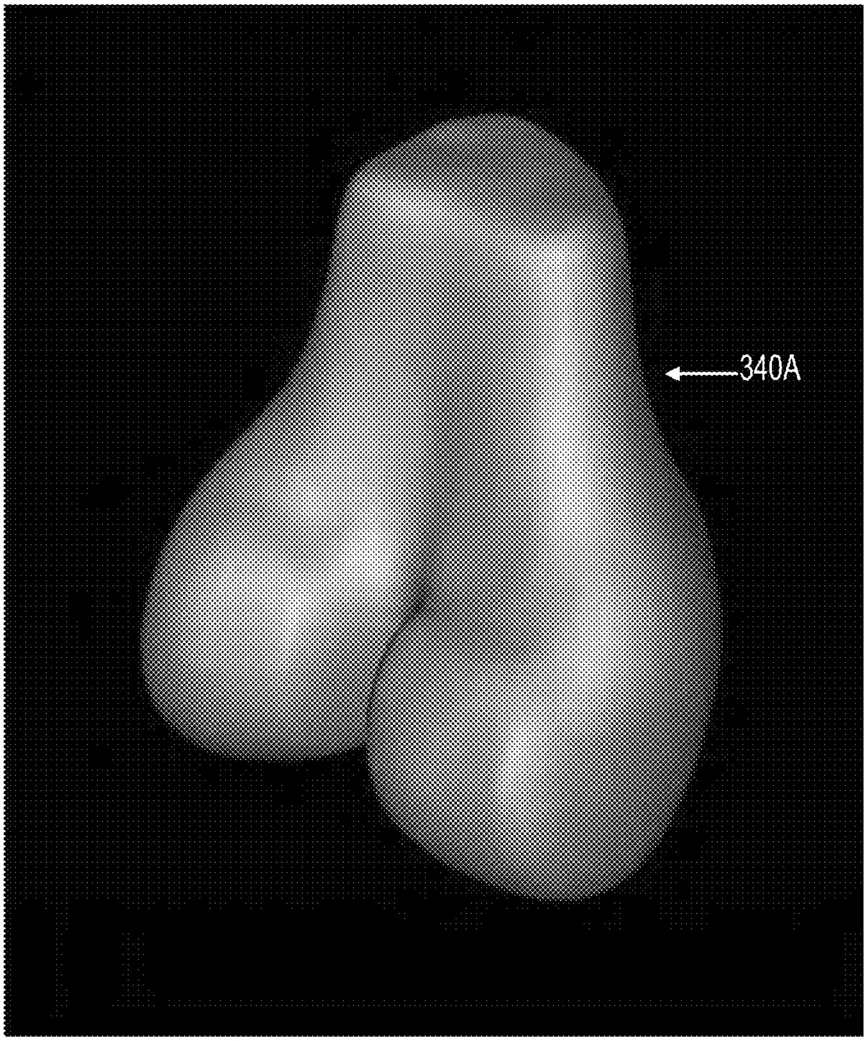
FIG. 13B depicts a golden femur 3D mesh.
Figure 14B:
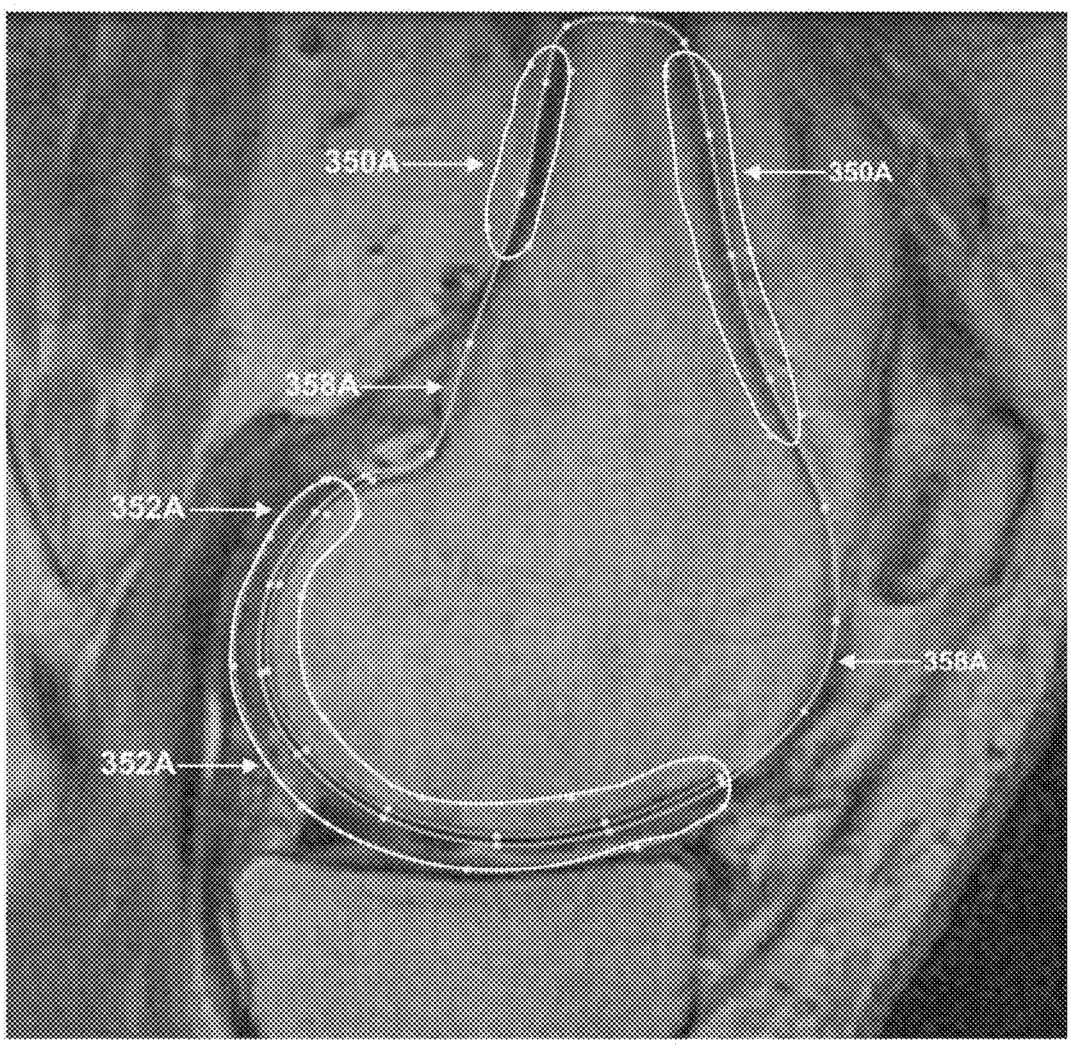
FIG. 14B is a sagittal plane image slice depicting anchor segmentation regions of a femur.
Figure 15B:
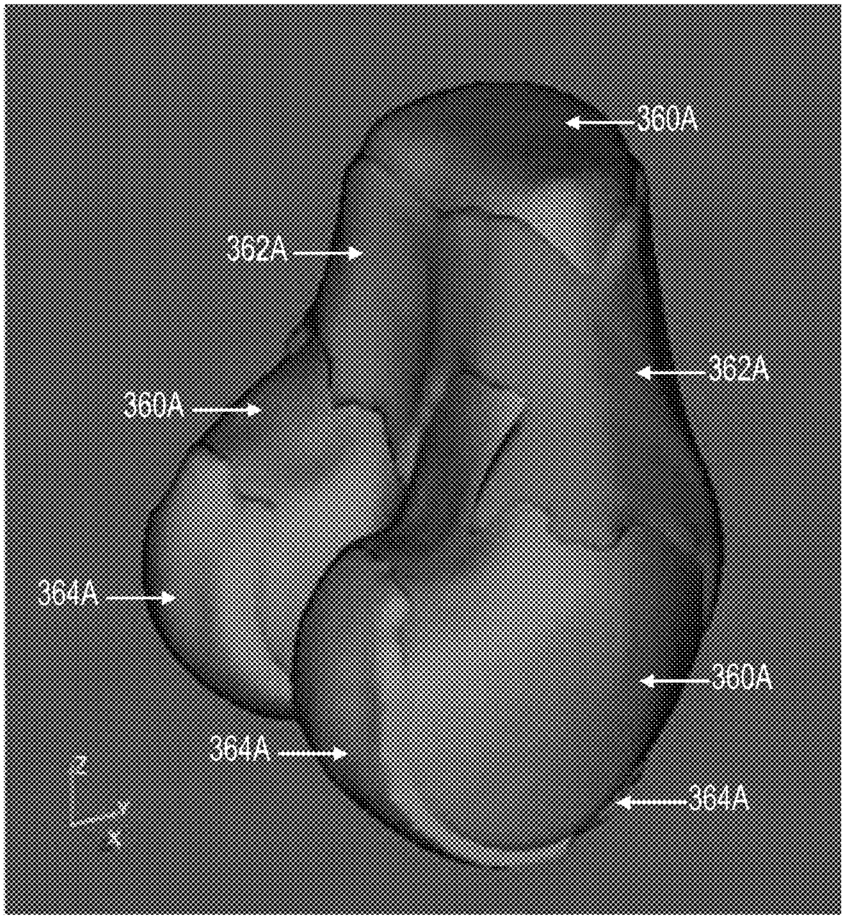
FIG. 15B is a 3D mesh geometry depicting the anchor segmentation mesh, the InDark-OutLight anchor mesh and the InLight-OutDark anchor mesh of a femur.

A golden template of a femur may also be generated in a similar manner using the method depicted by FIG. 11. FIG. 12B depicts the golden femur region, outlined by a contour curve 320A, the grown femur region, outlined by contour curve 328A, and the boundary golden femur region 330A bounded on the inside by contour curve 332A and the outside by contour curve 328A. FIG. 13B depicts the golden femur mesh 340A. FIG. 14B depicts the femur anchor segmentation curve 358A, the femur InDark-OutLight region 350A and the femur InLight-OutDark region 352A. Finally, FIG. 15B depicts the anchor segmentation mesh 360A, the InDark-OutLight anchor region mesh 362A and the InLight-OutDark anchor region mesh 364A for the femur.

Figure 16:
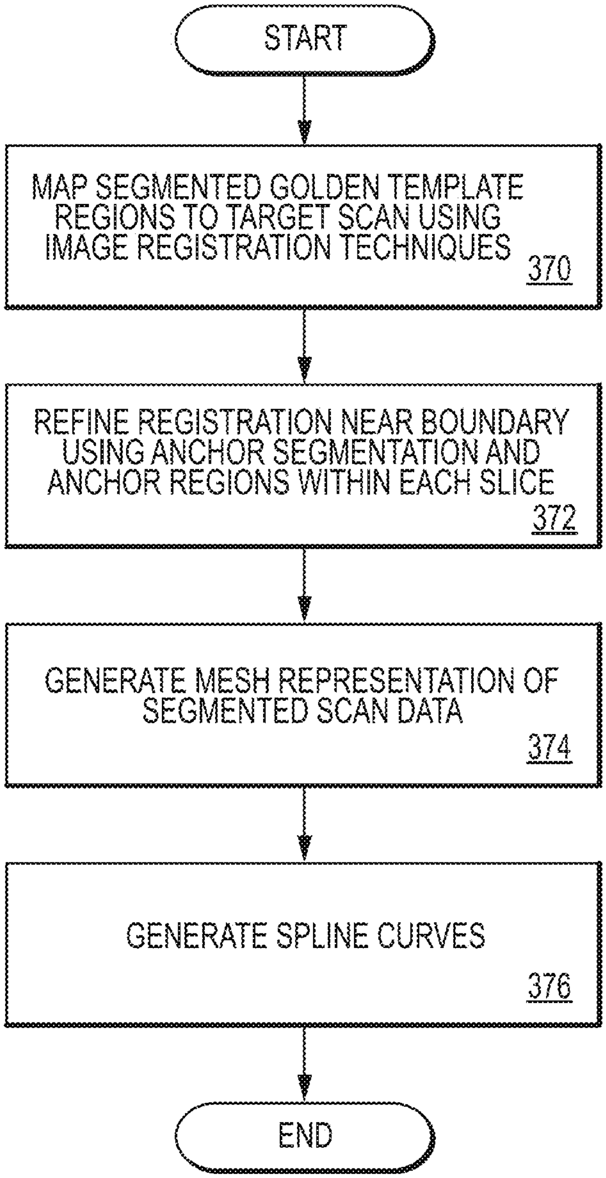
FIG. 16 depicts a flowchart illustrating one method for performing automatic segmentation of scan data using golden template registration.

FIG. 16 depicts a flowchart illustrating one method for performing automatic segmentation (e.g., operation 252 or operation 258 of FIG. 6) of the scan data of a joint (e.g., a MRI scan of a knee joint) using golden template registration. The segmentation method may be used to segment the femur (operation 252 of FIG. 6) and/or the tibia (operation 258 of FIG. 6) in either the left or right knee. Different golden template data may be used to segment the left tibia, right tibia, left femur or right femur. Additionally, other embodiments may segment other joints, including but not limited to, hip joints, elbow joints, by using an appropriate golden template of the feature of interest to be segmented.

Initially, operation 370 maps the segmented 3D golden template and marked regions (e.g., grown and boundary regions) to the target scan data using image registration techniques. This may be done to locate the corresponding feature of interest in the target scan (e.g., a target femur or tibia). Registration transforms the template image coordinate system into the target coordinate system. This allows the template image to be compared and/or integrated with the target image.

Next, operation 372 refines the registration near the feature (e.g., a bone) boundary of interest. Anchor segmentation and anchor regions may be used with a subset of 3D free-form deformations to move points within the plane of the slices (e.g., the yz plane) but not transversal (along the x axis) to the slices. Refinement of the initial registration operation may be necessary to correct errors caused by a high voxel aspect ratio. When a point from a golden template is mapped onto the target scan, it generally maps to a point between adjacent slices of the scan data. For example, if a translation occurs along the x direction, then the point being mapped may only align with a slice when the translation is a multiple of the inter-slice scan distance (e.g., a multiple of two-millimeters for an inter-slice spacing of two-millimeters). Otherwise, the point will be mapped to a point that falls between slices. In such cases, the intensity of the target scan point may be determined by averaging the intensities of corresponding points (voxels) in the two adjacent slices. This may further reduce image resolution. Additionally, refinement of the initial registration operation may correct for errors due to unhealthy areas and/or limited contrast areas. That is, the golden template may be partially pulled away from the actual bone boundary in diseased areas and/or minimal contrast areas (e.g., toward a diseased area having a different contrast) during the initial registration operation.

Next, operation 374 generates a polygon mesh representation of the segmented scan data. A polygon mesh typically is a collection of vertices, edges, and faces that may define the surface of a 3D object. The faces may consist of triangles, quadrilaterals or other simple convex polygons. In one embodiment, a polygon mesh may be generated by applying the registration transform found during operation 372 to all the vertices of a triangle golden template mesh (i.e., the surface of the mesh is composed of triangular faces). It is to be appreciated that the cumulative registration transform typically represents the transform that maps the golden template into the target MRI scan with minimal misalignment error.

Finally, operation 376 generates spline curves that approximate the intersection of the mesh generated by operation 374 with the target MRI slices. Note that these spline curves may be verified by the technician (during operation 254 or operation 260 of FIG. 6).

Figure 17:
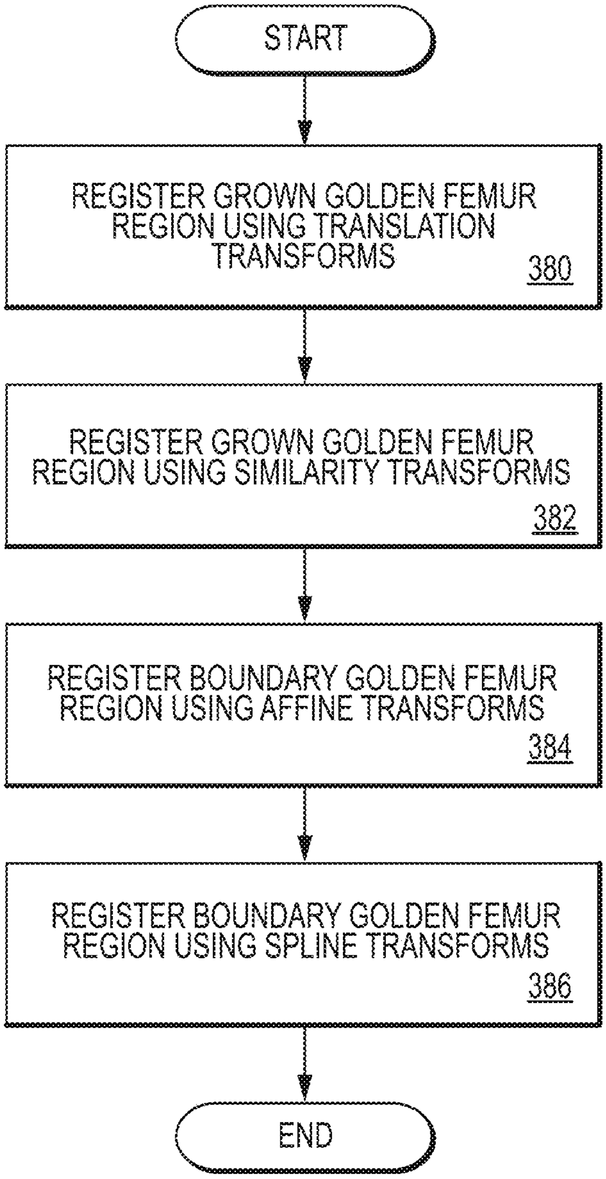
FIG. 17 depicts a flowchart illustrating one method for mapping the segmented golden femur template regions into the target scan data using image registration techniques.

FIG. 17 depicts a flowchart illustrating one method for mapping the segmented golden femur template regions into the target scan using image registration techniques. Registration may be thought of as an optimization problem with a goal of finding a spatial mapping that aligns a fixed image with a target image. Generally several registration operations may be performed, first starting with a coarse image approximation and a low-dimensional transformation group to find a rough approximation of the actual femur location and shape. This may be done to reduce the chance of finding wrong features instead of the femur of interest. For example, if a free-form deformation registration was initially used to register the golden femur template to the target scan data, the template might be registered to the wrong feature, e.g., to a tibia rather than the femur of interest. A coarse registration may also be performed in less time than a fine registration, thereby reducing the overall time required to perform the registration. Once the femur has been approximately located using a coarse registration, finer registration operations may be performed to more accurately determine the femur location and shape. By using the femur approximation determined by the prior registration operation as the initial approximation of the femur in the next registration operation, the next registration operation may find a solution in less time.

Figure 18:
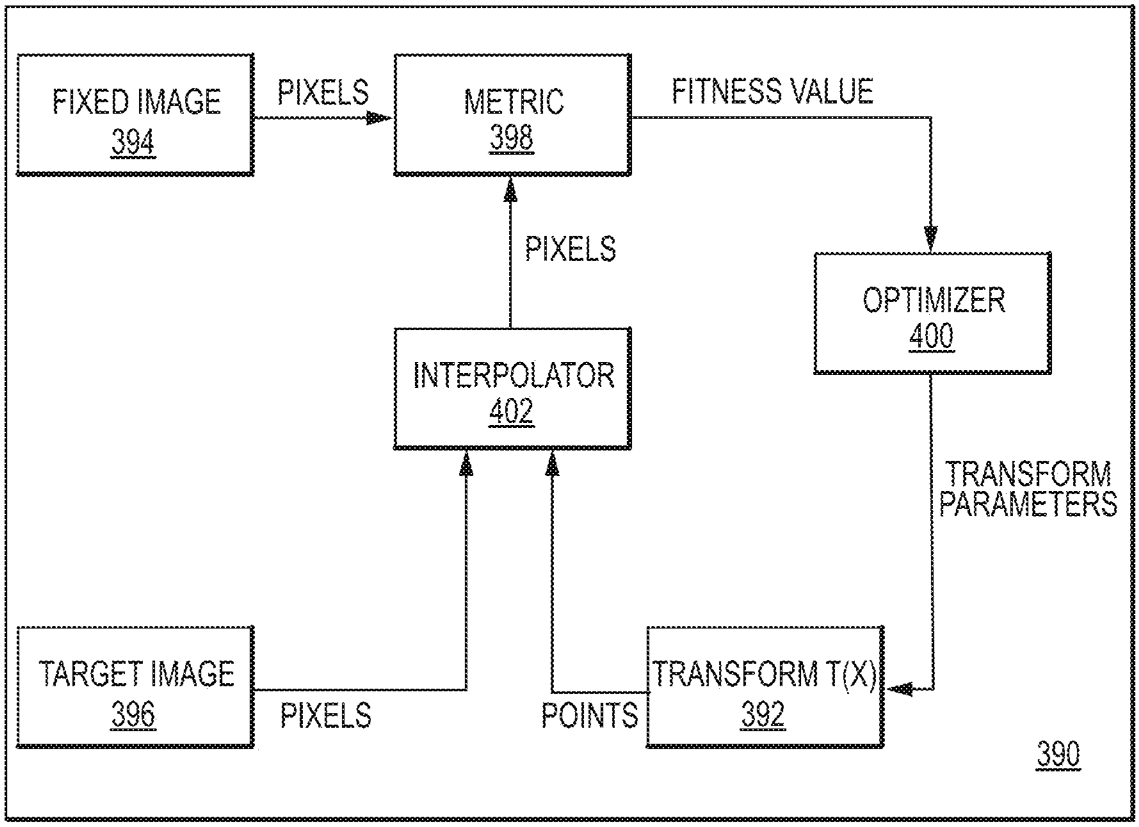
FIG. 18 depicts a registration framework that may be employed by one embodiment.

In one embodiment, each registration operation may employ a registration framework 390 as depicted in FIG. 18. The registration framework 390 may employ an image similarity-based method. Such a method generally includes a transformation model T(X) 392, which may be applied to coordinates of a fixed (or reference) image 394 (e.g., a golden femur template) to locate their corresponding coordinates in a target image 396 space (e.g., a MRI scan), an image similarity metric 398, which quantifies the degree of correspondence between features in both image spaces achieved by a given transformation, and an optimizer 400, which tries to maximize image similarity (or minimize an opposite function) by changing the parameters of the transformation model 392. An interpolator 402 may be used to evaluate target image intensities at non-grid locations (e.g., reference image points that are mapped to target image points that lie between slices). Thus, a registration framework typically includes two input images, a transform, a metric, an interpolator and an optimizer.

Referring again to FIG. 17, operation 380 may approximately register a grown femur region in a MRI scan using a coarse registration transformation. In one embodiment, this may be done by performing an exhaustive translation transform search on the MRI scan data to identify the appropriate translation transform parameters that minimizes translation misalignment of the reference image femur mapped onto the target femur of the target image. This coarse registration operation typically determines an approximate femur position in the MRI scan.

A translational transform, translates (or shifts) all elements of an image by the same 3D vector. That is, the reference femur may be mapped into the target image space by shifting the reference femur along one or more axes in the target image space to minimize misalignment. During this operation the reference femur is not rotated, scaled or deformed. In one embodiment, three parameters for the translation transformation may be generated: one parameter for each dimension that specifies the translation for that dimension. The final parameters of the translation transform minimizing the misalignment of the mapped reference femur image coordinates into the target image space may be stored.

Next, operation 382 further refines the image registration determined by operation 380. This may be done by approximately registering the grown femur region of the reference golden template femur into the target MRI scan data using a similarity transformation. In one embodiment, a similarity transformation may be performed in 3D space. The reference golden femur region may be rotated in 3D, translated in 3D and homogeneously scaled to map its coordinates into the target MRI scan data to minimize misalignment between the reference golden femur region and the corresponding region in the target MRI scan. In some embodiments, a center of rotation may be specified so that both the rotation and scaling operations are performed with respect to the specified center of rotation. In one embodiment, a 3D similarity transformation, specified by seven parameters, may be used. One parameter specifies the scaling factor, three parameters specify a versor that represents the 3D rotation and three parameters specify a vector that represents the 3D translation in each dimension. A versor is a unit quaternion that provides a convenient mathematical notation for representing orientations and rotations of objects in three dimensions.

In one embodiment, local minimization techniques may be employed with the similarity transformation to obtain a refined registration of the reference golden femur region onto the target MRI scan that is not far from the registration of the reference golden femur region onto the target MRI scan found in the previous operation 190 and used as the initial starting approximation. Registering the grown golden femur region may increase the distance where the metric function detects a feature during the registration process. When local optimization is used, the registration may be moved in a particular direction only when a small movement in that direction improves the metric function. When a golden femur template feature is farther away from the corresponding target femur feature (e.g., when there is a significant shape difference), the metric typically will not move toward that feature. Use of the larger grown femur region may allow the metric to detect the feature and move toward it.

After operation 382, operation 384 further refines the image registration of the golden femur into the target scan. In one embodiment, an affine transformation may be used to register coordinates of a boundary golden femur region of a golden femur template into the target MRI scan data. In one embodiment, the approximate femur registration found during operation 382 may be used as the initial starting approximation for the affine transformation.

An affine transformation typically is a linear transformation followed by a translation. The affine transformation preserves collinearity between points (i.e., three points which lie on a line continue to be collinear after the transformation) and ratios of distances along a line. In one embodiment, a 3D affine transformation, specified by 12 parameters, may be utilized. Nine parameters of the affine transformation specify the linear transformation (which may be represented by a three by three matrix) and three parameters of the affine transformation specify the 3D translation in each dimension. The parameters of the affine transform that minimizes the misalignment of the boundary golden femur region mapped into the target MRI scan data may be stored.

Finally, operation 386 further refines the image registration of the boundary golden femur region. In one embodiment, a spline transformation may be used to register the coordinates of the boundary golden femur region into the MRI scan data (target image space). In one embodiment, a 3D B-Spline deformable transformation may be employed and the transformation found in operation 384 may be used as the initial transformation values for the 3D B-Spline deformable transformation.

A B-Spline deformable transformation typically is a free form deformation of an object using a deformation field where a deformation vector is assigned to every point in space. For example, a 3D B-spline deformable transform T may specify a 3D vector V(P) for every point P in the original 3D space that is moved by T such that $T:P \rightarrow P+V(P)$.

In one embodiment, a B-Spline transformation may be specified with M×N parameters, where M is the number of nodes in the B-Spline grid and N is the dimension of the space. In one embodiment, a 3D B-Spline deformable transformation of order three may be used to map every reference image 3D point into the target MRI scan by a different 3D vector. The field of the vectors may be modeled using B-splines. Typically a grid J×K×L of control points may be specified where J, K, and L are parameters of the transformation.

In one embodiment, splines of order three may be used with a grid 9×6×6 of control points. That is, the transformation employs nine control points in the medial/lateral direction (i.e., the x direction), and six control points in the other directions (i.e., y and z directions). Two control points in each dimension (i.e., 2 of 9 in the x direction, 2 of 6 in the y direction and 2 of 6 in the z direction) may be used to specify boundary conditions. As such, the inner spline nodes may form a grid of size 7 by 4 by 4 and the boundary conditions increase the grid to size 9 by 6 by 6. The parametric set for this transformation has a dimension of 3×9×6×6=972 (i.e., each dimension may have a 9×6×6 grid of control points). The final parameters of the spline transformation that minimizes the misalignment between the reference golden femur template and the target MRI scan data may be stored. This may be referred to as the cumulative femur registration transform herein.

Figure 19:
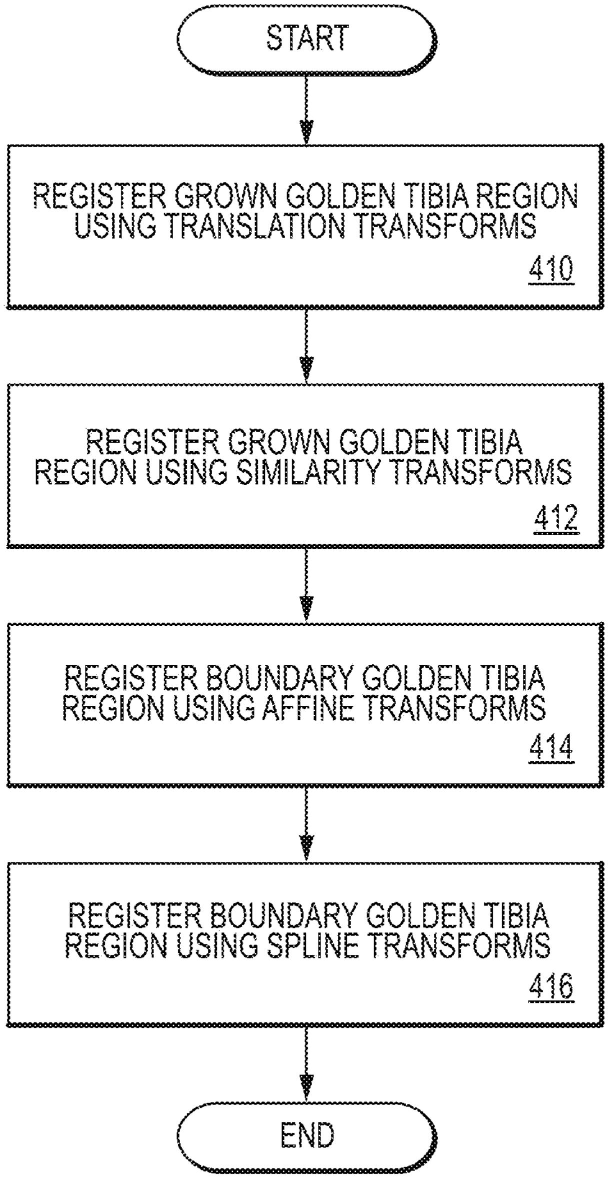
FIG. 19 depicts a flowchart illustrating one method for mapping the segmented golden tibia template regions into the target scan data using image registration techniques.

FIG. 19 depicts a flowchart illustrating one method for mapping the segmented golden tibia template regions into the target scan using image registration techniques. Generally several registration operations may be performed, first starting with a coarse image approximation and a low-dimensional transformation group to find a rough approximation of the actual tibia location and shape. This may be done to reduce the chance of finding wrong features instead of the tibia of interest. For example, if a free-form deformation registration was initially used to register the golden tibia template to the target scan data, the template might be registered to the wrong feature, e.g., to a femur rather than the tibia of interest. A coarse registration may also be performed in less time than a fine registration, thereby reducing the overall time required to perform the registration. Once the tibia has been approximately located using a coarse registration, finer registration operations may be performed to more accurately determine the tibia location and shape. By using the tibia approximation determined by the prior registration operation as the initial approximation of the tibia in the next registration operation, the next registration operation may find a solution in less time.

In one embodiment, each registration operation may employ a registration framework 390 as depicted in FIG. 18. The registration framework 390 may employ an image similarity-based method. Such a method generally includes a transformation model T(X) 392, which may be applied to coordinates of a fixed (or reference) image 394 (e.g., a golden tibia template) to locate their corresponding coordinates in a target image 396 space (e.g., a MRI scan), an image similarity metric 398, which quantifies the degree of correspondence between features in both image spaces achieved by a given transformation, and an optimizer 400, which tries to maximize image similarity by changing the parameters of the transformation model 392. An interpolator 402 may be used to evaluate target image intensities at non-grid locations (i.e., reference image points that are mapped to target image points that lie between slices). Thus, a registration framework typically includes two input images, a transform, a metric, an interpolator and an optimizer.

The automatic segmentation registration process will be described using scan data that includes a right tibia bone. This is by way of illustration and not limitation. Referring again to FIG. 19, operation 410 may approximately register a grown tibia region in a MRI scan using a coarse registration transformation. In one embodiment, this may be done by performing an exhaustive translation transform search on the MRI scan data to identify the appropriate translation transform parameters that minimizes translation misalignment of the reference image tibia mapped onto the target tibia of the target image. This coarse registration operation typically determines an approximate tibia position in the MRI scan. During this operation, the tibia of the reference image may be overlapped with the target tibia of the target image using a translation transformation to minimize translational misalignment of the tibias.

A translational transform, translates (or shifts) an image by the same 3D vector. That is, the reference tibia may be mapped into the target image space by shifting the reference tibia along one or more axes in the target image space to minimize misalignment. During this operation the reference tibia is not rotated, scaled or deformed. In one embodiment, three parameters for the translation transformation may be generated, one parameter for each dimension that specifies the translation for that dimension. The final parameters of the translation transform minimizing the misalignment of the mapped reference tibia image coordinates into the target image space may be stored.

Next, operation 412 further refines the image registration determined by operation 410. This may be done by approximately registering the grown tibia region of the reference golden tibia template into the target MRI scan data using a similarity transformation. In one embodiment, a similarity transformation may be performed in 3D space. The reference golden tibia region may be rotated in 3D, translated in 3D and homogeneously scaled to map its coordinates into the target MRI scan data to minimize misalignment between the reference golden tibia region and the corresponding region in the target MRI scan. In some embodiments, a center of rotation may be specified so that both the rotation and scaling operations are performed with respect to the specified center of rotation. In one embodiment, a 3D similarity transformation, specified by seven parameters, may be used. One parameter specifies the scaling factor, three parameters specify a versor that represents the 3D rotation and three parameters specify a vector that represents the 3D translation in each dimension. A versor is a unit quaternion that provides a convenient mathematical notation for representing orientations and rotations of objects in three dimensions.

In one embodiment, local minimization techniques may be employed with the similarity transformation to obtain a refined registration of the reference golden tibia region onto the target MRI scan that is not far from the registration of the reference golden tibia region onto the target MRI scan found in the previous operation 410 and used as the initial starting approximation. Registering the grown golden tibia region may increase the distance where the metric function detects a feature during the registration process. When local optimization is used, the registration may be moved in a particular direction only when a small movement in that direction improves the metric function. When a golden tibia template feature is farther away from the corresponding target tibia feature (e.g., when there is a significant shape difference), the metric typically will not move toward that feature. Use of the larger grown tibia region may allow the metric to detect the feature and move toward it.

After operation 412, operation 414 further refines the image registration. In one embodiment, an affine transformation may be used to register coordinates of a boundary golden tibia region of a golden tibia template into the target MRI scan data. In one embodiment, the approximate tibia registration found during operation 412 may be used as the initial starting approximation for the affine transformation.

An affine transformation typically is a linear transformation followed by a translation. The affine transformation preserves collinearity between points (i.e., three points which lie on a line continue to be collinear after the transformation) and ratios of distances along a line. In one embodiment, a 3D affine transformation, specified by 12 parameters, may be utilized. Nine parameters of the affine transformation specify the linear transformation (which may be represented by a three by three matrix) and three parameters of the affine transformation specify the 3D translation in each dimension. The parameters of the affine transform that minimizes the misalignment of the boundary golden tibia region mapped into the target MRI scan data may be stored.

Finally, operation 416 further refines the image registration of the boundary golden tibia region. In one embodiment, a spline transformation may be used to register the coordinates of the boundary golden tibia region into the MRI scan data (target image space). In one embodiment, a 3D B-Spline deformable transformation may be employed and the transformation found in operation 414 may be used as the initial transformation values for the 3D B-Spline deformable transformation.

A B-Spline deformable transformation typically is a free form deformation of an object using a deformation field where a deformation vector is assigned to every point in space. In one embodiment, a B-Spline transformation may be specified with M×N parameters, where M is the number of nodes in the B-Spline grid and N is the dimension of the space. In one embodiment, a 3D B-Spline deformable transformation of order three may be used to map every reference image 3D point into the target MRI scan by a different 3D vector. The field of the vectors may be modeled using B-splines. Typically a grid J×K×L of control points may be specified where J, K, and L are parameters of the transformation.

In one embodiment, splines of order three may be used with a grid 9×6×6 of control points. That is, the transformation employs nine control points in the medial/lateral direction (i.e., the x direction, and six control points in the other directions (i.e., the y and z directions). Two control points in each dimension (i.e., 2 of 9 in the x direction, 2 of 6 in the y direction and 2 of 6 in the z direction) may be used to specify boundary conditions. As such, the inner spline nodes may form a grid of size 7 by 4 by 4 and the boundary conditions increase the grid to size 9 by 6 by 6. The parametric set for this transformation has a dimension of 3×9×6×6=972. The final parameters of the spline transformation that minimizes the misalignment between the reference golden tibia template and the target MRI scan data may be stored. This may be referred to as the cumulative tibia registration transform herein.

The shape of the tibia may vary more from patient to patient than does the shape of the femur. As a result, the affine transformation may not provide a close enough registration of the golden tibia template to the target tibia in the target scan. This may cause the Spline transformation to find a local optimum that may be far from the actual tibia in some areas. In one embodiment, an additional registration operation between the affine transform and spline transform operations may be performed to more closely align the golden tibia and the target tibia, allowing the spline transform to converge to the correct local optimum rather than a nearby (but wrong) local optimum.

The class of transforms utilized generally should allow more flexibility (or degrees of freedom) than the Affine transform and less flexibility than the B-spline transforms. The number of degrees of freedom generally is equal to the number of transform parameters. In one embodiment, a class of transforms with more than 12 parameters and less than 3×9×6×6 parameters may be used. For example, a B-spline transform with fewer control points (than used in the subsequent spline transform) may be used for the additional transform operation. Alternatively, the deformations may be modeled using quadric rather than cubic functions.

In another embodiment, several golden tibia templates may be used that represent typical tibia variations, e.g., golden tibia templates for varum, valgum and normal tibia. In one embodiment, each of the golden tibia templates may be used during the translation, similarity and affine transform registration operations to find the template that provides the best match (e.g., best correlation) in the affine transform registration operation. This template may then be used in the remaining registration operations.

Finally, in one embodiment, the tibia registration may be improved by performing the tibia segmentation after the femur segmentation and adding a restriction on the tibia registration transformations such that the tibia may not penetrate the femur. In one embodiment, this may be implemented by introducing a penalty for the penetration. In the target MRI all the voxels that lie inside the femur splines may be marked. The metric functions, described in more detail below, that are used in the registration operations may be modified to include a penalty term. The penalty term may be computed by selecting a set of points on the boundary of the golden template segmentation, applying a transform to the set of points (in a similar way as the transform is applied to the sample points used in the correlation computations), determining if a transformed sample point falls into any of the marked voxels, and adding a large value to the penalty term for each transformed sample point that falls into any of the marked voxels.

In each of the above registration operations, a metric may be used to quantify the degree of correspondence between features in both the reference image and target image achieved by a given transformation. In one embodiment, the metric quantitatively measures how well the transformed golden template image fits the target image (e.g., a target MRI scan) and may compare the gray-scale intensity of the images using a set of sample points in the golden template region to be registered.

Figure 20:
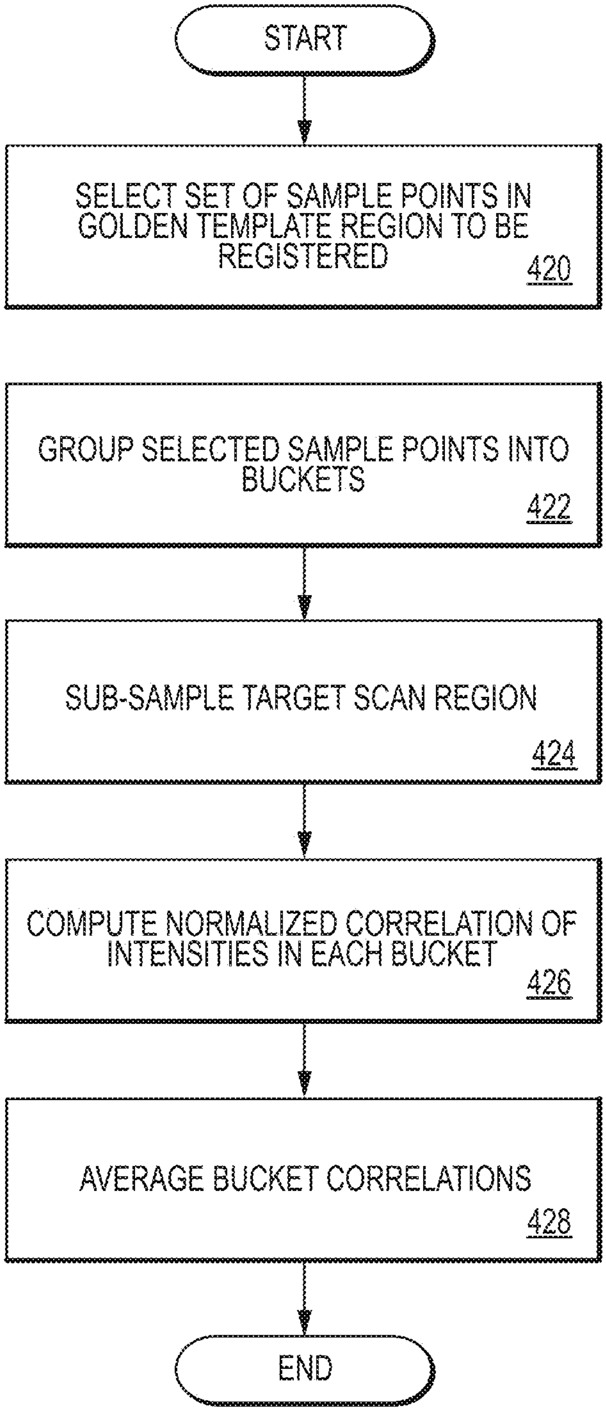
FIG. 20 depicts a flowchart illustrating one method for computing a metric for the registration framework of FIG. 18.

FIG. 20 depicts a flowchart illustrating one method for computing the metric used by the registration operations described above. For a particular registration operation, the metric may be computed in the same way, but the metric may have different parameters specified for the particular registration operation. The metric may be referred to herein as “local correlation in sample points.” Initially, operation 420 selects a set of sample points in the golden template region to be registered.

For the translation and similarity transformations, the sample points may be selected as follows. Initially, a rectilinear grid of L×M×N that covers the whole bone in 3D space may be used. L, M, and N may vary from one to 16. In one embodiment, an eight by eight grid in every image slice may be used to select uniform sample points in the grown golden region of the golden template. For each grid cell, the first sample point is selected. If the sample point falls within the grown golden region, it is used. If the sample point falls outside the golden region, it is discarded.

For the affine and spline transformations, the sample points may be determined by randomly selecting one out of every 32 points in the boundary golden region of the MRI slice.

Next, operation 422 groups the selected points into buckets. In one embodiment, buckets may be formed as follows. First, the 3D space may be subdivided into cells using a rectilinear grid. Sample points that belong to the same cell are placed in the same bucket. It should be noted that sample points may be grouped into buckets to compensate for non-uniform intensities in the MRI scan.

For example, MRI scan data may be brighter in the middle of the image and darker towards the edges of the image. This brightness gradient typically is different for different scanners and may also depend on other parameters including elapsed time since the scanner was last calibrated. Additionally, high aspect ratio voxels typically result in voxel volume averaging. That is, cortical bone may appear very dark in areas where its surface is almost perpendicular to the slice and generally will not be averaged with nearby tissues. However, cortical bone may appear as light gray in the areas where its surface is almost tangent to the slice and generally may be averaged with a large amount of nearby tissues.

Next, operation 424 sub-samples the target MRI slice. Sub-sampling the target space generally has the effect of smoothing the metric function. This may remove tiny local minima such that the local minimization algorithm converges to a deeper minimum. In one embodiment, during operations 410 and 412 (of FIG. 19), each slice may be sub-sampled with an eight by eight grid. During operations 414 and 416 (of FIG. 19), each slice may be sub-sampled with a four by four grid. That is, during the sub-sampling, one point from every grid cell may be selected (e.g., the first point) and the remaining points in the grid cells may be discarded.

Next, operation 426 computes a correlation of the intensities of the points in each bucket and their corresponding points in the target MRI scan (after mapping). The correlation (NC) metric may be expressed as:

$$NC(A, B) = \frac{\sum_{i=1}^{N} A_i B_i}{\sqrt{\left(\sum_{i=1}^{N} A_i^2\right)\left(\sum_{i=1}^{N} B_i^2\right)}} \frac{N\sum A_i B_i - \sum A_i \sum B_i}{\sqrt{N\sum A_i^2 - \left(\sum A_i\right)^2}\sqrt{N\sum B_i^2 - \left(\sum B_i\right)^2}}$$

where $A_i$ is the intensity in the $i^{th}$ voxel of image A, $B_i$ is the intensity in the corresponding $i^{th}$ voxel of image B and N is the number of voxels considered, and the sum is taken from i equals one to N. It should be appreciated that the metric may be optimal when image differences are minimized (or when the correlation of image similarities is maximized). The NC metric generally is insensitive to intensity shifts and to multiplicative factors between the two images and may produce a cost function with sharp peaks and well defined minima.

Finally, operation 428 averages the correlations computed in every bucket with weights proportional to the number of sample points in the bucket.

It is to be appreciated that the above process for computing the metric may compensate for non-uniform intensities, for example, those described above with respect to FIGS. 3A-3C, in the MRI scan data.

During the registration process, an optimizer may be used to maximize image similarity between the reference image and target image by adjusting the parameters of a given transformation model to adjust the location of reference image coordinates in the target image. In one embodiment, the optimizer for a registration operation may use the transformed image (e.g., the transformed golden template) from the previous registration operation as its initial approximation. Then, local optimization techniques may be used to search for a local optimum near the initial starting approximation. This may be done so that any potential matches farther away from the feature of interest (e.g., the femur or tibia in a knee joint) reliably found in an earlier operation may be eliminated.

For the translation transformation, an exhaustive search may be performed using a grid 10×10×10 of size 5-millimeter translation vectors. A translation for every vector in the grid may be performed and the translation providing a maximum local correlation in sample points may be selected as the optimum translation.

For the similarity transformation, a regular step gradient descent optimizer may be used by one embodiment. A regular step gradient descent optimizer typically advances transformation parameters in the direction of the gradient and a bipartition scheme may be used to compute the step size. The gradient of a function typically points in the direction of the greatest rate of change and whose magnitude is equal to the greatest rate of change.

For example, the gradient for a three dimensional space may be given by:

$$\nabla f(x, y, z) = \left(\frac{\partial f}{\partial x}, \frac{\partial f}{\partial y}, \frac{\partial f}{\partial z}\right).$$

That is, the gradient vector may be composed of partial derivatives of the metric function over all the parameters defining the transform. In one embodiment the metric function may be a composition of an outer and N inner functions. The outer function may compute a metric value according to operations 426 and 428 given the vectors $\{A_i\}$ and $\{B_i\}$. The N inner functions may map N sample points from the fixed (reference) image $A_i$ into the target image $B_i$ using the transform and evaluate intensities of the target image $B_i$ in the mapped points. Each of the inner functions generally depends on the transform parameters as well as on the point in the "from" space to which the transform is applied. When computing the partial derivatives, the chain rule for computing a derivative of the function composition may be used.

To find a local minimum, parameter steps may be taken in the direction of the negative of the metric gradient (or the approximate gradient) over the transform parameter space at the current point. This generally optimizes the metric which typically has a local minimum when features of the reference image mapped into corresponding features of the target image have minimal misalignment).

The initial center of rotation for the similarity transformation (e.g., operation 382 of FIG. 17) may be specified as the center of a bounding box (or minimum sized cuboid with sides parallel to the coordinate planes) that encloses the feature (e.g., a bone) registered in the translation registration (e.g., operation 380 of FIG. 17). Scaling coefficients of approximately 40-millimeters may be used for the scaling parameters when bringing them together with translation parameters. It is to be appreciated that the gradient computation generally relies on a customized metric function in the parameter space, due to the fact that with a similarity transformation, the transform parameters do not have the same dimensionality. The translation parameters have a dimension of millimeters, while the parameters for rotational angles and scaling do not have a dimension of millimeters. In one embodiment, a metric ρ may be defined as $$\rho = SQRT\left(X^2 + Y^2 + Z^2 + (\text{40-millimeter} * A1)^2 + \ldots\right)$$

where X is the translation along the x axis, Y is the translation along the y axis, Z is the translation along the z axis, A1 is the first rotation angle, etc. A scaling coefficient of approximately 40-millimeters may be used because it is approximately half the size of the bone (in the anterior/posterior and medial/lateral directions) of interest and results in a point being moved approximately 40-millimeters when performing a rotation of one radian angle.

In one embodiment, a maximum move of 1.5-millimeters may be specified for every point, a relaxation factor may be set to 0.98 and a maximum of 300 iterations may be performed to determine the parameters of the similarity transformation that results in minimal misalignment between the reference image and target MRI scan.

For the affine transformation, a regular step gradient optimizer may be used by one embodiment. Scaling coefficients of approximately 40-millimeters may be used for the matrix coefficients variations when bringing them together with translation parameters. A maximum 1.0-millimeter move for every point may be set for each iteration, the relaxation factor may be set to 0.98 and a maximum of 300 iterations may be performed to determine the parameters of the affine transformation that results in minimal misalignment.

For the B-spline transformation, a modified regular step gradient descent optimizer may be used by one embodiment when searching for the best B-spline deformable transformation. An MRI image gradient may often follow the bone surface in diseased areas (e.g., where the bone contact surface is severely damaged and/or where osteophytes have grown). Such a gradient may cause deformations of the golden template that would introduce large distortions in the segmented bone shape.

In one embodiment, the MRI image gradient may be corrected for such deformations by computing a normal to golden boundary vector field where every vector points towards the closest point in the golden template shape found during the affine transformation (e.g., operation 384 of FIG. 17). This may be done using a distance map (also referred to as a distance transform). A distance map supplies each voxel of the image with the distance to the nearest obstacle voxel (e.g., a boundary voxel in a binary image). In one embodiment, the gradient of the signed distance map of the golden tibia region may be mapped using the affine transformation found in operation 384 of FIG. 17. In one embodiment, a signed Danielsson distance map image filter algorithm may be used. Then, the MRI image gradient may be projected onto the vector field to obtain the corrected gradient field. This corrected gradient field is parallel to the normal to golden boundary field and typically defines a very thin subset of the set of B-spline transformations that may be spanned during the optimization.

Additionally, rather than computing one gradient vector for the transform space and taking a step along it, a separate gradient may be computed for every spline node. In one embodiment, order three B-splines (with J×K×L control nodes) may be used and J×K×L gradients may be computed, one for each control point. At every iteration, each of the spline nodes may be moved along its respective gradient. This may allow the spline curve to be moved in low contrast areas at the same time it is moved in high contrast areas. A relaxation factor of 0.95 may be used for each spline node. A maximum move of one-millimeter may be set for every point during an iteration and a maximum of 20 iterations may be performed to find the parameters of the B-spline transformation that provides minimal misalignment of the golden tibia region mapped into the target MRI scan.

Figure 21:
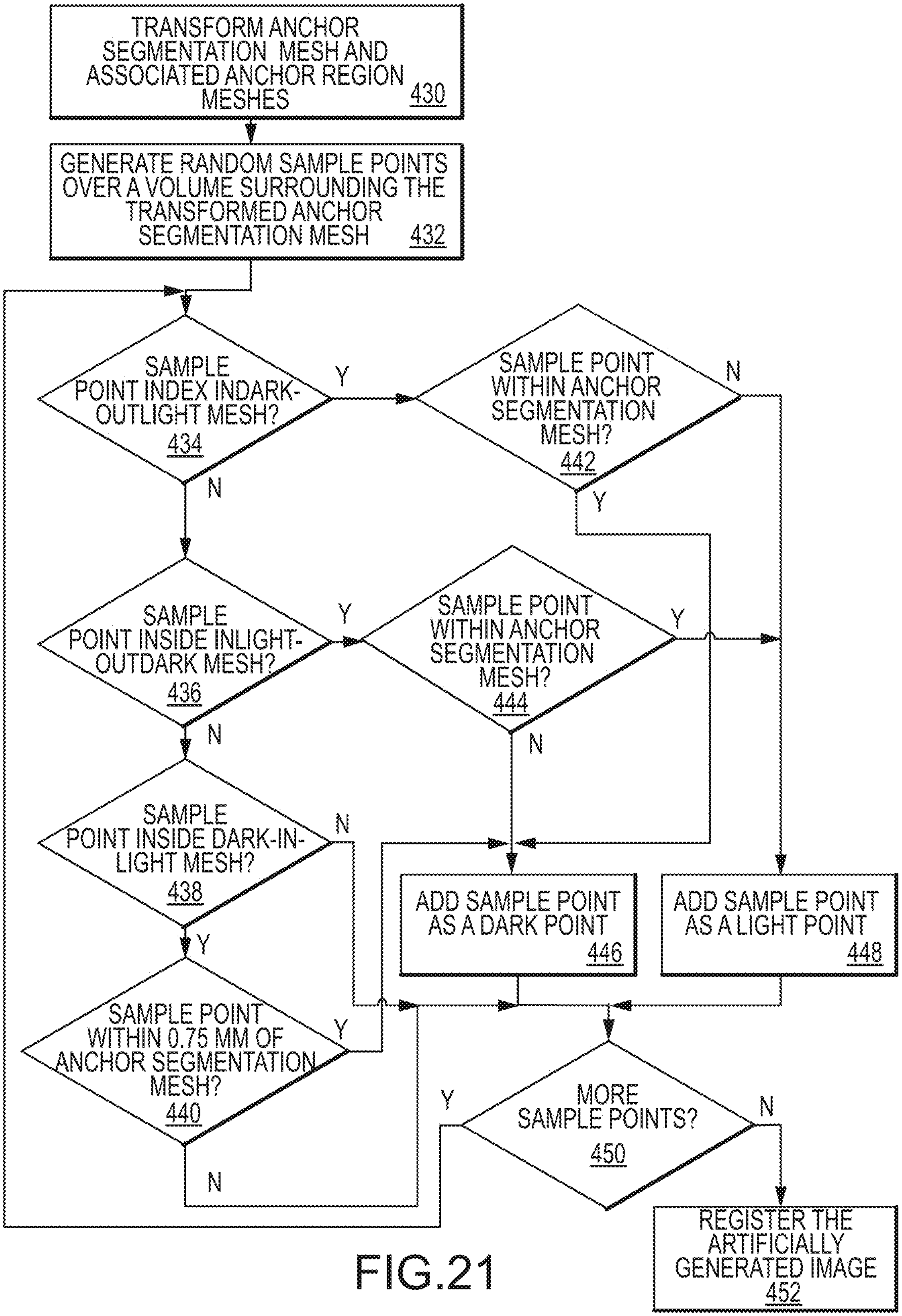
FIG. 21 depicts a flowchart illustrating one method for refining the registration results using anchor segmentation and anchor regions.

Once the position and shape of the feature of interest of the joint has been determined using image registration (operation 370 of FIG. 16), the registration results may be refined using anchor segmentation and anchor regions (operation 372 of FIG. 16). FIG. 21 depicts a flowchart illustrating one method for refining the registration results using anchor segmentation and anchor regions. Typically, during this operation, one more registration may be done using an artificially generated image for the fixed image 394 of the registration framework 390. Use of an artificial image may improve the overall segmentation by registering known good regions that typically do not change from scan to scan to correct for any errors due to diseased and/or low contrast areas that otherwise may distort the registration.

Additionally, the artificial image may be used to increase surface detection precision of articular surfaces and shaft middle regions. The image slices typically have higher resolution in two dimensions (e.g., 0.3-millimeter in the y and z dimensions) and lower resolution in the third dimension (e.g., 2-millimeters in the x dimension). The articular surfaces and shaft middle regions typically are well defined in the image slices due to these surfaces generally being perpendicular to the slices. The surface detection precision may be improved using a combination of 2D and 3D techniques that preserves the in-slice precision by only moving points within slices rather than between slices. Further, a 3D B-spline transform may be used such that the slices are not deformed independently of one another. Since each slice may not contain enough information, deforming each slice independently may result in the registration finding the wrong features. Instead, the slices as a whole may be deformed such that the registration remains near the desired feature. While each slice may be deformed differently, the difference in deformation between slices generally is small such that the changes from one slice to the next are gradual.

In one embodiment, the artificial image may comprise a set of dark and light sample points that may be used by the metric. All dark points in the artificial image may have the same intensity value (e.g., 100) and all light points in the artificial image may have the same intensity value (e.g., 200). It should be appreciated that the correlations are generally insensitive to scaling and zero shift. Thus, any intensity values may be used as long as the dark intensity value is less than the light intensity value.

Initially, operation 430 may apply the cumulative registration transform (computed by operation 370 of FIG. 16) to an anchor segmentation mesh and its three associated anchor region meshes (e.g., InDark-OutLight mesh, InLight-OutDark mesh and Dark-in-Light mesh) to generate a transformed anchor segmentation mesh and associated transformed anchor region meshes (transformed InDark-OutLight anchor mesh, transformed InLight-OutDark anchor mesh and transformed Dark-in-Light anchor mesh) that lie in a space identical to the target image space.

Then, operation 432 generates random sample points lying within a thin volume surrounding the transformed anchor segmentation mesh surface. In one embodiment, this may be a volume having an outer boundary defined by the anchor segmentation mesh surface plus 1.5-millimeters and an inner boundary defined by the anchor segmentation mesh surface minus 1.5-millimeters, which may be referred to herein as the 1.5-millimeter neighborhood. The random sample points may be generated such that they are within the image slices of the target scan but not between the slices. For example, the image slices may be transversal to the x-axis with a spacing of 2-millimeters (at x-axis locations 0.0, 2.0, 4.0, . . . ). When a sample point is selected, its x-coordinate may be one of 0.0, 2.0, 4.0, etc. but may not be 1.7, 3.0, or some non-multiple of 2.0.

In one embodiment, voxels may be marked in every image slice that belong to the 1.5-millimeter neighborhood as follows. First, the intersection of the transformed anchor mesh with every image slice may be found. It should be appreciated that the intersection of the anchor mesh with an image slice may be a polyline(s). Then, in each image slice, the polyline segments may be traversed and all pixels that intersect with the mesh may be marked. Next, a Dilate filter may be applied to the marked pixels of each image slice using a radius of 1.5-millimeters. The Dilate filter typically enlarges the marked region by adding all the points that lie within a 1.5-millimeter distance from the originally marked points.

After operation 432, operation 434 determines if a sample point lies inside the transformed InDark-OutLight mesh surface. If operation 434 determines that the sample point lies inside the transformed InDark-OutLight mesh surface, then operation 442 is performed. If operation 434 determines that the sample point does not lie inside the transformed InDark-OutLight mesh surface, then operation 436 is performed.

Operation 442 determines if the sample point lies inside the transformed anchor segmentation mesh surface. If operation 442 determines that the sample point lies inside the transformed anchor segmentation mesh surface, then operation 446 is performed. If operation 442 determines that the sample point does not lie inside the transformed anchor segmentation mesh surface, then operation 448 is performed.

Operation 436 determines if the sample point lies inside the transformed InLight-OutDark mesh surface. If operation 436 determines that the sample point lies inside the transformed InLight-OutDark mesh surface, then operation 444 is performed. If operation 436 determines that the sample point does not lie inside the transformed InLight-OutDark mesh surface, then operation 438 is performed.

Operation 444 determines if the sample point lies inside the transformed anchor segmentation mesh surface. If operation 444 determines that the sample point lies inside the transformed anchor segmentation mesh surface, then operation 448 is performed. If operation 444 determines sample point does not lie within the transformed anchor segmentation mesh surface, then operation 446 is performed.

Operation 438 determines if the sample point lies inside the transformed Dark-In-Light mesh surface. If operation 438 determines that the sample point lies inside the transformed Dark-In-Light mesh surface, then operation 440 is performed. If operation 438 determines that the sample point does not lie inside the transformed Dark-In-Light mesh surface, then operation 450 is performed.

Operation 440 determines if the sample point is within 0.75-millimeter of the surface of the transformed anchor segmentation mesh. If operation 440 determines that the sample point is within 0.75-millimeter of the surface of the transformed anchor segmentation mesh, then operation 446 is performed. If operation 440 determines that the sample point is not within 0.75-millimeter of the surface of the anchor segmentation mesh, then operation 450 is performed.

Operation 446 adds the sample point to the artificial image as a dark point. Then, operation 450 is performed.

Operation 448 adds the sample point to the artificial image as a light sample point. Then, operation 450 is performed.

Operation 450 determines if there are more randomly generated samples points to be added to the artificial image. If operation 450 determines that there are more randomly generated sample points to be added to the artificial image, then operation 434 is performed. If operation 450 determines that there are no more randomly generated sample points to be added to the artificial image, then operation 452 is performed.

Figure 22:
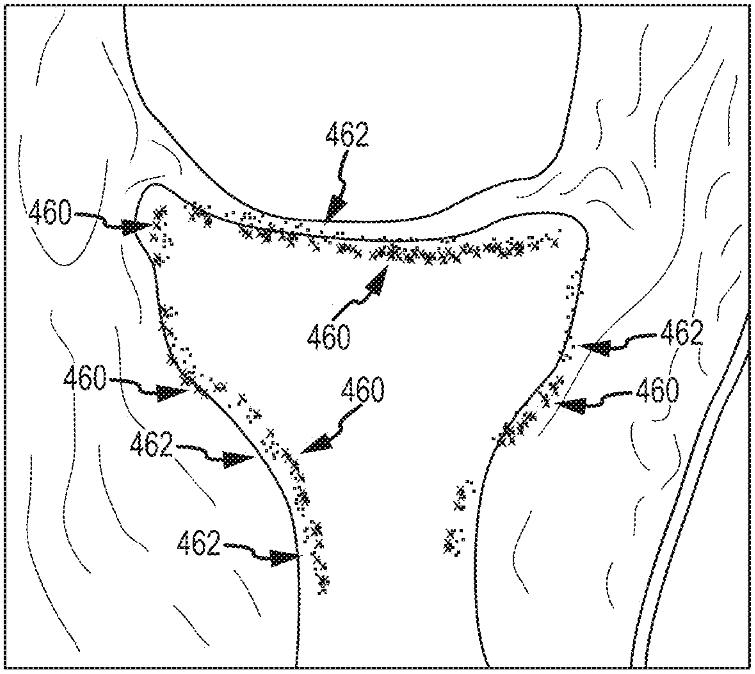
FIG. 22 depicts a set of randomly generated light sample points and dark sample points of a tibia.

FIG. 22 depicts a set of randomly generated light sample points 460 and dark sample points 462 over the target MRI 464. In one embodiment, approximately 8,000 sample points (light and dark) may be generated over the entire artificial image.

Referring again to FIG. 21, if operation 450 determines that there are no more randomly generated sample points to be added to the artificial image, operation 452 registers the set of dark and light points to the target MRI scan. This operation may perform a registration similar to the registration operation 196 (depicted in FIG. 17). In this transformation, a subset of B-spline deformable transformations may be performed that move points along their respective slices, but not transversal to their respective slices.

In a B-spline deformable transform, a translation vector for every control point (e.g., in the set of J×K×L control points) may be specified. To specify a transform that moves any point in 3D space along the y and z slice coordinates but not along the x coordinate, a restriction on the choice of translation vectors in the control points may be introduced. In one embodiment, only translation vectors with the x coordinate set equal to zero may be used to move points in the plane of the slice (e.g., the y and z directions) but not transversal to the slice (e.g., the x direction).

The use of anchor region meshes which typically are well pronounced in most image scans may reduce registration errors due to unhealthy areas and/or areas with minimal contrast differences between the feature to be segmented and surrounding image areas. For example, in the area where a healthy bone normally has cartilage, a damaged bone may or may not have cartilage. If cartilage is present in this damaged bone region, the bone boundary separates the dark cortical bone from the gray cartilage matter. If cartilage is not present in this area of the damaged bone, there may be white liquid matter next to the dark cortical bone or there may be another dark cortical bone next to the damage bone area. Thus, the interface from the cortical bone to the outside matter in this region of the damaged bone typically varies from MRI scan to MRI scan. In such areas, the interface between the cortical and the inner cancellous bone may be used as an anchor region.

The use of a subset of B-Spline deformable transforms may reduce errors due to the 2-millimeter spacing between image slices.

Figure 23:
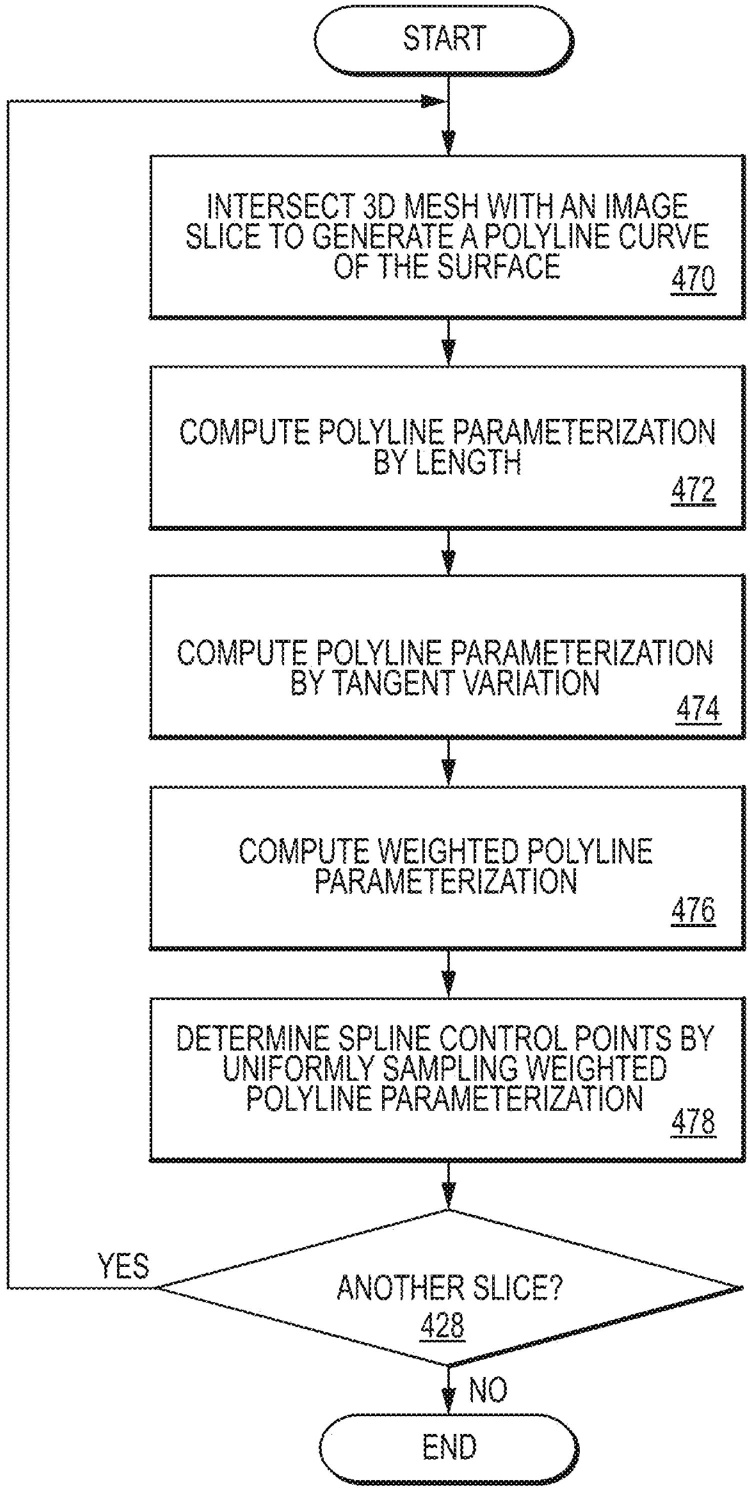
FIG. 23 depicts a flowchart illustrating one method for generating spline curves to outline features of interest in each target MRI slice.

FIG. 23 depicts a flowchart illustrating one method for generating spline curves outlining the surface of a feature of interest in each target MRI slice (e.g., operation 376 of FIG. 16). Initially, operation 470 intersects the generated 3D mesh model of the feature surface with a slice of the target scan data. The intersection defines a polyline curve of the surface of the feature (e.g., bone) in each slice. Two or more polyline curves may be generated in a slice when the bone is not very straightly positioned with respect to the slice direction.

A polyline curve is a piecewise linear approximation to a curved feature shape. Generally, this curve should be easy to manipulate with a set of control points. The polyline curve may have many segments, making it more difficult to manipulate the polyline curve (e.g., during operation 254 or 260 of FIG. 6). One embodiment may generate one or more Kochanek splines from the polyline curve. Each spline typically has a smaller number of control points and typically fits the polyline curve with about 0.2-millimeter deviation. Generally, a Kochanek spline may have more control points along the high curvature regions of the polyline curve and fewer control points along low curvature regions (i.e., where the curve tends to be flatter) of the polyline curve.

Figure 24:
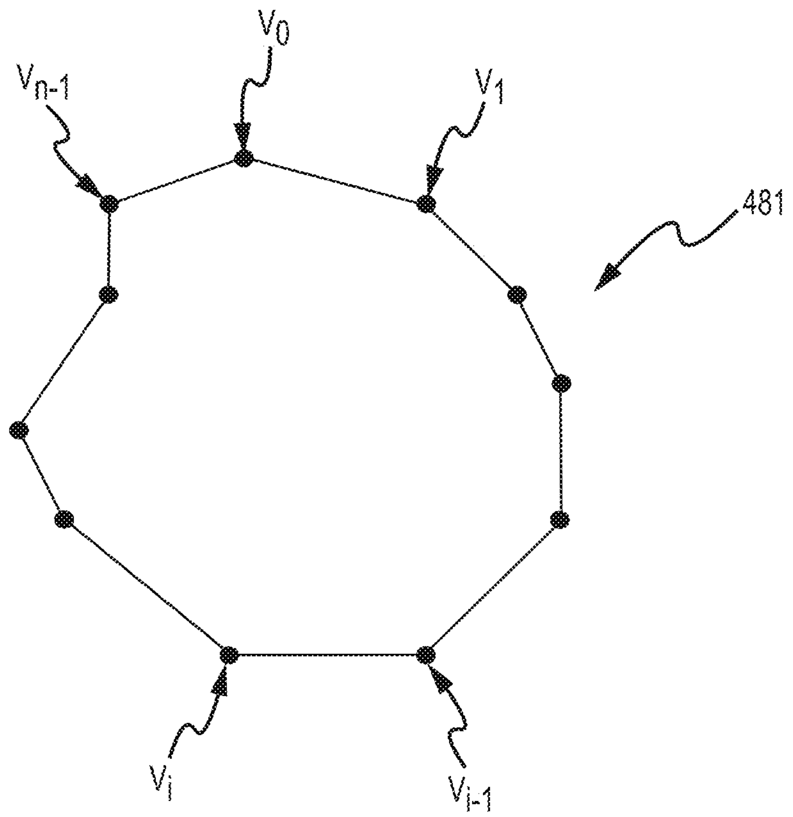
FIG. 24 depicts a polyline curve with n vertices.

Once a polyline curve has been generated, operation 472 may compute a polyline parameterization, $L_i$, as a function of the polyline's length. FIG. 24 depicts a polyline curve 48I with n vertices, $V_0, V_1, \ldots V_{i-1}, V_i \ldots V_{n-1}$. Note that vertex $V_0$ follows vertex $V_{n-1}$ to form a closed contour curve. The length of a segment connecting vertices $V_{i-1}$ and $V_i$ may be denoted by $\Delta L_i$ such that the length parameterization, $L_i$, of the polyline at vertex $V_i$ may be expressed as:

$$L_i = \Delta L_0 + \Delta L_1 + \ldots + \Delta L_i.$$

Next, operation 474 may compute a polyline parameterization, $A_i$, as a function of the polyline's tangent variation. The absolute value of the angle between a vector connecting vertices $V_{i-1}$ and $V_i$ and a vector connecting vertices $V_i$ and $V_{i+1}$ may be denoted by $\Delta A_i$ such that the tangent variation parameter A1 at vertex $V_i$ may be expressed as:

$$A_i = \Delta A_0 + \Delta A + \ldots + \Delta A_i.$$

Then, operation 476 determines a weighted sum parameterization of the polyline length and tangent variation parameterizations. In one embodiment the weighted sum parameterization, $W_i$, at vertex $V_i$ may be computed as:

$$W_i = \alpha * L_i + \beta * A_i$$

where $\alpha$ may be set to 0.2 and $\beta$ may be set to 0.8 in one embodiment.

Then, operation 478 may perform a uniform sampling of the polyline using the W parameterization results determined by operation 476. In one embodiment, a spacing interval of approximately 3.7 of the W parameter value may be used for positioning K new sample points. First, K may be computed as follows:

$$K = \text{ROUND}(W_n/3.7).$$

That is, the W parameter value, which is the last computed value $W_n$, may be divided by 3.7 and the result rounded to the nearest integer to get the number of new sample points. Then, the spacing of the sample points, $\Delta W$ may be computed as:

$$\Delta W = W_n/K.$$

Finally, the K new sample points, which are uniformly spaced, may be positioned at intervals $\Delta W$ of the parameter W. The resulting sample points may be used as control points for the Kochanek splines to convert the polyline into a spline. A Kochanek spline generally has a tension, a bias and a continuity parameter that may be used to change the behavior of the tangents. That is, a closed Kochanek spline with K control points typically is interpolated with K curve segments. Each segment has a starting point, an ending point, a starting tangent and an ending tangent. Generally, the tension parameter changes the length of the tangent vectors, the bias parameter changes the direction of the tangent vectors and the continuity parameter changes the sharpness in change between tangents. In certain embodiments, the tension, bias and continuity parameters may be set to zero to generate a Catmull-Rom spline.

In one embodiment, operation 478 may perform a linear interpolation of $W_i$ and $W_{i+1}$ to locate a sample point that lies between $W_i$ and $W_{i+1}$. The interpolated value of W may be used to determine the corresponding sample location in the segment connecting vertices $V_i$ and $V_{i+1}$.

In certain embodiments, operation 478 may divide the W parameter value by six to obtain the new number of sample points K. That is, $$K = \text{ROUND}(W_n/6).$$

Then, a measure of closeness (i.e., how closely the spline follows the polyline) may be computed as follows. First, the spline is sampled such that there are seven sample points in every arc of the spline (i.e., 7*K sample points). Then, the sum of the squared distances of the sample points to the polyline may be computed. Next, the coordinates of the K control points are varied (i.e., two*K parameters). Then, a local optimization algorithm is used to find the closest spline. If the closest spline found during the optimization is not within a certain precision (e.g., within approximately 0.4-millimeter of the polyline), then the number of control points, K, may be increased by one. The new number of control points may be uniformly distributed along the W parameter, and another optimization performed to find the new closest spline. Generally one to two optimizations provide a spline that follows the polyline with the desired degree of precision (e.g., within approximately 0.2-millimeter).

Finally, operation 480 determines if a spline curve(s) should be generated for another image slice. If operation 480 determines that a spline curve should be generated for another slice, then operation 472 is performed. If operation 480 determines that there are no more image slices to be processed, the method terminates.

As discussed above, in one embodiment, the output of the segmentation may be a triangular mesh (e.g., a 3D surface model) of the segmented bone(s) of a joint (e.g., the femur and tibia of a knee joint). The mesh generated generally represents a watertight surface that closely follows the segmentation contour curves of the slices, smoothly interpolates between the segmentation contour curves, and may have a low triangular count.

In one embodiment, a triangular mesh may be generated as follows. The segmentation data may be represented in 3D using (x, y, z) coordinates with the image slices transversal to the x direction. Thus, the segmentation contours lie in yz planes with fixed values of x. Initially, an in-slice distance image may be computed for each segmented slice. The value of each (y, z) pixel in an in-slice distance image is the distance to the closest point in the contours when the point is located inside one of the contours and is the inverse (i.e., negative) of the distance to the closest point in the contours when the point is outside all of the contours.

Then, a marching cubes algorithm may be applied to the in-slice distance images to generate the mesh. The marching cubes algorithm is a computer algorithm for extracting a polygonal mesh of an isosurface (i.e., the contours) from a three-dimensional scalar field (or voxels). The algorithm typically proceeds through the voxels, taking eight neighbor voxels at a time (thus forming an imaginary cube) and determines the polygon(s) needed to represent the part of the isosurface (i.e., contour) that passes through the imaginary cube. The individual polygons are then fused into the desired surface. The generated mesh generally passes through the zero level of the signed distance function in each slice such that the mesh lies close to the contours.

It is to be appreciated that the image resolution in the y and z directions typically determines how well the zero level of the signed distance function approximates the original contours and may also determine the triangular count in the resulting mesh. In one embodiment, a voxel size of 1.5-millimeters in the y and z directions may be used. This typically yields deviations within 0.1-millimeter of the original contours and produces a smooth mesh.

In one embodiment, a smoothing operation may be performed in the x direction (i.e., transversal to the image slices) to compensate for surface waviness that may have been introduced when the automatically generated contours were adjusted (e.g., during operation 260 of FIG. 6). Such waviness may occur in regions of an image slice where there is minimal contrast variation and the curve is positioned by the technician. Typically a smooth best guess mesh in uncertain areas may be desired when generating a planning model that may be used to locate the position of an implant. Alternatively, a smooth overestimation may be desired in uncertain areas such as in an arthritic model used to create a jig.

In one embodiment, simple smoothing may be used and the amount of smoothing (i.e., how much a voxel value may be modified) may be controlled by two user specified parameters, MaxUp and MaxDown. After an average is computed for a voxel, it is clamped using these values to limit the amount of smoothing. The smoothing operation typically does not change the image much in areas where the image contrast is good. For smooth best guess averaging in uncertain areas, MaxUp and MaxDown may each be set to 1 millimeter. For smooth overestimation averaging in uncertain regions, MaxUp may be set to 2-millimeters and MaxDown may be set to 0-millimeter.

Figure 25:
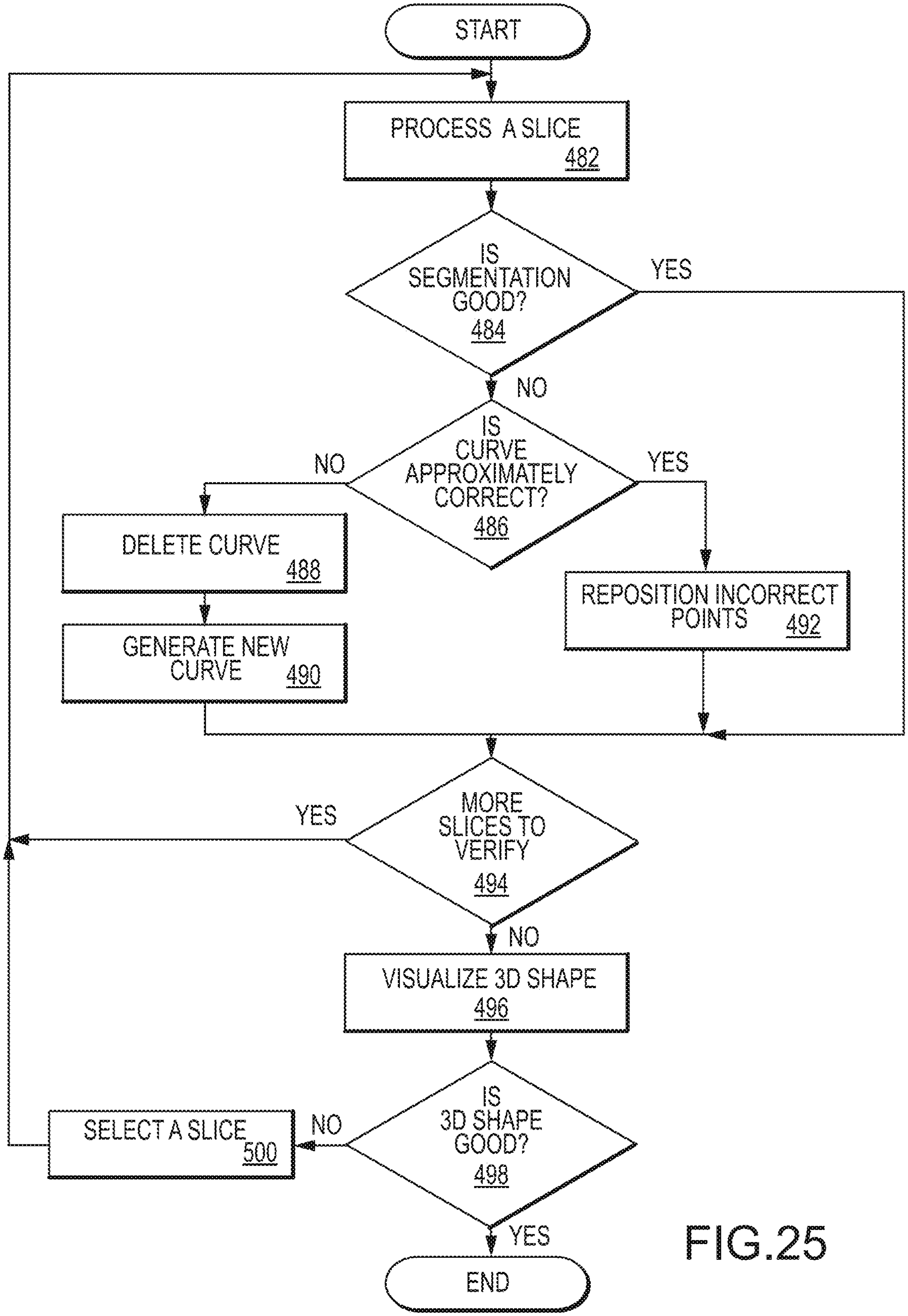
FIG. 25 depicts a flowchart illustrating one method for adjusting segments.

The operation of adjusting segments of the segmentation process will now be described with reference to FIG. 25, which depicts a flowchart for one method of adjusting segments (e.g., operation 254 or operation 260 of the flowchart depicted in FIG. 6). In one embodiment, the segmentation data may be manually adjusted by a trained technician sitting in front of a computer 6 and visually observing the automatically generated contour curves in the image slices on a computer screen 9. By interacting with computer controls 11, the trained technician may manually manipulate the contour curves. The trained technician may visually observe all of the contours as a 3D surface model to select an image slice for further examination.

Initially, in operation 482 a slice is selected for verification. In one embodiment, the slice may be manually selected by a technician.

Next, operation 484 determines if the segmentation contour curve in the selected slice is good. If operation 484 determines that the segmentation contour curve is good, then operation 494 is performed. If operation 484 determines that the segmentation contour curve is not good, then operation 486 is performed.

Operation 486 determines if the segmentation contour curve is approximately correct. If operation 486 determines that the contour curve is approximately correct, then operation 492 is performed.

Figure 26:
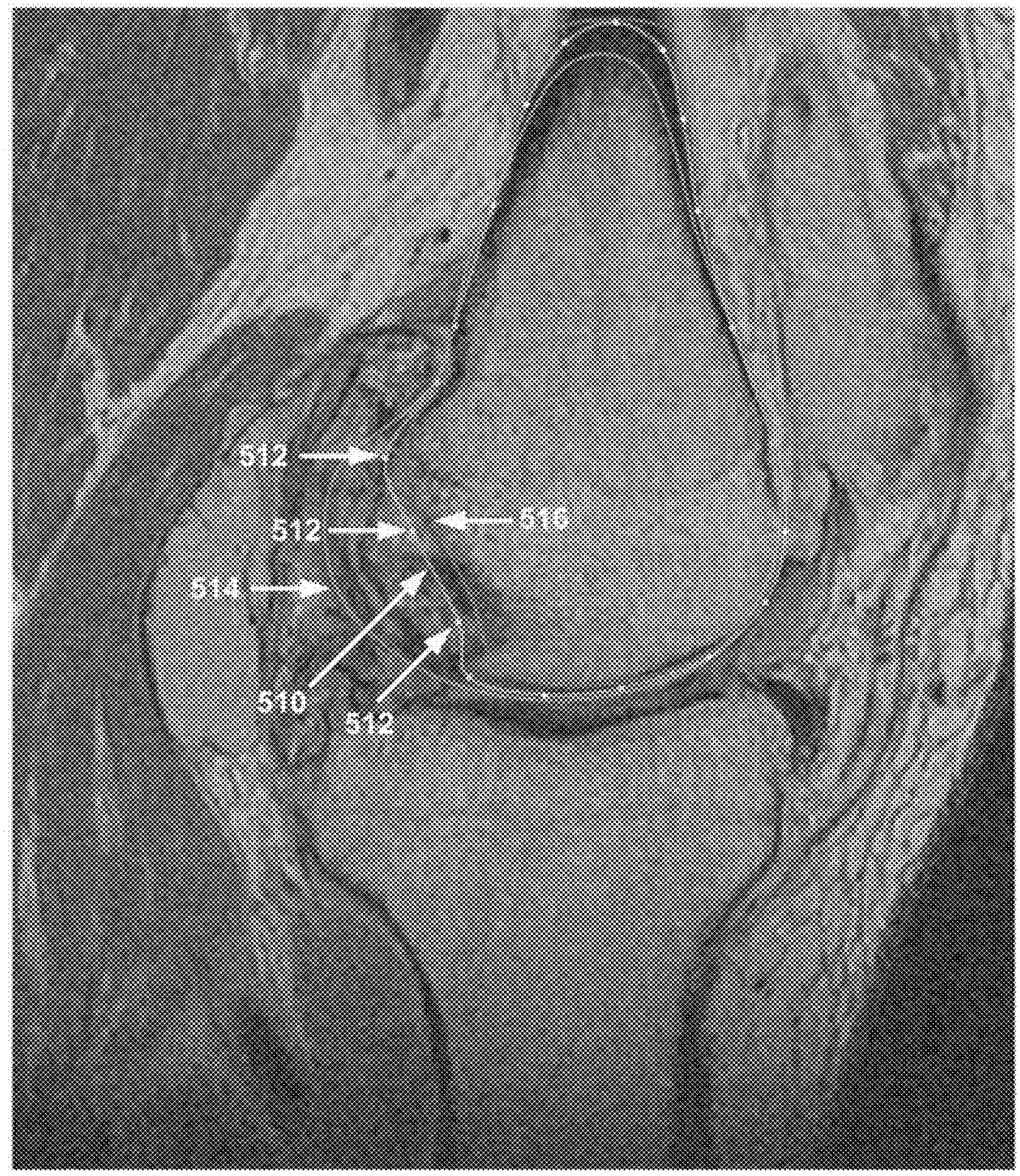
FIG. 26 is a sagittal plane image slice depicting a contour curve with control points outlining a femur with superimposed contour curves of the femur from adjacent image slices.

In operation 492 incorrect points of the segmentation contour curve may be repositioned. In one embodiment this may be performed manually by a trained technician. It is to be appreciated that it may be difficult for the technician to determine where the correct contour curve should be located in a particular slice. This may be due to missing or unclear bone boundaries and/or areas with little contrast to distinguish image features. In one embodiment, a compare function may be provided to allow the technician to visually compare the contour curve in the current slice with the contour curves in adjacent slices. FIG. 26 depicts an image showing the contour curve 510 (e.g., a spline curve) with control points 512 of the contour curve 510 for the current image slice as well the contour curves 514, 516 of the previous and next image slices, respectively, superimposed on the current image slice.

It may be difficult to determine where the correct segmentation contour curve should be located due to missing or unclear bone boundaries due to the presence of unhealthy areas, areas with limited contrast differences, and/or voxel volume averaging. When visually comparing adjacent slices, the technician may visualize the data in 2D planes (xy, yz, and xz) and in 3D. In one embodiment, the technician may select an area for examination by positioning a crosshair on a location in any window and clicking a mouse button to select that image point. The crosshair will be placed at the desired point and may be used to indicate the same location when the data is visualized in each window.

The technician may use the spline control points to manipulate the shape of the curve. This may be done by using a mouse to click on a control point and dragging it to a desired location. Additionally, the technician may add or delete spline curve control points. This may be done by using a mouse to select two existing control points between which a control point will be inserted or deleted. Alternatively, the technician may use a mouse cursor to point to the location on the curve where a control point is to be inserted. In one embodiment, by pressing the letter I on a keyboard and then positioning the cursor at the desired location, clicking the left mouse button will insert the control point. A control point may be deleted by pressing the letter D on the keyboard and then positioning the cursor over the desired control point to be deleted. The selected control point will change color. The selected control point will be deleted when the left mouse button is clicked.

Referring again to FIG. 25, if operation 486 determines that the contour curve is not approximately correct, operation 488 is performed to delete the curve. Then, operation 490 is performed.

Operation 490 generates a new segmentation contour curve for the image slice. In one embodiment, a technician may use a spline draw tool to insert a new spline curve. With the spline draw tool, the technician may click on consecutive points in the current slice to indicate where the spline curve should be located and a spline curve is generated that passes through all of the indicated points. A right mouse click may be used to connect the first and last points of the new spline curve. Alternatively, the technician may use a paste command to copy the spline curve(s) from the previous slice into the current slice. The spline control points may then be manipulated to adjust the spline curves to follow the feature in the current image slice.

In another embodiment, a paste similar command may be used by the technician to copy the spline curve from the previous slice into the current slice. Rather than pasting a copy of the spline curve from the previous slice, the spline curve may be automatically modified to pass through similar image features present in both slices. This may be done by registering a region around the spline curve in the previous slice that is from about 0.7-millimeter outside of the curve to about 5.0-millimeter within the curve. Initially, this region is registered using an affine transformation. Then, the result of the affine transform may be used as a starting value for a B-Spline deformable transformation. The metric used for the transform may be the local correlation in sample points metric described previously. Typically, more sample points may be taken closer to the curve and fewer sample points taken farther away from the curve. Next, the spline control points may be modified by applying the final transformation found to the spline control points. Additionally, the trained technician may adjust from zero to a few control points in areas where the bone boundary changes a lot from the slice due to the bone being tangent to the slice or in areas of limited contrast (e.g., where there is an osteophyte growth). Then, operation 492 is performed.

Operation 494 determines if there are additional slices to be verified. If operation 494 determines that there are additional slices to be verified, operation 482 is performed.

If operation 494 determines that there are no more slices to be verified, then operation 496 is performed. Operation 496 generates a 3D surface model of the segmented bone.

Figure 27:
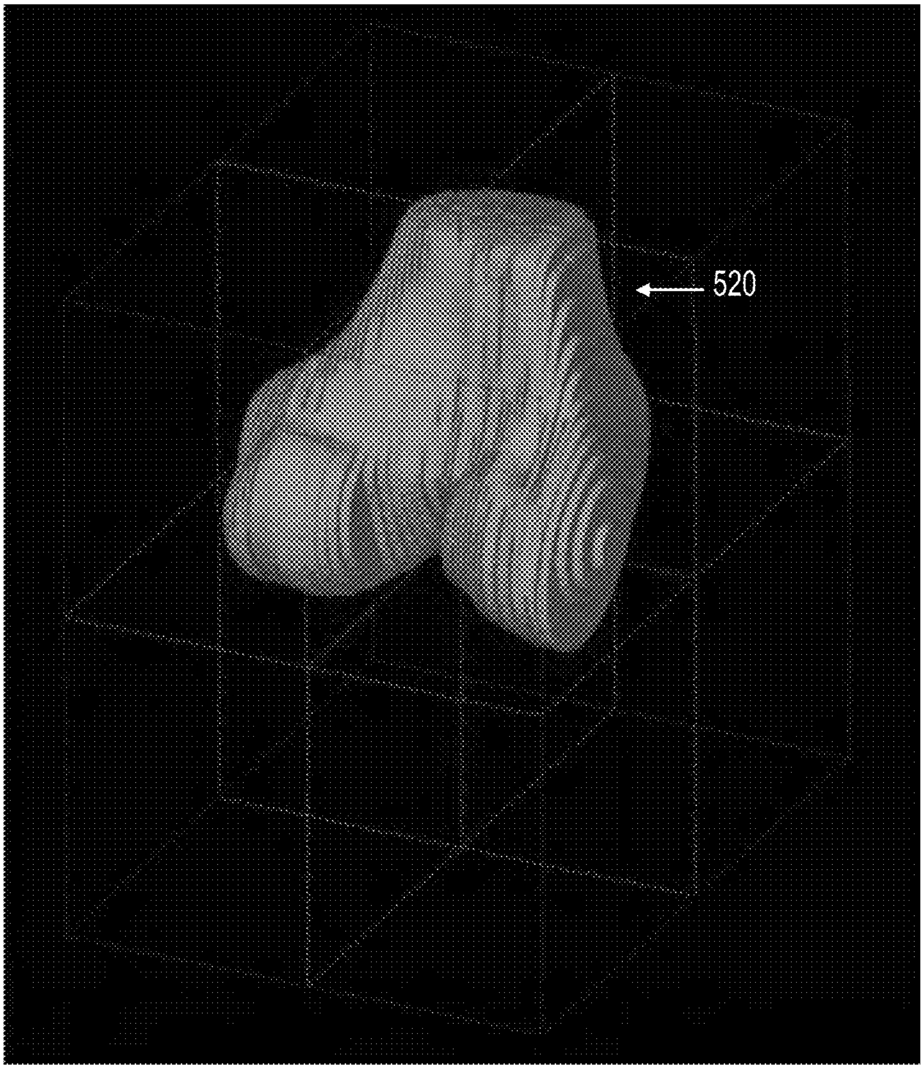
FIG. 27 depicts a 3D slice visualization of a femur showing the voxels inside of the spline curves.

Then, operation 498 determines if the 3D surface model is good. In one embodiment, a technician may manually determine if the 3D surface model is good. The technician may use a spline 3D visualization tool that generates a slice visualization showing the voxels inside all of the splines in 3D, as illustrated by the 3D shape 520 depicted in FIG. 27. This spline 3D visualization tool typically may be generated in real time to provide interactive updates to the technician as the spline curves are manually edited. Alternatively, a mesh visualization may be generated in response to a technician command. The mesh visualization typically generates a smooth mesh that passes close to all the spline curves, e.g., mesh 290 depicted in FIG. 9.

If operation 498 determines that the 3D model is not good, then operation 500 is performed. Operation 500 selects a slice lying in an area where the 3D shape is not good. In one embodiment, a technician may manually select the slice. Then, operation 482 is performed.

If operation 498 determines that the 3D model is good, then the method terminates.

The 3D surface models of the lower end of the femur and the upper end of the tibia of a patient's knee may be used to create arthroplasty jigs and/or implants. For example, the models may be used to create femur and tibia jigs that can be used with a patient's femur and tibia as disclosed in the various U.S. patent applications incorporated by reference herein in this Detailed Description and filed by Park and Park et al. Automatic segmentation of image data to generate 3D bone models may reduce the overall time required to perform a reconstructive surgery to repair a dysfunctional joint and may also provide improved patient outcomes.

B. Segmentation Using Landmarks of Scanner Modality Image Data to Generate 3D Surface Model of a Patient's Bone Now begins a discussion of an alternative embodiment of image segmentation. The alternative embodiment includes placing landmarks 777 (in FIG. 35A-FIG. 35H) on image contours. The landmarks 777 are then used to modify a golden bone model (e.g., golden femur or golden tibia), the resulting modified golden bone model being the output of segmentation.

Similar to the embodiment of image segmentation discussed above in section b. of this Detailed Discussion, in one version of the alternative embodiment of image segmentation, the 2D images 16 of the patient's joint 14 are generated via the imaging system 8 (see FIG. 1A and [block 100] of FIG. 1B). These images 16 are analyzed to identify the contour lines of the bones and/or cartilage surfaces that are of significance with respect to generating 3D models 22, 36, as discussed above in section a. of this Detailed Discussion with respect to [blocks 110 and 130] of FIGS. 1C and 1D. Specifically, a variety of image segmentation processes may occur with respect to the 2D images 16 and the data associated with such 2D images 16 to identify contour lines that are then compiled into 3D bone models, such as bone models 22, restored bone models 28, and arthritic models 36.

Algorithms and software are described in this Detailed Discussion for automatic and semi-automatic image segmentation. In the Detailed Description, alternative software tools and underlying methods are described, such alternative tools and methods helping a user to quickly generate bone models. Because the alternative software requires some user input such as, for example, initial Landmark positions, final verification and, in some instances, adjustment, this alternative segmentation process can be considered a semi-automatic segmentation process.

In some cases the alternative embodiment described in section c. of this Detailed Discussion may significantly reduce the user time spent on segmentation. In particular, compared to manual segmentation (where the user draws contour(s) by hand on each applicable slice for each applicable bone), the user time may be reduced by approximately five times when a user segments a planning model intended for communicating a preoperative planning model to a surgeon. For that purpose, a user may generate 3D bone models with high precision in particular areas and less precision in other areas. In some implementations, a user may get high precision (e.g., 0.5 mm) at well-defined bone contours in MRI images outside the implant regions and less precision (e.g., up to 2 mm) in the regions that will be replaced with implants by spending approximately 3-4 minutes in the user interface ("UI") setting landmarks for the algorithm. If improved precision is desired, the user may position more landmarks and thus spend more time in the UI.

In one embodiment, the software tool described in section c. of the Detailed Discussion is called "Segmentation using Landmarks". This tool may be implemented inside software application PerForm 1.0. A variety of processes and methods for performing image segmentation using landmarks are disclosed herein.

The imager 8 typically generates a plurality of image slices 16 via repetitive imaging operations. Depending on whether the imager 8 is a MRI or CT imager, each image slice will be a MRI or CT slice. As shown in FIG. 2A, the image slice may depict the cancellous bone 200, the cortical bone 202 surrounding the cancellous bone, and the articular cartilage lining portions of the cortical bone 202 of an object of interest of a joint, e.g., a femur 204 in a patient's knee joint 14. The image may further depict the cancellous bone 206, the cortical bone 208 of another object of interest in the joint, e.g., a tibia 210 of the knee joint 14. In one embodiment, each image slice 16 may be a two-millimeter 2D image slice.

One embodiment may segment one or more features of interest (e.g., bones) present in MRI or CT scans of a patient joint, e.g., knee, hip, elbow, etc. A typical scan of a knee joint may represent approximately a 100-millimeter by 150-millimeter by 150-millimeter volume of the joint and may include about 40 to 80 slices taken in sagittal planes. A sagittal plane is an imaginary plane that travels from the top to the bottom of the object (e.g., the human body), dividing it into medial and lateral portions. It is to be appreciated that a large inter-slice spacing may result in voxels (volume elements) with aspect ratios of about one to seven between the resolution in the sagittal plane (e.g., the y z plane) and the resolution along the x axis (i.e., each scan slice lies in the yz plane with a fixed value of x). For example, a two-millimeter slice that is 150-millimeters by 150-millimeters may be comprised of voxels that are approximately 0.3-millimeter by 0.3-millimeter by 2-millimeters (for a 512 by 512 image resolution in the sagittal plane).

In one embodiment, each slice may be a gray scale image with a resolution of 512 by 512 voxels where the voxel value represents the brightness (intensity) of the voxel. The intensity may be stored as a 16-bit integer resulting in an intensity range from 0 to 65,535, where 0 may represent black and 65,535 may represent white. The intensity of each voxel typically represents the average intensity of the voxel volume. Other embodiments may employ scans having higher or lower resolutions in the sagittal plane, different inter-slice spacing, or images where the intensity may be represented by a 24 bit vector (e.g., eight bits each for a red component, green component and blue component). Additionally, other embodiments may store intensity values as 8-bit or 32-bit signed or unsigned integers or floating point values.

Typical MRI and CT scan data generally provide images where parts of a bone boundary of interest may be well defined while other parts of the bone boundary may be difficult to determine due to voxel volume averaging, the presence of osteophyte growth, the presence of tissue having similar image intensities in neighboring areas to the object to be segmented, amongst other things. Such poor definition of parts of the bone boundary in the images may cause fully automated segmentation techniques to fail. For example, FIG. 2A depicts regions 212 within a slice where an object boundary may not be visible due to neighboring tissue having about the same intensity as the feature of interest. Depicted in FIG. 2B are regions 214 that may be extended into the slice from adjacent slices due to a high voxel aspect ratio. Depicted in FIG. 2C is a region 216 of the bone boundary 218 that may disappear or lose regularity when the bone boundary 218 is approximately tangent to the slice.

In one embodiment, a user may provide some additional input to the auto-segmentation algorithm, and the algorithm could use the additional user input for more accurate and faster segmentation of features of interest. For example, the additional user input may be a set of points on the boundary of the feature of interest. In the context of a knee procedure, the points might be on the Femur knee bone boundary or on the Tibia knee bone boundary. These can be called landmark points or simply landmarks 777.

In order for a user to provide particular landmark points, the software may allow loading MRI or CT image data, viewing and scrolling over image slices, specifying landmark points in the slices and editing them. The software may also allow visualization of the segmentation results (i.e., segmentation curves drawn in the image slices). The software may also generate a 3D model from 2D outlining curves in 2D slices.

In one embodiment, PerForm software may be used to provide functionality for loading MRI or CT scanned data, visualizing sagittal, coronal and axial slices and scrolling over them, drawing spline curves in slices, and generating a 3D mesh model passing through a set of spline curves. In one embodiment, a 3D mesh typically is a collection of vertices, edges, and faces that may define the surface of a 3D object. The faces may consist of triangles, quadrilaterals or other simple convex polygons. It should be appreciated that any other curve types may be employed instead of spline curves. For example, polyline curves may be used.

In one embodiment, a tool called "Segmentation using Landmarks" is added to PerForm software. Such a tool provides a UI for landmarks positioning and editing. The tool also provides a button "Segment", which invokes the segmentation algorithm. The algorithm uses 3D image and landmarks and generates spline curves outlining the required bone.

Figure 28:
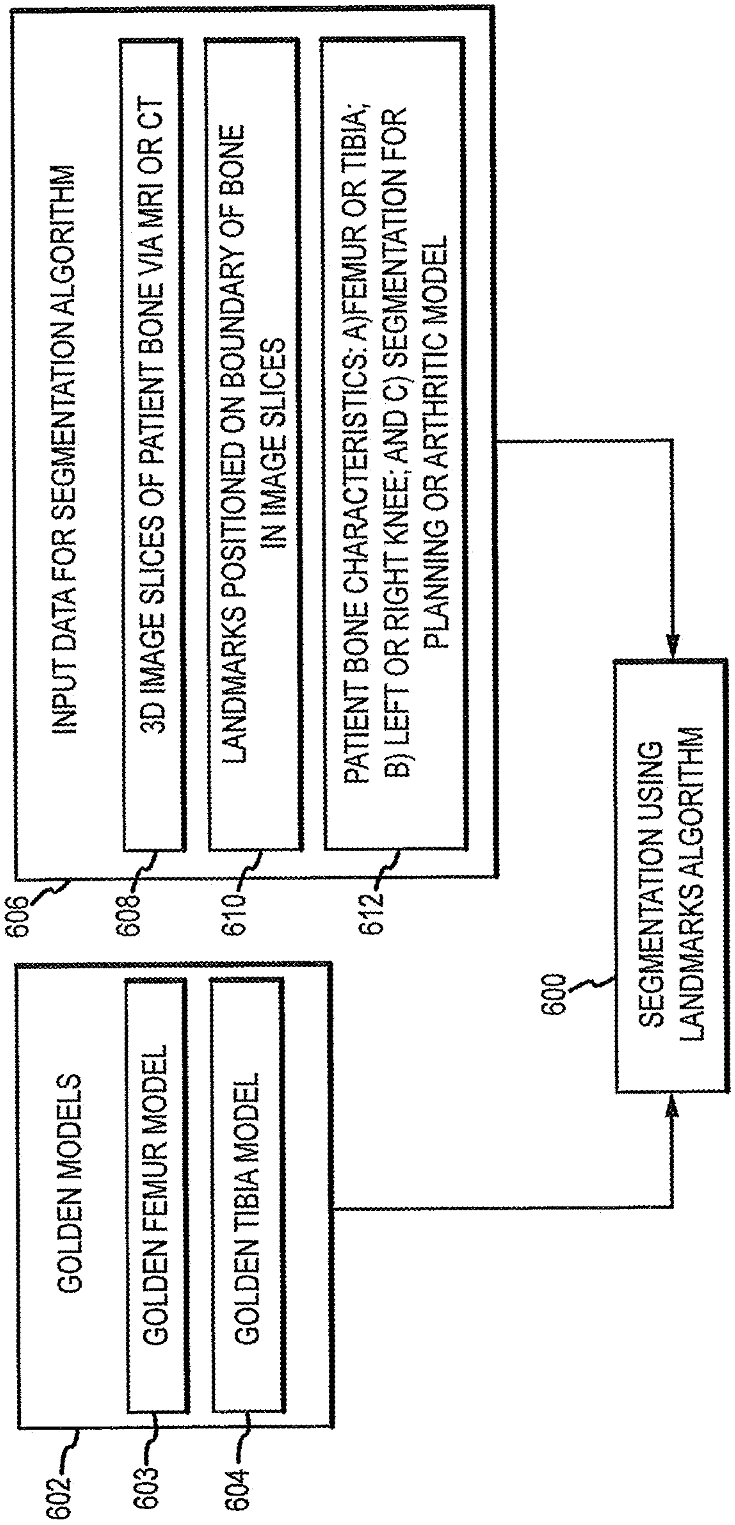
FIG. 28 is a diagram depicting types of data employed in the image segmentation algorithm that uses landmarks.

To begin the detailed discussion of the alternative embodiment of image segmentation described in this section c. of the Detailed Description, wherein landmarks 777 placed on image contours are used to modify a golden bone model (e.g., golden femur or golden tibia), the resulting modified golden bone model being segmented, reference is made to FIG. 28, which is a diagram depicting types of data employed in the image segmentation algorithm that uses landmarks. As shown in FIG. 28, the data employed in the segmentation algorithm 600 may be characterized as being two types of data. The first type of data exists in the system once generated and is for use with multiple patients and is not generated specifically for the patient for which the current image segmentation is being undertaken. This type of data may be called golden model data 602 and is derived similar to as discussed above with respect to FIG. 11, etc. and as generally reiterated below. The golden model data 602 may include, for example, one or more golden femur models 603 and one or more golden tibia models 604. If the joint being treated is something other than a knee, for example, the patient's arm, then the golden model data 602 may include another type of golden bone model, for example, a golden radius or golden ulna.

The second type of data is specific to the patient for which the current image segmentation is being undertaken. This type of data may be called input data for segmentation algorithm 606. The input data 606 includes 3D image slices data 608, which is 3D image slice data of the patient bone via MRI, CT or another type of medical imaging. The input data 606 also includes landmark data 610, which is landmarks 777 positioned on boundaries of the patient bone in the image slices. The input data 606 further includes patient bone characteristics 612 such as bone type (e.g., whether the bone is a tibia or femur), bone right or left handedness, and whether the segmentation is being done to generate an arthritic model 36 (see FIG. 1D) or a planning or restored bone model 28 (see FIG. 1C). As explained below, the golden model data 602 and the input data 606 are used in the segmentation algorithm 600 to segment the 3D image employing landmarks 777.

Figure 29:
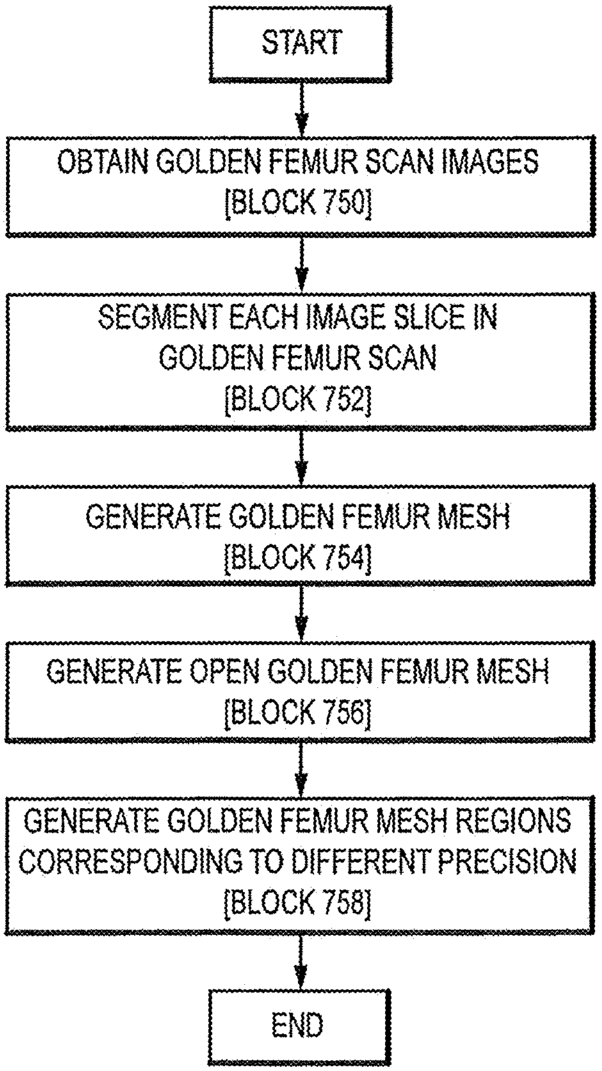
FIG. 29 is a flowchart illustrating the overall process for generating a golden femur model of FIG. 28.

As shown in FIG. 29, which is a flowchart illustrating the overall process for generating a golden femur model 603 of FIG. 28, golden femur scan image slices 616 are obtained in operation 750. For example, as discussed above with respect to FIG. 11 above, a representative femur 618 that is free of damage and disease may be scanned via medical imaging, such as, for example, MRI or CT. Where the golden femur model 603 is to be employed in generating a bone model 22 (see block 110 of FIG. 1C) and cartilage geometry is not of interest, the golden femur scan images slices 616 may be of a femur having damaged cartilage as long as the bone shape is otherwise desirable (e.g., normal) and free of deterioration or damage. Where the golden femur model 603 is to be employed in generating an arthritic model 36 (see block 130 of FIG. 1D) and cartilage geometry is of interest, the golden femur scan images slices 616 may be of a femur having both cartilage and bone shape that are desirable (e.g., normal) and free of deterioration or damage.

The appropriate femur scan may be selected by screening multiple MRI femur scans to locate an MRI femur scan having a femur that does not have damaged cancellous and cortical matter (i.e., no damage in femur regions that should be present in this particular model), which has good MRI image quality, and which has a relatively average shape, e.g., the shaft width relative to the largest part is not out of proportion (which may be estimated by eye-balling the images). This femur scan data, referred to herein as a golden femur scan, may be used to create a golden femur template.

It is to be appreciated that several MRI scans of a femur (or other bone of interest) may be selected, a template generated for each scan, statistics gathered on the success rate when using each template to segment target MRI scans, and selecting the one with the highest success rate as the golden femur template.

In other embodiments, a catalog of golden models may be generated for any given feature, with distinct variants of the feature depending on various patient attributes, such as (but not limited to) weight, height, race, gender, age, and diagnosed disease condition. The appropriate golden mesh would then be selected for each feature based on a given patient's characteristics.

Figure 30:
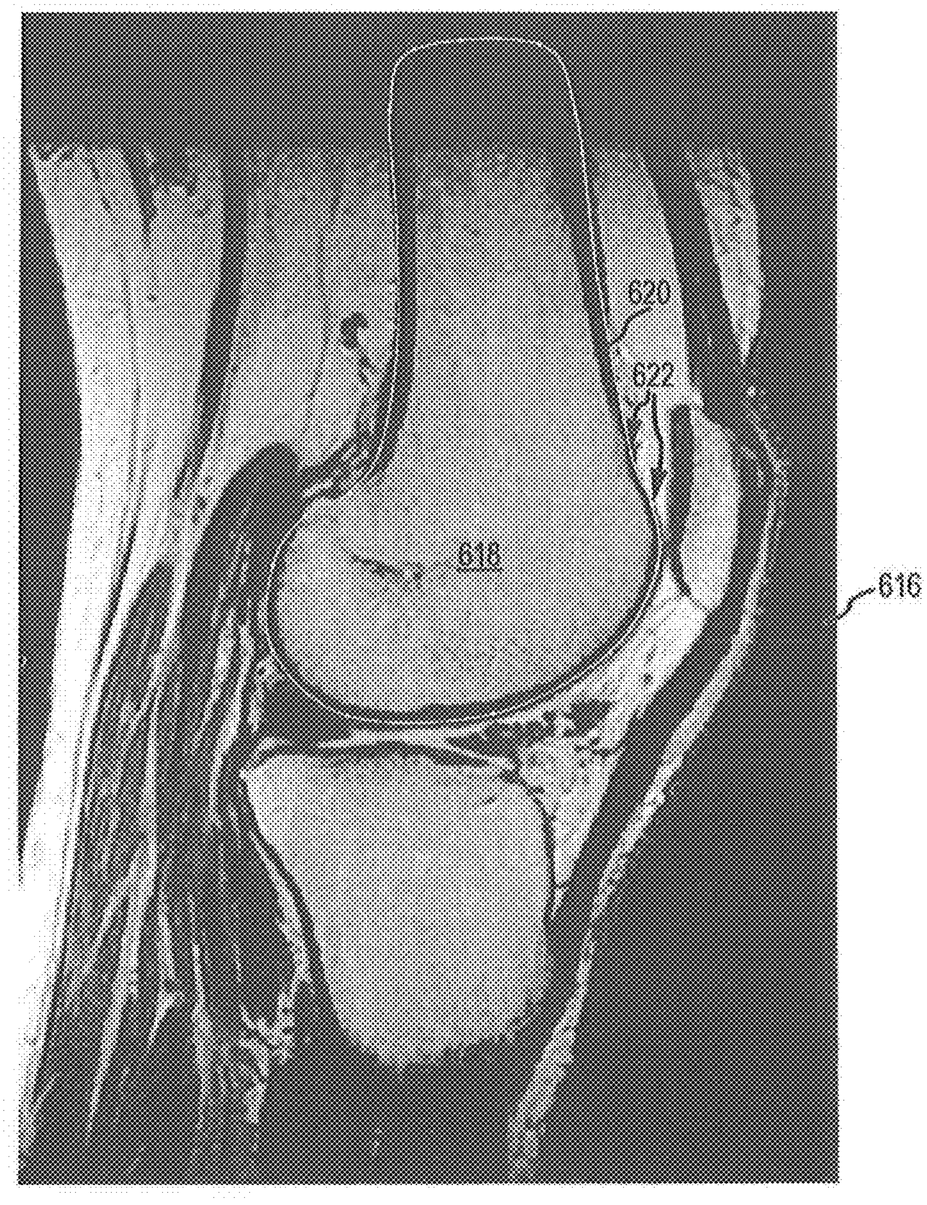
FIG. 30 is an image slice of the representative femur to be used to generate a golden femur mesh.

In operation 752 and as indicated in FIG. 30, each of the image slices 616 of the representative femur 618 are segmented with a contour curve or spline 620 having control points 622 and in a manner similar to that discussed above with respect to FIG. 12A, etc. For example and as shown in FIG. 30, where the golden model is to be used in the generation of a bone model 22 (see block 110 of FIG. 1C) and cartilage geometry is not of interest, each segmentation region includes cancellous matter and cortical matter of the femur in a manner similar to that discussed above with respect to the cancellous matter 322 and cortical matter 324 of the tibia depicted in FIG. 12A, etc. Thus, as shown in FIG. 30, the contour curve 620 excludes any cartilage matter in outlining a golden femur region.

On the other hand, where the golden model is to be used in the generation of an arthritic model 36 (see block 130 of FIG. 1D) and cartilage geometry is of interest, each segmentation region the contour curve would include cartilage matter in outlining a golden femur region.

If the golden femur scan does not contain a sufficiently long shaft of the femur bone (e.g., it may be desired to segment a femur in a target MRI that may have a longer shaft), then the image segmentation can be extrapolated beyond the image to approximate a normal bone shape. This can be done because the femoral shaft is quite straight and, generally, all that is needed is to continue the straight lines beyond the MRI image, as can be understood from the extension of the contour line 620 proximal of the proximal edge of the femur image 616 of FIG. 30.

Figure 31C:
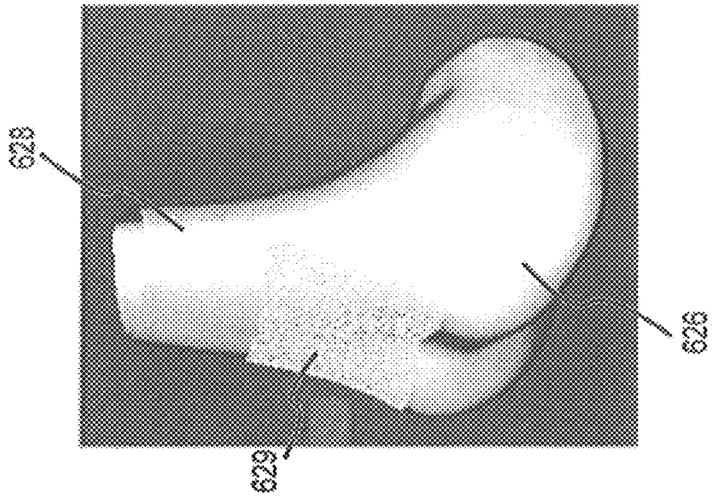
FIG. 31C is the open femur mesh of FIG. 31B with regions of a different precision indicated.
Figure 31B:
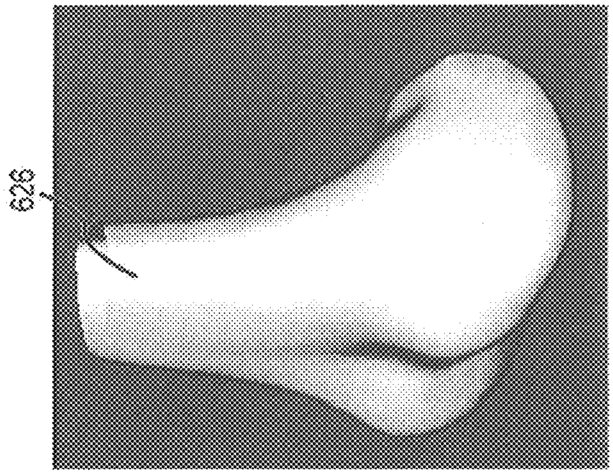
FIG. 31B is an isometric view of an open golden femur mesh created from the closed golden femur mesh of FIG. 31A.
Figure 31A:
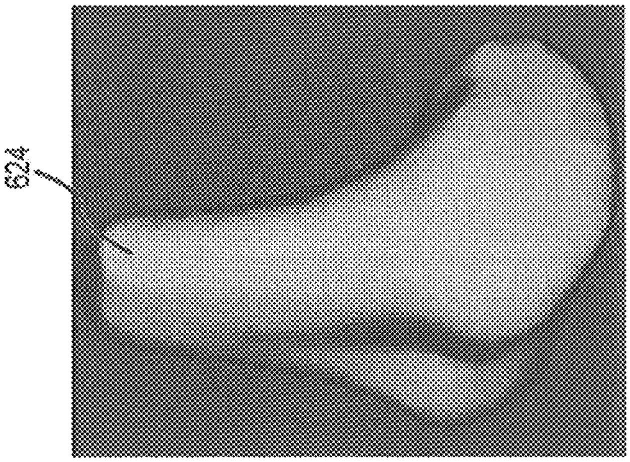
FIG. 31A is an isometric view of a closed golden femur mesh.

In operation 754 and as illustrated in FIG. 31A, the contour curves or splines 620 are compiled and smoothed into a golden femur mesh 624 as discussed above with respect to FIG. 13A, etc. As indicated in FIG. 30, in one embodiment, the segmentation curve 620 is a closed curve. Thus, the resulting golden femur mesh 624 is a closed mesh as depicted in FIG. 31A.

In operation 756 and as shown in FIG. 31B, the golden femur mesh 624 is converted into an open golden femur mesh 626, wherein the proximal portion of the golden femur mesh 624 is removed to create the open surface model called the open golden femur mesh 626. In other words, in operation 756 the artificial part of the femur mesh 626 is cut off, namely the proximally extending shaft portion that results from the proximal extrapolated extension of the contour line 620, so as to obtain the open golden femur mesh 626 of FIG. 31B.

In operation 758 and as indicated in FIG. 31C, regions 628, 629 of a different precision are generated for the golden femur mesh 626. For example, when segmenting the image slices 16 for the purpose of generating a golden femur mesh 626 that is used to create a 3D computer generated bone model used to show the preoperative planning ("POP") images to a surgeon, it is desirable that the bone geometry of the mesh 626 be generated with a relatively high degree of accuracy in certain regions 628 of the mesh 626 such that the resulting 3D computer generated bone model allows the physician to verify the POP with a desired degree of accuracy, while other regions 629 of the mesh 626 may not be generated to such a high degree of accuracy. For example, such a degree of accuracy in the certain regions 628 of the mesh 626 can be achieved via relatively precise image segmentation. The certain regions 628 of the mesh 626 having the relatively high degree of accuracy could include, among others, the lower shaft area, as depicted in FIG. 31C. In one embodiment, the relatively high accuracy of the certain regions 628 of the mesh 626 should allow the physician to verify the POP within 0.5 mm accuracy.

As can be understood from FIG. 31C, in one embodiment, the high precision region(s) 628 of the mesh 626 represent a portion of the distal anterior femoral shaft that would be contacted by the anterior flange of a candidate femoral implant. The rest of the mesh 626 may form the region 629 that has an accuracy that is not as precise as the high precision region 628. Such a lower precision region 629 of the mesh 626 may include the entire distal femur excluding the distal anterior region of the shaft included within the high precision region 628. Where the golden femur mesh 626 is employed to form other 3D computer generated bone models, such as, for example, the bone model 22 or arthritic model 36, the mesh 626 may have a different number of high precision regions 628 (e.g., none, one, two, three, or more such regions 628). Also, such regions 628 may have precisions that are greater or less than stated above. Finally, such regions 628 may correspond to different regions of the bone, encompass generally the entirety of the mesh surface, or include other regions in addition to the region 628 depicted in FIG. 31C.

Figure 32B:
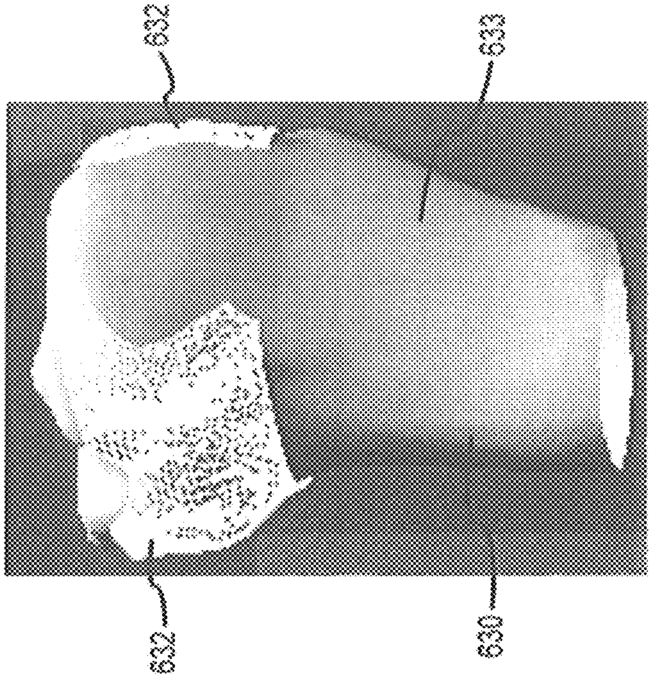
FIGS. 32A-32B are isometric views of an open golden tibia mesh with regions of a different precision indicated.
Figure 32A:
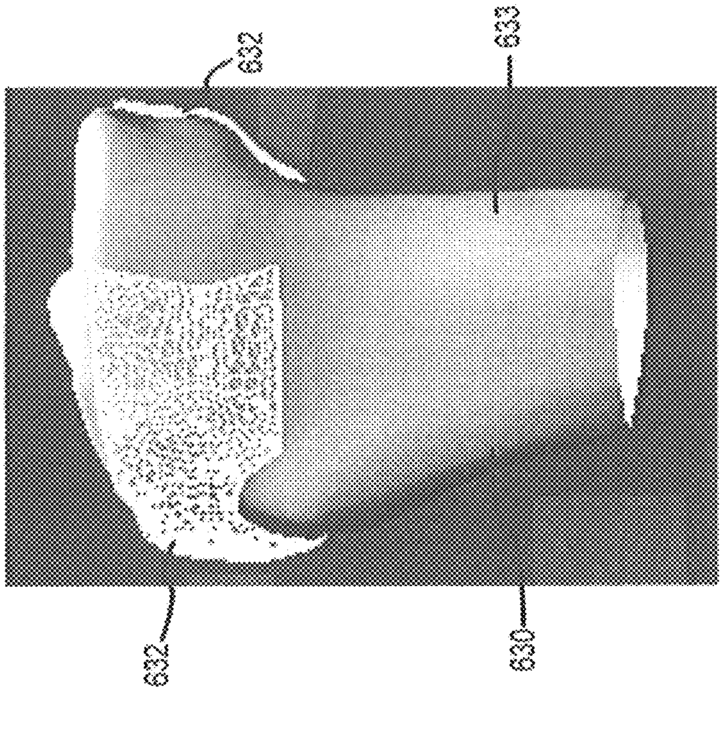

While the preceding discussion regarding the open golden bone mesh is given in the context of the open golden bone mesh being an open golden femur mesh 626, as can be understood from FIG. 32A-B, the open golden bone mesh may be an open golden tibia mesh 630 having regions 632, 633 of a different precision, all of which are generated in a manner similar to that discussed with respect to FIGS. 28-31C above.

For example, as can be understood from FIGS. 32A-32B, in one embodiment, the high precision region(s) 632 of the open golden tibia mesh 630 represent a portion of the proximal anterior tibial shaft immediately distal the tibial plateau and running medial to lateral generally proximal the tibial tuberosity. Another high precision region 632 may occupy a space similar in location and size, except on the posterior of the tibial shaft. The rest of the mesh 630 may form the region 633 that has an accuracy that is not as precise as the high precision region 632. Such a lower precision region 633 of the mesh 630 may include the entire proximal tibia excluding the regions of the shaft included within the high precision regions 632. Where the golden tibia mesh 630 is employed to form other 3D computer generated bone models, such as, for example, the bone model 22 or arthritic model 36, the mesh 630 may have a different number of high precision regions 632 (e.g., none, one, two, three, or more such regions 632). Also, such regions 630 may have precisions that are greater or less than stated above. Finally, such regions 630 may correspond to different regions of the bone, encompass generally the entirety of the mesh surface, or include other regions in addition to the regions 632 depicted in FIGS. 32A-32B.

Figure 33:
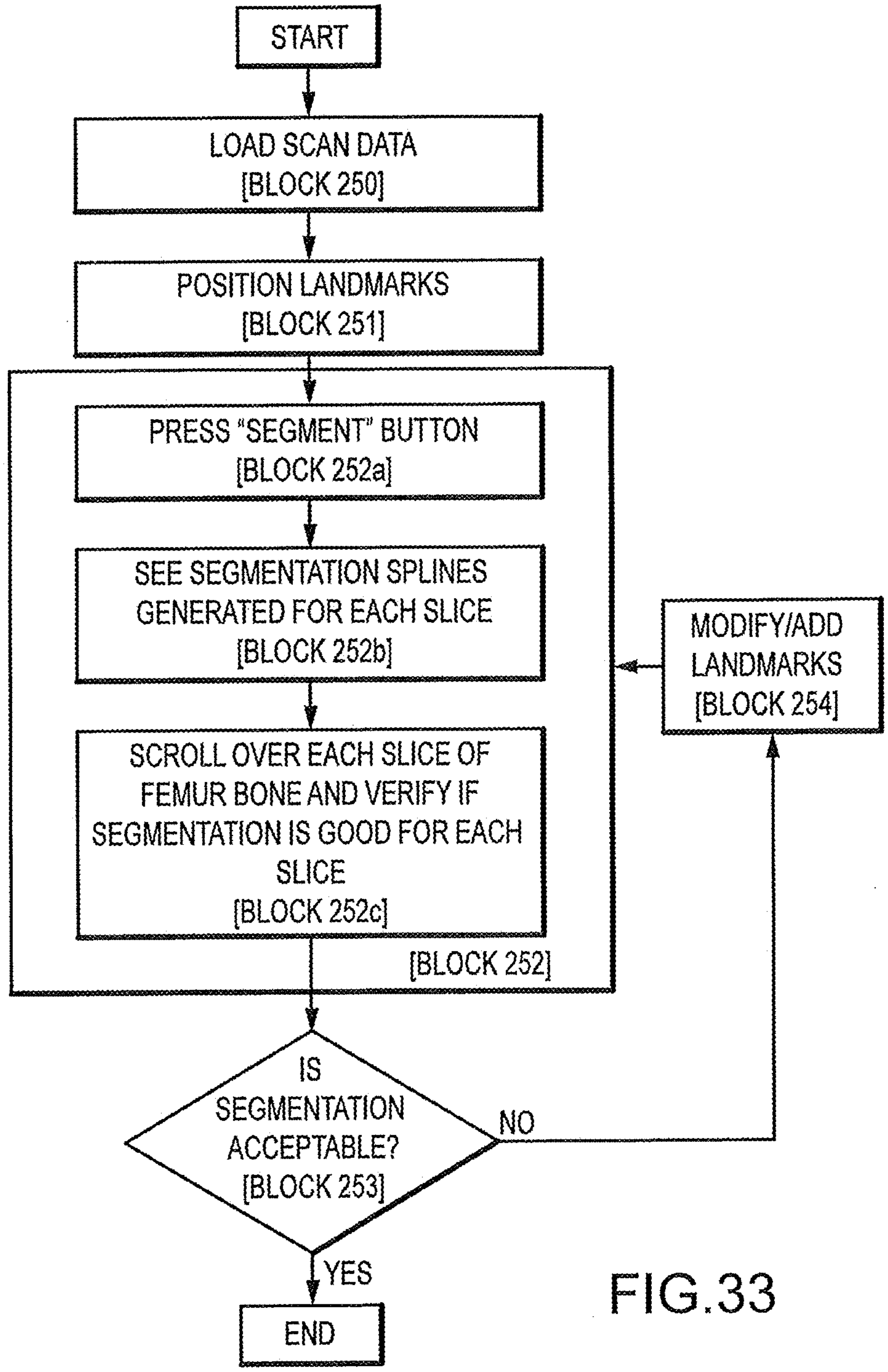
FIG. 33 is a flow chart illustrating an alternative method of segmenting an image slice, the alternative method employing landmarks.

For a discussion of an alternative embodiment of operations 250-254 of FIG. 6, reference is first made to FIG. 33, which is a flowchart illustrating the alternative embodiment of segmenting a target bone. In this example, the target bone is a femur 204, but may be a tibia 210 or any other type of bone.

Figure 34:
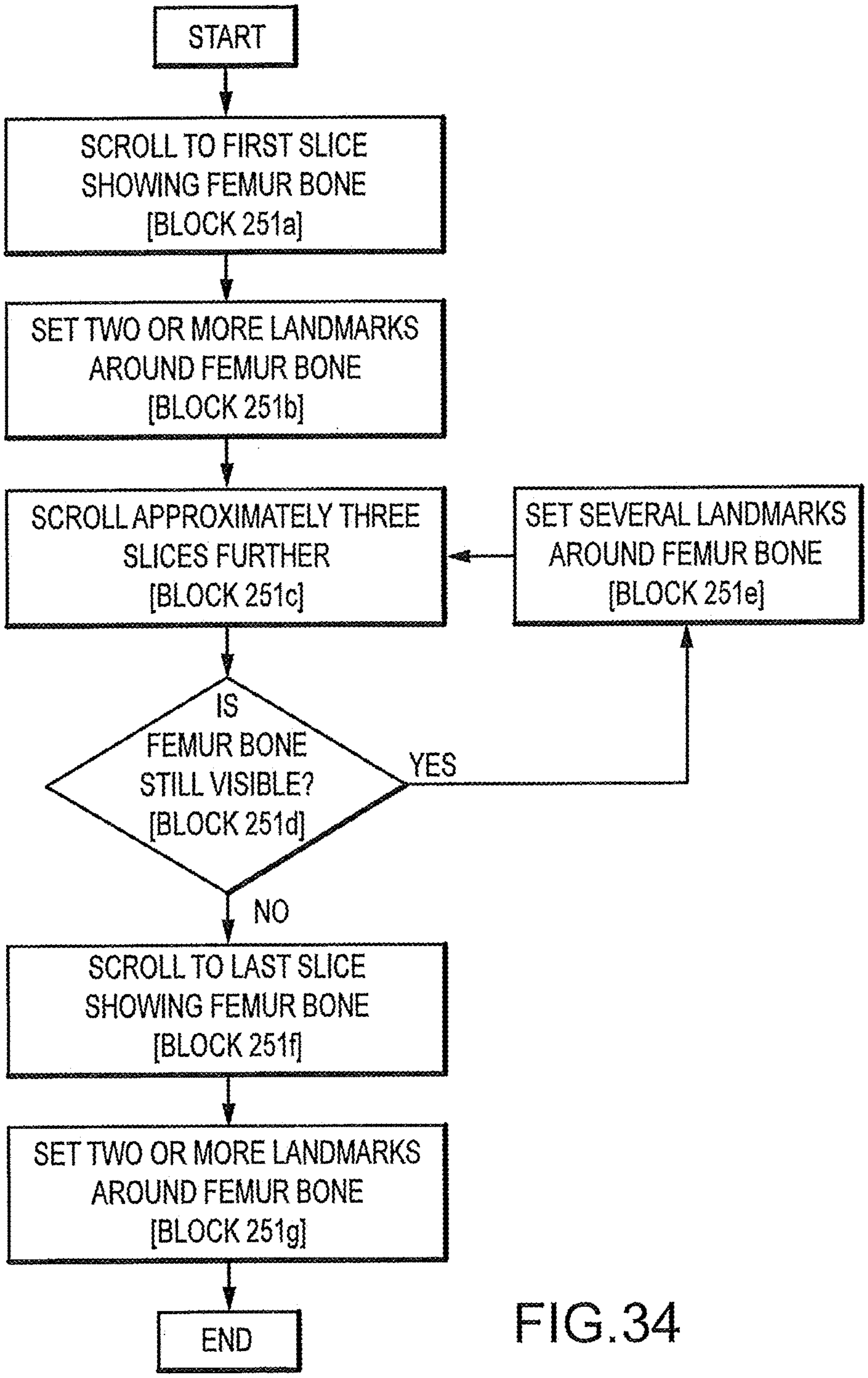
FIG. 34 is a flow chart illustrating the process involved in operation "position landmarks" of the flow chart of FIG. 33.
Figure 35A:
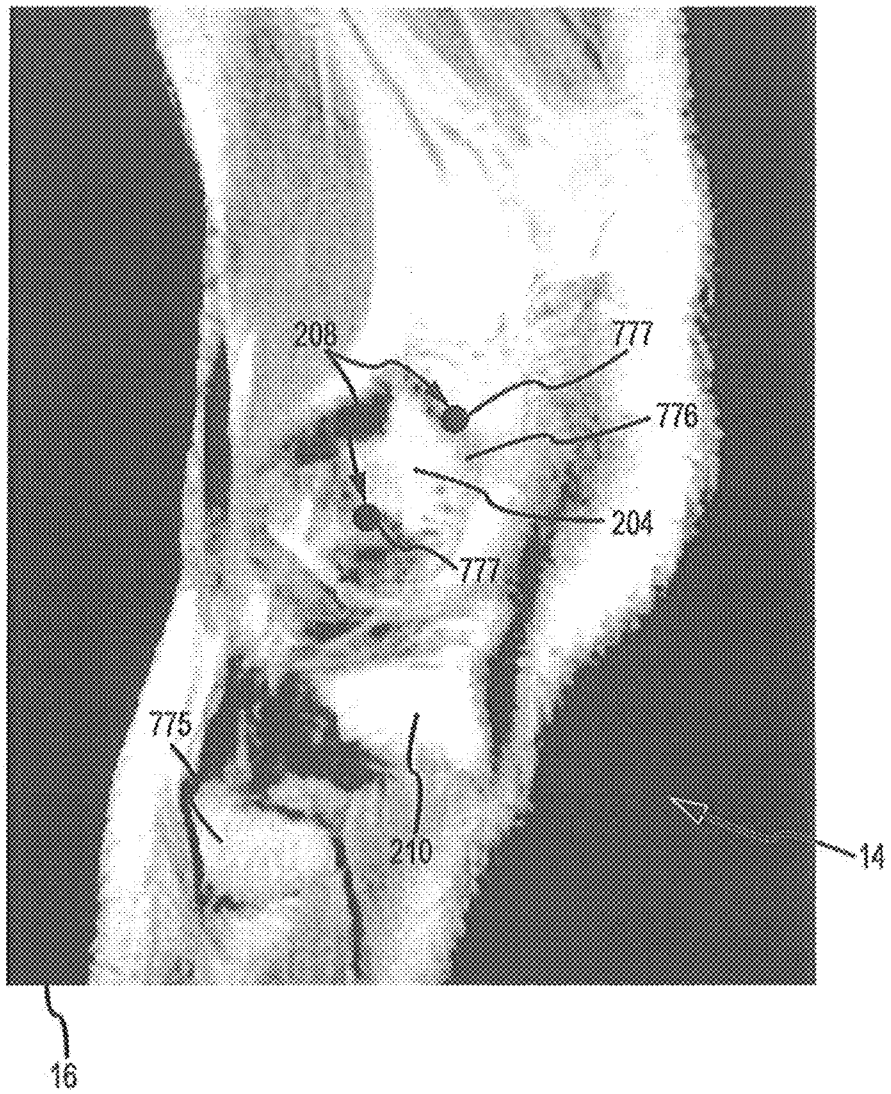
FIGS. 35A-35H are a series of sagittal image slices wherein landmarks have been placed according the process of FIG. 34.

As indicated in FIG. 33, operation 250 obtains or, more specifically, loads the scan data (e.g., scan images 16) generated by imager 8 of the patient's joint 14 to be analyzed. In operation 251 the landmarks are positioned in the scan images. In other words, as can be understood from FIG. 34, which is a flowchart illustrating the steps of operation 251, operation 251 begins with operation 251*a*, wherein the images 16 are scrolled through (e.g., medial to lateral or lateral to medial) to the most medial or lateral image slice were the femur bone 204 first appears, as shown in FIG. 35A, which, in this example, is a most lateral sagittal MRI image slice 16 where the femur bone 204 or, more specifically, the lateral epicondyle 776 first appears. Since the slice 16 of FIG. 35A is the most lateral image where bone has begun to appear, the fibula 775 can be seen adjacent the tibia 210 in such instances where the image slice is positioned so as to show both the femur 204 and the tibia 210. In operation 251*b*, two or more landmarks 777 are positioned on the outer rim of the black cortical bone 208 of the image slice 16 depicted in FIG. 35A. As is the case with all of the images depicted in FIGS. 35A-35H, in one embodiment, the landmarks are placed via an operator sitting at a work station. In one embodiment, the operator or user is able to add landmarks by simply clicking onto the slice image, the landmark (point) being created at the exact coordinates where the click has occurred. The operator is able to move existing landmarks within the slice by selecting them and moving them with the mouse, a keyboard, a pen-and-tablet system, or similar. The user is able to delete existing landmarks by selecting them and indicating to the software that they should be deleted.

In another embodiment, a touch-screen surface may be used to provide input and display for interactive editing of landmarks and segmentation curves. Specialized gestures may be adopted for various editing operations.

In another embodiment, a spatial input device may be used for manipulation of landmarks, segmentation curves, and other operations involving POP and jig design activities.

Figure 35B:
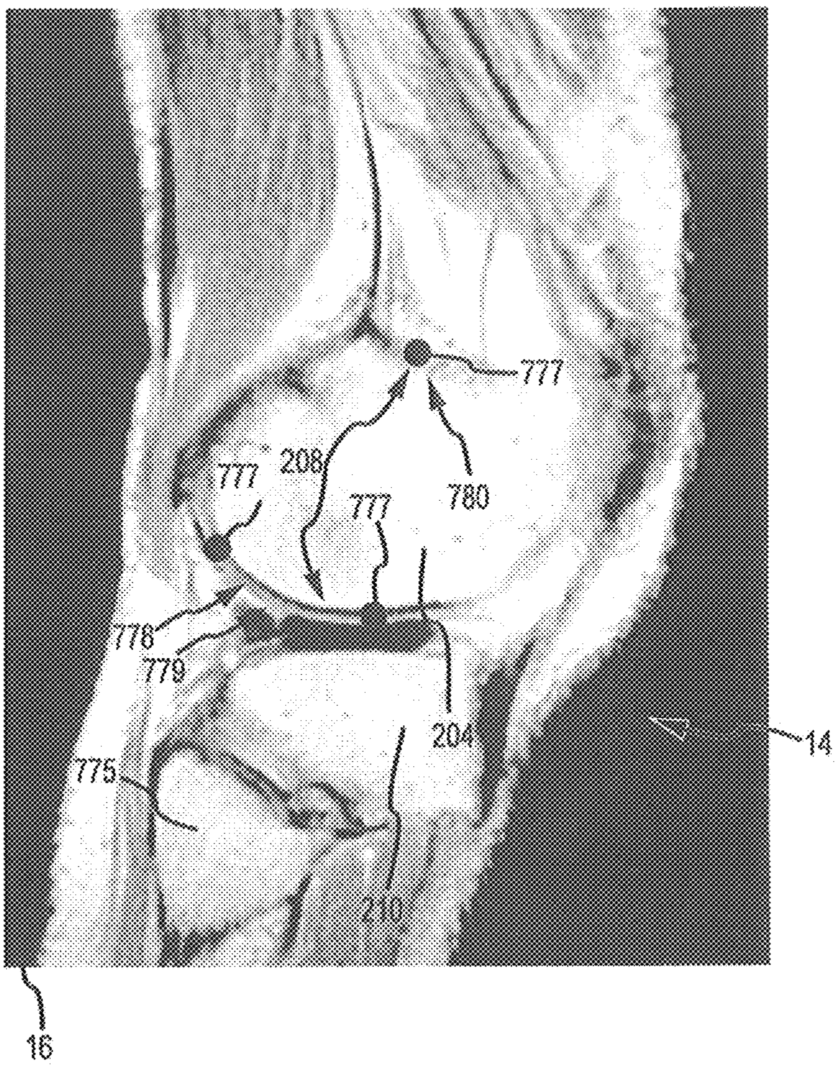

In operation 251*c*, the image slices 16 are scrolled lateral to medial through approximately three slices 16 further to a new image slice 16 and, at operation 251*d*, it is determined if the femur bone 204 is still visible in the new image slice 16, which is depicted in FIG. 35B. If so, then operation 251*e* adds landmarks 777 to the new image slice 16 as indicated in FIG. 35B. Specifically, as indicated in FIG. 35B, this new image slice 16 may show the femur lateral condyle 778 and be the first image slice having a clear boundary 779 of the femur lateral condyle. As can be seen in FIG. 35B, the fibula 775 and tibia 210 are also more fully shown. Landmarks 777 are set on the clear boundary 779 of the outer rim of the dark cortical bone of the femur lateral condyle, and an additional landmark 777 is set on the opposite side 780 on the rim of the black cortical bone 208. As is the case with the placement of landmarks 777 in any of the images 16, more or fewer landmarks 777 may be placed along the rim of the black cortical bone depicted in the image 16, including landmarks being placed on the rim of the black cortical cone of the entirety of the distal femur, including the distal femur condyle and distal femur shaft.

Figure 35C:
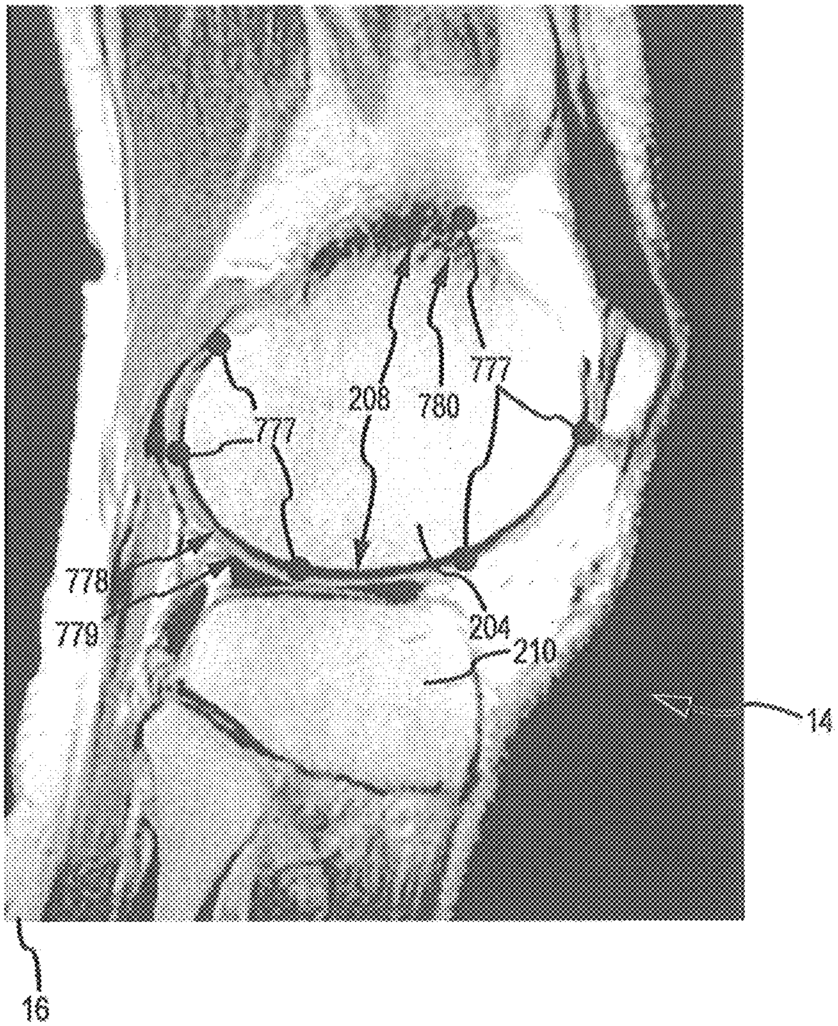

Operations 251*c* through 251*e* are repeated to set landmarks 777 at the bone contour boundaries of approximately every third image slice 16 moving lateral to medial until eventually at operation 251*d* it is determined that bone no longer appears in the present image slice. Thus, as operation 251 of FIG. 33 loops through operations 251*c*-251*e* of FIG. 34, landmarks 777 are set at the bone contour boundaries in each of the sagittal image slices 16 depicted in FIGS. 35C-35H, which are, respectively, approximately every third sagittal image slice 16 tabbing lateral to medial through all the sagittal image slices 16 loaded in operation 250 of FIG. 33. Thus, as shown in FIG. 35C, which represents a sagittal image slice 16 approximately three slices more medial than the image slice 16 of FIG. 35B, the femur lateral condyle 778 has a clear bone contour boundary 779, and landmarks 777 are set along the boundary 779 on the rim of the dark cortical bone 208. A landmark 777 is also set on the top region 780 of the cortical bone boundary 779 where the bone contour boundary is less clear, the landmark being positioned on the rim of the dark cortical bone 208.

Figure 35D:
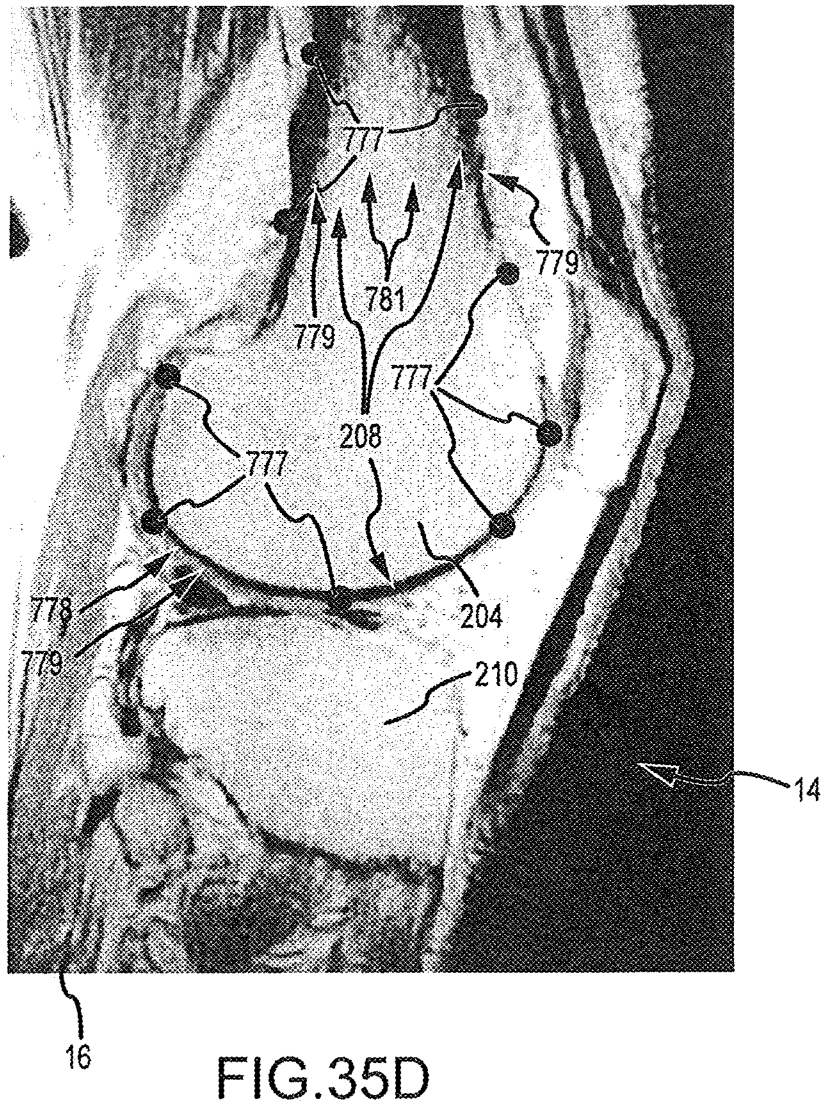

As illustrated in FIG. 35D, which represents a sagittal image slice 16 approximately three slices 16 more medial than the image slice 16 of FIG. 35C, the femur shaft 781 has now appeared in an image slice 16 and both the femur shaft 781 and femur lateral condyle 778 have clear bone contour boundaries 779. Landmarks 777 are set along the bone contour boundaries 779 on the rim of the dark cortical bone 208.

Figure 35E:
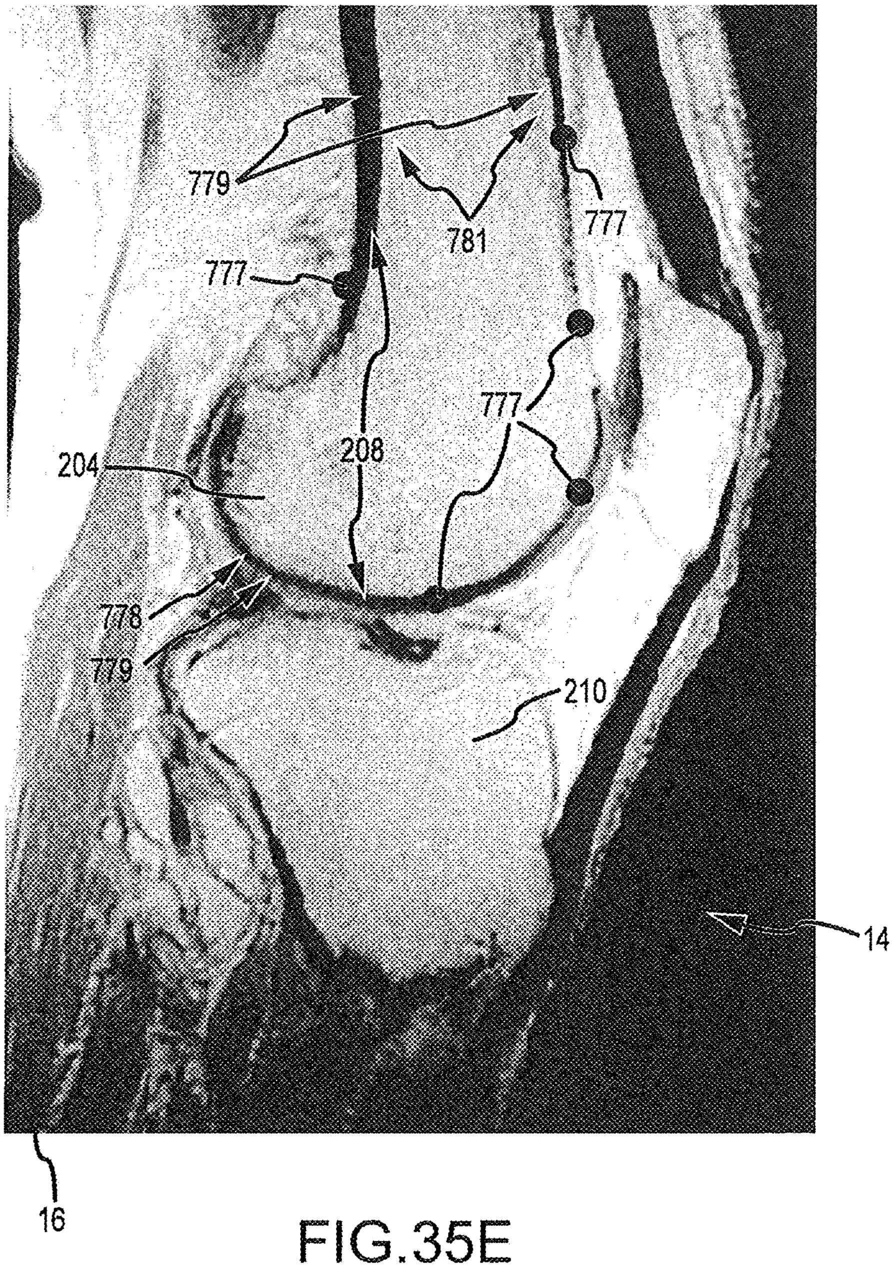

As shown in FIG. 35E, which represents a sagittal image slice 16 approximately three slices 16 more medial than the image slice 16 of FIG. 35D, the femur lateral condyle 778 is starting to disappear, and part of its cortical bone contour boundary 779 is not clear. Landmarks 777 are only set outside the dark cortical bone 208 in the regions where the contour boundary 779 is clear.

Figure 35F:
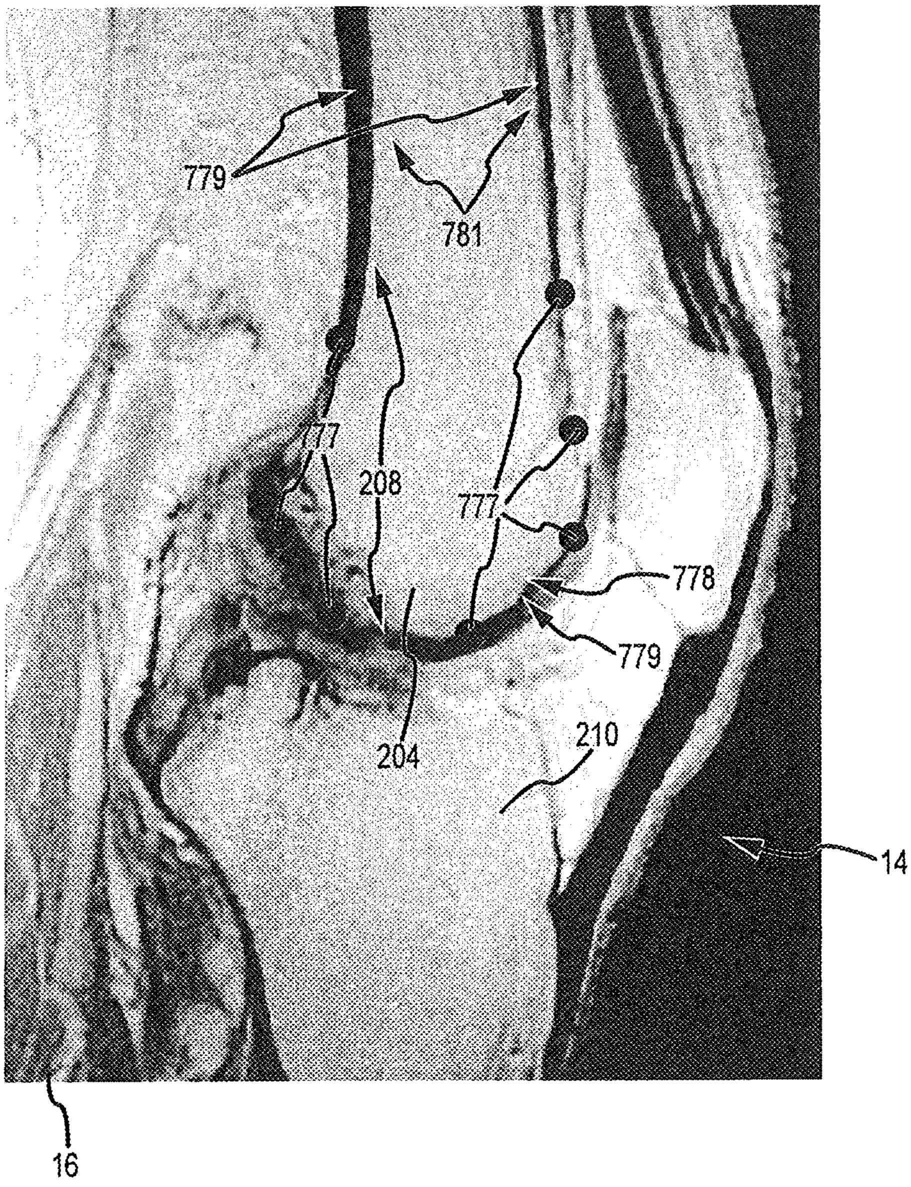

As illustrated in FIG. 35F, which represents a sagittal image slice 16 approximately three slices 16 more medial than the image slice 16 of FIG. 35E, the bone contour boundary 779 has become less clear as the femur lateral condyle 778 has decreased in size as compared to the femur lateral condyle 778 of slice 16 in FIG. 35E. The slice 16 of FIG. 30F is just lateral of the trochlear groove 782 between the femur lateral condyle 778 and femur medial condyle 783. The bone contour boundary 779 is clear in the anterior region of the femur lateral condyle 778 and two landmarks 777 are placed there. Additional landmarks 777 are set along the bone contour boundaries 779 on the rim of the dark cortical bone 208.

Figure 35G:
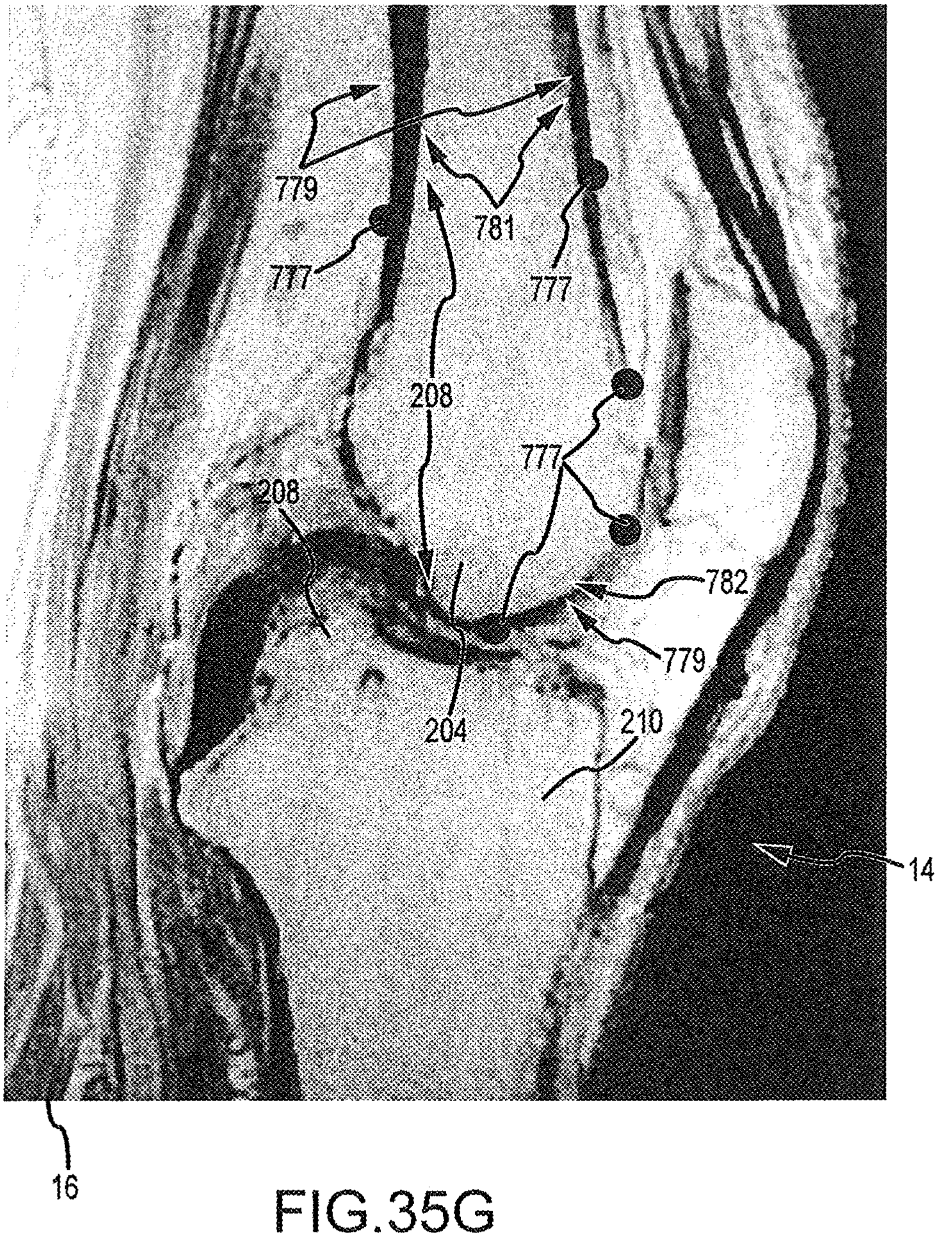

As indicated in FIG. 35G, which represents a sagittal image slice 16 approximately three slices 16 more medial than the image slice 16 of FIG. 35F, landmarks 777 are set along the bone contour boundaries 779 on the rim of the dark cortical bone 208. The slice 16 of FIG. 35G is in the trochlear groove 782 between the femur lateral condyle 778 and femur medial condyle 783. The intercondylar eminence 784 of the tibia 210 can be seen in the slice 16 of FIG. 35G.

Figure 35H:
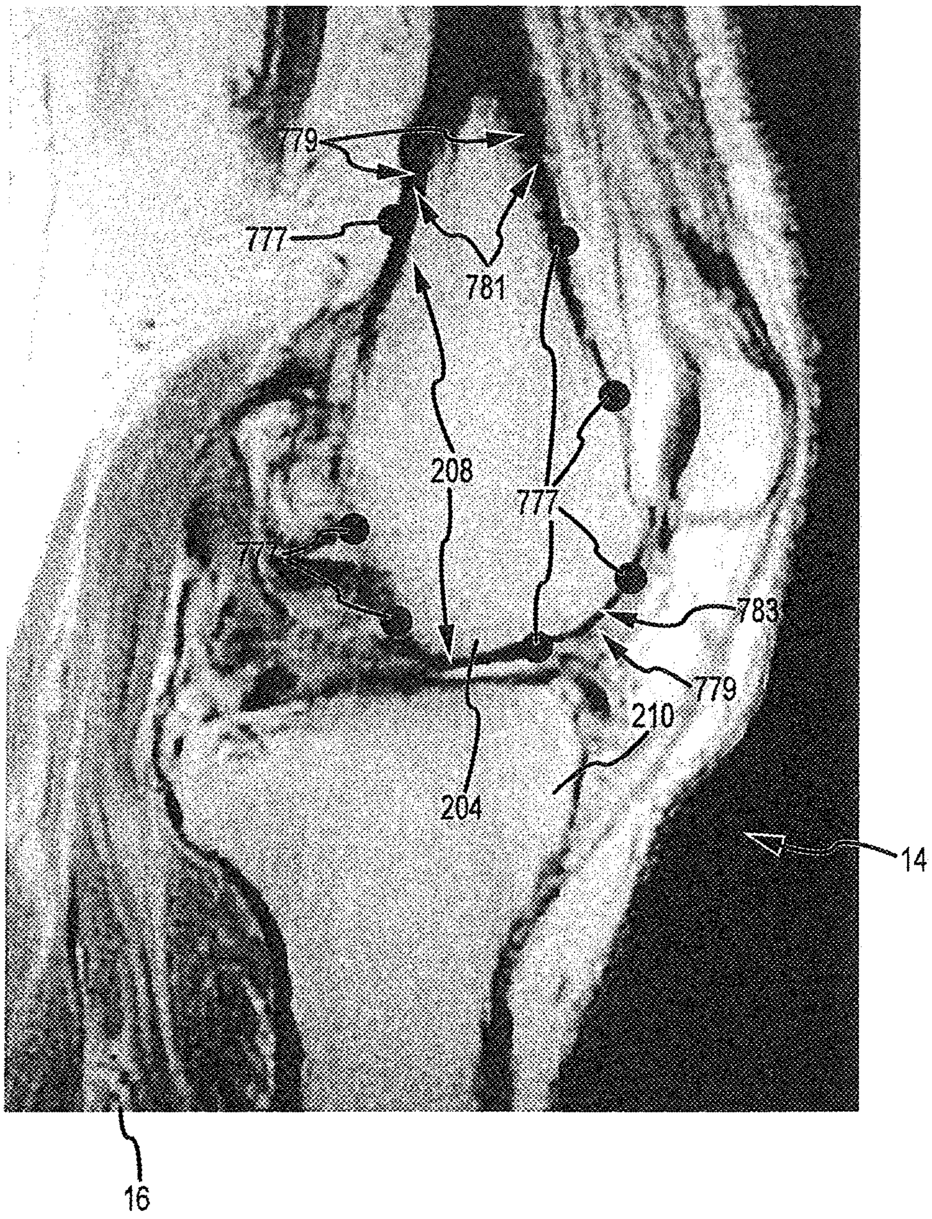

As indicated in FIG. 35H, which represents a sagittal image slice 16 approximately three slices 16 more medial than the image slice 16 of FIG. 35G, the femur shaft 781 has begun to disappear and the femur medial condyle 783 has begun to appear as the slice of FIG. 35H is medial of the trochlear groove 782 depicted in the slice of FIG. 35G. The bone contour boundary 779 is clear in the anterior region of the femur medial condyle 783 and two landmarks 777 are placed there. Additional landmarks 777 are set along the bone contour boundaries 779 on the rim of the dark cortical bone 208.

As stated above, operations 251*c* through 251*e* continue to be repeated as the slices 16 continue to be tabbed through lateral to medial to set landmarks 777 at the bone contour boundaries of approximately every third image slice 16 until eventually at operation 251*d* it is determined that bone no longer appears in the present image slice. Operation 251*f* then scrolls medial to lateral through the image slices 16 until arriving at the image slice 16 where the most medial portion of the femur is depicted. Operation 251*g* then sets two or more landmarks 777 around the bone (e.g., the medial epicondyle) in a manner similar to that depicted in FIG. 35A with respect to the lateral epicondyle 776. This is the end of operation 251 and, as can be understood from FIG. 33, operation 252 begins by pressing the "segment" button (operation 252*a*), which causes segmentation lines to be generated for each slice 16 with landmarks 777 (operation 252*b*) in a manner similar to that illustrated and discussed above with respect to FIGS. 7A-7K or as now will be discussed below beginning with FIG. 36.

When positioning landmarks, a user needs to distribute them over the cortical bone outer surface, favoring areas where the cortical bone boundary is sharp and is more orthogonal to the slice plane, particularly favoring certain "important" areas of the bone surface (where importance is dictated by eventual contact between bone and implant or by other requirements from POP procedure.) The user should only sparsely mark up the remaining parts of the bone, particularly where there is a lot of volume averaging (and/or the bone surface is more parallel to slice plane.) While the image slices depicted in FIGS. 35A-35H are MRI generated image slices, in other embodiments the imaging slices may be via other medical imaging methods, such as, for example, CT.

In one embodiment, the landmark-driven segmentation algorithm described below is deliberately sensitive to the number of landmarks (points) placed at a given area of the bone. So for instance, if the user desires the auto-generated bone mesh to very accurately pass through particular spots on the slice, the user can place more than one landmark on that same spot or very near that spot. When there is a high concentration of landmarks in a small area of the bone, the auto-generated mesh will be biased to more accurately model that area. The software indicates to the user, making it visible at a glance whenever more than one landmark is located within the same small area of the image.

In one embodiment, instead of putting landmarks in every three slices, a user may position landmarks in every slice but use three times fewer landmarks in each slice. The result of the segmentation usually varies very little depending on how a user distributes landmarks around the bone surface as long as the entire surface is covered.

While much of the following discussion takes place in reference to the segmentation of a femur (operation 252 of FIG. 6), the concepts discussed herein are readily applicable to the segmentation of a tibia (operation 258 of FIG. 6). Additionally, the concepts discussed herein are readily applicable to both the left or right knee. Different golden template data may be used to segment the left tibia, right tibia, left femur or right femur for bone models 22 or planning models 28. Additionally, other embodiments may segment other models and or joints, including but not limited to, arthritic models 36, hip joints, elbow joints, etc. by using an appropriate golden template of the feature of interest to be segmented.

Figure 36:
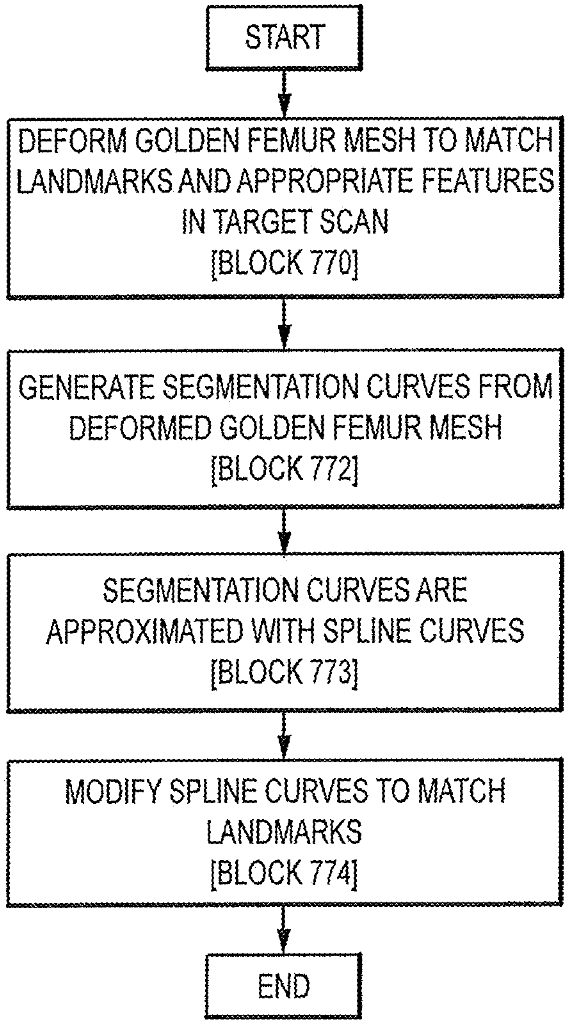
FIG. 36 is a flowchart illustrating the process of segmenting the target images that were provided with landmarks in operation "position landmarks" of the flow chart of FIG. 33.

As shown in FIG. 36, which is a flowchart illustrating the process of segmenting the target images 16 that were provided with landmarks 777 in operation 251, the full or entire golden femur mesh 626, including its regions 628, 629 in FIG. 31C, is deformed in operation 770 to match landmarks 777 and appropriate features, such as, for example, the outer edges of dark cortical bone, in the target scan images 16.

As discussed below with respect to FIG. 37, a method is provided for mapping the golden femur mesh into the target scan using registration techniques. Registration may be thought of as an optimization problem with a goal of finding a spatial mapping that aligns a fixed object with a target object. Generally, several registration operations may be performed, first starting with a low-dimensional transformation group to find a rough approximation of the actual femur location and shape in the target image. This may be done to reduce the chance of finding wrong features instead of the femur of interest. For example, if a free-form deformation registration was initially used to register the golden femur mesh to the target scan data, the template might be registered to the wrong feature, e.g., to a tibia rather than the femur of interest. A coarse registration may also be performed in less time than a fine registration, thereby reducing the overall time required to perform the registration. Once the femur has been approximately located using a coarse registration, finer registration operations may be performed to more accurately determine the femur location and shape. By using the femur approximation determined by the prior registration operation as the initial approximation of the femur in the next registration operation, the next registration operation may find a solution in less time. It is to be understood that similar considerations apply to segmentation of other entities (and not just the femur.)

In one embodiment, each registration operation may employ a registration framework. The registration framework may be based on three general blocks. The first block defines a transformation model (or a class of transforms) T(X), which may be applied to coordinates of a fixed (or reference) object (e.g., a golden femur template) to locate their corresponding coordinates in a target image space (e.g., an MRI scan). The second block defines a metric, which quantifies the degree of correspondence or similarity between features of a fixed (or reference) object and the target object (that is landmarks and appropriate target image features) achieved by a given transformation. It should be noted that instead of a metric that defines the degree of correspondence, an opposite to it function is defined, which is call the defect function. The third block defines an optimization algorithm (optimizer), which tries to maximize the reference and the target objects similarity (or minimize the opposite defect function) by changing the parameters of the transformation model. Thus, as discussed below in detail with reference to FIG. 37, in every registration operation 770*a*-770*c* and 770*e* there is a need to specify three blocks: (1) class of transforms; (2) metric (or defect) function; and (3) optimization algorithm. In one embodiment, the same third block may be used in all four registration steps. For instance, a gradient descent optimizer or conjugate gradient descend optimizer may be used. Alternatively, any other appropriate optimization algorithm, such as Monte Carlo, simulated annealing, genetic algorithms, neural networks, and so on, may be used.

Figure 37:
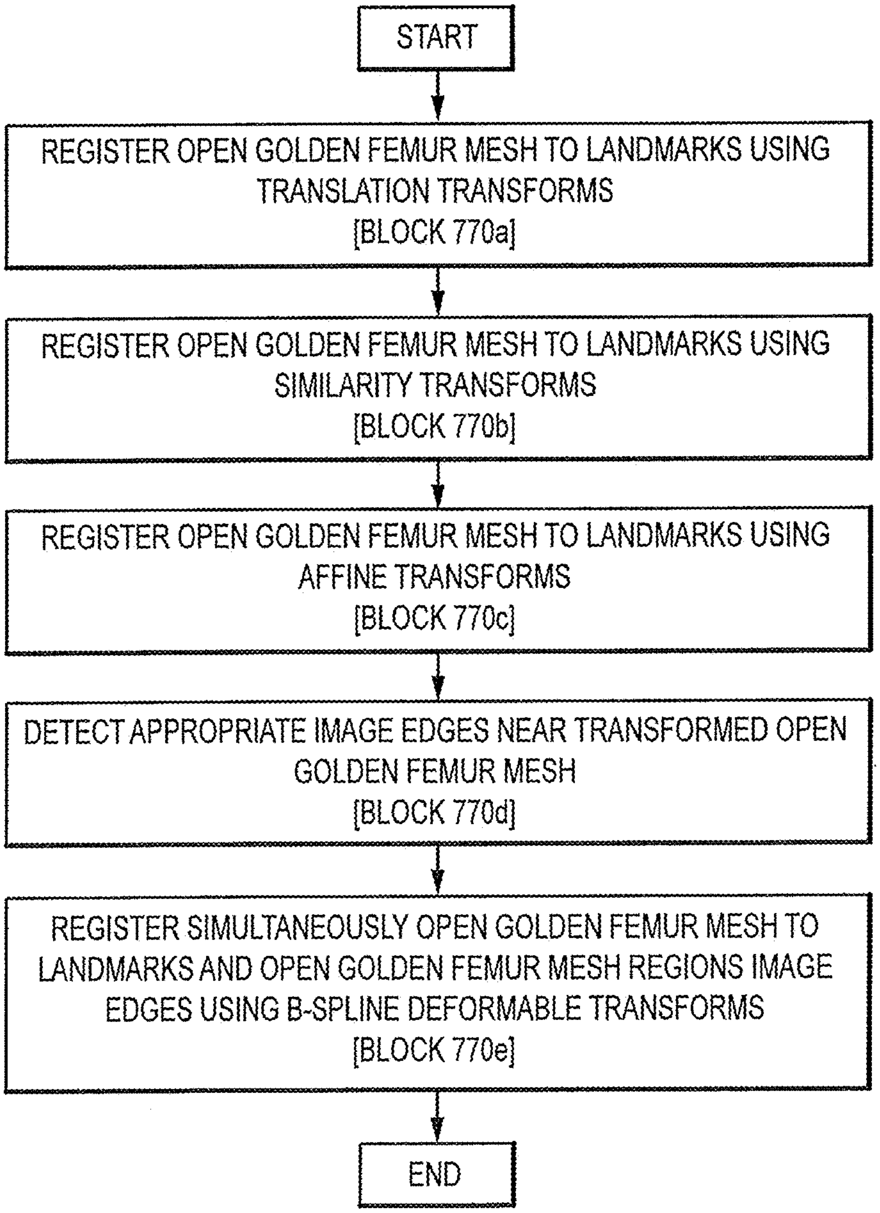
FIG. 37 is a flowchart illustrating the process of operation "Deform Golden Femur Mesh" of FIG. 36, the process including mapping the golden femur mesh into the target scan using registration techniques.

As shown in FIG. 37, which is a flowchart illustrating the process of operation 770 of FIG. 36, in operation 770*a* translation transforms are used to register the full or entire open golden femur mesh 626 to the landmarks 777. More specifically, in operation 770*a*, the open golden femur mesh 626 may be approximately registered to landmarks 777 using a coarse registration transformation. In one embodiment, this may be done by finding appropriate translation transform parameters that minimize translation misalignment with landmarks of the reference open golden femur mesh mapped onto the target femur of the target image, where landmarks 777 are positioned. This coarse registration operation typically determines an approximate femur position in the MRI scan. During this operation, the reference open golden femur mesh 626 may be overlapped with the target femur of the target image using a translation transformation to minimize translational misalignment of the femurs. A translation transform, translates (or shifts) all the points in 3D space by the same 3D vector. That is, the reference femur may be mapped into the target image space by shifting the reference open golden femur mesh along one or more axes in the target image space to minimize misalignment. During this operation the reference object is not rotated, scaled or deformed. In one embodiment, three parameters for the translation transformation may be generated: one parameter for each dimension that specifies the translation for that dimension. In one embodiment, the final parameters of the translation transform minimizing the misalignment of the mapped reference femur image coordinates into the target image space may be found using a gradient descent optimizer. In other embodiments, other types of optimizers may be utilized, such as for instance an Iterative Closest Point (ICP) algorithm.

Optimization of mesh alignment with respect to landmarks is based on minimizing a cost function D, which in one embodiment can be the sum, across all landmarks, of the squared distance from each landmark point 777 to the transformed open golden mesh. The same cost function may be used for steps 770*a*-770*c*. Methods for computing this cost function and its gradient are covered in more detail later in this disclosure.

After an optimal transform has been found, it is applied to all the golden femur data (i.e., the closed golden femur mesh 624, open golden femur mesh 626, and golden femur mesh regions 628, 629. The next operation (i.e., operation 770*b* of FIG. 37, which is discussed immediately below) is then started with transformed golden femur data. As can be understood from the following discussion, after every consecutive operation 770*a*, 770*b*, 770*c* and 770*e* of FIG. 37, the transform found during the registration step is applied to all the golden femur data. As a result, after each operation the golden femur data is successively made more closely aligned with the femur in the target image.

In operation 770*b* of FIG. 37 similarity transforms are used to register the full or entire open golden femur mesh 626 to the landmarks 777. Specifically, operation 770*b* further refines the object's registration determined by operation 770*a*. This may be done by approximately registering the open golden femur mesh 626 to landmarks 777 using a similarity transformation. In one embodiment, a similarity transformation may be performed in 3D space. The reference open golden femur mesh may be rotated in 3D, translated in 3D and homogeneously scaled to map its coordinates into the target MRI scan data to minimize misalignment between the open golden femur mesh and the landmarks in the target MRI scan. In some embodiments, a center of rotation may be specified so that both the rotation and scaling operations are performed with respect to the specified center of rotation. In one embodiment, a 3D similarity transformation, specified by seven parameters, may be used. One parameter specifies the scaling factor, three parameters specify a versor that represents the 3D rotation, and three parameters specify a vector that represents the 3D translation in each dimension. A versor is a unit quaternion that provides a convenient mathematical notation for representing rotations of objects in three dimensions.

In one embodiment, local minimization techniques may be employed with the similarity transformation to obtain a refined registration of the reference open golden femur mesh onto the target MRI scan that is not far from the registration of the reference open golden femur mesh onto the target MRI scan found in previous operation 770*a* and used as the initial starting approximation. For instance, gradient descent, conjugate gradient descent, or ICP optimization may be used. After the best transform is found for operation 770*b* of FIG. 37, the transform is applied to the golden femur data in a manner similar to that of operation 770*a*.

In operation 770*c* of FIG. 37 affine transforms are used to register the full or entire open golden femur mesh 626 to the landmarks 777. Specifically, operation 770*c* further refines the image registration determined by operation 770*b*. In one embodiment, an affine transformation may be used to register the open golden femur mesh 626 to landmarks 777 in the target MRI scan data. In one embodiment, the approximate femur registration found during operation 770*b* may be used as the initial starting approximation for the affine transformation of operation 770*c*.

An affine transformation typically is a linear transformation followed by a translation. The affine transformation preserves collinearity between points (i.e., three points which lie on a line continue to be collinear after the transformation) and ratios of distances along a line. In one embodiment, a 3D affine transformation, specified by 12 parameters, may be utilized. Nine parameters of the affine transformation specify the linear transformation (which may be represented by a three by three matrix) and three parameters of the affine transformation specify the 3D translation in each dimension. The parameters of the affine transform that minimizes the misalignment of the open golden femur mesh with landmarks may be found using again local minimization techniques, such as gradient descent or conjugate gradient descent optimization.

After the best transform is found for operation 770*c* of FIG. 37, the transform is applied to the golden femur data. The transformed golden femur data from operation 770*c* is then employed in the preparatory step of detecting appropriate image edges, namely, operation 770*d*, which is discussed below. Those edges will be later used in operation 770*e* of FIG. 37, as discussed below. The transformed golden femur data from operation 770*c* is used as reference data similar to the previous operations.

A discussion of image edges is now provided before discussing the details of operation 770*d* of FIG. 37. Image edges consist of those points in the image where the image contrast significantly changes between neighbor pixels (or voxels) and this contrast change is consistent along several neighboring points distributed over a smooth curve. For example, points that lie between the light cancellous bone pixels and dark cortical bone pixels form an image edge. Similarly, the points that lie between the dark cortical bone pixels and the grayish cartilage pixels form an image edge. Yet a configuration involving a one-pixel black spot and the surrounding light pixels does not form an image edge because the light points represent a curve with too much curvature, whereas the dark point represents a curve that is too discontinuous (spanning only a single voxel.) Usually there is an image edge that separates one type of the body tissue from a neighboring different type of body tissue.

The purpose of segmenting an image is to be able to separate in the image certain body tissues from the surrounding tissues. Ideally, the segmentation boundaries (or curves) should lie mostly in the image edges. A general MRI or CT image contains lots of edges separating various body tissues from the neighboring tissues. Yet when segmenting, there is only interest in certain tissues and thus particular edges only. Operation 770*d* is intended to find those edges that are of interest for segmenting a particular body object.

In particular in case of the segmentation of any of the versions of the femur planning model 22, 28 (shown in blocks 110 and 115, respectively, of FIG. 1C), operation 770*d* of FIG. 37 will find the edges that separate the cortical femur bone from the outside knee tissues (i.e., the tendons, ligaments, cartilage, fluid, etc.). In some embodiments, operation 770*d* will not find the edges that separate the femur cancellous bone from the femur cortical bone. In other embodiments, operation 770*d* will find the edges that separate the femur cancellous bone form the cortical bone.

Operation 770*d* may also find some edges that are of no interest to the femur planning segmentation. Most of those edges of no interest will lie at significant distance from the femur boundary surface and, as a result, the edges of no interest will not influence the next operation in the algorithm, namely, operation 770*e* of FIG. 37.

In some cases, some of the edges of no interest might happen to be very close to the edges of interest. Such nearby edges of no interest are likely to be the edges separating the cartilage tissue from the other tissues outside the bone. Such edges might adversely influence the next operation in the algorithm, namely, operation 770*e* of FIG. 37, and lead to inaccurate segmentation. In some embodiments, this inaccuracy can be remedied by the user providing extra landmarks 777 in the area that is likely to cause such inaccuracies or manually fixing the spline curves during the verification and adjustment operations.

The result of the operation 770*e* of FIG. 37 will be a 3D image of the same size as the target scan data. The resulting 3D image can be called an edges image. The voxels in the edges image correspondent to strong edges will have highest intensities, the non-edge voxels will have low intensities, and the voxels correspondent to weak edges will have intermediate intensities. Discussion of the operation 770*d* of FIG. 37 is now provided.

Figure 38A:
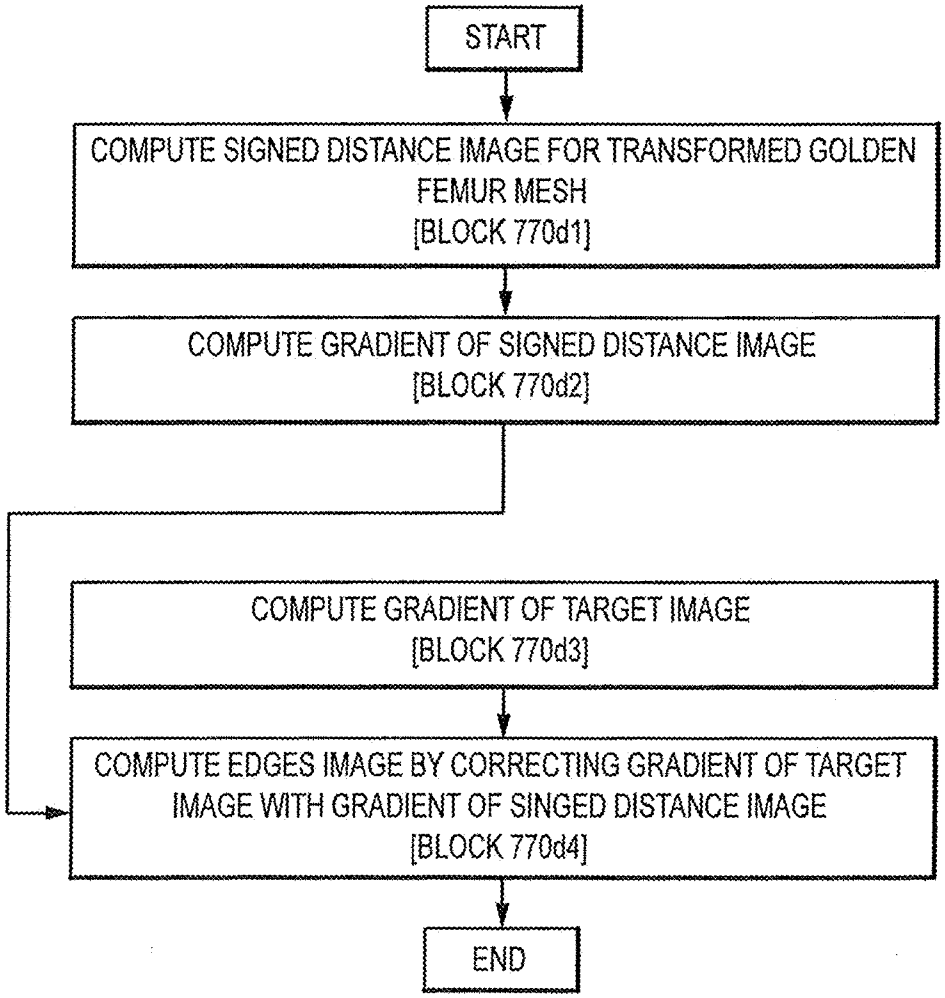
FIG. 38A is a flowchart illustrating the process of operation "Detect Appropriate Image Edges" of FIG. 37.

In operation 770*d* of FIG. 37 appropriate edges of the target images are detected near the transformed open golden femur mesh 626. For example, as indicated in FIG. 38A, which is a flowchart illustrating the process of operation 770*d* of FIG. 37, in operation 770*d*1 the signed distance image is computed for the transformed golden femur mesh 626. A signed distance map is a distance map of a region in 2D (or 3D) and is a function in 2D (or 3D). The signed distance value for a point equals the distance from the point to the boundary of a region. A signed distance value can have a positive or negative value. For example, when a point is inside the region, the signed distance value of the point is the distance from the point to the boundary of the region in the form of a negative value. When a point is outside the region, the signed distance value of the point is the distance from the point to the boundary of the region in the form of a positive value. If the signed distance map function is computed in a regular grid of points in 2D (or 3D) correspondent to image pixels (or voxels) and stored as a 2D (or 3D) image representation, the result can be said to be a 2D (or 3D) signed distance image.

Thus, from the preceding discussion, it can be understood that the signed distance for a watertight surface is a function that has absolute values equal to the regular (Euclidean) distance, but the values also have a sign. The sign is negative for the points inside the surface, and the sign is positive for the points outside the surface. The open golden femur mesh 626 transformed in operations 770*a*-770*c* of FIG. 37 is used in operation 770*d*1 of FIG. 38A. By the time of operation 770*d*1, the open golden femur mesh 626 may quite closely match the landmarks 777 positioned in the target image and, as a result, the open golden femur mesh 626 also matches quite closely the target femur bone in the target image. Since the golden femur mesh 626 is a watertight mesh, the mask image marking may be computed as "1" for all voxels that lie inside the open golden femur mesh 626 and as "0" for all the voxels that lie outside the mesh. The Signed Danielsson Distance Map Image Filter from the ITK library can then be used to compute the signed distance to the mask boundary, which is approximately the same as the signed distance to the mesh. It may be desired to have greater accuracy close to the mesh. If so, then for the voxels where the absolute value of the signed distance is small, the distance to the mesh may be recomputed by finding the closest points via a more exact method, as detailed later in this specification.

In operation 770*d*2 the gradient of the signed distance image is computed. As can be understood from FIGS. 38B, the gradient of the signed distance image contains a vector 1000 in every voxel. The vector 1000 represents the gradient of the signed distance image at the particular point of the voxel. Because the signed distance image represents the signed distance to the transformed open golden femur mesh 626, which follows closely the boundary of the femur bone in the target image, the gradient image has gradient vectors nearly orthogonal to the boundary of the target femur in the voxels close to the boundary.

Figure 38B:
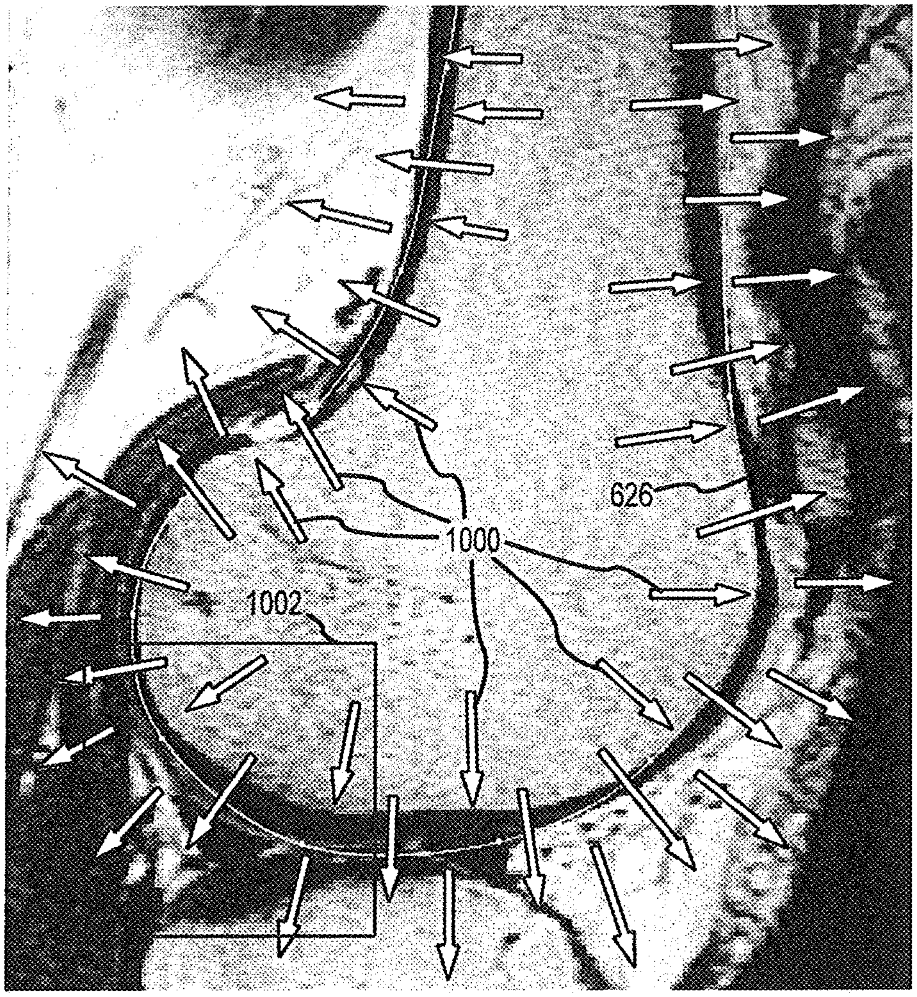
FIG. 38B is an image slice with a contour line representing the approximate segmentation mesh surface found in operation 770*c* of FIG. 37, the vectors showing the gradient of the signed distance for the contour.

The contour line 626 in FIG. 38B represents the approximate segmentation mesh surface found in the previous registration step of operation 770*c* of FIG. 37. The vectors 1000 show the gradient of the signed distance for the contour 626. The starting end of the vector 1000 is the point or voxel where the vector 1000 is computed. The gradient of a signed distance has a vector direction in every point or voxel toward the closest point in the contour 626. Vectors 1000 are oriented from inside to outside the contour 626. Each vector 1000 has a unit length.

In operation 770*d*3 the gradient of the target image is computed. As can be understood from FIG. 38C, which is an enlarged view of the area in FIG. 38B enclosed by the square 1002, the gradient of the target image has gradient vectors 1004 orthogonal to the edges 1006, 1008 in the target image, and the length of those vectors 1004 is larger for stronger edges and smaller for weaker edges. Such vectors 1004 are always oriented from the darker image region to the lighter image region or, in other words, from darker pixels towards brighter pixels. The vectors 1004 are longer where the contrast is higher. For purposes of illustration in FIG. 38C, the vectors 1004 illustrated are only long vectors corresponding to high contrast pixels associated with strong edges. The gradient vectors 1004 can be used to identify the outer cortical bone boundary 1006 and other edges 1008, 1010 that are not of interest for the analysis.

Figure 38C:
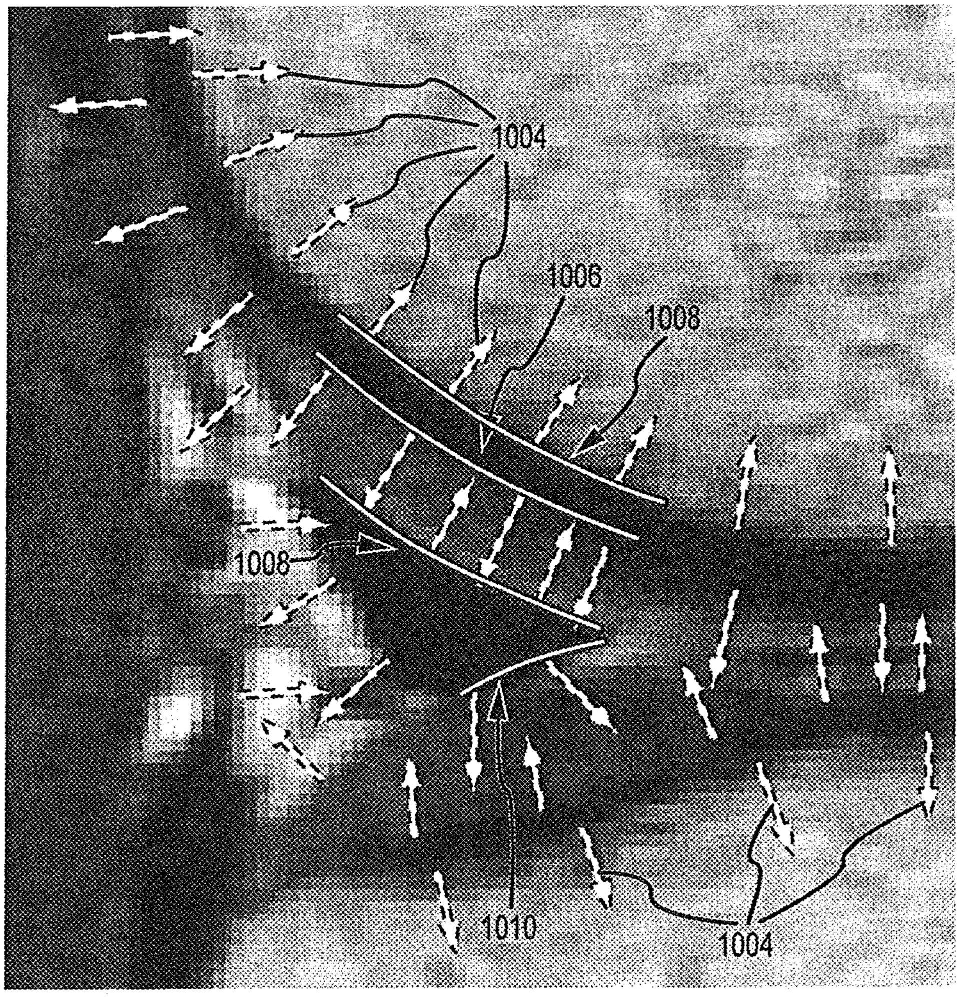
FIG. 38C is an enlarged view of the area in FIG. 38B enclosed by the square 1002, the vectors showing the computed gradient of the target image.

Finally, operation 770*d* of FIG. 37 is completed via operation 770*d*4 of FIG. 38A, wherein the edges image is computed by correcting the gradient of the target image with the gradient of the signed distance image. As can be understood from FIG. 38D, the edges image is computed by combining the results from operations 770*d*2 and 770*d*3. Depending on the type of 3D computer generated bone model being generated from the segmented images, different boundary edges may be of relevance. For example, if the images are being segmented to generate a bone model 22, the boundary edges that are of interest contain dark cortical voxels inside and lighter cartilage or other voxels outside. As a result, the voxels that are of interest are those voxels that have similarly oriented gradients 1000, 1004 computed in operations 770*d*2 and 770*d*3 as shown in FIGS. 38B and 38C, respectively. In every voxel the vector 1004 from operation 770*d*3 is projected onto the vector 1000 from operation 770*d*2. When the projection of image gradient vector onto a signed distance gradient vector points in the same direction as the signed distance vector, its magnitude is taken as the voxel value for the resulting edges image. When it points in the opposite direction (or has no magnitude at all), "0" is taken as the voxel value for the resulting edges image.

The resulting edges image has high values in the target femur cortical bone outer boundary 1006. However, the edges image does not have many other high values close to the transformed open golden femur mesh with one exception, namely, the voxels on the boundary between the target femur cartilage and the outsight bright voxels (for example fluid voxels) might have high values.

Figure 38D:
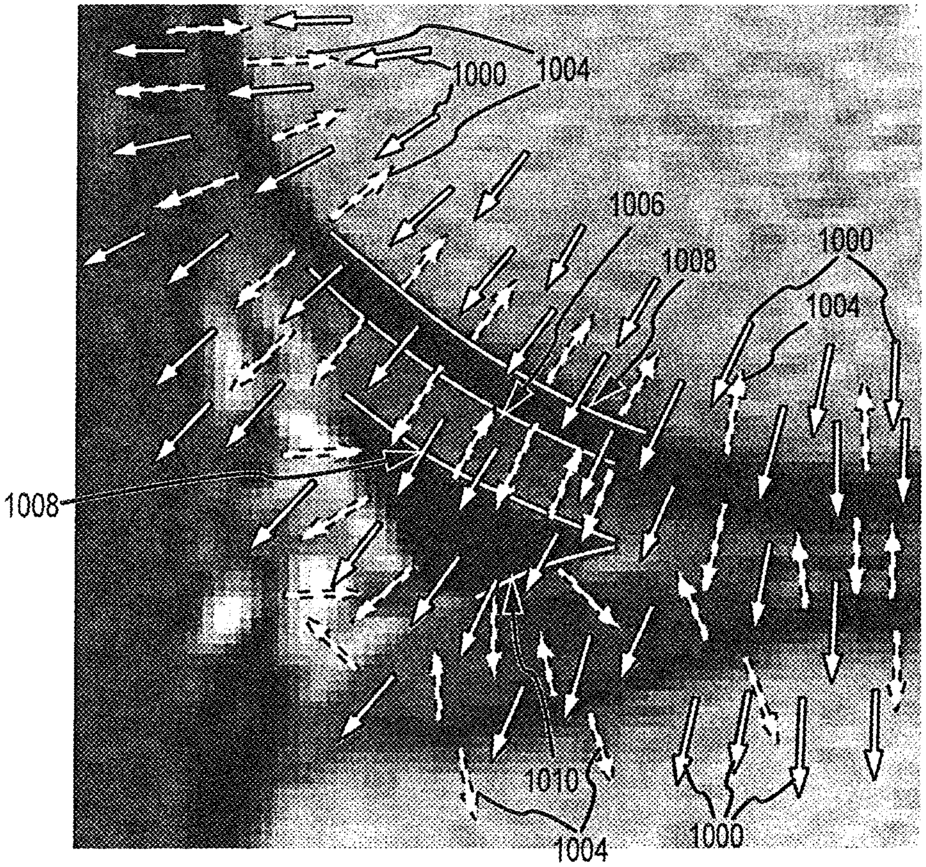
FIG. 38D is the same view as FIG. 38C, except the vectors of FIGS. 38B and 38C are superimposed.

As can be understood from FIG. 38D, the gradient of the signed distance vectors 1000 are uniformly oriented orthogonal to the bone surface and go from inside to outside of the bone. The image gradient vectors 1004 are oriented differently near different image details. For the points in the bone outer boundary 1006, the vectors 1004 are almost parallel to the vectors 1000. For two of the other boundaries 1008, the vectors 1000, 1004 are generally oppositely oriented. Finally, for the last boundary 1010, the vectors 1000, 1004 are quite differently oriented from each other. As a result of the combination of the vectors 1000, 1004 and an analysis of their directional relationships to each other, the edges image will be for FIG. 38D as follows. For points associated with the bone contour line 1006, the edges image will reflect the length of the image gradient vector. For points associated with contour lines 1008, the edges image will be zero. For points associated with the contour line 1010, the edges image values will be smaller than the length of the image gradient vector associated with the bone contour line 1006. Thus, the edges image will tend to have the largest values for the points of the bone contour line 1006.

The high values correspondent to a cartilage/fluid boundary might negatively impact operation 770*e* of the registration in FIG. 37. Consequently, it may be desirable to suppress those values. This can be done in the beginning of operation 770*d*3 of FIG. 38A. Specifically, a windowing filter may be applied to the whole target image. A window [w0, w1] may be used, where w0 will be the minimum value in the image, and w1 will be approximately the value correspondent to the cartilage intensity. The filter will replace the high intensity values in the image with w1 value, and thus the boundary between the cartilage and the lighter matters will disappear. For the type of MRI images that may be used, the w1 value correspondent to the median of all the values in the image works quite well. Although such a filter may not always suppress the cartilage boundary entirely, it makes cartilage outer boundary very much weaker in the image and, as a result, the cartilage has less of an impact in operation 770*e* of FIG. 37.

In one embodiment, a more sophisticated method for suppressing the cartilage boundary may be employed. The cartilage intensity values may be estimated by comparing the voxel values near landmarks 777 along the signed distance gradient direction. The values before a landmark correspond to the cortical bone intensities, while the values after the landmark correspond to the cartilage intensity. Thus for every landmark, a value may be found that represents an "Out of cortical bone" intensity. Such values may be interpolated into the whole image and this windowing function may be applied rather than the constant windowing value w1.

It should be appreciated that a lesser resolution than the target image resolution may be used in all the images participating in the edges image computation. For example, an in-slice voxel size of 1 mm may be used rather than ~0.3 mm in the target image. Using coarser resolution in effect smoothes out the data, allowing a more stable edges computation. It also significantly speeds up the computation. In case of very noisy target images, an additional smoothing step may be applied.

Operation 770 of FIG. 36 is completed via operation 770*e* of FIG. 37, wherein the full or entire golden femur mesh 626, including its regions 628, 629, are simultaneously registered to landmarks 777 and image edges respectively using B-spline deformable transforms. Specifically, operation 770*e* of FIG. 37 further refines the image registration of the boundary golden femur region. In one embodiment, a spline transformation may be used to register the open golden femur mesh 626 into the MRI scan data (target image space). In one embodiment, 3D B-Spline deformable transforms may be employed.

A B-Spline deformable transformation typically is a free form deformation of an object using a deformation field where a deformation vector is assigned to every point in space. For example, a 3D B-spline deformable transform T may specify a 3D vector V(P) for every point P in the original 3D space that is moved by T such that T:P→P+V (P).

In one embodiment, a B-Spline transformation may be specified with M×N parameters, where M is the number of nodes in the B-Spline grid and N is the dimension of the space. In one embodiment, a 3D B-Spline deformable transformation of order three may be used to map every reference image 3D point into the target MRI scan by a different 3D vector. The field of vectors may be modeled using B-splines. Typically a grid J×K×L of control points may be specified where J, K, and L are parameters of the transformation.

In one embodiment, splines of order three may be used with a grid 27×9×11 of control points. That is, the transformation employs 27 control points in the medial/lateral direction (i.e., the x direction), 9 control points in posterior/anterior direction, and 11 control points in distal/proximal direction. Two control points in each dimension (i.e., 2 of 27 in the x direction, 2 of 9 in the y direction and 2 of 11 in the z direction) may be used to specify boundary conditions. As such, the inner spline nodes may form a grid of size 25 by 7 by 9 and the boundary conditions increase the grid to size 27 by 9 by 11. The parametric set for this transformation has a dimension of 3×27×9×11=8019 (i.e., at each node of a 27×9×11 grid of control points, there is specified a 3-dimensional transformation vector; a nonlinear interpolation of transformation vectors for points located between adjacent nodes, is governed by spline equations.) The final parameters of the spline transformation that minimizes the misalignment between the reference golden femur template and the target MRI scan data may be found.

In operation 770*e* of FIG. 37 a different metric (or defect function) may be used as compared to what was used in operations 770*a*, 770*b*, and 770*c*. Specifically, a combined defect function may be used. The combined defect function may be defined as a linear combination of the defect function D (same as in operations 770*a*, 770*b*, and 770*c*) and defect functions D_i that evaluate the discrepancy between the golden mesh regions 628, 629 and the scan image edges defined in operation 770*d* of FIG. 37.

The defect function D_i, or rather its opposite metric function M_i=−D_i, for a given Golden Mesh Region R_i may be defined as follows. All the vertices in the golden mesh region R_i, are taken, a transform is applied to them, and the correspondent intensities are evaluated in the edges image. M_i may be set to be the sum of those intensities. Thus, when more vertices from the transformed golden mesh region R_i come close to the image edges, a higher metric value is the result.

When defining the combined metric or defect, that is when taking the linear combination of D and all the D_i, the coefficients in the linear combination need to be specified. It may be desirable to use a very high coefficient with D because we want to follow very precisely the landmarks 777 provided by a user. Smaller coefficients may be employed with D_i. The latter coefficients might be also different. The higher coefficients may be used for those regions of the bone that require a greater degree of precision, the associated image segmentation needing to result in more clearly defined regions. The lower coefficients may be used for those regions of the bone that do not require a high degree of precision, the associated image segmentation resulting in less clearly defined regions.

Some bones may have a higher degree of shape variations across the population than is found with the knee region of the femur. For example, the shape of the tibia may vary more from patient to patient than does the shape of the femur. As a result, the affine transformation may not provide a close enough registration of the golden tibia template to the target tibia in the target scan. This may cause the Spline transformation to find a local optimum that may be far from the actual tibia in some areas. In one embodiment, an additional registration operation between the affine transform and spline transform operations may be performed to more closely align the golden tibia and the target tibia, allowing the spline transform to converge to the correct local optimum rather than a nearby, but wrong, local optimum.

The class of transforms utilized generally should allow more flexibility (or degrees of freedom) than the Affine transform and less flexibility than the B-spline transforms. The number of degrees of freedom generally is equal to the number of transform parameters. In one embodiment, a class of transforms with more than 12 parameters and less than $3\times27\times9\times11$ parameters may be used. For example, a B-spline transform with fewer control points than used in the subsequent spline transform may be used for the additional transform operation. Alternatively, the deformations may be modeled using quadric rather than cubic functions.

In another embodiment, several golden tibia templates may be used that represent typical tibia variations, e.g., golden tibia templates for varus, valgus, and normal tibia. In one embodiment, each of the golden tibia templates may be used during the translation, similarity and affine transform registration operations to find the template that provides the best match (e.g., best correlation) in the affine transform registration operation. This template may then be used in the remaining registration operations.

Finally, in one embodiment, the tibia registration may be improved by performing the tibia segmentation after the femur segmentation and adding a restriction on the tibia registration transformations such that the tibia may not penetrate the femur. In one embodiment, this may be implemented by introducing a penalty for the penetration. In the target MRI all the voxels that lie inside the femur segmentation curves may be marked. The metric functions, described in more detail below, that are used in the registration operations may be modified to include a penalty term. The penalty term may be computed by taking points in the golden tibia mesh, applying a transform to the set of points, determining if a transformed sample point falls into any of the marked voxels, and adding a large value to the penalty term for each transformed sample point that falls into any of the marked voxels.

In each of the above registration operations, a metric may be used to quantify the degree of correspondence between the reference objects and target image achieved by a given transformation. In one embodiment, the metric quantitatively measures how well the transformed golden femur data fits the target image (e.g., a target MRI scan) and landmarks positioned there.

As discussed above, metrics M=−D, M_i=−D_i, and their linear combination are used in operations 770*a*-770*d* of the registration. An explanation is now given regarding the details on how to compute those metrics. As far as using those metrics with optimizers that require computations of the gradient of the metric, it is also explained how to compute the gradient of those metrics.

When computing the metric M or rather the defect D, such a computation can include finding the sum of the squared distances from each landmark point 777 to the transformed open golden mesh. In order to make this computation as quickly and efficiently as possible, the following can be done. First, a B-Spline transformation of a mesh is no longer a mesh. The plane triangles forming the original mesh get curved over the transformation, and the triangles are no longer planar. Rather than computing distances to curved triangles, which would be very computationally expensive, planar triangles connecting the transformed vertices are used. Very little precision is lost with this substitution because the triangles are very small.

Next, after finding the transformed mesh, it is desirable for every Landmark point to find the closest point in the transformed mesh triangles and take the squared distance to it. A spatial subdivision scheme is used to sort all the triangles by spatial location. An octree subdivision is used, although other schemes (kd-tree, fixed size grid, etc.) would work as well. The spatial subdivision helps to find a closest mesh triangle and a closest point in it using an order of LOG(n) operations where n is the number of triangles in the mesh.

The optimizers used in the registration steps require the computation of the gradient of the metric function, which depends on the applied transform, over the transform parameters.

In one embodiment the metric function may be a composition of several functions. For the metric M (or cost function D), for example, the following functions are used in the composition: a) mesh transformation, b) distance from a Landmark point to the transformed mesh, c) squared distance, d) sum of squares, e) inverse of the sum.

For a composition of functions, determining the gradient involves finding partial derivatives for each function and then applying the chain rule. The derivatives of the algebraic functions are computed by standard formulae. The only non-trivial computation in the above functions is the computation of the partial derivative of a distance from a point to the transformed mesh.

For the latter computation, it may involve using an approximate method. Namely, take the closest triangle found in the metric computation followed by taking the plane containing that triangle. This plane approximates the transformed mesh surface in some small neighborhood of the closest point. One of the transform parameters is changed by a very small amount. It is observed where the former closest triangle is mapped after the variation.

The plane containing the varied triangle is taken. This plane approximates the varied transformed mesh surface in some small neighborhood of the varied closest point. The distance from the landmark point to this varied plane is taken. It is approximately the distance from the landmark point to the whole varied transformed mesh surface. Now the difference between the varied distance and the original distance is taken and divided by the value of the parameters variation. This gives approximately the partial derivative for this parameter.

In order to compute the gradient of the metric D_i with respect to the transform parameters, the gradient image of the edges image is computed right after the computation of the edges image itself. To compute the partial derivative of D_i over a transform parameter, the computation may take place for the derivative of every transformed vertex motion over that parameter using the chain rule. This derivative will be a 3D vector. Its dot product is taken with the correspondent Gradient vector of the Gradient Image of the Edges Image and the values are summed all over the vertices.

Finally, since the combined defect function is a linear combination of defect functions D and D_i, then the gradient of the combined defect function with respect to a given transform, is correspondingly a linear combination (with the same coefficients) of the gradients of D and D_i with respect to that same transform.

In summary and as can be understood from the immediately preceding discussion regarding operations 770*a*-770*c* and 770*e* of FIG. 37, translation transforms (operation 770*a*), similarity transforms (operation 770*b*), affine transforms (operation 770*c*), and B-Spline deformable transforms (operation 770*e*) are employed as part of accomplishing operation 770 of FIG. 36. Because in operations 770*a*-770*c* of FIG. 37 it is intended to register the open golden femur mesh to landmarks, the metric (or defect) function should evaluate how close the transformed open golden femur mesh is to landmarks. Thus, in operations 770*a*-770*c*, there is a selection of the defect function D to be the sum of squared distances from landmarks to the deformed open golden mesh. In the operation 770*e*, a simultaneous registering of several parameters may be defined as a combined metric that will take into account all the parameters. The combined defect function may be defined as a linear combination of the defect function D (same as in operations 770*a*-770*c*) and defect functions D_i that evaluate the discrepancy between the golden mesh regions and the scan image edges defined in operation 770*d* of FIG. 37.

Once operation 770 of FIG. 36 is completed, the process of FIG. 36 then continues with operation 772, wherein the deformed open golden femur mesh 626 and associated regions 628, 629 are segmented followed by operation 773, wherein the resulting segmentation curves are approximated with splines. The process continues with operation 774, wherein the contour lines or splines generated in operation 773 are modified to match landmarks.

In other words, in operation 774 the segmentation curves are refined to more precisely match the landmarks. Typically, the segmentation curves created via the above-described algorithms match the landmarks quite closely. Accordingly, most any simple algorithm for a local curve adjustment can work to further refine the precision of the match of the segmentation curves with the landmarks.

In one embodiment of operation 774 when further refining the segmentation curves to match landmarks, only those curves that belong to slices that contain landmarks are considered. When a curve belongs to a slice with landmarks, it is assumed that it should rather precisely go through all the Landmarks. In one embodiment, a curve may be considered to be precisely enough located relative to a landmark if its distance from the landmark ("Tol") is Tol=0.3 mm or less. Most often all the landmarks are within the Tol distance from the curve. However, sometimes a few of the landmarks are further than the Tol distance from the curve. As can be understood from the following discussion regarding operation 774, for every curve generated via the above-described algorithms, each landmark in a slice is iterated. If a landmark is not within Tol distance from the curve, a correction algorithm is applied to the curve as described below with respect to operation 774.

Operation 774 locally modifies the spline curve to fit a selected landmark. Specifically, as can be understood from FIG. 39, which is a flowchart illustrating the process of operation 774 of FIG. 36 in the context of a particular image slice containing landmarks and a segmentation contour, in operation 774*a* a landmark 777 is identified. In operation 774*b*, the distance of the identified landmark 777 to the spline generated from the golden femur mesh 626 is computed. More specifically, the algorithm of operation 774 first computes distances for all the other landmarks in the same slice to avoid making the distance relationships of the landmarks and curve worse.

In operation 774*c*, an arc of the contour line or spline that is the closest to the landmark is identified. Specifically, the closest spline arc [A, B] to the selected landmark L is located, where A and B are consecutive vertices in the spline curve.

In operation 774*d*, the arc is modified to include the identified landmark, resulting in a modified contour line or spline. Specifically, the vertices A and B are moved iteratively so that the arc [A, B] fits L. For each iteration, the closest point C in [A, B] to L is found. The ratio $\alpha:(1-\alpha)$ is then found in which C divides [A, B]. Next, A is moved by $(1-\alpha)*(L-C)$, and B is moved by $\alpha*(L-C)$. The process stops when 0.5*Tol distance is achieved.

Figure 39:
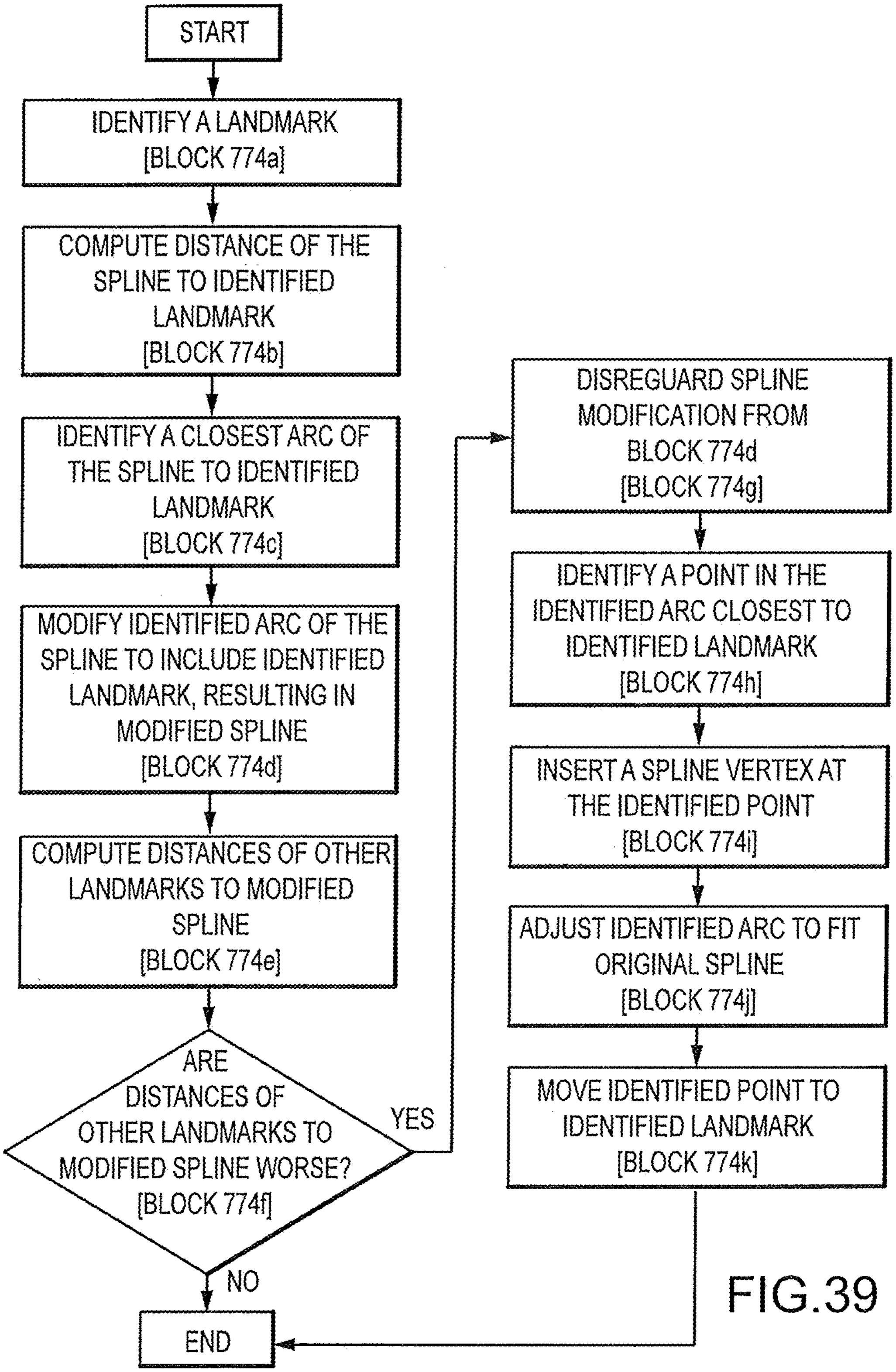
FIG. 39 is a flowchart illustrating the process of operation "Modify Splines" of FIG. 36.

In operation 774*e*, distances of other landmarks to the modified spline are computed and reviewed in operation 774*f* to verify operations 774*a*-774*d* have not made the fit between the spline and other landmarks worse. In other words, the following is checked for every landmark. First, it is checked to see if the new distance between the spline and landmark is within Tol and, if it is, then the relationship between the spline and landmark is acceptable. Second, it is checked to see if the new distance between the spline and landmark is smaller than the old distance and, if it is, then the relationship between the spline and landmark is acceptable. Third, it is checked to see if the new distance is higher than Tol, the old distance was higher than Tol, and the new distance increased by less than 0.5*Tol. If the answer is yes with respect to all three of the elements of the third check, then the relationship between the spline and landmark is acceptable. For all the other cases, the relationship between the spline and landmark is not acceptable. If the distance relationships between the spline and all of the landmarks are considered acceptable, the process outlined in FIG. 39 is completed for the identified landmark, and the process of FIG. 39 can then be run for another identified landmark until all landmarks have gone through the process of FIG. 39.

If any of the distance relationships between any landmark and the spline are found to be unacceptable in operation 774*f* due to a modification of the spline with respect to a selected landmark according to operations 774*a*-774*d*, then per operation 774*g* the spline modification from operation 774*d* is disregarded and a more local modification is employed, as described below with respect to operations 774*h*-774*k* of FIG. 39. The more local modification will add a new vertex into the spline making the spline more flexible in this region. The more local modification will then move the new vertex to L, and this will affect a very small area of the spline. Thus, the chance of decreasing the fit to other landmarks will be very small. The more local modification occurs as follows.

In operation 774*h*, a point in the identified arc closest to the identified landmark is identified. Specifically, the point C in arc [A, B] that is the closest to landmark L is found.

In operation 774*i*, a spline vertex is inserted at the identified point C. With the insertion of a new vertex, the spline shape usually changes in the two immediately adjacent neighbor arcs on both sides of the arc [A, B]. As a result, the arc spline can become too wavy in the vicinity of the arc [A, B].

To remedy the situation, the arc [A, B] is adjusted to fit the original spline in operation 774*j*. Specifically, the vertices A and B are modified to try to fit the new spline as closely as possible to the original spline. In doing so, a measure of closeness (i.e., how closely the new spline follows the original spline in the six neighboring arcs—three to each side of the new control point C) may be computed as follows. In one embodiment, the six spline arcs are sampled such that there are twenty or so sample points in every arc of the spline (i.e., 20*6 sample points). Then, the sum of the squared distances from the sample points to the original spline may be computed. Next, the coordinates of the A and B vertices (control points) are varied (i.e., two parameters for each of A and B, that is four parameters). Then, a local optimization algorithm is used to find the closest spline. This process may be similar to the process of fitting a spline to a polyline, as described elsewhere in this Detailed Description.

Per operation 774*k*, the identified point is moved to the identified landmark. Specifically, the spline vertex C is moved into the landmark point L.

The process outlined in FIG. 39 is completed for the identified landmark, and the process of FIG. 39 can then be run for another identified landmark until all landmarks have gone through the process of FIG. 39.

Once the process of FIG. 39 is completed for all landmarks and the associated contour lines or splines, the process of operation 774 of FIG. 36 is considered complete, which completes the process of FIG. 36 for the operation 252*a* of FIG. 33. The process of operation 252*a* in FIG. 33 is now complete. The image slices 16 are then scrolled over to verify if the segmentation results are acceptable, as indicated by operation 252*c*. In operation 253, if the segmentation is acceptable, then the segmentation process of FIG. 33 ends.

As can be understood from FIG. 33, if in operation 253 the segmentation is not acceptable, then the segmentation of each offending slice 16 is modified by adding additional landmarks 777 and/or modifying the locations of existing landmarks 777 per operation 254 of FIG. 33. For example and as can be understood from FIG. 40, a first spline 800, which is generated via a first run through operation 252 of FIG. 33, has control points 802 and extends along first landmarks 777*a* placed in the slice 16 of FIG. 40 during operation 251 of FIG. 33.

Figure 40:
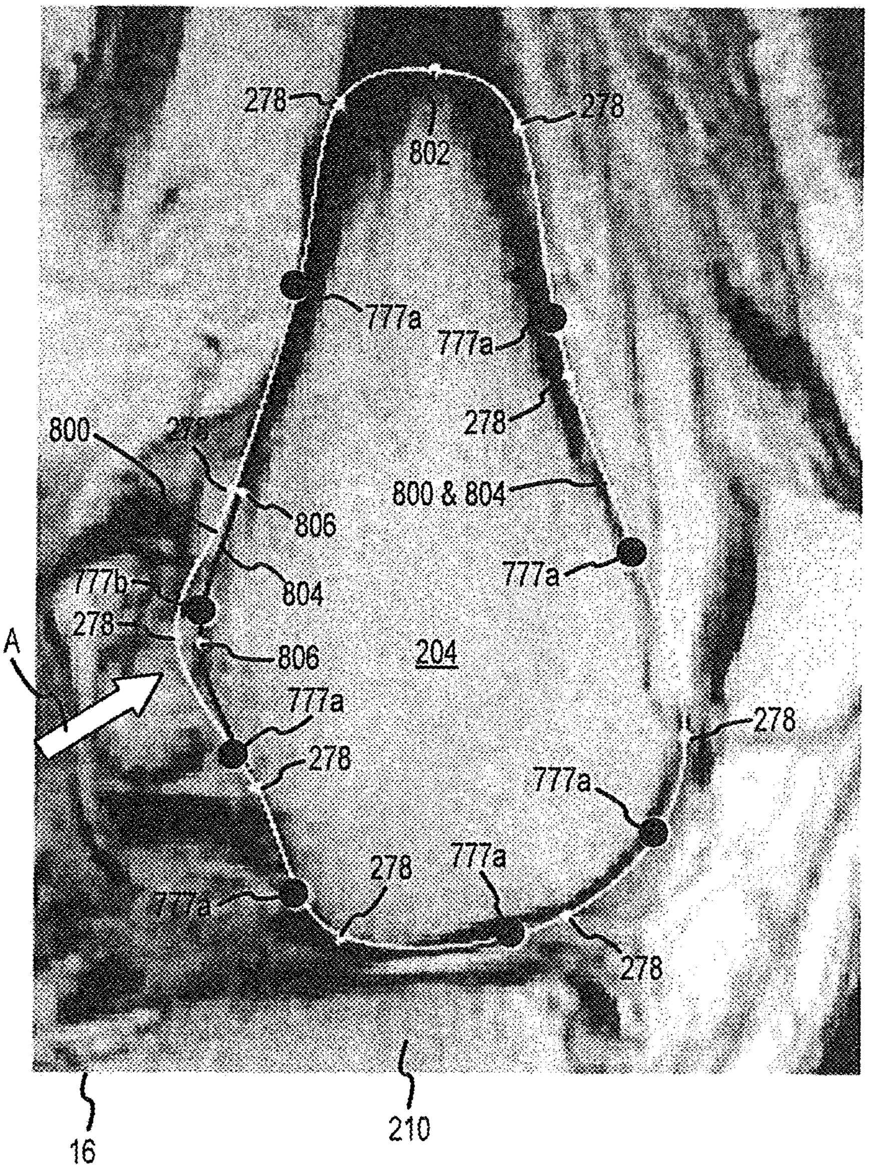
FIG. 40 is an image slice with a spline being modified according to the operations of the flow chart of FIG. 39.

During operation 253 of FIG. 33 the segmentation of the slice 16 of FIG. 40 is identified as being unsatisfactory in the location called out by arrow A in FIG. 40. A new landmark 777*b* is added in the location called out by arrow A per operation 254 and operation 252, or more specifically, operations 774*b*-774*e* of the algorithm of FIG. 39, are repeated to generate a second spline 804, which has control points 806 and extends along both the first landmarks 777*a* and the second landmark 777*b*. As can be understood from FIG. 40, the first spline 800 and the second spline 804 are generally identical and coextensive, except in the region identified by arrow A. The segmentation of the second spline 804 is then approved or disapproved per operation 253. If approved, then the segmentation process of FIG. 33 ends. If disapproved, then the second spline 804 is further modified per operation 254 in a manner similar to as discussed above with respect to FIG. 40.

In one embodiment of operation 254 of FIG. 33, the spline may be simultaneously modified near a new added landmark or near moving landmarks to fit the moving landmarks. In doing so, it may be the case that the user is satisfied with the corrected splines. As a result, the process of FIG. 33 may simply end at operation 254 as if the entirety of operation 252 had been completed and the segmentation was found acceptable at operation 253.

In one embodiment, when a user adds a new landmark into a slice with a spline, the spline is immediately modified using precisely the same algorithm of FIG. 39, namely operations 774*b*-774*e*. When a user moves a landmark, the spline is updated during the motion using operations 774*b*-774*e* of the algorithm of FIG. 39. Adding landmarks (operations 774*g*-774*k* of the algorithm of FIG. 39) is avoided during the motion phase as it may lead to multiple updates during motions, resulting in too many points.

Once the contour lines or splines are successfully segmented from each target image slice, the contour lines or splines are compiled as discussed above into a 3D mesh that may be used as an arthritic bone model 36 (see FIG. 1D) or bone models 22 (see FIG. 1C).

In one embodiment of the registration process discussed above, an optimizer may be used during the registration process to maximize similarity between the open golden mesh and landmarks in the target image (and possibly edges image) by adjusting the parameters of a given transformation model to adjust the location of reference image coordinates in the target image. In one embodiment, the optimizer for a registration operation may use the transformed golden femur data from the previous registration operation as its initial approximation. Then, local optimization techniques may be used to search for a local optimum near the initial starting approximation. This may be done so that any potential matches farther away from the feature of interest (e.g., the femur or tibia in a knee joint) reliably found in an earlier operation may be eliminated.

In operation 770*a* of FIG. 37, when optimizing the translation transformation, a regular step gradient descent optimizer may be used by one embodiment. Other embodiments may use different optimization techniques.

To find a local minimum, parameter steps may be taken in the direction of the negative of the metric gradient (or the approximate gradient) over the transform parameter space at the current point. This generally optimizes the metric which typically has a local minimum when features of the reference image mapped into corresponding features of the target image have minimal misalignment).

In one embodiment, initial gradient step of 3 millimeters may be specified, a relaxation factor may be set to 0.95 and a maximum of 50 iterations may be used in the regular step gradient descent optimization method to determine the parameters of the translation transformation that results in minimal misalignment between the reference Open Golden Femur mesh and the Landmarks in the target MRI scan.

In operation 770*b* of FIG. 37, when optimizing the similarity transformation, a regular step gradient descent optimizer may be used again by one embodiment. When applying the regular step gradient descent optimizer to similarity transformation, the result and the convergence rate depend on the proper choice of parameters representing the similarity transforms. A good choice of parameters when used with gradient computations is such that a variation of every parameter by one unit leads to approximately equal displacement of object points. In order to ensure similar displacement of points with respect to three rotational parameters in the similarity transform, the initial center of rotation for the similarity transformation may be specified as the center of a bounding box (or minimum sized cuboid with sides parallel to the coordinate planes) that encloses the feature (e.g., a bone) registered in the translation registration (e.g., operation 770*a* in FIG. 37). For knee segmentation, scaling coefficients of approximately 40-millimeters may be used for the scaling parameters when bringing the rotational angle parameters together with translation parameters. A scaling coefficient of approximately 40-millimeters may be used because it is approximately half the size of the bone (in the anterior/posterior and medial/lateral directions) of interest and results in a point being moved approximately 40-millimeters when performing a rotation of one radian angle. By the same reason a scaling coefficient of 40 millimeters may be used in the similarity transform scaling parameter together with its translational parameters.

In one embodiment, an initial gradient step of 1.5 millimeters may be specified, a relaxation factor may be set to 0.95 and a maximum of 50 iterations may be performed in the regular step gradient descent optimization method to determine the parameters of the similarity transformation that results in minimal misalignment between the reference open golden template mesh and landmarks in the target MRI scan.

In operation 770*c* of FIG. 37, when optimizing the affine transformation, a regular step gradient optimizer may be used again by one embodiment. For knee bones, scaling coefficients of approximately 40 millimeters may be used for the matrix coefficients variations when bringing them together with translation parameters. An initial gradient step of 1 millimeter may be specified, the relaxation factor may be set to 0.95 and a maximum of 50 iterations may be performed to determine the parameters of the affine transformation that results in minimal misalignment.

In operation 770*e* of FIG. 37, when optimizing the B-spline transformation, a modified regular step gradient descent optimizer may be used by one embodiment when searching for the best B-spline deformable transformation. Namely, a combination of regular step gradient descent optimizer with by coordinate descent may be used here. Rather than computing one gradient vector for the transform space and taking a step along it, a separate gradient may be computed for every B-spline transform node. In one embodiment, order three B-splines (with J×K×L control nodes) may be used and J×K×L gradients may be computed, one for each control point. At every iteration, each of the spline nodes may be moved along its respective gradient. This may enable faster convergence of the optimization scheme. A relaxation factor of 0.95 may be used for each spline node. A an initial gradient step of one-millimeter may be set for every B-spline grid node, and a maximum of 50 iterations may be used in the regular step gradient descent optimization method to find the parameters of the B-spline transformation that provides minimal misalignment of the open golden femur mesh and landmarks and feature edges in the target MRI scan.

FIG. 23 depicts a flowchart illustrating one method for generating spline curves outlining the surface of an object of interest in each target MRI slice (e.g., as discussed above with respect to operation 772 of FIG. 36) after the transformed golden femur mesh is found in operation 770*e* in FIG. 37. Initially, operation 470 intersects the transformed golden femur mesh with a slice of the target scan data. The intersection defines a polyline curve of the surface of the feature (e.g., bone) in each slice. Two or more polyline curves may be generated in a slice when the bone is not very straightly positioned with respect to the slice direction.

A polyline curve is a piecewise linear approximation to a curved feature shape. Generally, this curve should be easy to manipulate with a set of control points. The polyline curve may have many segments, making it more difficult to manipulate the polyline curve (e.g., during operation 254 or 260 of FIG. 6). One embodiment may generate one or more Kochanek splines from the polyline curve. Each spline typically has a smaller number of control points and typically fits the polyline curve with about 0.3-millimeter deviation. See previous description in this Detailed Description for a detailed discussion regarding spline generation.

As discussed above, in one embodiment, the output of the segmentation may be a triangular mesh (e.g., a 3D surface model) of the segmented bone(s) of a joint (e.g., the femur and tibia of a knee joint). The mesh generated generally represents a watertight surface that closely follows the segmentation contour curves of the slices, smoothly interpolates between the segmentation contour curves, and may have a low triangular count. See previous description in this Detailed Description for a detailed discussion regarding mesh generation and the manual adjustment of segmentation splines.

The 3D surface models of the lower end of the femur and the upper end of the tibia of a patient's knee may be used to create arthroplasty jigs and/or implants. For example, the models may be used to create femur and tibia jigs that can be used with a patient's femur and tibia as disclosed in the various U.S. patent applications incorporated by reference herein in this Detailed Description and filed by Park and Park et al. The automatic or semi-automatic processes described herein for segmentation of image data to generate 3D bone models may reduce the overall time required to perform a reconstructive surgery to repair a dysfunctional joint and may also provide improved patient outcomes.

III. Overview of Overestimation Process

The description in Section II. focused on the acquisition of medical images, the segmentation or auto-segmentation of the medical images, and the generation of a patient bone model from the segmented images that is representative of the bones of the patient in a deteriorated or degenerated state. Beginning in Section III., the present disclosure describes an overestimation process where certain areas of the bone in the medical images are identified for generating mating jig surfaces, and certain areas of the bone in the medical images are identified as non-mating areas between a jig and the bone surface. Subsequently, Section IV. will describe an overview of the pre-operative surgical planning process that may take place on the patient's image data.

a. Overview of System and Method for Manufacturing Customized Arthroplasty Cutting Jigs This section continues and expands upon the previous description of the overview of systems and methods for manufacturing custom arthroplasty jigs of FIGS. 1A-1E. Referring back to FIG. 1D, to coordinate the positions/orientations of the bone and arthritic models 36, 36 and their respective descendants, any movement of the restored bone models 28 from point P to point P' is tracked to cause a generally identical displacement for the "arthritic models" 36 [block 135].

As depicted in FIG. 1D, computer generated 3D surface models 40 of the arthroplasty target areas 42 of the arthritic models 36 are imported into computer generated 3D arthroplasty jig models 38 [block 140]. Thus, the jig models 38 are configured or indexed to matingly receive the arthroplasty target areas 42 of the arthritic models 36. Jigs 2 manufactured to match such jig models 38 will then matingly receive the arthroplasty target areas of the actual joint bones during the arthroplasty surgical procedure.

In some embodiments, the 3D surface models 40 may be modified to account for irregularities in the patient's bone anatomy or limitations in the imaging process. For example, the 3D surface models 40 may be subjected to, or the result of, an "overestimation" process. The "overestimated" 3D surface models 40 may result in bone mating surfaces of the actual jigs that matingly receive and contact certain portions of the arthroplasty target areas of the actual joint bones while other portions of the jigs are spaced apart from the bones, including, for example, some regions of the arthroplasty target areas of the actual joint bones. Thus, the bone mating surfaces of the actual jigs may matingly contact certain specific portions of the arthroplasty target areas of the actual joint bones while other areas of the arthroplasty target areas are not matingly contacted. In some embodiments, the specific portions of the arthroplasty target areas contacted by the jig's bone mating surfaces may be those areas that are most likely to be accurately 3D computer modeled and most likely to result in a reliably accurate mating contact between the jig's bone mating surface and the arthroplasty target areas, and the portions of the arthroplasty target areas not contacted by the jig's bone mating surfaces may be those areas that are the least likely to be accurately 3D computer modeled.

In other words, for some embodiments, overestimation may result in areas of mating contact for the bone mating surfaces of the actual jigs being based on the areas of the 3D surface models that are most reliably accurate with respect to the image scan data and most readily machined via the tooling of the CNC machine. Conversely, for some embodiments, overestimation may result in areas of non-contact for the bone mating or other surfaces of the actual jigs for those areas of the jig pertaining to those areas of the 3D surface models that result from image scan data that is less accurate or reliable and/or represent bone features that are too small to be readily machined via the tooling of the CNC machine. The result of the overestimation process described below is actual jigs with a bone mating surfaces that matingly contact certain reliable regions of the arthroplasty target areas of the actual joint bones while avoiding contact with certain less reliable regions of the arthroplasty target areas, resulting in jigs with bone mating surfaces that accurately and reliably matingly receive the arthroplasty target regions.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly receive the arthroplasty target areas 42 of the arthritic models 36. Point P' ($X_{0-k}$, $Y_{0-k}$, $Z_{0-k}$) can also be imported into the jig models 38, resulting in jig models 38 positioned and oriented relative to point P' ($X_{0-k}$, $Y_{0-k}$, $Z_{0-k}$) to allow their integration with the bone cut and drill hole data 44 of [block 125].

In one embodiment, the procedure for indexing the jig models 38 to the arthroplasty target areas 42 is generally or completely automated, as discussed in detail later in this Detailed Description. For example, a computer program may create 3D computer generated surface models 40 of the arthroplasty target areas 42 of the arthritic models 36. The computer program may then import the surface models 40 and point P' ($X_{0-k}$, $Y_{0-k}$, $Z_{0-k}$) into the jig models 38, resulting in the jig models 38 being indexed to matingly receive the arthroplasty target areas 42 of the arthritic models 36. In some embodiments, the surface models 40 may include accounting for irregularities in the patient's bone anatomy and/or limitations in the imaging technology by creating deliberate gaps between the jig's surface and the patient's bone. The resulting jig models 38 are also positioned and oriented relative to point P' ($X_{0-k}$, $Y_{0-k}$, $Z_{0-k}$) to allow their integration with the bone cut and drill hole data 44 of [block 125].

In one embodiment, the arthritic models 36 may be 3D volumetric models as generated from the closed-loop process discussed below with respect to FIGS. 41D-41F. In other embodiments, the arthritic models 36 may be 3D surface models as generated from the open-loop process discussed below with respect to FIGS. 41A-41C and 43A-43C.

As indicated in FIG. 1E, in one embodiment, the data regarding the jig models 38 and surface models 40 relative to point P' ($X_{0-k}$, $Y_{0-k}$, $Z_{0-k}$) is packaged or consolidated as the "jig data" 46 [block 145]. The "jig data" 46 is then used as discussed below with respect to [block 150] in FIG. 1E.

As can be understood from FIG. 1E, the "saw cut and drill hole data" 44 is integrated with the "jig data" 46 to result in the "integrated jig data" 48 [block 150]. As explained above, since the "saw cut and drill hole data" 44, "jig data" 46 and their various ancestors (e.g., models 22, 28, 36, 38) are matched to each other for position and orientation relative to point P and P', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated or natural alignment state.

As can be understood from FIGS. 1A and 1E, the "integrated jig data" 48 is transferred from the computer 6 to the CNC machine 10 [block 155]. Jig blanks 50 are provided to the CNC machine 10 [block 160], and the CNC machine 10 employs the "integrated jig data" to machine the arthroplasty jigs 2 from the jig blanks 50.

For a discussion of example customized arthroplasty cutting jigs 2 capable of being manufactured via the above-discussed process, reference is made to FIGS. 1F-1I. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 1F-1I are for total knee replacement ("TKR") procedures. Thus, FIGS. 1F and 1G are, respectively, bottom and top perspective views of an example customized arthroplasty femur jig 2A, and FIGS. 1H and 1I are, respectively, bottom and top perspective views of an example customized arthroplasty tibia jig 2B.

As indicated in FIGS. 1F and 1G, a femur arthroplasty jig 2A may include an interior side or portion 100 and an exterior side or portion 102. When the femur cutting jig 2A is used in a TKR procedure, the interior side or portion 100 faces and matingly receives the arthroplasty target area 42 of the femur lower end, and the exterior side or portion 102 is on the opposite side of the femur cutting jig 2A from the interior portion 100.

The interior portion 100 of the femur jig 2A is configured to match the surface features of the damaged lower end (i.e., the arthroplasty target area 42) of the patient's femur 18. Thus, when the target area 42 is received in the interior portion 100 of the femur jig 2A during the TKR surgery, the surfaces of the target area 42 and the interior portion 100 match.

The surface of the interior portion 100 of the femur cutting jig 2A is machined or otherwise formed into a selected femur jig blank 50A and is based or defined off of a 3D surface model 40 of a target area 42 of the damaged lower end or target area 42 of the patient's femur 18. In some embodiments, the 3D surface model 40 may modified via the "overestimation" process described below to account for limitations in the medical imaging process and/or limitations in the machining process.

As indicated in FIGS. 1H and 1I, a tibia arthroplasty jig 2B may include an interior side or portion 104 and an exterior side or portion 106. When the tibia cutting jig 2B is used in a TKR procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR surgery, the surfaces of the target area 42 and the interior portion 104 match.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient's tibia 20. In some embodiments, the 3D surface model 40 may modified via the "overestimation" process described below to account for limitations in the medical imaging process and/or limitations in the machining process.

b. Overview of Automated Process for Indexing 3D Arthroplasty Jig Models to Arthroplasty Target Areas As mentioned above with respect to [block 140] of FIG. 1D, the process for indexing the 3D arthroplasty jig models 38 to the arthroplasty target areas 42 can be automated. A discussion of an example of such an automated process will now concern the remainder of this Detailed Description, beginning with an overview of the automated indexing process.

As can be understood from FIG. 1A and [blocks 100-105] of FIG. 1B, a patient 12 has a joint 14 (e.g., a knee, elbow, ankle, wrist, shoulder, hip, vertebra interface, etc.) to be replaced. The patient 12 has the joint 14 scanned in an imaging machine 8 (e.g., a CT, MRI, etc. machine) to create a plurality of 2D scan images 16 of the bones (e.g., femur 18 and tibia 20) forming the patient's joint 14 (e.g., knee). Each scan image 16 is a thin slice image of the targeted bone(s) 18, 20. The scan images 16 are sent to the CPU 7, which employs an open-loop image analysis along targeted features 42 of the scan images 16 of the bones 18, 20 to generate a contour line for each scan image 16 along the profile of the targeted features 42.

As can be understood from FIG. 1A and [block 110] of FIG. 1C, the CPU 7 compiles the scan images 16 and, more specifically, the contour lines to generate 3D computer surface models ("arthritic models") 36 of the targeted features 42 of the patient's joint bones 18, 20. In the context of total knee replacement ("TKR") surgery, the targeted features 42 may be the lower or knee joint end of the patient's femur 18 and the upper or knee joint end of the patient's tibia 20. More specifically, the targeted features 42 may be the tibia contacting articulating surface of the patient's femur 18 and the femur contacting articulating surface of the patient's tibia 20.

In some embodiments, the "arthritic models" 36 may be surface models or volumetric solid models respectively formed via an open-loop or closed-loop process such that the contour lines are respectively open or closed loops. In one embodiment discussed in detail herein, the "arthritic models" 36 may be surface models formed via an open-loop process. By employing an open-loop and surface model approach, as opposed to a closed-loop and volumetric solid model approach, the computer modeling process requires less processing capability and time from the CPU 7 and, as a result, is more cost effective.

The system 4 measures the anterior-posterior extent and medial-lateral extent of the target areas 42 of the "arthritic models" 36. The anterior-posterior extent and medial-lateral extent may be used to determine an aspect ratio, size and/or configuration for the 3D "arthritic models" 36 of the respective bones 18, 20. In one embodiment of a jig blank grouping and selection method discussed below, the aspect ratio, size and/or configuration of the 3D "arthritic models" 36 of the respective bones 18, 20 may be used for comparison to the aspect ratio, size and/or configuration of 3D computer models of candidate jig blanks 50 in a jig blank grouping and selection method discussed below. In one embodiment of a jig blank grouping and selection method discussed below, the anterior-posterior and medial-lateral dimensions of the 3D "arthritic models" 36 of the respective bones 18, 20 may be used for comparison to the anterior-posterior and medial-lateral dimensions of 3D computer models of candidate jig blanks 50.

In the context of TKR, the jigs 2 will be femur and tibia arthroplasty cutting jigs 2A, 2B, which are machined or otherwise formed from femur and tibia jig blanks 50A, 50B. A plurality of candidate jig blank sizes exists, for example, in a jig blank library. While each candidate jig blank may have a unique combination of anterior-posterior and medial-lateral dimension sizes, in some embodiments, two or more of the candidate jig blanks may share a common aspect ratio or configuration. The candidate jig blanks of the library may be grouped along sloped lines of a plot according to their aspect ratios. The system 4 employs the jig blank grouping and selection method to select a jig blank 50 from a plurality of available jig blank sizes contained in the jig blank library. For example, the configurations, sizes and/or aspect ratios of the tibia and femur 3D arthritic models 36 are compared to the configurations, sizes and/or aspect ratios of the 3D models of the candidate jig blanks with or without a dimensional comparison between the arthritic models 36 and the models of the candidate jig blanks.

Alternatively, in one embodiment, the anterior-posterior and medial-lateral dimensions of the target areas of the arthritic models 36 of the patient's femur and tibia 18, 20 are increased via a mathematical formula. The resulting mathematically modified anterior-posterior and medial-lateral dimensions are then compared to the anterior-posterior and medial-lateral dimensions of the models of the candidate jig blanks 50A, 50B. In one embodiment, the jig blanks 50A, 50B selected are the jig blanks having anterior-posterior and medial-lateral dimensions that are the closest in size to the mathematically modified anterior-posterior and medial-lateral dimensions of the patient's bones 18, 20 without being exceeded by the mathematically modified dimensions of the patient's bones 18, 20. In one embodiment, the jig blank selection method results in the selection of a jig blank 50 that is as near as possible in size to the patient's knee features, thereby minimizing the machining involved in creating a jig 2 from a jig blank.

In one embodiment, as discussed with respect to FIGS. 1F-1I, each arthroplasty cutting jig 2 includes an interior portion and an exterior portion. The interior portion is dimensioned specific to the surface features of the patient's bone that are the focus of the arthroplasty. Thus, where the arthroplasty is for TKR surgery, the jigs will be a femur jig and/or a tibia jig. The femur jig will have an interior portion custom configured to match the damaged surface of the lower or joint end of the patient's femur. The tibia jig will have an interior portion custom configured to match the damaged surface of the upper or joint end of the patient's tibia.

In one embodiment, because of the jig blank grouping and selection method, the exterior portion of each arthroplasty cutting jig 2 is substantially similar in size to the patient's femur and tibia 3D arthritic models 36. However, to provide adequate structural integrity for the cutting jigs 2, the exterior portions of the jigs 2 may be mathematically modified to cause the exterior portions of the jigs 2 to exceed the 3D femur and tibia models in various directions, thereby providing the resulting cutting jigs 2 with sufficient jig material between the exterior and interior portions of the jigs 2 to provide adequate structural strength.

As can be understood from [block 140] of FIG. 1D, once the system 4 selects femur and tibia jig blanks 50 of sizes and configurations sufficiently similar to the sizes and configurations of the patient's femur and tibia computer arthritic models 36, the system 4 superimposes the 3D computer surface models 40 of the targeted features 42 of the femur 18 and tibia 20 onto the interior portion of the respective 3D computer models of the selected femur and tibia jigs 38, or more appropriately in one version of the present embodiment, the jig blanks 50. The result, as can be understood from [block 145] of FIG. 1E, is computer models of the femur and tibia jigs 2 in the form of "jig data" 46, wherein the femur and tibia jig computer models have: (1) respective exterior portions closely approximating the overall size and configuration of the patient's femur and tibia; and (2) respective interior portions having surfaces that match the targeted features 42 of the patient's femur 18 and tibia 20.

The system 4 employs the data from the jig computer models (i.e., "jig data" 46) to cause the CNC machine 10 to machine the actual jigs 2 from actual jig blanks. The result is the automated production of actual femur and tibia jigs 2 having: (1) exterior portions generally matching the patient's actual femur and tibia with respect to size and overall configuration; and (2) interior portions having patient-specific dimensions and configurations corresponding to the actual dimensions and configurations of the targeted features 42 of the patient's femur and tibia. The systems 4 and methods disclosed herein allow for the efficient manufacture of arthroplasty jigs 2 customized for the specific bone features of a patient.

The jigs 2 and systems 4 and methods of producing such jigs are illustrated herein in the context of knees and TKR surgery. However, those skilled in the art will readily understand the jigs 2 and system 4 and methods of producing such jigs can be readily adapted for use in the context of other joints and joint replacement surgeries, e.g., elbows, shoulders, hips, etc. Accordingly, the disclosure contained herein regarding the jigs 2 and systems 4 and methods of producing such jigs should not be considered as being limited to knees and TKR surgery, but should be considered as encompassing all types of joint surgeries.

c. Defining a 3D Surface Model of an Arthroplasty Target Area of a Femur Lower End for Use as a Surface of an Interior Portion of a Femur Arthroplasty Cutting Jig.

Figure 41C:
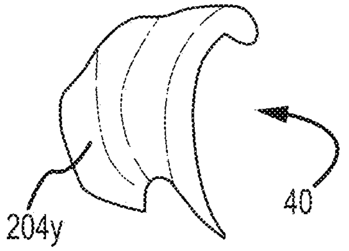
FIG. 41C is a 3D model of the targeted region of the damaged lower end as generated using the open-loop contour line segments depicted in FIG. 41B.
Figure 41D:
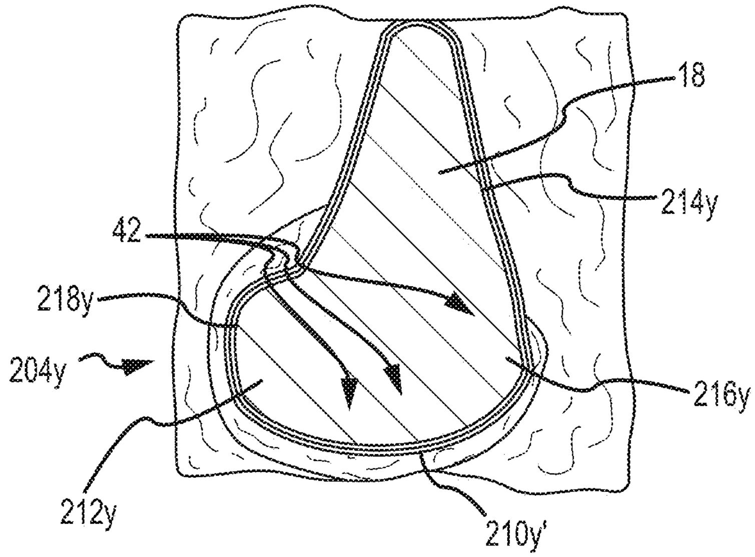
FIG. 41D is an anterior-posterior image slice of the damaged lower or knee joint end of the patient's femur, wherein the image slice includes a closed-loop contour line corresponding to the femur lower end, including the targeted region.
Figure 41E:
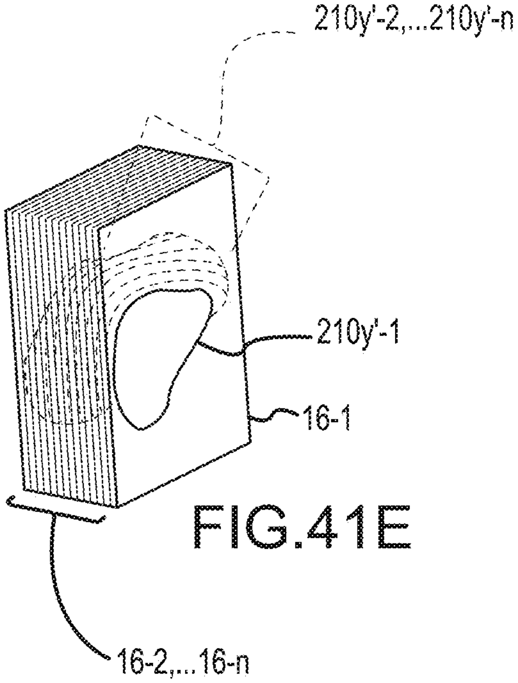
FIG. 41E is a plurality of image slices with their respective closed-loop contour line segments, the closed-loop contour lines being accumulated to generate the 3D model of the femur lower end, including the targeted region.
Figure 41F:
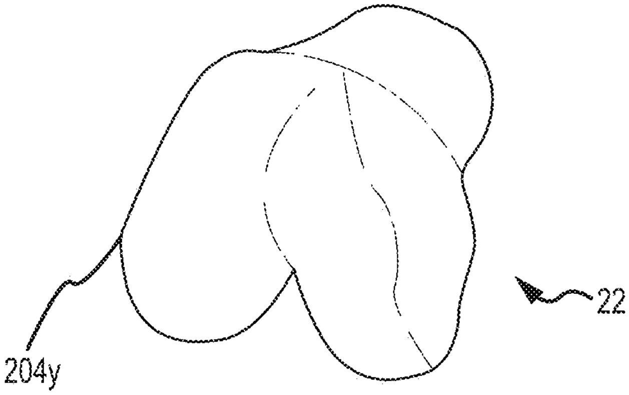
FIG. 41F is a 3D model of the femur lower end, including the targeted region, as generated using the closed-loop contour lines depicted in FIG. 41B.
Figure 41G:
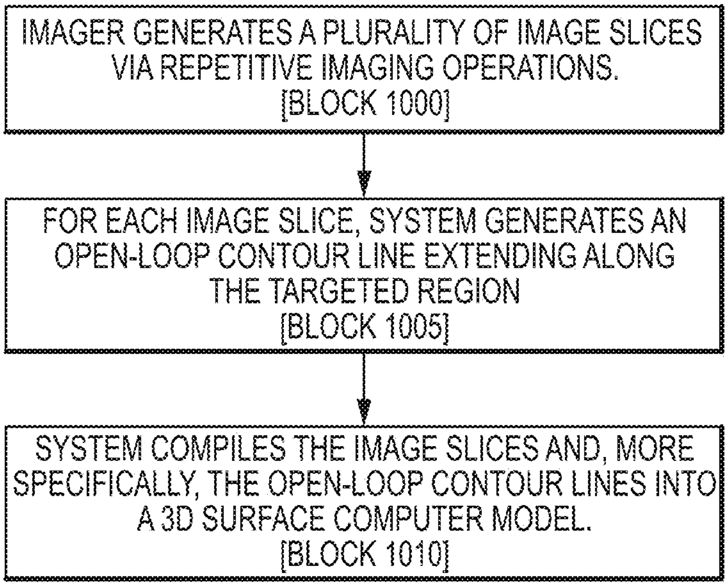
FIG. 41G is a flow chart illustrating an overview of the method of producing a femur jig.

For a discussion of a method of generating a 3D model 40 of a target area 42 of a damaged lower end 204*y* of a patient's femur 18, reference is made to FIGS. 41A-41G. FIG. 41A is an anterior-posterior ("AP") image slice 208*y* of the damaged lower or knee joint end 204*y* of the patient's femur 18, wherein the image slice 208*y* includes an open-loop contour line segment 210*y* corresponding to the target area 42 of the damaged lower end 204*y*. FIG. 41B is a plurality of image slices (16-1, 16-1, 16-2, . . . 16-*n*) with their respective open-loop contour line segments (210*y*-1, 210*y*-2, . . . 210*y*-*n*), the open-loop contour line segments 210*y* being accumulated to generate the 3D model 40 of the target area 42. FIG. 41C is a 3D model 40 of the target area 42 of the damaged lower end 204*y* as generated using the open-loop contour line segments (16-1, 16-2, . . . 16-*n*) depicted in FIG. 41B. FIGS. 41D-41F are respectively similar to FIGS. 41A-41C, except FIGS. 41D-41F pertain to a closed-loop contour line as opposed to an open-loop contour line. FIG. 41G is a flow chart illustrating an overview of the method of producing a femur jig 2A.

As can be understood from FIGS. 1A, 1B and 41A, the imager 8 is used to generate a 2D image slice 16 of the damaged lower or knee joint end 204*y* of the patient's femur 18. As depicted in FIG. 41A, the 2D image 16 may be an AP view of the femur 18. Depending on whether the imager 8 is a MRI or CT imager, the image slice 16 will be a MRI or CT slice. The damaged lower end 204*y* includes the posterior condyle 212*y*, an anterior femur shaft surface 214*y*, and an area of interest or targeted area 42 that extends from the posterior condyle 212*y* to the anterior femur shaft surface 214*y*. The targeted area 42 of the femur lower end may be the articulating contact surfaces of the femur lower end that contact corresponding articulating contact surfaces of the tibia upper or knee joint end.

As shown in FIG. 41A, the image slice 16 may depict the cancellous bone 216*y*, the cortical bone 218*y* surrounding the cancellous bone, and the articular cartilage lining portions of the cortical bone 218*y*. The contour line 210*y* may extend along the targeted area 42 and immediately adjacent the cortical bone and cartilage to outline the contour of the targeted area 42 of the femur lower end 204*y*. The contour line 210*y* extends along the targeted area 42 starting at point A on the posterior condyle 212*y* and ending at point B on the anterior femur shaft surface 214*y*.

In one embodiment, as indicated in FIG. 41A, the contour line 210*y* extends along the targeted area 42, but not along the rest of the surface of the femur lower end 204*y*. As a result, the contour line 210*y* forms an open-loop that, as will be discussed with respect to FIGS. 41B and 41C, can be used to form an open-loop region or 3D computer model 40, which is discussed with respect to [block 140] of FIG. 1D and closely matches the 3D surface of the targeted area 42 of the femur lower end. Thus, in one embodiment, the contour line is an open-loop and does not outline the entire cortical bone surface of the femur lower end 204*y*. Also, in one embodiment, the open-loop process is used to form from the 3D images 16 a 3D surface model 36 that generally takes the place of the arthritic model 36 discussed with respect to [blocks 125-140] of FIG. 1D and which is used to create the surface model 40 used in the creation of the "jig data" 46 discussed with respect to [blocks 145-150] of FIG. 1E.

In one embodiment and in contrast to the open-loop contour line 210*y* depicted in FIGS. 41A and 41B, the contour line is a closed-loop contour line 210*y*' that outlines the entire cortical bone surface of the femur lower end and results in a closed-loop area, as depicted in FIG. 41D. The closed-loop contour lines 210*y*'-2, . . . 210*y*'-*n* of each image slice 16-1, . . . 16-*n* are combined, as indicated in FIG. 41E. A closed-loop area may require the analysis of the entire surface region of the femur lower end 204*y* and result in the formation of a 3D model of the entire femur lower end 204*y* as illustrated in FIG. 41F. Thus, the 3D surface model resulting from the closed-loop process ends up having in common much, if not all, the surface of the 3D arthritic model 36. In one embodiment, the closed-loop process may result in a 3D volumetric anatomical joint solid model from the 2D images 16 via applying mathematical algorithms. U.S. Pat. No. 5,682,886, which was filed Dec. 26, 1995 and is incorporated by reference in its entirety herein, applies a snake algorithm forming a continuous boundary or closed-loop. After the femur has been outlined, a modeling process is used to create the 3D surface model, for example, through a Bezier patches method. Other 3D modeling processes, e.g., commercially-available 3D construction software as listed in other parts of this Detailed Description, are applicable to 3D surface model generation for closed-loop, volumetric solid modeling.

In one embodiment, the closed-loop process is used to form from the 3D images 16 a 3D volumetric solid model 36 that is essentially the same as the arthritic model 36 discussed with respect to [blocks 125-140] of FIG. 1D. The 3D volumetric solid model 36 is used to create the surface model 40 used in the creation of the "jig data" 46 discussed with respect to [blocks 145-150] of FIG. 1E.

The formation of a 3D volumetric solid model of the entire femur lower end employs a process that may be much more memory and time intensive than using an open-loop contour line to create a 3D model of the targeted area 42 of the femur lower end. Accordingly, although the closed-loop methodology may be utilized for the systems and methods disclosed herein, for at least some embodiments, the open-loop methodology may be preferred over the closed-loop methodology.

An example of a closed-loop methodology is disclosed in U.S. patent application Ser. No. 11/641,569 to Park, which is entitled "Improved Total Joint Arthroplasty System" and was filed Jan. 19, 2007. This application is incorporated by reference in its entirety into this Detailed Description.

As can be understood from FIGS. 41B and 41G, the imager 8 generates a plurality of image slices (16-1, 16-2 . . . 16-*n*) via repetitive imaging operations [block 1000]. Each image slice 16 has an open-loop contour line (210*y*-1, 210*y*-2 . . . 210*y*-*n*) extending along the targeted region 42 in a manner as discussed with respect to FIG. 41A [block 1005]. In one embodiment, each image slice is a two-millimeter 2D image slice 16. The system 4 compiles the plurality of 2D image slices (16-1, 16-2 . . . 16-*n*) and, more specifically, the plurality of open-loop contour lines (210*y*-1, 210*y*-2, . . . 210*y*-*n*) into the 3D femur surface computer model 40 depicted in FIG. 41C [block 1010]. This process regarding the generation of the surface model 40 is also discussed in the overview section with respect to [blocks 100-105] of FIG. 1B and [blocks 130-140] of FIG. 1D. A similar process may be employed with respect to the closed-loop contour lines depicted in FIGS. 41D-41F.

As can be understood from FIG. 41C, the 3D femur surface computer model 40 is a 3D computer representation of the targeted region 42 of the femur lower end. In one embodiment, the 3D representation of the targeted region 42 is a 3D representation of the articulated tibia contact surfaces of the femur distal end. As the open-loop generated 3D model 40 is a surface model of the relevant tibia contacting portions of the femur lower end, as opposed to a 3D model of the entire surface of the femur lower end as would be a result of a closed-loop contour line, the open-loop generated 3D model 40 is less time and memory intensive to generate.

In one embodiment, the open-loop generated 3D model 40 is a surface model of the tibia facing end face of the femur lower end, as opposed a 3D model of the entire surface of the femur lower end. The 3D model 40 can be used to identify the area of interest or targeted region 42, which, as previously stated, may be the relevant tibia contacting portions of the femur lower end. Again, the open-loop generated 3D model 40 is less time and memory intensive to generate as compared to a 3D model of the entire surface of the femur distal end, as would be generated by a closed-loop contour line. Thus, for at least some versions of the embodiments disclosed herein, the open-loop contour line methodology is preferred over the closed-loop contour line methodology. However, the system 4 and method disclosed herein may employ either the open-loop or closed-loop methodology and should not be limited to one or the other.

Regardless of whether the 3D model 40 is a surface model of the targeted region 42 (i.e., a 3D surface model generated from an open-loop process and acting as the arthritic model 22) or the entire tibia facing end face of the femur lower end (i.e., a 3D volumetric solid model generated from a closed-loop process and acting as the arthritic model 22), the data pertaining to the contour lines 210*y* can be converted into the 3D contour computer model 40 via the surface rendering techniques disclosed in any of the aforementioned U.S. patent applications to Park. For example, surface rending techniques employed include point-to-point mapping, surface normal vector mapping, local surface mapping, and global surface mapping techniques. Depending on the situation, one or a combination of mapping techniques can be employed.

In one embodiment, the generation of the 3D model 40 depicted in FIG. 41C may be formed by using the image slices 16 to determine location coordinate values of each of a sequence of spaced apart surface points in the open-loop region of FIG. 41B. A mathematical model may then be used to estimate or compute the 3D model 40 in FIG. 41C. Examples of other medical imaging computer programs that may be used include, but are not limited to: Analyze from AnalyzeDirect, Inc. of Overland Park, KS; open-source software such as Paraview of Kitware, Inc.; Insight Toolkit ("ITK") available at www.itk.org; 3D Slicer available at www.slicer.org; and Mimics from Materialise of Ann Arbor, MI.

Alternatively or additionally to the aforementioned systems for generating the 3D model 40 depicted in FIG. 41C, other systems for generating the 3D model 40 of FIG. 41C include the surface rendering techniques of the Non-Uniform Rational B-spline ("NURB") program or the Bézier program. Each of these programs may be employed to generate the 3D contour model 40 from the plurality of contour lines 210y.

In one embodiment, the NURB surface modeling technique is applied to the plurality of image slices 16 and, more specifically, the plurality of open-loop contour lines 210y of FIG. 41B. The NURB software generates a 3D model 40 as depicted in FIG. 41C, wherein the 3D model 40 has areas of interest or targeted regions 42 that contain both a mesh and its control points. For example, see Ervin et al., Landscape Modeling, McGraw-Hill, 2001, which is hereby incorporated by reference in its entirety into this Detailed Description.

In one embodiment, the NURB surface modeling technique employs the following surface equation:

$$G(s,t)=\frac{\sum_{i=0}^{k1}\sum_{j=0}^{k2}W(i,j)P(i,j)b_i(s)b_j(t)}{\sum_{i=0}^{k1}\sum_{j=0}^{k2}W(i,j)b_i(s)b_j(t)},$$

wherein P(i,j) represents a matrix of vertices with nrows=(k1+1) and ncols=(k2+1), W(i,j) represents a matrix of vertex weights of one per vertex point, $b_i(s)$ represents a row-direction basis or blending of polynomial functions of degree M1, $b_j(t)$ represents a column-direction basis or blending polynomial functions of degree M2, s represents a parameter array of row-direction knots, and t represents a parameter array of column-direction knots.

In one embodiment, the Bézier surface modeling technique employs the Bézier equation (1972, by Pierre Bézier) to generate a 3D model 40 as depicted in FIG. 41C, wherein the model 40 has areas of interest or targeted regions 42. A given Bézier surface of order (n, m) is defined by a set of (n+1)(m+1) control points $k_{i,j}$). It maps the unit square into a smooth-continuous surface embedded within a space of the same dimensionality as ($k_{i,j}$). For example, if k are all points in a four-dimensional space, then the surface will be within a four-dimensional space. This relationship holds true for a one-dimensional space, a two-dimensional space, a fifty-dimensional space, etc.

A two-dimensional Bézier surface can be defined as a parametric surface where the position of a point p as a function of the parametric coordinates u, v is given by:

$$p(u,v)=\sum_{i=0}^{n}\sum_{j=0}^{m}B_i^n(u)B_j^m(v)k_{i,j}$$

evaluated over the unit square, where $$B_i^n(u)=\binom{n}{i}u^i(1-u)^{n-i}$$

is a Bernstein polynomial and $$\binom{n}{i}=\frac{n!}{i!*(n-i)!}$$

is the binomial coefficient. See Grune et al, *On Numerical Algorithm and Interactive Visualization for Optimal Control Problems*, Journal of Computation and Visualization in Science, Vol. 1, No. 4, July 1999, which is hereby incorporated by reference in its entirety into this Detailed Description.

Various other surface rendering techniques are disclosed in other references. For example, see the surface rendering techniques disclosed in the following publications: Lorensen et al., *Marching Cubes: A high Resolution 3d Surface Construction Algorithm*, Computer Graphics, 21-3: 163-169, 1987; Farin et al., *NURB Curves & Surfaces: From Projective Geometry to Practical Use*, Wellesley, 1995; Kumar et al, *Robust Incremental Polygon Triangulation for Surface Rendering*, WSCG, 2000; Fleischer et al., *Accurate Polygon Scan Conversion Using Half-Open Intervals*, Graphics Gems III, p. 362-365, code: p. 599-605, 1992; Foley et al., *Computer Graphics: Principles and Practice*, Addison Wesley, 1990; Glassner, *Principles of Digital Image Synthesis*, Morgan Kaufmann, 1995, all of which are hereby incorporated by reference in their entireties into this Detailed Description.

d. Selecting a Jig Blank Most Similar in Size and/or Configuration to the Size of the Patient's Femur Lower End.

As mentioned above, an arthroplasty jig 2, such as a femoral jig 2A includes an interior portion 100 and an exterior portion 102. The femoral jig 2A is formed from a femur jig blank 50A, which, in one embodiment, is selected from a finite number of femur jig blank sizes. The selection of the femur jig blank 50A is based on a comparison of the dimensions of the patient's femur lower end 204y to the dimensions and/or configurations of the various sizes of femur jig blanks 50A to select the femur jig blank 50A most closely resembling the patient's femur lower end 204y with respect to size and/or configuration. This selected femur jig blank 50A has an outer or exterior side or surface 232y that forms the exterior portion 232y of the femur jig 2A. The 3D surface computer model 40 discussed with respect to the immediately preceding section of this Detail Description is used to define a 3D surface 40 into the interior side 230y of computer model of a femur jig blank 50A. Furthermore, in some embodiments, the overestimation of the procedure described below may be used to adjust the 3D surface model 40.

By selecting a femur jig blank 50A with an exterior portion 232y close in size to the patient's lower femur end 204y, the potential for an accurate fit between the interior portion 230y and the patient's femur is increased. Also, the amount of material that needs to be machined or otherwise removed from the jig blank 50A is reduced, thereby reducing material waste and manufacturing time.

Figure 41H:
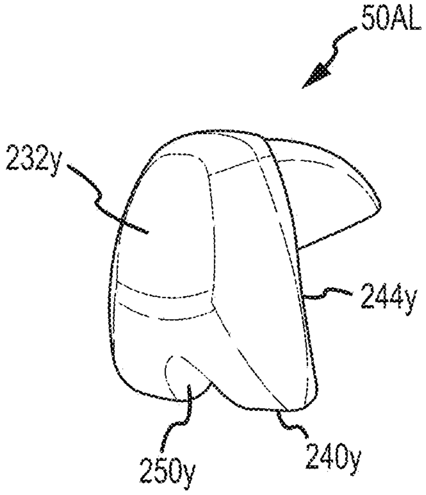
FIG. 41H is a top perspective view of a left femoral cutting jig blank having predetermined dimensions.
Figure 41I:
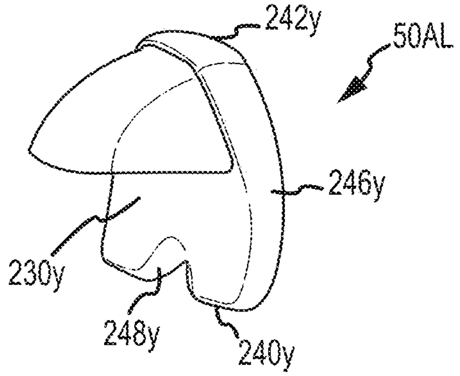
FIG. 41I is a bottom perspective view of the jig blank depicted in FIG. 41H.
Figure 41J:
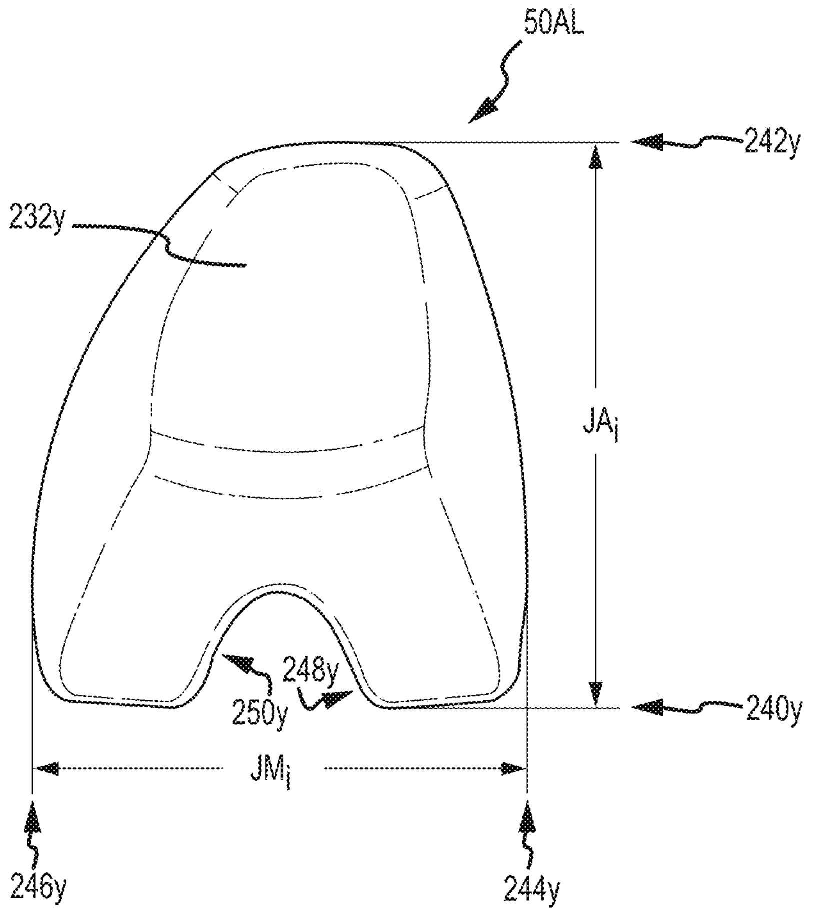
FIG. 41J is plan view of an exterior side or portion of the jig blank depicted in FIG. 41H.
Figure 41K:
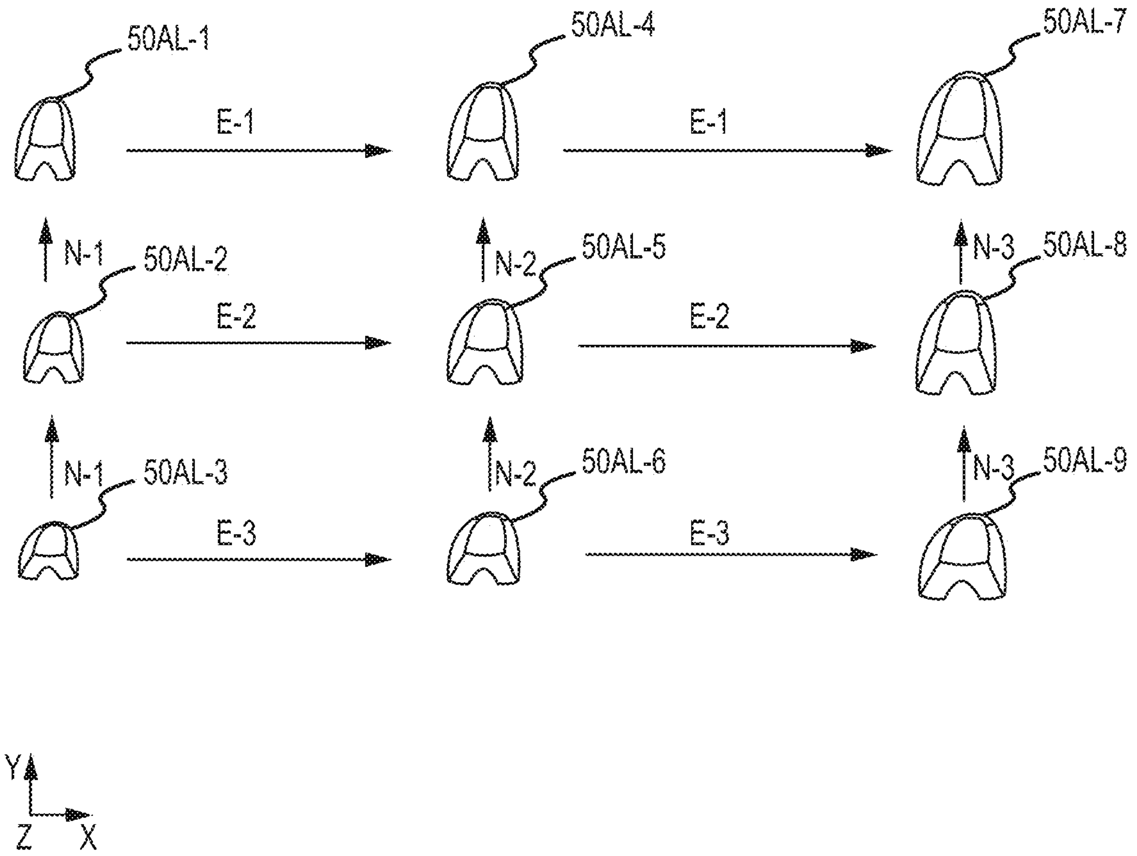
FIG. 41K is a plurality of available sizes of left femur jig blanks, each depicted in the same view as shown in FIG. 41J.
Figure 41L:
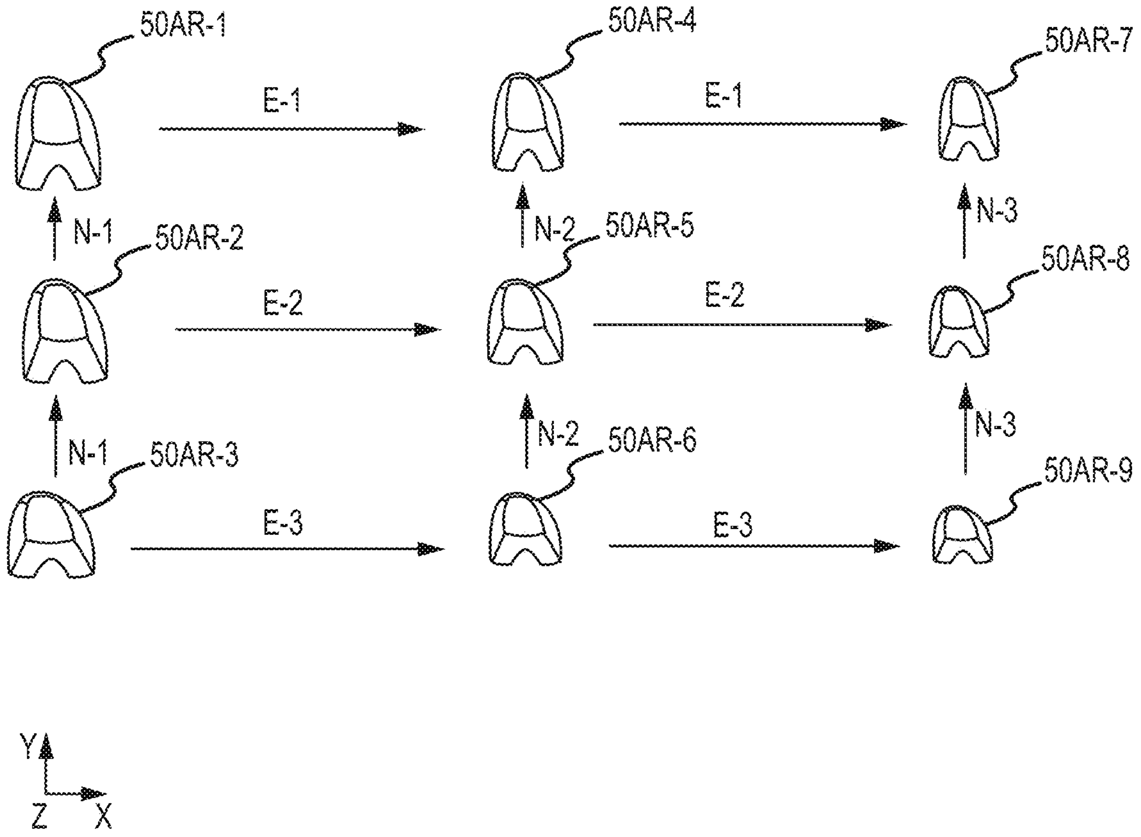
FIG. 41L is a plurality of available sizes of right femur jig blanks, each depicted in the same view as shown in FIG. 41J.

For a discussion of a method of selecting a jig blank 50 most closely corresponding to the size and/or configuration of the patient's lower femur end, reference is first made to FIGS. 3-41L. FIG. 41H is a top perspective view of a left femoral cutting jig blank 50AL having predetermined dimensions. FIG. 41I is a bottom perspective view of the jig blank 50AL depicted in FIG. 41H. FIG. 41J is plan view of an exterior side or portion 232*y* of the jig blank 50AL depicted in FIG. 41H. FIG. 41K is a plurality of available sizes of left femur jig blanks 50AL, each depicted in the same view as shown in FIG. 41J. FIG. 41L is a plurality of available sizes of right femur jig blanks 50AR, each depicted in the same view as shown in FIG. 41J.

A common jig blank 50, such as the left jig blank 50AL depicted in FIGS. 41H-41J and intended for creation of a left femur jig that can be used with a patient's left femur, may include a posterior edge 240*y*, an anterior edge 242*y*, a lateral edge 244*y*, a medial edge 246*y*, a lateral condyle portion 248*y*, a medial condyle portion 250*y*, the exterior side 232*y* and the interior side 230*y*. The jig blank 50AL of FIGS. 41H-41J may be any one of a number of left femur jig blanks 50AL available in a limited number of standard sizes. For example, the jig blank 50AL of FIGS. 41H-41J may be an i-th left femur jig blank, where i=1, 2, 3, 4, . . . m and m represents the maximum number of left femur jig blank sizes.

As indicated in FIG. 41J, the anterior-posterior extent JAi of the jig blank 50AL is measured from the anterior edge 242*y* to the posterior edge 240*y* of the jig blank 50AL. The medial-lateral extent JMi of the jig blank 50AL is measured from the lateral edge 244*y* to the medial edge 246*y* of the jig blank 50AL.

As can be understood from FIG. 41K, a limited number of left femur jig blank sizes may be available for selection as the left femur jig blank size to be machined into the left femur cutting jig 2A. For example, in one embodiment, there are nine sizes (m=9) of left femur jig blanks 50AL available. As can be understood from FIG. 41J, each femur jig blank 50AL has an anterior-posterior/medial-lateral aspect ratio defined as JAi to JMi (e.g., "JAi/JMi" aspect ratio). Thus, as can be understood from FIG. 41K, jig blank 50AL-1 has an aspect ratio defined as "$JA_1/JM_1$", jig blank 50AL-2 has an aspect ratio defined as "$JA_2/JM_2$", jig blank 50AL-3 has an aspect ratio defined as "$JA_3/JM_3$", jig blank 50AL-4 has an aspect ratio defined as "$JA_4/JM_4$", jig blank 50AL-5 has an aspect ratio defined as "$JA_5/JM_5$", jig blank 50AL-6 has an aspect ratio defined as "JA/JM", jig blank 50AL-7 has an aspect ratio defined as "$JA_7/JM_7$", jig blank 50AL-8 has an aspect ratio defined as "$JA_8/JM_8$", and jig blank 50AL-9 has an aspect ratio defined as "$JA_9/JM_9$".

The jig blank aspect ratio is utilized to design left femur jigs 2A dimensioned specific to the patient's left femur features. In one embodiment, the jig blank aspect ratio can be the exterior dimensions of the left femur jig 2A. In another embodiment, the jig blank aspect ratio can apply to the left femur jig fabrication procedure for selecting the left jig blank 50AL having parameters close to the dimensions of the desired left femur jig 2A. This embodiment can improve the cost efficiency of the left femur jig fabrication process because it reduces the amount of machining required to create the desired jig 2 from the selected jig blank 50.

In FIG. 41K, the N−1 direction represents increasing jig aspect ratios moving from jig 50AL-3 to jig 50AL-2 to jig 50AL-1, where "$JA_3/JM_3$"<"$JA_2/JM_2$"<"$JA_1/JM_1$". The increasing ratios of the jigs 50AL represent the corresponding increment of JAi values, where the jigs' JMi values remain the same. In other words, since $JA_3<JA_2<JA_1$, and $JM_3=JM_2=JM_1$, then "$JA_3/JM_3$"<"$JA_2/JM_2$"<"$JA_1/JM_1$". One example of the increment level can be an increase from 5% to 20%.

The same rationale applies to the N−2 direction and the N−3 direction. For example, the N−2 direction represents increasing jig aspect ratios from jig 50AL-6 to jig 50AL-5 to jig 50AL-4, where "$JA_4/JM_4$"<"$JA_5/JM_5$"<"$JA_6/JM_6$". The increasing ratios of the jigs 50AL represent the corresponding increment of JAi values, where the JMi values remain the same. The N−3 direction represents increasing jig aspect ratios from jig 50AL-9 to jig 50AL-8 to jig 50AL-7, where "$JA_7/JM_7$"<"$JA_8/JM_8$"<"$JA_9/JM_9$". The increasing ratios of the jigs 50AL represent the corresponding increment of JAi values, where the JMi values remain the same.

As can be understood from the plot 300*y* depicted in FIG. 42C and discussed later in this Detailed Discussion, the E-1 direction corresponds to the sloped line joining Group 1, Group 4 and Group 7. Similarly, the E-2 direction corresponds to the sloped line joining Group 2, Group 5 and Group 8. Also, the E-3 direction corresponds to the sloped line joining Group 3, Group 6 and Group 9.

As indicated in FIG. 41K, along direction E-2, the jig aspect ratios remain the same among jigs 50AL-2, 50AL-5 and jig 50AL-8, where "$JA_2/JM_2$"="$JA_5/JM_5$"="$JA_8/JM_8$". However, comparing to jig 50AL-2, jig 50AL-5 is dimensioned larger and longer than jig 50AL-2. This is because the $JA_5$ value for jig 50AL-5 increases proportionally with the increment of its $JM_5$ value in certain degrees in all X, Y, and Z-axis directions. In a similar fashion, jig 50AL-8 is dimensioned larger and longer than jig 50AL-5 because the $JA_8$ increases proportionally with the increment of its $JM_8$ value in certain degrees in all X, Y, and Z-axis directions. One example of the increment can be an increase from 5% to 20%.

The same rationale applies to directions E-1 and E-3. For example, in E-3 direction the jig ratios remain the same among the jigs 50AL-3, 50AL-6 and jig 50AL-9. Compared to jig 50AL-3, jig 50AL-6 is dimensioned bigger and longer because both $JM_6$ and $JA_6$ values of jig 50AL-6 increase proportionally in all X, Y, and Z-axis directions. Compared to jig 50AL-6, jig 50AL-9 is dimensioned bigger and longer because both $JM_9$ and $JA_9$ values of jig 50AL-9 increase proportionally in all X, Y, and Z-axis.

As can be understood from FIG. 41L, a limited number of right femur jig blank sizes may be available for selection as the right femur jig blank size to be machined into the right femur cutting jig 2A. For example, in one embodiment, there are nine sizes (m=9) of right femur jig blanks 50AR available. As can be understood from FIG. 3, each femur jig blank 50AR has an anterior-posterior/medial-lateral aspect ratio defined as JAi to JMi (e.g., "JAi/JMi" aspect ratio). Thus, as can be understood from FIG. 41L, jig blank 50AR-1 has an aspect ratio defined as "$JA_1/JM_1$", jig blank 50AR-2 has an aspect ratio defined as "$JA_2/JM_2$", jig blank 50AR-3 has an aspect ratio defined as "$JA_3/JM_3$", jig blank 50AR-4 has an aspect ratio defined as "$JA_4/JM_4$", jig blank 50AR-5 has an aspect ratio defined as "$JA_5/JM_5$", jig blank 50AR-6 has an aspect ratio defined as "$JA_6/JM_6$", jig blank 50AR-7 has an aspect ratio defined as "$JA_7/JM_7$", jig blank 50AR-8 has an aspect ratio defined as "$JA_8/JM_8$", and jig blank 50AR-9 has an aspect ratio defined as "$JA_9/JMe_9$".

The jig blank aspect ratio may be utilized to design right femur jigs 2A dimensioned specific to the patient's right femur features. In one embodiment, the jig blank aspect ratio can be the exterior dimensions of the right femur jig 2A. In another embodiment, the jig blank aspect ratio can apply to the right femur jig fabrication procedure for selecting the right jig blank 50AR having parameters close to the dimensions of the desired right femur jig 2A. This embodiment can improve the cost efficiency of the right femur jig fabrication process because it reduces the amount of machining required to create the desired jig 2 from the selected jig blank 50.

In FIG. 41L, the N−1 direction represents increasing jig aspect ratios moving from jig 50AR-3 to jig 50AR-2 to jig 50AR-1, where "$JA_3/JM_3$"<"$JA_2/JM_2$"<"$JA_1/JM_1$". The increasing ratios of the jigs 50AR represent the corresponding increment of JAi values, where the jigs' JMi values remain the same. In other words, since $JA_3<JA_2<JA_1$, and $JM_3=JM_2=JM_1$, then "$JA_3/JM_3$"<"$JA_2/JM_2$"<"$JA_1/JM_1$". One example of the increment level can be an increase from 5% to 20%.

The same rationale applies to the N−2 direction and the N−3 direction. For example, the N−2 direction represents increasing jig aspect ratios from jig 50AR-6 to jig 50AR-5 to jig 50AR-4, where "$JA_4/JM_4$"<"$JA_5/JM_5$"<"$JA_6/JM_6$". The increasing ratios of the jigs 50AR represent the corresponding increment of JAi values, where the JMi values remain the same. The N−3 direction represents increasing jig aspect ratios from jig 50AR-9 to jig 50AR-8 to jig 50AR-7, where "$JA_7/JM_7$"<"$JA_8/JM_8$"<"$JA_9/JM_9$". The increasing ratios of the jigs 50AR represent the corresponding increment of JAi values, where the JMi values remain the same.

As indicated in FIG. 41L, along direction E-2, the jig aspect ratios remain the same among jigs 50AR-2, 50AR-5 and jig 50AR-8, where "$JA_2/JM_2$"="$JA_5/JM_5$"="$JA_8/JM_8$". However, comparing to jig 50AR-2, jig 50AR-5 is dimensioned larger and longer than jig 50AR-2. This is because the $JA_5$ value for jig 50AR-5 increases proportionally with the increment of its $JM_5$ value in certain degrees in all X, Y, and Z-axis directions. In a similar fashion, jig 50AR-8 is dimensioned larger and longer than jig 50AR-5 because the $JA_8$ increases proportionally with the increment of its $JM_8$ value in certain degrees in all X, Y, and Z-axis directions. One example of the increment can be an increase from 5% to 20%.

The same rationale applies to directions E-1 and E-3. For example, in E-3 direction the jig ratios remain the same among the jigs 50AR-3, 50AR-6 and jig 50AR-9. Compared to jig 50AR-3, jig 50AR-6 is dimensioned bigger and longer because both $JM_6$ and $JA_8$ values of jig 50AR-6 increase proportionally in all X, Y, and Z-axis directions. Compared to jig 50AR-6, jig 50AR-9 is dimensioned bigger and longer because both $JM_9$ and $JA_9$ values of jig 50AR-9 increase proportionally in all X, Y, and Z-axis.

The dimensions of the lower or knee joint forming end 204*y* of the patient's femur 18 can be determined by analyzing the 3D surface model 40 or 3D arthritic model 36 in a manner similar to those discussed with respect to the jig blanks 50. For example, as depicted in FIG. 42A, which is an axial view of the 3D surface model 40 or arthritic model 36 of the patient's left femur 18 as viewed in a direction extending distal to proximal, the lower end 204*y* of the surface model 40 or arthritic model 36 may include an anterior edge 262*y*, a posterior edge 260*y*, a medial edge 264*y*, a lateral edge 266*y*, a medial condyle 268*y*, and a lateral condyle 270*y*. The femur dimensions may be determined for the bottom end face or tibia articulating surface 204*y* of the patient's femur 18 via analyzing the 3D surface model 40 of the 3D arthritic model 36. These femur dimensions can then be utilized to configure femur jig dimensions and select an appropriate femur jig.

As shown in FIG. 42A, the anterior-posterior extent fAP of the lower end 204*y* of the patient's femur 18 (i.e., the lower end 204*y* of the surface model 40 of the arthritic model 36, whether formed via open or closed-loop analysis) is the length measured from the anterior edge 262*y* of the femoral lateral groove to the posterior edge 260*y* of the femoral lateral condyle 270*y*. The medial-lateral extent fML of the lower end 204*y* of the patient's femur 18 is the length measured from the medial edge 264*y* of the medial condyle 268*y* to the lateral edge 266*y* of the lateral condyle 270*y*.

In one embodiment, the anterior-posterior extent fAP and medial-lateral extent fML of the femur lower end 204*y* can be used for an aspect ratio fAP/fML of the femur lower end. The aspect ratios fAP/fML of a large number (e.g., hundreds, thousands, tens of thousands, etc.) of patient knees can be compiled and statistically analyzed to determine the most common aspect ratios for jig blanks that would accommodate the greatest number of patient knees. This information may then be used to determine which one, two, three, etc. aspect ratios would be most likely to accommodate the greatest number of patient knees.

The system 4 analyzes the lower ends 204*y* of the patient's femur 18 as provided via the surface model 40 of the arthritic model 36 (whether the arthritic model 36 is an 3D surface model generated via an open-loop or a 3D volumetric solid model generated via a closed-loop process) to obtain data regarding anterior-posterior extent fAP and medial-lateral extent fML of the femur lower ends 204*y*. As can be understood from FIG. 42B, which depicts the selected model jig blank 50AL of FIG. 41J superimposed on the model femur lower end 204*y* of FIG. 42A, the femur dimensional extents fAP, fML are compared to the jig blank dimensional extents jAP, jML to determine which jig blank model to select as the starting point for the machining process and the exterior surface model for the jig model.

Figure 42B:
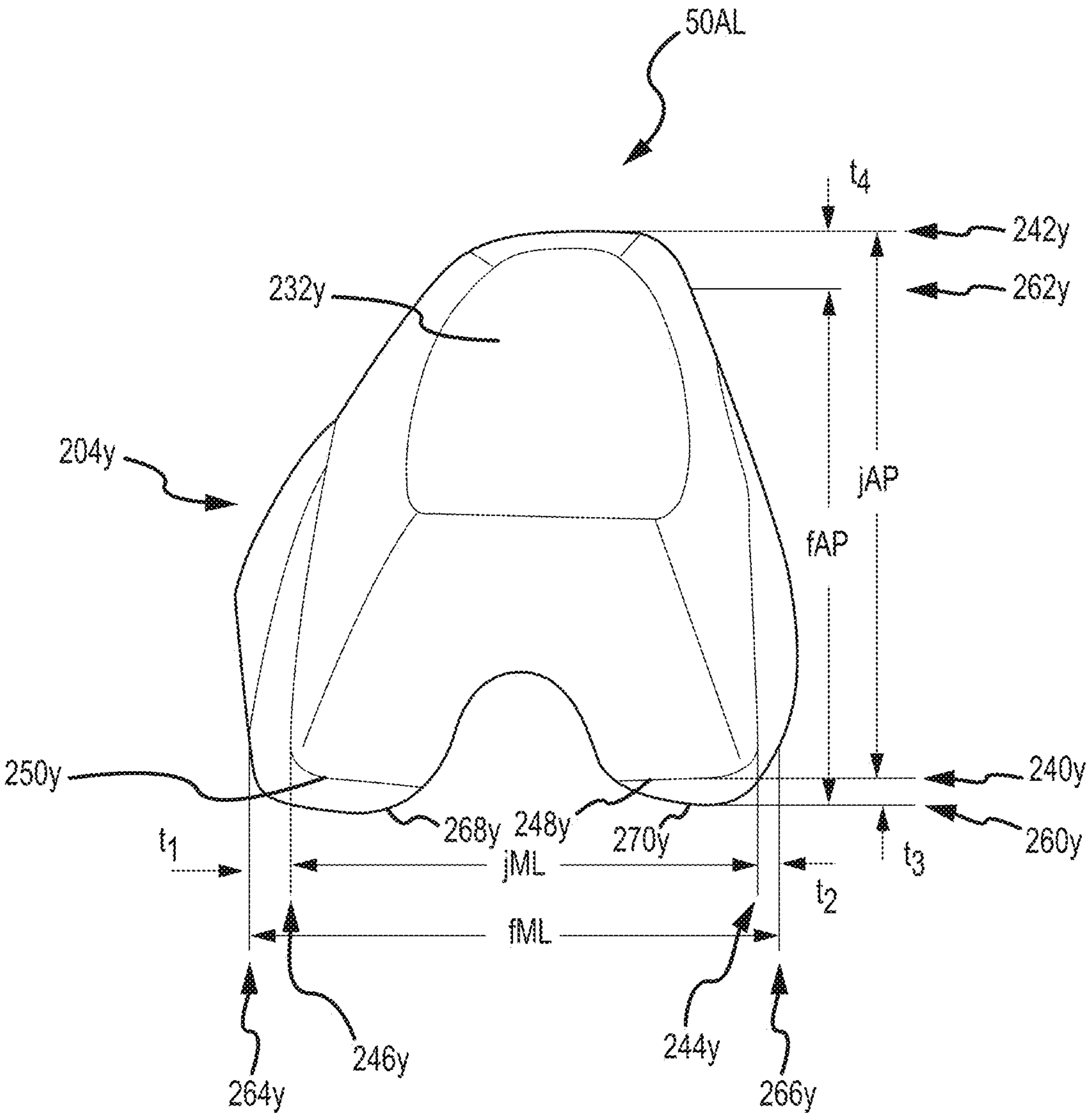
FIG. 42B depicts the selected model jig blank of FIG. 3C superimposed on the model femur lower end of FIG. 42A.

As shown in FIG. 42B, a prospective left femoral jig blank 50AL is superimposed to mate with the left femur lower end 204*y* of the patient's anatomical model as represented by the surface model 40 or arthritic model 36. The jig blank 50AL covers most of medial condyle 268*y* and the lateral condyle 270*y*, leaving small exposed condyle regions including t1, t2, t3. The medial medial-lateral condyle region t1 represents the region between the medial edge 264*y* of the medial condyle 268*y* and the medial edge 246*y* of the jig blank 50AL. The lateral medial-lateral condyle region t2 represents the region between the lateral edge 266*y* of the lateral condyle 270*y* and the lateral edge 244*y* of the jig blank 50AL. The posterior anterior-posterior region t3 represents the condyle region between the posterior edge 260*y* of the lateral condyle 270*y* and the posterior edge 240*y* of the jig blank 50AL.

The anterior edge 242*y* of the jig blank 50AL extends past the anterior edge 262*y* of the left femur lower end 204*y* as indicated by anterior anterior-posterior overhang t4. Specifically, the anterior anterior-posterior overhang t4 represents the region between the anterior edge 262*y* of the lateral groove of femur lower end 204*y* and the anterior edge 242*y* of the jig blank 50AL. By obtaining and employing the femur anterior-posterior fAP data and the femur medial-lateral fML data, the system 4 can size the femoral jig blank 50AL according to the following formulas: as $jFML=fML-t1-t2$ and $jFAP=fAP-t3+t4$, wherein jFML is the medial-lateral extent of the femur jig blank 50AL and jFAP is the anterior-posterior extent of the femur jig blank 50AL. In one embodiment, t1, t2, t3 and t4 will have the following ranges: 2 mm≤t1≤6 mm; 2 mm≤t2≤6 mm; 2 mm≤t3≤12 mm; and 15 mm≤t4≤25 mm. In another embodiment, t1, t2, t3 and t4 will have the following values: t1=3 mm; t2=3 mm; t3=6 mm; and t4=20 mm.

Figure 42C:
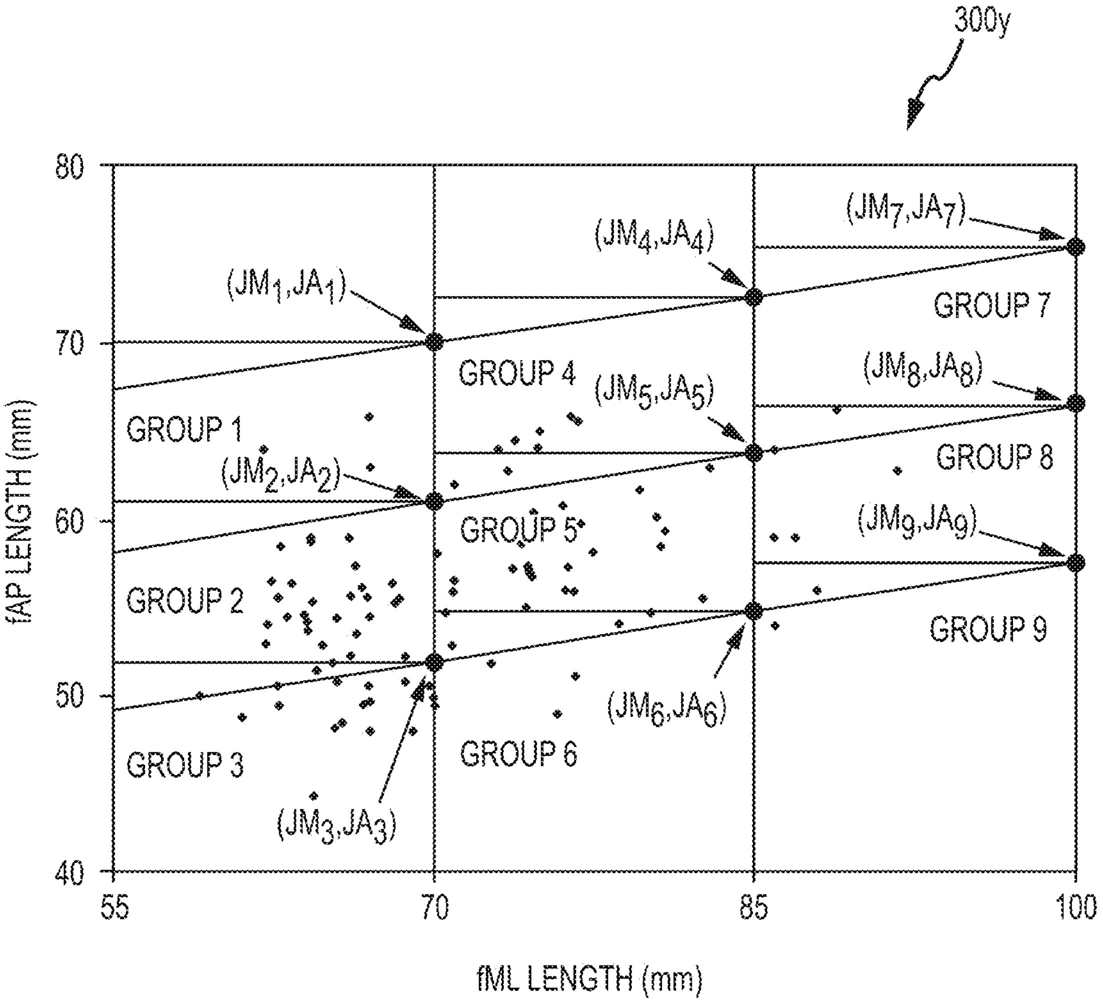
FIG. 42C is an example scatter plot for selecting from a plurality of candidate jig blanks sizes a jig blank size appropriate for the lower end of the patient's femur.

FIG. 42C is an example scatter plot 300y for selecting from a plurality of candidate jig blanks sizes a jig blank size appropriate for the lower end 204y of the patient's femur 18. In one embodiment, the X-axis represents the patient's femoral medial-lateral length fML in millimeters, and the Y-axis represents the patient's femoral anterior-posterior length fAP in millimeters. In one embodiment, the plot is divided into a number of jig blank size groups, where each group encompasses a region of the plot 300y and is associated with specific parameters $JM_r$, $JA_r$ of a specific candidate jig blank size.

In one embodiment, the example scatter plot 300y depicted in FIG. 42C has nine jig blank size groups, each group pertaining to a single candidate jig blank size. However, depending on the embodiment, a scatter plot 300y may have a greater or lesser number of jig blank size groups. The higher the number of jig blank size groups, the higher the number of the candidate jig blank sizes and the more dimension specific a selected candidate jig blank size will be to the patient's knee features and the resulting jig 2. The more dimension specific the selected candidate jig blank size, the lower the amount of machining required to produce the desired jig 2 from the selected jig blank 50.

Conversely, the lower the number of jig blank size groups, the lower the number of candidate jig blank sizes and the less dimension specific a selected candidate jig blank size will be to the patient's knee features and the resulting jig 2. The less dimension specific the selected candidate jig blank size, the higher the amount of machining required to produce the desired jig 2 from the selected jig blank 50, adding extra roughing during the jig fabrication procedure.

As can be understood from FIG. 42C, in one embodiment, the nine jig blank size groups of the plot 300y have the parameters $JM_r$, $JA_r$ as follows. Group 1 has parameters $JM_1$, $JA_1$. $JM_1$ represents the medial-lateral extent of the first femoral jig blank size, wherein $JM_1$=70 mm. $JA_1$ represents the anterior-posterior extent of the first femoral jig blank size, wherein $JA_1$=70.5 mm. Group 1 covers the patient's femur fML and fAP data wherein 55 mm<fML<70 mm and 61 mm<fAP<70.5 mm.

Group 2 has parameters $JM_2$, $JA_2$. $JM_2$ represents the medial-lateral extent of the second femoral jig blank size, wherein $JM_2$=70 mm. $JA_2$ represents the anterior-posterior extent of the second femoral jig blank size, wherein $JA_2$=61.5 mm. Group 2 covers the patient's femur fML and fAP data wherein 55 mm<fML<70 mm and 52 mm<fAP<61.5 mm.

Group 3 has parameters $JM_3$, $JA_3$. $JM_3$ represents the medial-lateral extent of the third femoral jig blank size, wherein $JM_3$=70 mm. $JA_3$ represents the anterior-posterior extent of the third femoral jig blank size, wherein $JA_3$=52 mm. Group 3 covers the patient's femur fML and fAP data wherein 55 mm<fML<70 mm and 40 mm<fAP<52 mm.

Group 4 has parameters $JM_4$, $JA_4$. $JM_4$ represents the medial-lateral extent of the fourth femoral jig blank size, wherein $JM_4$=85 mm. $JA_4$ represents the anterior-posterior extent of the fourth femoral jig blank size, wherein $JA_4$=72.5 mm. Group 4 covers the patient's femur fML and fAP data wherein 70 mm<fML<85 mm and 63.5 mm<fAP<72.5 mm.

Group 5 has parameters $JM_5$, $JA_8$. $JM_5$ represents the medial-lateral extent of the fifth femoral jig blank size, wherein $JM_5$=85 mm. $JA_5$ represents the anterior-posterior extent of the fifth femoral jig blank size, wherein $JA_5$=63.5 mm. Group 5 covers the patient's femur fML and fAP data wherein 70 mm<fML<85 mm and 55 mm<fAP<63.5 mm.

Group 6 has parameters $JM_6$, $JA_6$. $JM_6$ represents the medial-lateral extent of the sixth femoral jig blank size, wherein $JM_6$=85 mm. $JA_6$ represents the anterior-posterior extent of the sixth femoral jig blank size, wherein $JA_6$=55 mm. Group 6 covers the patient's femur fML and fAP data wherein 70 mm<fML<85 mm and 40 mm<fAP<55 mm.

Group 7 has parameters $JM_7$, $JA_7$. $JM_7$ represents the medial-lateral extent of the seventh femoral jig blank size, wherein $JM_7$=100 mm. $JA_7$ represents the anterior-posterior extent of the seventh femoral jig blank size, wherein $JA_7$=75 mm. Group 7 covers the patient's femur fML and fAP data wherein 85 mm<fML<100 mm and 65 mm<fAP<75 mm.

Group 8 has parameters $JM_8$, $JA_8$. $JM_8$ represents the medial-lateral extent of the eighth femoral jig blank size, wherein $JM_8$=100 mm. $JA_8$ represents the anterior-posterior extent of the eighth femoral jig blank size, wherein $JA_8$=65 mm. Group 8 covers the patient's femur fML and fAP data wherein 85 mm<fML<100 mm and 57.5 mm<fAP<65 mm.

Group 9 has parameters $JM_9$, $JA_9$. $JM_9$ represents the medial-lateral extent of the ninth femoral jig blank size, wherein $JM_9$=100 mm. $JA_9$ represents the anterior-posterior extent of the ninth femoral jig blank size, wherein $JA_9$=57.5 mm. Group 9 covers the patient's femur fML and fAP data wherein 85 mm<fML<100 mm and 40 mm<fAP<57.5 mm.

Figure 42D:
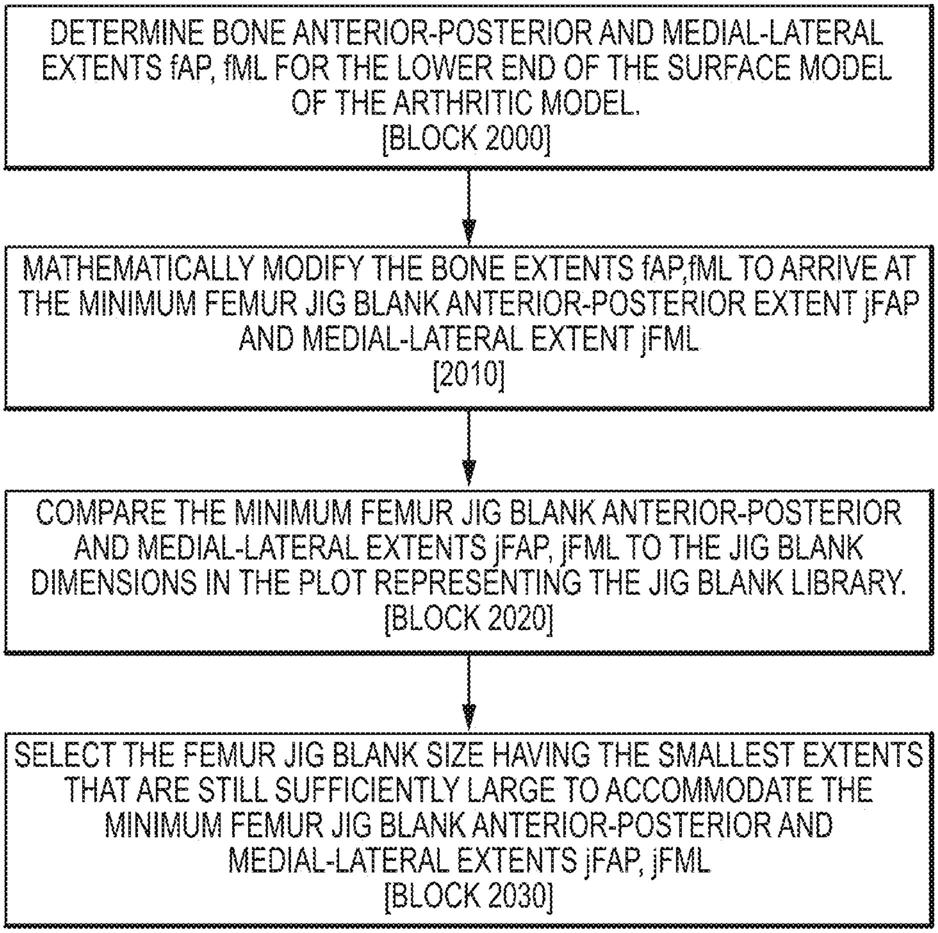
FIG. 42D is a flow diagram illustrating an embodiment of a process of selecting an appropriately sized jig blank.

As can be understood from FIG. 42D, which is a flow diagram illustrating an embodiment of a process of selecting an appropriately sized jig blank, bone anterior-posterior and medial-lateral extents fAP, fML are determined for the lower end 204y of the surface model 40 of the arthritic model 36 [block 2000]. The bone extents fAP, fML of the lower end 204y are mathematically modified according to the above discussed jFML and jFAP formulas to arrive at the minimum femur jig blank anterior-posterior extent jFAP and medial-lateral extent jFML [block 2010]. The mathematically modified bone extents fAP, fML or, more specifically, the minimum femur jig blank anterior-posterior and medial-lateral extents jFAP, jFML are referenced against the jig blank dimensions in the plot 300y of FIG. 42C [block 2020]. The plot 300y may graphically represent the extents of candidate femur jig blanks forming a jig blank library. The femur jig blank 50A is selected to be the jig blank size having the smallest extents that are still sufficiently large to accommodate the minimum femur jig blank anterior-posterior and medial-lateral extents JFAP, jFML [block 2030].

In one embodiment, the exterior of the selected jig blank size is used for the exterior surface model of the jig model, as discussed below. In one embodiment, the selected jig blank size corresponds to an actual jig blank that is placed in the CNC machine and milled down to the minimum femur jig blank anterior-posterior and medial-lateral extents jFAP, jFML to machine or otherwise form the exterior surface of the femur jig 2A.

The method outlined in FIG. 42D and in reference to the plot 300y of FIG. 42C can be further understood from the following example. As measured in FIG. 42B with respect to the lower end 204y of the patient's femur 18, the extents of the patient's femur are as follows: fML=79.2 mm and fAP=54.5 mm [block 2000]. As previously mentioned, the lower end 204y may be part of the surface model 40 of the arthritic model 36. Once the fML and fAP measurements are determined from the lower end 204y, the corresponding jig jFML data and jig jFAP data can be determined via the above-described jFML and jFAP formulas: jFML=fML−t1−t2, wherein t1=3 mm and t2=3 mm; and jFAP=fAP−t3+t4, wherein t3=6 mm and t4=20 mm [block 2010]. The result of the jFML and jFAP formulas is jFML=73.2 mm and jFAP=68.5 mm.

As can be understood from the plot 300*y* of FIG. 42C, the determined jig data (i.e., jFML=73.2 mm and jFAP=68.5 mm) falls in Group 4 of the plot 300*y*. Group 4 has the predetermined femur jig blank parameters ($JM_4$, $JA_4$) of $JM_4$=85 mm and $JA_4$=72.5 mm. These predetermined femur jig blank parameters are the smallest of the various groups that are still sufficiently large to meet the minimum femur blank extents jFAP, jFML [block 2020]. These predetermined femur jig blank parameters ($JM_4$=85 mm and $JA_4$=72.5 mm) may be selected as the appropriate femur jig blank size [block 2030].

In one embodiment, the predetermined femur jig blank parameters (85 mm, 72.5 mm) can apply to the femur exterior jig dimensions as shown in FIG. 41J. In other words, the jig blank exterior is used for the jig model exterior as discussed with respect to FIGS. 42E-42I. Thus, the exterior of the femur jig blank 50A undergoes no machining, and the unmodified exterior of the jig blank 50A with its predetermined jig blank parameters (85 mm, 72.5 mm) serves as the exterior of the finished femur jig 2A.

In another embodiment, the femur jig blank parameters (85 mm, 72.5 mm) can be selected for jig fabrication in the machining process. Thus, a femur jig blank 50A having predetermined parameters (85 mm, 72.5 mm) is provided to the machining process such that the exterior of the femur jig blank 50A will be machined from its predetermined parameters (85 mm, 72.5 mm) down to the desired femur jig parameters (73.2, 68.5 mm) to create the finished exterior of the femur jig 2A. As the predetermined parameters (85 mm, 72.5 mm) are selected to be relatively close to the desired femur jig parameters (73.2, 68.5 mm), machining time and material waste are reduced.

While it may be advantageous to employ the above-described jig blank selection method to minimize material waste and machining time, in some embodiments, a jig blank will simply be provided that is sufficiently large to be applicable to all patient bone extents fAP, fML. Such a jig blank is then machined down to the desired jig blank extents jFAP, jFML, which serve as the exterior surface of the finished jig 2A.

In one embodiment, the number of candidate jig blank size groups represented in the plot 300*y* is a function of the number of jig blank sizes offered by a jig blank manufacturer. For example, a first plot 300*y* may pertain only to jig blanks manufactured by company A, which offers nine jig blank sizes. Accordingly, the plot 300*y* has nine jig blank size groups. A second plot 300*y* may pertain only to jig blanks manufactured by company B, which offers twelve jig blank size groups. Accordingly, the second plot 300*y* has twelve jig blank size groups.

A plurality of candidate jig blank sizes exist, for example, in a jig blank library as represented by the plot 300*y* of FIG. 42D. While each candidate jig blank may have a unique combination of anterior-posterior and medial-lateral dimension sizes, in some embodiments, two or more of the candidate jig blanks may share a common aspect ratio jAP/jML or configuration. The candidate jig blanks of the library may be grouped along sloped lines of the plot 300*y* according to their aspect ratios jAP/jML.

In one embodiment, the jig blank aspect ratio jAP/jML may be used to take a workable jig blank configuration and size it up or down to fit larger or smaller individuals.

As can be understood from FIG. 42C, a series of 98 OA patients having knee disorders were entered into the plot 300*y* as part of a femur jig design study. Each patient's femur fAP and fML data was measured and modified via the above-described jFML and jFAP formulas to arrive at the patient's jig blank data (jFML, jFAP). The patient's jig blank data was then entered into the plot 300*y* as a point. As can be understood from FIG. 42C, no patient point lies outside the parameters of an available group. Such a process can be used to establish group parameters and the number of needed groups.

In one embodiment, the selected jig blank parameters can be the femoral jig exterior dimensions that are specific to patient's knee features. In another embodiment, the selected jig blank parameters can be chosen during fabrication process.

e. Formation of 3D Femoral Jig Model.

Figure 42E:
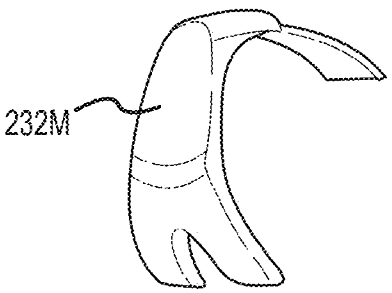
FIG. 42E is an exterior perspective view of a femur jig blank exterior surface model.
Figure 42F:
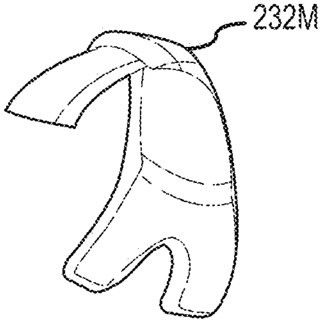
FIG. 42F is an interior perspective view of the femur jig blank exterior surface model of FIG. 42E.
Figure 42G:
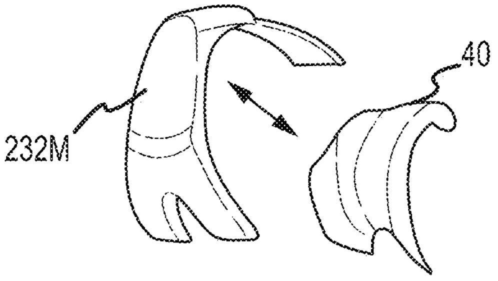
FIG. 42G is a perspective view of the extracted jig blank exterior surface model being combined with the extracted femur surface model.
Figure 42H:
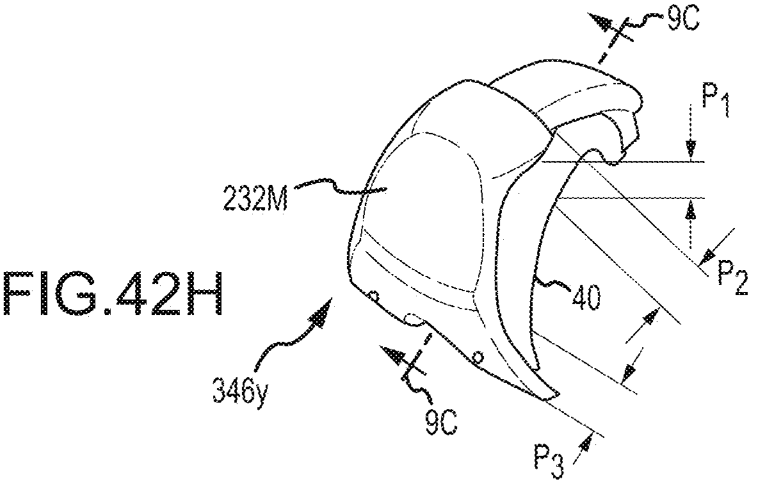
FIG. 42H is a perspective view of the extracted jig blank exterior surface model combined with the extracted femur surface model.
Figure 42I:
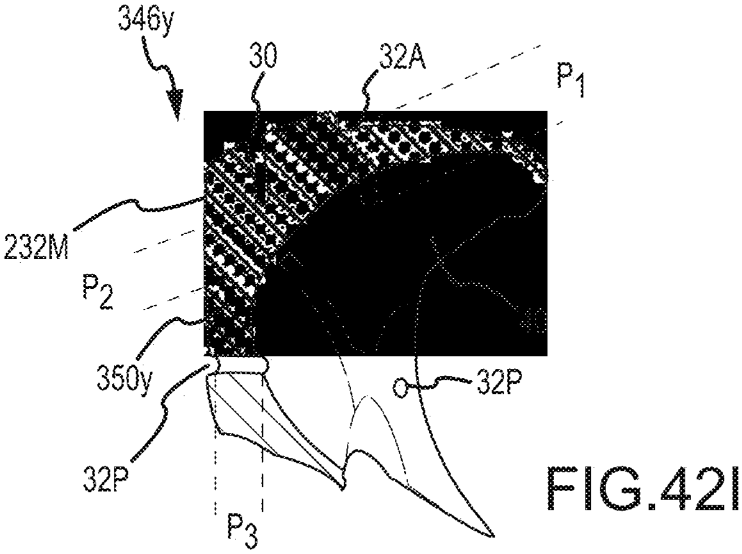
FIG. 42I is a cross section of the combined jig blank exterior surface model and the femur surface model as taken along section line 42I-42I in FIG. 42H.
Figure 42J:
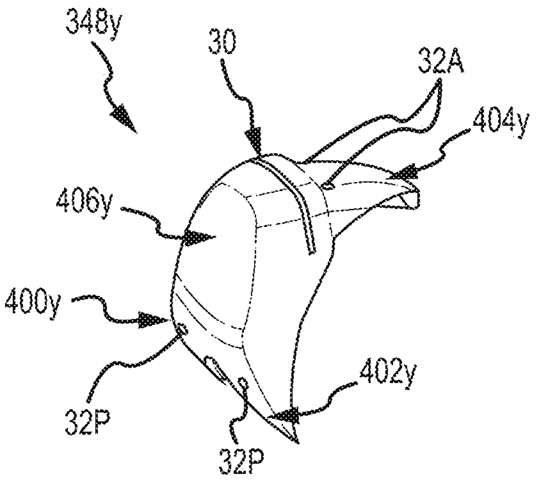
FIG. 42J is an exterior perspective view of the resulting femur jig model.
Figure 42K:
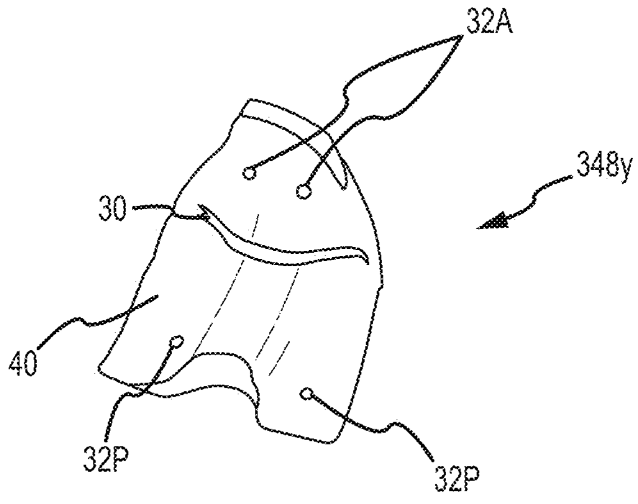
FIG. 42K is an interior perspective view of the femur jig model of FIG. 42J.

For a discussion of an embodiment of a method of generating a 3D femur jig model 346*y* generally corresponding to the "integrated jig data" 48 discussed with respect to [block 150] of FIG. 1E, reference is made to FIGS. 41H-41J, FIGS. 42E-42F, FIGS. 42G-42I and FIG. 42J-42K. FIGS. 41H-41J are various views of a femur jig blank 50A. FIGS. 42E-42F are, respectively, exterior and interior perspective views of a femur jig blank exterior surface model 232M. FIGS. 42G and 42H are exterior perspective views of the jig blank exterior model 232M and bone surface model 40 being combined, and FIG. 42I is a cross section through the combined models 232M, 40 as taken along section line 42I-42I in FIG. 42H. FIGS. 42J and 42K are, respectively, exterior and interior perspective views of the resulting femur jig model 346*y* after having "saw cut and drill hole data" 44 integrated into the jig model 346*y* to become an integrated or complete jig model 348*y* generally corresponding to the "integrated jig data" 48 discussed with respect to [block 150] of FIG. 1E.

As can be understood from FIGS. 41H-41J, the jig blank 50A, which has selected predetermined dimensions as discussed with respect to FIG. 42C, includes an interior surface 230*y* and an exterior surface 232*y*. The exterior surface model 232M depicted in FIGS. 42E and 42F is extracted or otherwise created from the exterior surface 232*y* of the jig blank model 50A. Thus, the exterior surface model 232M is based on the jig blank aspect ratio of the femur jig blank 50A selected as discussed with respect to FIG. 42C and is dimensioned specific to the patient's knee features. The femoral jig surface model 232M can be extracted or otherwise generated from the jig blank model 50A of FIGS. 41H-41J by employing any of the computer surface rendering techniques described above.

As can be understood from FIGS. 42G-42I, the exterior surface model 232M is combined with the femur surface model 40 to respectively form the exterior and interior surfaces of the femur jig model 346*y*. The femur surface model 40 represents the interior or mating surface of the femur jig 2A and corresponds to the femur arthroplasty target area 42. Thus, the model 40 allows the resulting femur jig 2A to be indexed to the arthroplasty target area 42 of the patient's femur 18 such that the resulting femur jig 2A will matingly receive the arthroplasty target area 42 during the arthroplasty procedure. The two surface models 232M, 40 combine to provide a patient-specific jig model 346*y* for manufacturing the femur jig 2A. In some embodiments, this patient-specific jig model 346*y* may include one or more areas of overestimation (as described below) to accommodate for irregularities in the patient's bone surface and/or limitations in jig manufacturing capabilities.

As can be understood from FIGS. 42H and 42I, once the models 232M, 40 are properly aligned, a gap will exist between the two models 232M, 40. An image sewing method or image sewing tool is applied to the aligned models 232M, 40 to join the two surface models together to form the 3D computer generated jig model 346*y* of FIG. 42H into a single-piece, joined-together, and filled-in jig model 346*y* similar in appearance to the integrated jig model 348*y* depicted in FIGS. 42J and 42K. In one embodiment, the jig model 346*y* may generally correspond to the description of the "jig data" 46 discussed with respect [block 145] of FIG. 1E.

As can be understood from FIGS. 42H and 42I, the geometric gaps between the two models 232M, 40, some of which are discussed below with respect to thicknesses $P_1$, $P_2$ and $P_3$, may provide certain space between the two surface models 232M, 40 for slot width and length and drill bit length for receiving and guiding cutting tools during TKA surgery. Because the resulting femur jig model 348*y* depicted in FIGS. 42J and 42K may be a 3D volumetric model generated from 3D surface models 232M, 40, a space or gap should be established between the 3D surface models 232M, 40. This allows the resulting 3D volumetric jig model 348*y* to be used to generate an actual physical 3D volumetric femur jig 2.

In some embodiments, the image processing procedure may include a model repair procedure for repairing the jig model 346*y* after alignment of the two models 232M, 40. For example, various methods of the model repairing include, but are not limit to, user-guided repair, crack identification and filling, and creating manifold connectivity, as described in: Nooruddin et al., *Simplification and Repair of Polygonal Models Using Volumetric Techniques* (IEEE Transactions on Visualization and Computer Graphics, Vol. 9, No. 2, April-June 2003); C. Erikson, *Error Correction of a Large Architectural Model: The Henderson County Courthouse* (Technical Report TR95-013, Dept. of Computer Science, Univ. of North Carolina at Chapel Hill, 1995); D. Khorramabdi, *A Walk through the Planned CS Building* (Technical Report UCB/CSD 91/652, Computer Science Dept., Univ. of California at Berkeley, 1991); Morvan et al., *IVECS: An Interactive Virtual Environment for the Correction of .STL files* (Proc. Conf. Virtual Design, August 1996); Bohn et al., *A Topology-Based Approach for Shell-Closure*, Geometric Modeling for Product Realization, (P. R. Wilson et al., pp. 297-319, North-Holland, 1993); Barequet et al., *Filling Gaps in the Boundary of a Polyhedron*, Computer Aided Geometric Design (vol. 12, no. 2, pp. 207-229, 1995); Barequet et al., *Repairing CAD Models* (*Proc. IEEE Visualization* '97, pp. 363-370, October 1997); and Gueziec et al., *Converting Sets of Polygons to Manifold Surfaces by Cutting and Stitching*, (*Proc. IEEE Visualization* 1998, pp. 383-390, October 1998). Each of these references is incorporated into this Detailed Description in their entireties.

As can be understood from FIGS. 42J and 42K, the integrated jig model 348*y* may include several features based on the surgeon's needs. For example, the jig model 348*y* may include a slot feature 30 for receiving and guiding a bone saw and drill holes 32 for receiving and guiding bone drill bits. As can be understood from FIGS. 42H and 42I, to provide sufficient structural integrity to allow the resulting femur jig 2A to not buckle or deform during the arthroplasty procedure and to adequately support and guide the bone saw and drill bits, the gap 350*y* between the models 232M, 40 may have the following offsets $P_1$, $P_2$, and $P_3$.

As can be understood from FIGS. 42H-42K, in one embodiment, thickness $P_1$ extends along the length of the anterior drill holes 45N between the models 232M, 40 and is for supporting and guiding a bone drill received therein during the arthroplasty procedure. Thickness $P_1$ may be at least approximately four millimeters or at least approximately five millimeters thick. The diameter of the anterior drill holes 45N may be configured to receive a cutting tool of at least one-third inches.

Thickness $P_2$ extends along the length of a saw slot 30 between the models 232M, 40 and is for supporting and guiding a bone saw received therein during the arthroplasty procedure. Thickness $P_2$ may be at least approximately 10 mm or at least 15 mm thick.

Thickness $P_3$ extends along the length of the posterior drill holes 32P between the models 232M, 40 and is for supporting and guiding a bone drill received therein during the arthroplasty procedure. Thickness $P_3$ may be at least approximately five millimeters or at least eight millimeters thick. The diameter of the drill holes 32 may be configured to receive a cutting tool of at least one-third inches.

In addition to providing sufficiently long surfaces for guiding drill bits or saws received therein, the various thicknesses $P_1$, $P_2$, $P_3$ are structurally designed to enable the femur jig 2A to bear vigorous femur cutting, drilling and reaming procedures during the TKR surgery.

As indicated in FIGS. 42J and 42K, the integrated jig model 348*y* may include: feature 400*y* that matches the patient's distal portion of the medial condyle cartilage; feature 402*y* that matches the patient's distal portion of the lateral condyle cartilage; projection 404*y* that can be configured as a contact or a hook and may securely engage the resulting jig 2A onto the patient's anterior femoral joint surface during the TKR surgery; and the flat surface 406*y* that provides a blanked labeling area for listing information regarding the patient, surgeon or/and the surgical procedure. Also, as discussed above, the integrated jig model 348*y* may include the saw cut slot 30 and the drill holes 32. The inner portion or side 100 of the jig model 348*y* (and the resulting femur jig 2A) is the femur surface model 40, which will matingly receive the arthroplasty target area 42 of the patient's femur 18 during the arthroplasty procedure. In some embodiments, the overestimation of the procedure described below may be used to adjust the 3D surface model 40.

As can be understood by referring to [block 105] of FIG. 1B and FIGS. 41A-41F, in one embodiment when cumulating the image scans 16 to generate the one or the other of the models 40, 22, the models 40, 22 are referenced to point P, which may be a single point or a series of points, etc. to reference and orient the models 40, 22 relative to the models 22, 28 discussed with respect to FIG. 1C and utilized for POP. Any changes reflected in the models 22, 28 with respect to point P (e.g., point P becoming point P') on account of the POP is reflected in the point P associated with the models 40, 22 (see [block 135] of FIG. 1D). Thus, as can be understood from [block 140] of FIG. 1D and FIGS. 42G-421, when the jig blank exterior surface model 232M is combined with the surface model 40 (or a surface model developed from the arthritic model 22) to create the jig model 346*y*, the jig model 346*y* is referenced and oriented relative to point P' and is generally equivalent to the "jig data" 46 discussed with respect to [block 145] of FIG. 1E.

Because the jig model 346*y* is properly referenced and oriented relative to point P', the "saw cut and drill hole data" 44 discussed with respect to [block 125] of FIG. 1E can be properly integrated into the jig model 346*y* to arrive at the integrated jig model 348*y* depicted in FIGS. 42J-42K. The integrated jig model 348*y* includes the saw cuts 30, drill holes 32 and the surface model 40. Thus, the integrated jig model 348*y* is generally equivalent to the "integrated jig data" 48 discussed with respect to [block 150] of FIG. 1E.

Figure 42L:
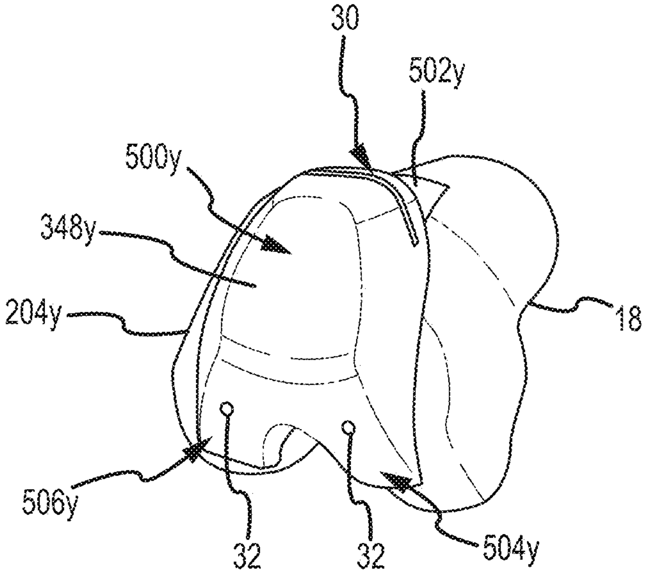
FIG. 42L illustrates a perspective view of the integrated jig model mating with the "arthritic model".

As can be understood from FIG. 42L, which illustrates a perspective view of the integrated jig model 348*y* mating with the "arthritic model" 22, the interior surface 40 of the jig model 348*y* matingly receives the arthroplasty target area 42 of the femur lower end 204*y* such that the jig model 348*y* is indexed to mate with the area 42. (In some embodiments, the interior surface 40 includes areas of overestimation, described below, to accommodate for irregularities in the patient's bone surface.) Because of the referencing and orientation of the various models relative to the points P, P' throughout the procedure, the saw cut slot 30 and drill holes 32 are properly oriented to result in saw cuts and drill holes that allow a resulting femur jig 2A to restore a patient's joint to a pre-degenerated or natural alignment condition.

As indicated in FIG. 42L, the integrated jig model 348*y* may include a jig body 500*y*, a projection 502*y* on one side, and two projections 504*y*, 506*y* the other side of jig body 500*y*. The projections 504*y*, 506*y* match the medial and lateral condyle cartilage. The projections 502*y*, 504*y*, 506*y* extend integrally from the two opposite ends of the jig body 500*y*.

As can be understood from [blocks 155-165] of FIG. 1E, the integrated jig 348*y* or, more specifically, the integrated jig data 48 can be sent to the CNC machine 10 to machine the femur jig 2A from the selected jig blank 50A. For example, the integrated jig data 48 may be used to produce a production file that provides automated jig fabrication instructions to a rapid production machine 10, as described in the various Park patent applications referenced above. The rapid production machine 10 then fabricates the patient-specific arthroplasty femur jig 2A from the femur jig blank 50A according to the instructions.

The resulting femur jig 2A may have the features of the integrated jig model 348*y*. Thus, as can be understood from FIG. 42L, the resulting femur jig 2A may have the slot 30 and the drilling holes 32 formed on the projections 502*y*, 504*y*, 506*y*, depending on the needs of the surgeon. The drilling holes 32 are configured to prevent the possible IR/ER (internal/external) rotational axis misalignment between the femoral cutting jig 2A and the patient's damaged joint surface during the distal femur cut portion of the TKR procedure. The slot 30 is configured to accept a cutting instrument, such as a reciprocating slaw blade for transversely cutting during the distal femur cut portion of the TKR.

f. Defining a 3D Surface Model of an Arthroplasty Target Area of a Tibia Upper End for Use as a Surface of an Interior Portion of a Tibia Arthroplasty Cutting Jig.

For a discussion of a method of generating a 3D model 40 of a target area 42 of a damaged upper end 604*y* of a patient's tibia 20, reference is made to FIGS. 43A-43C. FIG. 43A is an anterior-posterior ("AP") image slice 608*y* of the damaged upper or knee joint end 604*y* of the patient's tibia 20, wherein the image slice 608*y* includes an open-loop contour line segment 610*y* corresponding to the target area 42 of the damaged upper end 604*y*. FIG. 43B is a plurality of image slices (16-1, 16-1, 16-2, . . . 16-*n*) with their respective open-loop contour line segments (610*y*-1, 610*y*-2, . . . 610*y*-*n*), the open-loop contour line segments 610*y* being accumulated to generate the 3D model 40 of the target area 42. FIG. 43C is a 3D model 40 of the target area 42 of the damaged upper end 604*y* as generated using the open-loop contour line segments (16-1, 16-2, . . . 16-*n*) depicted in FIG. 43B.

As can be understood from FIGS. 1A, 1B and 43A, the imager 8 is used to generate a 2D image slice 16 of the damaged upper or knee joint end 604*y* of the patient's tibia 20. As depicted in FIG. 43A, the 2D image 16 may be an AP view of the tibia 20. Depending on whether the imager 8 is a MRI or CT imager, the image slice 16 will be a MRI or CT slice. The damaged upper end 604*y* includes the tibia plateau 612*y*, an anterior tibia shaft surface 614*y*, and an area of interest or targeted area 42 that extends along the tibia meniscus starting from a portion of the lateral tibia plateau surface to the anterior tibia surface 614*y*. The targeted area 42 of the tibia upper end may be the articulating contact surfaces of the tibia upper end that contact corresponding articulating contact surfaces of the femur lower or knee joint end.

As shown in FIG. 43A, the image slice 16 may depict the cancellous bone 616*y*, the cortical bone 618*y* surrounding the cancellous bone, and the articular cartilage lining portions of the cortical bone 618*y*. The contour line 610*y* may extend along the targeted area 42 and immediately adjacent the cortical bone and cartilage to outline the contour of the targeted area 42 of the tibia upper end 604*y*. The contour line 610*y* extends along the targeted area 42 starting at point C on the lateral or medial tibia plateau 612*y* (depending on whether the slice 16 extends through the lateral or medial portion of the tibia) and ends at point D on the anterior tibia shaft surface 614*y*.

In one embodiment, as indicated in FIG. 43A, the contour line 610*y* extends along the targeted area 42, but not along the rest of the surface of the tibia upper end 604*y*. As a result, the contour line 610*y* forms an open-loop that, as will be discussed with respect to FIGS. 43B and 43C, can be used to form an open-loop region or 3D computer model 40, which is discussed with respect to [block 140] of FIG. 1D and closely matches the 3D surface of the targeted area 42 of the tibia upper end. (In some embodiments, the 3D model 40 may be deliberately configured to be larger than the bone surface, in one or more areas, to accommodate for irregularities. See description below in the context of overestimating the tibial mating surface.) Thus, in one embodiment, the contour line is an open-loop and does not outline the entire cortical bone surface of the tibia upper end 604*y*. Also, in one embodiment, the open-loop process is used to form from the 2D images 16 a 3D surface model 36 that generally takes the place of the arthritic model 36 discussed with respect to [blocks 125-140] of FIG. 1D and which is used to create the surface model 40 used in the creation of the "jig data" 46 discussed with respect to [blocks 145-150] of FIG. 1E.

In one embodiment and in contrast to the open-loop contour line 610*y* depicted in FIGS. 43A and 43B, the contour line is a closed-loop contour line generally the same as the closed-loop contour line 210*y*' discussed with respect to FIGS. 41D-41E, except the closed-loop contour line pertains to a tibia instead of a femur. Like the femur closed-loop contour line discussed with respect to FIG. 41D, a tibia closed-loop contour line may outline the entire cortical bone surface of the tibia upper end and results in a closed-loop area. The tibia closed-loop contour lines are combined in a manner similar that discussed with respect to the femur contour lines in FIG. 41E. As a result, the tibia closed-loop area may require the analysis of the entire surface region of the tibia upper end 604*y* and result in the formation of a 3D model of the entire tibia upper end 604*y* in a manner similar to the femur lower end 204*y* illustrated in FIG. 41F. Thus, the 3D surface model resulting from the tibia closed-loop process ends up having in common much, if not all, the surface of the 3D tibia arthritic model 36. In one embodiment, the tibia closed-loop process may result in a 3D volumetric anatomical joint solid model from the 2D images 16 via applying mathematical algorithms. U.S. Pat. No. 5,682,886, which was filed Dec. 26, 1995 and is incorporated by reference in its entirety herein, applies a snake algorithm forming a continuous boundary or closed-loop. After the tibia has been outlined, a modeling process is used to create the 3D surface model, for example, through a Bezier patches method. Other 3D modeling processes, e.g., commercially-available 3D construction software as listed in other parts of this Detailed Description, are applicable to 3D surface model generation for closed-loop, volumetric solid modeling.

In one embodiment, the closed-loop process is used to form from the 2D images 16 a 3D volumetric solid model 36 that is essentially the same as the arthritic model 36 discussed with respect to [blocks 125-140] of FIG. 1D. The 3D volumetric solid model 36 is used to create the surface model 40 used in the creation of the "jig data" 46 discussed with respect to [blocks 145-150] of FIG. 1E.

The formation of a 3D volumetric solid model of the entire tibia upper end employs a process that may be much more memory and time intensive than using an open-loop contour line to create a 3D model of the targeted area 42 of the tibia upper end. Accordingly, although the closed-loop methodology may be utilized for the systems and methods disclosed herein, for at least some embodiments, the open-loop methodology may be preferred over the closed-loop methodology.

An example of a closed-loop methodology is disclosed in U.S. patent application Ser. No. 11/641,569 to Park, which is entitled "Improved Total Joint Arthroplasty System" and was filed Jan. 19, 2007. This application is incorporated by reference in its entirety into this Detailed Description.

As can be understood from FIGS. 43B and 41G, the imager 8 generates a plurality of image slices (16-1, 16-2 . . . 16-*n*) via repetitive imaging operations [block 1000]. Each image slice 16 has an open-loop contour line (610*y*-1, 610*y*-2 . . . 610*y*-*n*) extending along the targeted region 42 in a manner as discussed with respect to FIG. 43A [block 1005]. In one embodiment, each image slice is a two-millimeter 2D image slice 16. The system 4 compiles the plurality of 2D image slices (16-1, 16-2 . . . 16-*n*) and, more specifically, the plurality of open-loop contour lines (610*y*-1, 610*y*-2, . . . 610*y*-*n*) into the 3D femur surface computer model 40 depicted in FIG. 43C [block 1010]. This process regarding the generation of the surface model 40 is also discussed in the overview section with respect to [blocks 100-105] of FIG. 1B and [blocks 130-140] of FIG. 1D. A similar process may be employed with respect to tibia closed-loop contour lines As can be understood from FIG. 43C, the 3D tibia surface computer model 40 is a 3D computer representation of the targeted region 42 of the tibia upper end. In one embodiment, the 3D representation of the targeted region 42 is a 3D representation of the articulated femur contact surfaces of the tibia proximal end. As the open-loop generated 3D model 40 is a surface model of the relevant femur contacting portions of the tibia upper end, as opposed to a 3D model of the entire surface of the tibia upper end as would be a result of a closed-loop contour line, the open-loop generated 3D model 40 is less time and memory intensive to generate.

In one embodiment, the open-loop generated 3D model 40 is a surface model of the femur facing end face of the tibia upper end, as opposed a 3D model of the entire surface of the tibia upper end. The 3D model 40 can be used to identify the area of interest or targeted region 42, which, as previously stated, may be the relevant femur contacting portions of the tibia upper end. Again, the open-loop generated 3D model 40 is less time and memory intensive to generate as compared to a 3D model of the entire surface of the tibia proximal end, as would be generated by a closed-loop contour line. Thus, for at least some versions of the embodiments disclosed herein, the open-loop contour line methodology is preferred over the closed-loop contour line methodology. However, the system 4 and method disclosed herein may employ either the open-loop or closed-loop methodology and should not be limited to one or the other.

Regardless of whether the 3D model 40 is a surface model of the targeted region 42 (i.e., a 3D surface model generated from an open-loop process and acting as the arthritic model 22) or the entire femur facing end face of the tibia upper end (i.e., a 3D volumetric solid model generated from a closed-loop process and acting as the arthritic model 22), the data pertaining to the contour lines 610*y* can be converted into the 3D contour computer model 40 via the surface rendering techniques disclosed in any of the aforementioned U.S. patent applications to Park. For example, surface rending techniques employed include point-to-point mapping, surface normal vector mapping, local surface mapping, and global surface mapping techniques. Depending on the situation, one or a combination of mapping techniques can be employed.

In one embodiment, the generation of the 3D model 40 depicted in FIG. 43C may be formed by using the image slices 16 to determine location coordinate values of each of a sequence of spaced apart surface points in the open-loop region of FIG. 43B. A mathematical model may then be used to estimate or compute the 3D model 40 in FIG. 43C. Examples of other medical imaging computer programs that may be used include, but are not limited to: Analyze from AnalyzeDirect, Inc. of Overland Park, KS; open-source software such as Paraview of Kitware, Inc.; Insight Toolkit ("ITK") available at www.itk.org; 3D Slicer available at www.slicer.org; and Mimics from Materialise of Ann Arbor, MI.

Alternatively or additionally to the aforementioned systems for generating the 3D model 40 depicted in FIG. 43C, other systems for generating the 3D model 40 of FIG. 43C include the surface rendering techniques of the Non-Uniform Rational B-spline ("NURB") program or the Bézier program. Each of these programs may be employed to generate the 3D contour model 40 from the plurality of contour lines 610*y*.

In one embodiment, the NURB surface modeling technique is applied to the plurality of image slices 16 and, more specifically, the plurality of open-loop contour lines 610*y* of FIG. 41B. The NURB software generates a 3D model 40 as depicted in FIG. 43C, wherein the 3D model 40 has areas of interest or targeted regions 42 that contain both a mesh and its control points. For example, see Ervin et al., Landscape Modeling, McGraw-Hill, 2001, which is hereby incorporated by reference in its entirety into this Detailed Description.

In one embodiment, the NURB surface modeling technique employs the following surface equation:

$$G(s,t)=\frac{\sum_{i=0}^{k1}\sum_{j=0}^{k2}W(i,j)P(i,j)b_i(s)b_j(t)}{\sum_{i=0}^{k1}\sum_{j=0}^{k2}W(i,j)b_i(s)b_j(t)},$$

wherein P(i,j) represents a matrix of vertices with nrows=(k1+1) and ncols=(k2+1), W(i,j) represents a matrix of vertex weights of one per vertex point, $b_i(s)$ represents a row-direction basis or blending of polynomial functions of degree M1, $b_j(t)$ represents a column-direction basis or blending polynomial functions of degree M2, s represents a parameter array of row-direction knots, and t represents a parameter array of column-direction knots.

In one embodiment, the Bézier surface modeling technique employs the Bézier equation (1972, by Pierre Bézier) to generate a 3D model 40 as depicted in FIG. 43C, wherein the model 40 has areas of interest or targeted regions 42. A given Bézier surface of order (n, m) is defined by a set of (n+1)(m+1) control points $k_{i,j}$. It maps the unit square into a smooth-continuous surface embedded within a space of the same dimensionality as ($k_{i,j}$). For example, if k are all points in a four-dimensional space, then the surface will be within a four-dimensional space. This relationship holds true for a one-dimensional space, a two-dimensional space, a fifty-dimensional space, etc.

A two-dimensional Bézier surface can be defined as a parametric surface where the position of a point p as a function of the parametric coordinates u, v is given by:

$$p(u, v) = \sum_{i=0}^{n}\sum_{j=0}^{m} B_i^n(u) B_j^m(v) k_{i,j}$$

evaluated over the unit square, where $$B_i^n(u) = \binom{n}{i} u^i (1-u)^{n-i}$$

is a Bernstein polynomial and $$\binom{n}{i} = \frac{n!}{i! * (n-i)!}$$

is the binomial coefficient. See Grune et al, *On Numerical Algorithm and Interactive Visualization for Optimal Control Problems*, Journal of Computation and Visualization in Science, Vol. 1, No. 4, July 1999, which is hereby incorporated by reference in its entirety into this Detailed Description.

Various other surface rendering techniques are disclosed in other references. For example, see the surface rendering techniques disclosed in the following publications: Lorensen et al., *Marching Cubes: A high Resolution 3d Surface Construction Algorithm*, Computer Graphics, 21-3: 163-169, 1987; Farin et al., *NURB Curves & Surfaces: From Projective Geometry to Practical Use*, Wellesley, 1995; Kumar et al, *Robust Incremental Polygon Triangulation for Surface Rendering*, WSCG, 2000; Fleischer et al., *Accurate Polygon Scan Conversion Using Half-Open Intervals*, Graphics Gems III, p. 362-365, code: p. 599-605, 1992; Foley et al., *Computer Graphics: Principles and Practice*, Addison Wesley, 1990; Glassner, *Principles of Digital Image Synthesis*, Morgan Kaufmann, 1995, all of which are hereby incorporated by reference in their entireties into this Detailed Description.

g. Selecting a Jig Blank Most Similar in Size and/or Configuration to the Size of the Patient's Tibia Upper End.

As mentioned above, an arthroplasty jig 2, such as a tibia jig 2B includes an interior portion 104 and an exterior portion 106. The tibia jig 2B is formed from a tibia jig blank 50B, which, in one embodiment, is selected from a finite number of femur jig blank sizes. The selection of the tibia jig blank 50B is based on a comparison of the dimensions of the patient's tibia upper end 604*y* to the dimensions and/or configurations of the various sizes of tibia jig blanks 50B to select the tibia jig blank 50B most closely resembling the patient's tibia upper end 604*y* with respect to size and/or configuration. This selected tibia jig blank 50B has an outer or exterior side or surface 632*y* that forms the exterior portion 632*y* of the tibia jig 2B. The 3D surface computer model 40 discussed with respect to the immediately preceding section of this Detail Description is used to define a 3D surface 40 into the interior side 630*y* of the computer model of a tibia jig blank 50B. Furthermore, in some embodiments, the overestimation of the procedure described below may be used to adjust the 3D surface model 40.

By selecting a tibia jig blank 50B with an exterior portion 632*y* close in size to the patient's upper tibia end 604*y*, the potential for an accurate fit between the interior portion 630*y* and the patient's tibia is increased. Also, the amount of material that needs to be machined or otherwise removed from the jig blank 50B is reduced, thereby reducing material waste and manufacturing time.

For a discussion of a method of selecting a jig blank 50 most closely corresponding to the size and/or configuration of the patient's upper tibia end, reference is first made to FIGS. 43D-43H. FIG. 43D is a top perspective view of a right tibia cutting jig blank 50BR having predetermined dimensions. FIG. 43E is a bottom perspective view of the jig blank 50BR depicted in FIG. 43D. FIG. 43F is plan view of an exterior side or portion 232*y* of the jig blank 50BR depicted in FIG. 43D. FIG. 43G is a plurality of available sizes of right tibia jig blanks 50BR, each depicted in the same view as shown in FIG. 43F. FIG. 43H is a plurality of available sizes of left tibia jig blanks, each depicted in the same view as shown in FIG. 43F.

A common jig blank 50, such as the right jig blank 50BR depicted in FIGS. 43D-43F and intended for creation of a right tibia jig that can be used with a patient's right tibia, may include a medial tibia foot projection 648*y* for mating with the medial tibia plateau, a lateral tibia foot projection 650*y* for mating with the lateral tibia plateau, a posterior edge 640*y*, an anterior edge 642*y*, a lateral edge 644*y*, a medial edge 646*y*, the exterior side 632*y* and the interior side 630*y*. The jig blank 50BR of FIGS. 43D-43F may be any one of a number of right tibia jig blanks 50BR available in a limited number of standard sizes. For example, the jig blank 50BR of FIGS. 43D-43F may be an i-th right tibia jig blank, where i=1, 2, 3, 4, . . . m and m represents the maximum number of right tibia jig blank sizes.

As indicated in FIG. 43F, the anterior-posterior extent TAi of the jig blank 50BR is measured from the anterior edge 642*y* to the posterior edge 640*y* of the jig blank 50BR. The medial-lateral extent TMi of the jig blank 50BR is measured from the lateral edge 644*y* to the medial edge 646*y* of the jig blank 50BR.

As can be understood from FIG. 43G, a limited number of right tibia jig blank sizes may be available for selection as the right tibia jig blank size to be machined into the right tibia cutting jig 2B. For example, in one embodiment, there are three sizes (m=3) of right tibia jig blanks 50BR available. As can be understood from FIG. 43F, each tibia jig blank 50BR has an anterior-posterior/medial-lateral aspect ratio defined as TAi to TMi (e.g., "TAi/TMi" aspect ratio).

Thus, as can be understood from FIG. 43G, jig blank 50BR-1 has an aspect ratio defined as "$TA_1/TM_1$", jig blank 50BR-2 has an aspect ratio defined as "$TA_2/TM_2$", and jig blank 50BR-3 has an aspect ratio defined as "$TA_3/TM_3$".

The jig blank aspect ratio is utilized to design right tibia jigs 2B dimensioned specific to the patient's right tibia features. In one embodiment, the jig blank aspect ratio can be the exterior dimensions of the right tibia jig 2B. In another embodiment, the jig blank aspect ratio can apply to the right tibia jig fabrication procedure for selecting the right jig blank 50BR having parameters close to the dimensions of the desired right tibia jig 2B. This embodiment can improve the cost efficiency of the right tibia jig fabrication process because it reduces the amount of machining required to create the desired jig 2 from the selected jig blank 50.

In FIG. 43G there is a single jig blank aspect ratio depicted for the candidate tibia jig blank sizes. In embodiments having a greater number of jig blank aspect ratios for the candidate tibia jig blank sizes, FIG. 43G would be similar to FIG. 41K and would have an N−1 direction, and potentially N−2 and N−3 directions, representing increasing jig blank aspect ratios. The relationships between the various tibia jig blank aspect ratios would be similar to those discussed with respect to FIG. 41K for the femur jig blank aspect ratios.

As can be understood from the plot 900 depicted in FIG. 17 and discussed later in this Detailed Discussion, the E-1 direction corresponds to the sloped line joining Group 1, Group 2 and Group 3 in the plot 900.

As indicated in FIG. 43G, along direction E-1, the jig blank aspect ratios remain the same among jigs blanks 50BR-1, 50BR-2 and 50BR-3, where "$TA_1/TM_1$"="$TA_2/TM_2$"="$TA_3/TM_3$". However, comparing to jig blank 50BR-1, jig blank 50BR-2 is dimensioned larger and longer than jig blank 50BR-1. This is because the $TA_2$ value for jig blank 50BR-2 increases proportionally with the increment of its $TM_2$ value in certain degrees in all X, Y, and Z-axis directions. In a similar fashion, jig blank 50BR-3 is dimensioned larger and longer than jig blank 50BR-2 because the $TA_3$ increases proportionally with the increment of its $TM_3$ value in certain degrees in all X, Y, and Z-axis directions. One example of the increment can be an increase from 5% to 20%. In embodiments where there are additional aspect ratios available for the tibia jig blank sizes, as was illustrated in FIG. 41K with respect to the femur jig blank sizes, the relationship between tibia jig blank sizes may be similar to that discussed with respect to FIGS. 41K and 43G.

As can be understood from FIG. 43H, a limited number of left tibia jig blank sizes may be available for selection as the left tibia jig blank size to be machined into the left tibia cutting jig 2B. For example, in one embodiment, there are three sizes (m=3) of left tibia jig blanks 50BL available. As can be understood from FIG. 43F, each tibia jig blank 50BL has an anterior-posterior/medial-lateral aspect ratio defined as TAi to TMi (e.g., "TAi/TMi" aspect ratio). Thus, as can be understood from FIG. 43H, jig blank 50BL-1 has an aspect ratio defined as "$TA_1/TM_1$", jig blank 50BL-2 has an aspect ratio defined as "$TA_2/TM_2$", and jig blank 50BL-3 has an aspect ratio defined as "$TA_3/TM_3$".

The jig blank aspect ratio is utilized to design left tibia jigs 2B dimensioned specific to the patient's left tibia features. In one embodiment, the jig blank aspect ratio can be the exterior dimensions of the left tibia jig 2B. In another embodiment, the jig blank aspect ratio can apply to the left tibia jig fabrication procedure for selecting the left jig blank 50BL having parameters close to the dimensions of the desired left tibia jig 2B. This embodiment can improve the cost efficiency of the left tibia jig fabrication process because it reduces the amount of machining required to create the desired jig 2 from the selected jig blank 50.

In FIG. 43H there is a single jig blank aspect ratio depicted for the candidate tibia jig blank sizes. In embodiments having a greater number of jig blank aspect ratios for the candidate tibia jig blank sizes, FIG. 43H would be similar to FIG. 41L and would have an N−1 direction, and potentially N−2 and N−3 directions, representing increasing jig blank aspect ratios. The relationships between the various tibia jig blank aspect ratios would be similar to those discussed with respect to FIG. 41L for the femur jig blank aspect ratios.

As indicated in FIG. 43H, along direction E-1, the jig blank aspect ratios remain the same among jigs blanks 50BL-1, 50BL-2 and 50BL-3, where "$TA_1$/TMi"="$TA_2/TM_2$"="$TA_3/TM_3$". However, comparing to jig blank 50BL-1, jig blank 50BL-2 is dimensioned larger and longer than jig blank 50BL-1. This is because the $TA_2$ value for jig blank 50BL-2 increases proportionally with the increment of its $TM_2$ value in certain degrees in all X, Y, and Z-axis directions. In a similar fashion, jig blank 50BL-3 is dimensioned larger and longer than jig blank 50BL-2 because the $TA_3$ increases proportionally with the increment of its $TM_3$ value in certain degrees in all X, Y, and Z-axis directions. One example of the increment can be an increase from 5% to 20%. In embodiments where there are additional aspect ratios available for the tibia jig blank sizes, as was illustrated in FIG. 41L with respect to the femur jig blank sizes, the relationship between tibia jig blank sizes may be similar to that discussed with respect to FIGS. 41L and 43H.

The dimensions of the upper or knee joint forming end 604*y* of the patient's tibia 20 can be determined by analyzing the 3D surface model 40 or 3D arthritic model 36 in a manner similar to those discussed with respect to the jig blanks 50. For example, as depicted in FIG. 43I, which is an axial view of the 3D surface model 40 or arthritic model 36 of the patient's right tibia 20 as viewed in a direction extending proximal to distal, the upper end 604*y* of the surface model 40 or arthritic model 36 may include an anterior edge 660*y*, a posterior edge 662*y*, a medial edge 664*y* and a lateral edge 666*y*. The tibia dimensions may be determined for the top end face or femur articulating surface 604*y* of the patient's tibia 20 via analyzing the 3D surface model 40 of the 3D arthritic model 36. These tibia dimensions can then be utilized to configure tibia jig dimensions and select an appropriate tibia jig.

As shown in FIG. 43I, the anterior-posterior extent tAP of the upper end 604*y* of the patient's tibia 20 (i.e., the upper end 604*y* of the surface model 40 of the arthritic model 36, whether formed via open or closed-loop analysis) is the length measured from the anterior edge 660*y* of the tibia plateau to the posterior edge 662*y* of the tibia plateau. The medial-lateral extent tML of the upper end 604*y* of the patient's tibia 20 is the length measured from the medial edge 664*y* of the medial tibia plateau to the lateral edge 666*y* of the lateral tibia plateau.

In one embodiment, the anterior-posterior extent tAP and medial-lateral extent tML of the tibia upper end 604*y* can be used for an aspect ratio tAP/tML of the tibia upper end. The aspect ratios tAP/tML of a large number (e.g., hundreds, thousands, tens of thousands, etc.) of patient knees can be compiled and statistically analyzed to determine the most common aspect ratios for jig blanks that would accommodate the greatest number of patient knees. This information may then be used to determine which one, two, three, etc.

aspect ratios would be most likely to accommodate the greatest number of patient knees.

The system 4 analyzes the upper ends 604*y* of the patient's tibia 20 as provided via the surface model 40 of the arthritic model 36 (whether the arthritic model 36 is an 3D surface model generated via an open-loop or a 3D volumetric solid model generated via a closed-loop process), to obtain data regarding anterior-posterior extent tAP and medial-lateral extent tML of the tibia upper ends 604*y*. As can be understood from FIG. 43J, which depicts the selected model jig blank 50BR of FIG. 43F superimposed on the model tibia upper end 604*y* of FIG. 43I, the tibia dimensional extents tAP, tML are compared to the jig blank dimensional extents TAi, TMi to determine which jig blank model to select as the starting point for the machining process and the exterior surface model for the jig model.

Figure 43J:
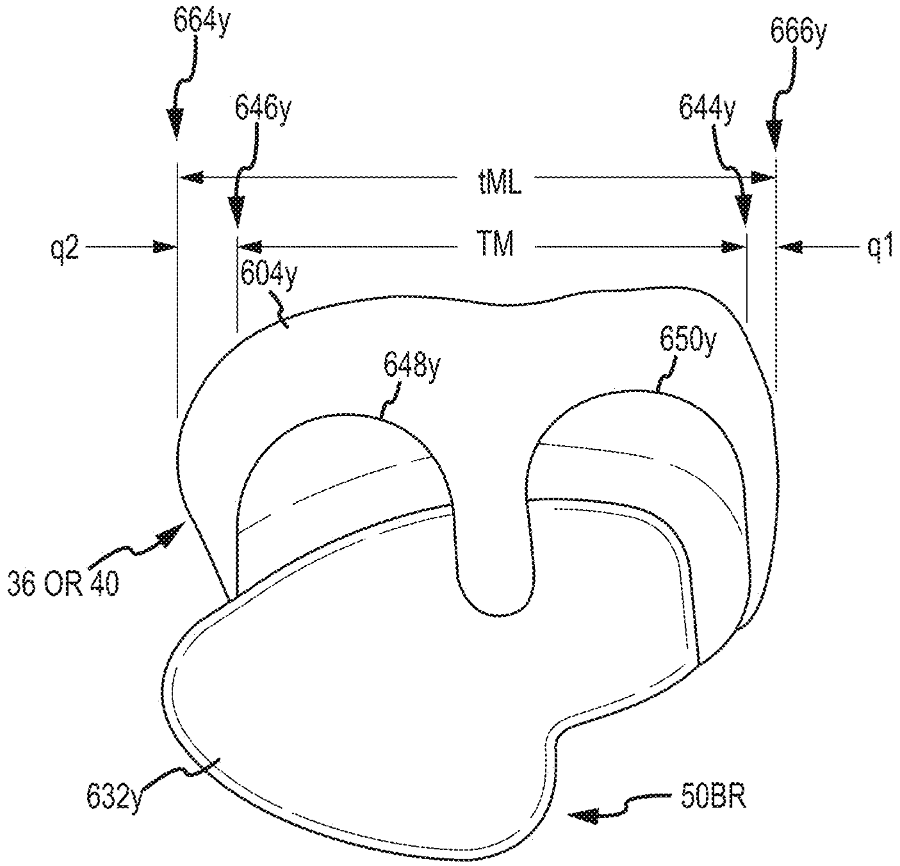
FIG. 43J depicts the selected model jig blank of FIG. 43F superimposed on the model tibia upper end of FIG. 43I.

As shown in FIG. 43J, a prospective right tibia jig blank 50BR is superimposed to mate with the right tibia upper end 604*y* of the patient's anatomical model as represented by the surface model 40 or arthritic model 36. In one embodiment, the jig blank 50BR may cover the anterior approximately two thirds of the tibia plateau, leaving the posterior approximately one third of the tibia exposed. Included in the exposed portion of the tibia plateau are lateral and medial exposed regions of the tibia plateau, as respectively represented by regions q1 and q2 in FIG. 43J. Specifically, exposed region q1 is the region of the exposed tibia plateau between the tibia and jig blank lateral edges 666*y*, 644*y*, and exposed region q2 is the region of the exposed tibia plateau between the tibia and jig blank medial edges 664*y*, 646*y*.

By obtaining and employing the tibia anterior-posterior tAP data and the tibia medial-lateral tML data, the system 4 can size the tibia jig blank 50BR according to the following formula: jTML=tML−q1−q2, wherein jTML is the medial-lateral extent of the tibia jig blank 50BR. In one embodiment, q1 and q2 will have the following ranges: 2 mm≤q1≤4 mm; and 2 mm≤q2≤4 mm. In another embodiment, q1 will be approximately 3 mm and q2 will approximately 3 mm.

Figure 43K:
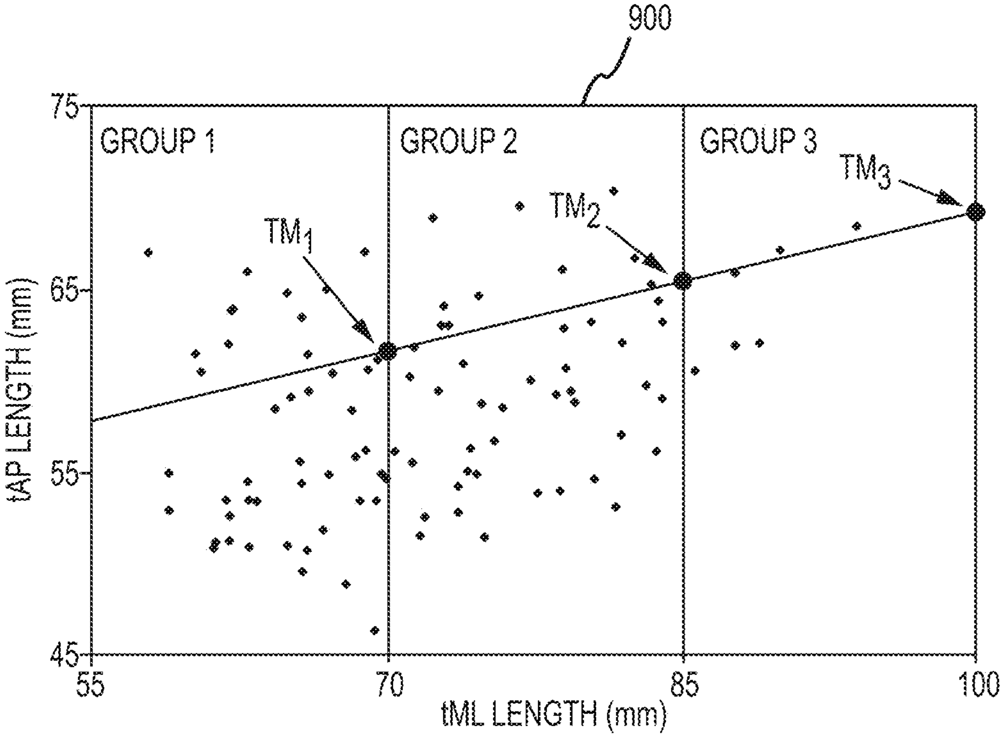
FIG. 43K is an example scatter plot for selecting from a plurality of candidate jig blanks sizes a jig blank size appropriate for the upper end of the patient's tibia.

FIG. 43K is an example scatter plot 900 for selecting from a plurality of candidate jig blanks sizes a jig blank size appropriate for the upper end 604*y* of the patient's tibia 20. In one embodiment, the X-axis represents the patient's tibia medial-lateral length tML in millimeters, and the Y-axis represents the patient's tibia anterior-posterior length tAP in millimeters. In one embodiment, the plot 900 is divided into a number of jig blank size groups, where each group encompasses a region of the plot 900 and is associated with a specific parameter $TM_r$ of a specific candidate jig blank size.

In one embodiment, the example scatter plot 900 depicted in FIG. 43K has three jig blank size groups, each group pertaining to a single candidate jig blank size. However, depending on the embodiment, a scatter plot 900 may have a greater or lesser number of jig blank size groups. The higher the number of jig blank size groups, the higher the number of the candidate jig blank sizes and the more dimension specific a selected candidate jig blank size will be to the patient's knee features and the resulting jig 2. The more dimension specific the selected candidate jig blank size, the lower the amount of machining required to produce the desired jig 2 from the selected jig blank 50.

Conversely, the lower the number of jig blank size groups, the lower the number of candidate jig blank sizes and the less dimension specific a selected candidate jig blank size will be to the patient's knee features and the resulting jig 2. The less dimension specific the selected candidate jig blank size, the higher the amount of machining required to produce the desired jig 2 from the selected jig blank 50, adding extra roughing during the jig fabrication procedure.

The tibia anterior-posterior length tAP may be relevant because it may serve as a value for determining the aspect ratio $TA_i/TM_i$ for tibia jig blanks 50B such as those discussed with respect to FIGS. 43F-43H and 43K. Despite this, in some embodiments, tibia anterior-posterior length $TA_i$ of the candidate jig blanks may not be reflected in the plot 900 depicted in FIG. 43K or the relationship depicted in FIG. 43J because in a practical setting for some embodiments, tibia jig anterior-posterior length may be less significant than tibia jig medial-lateral length. For example, although a patient's tibia anterior-posterior distance varies according to their knee features, the length of the foot projection 800*y*, 802*y* (see FIG. 44G) of a tibia jig 2B is simply increased without the need to create a jig blank or jig that is customized to correspond to the tibia anterior-posterior length TAi. In other words, in some embodiments, the only difference in anterior-posterior length between various tibia jigs is the difference in the anterior-posterior length of their respective foot projections 800*y*, 802*y*.

Figure 44A:
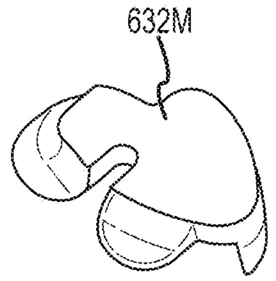
FIG. 44A is an exterior perspective view of a tibia jig blank exterior surface model.
Figure 44B:
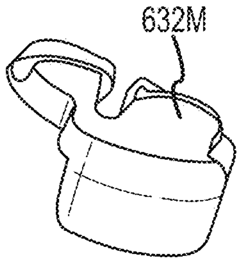
FIG. 44B is an interior perspective view of the tibia jig blank exterior surface model of FIG. 44A.
Figure 44C:
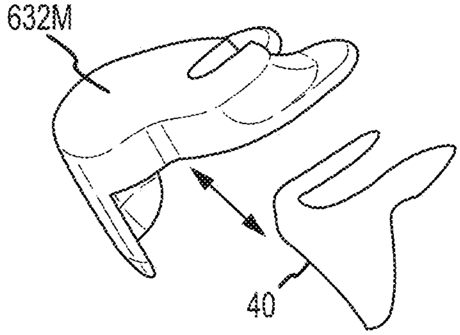
FIG. 44C is a perspective view of the extracted jig blank exterior surface model being combined with the extracted tibia surface model.
Figure 44D:
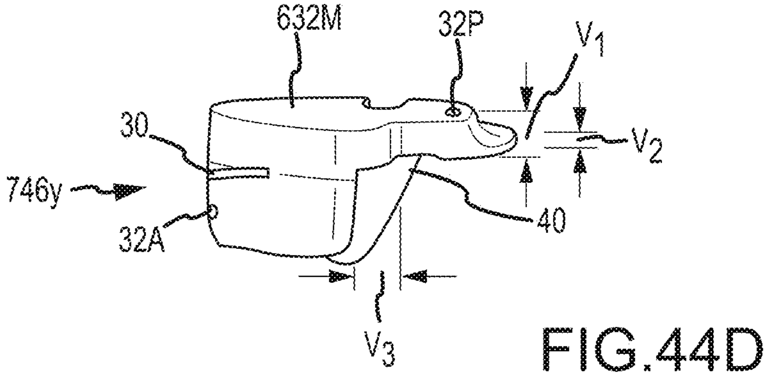
FIGS. 44D-44F are perspective views of the extracted jig blank exterior surface model combined with the extracted tibia surface model.
Figure 44E:
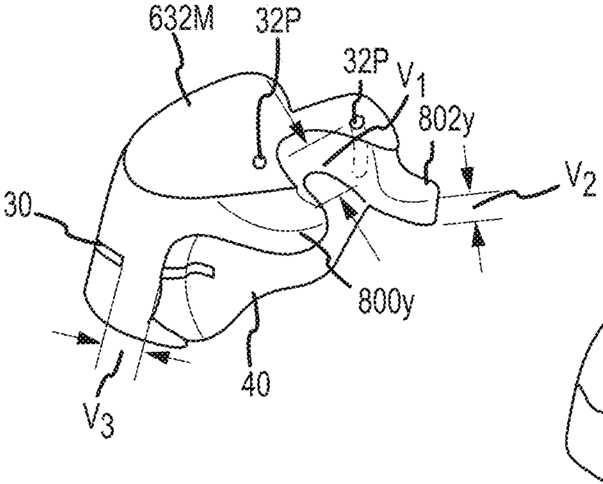
Figure 44F:
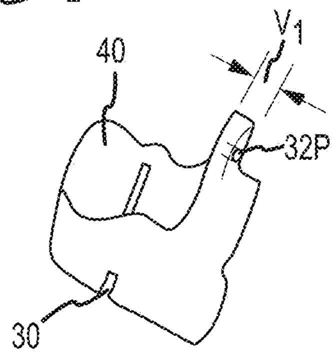
Figure 44G:
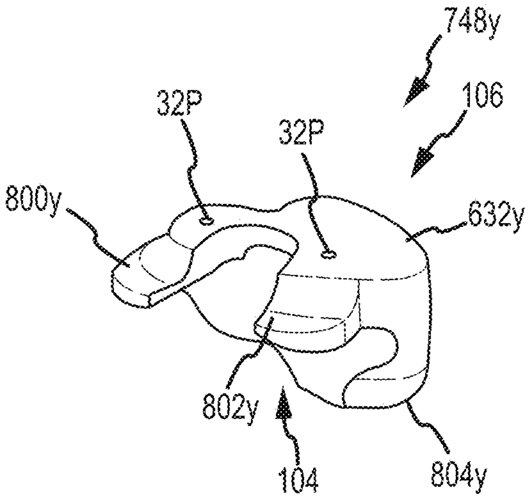
FIG. 44G is an exterior perspective view of the resulting tibia jig model.
Figure 44H:
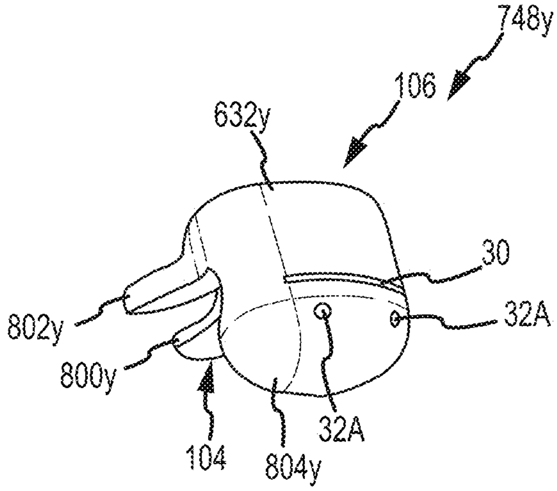
FIG. 44H is an interior perspective view of the tibia jig model of FIG. 44G.
Figure 44I:
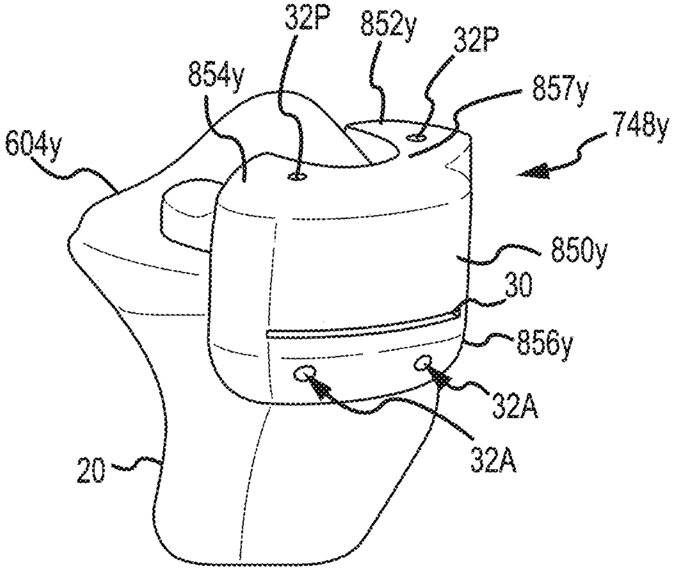
FIG. 44I illustrates a perspective view of the integrated jig model mating with the "arthritic model".

In some embodiments, as can be understood from FIGS. 43J and 44I, the anterior-posterior length of a tibia jig 2B, with its foot projection 800*y*, 802*y*, covers approximately half of the tibia plateau. Due in part to this "half" distance coverage, which varies from patient-to-patient by only millimeters to a few centimeter, in one embodiment, the anterior-posterior length of the jig may not be of a significant concern. However, because the jig may cover a substantial portion of the medial-lateral length of the tibia plateau, the medial-lateral length of the jig may be of substantial significance as compared to the anterior-posterior length.

While in some embodiments the anterior-posterior length of a tibia jig 2B may not be of substantial significance as compared to the medial-lateral length, in some embodiments the anterior-posterior length of the tibia jig is of significance. In such an embodiment, jig sizes may be indicated in FIG. 43K by their aspect ratios $TA_i/TM_i$ as opposed to just $TM_i$. In other words, the jig sizes may be depicted in FIG. 43K in a manner similar to that depicted in FIG. 42C. Furthermore, in such embodiments, FIGS. 43G and 43H may have additional jig blank ratios similar to that depicted in FIGS. 41K and 41L. As a result, the plot 900 of 43K may have additional diagonal lines joining the jig blank sizes belonging to each jig blank ratio in a manner similar to that depicted in plot 300*y* of FIG. 42C. Also, in FIG. 43K and in a manner similar to that shown in FIG. 42C, there may be additional horizontal lines dividing plot 900 according to anterior-posterior length to represent the boundaries of the various jig blank sizes.

As can be understood from FIG. 43K, in one embodiment, the three jig blank size groups of the plot 900 have parameters $TM_r$, $TA_r$ as follows. Group 1 has parameters $TM_1$, $TA_1$. $TM_1$ represents the medial-lateral extent of the first tibia jig blank size, wherein $TM_1$=70 mm. $TA_1$ represents the anterior-posterior extent of the first femoral jig blank size, wherein $TA_1$=62 mm. Group 1 covers the patient's tibia tML and tAP data wherein 55 mm<tML<70 mm and 45 mm<tAP<75 mm.

Group 2 has parameters $TM_2$, $TA_2$. $TM_2$ represents the medial-lateral extent of the second tibia jig blank size, wherein $TM_{2=85}$ mm. $TA_2$ represents the anterior-posterior extent of the second femoral jig blank size, wherein $TA_2$=65 mm. Group 2 covers the patient's tibia tML and tAP data wherein 70 mm<tML<85 mm and 45 mm<tAP<75 mm.

Group 3 has parameters $TM_3$, $TA_3$. $TM_3$ represents the medial-lateral extent of the third tibia jig blank size, wherein $TM_3$=100 mm. $TA_3$ represents the anterior-posterior extent of the second femoral jig blank size, wherein $TA_3$=68.5 mm. Group 3 covers the patient's tibia tML and tAP data wherein 85 mm<tML<100 mm and 45 mm<tAP<75 mm.

In some embodiments and in contrast to the selection process for the femur jig blanks discussed with respect to FIGS. 41H-42D, the tibia jig blank selection process discussed with respect to FIGS. 43D-43L may only consider or employ the medial-lateral tibia jig value jTML and related medial-lateral values $TM_i$, tML. Accordingly, in such embodiments, the anterior-posterior tibia jig value JTAP and related anterior-posterior values $TA_i$, tAP for the tibia jig and tibia plateau are not considered.

Figure 43L:
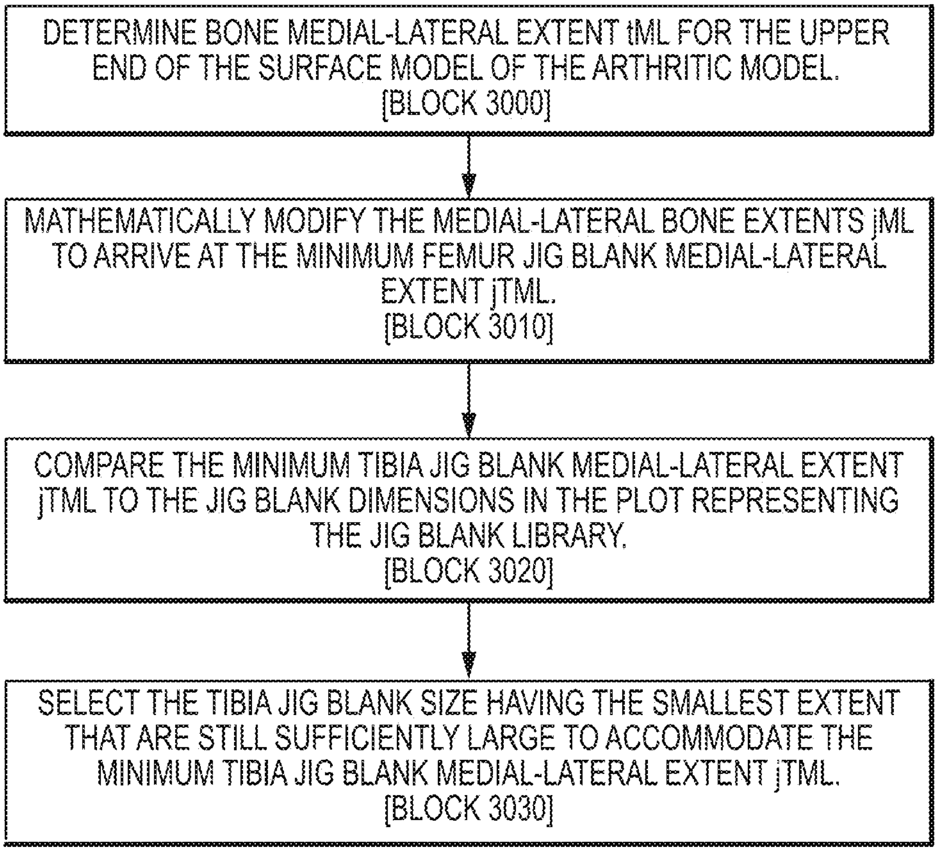
FIG. 43L is a flow diagram illustrating an embodiment of a process of selecting an appropriately sized jig blank.

As can be understood from FIG. 43L, which is a flow diagram illustrating an embodiment of a process of selecting an appropriately sized jig blank, the bone medial-lateral extent tML is determined for the upper end 604*y* of the surface model 40 of the arthritic model 36 [block 3000]. The medial-lateral bone extent tML of the upper end 604*y* is mathematically modified according to the above discussed jTML formula to arrive at the minimum tibia jig blank medial-lateral extent jTML [block 3010]. The mathematically modified bone medial-lateral extent tML or, more specifically, the minimum tibia jig blank medial-lateral extent jTML is referenced against the jig blank dimensions in the plot 900 of FIG. 43K [block 3020]. The plot 900 may graphically represent the extents of candidate tibia jig blanks forming a jig blank library. The tibia jig blank 50B is selected to be the jig blank size having the smallest extents that are still sufficiently large to accommodate the minimum tibia jig blank medial-lateral extent jTML [block 3030].

In one embodiment, the exterior of the selected jig blank size is used for the exterior surface model of the jig model, as discussed below. In one embodiment, the selected jig blank size corresponds to an actual jig blank that is placed in the CNC machine and milled down to the minimum tibia jig blank anterior-posterior and medial-lateral extents jTAP, jTML to machine or otherwise form the exterior surface of the tibia jig 2B.

The method outlined in FIG. 43L and in reference to the plot 900 of FIG. 43K can be further understood from the following example. As measured in FIG. 43J with respect to the upper end 604*y* of the patient's tibia 20, the extents of the patient's tibia are as follows: tML=85.2 mm [block 3000]. As previously mentioned, the upper end 604*y* may be part of the surface model 40 of the arthritic model 36. Once the tML measurement is determined from the upper end 604*y*, the corresponding jig jTML data can be determined via the above-described jTML formula: jTML=tML−q1−q2, wherein q1=3 mm and q2=3 mm [block 3010]. The result of the jTML formula is jTML=79.2 mm.

As can be understood from the plot 900 of FIG. 43K, the determined jig data (i.e., jTML=79.2 mm) falls in Group 2 of the plot 900. Group 2 has the predetermined tibia jig blank parameters ($TM_2$) of $TM_2$=85 mm. This predetermined tibia jig blank parameter is the smallest of the various groups that are still sufficiently large to meet the minimum tibia blank extents jTML [block 3020]. This predetermined tibia jig blank parameters ($TM_2$=85 mm) may be selected as the appropriate tibia jig blank size [block 3030].

In one embodiment, the predetermined tibia jig blank parameter (85 mm) can apply to the tibia exterior jig dimensions as shown in FIG. 43F. In other words, the jig blank exterior is used for the jig model exterior as discussed with respect to FIGS. 44A-44E. Thus, the exterior of the tibia jig blank 50B undergoes no machining, and the unmodified exterior of the jig blank 50B with its predetermined jig blank parameter (85 mm) serves as the exterior of the finished tibia jig 2B.

In another embodiment, the tibia jig blank parameter (85 mm) can be selected for jig fabrication in the machining process. Thus, a tibia jig blank 50B having a predetermined parameter (85 mm) is provided to the machining process such that the exterior of the tibia jig blank 50B will be machined from its predetermined parameter (85 mm) down to the desired tibia jig parameter (79.2 mm) to create the finished exterior of the tibia jig 2B. As the predetermined parameter (85 mm) is selected to be relatively close to the desired femur jig parameter (79.2 mm), machining time and material waste are reduced.

While it may be advantageous to employ the above-described jig blank selection method to minimize material waste and machining time, in some embodiments, a jig blank will simply be provided that is sufficiently large to be applicable to all patient bone extents tML. Such a jig blank is then machined down to the desired jig blank extent jTML, which serve as the exterior surface of the finished jig 2B.

In one embodiment, the number of candidate jig blank size groups represented in the plot 900 is a function of the number of jig blank sizes offered by a jig blank manufacturer. For example, a first plot 900 may pertain only to jig blanks manufactured by company A, which offers three jig blank sizes. Accordingly, the plot 900 has three jig blank size groups. A second plot 900 may pertain only to jig blanks manufactured by company B, which offers six jig blank size groups. Accordingly, the second plot 900 has six jig blank size groups.

A plurality of candidate jig blank sizes exist, for example, in a jig blank library as represented by the plot 900 of FIG. 43L. While each candidate jig blank may have a unique combination of anterior-posterior and medial-lateral dimension sizes, in some embodiments, two or more of the candidate jig blanks may share a common aspect ratio tAP/tML or configuration. The candidate jig blanks of the library may be grouped along sloped lines of the plot 900 according to their aspect ratios tAP/tML.

In one embodiment, the jig blank aspect ratio tAP/tML may be used to take a workable jig blank configuration and size it up or down to fit larger or smaller individuals.

As can be understood from FIG. 43K, a series of 98 OA patients having knee disorders were entered into the plot 900 as part of a tibia jig design study. Each patient's tibia tAP and tML data was measured. Each patient tibia tML data was modified via the above-described jTML formula to arrive at the patient's jig blank data (jFML). The patient's jig blank data was then entered into the plot 900 as a point. As can be understood from FIG. 43K, no patient point lies outside the parameters of an available group. Such a process can be used to establish group parameters and the number of needed groups.

In one embodiment, the selected jig blank parameters can be the tibia jig exterior dimensions that are specific to patient's knee features. In another embodiment, the selected jig blank parameters can be chosen during fabrication process.

h. Formation of 3D Tibia Jig Model.

For a discussion of an embodiment of a method of generating a 3D tibia jig model 746*y* generally corresponding to the "integrated jig data" 48 discussed with respect to [block 150] of FIG. 1E, reference is made to FIGS. 43D-43F, FIGS. 44A-44B, FIGS. 44C-44F and FIG. 44G-44H. FIGS. 43D-43F are various views of a tibia jig blank 50B. FIGS. 44A-44B are, respectively, exterior and interior perspective views of a tibia jig blank exterior surface model 632M. FIGS. 44C-44F are exterior perspective views of the tibia jig blank exterior model 632M and bone surface model 40 being combined. FIGS. 44G and 44H are, respectively, exterior and interior perspective views of the resulting tibia jig model 746*y* after having "saw cut and drill hole data" 44 integrated into the jig model 746*y* to become an integrated or complete jig model 748*y* generally corresponding to the "integrated jig data" 48 discussed with respect to [block 150] of FIG. 1E.

As can be understood from FIGS. 43D-43F, the jig blank 50B, which has selected predetermined dimensions as discussed with respect to FIGS. 43K and 43L, includes an interior surface 630*y* and an exterior surface 632*y*. The exterior surface model 632M depicted in FIGS. 44A and 44B is extracted or otherwise created from the exterior surface 632*y* of the jig blank model 50B. Thus, the exterior surface model 632M is based on the jig blank aspect ratio of the tibia jig blank 50B selected as discussed with respect to FIGS. 43K and 43L and is dimensioned specific to the patient's knee features. The tibia jig surface model 632M can be extracted or otherwise generated from the jig blank model 50B of FIGS. 43D-43F by employing any of the computer surface rendering techniques described above.

As can be understood from FIGS. 44C-44E, the exterior surface model 632M is combined with the tibia surface model 40 to respectively form the exterior and interior surfaces of the tibia jig model 746*y*. The tibia surface model 40 represents the interior or mating surface of the tibia jig 2B and corresponds to the tibia arthroplasty target area 42. Thus, the model 40 allows the resulting tibia jig 2B to be indexed to the arthroplasty target area 42 of the patient's tibia 20 such that the resulting tibia jig 2B will matingly receive the arthroplasty target area 42 during the arthroplasty procedure. The two surface models 632M, 40 combine to provide a patient-specific jig model 746*y* for manufacturing the tibia jig 2B.

As can be understood from FIGS. 44D and 44E, once the models 632M, 40 are properly aligned, a gap will exist between the two models 632M, 40. An image sewing method or image sewing tool is applied to the aligned models 632M, 40 to join the two surface models together to form the 3D computer generated jig model 746*y* of FIG. 44D into a single-piece, joined-together, and filled-in jig model 746*y* similar in appearance to the integrated jig model 748*y* depicted in FIGS. 44G and 44H. In one embodiment, the jig model 746*y* may generally correspond to the description of the "jig data" 46 discussed with respect [block 145] of FIG. 1E.

As can be understood from FIGS. 44D-44F, 44G and 44H, the geometric gaps between the two models 632M, 40, some of which are discussed below with respect to thicknesses $V_1$, $V_2$ and $V_3$, may provide certain space between the two surface models 632M, 40 for slot width and length and drill bit length for receiving and guiding cutting tools during TKA surgery. Because the resulting tibia jig model 748*y* depicted in FIGS. 44G and 44H may be a 3D volumetric model generated from 3D surface models 632M, 40, a space or gap should be established between the 3D surface models 632M, 40. This allows the resulting 3D volumetric jig model 748*y* to be used to generate an actual physical 3D volumetric tibia jig 2B.

In some embodiments, the image processing procedure may include a model repair procedure for repairing the jig model 746*y* after alignment of the two models 632M, 40. For example, various methods of the model repairing include, but are not limit to, user-guided repair, crack identification and filling, and creating manifold connectivity, as described in: Nooruddin et al., *Simplification and Repair of Polygonal Models Using Volumetric Techniques* (IEEE Transactions on Visualization and Computer Graphics, Vol. 9, No. 2, April-June 2003); C. Erikson, *Error Correction of a Large Architectural Model: The Henderson County Courthouse* (Technical Report TR95-013, Dept. of Computer Science, Univ. of North Carolina at Chapel Hill, 1995); D. Khorramabdi, *A Walk through the Planned CS Building* (Technical Report UCB/CSD 91/652, Computer Science Dept., Univ. of California at Berkeley, 1991); Morvan et al., *IVECS: An Interactive Virtual Environment for the Correction of .STL files* (Proc. Conf. Virtual Design, August 1996); Bohn et al., *A Topology-Based Approach for Shell-Closure*, Geometric Modeling for Product Realization, (P. R. Wilson et al., pp. 297-319, North-Holland, 1993); Barequet et al., *Filling Gaps in the Boundary of a Polyhedron*, Computer Aided Geometric Design (vol. 12, no. 2, pp. 207-229, 1995); Barequet et al., *Repairing CAD Models* (Proc. IEEE Visualization '97, pp. 363-370, October 1997); and Gueziec et al., *Converting Sets of Polygons to Manifold Surfaces by Cutting and Stitching*, (*Proc. IEEE Visualization* 1998, pp. 383-390, October 1998). Each of these references is incorporated into this Detailed Description in their entireties.

As can be understood from FIGS. 44G and 44H, the integrated jig model 748*y* may include several features based on the surgeon's needs. For example, the jig model 748*y* may include a slot feature 30 for receiving and guiding a bone saw and drill holes 32 for receiving and guiding bone drill bits. As can be understood from FIGS. 44D and 44E, to provide sufficient structural integrity to allow the resulting tibia jig 2B to not buckle or deform during the arthroplasty procedure and to adequately support and guide the bone saw and drill bits, the gap between the models 232M, 40 may have the following offsets $V_1$, $V_2$, and $V_3$.

As can be understood from FIGS. 44D-44H, in one embodiment, thickness $V_1$ extends along the length of the posterior drill holes 32P between the models 632M, 40 and is for supporting and guiding a bone drill received therein during the arthroplasty procedure. Thickness $V_1$ may be at least approximately four millimeters or at least approximately five millimeters thick. The diameter of the posterior drill holes 32P may be configured to receive a cutting tool of at least one-third inches.

Thickness $V_2$ extends is the thickness of the jig foots 800*y*, 802*y* between the inner and exterior surfaces 40, 632M. The thickness provides adequate structural strength for jig foots 800*y*, 802*y*, to resist buckling and deforming of the jig to manufacture and use. Thickness $V_2$ may be at least approximately five millimeters or at least eight millimeters thick.

Thickness $V_3$ extends along the length of a saw slot 30 between the models 632M, 40 and is for supporting and guiding a bone saw received therein during the arthroplasty procedure. Thickness $V_3$ may be at least approximately 10 mm or at least 15 mm thick.

In addition to providing sufficiently long surfaces for guiding drill bits or saws received therein, the various thicknesses $V_1$, $V_2$, $V_3$ are structurally designed to enable the tibia jig 2B to bear vigorous tibia cutting, drilling and reaming procedures during the TKR surgery.

As indicated in FIGS. 44G and 44H, the exterior portion or side 106 of the integrated jig model 748*y* may include: feature or jig foot 800*y* that extends over and matches the patient's medial portion of the tibia plateau; feature or jig foot 802*y* that extends over and matches the patient's lateral portion of the tibia plateau; projection 804*y* that extends downward from the upper exterior surface 632*y* of the tibia jig 2B; and a flat portion of the exterior surface 632*y* that provides a blanked labeling area for listing information regarding the patient, surgeon or/and the surgical procedure. Also, as discussed above, the integrated jig model 748*y* may include the saw cut slot 30 and the drill holes 32. The inner portion or side 104 of the jig model 748*y* (and the resulting tibia jig 2B) is the tibia surface model 40, which will matingly receive the arthroplasty target area 42 of the patient's tibia 20 during the arthroplasty procedure.

As can be understood by referring to [block 105] of FIG. 1B and FIGS. 43A-43C, in one embodiment when cumulating the image scans 16 to generate the one or the other of the models 40, 22, the models 40, 22 are referenced to point P, which may be a single point or a series of points, etc. to reference and orient the models 40, 22 relative to the models 22, 28 discussed with respect to FIG. 1C and utilized for POP. Any changes reflected in the models 22, 28 with respect to point P (e.g., point P becoming point P') on account of the POP is reflected in the point P associated with the models 40, 22 (see [block 135] of FIG. 1D). Thus, as can be understood from [block 140] of FIG. 1D and FIGS. 44C-44E, when the jig blank exterior surface model 632M is combined with the surface model 40 (or a surface model developed from the arthritic model 22) to create the jig model 746*y*, the jig model 746*y* is referenced and oriented relative to point P' and is generally equivalent to the "jig data" 46 discussed with respect to [block 145] of FIG. 1E.

Because the jig model 746*y* is properly referenced and oriented relative to point P', the "saw cut and drill hole data" 44 discussed with respect to [block 125] of FIG. 1E can be properly integrated into the jig model 746*y* to arrive at the integrated jig model 748*y* depicted in FIGS. 44G-44H. The integrated jig model 748*y* includes the saw cuts 30, drill holes 32 and the surface model 40. Thus, the integrated jig model 748*y* is generally equivalent to the "integrated jig data" 48 discussed with respect to [block 150] of FIG. 1E.

As can be understood from FIG. 44I, which illustrates a perspective view of the integrated jig model 748*y* mating with the "arthritic model" 22, the interior surface 40 of the jig model 748*y* matingly receives the arthroplasty target area 42 of the tibia upper end 604*y* such that the jig model 748*y* is indexed to mate with the area 42. Because of the referencing and orientation of the various models relative to the points P, P' throughout the procedure, the saw cut slot 30 and drill holes 32 are properly oriented to result in saw cuts and drill holes that allow a resulting tibia jig 2B to restore a patient's joint to a pre-degenerated condition.

As indicated in FIG. 44I, the integrated jig model 748*y* may include a jig body 850*y*, a medial tibia plateau covering projection 852*y*, a lateral tibia plateau covering projection 854*y*, a lower portion 856*y* extending form the body 850*y*, posterior drill holes 32P, anterior drill holes 45N, a saw slot 30 and an upper flat portion 857*y* for receiving thereon patient, surgery and physician data. The projections 852*y*, 854*y* extend over their respective medial and lateral tibia plateau portions. The projections 852*y*, 854*y*, 856*y*, 857*y* extend integrally from the jig body 850*y*.

As can be understood from [blocks 155-165] of FIG. 1E, the integrated jig 748*y* or, more specifically, the integrated jig data 48 can be sent to the CNC machine 10 to machine the tibia jig 2B from the selected jig blank 50B. For example, the integrated jig data 48 may be used to produce a production file that provides automated jig fabrication instructions to a rapid production machine 10, as described in the various Park patent applications referenced above. The rapid production machine 10 then fabricates the patient-specific arthroplasty tibia jig 2B from the tibia jig blank 50B according to the instructions.

The resulting tibia jig 2B may have the features of the integrated jig model 748*y*. Thus, as can be understood from FIG. 44I, the resulting tibia jig 2B may have the slot 30 and the drilling holes 32 formed on the projections 852*y*, 854*y*, 856*y*, 857*y*, depending on the needs of the surgeon. The drilling holes 32 are configured to prevent the possible IR/ER (internal/external) rotational axis misalignment between the tibia cutting jig 2B and the patient's damaged joint surface during the proximal tibia cut portion of the TKR procedure. The slot 30 is configured to accept a cutting instrument, such as a reciprocating slaw blade for transversely cutting during the proximal tibia cut portion of the TKR.

i. Overestimation Process

As mentioned above in Subsection a of this Detailed Description, certain regions of the 3D surface models 40 may be a more accurate representation of the actual patient bone surface than other regions and/or may be more readily machined. For example, because of limitations in the medical imaging process (e.g., having to rely on a finite number of image slices 16 as opposed to an infinite number of image slices, volume averaging issues, and issues presented by irregular contours due to the presence of osteophytes, fat tissue, broken cartilage, etc.), the 3D surface models 40 in certain regions may not be an accurate representation of the corresponding actual bone surfaces of the arthroplasty target areas. As a result, a bone mating surface of an actual jig 2 based upon such less accurate data may end up having an interfering fit as opposed to a mating fit with the arthroplasty target area of the actual bone surfaces.

With respect to machining, the size of the tooling used to machine the bone mating surface of the actual jig may exceed the size of certain features in the 3D surface models 40. As a result, the CNC machine may not be able to accurately machine the bone mating surface of the actual jig to match the 3D surface models.

To address these issues presented by the imaging and machining limitations, the 3D surface models 40, or more specifically, the contour lines 210*y*, 210*y*' used to generate the 3D surface models, may be subjected to the overestimation process described below. The result of the overestimation process is an actual jig with: (1) bone mating surfaces that matingly receive and contact certain regions of the actual bone surface of the arthroplasty target region, wherein the certain regions correspond to regions of the actual bone surface that can be accurately and reliably 3D computer modeled and actually machined; and (2) bone-facing surfaces of the jig (i.e., those surfaces of the jig that face the bone when the bone mating surfaces of the jig matingly receive and contact the bone surfaces of the arthroplasty target region) that avoid contact with certain other regions of the actual bone surface of the arthroplasty target region, wherein the certain other regions correspond to regions of the actual bone surface that are less likely to be accurately and reliably 3D computer modeled and/or less likely to be actually machined.

In creating bone-facing surfaces of the jig that correspond to bone surface regions that are less likely to be accurately 3D modeled and/or actually machined, the overestimation process overestimates or moves the contour lines 210*y* away or outward from the bone area of the image slice 16 such that the CNC machine will be caused to over-machine along the overestimated contour line. This outward displacement of the contour line 210*y* results in the jig's bone-facing surface corresponding to the overestimated contour line being spaced apart from the corresponding actual bone surface of the arthroplasty target region when the jig's bone mating surface matingly receives and contacts the arthroplasty target region.

Due to the overestimation process, in one embodiment, the contact between the jig's bone mating surface and the bone surface of the arthroplasty target region is limited to those regions of the arthroplasty target region that can be accurately and reliably 3D computer modeled and actually machined. All other bone-facing surfaces of the jig may be the result of the overestimation process such that these other bone-facing surfaces are spaced apart from, and do not contact, their corresponding regions of the bone surface of the arthroplasty target region, as these bone regions correspond to regions that are less likely to be accurately 3D computer modeled and/or less likely to be actually machined. The result of the overestimated bone-facing surfaces of the jig 2 is a jig that is more likely to accurately and reliably matingly receive the arthroplasty target region during an arthroplasty procedure.

Example overestimation processes are provided below in the context of generating bone-facing surfaces for a femur jig and a tibia jig, wherein some of the bone-facing surfaces are bone mating surfaces and other bone-facing surfaces are the result of overestimation. While the following examples are provided in the context of jigs for knee arthroplasty, the overestimation process should not be considered as being limited to the knee context. Instead, the overestimation concepts disclosed herein should be considered to be applicable to all types of orthopedic surgeries by those skilled in the art, including those surgeries for other types of bone-to-bone interfaces such as ankle, hip, wrist, elbow, shoulder, toe, finger and other types of joints, vertebrae-to-vertebrae interfaces, vertebrae-to-hip structure interfaces, vertebrae-to-skull interfaces, etc.

1. Overestimating the 3D Femur Surface Models

As described above with regard to block 140 of FIG. 1D, the "jig data" 46 is used to produce a jigs having bone mating surfaces customized to matingly receive the target areas 42 of the respective bones of the patent's joint. Data for the target areas 42 may be based, at least in part, on the 3D computer generated surface models 40 of the patient's joint bones. Furthermore, as described above with regard to FIG. 1A and [blocks 100-105] of FIG. 1B, these 3D computer generated surface models 40 may be based on the plurality of 2D scan image slices 16 taken from the imaging machine 8 and, more precisely, from the contour lines derived from those 2D scan image slices via image segmentation processes known in the art or, alternatively, as disclosed in U.S. Provisional Patent Application 61/126,102, which was filed Apr. 30, 2008 and is incorporated by reference herein in its entirety.

Each scan image slice 16 represents a thin slice of the desired bones. FIG. 45A illustrates the distal axial view of the 3D model of the patient's femur shown in FIG. 42A with the contour lines 2301 of the image slices shown and spaced apart by the thickness DT of the slices. FIG. 45B represents a coronal view of a 3D model of the patient's femur with the contour lines 2301 of the image slices shown and spaced apart by the thickness DT of the slices.

The slices shown in FIGS. 45A-B have contour lines 2301 similar to the open and closed loop contour line segments 210*y*, 210*y*' depicted in FIGS. 41B and 41E. The contour lines 2301 of each respective image slice 16 are compiled together to form the 3D model of the patient's femur. The overall resolution or preciseness of the 3D models 40 (shown in FIGS. 41C and 41F) resulting from compiling together the contour lines of each of these slices (shown in [block 1010]) may be impacted by the thickness DT of the slices shown in FIGS. 45A-B. Specifically, the greater the thickness DT of the slices, the lower the resolution/preciseness of the resulting 3D models, and the smaller the thickness DT of the slices, the higher the resolution/preciseness of the resulting 3D models.

As the resolution/preciseness of the 3D models increases, more accurate customized arthroplasty jigs 2 may be generated. Thus, the general impetus is to have thinner slices rather than thicker slices. However, depending upon the imaging technology used, the feasible thickness DT of the image slices may vary and may be limited due a variety of reasons. For example, an imaging thickness DT that is sufficiently precise to provide the desired imaging resolution may also need to be balanced with an imaging duration that is sufficiently brief to allow a patient to remain still for the entire imaging duration.

In embodiments utilizing MRI technology, the range of slice thickness DT may be from approximately 0.8 mm to approximately 5 mm. MRI slice thicknesses DT below this range may be unfeasible because they have associated imaging durations that are too long for most patients to remain still. Also, MRI slice thicknesses DT below this range may be unfeasible because they may result in higher levels of noise with regard to actual signals present, residuals left between slices, and volume averaging limitations of the MRI machine. MRI slice thicknesses above this range may not provide sufficient image resolution/preciseness. In one embodiment, the MRI slice thicknesses DT is approximately 2 mm.

While embodiments utilizing CT technology may have a range of slice thicknesses DT from approximately 0.3 mm to approximately 5 mm, CT imaging may not capture the cartilage present in the patient's joints to generate the arthritic models mentioned above.

Regardless of the imaging technology used and the resulting resolution/preciseness of the 3D models, the CNC machine 10 may be incapable of producing the customized arthroplasty jigs 2 due to mechanical limitations, especially where irregularities in the bone surface are present. This, for example, may result where a milling tool bit has dimensions that exceed those of the feature to be milled.

FIG. 45C illustrates an example sagittal view of compiled contour lines of successive sagittal 2D MRI images based on the slices shown in FIGS. 45A-B with a slice thickness DT of 2 mm. As can be understood from FIGS. 45A-23, the contour lines shown begin on the medial side of the knee at the image slice corresponding to contour line 2310 and conclude on the lateral side of the knee at the image slice corresponding to contour line 2330. Thus, in one embodiment, contour lines 2310 and 2330 represent the contour lines of the first and last images slices taken of the femur, with the other contour lines between contour lines 2310, 2330 representing the contour lines of the intermediate image slices taken of the femur. Each of the contour lines is unique is size and shape, may be either open-loop or closed-loop, and corresponds to a unique image slice 16.

FIG. 45D illustrates an example contour line 2400 of one of the contour lines depicted in FIGS. 45A-23, wherein the contour line 2400 is depicted in a sagittal view and is associated with an image slice 16 of the femoral condyle. As shown, the contour line 2400 includes a plurality of surface coordinate points (e.g., h−n, . . . , h−3, h−2, h−1, h, h+1, h+2, h+3, . . . , h+n; j−n, . . . , j−3, j−2, j−1, j, j+1, j+2, j+3, . . . , j+n; k−n, . . . , k−3, k−2, k−1, k, k+1, k+2, k+3, . . . , k+n; and i−n, . . . , i−3, i−2, i−1, i, i+1, i+2, i+3, . . . , i+n). The contour line and associated points may be generated by imaging technology, for example, via an image segmentation process that may employ, for example, a shape recognition process and/or a pixel intensity recognition process. In one embodiment, the contour line 2400 may represent the boundary line along the cortical-cancellous bone edge. In one embodiment, the boundary line may represent the outer boundary line of the cartilage surface.

Each of the surface contour points in the plurality may be separated by a distance "d". In one embodiment, distance "d" may be a function of the minimum imaging resolution. In some embodiments, distance "d" may be function of, or associated with, the size of the milling tool used to manufacture the jig. For example, the distance "d" may be set to be approximately 10 times smaller than the diameter of the milling tool. In other words, the distance "d" may be set to be approximately $1/10^{th}$ or less of the diameter of the milling tool. In other embodiments, the distance "d" may be in the range of between approximately one half of the diameter of the milling tool to approximately $1/100^{th}$ or less of the diameter of the milling tool.

Depending on the embodiment, the separation distance d may be either uniform along the contour line 2400, or may be non-uniform. For example, in some embodiments, areas of bone irregularities may have points that are closer together than areas where no irregularities are present. In one embodiment, the points shown along the example contour line 2400 may have a separation distance d of approximately 2 mm. In other embodiments, distance d may be in the range of approximately 0.8 mm to approximately 5 mm.

The bone surface of the example contour line 2400 includes a regular region 2402A on the distal-posterior portion of the contour line 2400 as well as an irregular region 2402B of the same. The contour line 2400 also includes irregular regions 2402C-D on the distal and distal-anterior portions, respectively. The irregular regions 2402B-D may be due to a variety of patient specific factors. For example, irregular region 2402B illustrates a type of bone irregularity, referred to as an "osteophyte", where a bony outgrowth has occurred in the femoral condyle. Osteophytes may be present in patients that have undergone trauma to the bone or who have experienced degenerative joint disease.

The irregular regions 2402C-D illustrate areas of the femoral condyle that have experienced cartilage damage and appear as notches in the contour line 2400. Regardless of the cause of the irregularity, the presence of irregularities in the contour line 2400 may adversely impact the ability to generate a mating surface in the actual arthroplasty jig that accurately and reliably mates with the corresponding bone surface of the patient during the arthroplasty procedure. This may be the result of the imaging impreciseness in the vicinity of the contour irregular regions 2402B-D or because the contour irregular regions 2402B-D represent surface contours that are too small for the tooling of the CNC machine 10 to generate. To account for contour line regions associated with imaging impreciseness and/or features too small to be milled via the tooling of the CNC machine, in some embodiments, such contour line regions may be identified and corrected or adjusted via the overestimation process prior to being compiled to form the 3D models 40.

FIG. 45E represents an example overestimation algorithm 2500 that may be used to identify and adjust for irregular regions 2402B-D when forming the 3D models 40. In block 2502, medical imaging may be performed on the damaged bone at desired slice thicknesses DT, which in some embodiments may be equal to those slice thicknesses DT mentioned above with regard to FIGS. 45A-45B. For example, MRI and/or CT scans may be performed at predetermined thicknesses DT as shown in FIGS. 45A-B. In some embodiments, the desired thickness DT used in block 2502 is set at 2 mm or any other thickness DT within the range of thicknesses DT mentioned above.

From this medical imaging, a series of slices 16 may be produced and image segmentation processes can be used to generate the contour lines 210*y*, 210*y*', 2301, 2310, 2330, 2400 discussed with respect to FIGS. 2, 45A-B, and 24 (see block 2504). Also in block 2504, a plurality of surface coordinate points along each contour line segment 2402A-D may be identified as shown in FIG. 45D with respect to contour line 2400. For example, the points in the irregular region corresponding to contour line segment 2402B may be identified and indexed as i-n, . . . , i-1, i, i+1, i+2, i+3, . . . , i+n.

With the surface coordinate points along the contour 2400 defined, an analysis may be performed on two or more of the points (e.g., i and i+1) to determine if an irregularity exists in the contour line segment per block 2506.

Figure 45F:
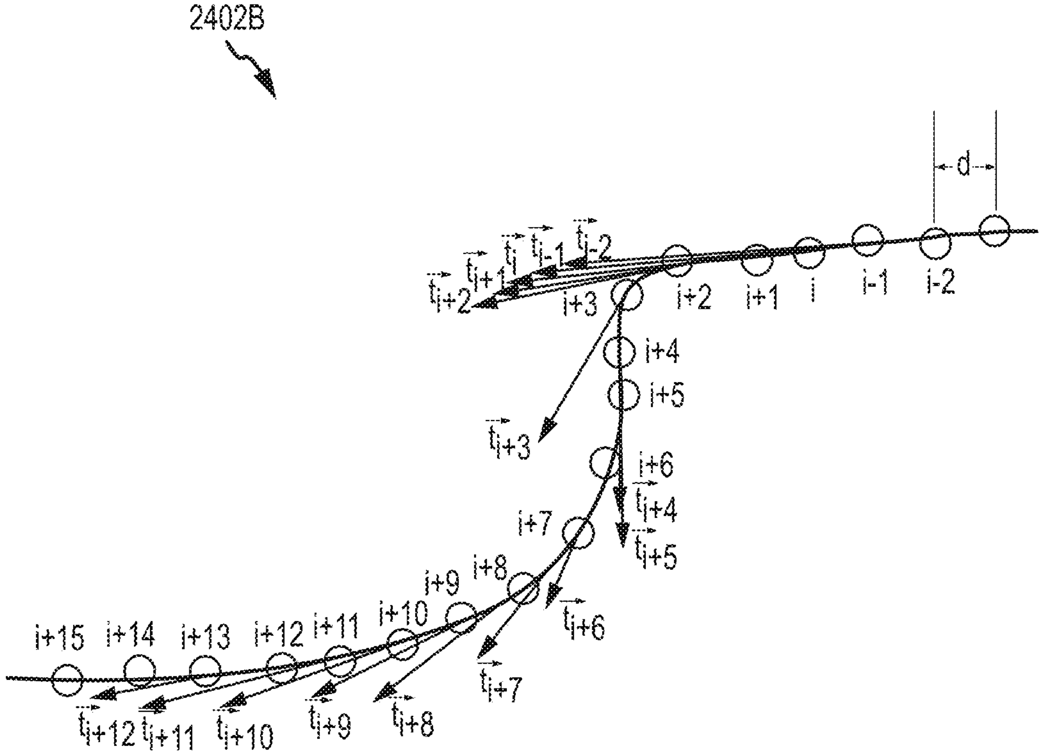
FIG. 45F depicts implementing an example analysis scheme (according to block 2506) on the irregular contour line region 2402B of FIG. 45D.

FIG. 45F depicts implementing an example analysis scheme (according to block 2506) on the irregular contour line region 2402B of FIG. 45D. As shown, the analysis may include constructing one or more tangent lines (labeled as $t_{i-1}$, $t_i$, $t_{i+1}$, $t_{i+2}$, $t_{i+3}$, $t_{i+4}$, etc.), corresponding to the points in the irregular region 2402B. The analysis of block 2506 may further include calculating differences between the angles formed by one or more of the tangent lines. For example, the difference between the angles formed by the tangent lines $t_i$ and $t_{i+1}$, may be defined as $w_i$, where $$w_i = \cos^{-1}\left(\frac{t_{i+1} \cdot t_i}{|t_{i+1}||t_i|}\right).$$

In some embodiments, the operations of block 2506 may be performed repetitively on each point within the contour segment.

The operations of block 2506 may be calculated on subsequent points (e.g., between $t_i$ and $t_{i+1}$) in some embodiments, and on non-subsequent points in other embodiments (e.g., $t_{i+2}$ and $t_{i+4}$).

The angular difference w; may indicate whether portions of the contour line segment are too eccentric for use in constructing the 3D models 40. In block 2508, the angular difference $w_i$ may be compared to a predetermined angular criterion $w_c$. The angular criterion $w_c$ may be determined based on several factors, including the physical dimensions and characteristics of the CNC machine 10. In some embodiments, the predetermined angular criterion $w_c$ is set at approximately 5 degrees. In other embodiments, the predetermined angular criterion $w_c$ is set at between approximately 5 degrees and approximately 20 degrees.

For the sake of discussing the example irregular region 2402B shown in FIG. 45F, the angular criterion $w_c$ is set to 5 degrees in one embodiment. The angular differences between tangent lines associated with adjacent points i-2, i-1, i, i+1, i+2 are within the predetermined angular criterion $w_c$ of 5 degrees, but the differences between tangent lines associated with adjacent points i+2 and i+3 and adjacent points i+3 and i+4 exceeds the predetermined angular criterion $w_c$ of 5 degrees and therefore indicates an irregular region of the contour line. The difference between tangent lines associated with adjacent points, such as i+5 and i+6, may indicate similar irregular regions. As mentioned above, these irregularities may result from conditions of the patient's bone such as arthritis or osteoarthritis and generally result in a contour line segment being unsuitable for using when forming the 3D models 40. Accordingly, if the comparison from block 2508 indicates that the angular difference w; is greater than the predetermined criterion $w_c$, then the data associated with the irregular contour line segment may be modified by overestimating (e.g., adjusting the irregular contour line segment outward or away from the bone portion of the image slice 16) as discussed in greater detail below with respect to FIG. 45G (see block 2510).

Figure 45G:
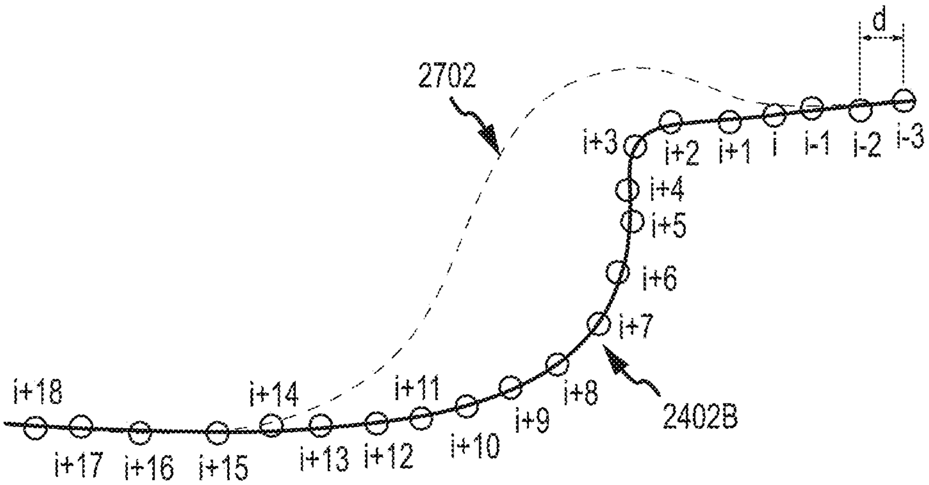
FIG. 45G depicts the irregular region 2402B from FIG. 45F including a proposed area of overestimation, wherein an overestimation procedure creates an adjusted contour line and positionally deviates the adjusted contour line from the original surface profile contour line.

FIG. 45G depicts the irregular region 2402B from FIG. 45F including a proposed area of overestimation, wherein an overestimation procedure creates an adjusted contour line 2702 and positionally deviates the adjusted contour line 2702 from the original surface profile contour line 2402B. In the event that the comparison performed in block 2508 indicates that the angular differences between any of the points i through i+14 exceed the predetermined angular criterion $w_c$, then the contour line segment may be overestimated between these points as shown by the dashed line 2702. As can be understood from a comparison of contour line 2402B to the overestimated or adjusted line 2702, the adjusted line 2702 is adjusted or moved outward or away from the location of the contour line 2402B by an offset distance. Depending on the embodiment, the offset distance between the contour line 2402B and the adjusted line 2702 may range between a few millimeters to a few centimeters. This overestimation may be built into the data used to construct 3D surface models 40 and result in a gap between the respective region of the bone mating surface of the jig 2 and the corresponding portion of the patient's bone surface, thereby avoiding contact between these respective areas of the jig and bone surface. The other areas, such as i-1, i-2, i-3, i+15, i+16, i+17, and i+18, need not be overestimated, per block 2510, because the differences between their tangent lines fall within the angular difference criterion $w_c$. These areas may be designated as potential target areas that may later be used as the 3D surface models 40 if other angular criteria (described below) are satisfied.

By building overestimation data into the 3D surface models 40, deliberate spaces may be created in regions of the custom arthroplasty jig 2 corresponding to irregularities in the patient's bone, where it is often difficult to predict the size and shape of these irregularities from 2D MRI or where it is difficult to accurately machine the contour line into the jig's bone mating surface because of the largeness of the milling tool relative to the changes in contour. Thus, the jig 2 may include one or more deliberate spaces to accommodate these irregularities or inability to machine. Without these deliberate spaces, the jig 2 may be potentially misaligned during the TKR surgery and may reduce the chances of the surgery's success.

Figure 45H:
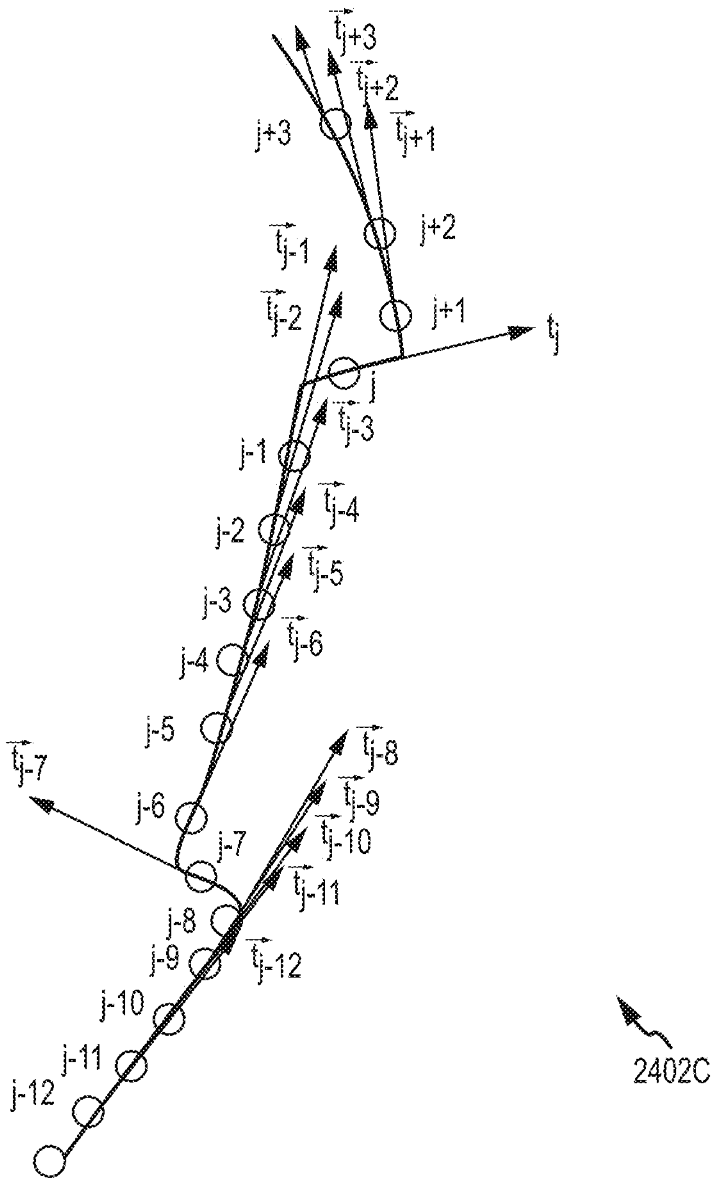
FIG. 45H illustrates the example analysis scheme according to the algorithm of FIG. 45E implemented on the irregular region 2402C from FIG. 45D where an irregular surface of the condylar contour is observed.

The image generation, analysis and overestimation of blocks 2506, 2508 and 2510 may be performed on the other irregularities shown in FIG. 45D. FIG. 45H illustrates the example analysis scheme according to algorithm 2500 implemented on the irregular region 2402C where an irregular surface of the condylar contour is observed. Akin to the analysis of irregular region 2402B, the analysis may include constructing one or more tangent lines (labeled as $t_{j-1}$, $t_j$, $t_{j+1}$, $t_{j+2}$, $t_{j+3}$, etc.), corresponding to the points in the irregular region 2402C. The analysis of block 2506 may further include calculating differences between the angles formed by one or more of the tangent lines, defined as $w_j$, where $$w_j = \cos^{-1}\left(\frac{t_{j+1} \cdot t_j}{|t_{j+1}||t_j|}\right)$$

between subsequent points $t_j$ and $t_{j+1}$. Other embodiments include analysis between non-subsequent points (e.g., $t_{j+2}$ and $t_{j+4}$).

Akin to the analysis of irregular region 2402B, the angular difference $w_j$ may indicate whether portions of the contour line segment in the irregular region 2402C are too eccentric for use in constructing the 3D models 40. In block 2508, the angular difference $w_j$ may be compared to a predetermined angular criterion $w_c$. If the angular criterion $w_c$ is set to 5 degrees, the angular differences between adjacent tangent lines associated with j-6, j-5, j-4, j-3, j-2 and j-1 are within the predetermined angular criterion $w_c$. The difference between j-1, j, and j+1, however, may exceed the predetermined angular criterion $w_c$ of 5 degrees and therefore may indicate an irregular region of the contour line 2400. In a similar fashion, the angular criterion $w_c$ for angular differences between tangent lines associated with subsequent points j-6, j-7, and j-8 may indicate similar irregular regions.

As mentioned above, these irregularities may result from conditions in the patient's bone such as arthritis or osteoarthritis and generally result in a contour line segment being unsuitable for using when forming the 3D models 40. Accordingly, if the comparison from block 2508 indicates that the angular difference w; is greater than the predetermined criterion $w_c$, such as the case at points j-1, j, and j+1 as well as j-6, j-7, and j-8, then the data used in forming 3D models 40 may be adjusted by the overestimating process prior to being used in forming the 3D models 40.

Figure 45I:
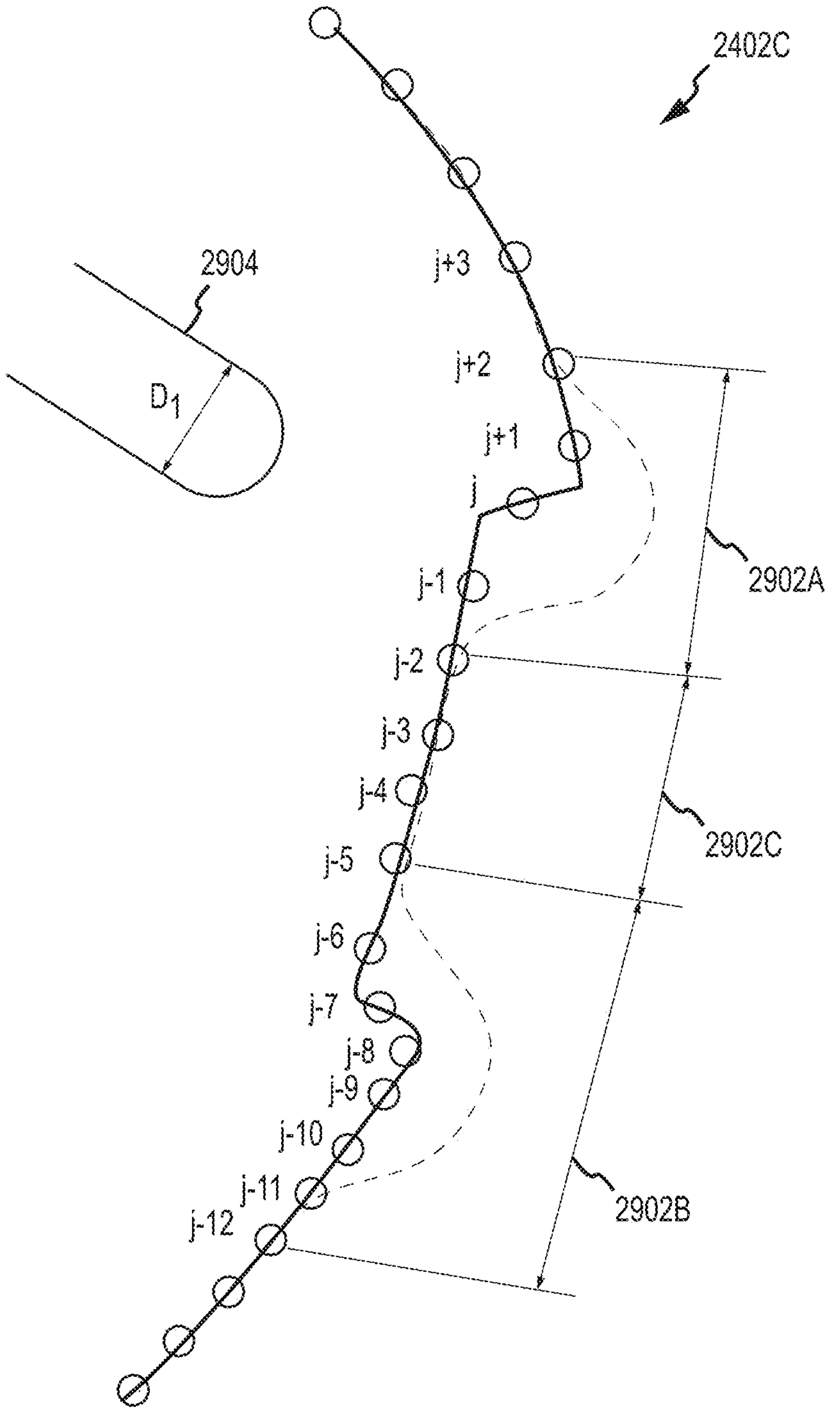
FIG. 45I depicts the irregular region 2402C from FIG. 45H including a proposed area of overestimation indicated by the dashed line areas 2902A-B.

FIG. 45I depicts the irregular region 2402C from FIG. 45H including a proposed area of overestimation indicated by the dashed line areas 2902A-B, wherein the dashed line areas 2902A-B are deviated from the original cortical-cancellous boundary or contour line 2402C. Since the comparison performed in block 2508 indicates that the angular difference w; is greater than the predetermined criterion $w_c$ at points j-1, j, and j+1 as well as at points j-6, j-7, and j-8, overestimation is performed at these points (labeled as regions 2902A-B respectively). In some embodiments to allow for an adequate transition from the non-overestimate regions to the overestimated regions in view of the diameter of the tool to be used, the overestimation may include additional points to either side of the points falling outside of the predetermined criterion $w_c$ (i.e., points j-1, j, and j+1 as well as at points j-6, j-7, and j-8). Thus, the overestimation in region 2902A may extend from j-2 through j+2, and the overestimation in region 2902B may extend from j-10 through j-5. Furthermore, since the comparison performed in block 2508 indicates that the angular difference w; is less than the predetermined criterion $w_c$ at points j-6, j-5, j-4, j-3, and j-2, (labeled as region 2902C) these points j-5, j-4, and j-3 (adjusting for the addition of points j-6 and j-2 to the regions 2902A-B) may be used in constructing the 3D models 40 as long as other criteria (described below in the context of blocks 2514-2520) are met.

A tool 2904 may be used to form the surface of the jig's bone mating surface from the 3D models 40 formed from the compiled contour lines, some of which may have been modified via the overestimation process. The tool 2904 may be part of the CNC machine 10 or any other type of machining or manufacturing device having any type of tool or device for forming a surface in a jig blank. Regardless of the type of the device used to mill or form the jigs 2, the tool 2904 may have certain attributes associated with jig machining process that are taken into account when performing the overestimating per block 2510. The associated attributes may include the accessible space for the machining tools to reach and machine the jig's bone mating surface. Examples of such attributes may include the collar diameter of the drilling cutter device, the allowable angle the drilling device can make with the surface to be drilled (e.g., 45 degrees±10%), and/or the overall length of the drilling cutter head.

For example, if the minimum diameter of the overestimated regions 2902A-B is larger than the diameter D, of the tool 2904, then overestimation of block 2510 may not need to account for the dimensions of the tool 2904, except to provide adequate transitions leading to the overestimated regions as illustrated above by the addition of a single or few points (e.g., points j-2, j+2, j-5, and j-10) to either side of the points outside predetermined criterion $w_c$.

Figure 45J:
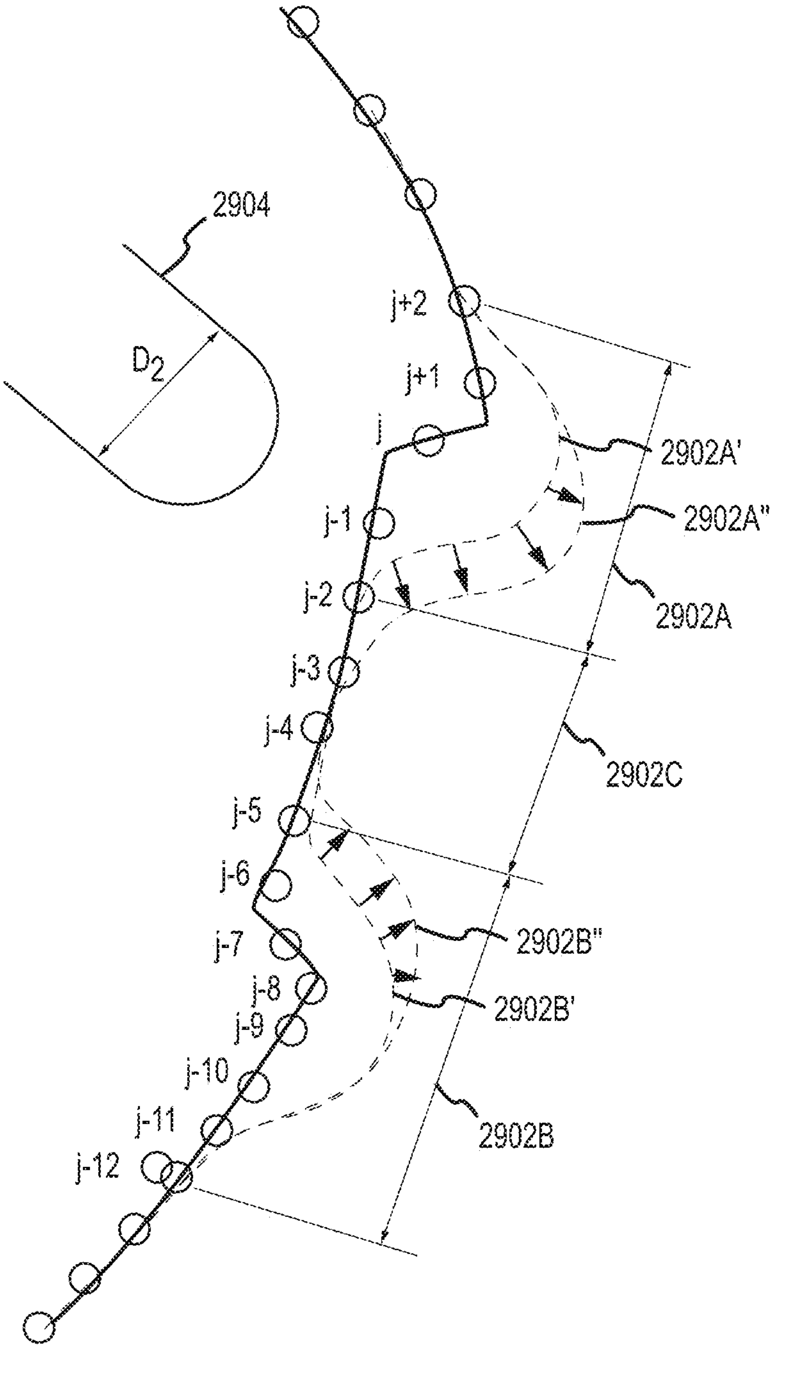

If, on the other hand, the tool 2904 has a larger diameter $D_2$ as shown in the example implementation of FIG. 45J, then the overestimation performed in block 2510 may include accounting for this larger tool size in its overestimation. To determine if the overestimation needs to be adjusted to accommodate the larger diameter $D_2$, a first measurement of the minimum diameter of curvatures 2902A' and 2902B' for regions 2902A-B may be made. In addition, a second measurement of half of the distance associated with region 2902C plus the minimum diameter of curvatures 2902A' and 2902B' for regions 2902A-B may be made. If both the first and second measurements are less than the diameter $D_2$, then the amount of overestimation implemented in block 2510 may be set such that the minimum curvatures of regions 2902A-B, respectively, are greater than or equal to $D_2$ and are increased to 2902A" and 2902B", respectively. Logically, this example curvature requirement may be expressed as: if $diameter_{MIN}$(2902A OR 2902B)<$D_2$ AND ($diameter_{MIN}$(2902A OR 2902B)+(2902C)/2)<$D_2$, then overestimate so that $diameter_{MIN}$ (2902A and/or 2902B) $D_2$. Also, in the event that the overestimation needs to account for the tool diameter $D_2$, one or more additional points, over what would normally be required absent the need to account for tool diameter, may be included such that the regions 2902A-B respectively extend through points j-4 through j+2 and j-12 through j-4. The curvatures 2902A' and 2902B' for the respective regions 2902A-B may be further adjusted outward (as indicated by the arrows in FIG. 45J) to the respective diameter-accounted curvatures 2902A" and 2902B" to define the potential jig mating surface for the 3D models 40. Thus, regions 2902A-B may increase in size to accommodate the diameter $D_2$ of the tool 2904 by sacrificing the area of region 2902C. It should be noted that, if adding a one or more points on either side of an overestimation region 2902A, 2902B in the course of accounting for tool diameter does not result in a smooth transition into the resulting curvature 2902A", 2902B", then still further points can be added to the overestimation region until a smooth transition is achieved.

Figure 45K:
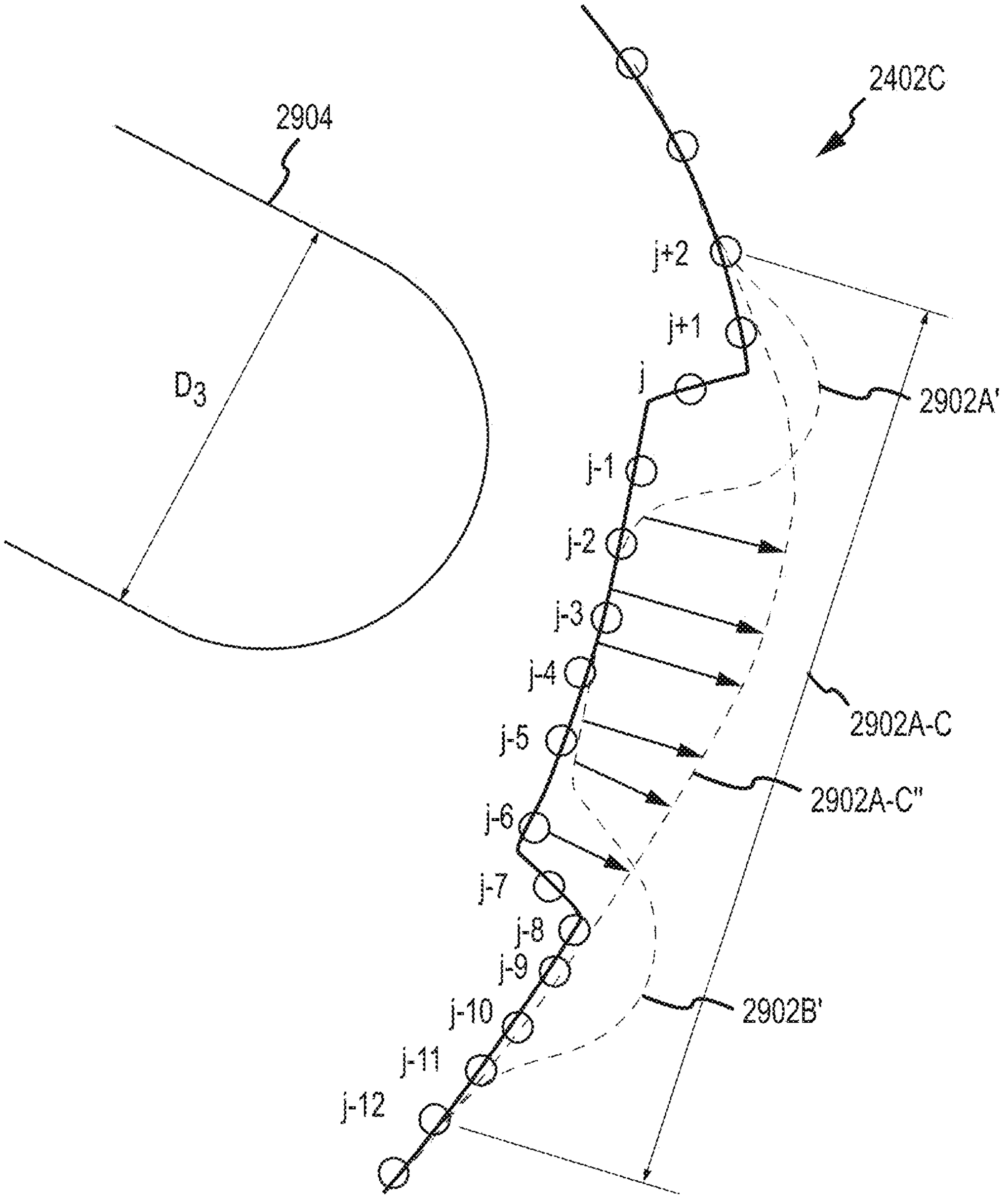

FIG. 45K shows an example implementation of the tool 2904 having an even larger diameter $D_3$ than what is shown in FIGS. 45I-J. In this scenario, if $diameter_{MIN}$(2902A OR 2902B)<$D_3$ AND ($diameter_{MIN}$(2902A OR 2902B)+(2902C)/2)<$D_3$, then overestimate so that $diameter_{MIN}$ (2902A-C)<$D_3$. As illustrated by the arrows, all three regions 2902A-C may need to be overestimated if the size of tool diameter is large enough, sacrificing the entirety of region 2902C to the overestimation associated with regions 2902A-B. Thus, the initial overestimation curvatures 2902A' and 2902B' end up being a single curvature 2902A-C" encompassing all of regions 2902A-C. Of course, additional points can be added as needed to either side of overestimation region 2902A-C to provide a smooth transition into the resulting curvature 2902A-C".

With the curves overestimated to account for factors related to the tool 2904, the resulting overestimated surface profile or contour may be saved for generating the 3D model 40 as long as other criteria (described below in the context of block 2514-2520) are met.

Figure 45L:
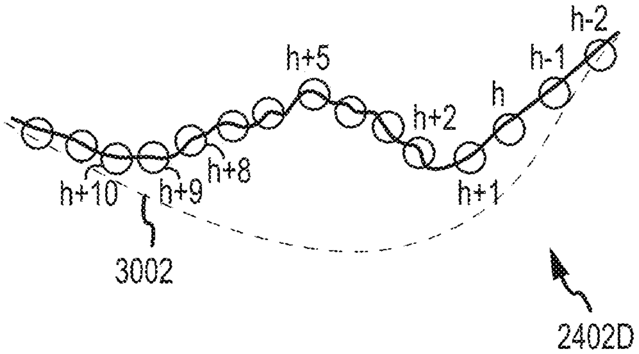

Referring briefly back to FIG. 45D, the analysis and overestimation of algorithm 2500 may be performed on the irregular region 2402D, where the boundary between the cortical and cancellous bone in the femoral condyle is irregular and may not be clearly identified by the imaging slices. FIG. 45L illustrates the example overestimation scheme on the irregular region 2402D according to block 2510. As shown in FIG. 45L, the irregular region 2402D extends between points h+1 to h+10. The tangent lines (not shown in FIG. 45L) of every two adjacent coordinate points shown have an angular difference greater than $w_c$, and therefore, overestimation may be performed as shown by the dashed line 3002 between points h−2 to h+13.

Figure 45M:
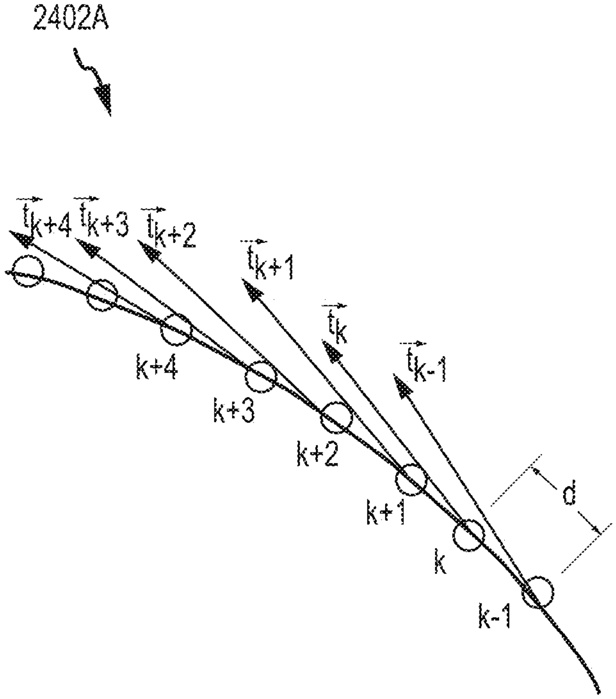

FIG. 45M shows a similar analysis of the regular region 2402A (from FIG. 45D). As was the case with the irregular regions 2402B-D, points along the contour line k−1 through k+4 may be identified and then tangent lines (labeled as $t_{k-1}$, $t_k$, $t_{k+1}$, $t_{k+2}$, $t_{k+3}$, etc.) may be constructed per block 2506. Per block 2508, comparing the angular differences $w_k$ between these tangent lines using the formula $$w_k = \cos^{-1}\left(\frac{t_{k+1} \cdot t_k}{|t_{k+1}||t_k|}\right)$$

shows that they are within the angular criterion $w_c$, which in this example is 5 degrees. Thus, the points shown in FIG. 45M may be saved and used as a potential surface profile for the mating surface of the femoral jig if the surface variations between these points and points on contour lines of adjacent slices are not too extreme. That is, if the angular differences associated with a contour line of a particular slice fall within the angular criterion $w_c$, and the points are used as a potential jig surface, then surface variation between contour lines of adjacent slices may be checked in block 2514. This approach may help to identify certain areas where no cartilage damage or osteophyte is observed in the imaging, yet there is a need to overestimate because the surface variation, between the adjacent slices shown in FIGS. 45A-B, may be too great to be used as an accurate representation of the actual bone surface to be a potential femoral jig surface. Example areas falling within this category for the femoral condyle include, the area of anterior condylar portion close to the trochlear groove and the area of distal condylar portion close to the intercondylar notch to name a few examples.

Figure 45N:
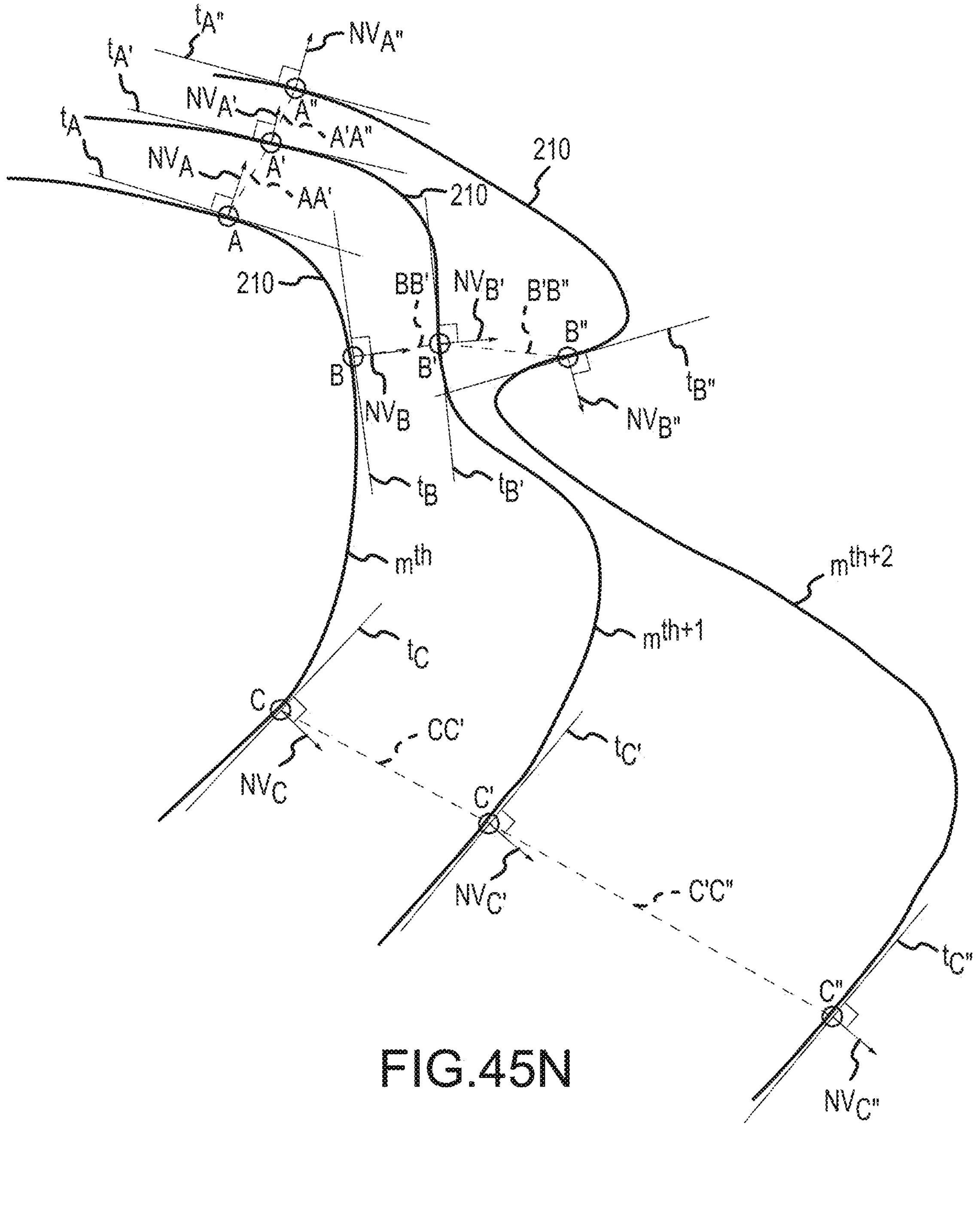

FIG. 45N is a diagrammatic sagittal-coronal-distal isometric view of three contour lines 210*y* of three adjacent image slices 16 depicting angular relationships that may be used to determine whether portions of the one or more contour lines may be employed to generate 3D computer models 40. As mentioned above, despite contour line segments and their associated coordinate points meeting the angular criterion $w_c$ so as to not require overestimation as discussed with respect to blocks 2508 and 2510, such contour line segments and associated coordinate points may still require overestimation if the surface variations between surface contour lines 210*y* of adjacent imaging slices 16 is excessive. Excessive surface variation may result in volume averaging error in the regions of the 3D computer generated models corresponding to the excessive surface variation. Jig mating surfaces based on regions of the 3D computer generated models that are the result of volume averaging error are may have difficulty accurately matingly receiving the associated bone surfaces of the arthroplasty target region.

Such excessiveness is typically the result of variations in the patient's knee features. For example, in the majority of cases, the area of the anterior condylar portion close to the trochlear groove is observed as a smooth depression. However, in other patients, a sharp edge is present in place of the smooth depression. Because of the variation in anatomy between various patients for these varying surface areas and/or other varying surface areas (e.g., the area of distal condylar portion close to the intercondylar notch), these varying surface areas may be generally excluded from being a potential contour line for generating a 3D model 40. In other words, such varying surface areas may be subjected to an overestimation process as described below.

The three contour line segments are respectively labeled in FIG. 45N as the $m^{th}$, $m^{th+1}$, $m^{th+2}$ contour line segments corresponding to three consecutive image slices 16 spaced apart from each other by slice thickness $D_T$. Each contour line includes surface contour points A-C, A'-C' and A"-C" that are saved for use in the potential jig surface profile because, for example, the points fall within the angular criteria discussed with respect to blocks 2506 and 2508. The points A-C, A'-C' and A"-C" now may be used to determine if the slice-to-slice surface variation exceeds a predetermined threshold. For example, on the $m^{th}$ contour line in FIG. 45N, points A, B, and C may have been identified in blocks 2506 and 2508 as defining potential jig mating surfaces. Similarly, in the $m^{th+1}$ contour line in FIG. 45N, points A', B', and C' may have been identified in blocks 2506 and 2508 as defining potential jig mating surfaces. Likewise, in the $m^{th+2}$ contour line in FIG. 45N, points A", B", and C" may have been identified in blocks 2506 and 2508 as defining potential jig mating surfaces.

Because each patient's bone anatomy may be unique, changes in surface contour between corresponding points on contour lines of adjacent slices (i.e., from A-A', A'-A", B-B', B'-B", C-C', or C'-C") may be too significant for use as potential jig surfaces, resulting in volume averaging errors that may lead to surface inaccuracies for the 3D computer models. As will be described in detail below with respect to the example bone contour lines depicted in FIG. 45N, the bone surface defined by points A-A'-A" may provide a potential jig mating surface, the bone surface defined by points B-B'-B" may have too much associated normal vector angular deviation to be used as potential jig mating surface, and the bone surface defined by points C-C'-C" may have too much associate angular deviation between corresponding points of contour lines of adjacent image slices to be used as a potential jig mating surface.

As discussed above with respect to FIG. 45D, a contour line 2400 may have a plurality of coordinate points. According to the operation of block 2508 of FIG. 45E, the coordinate points may fall into one of two classifications, namely, those coordinate points within a potential jig mating area 2402A and those coordinate points within a non-jig mating area 2402B, 2402C and 2402D. Via the criteria of block 2514 of FIG. 45E, the surface coordinate points of one contour line 2400 in potential jig mating area 2402A may be further investigated by a multi-slice (e.g., three-slice) check. For example, coordinate point k+1 located within area 2402A may be coordinate point A in FIG. 45N. Similarly, coordinate points k and k−1 within area 2402A may be coordinate points B and C, respectively. Coordinate points A, A' and A" may correspond to each other, coordinate points B, B' and B" may correspond to each other, and coordinate points C, C' and C" may correspond to each other. Corresponding points A', A", B', B", C', C" for respective points A, B, C may be identified via a variety of methods, including the three methods discussed below with respect to FIGS. 46A-46F.

Block 2514 in FIG. 45E illustrates example comparisons and/or determinations that may be made between corresponding points on contour lines of adjacent image slices to determine if surface variation is too great for the points and contour line segments to be used in generating jig mating surfaces. The comparisons and/or determinations may involve two facets, which are: (1) determining the angular deviation θ between corresponding coordinate points of contour lines of adjacent image slices; and (2) comparing the angular differences φ of normal vectors associated with corresponding coordinate points of contour lines of adjacent image slices. These two facets of the determination are explained in turn below, followed by an application of these two facets of the determination to the contours depicted in FIG. 45N.

As can be understood from FIG. 45N, in one embodiment, the comparisons of the contour lines with respect to angular deviation θ and angular differences φ may take place relative to the contour lines of three adjacent image slices. In other embodiments, the comparisons of the contour lines with respect to angular deviation θ and angular differences φ may take place relative to the contour lines of two, four or more adjacent image slices. In other words, depending on the embodiment, the comparison of the contour lines may be accomplished in groups of two, three, four or more contour lines. In one embodiment, the groups of contour lines evaluated together may be made up of adjacent contour lines. In other embodiments, one or more of the contour lines of a group of contour lines may not be an adjacent contour line (e.g. a contour line falling within a group may be skipped).

Where the image slices 16 are sagittal slices such as those slices 2301, 2310 and 2330 depicted in FIGS. 45A-23, in one embodiment as provided below with respect to FIG. 45N and then again with respect to FIGS. 46A-46B, corresponding coordinate points on contour lines 210*y* of adjacent image slices 16 may be those coordinate points that all exist in a single plane that is generally perpendicular to the sagittal image slices. Thus, as can be understood from FIG. 45N, points A, A' and A" may all exist in a single plane that is perpendicular to the respective image slices. Line segment ΔA' extends between points A and A', and line segment A'A" extends between points A' and A". Although the line segments ΔA' and A'A" may all exist in the same single plane that is perpendicular to the respective image slices, the line segments ΔA' and A'A" may be angularly deviated from each other such that they do not extend along a common line. This angular deviation may be the result of each point A, A' and A" being located on its respective contour line $m^{th}$, $m^{th+1}$, and $m^{th+2}$ and each contour line having a different elevation at its respective point relative to the corresponding points on the adjacent contour lines. This elevation difference between the points A, A' and A" may be because the bone contour geometric shape changes from contour line $m^{th}$, $m^{th+1}$, $m^{th+2}$ to contour line. The order of the contour lines $m^{th}$, $m^{th+1}$, $m^{th+2}$ may correspond to the order of the respective image slices, the image slice order corresponding to the movement of the MRI scan along the knee. Similar relationships exist for points B, B' and B" and for points C, C' and C", resulting in similar line segments BB', B'B" and CC', C'C", respectively.

Once corresponding coordinate points are identified via the method already discussed above and below with respect to FIGS. 45N and 46A-46B or via any of the methods discussed below with respect to FIGS. 46C-46F, the surface variation between adjacent contour lines may be analyzed by: (1) determining the angular deviation θ between corresponding coordinate points of contour lines of adjacent image slices; and (2) comparing the angular differences φ of normal vectors associated with corresponding coordinate points of contour lines of adjacent image slices.

As can be understood from FIG. 45N and already mentioned above, in one embodiment, the comparisons of the contour lines with respect to angular deviation θ and angular differences φ may take place relative to the contour lines of three adjacent image slices. In other embodiments, the comparisons of the contour lines with respect to angular deviation θ and angular differences φ may take place relative to the contour lines of two, four or more adjacent image slices. In other words, depending on the embodiment, the comparison of the contour lines may be accomplished in groups of two, three, four or more contour lines. In one embodiment, the groups of contour lines evaluated together may be made up of adjacent contour lines. In other embodiments, one or more of the contour lines of a group of contour lines may not be an adjacent contour line (e.g. a contour line falling within a group may be skipped).

As can be understood from FIG. 45N, in one embodiment, the contour lines $m^{th}$, $m^{th+1}$, $m^{th+2}$ may be evaluated as a group of three contour lines, wherein contour line $m^{th}$ is compared to contour lines $m^{th+1}$ and $m^{th+2}$. Contour line $m^{th+1}$ may then be compared to contour lines $m^{th+2}$ and $m^{th+3}$, and contour line $m^{th+2}$ may then be compared to contour line $m^{th+3}$ and contour line $m^{th+4}$. Alternatively, once contour line $m^{th}$ is compared to contour lines $m^{th+1}$ and $m^{th+2}$, the comparison may begin again with a comparison of contour line $m^{th+2}$ to contour line $m^{th+3}$ and contour line $m^{th+4}$. Alternatively, once contour line $m^{th}$ is compared to contour lines $m^{th+1}$ and $m^{th+2}$, the comparison may begin again with a comparison of contour line $m^{th+4}$ to contour line $m^{th+5}$ and contour line $m^{th+6}$. Similar orders for comparing the contour lines may be used regardless of whether the contour lines are compared in groups of two, four or more.

Figure 45O:
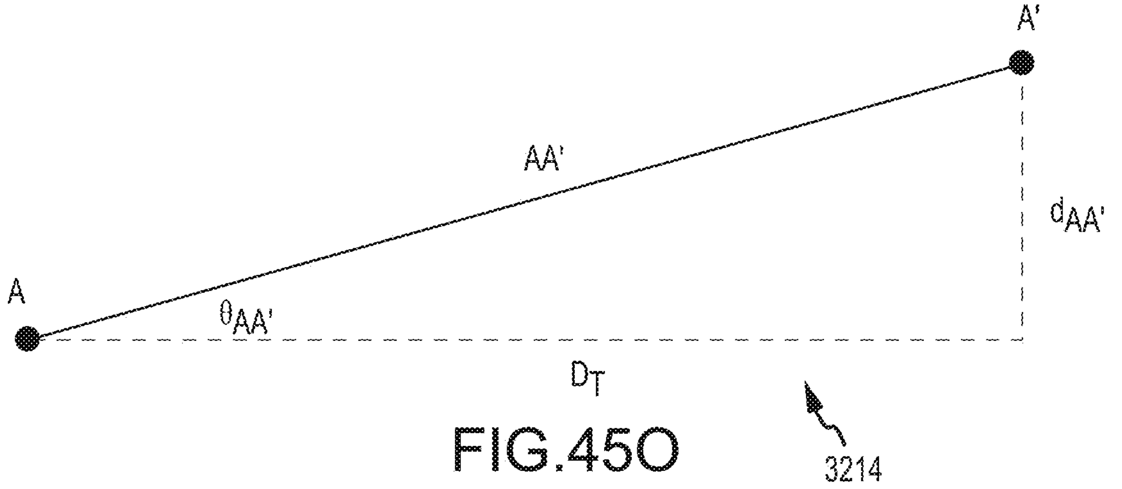

A discussion will now be given regarding the first facet of the surface variation analysis, namely, the determination of the angular deviation θ between corresponding coordinate points of contour lines of adjacent image slices per block 2514. FIG. 45O is an example right triangle 3214 that may be used for determining the angular deviation θ between corresponding coordinate points of contour lines of adjacent image slices per block 2514. The right triangle 3214 illustrates points A and A' with the line segment AA' extending between these two points. The points A and A' lie on respective contour lines $m^{th}$ and $m^{th+1}$. The image slices containing the two contour lines $m^{th}$ and $m^{th+1}$ are separated by the slice thickness DT, which is the perpendicular distance between the two image slices. Thus, the slice thickness DT can be represented in the right triangle 3214 as the long leg of the right triangle 3214, wherein the line segment AA' is the hypotenuse of the right triangle 3214. The rise or fall distance $d_{AA'}$ between the two points A and A' is a distance perpendicular to the slice thickness $D_T$ and is represented on the right triangle 3214 by the short leg of the right triangle 3214. The small angle $\theta_{AA'}$ of the right triangle 3214 represents the angular deviation $\theta_{AA'}$ between the corresponding coordinate points A and A' of contour lines $m^{th}$ and $m^{th+1}$ of adjacent image slices per block 2514. Thus, as can be understood from the triangle 3214, the angular deviation $\theta_{AA'}$ between the corresponding coordinate points A and A' of contour lines $m^{th}$ and $m^{th+1}$ of adjacent image slices may be calculated by any of the following three formulas:

$$\theta_{AA'} = \tan^{-1}\left(\frac{d_{AA'}}{D_T}\right);\ \theta_{AA'} = \cos^{-1}\left(\frac{D_T}{AA'}\right);\ \text{or}\ \theta_{AA'} = \sin^{-1}\left(\frac{d_{AA'}}{AA'}\right).$$

Ideally if there were no surface variation between points A and A', then the length of line segment AA' would be equal to the slice thickness $D_T$ and the angular deviation $\theta_{AA'}$ between the corresponding coordinate points A and A' of contour lines $m^{th}$ and $m^{th+1}$ would be zero.

Determining the angular deviation $\theta_{AA'}$ between the corresponding coordinate points A and A' in this manner may indicate if the surface between points A and A' is too steep or varied to be used as a potential jig mating surface. For example, the angular deviation θ between the coordinate points may be compared to an angular criterion $\theta_C$, and the surface corresponding to the coordinate points may be considered unsuitable for the creation of the jig's bone mating surfaces where the angular deviation θ between the coordinate points is greater than the angular criterion $\theta_C$. Stated in the reverse and in the context of coordinate points A and A', the surface corresponding to coordinate points A and A' may be a potential candidate for creation of the jig's bone mating surfaces if the angular deviation $\theta_{AA'}$ is less than the angular criterion $\theta_C$ (i.e., $[\theta_{AA'}<\theta_C]$=surface corresponding to coordinate points A and A' being a potential candidate for the creation of the jig's bone mating surfaces).

In one embodiment, the angular criterion $\theta_C$ may be approximately one degree. However, in some embodiments, the angular criterion $\theta_C$ may be in the range of approximately one to approximately five degrees. In other embodiments, the angular criterion $\theta_C$ may be less than or greater than these recited values for the angular criterion $\theta_C$.

Figure 45P:
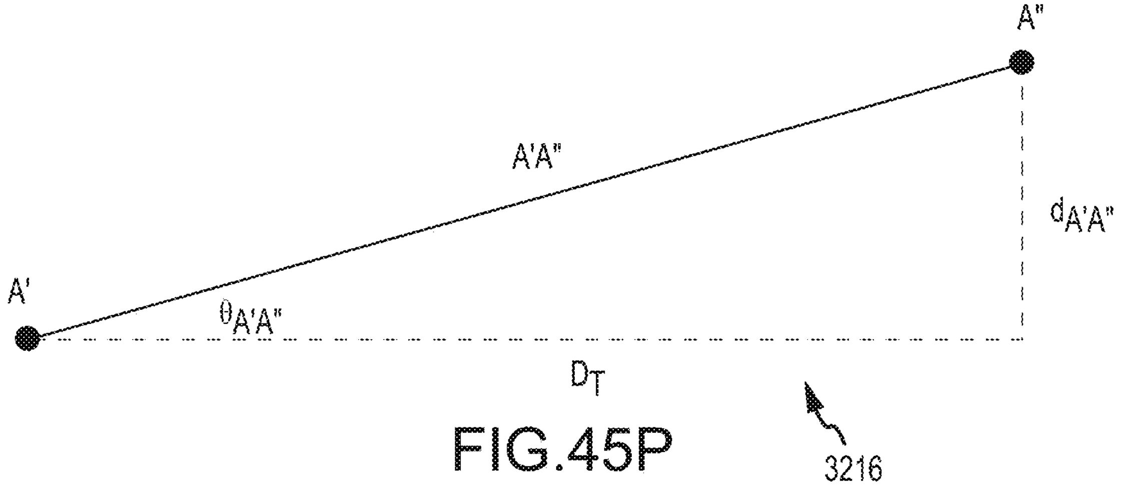

As can be understood from FIG. 45P, the example right triangle 3214 of FIG. 45O can be modified to become another example right triangle 3216 and used in determining the angular deviation $\theta_{A'A''}$ between corresponding coordinate points A' and A" of contour lines $m^{th+1}$ and $m^{th+2}$ of adjacent image slices per block 2514. The preceding three $\tan^{-1}$, $\sin^{-1}$ and $\cos^{-1}$ functions may be modified to match the circumstances of the example right triangle 3216 of FIG. 45P to calculate the respective angular deviation $\theta_{A'A''}$. Thus, as can be understood from FIG. 45P, the angular deviation $\theta_{A'A''}$ between the corresponding coordinate points A' and A" of contour lines $m^{th+1}$ and $m^{th+2}$ of adjacent image slices may be calculated by any of the following three formulas $$\theta_{A'A''} = \tan^{-1}\left(\frac{d_{A'A''}}{D_T}\right);\ \theta_{A'A''} = \cos^{-1}\left(\frac{D_T}{A'A''}\right);\ \text{or}\ \theta_{A'A''} = \sin^{-1}\left(\frac{d_{A'A''}}{A'A''}\right).$$

As can be understood from FIGS. 45Q-45T, the right triangle 3214 of FIG. 45O can be similarly modified into the respective example right triangles 3218, 3220, 3222 and 3224 of FIGS. 45Q-45T, which respectively will facilitate the determination of the angular deviations $\theta_{BB'}$, $\theta_{B'B''}$, $\theta_{CC'}$, and $\theta_{C'C''}$ between corresponding coordinate points B and B', B' and B", C and C', and C' and C", respectively. The preceding three $\tan^{-1}$, $\sin^{-1}$ and $\cos^{-1}$ functions may be modified to match the circumstances of the respective example right triangles 3218, 3220, 3222 and 3224 of FIGS. 45Q-45T to calculate the respective angular deviations $\theta_{BB'}$, $\theta_{B'B''}$, $\theta_{CC'}$, and $\theta_{C'C''}$.

In a manner like that discussed with respect to the angular deviation $\theta_{AA'}$ between the corresponding coordinate points A and A', the angular deviation θ between any of the other pairs of corresponding coordinate points (i.e., A' and A", B and B', B' and B", C and C', and C' and C") may be compared to an angular criterion $\theta_C$. Thus, where the angular deviation θ between corresponding coordinate points exceeds the angular criterion $\theta_C$, the surface associated with the coordinate points may be considered unsuitable for use in the creation of the jig's bone mating surfaces. Stated in the reverse, the surface corresponding to the coordinate points may be a potential candidate for creation of the jig's bone mating surfaces if the angular deviation θ is less than the angular criterion $\theta_C$ (i.e., [$\theta<\theta_C$]=surface corresponding to the coordinate points being a potential candidate for the creation of the jig's bone mating surfaces).

In one embodiment, the angular criterion $\theta_C$ may be approximately one degree. However, in some embodiments, the angular criterion $\theta_C$ may be in the range of approximately one to approximately four degrees. In other embodiments, the angular criterion $\theta_C$ may be less than or greater than these recited values for the angular criterion $\theta_C$.

A discussion will now be given regarding the second facet of the surface variation analysis, namely, comparing the angular differences φ of normal vectors associated with corresponding coordinate points of contour lines of adjacent image slices. As indicated in FIG. 45N, each contour line surface coordinate point A, A', A", B, B', B", C, C' and C" includes a respective tangent line $t_A$, $t_{A'}$, $t_{A''}$, $t_B$, $t_{B'}$, $t_{B''}$, $t_C$, $t_{C'}$, and $t_{C''}$ that is parallel to the plane in which the associated contour line $m^{th}$, $m^{th+1}$ and $m^{th+2}$ resides and tangent to the curvature of the associated contour line $m^{th}$, $m^{th+1}$ and $m^{th+2}$ at the respective coordinate point A, A', A", B, B', B", C, C' and C". A normal vector line $NV_A$, $NV_{A'}$, $NV_{A''}$, $NV_B$, $NV_{B'}$, $NV_{B''}$, $NV_C$, $NV_{C'}$, and $NV_{C''}$ extends from each respective coordinate point A, A', A", B, B', B", C, C' and C" and is perpendicular to each respective tangent line $t_A$, $t_{A'}$, $t_{A''}$, $t_B$, $t_{B'}$, $t_{B''}$, $t_C$, $t_{C'}$, and $t_{C''}$. The angular differences $\varphi_{A-A'}$ of normal vectors $NV_A$ and $NV_{A'}$ associated with respective corresponding coordinate points A and A' of respective contour lines $m^{th}$ and $m^{th+1}$ may be determined with the following formula:

$$\varphi_{A-A'} = \cos^{-1}\left(\frac{NV_A \cdot NV_{A'}}{|NV_A||NV_{A'}|}\right).$$

Similarly, the angular differences $\varphi_{A'-A''}$ of normal vectors $NV_{A'}$ and $NV_{A''}$ associated with respective corresponding coordinate points A' and A" of respective contour lines $m^{th+1}$ and $m^{th+2}$ may be determined with the following formula:

$$\varphi_{A'-A''} = \cos^{-1}\left(\frac{NV_{A'} \cdot NV_{A''}}{|NV_{A'}||NV_{A''}|}\right).$$

The angular differences $\varphi_{B-B'}$ of normal vectors $NV_B$ and $NV_{B'}$ associated with respective corresponding coordinate points B and B of respective contour lines $m^{th}$ and $m^{th+1}$ may be determined with the following formula:

$$\varphi_{B-B'} = \cos^{-1}\left(\frac{NV_B \cdot NV_{B'}}{|NV_B||NV_{B'}|}\right).$$

Similarly, the angular differences $\varphi_{B'-B''}$ of normal vectors $NV_{B'}$ and $NV_{B''}$ associated with respective corresponding coordinate points B' and B" of respective contour lines $m^{th+1}$ and $m^{th+2}$ may be determined with the following formula:

$$\varphi_{B'-B''} = \cos^{-1}\left(\frac{NV_{B'} \cdot NV_{B''}}{|NV_{B'}||NV_{B''}|}\right).$$

The angular differences $\varphi_{C-C'}$ of normal vectors $NV_C$ and $NV_{C'}$ associated with respective corresponding coordinate points C and C' of respective contour lines $m^{th}$ and $m^{th+1}$ may be determined with the following formula:

$$\varphi_{C-C'} = \cos^{-1}\left(\frac{NV_C \cdot NV_{C'}}{|NV_C||NV_{C'}|}\right).$$

Similarly, the angular differences $\varphi_{C'-C''}$ of normal vectors $NV_{C'}$ and $NV_{C''}$ associated with respective corresponding coordinate points C' and C" of respective contour lines $m^{th+1}$ and $m^{th+2}$ may be determined with the following formula:

$$\varphi_{C'-C''} = \cos^{-1}\left(\frac{NV_{C'} \cdot NV_{C''}}{|NV_{C'}||NV_{C''}|}\right).$$

Determining in this manner the angular differences φ of normal vectors associated with respective corresponding coordinate points of respective contour lines may indicate if the surface between the corresponding points is too varied to be used as a potential jig mating surface. For example, the angular differences φ of normal vectors associated with respective corresponding coordinate points may be compared to an angular criterion $\varphi_C$, and the surface associated with the corresponding points may be considered unsuitable for use in the creation of the jig's bone contacting surfaces where values for the angular differences φ are greater than the angular criterion $\varphi_C$. Stated in the reverse, where the angular differences φ of normal vectors associated with respective corresponding coordinate points is less than an angular criterion $\varphi_C$, the surface corresponding to the coordinate points may be a potential candidate for the creation of the jig's bone mating surfaces (i.e., $\varphi<\varphi_C$=surface corresponding to the coordinate points being a potential candidate for the creation of the jig's bone mating surfaces). In one embodiment, the angular criterion $\varphi_C$ may be approximately two degrees. In some embodiments, the angular criterion $\varphi_C$ may be in the range of approximately two to approximately six degrees. In other embodiments, the angular criterion $\varphi_C$ may be greater or less than these recited values for the angular criterion $\varphi_C$.

Thus, although one or more coordinate points of a contour line may satisfy the tangent angle criterion $w_c$ of block 2508 as discussed above with respect to FIGS. 45D and 45F-45M, the coordinate points may still be inadequate for use in generating the jig's bone contacting surfaces. This inadequateness may result from the failure of the coordinate points to meet the criterion of block 2514, namely, the failure of the angular deviation θ between any of the corresponding coordinate points to meet the angular deviation criterion $\theta_C$ and/or the failure of the angular differences φ of normal vectors associated with respective corresponding coordinate points to meet the angular differences criterion $\varphi_C$. In some embodiments, when one or more coordinate points fail to meet both the criterion $\theta_C$ and $\varphi_C$ of block 2508, the contour lines in the locations of those failed coordinate points may be modified via an overestimation process similar to that discussed above with respect block 2510 and FIGS. 45I-45L.

In other embodiments as reflected in block 2516, when one or more coordinate points fail to meet both the criterion $\theta_C$ and $\varphi_C$ of block 2508, a determination may be made regarding whether or not the slice thickness $D_T$ may be adjusted to a thinner slice thickness $D_T$. Reducing the slice thickness $D_T$ per block 2518 may reduce the variations between adjacent contour lines, making it more likely that the criterion $\theta_C$ and $\varphi_C$ will be satisfied for the coordinate points were the entire process started over at block 2502 with a new slice thickness $D_T$. If it is determined that modifying the slice thickness $D_T$ would not be beneficial (e.g., due to slice thickness $D_T$ already being at a minimum because further reduction in slice thickness $D_T$ may generate significant high interferences, residuals, signal-to-noise ratios and unreliable volume-averaging in the pixels), then the contour lines may be subjected to overestimation per block 2510.

If the one or more coordinate points of a contour line satisfy the tangent angle criterion $w_c$ of block 2508 and both of the angular criterion $\theta_C$ and $\varphi_C$ of block 2514, then such one or more coordinate points may be recorded for the generation of the jig's bone mating surface, as indicated in block 2520 of FIG. 45E. In other words, if the one or more coordinate points of a contour line satisfy the tangent angle criterion $w_c$ of block 2508 and both of the angular criterion $\theta_C$ and $\varphi_C$ of block 2514, then the surfaces associated with such one or more coordinate points may be employed in the generation of corresponding bone mating surfaces of the jig, as indicated in block 2520.

An example application of the functions of block 2514 with respect to the contour lines $m^{th}$, $m^{th+1}$ and $m^{th+2}$ depicted in FIG. 45N will now be provided. In this example, it is assumed the coordinate points A, A', A", B, B', B", C, C' and C" and their respective contour lines portions have already satisfied the tangent angle criterion $w_c$ of block 2508.

As can be understood from FIGS. 45N-P, points A, A' and A" are in close proximity to each other due to the close proximity of their respective contour line segments. The close proximity of the respective contour lines is a result of the rise or fall distances $d_{AA'}$ and $d_{A'A''}$ being small at points A, A' and A", as the contour lines $m^{th}$, $m^{th+1}$ and $m^{th+2}$ at all points A, A', A", B, B', B", C, C' and C" are evenly spaced medially-laterally due to having equal slice thicknesses $D_T$. Due to the close proximity of points A, A' and A", line segments AA' and A'A" are relatively short, resulting in angular deviations $\theta_{AA'}$ and $\theta_{A'A''}$ that are less than the angular criterion $\theta_C$, which in one embodiment, may be in the range of approximately one to approximately four degrees. As the angular deviations $\theta_{AA'}$ and $\theta_{A'A''}$ are less than the angular criterion $\theta_C$, the angular criterion $\theta_C$ is satisfied for points A, A' and A", and these points are potential candidates for the generation of the jig's bone mating surfaces.

As indicated in FIG. 45N, the angular differences $\varphi_{A-A'}$ and $\varphi_{A'-A''}$ between the normal vectors $NV_A$, $NV_{A'}$ and $NV_{A''}$ is small, resulting in angular differences $\varphi_{A-A'}$ and $\varphi_{A'-A''}$ that are less than the angular criterion $\varphi_C$, which in one embodiment, may be in the range of approximately two to approximately five degrees. As the angular differences $\varphi_{A-A'}$ and $\varphi_{A'-A''}$ are less than the angular criterion $\varphi_C$, the angular criterion $\varphi_C$ is satisfied. Because the points A, A' and A" have satisfied both of the angular criterion $\theta_C$ and $\varphi_C$ of block 2514, the surface represented by the points A, A' and A" may be employed to generate the jig's surfaces that matingly contact the patient's arthroplasty target surfaces per block 2520.

Figure 45Q:
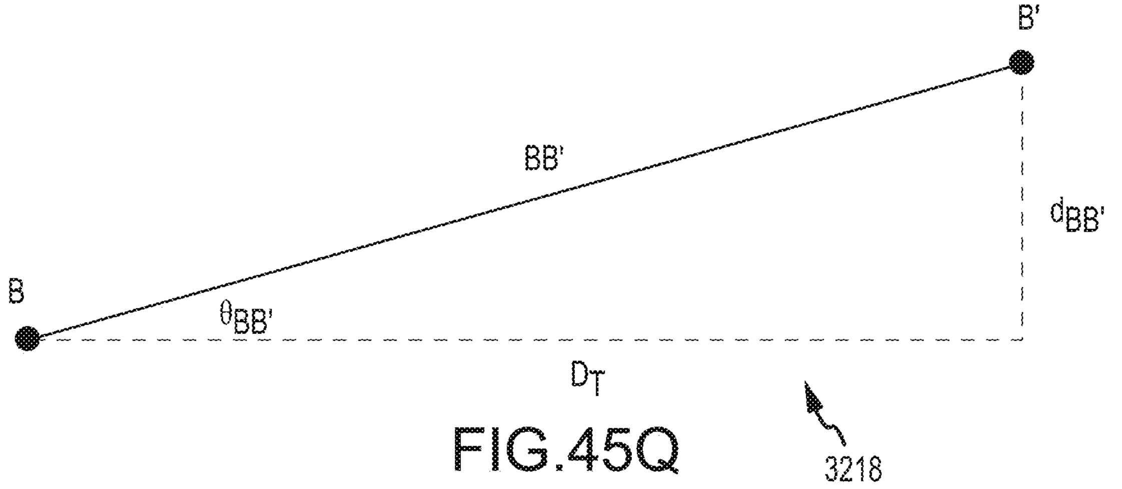
Figure 45R:
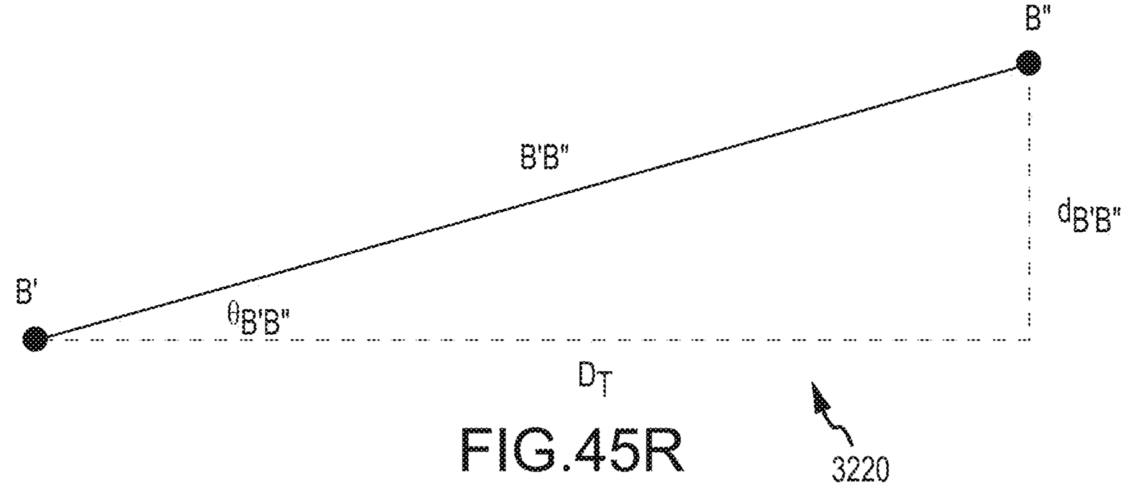

As can be understood from FIGS. 45N and 45Q-R and for reasons similar to those discussed with respect to points A, A' and A", points B, B' and B" are in close proximity to each other due to the close proximity of their respective contour line segments. Consequently, line segments BB' and B'B" are relatively short, resulting in angular deviations $\theta_{BB'}$ and $\theta_{BB''}$ that are less than the angular criterion $\theta_C$. As the angular deviations $\theta_{BB'}$ and $\theta_{B'B''}$ are less than the angular criterion $\theta_C$, the angular criterion $\theta_C$ is satisfied for points B, B' and B", and these points are potential candidates for the generation of the jig's bone mating surfaces.

As indicated in FIG. 45N, the angular difference $\varphi_{B-B'}$ between the normal vectors $NV_B$ and $NV_{B'}$ is small such that it is less than the angular criterion $\varphi_C$ and, therefore, satisfies the angular criterion $\varphi_C$. However, the angular difference $\varphi_{B'-B''}$ between the normal vectors $NV_{B'}$ and $NV_{B''}$ is large such that it is greater than the angular criterion $\varphi_C$ and, therefore, does not satisfy the angular criterion $\varphi_C$. As the points B and B' have satisfied both of the angular criterion $\theta_C$ and $\varphi_C$ of block 2514, the surface represented by the points B and B' may be employed to generate the jig's surfaces for matingly contacting the patient's arthroplasty target surfaces per block 2520. However, as the points B' and B" have failed to satisfy both of the angular criterion $\theta_C$ and $\varphi_C$ of block 2514, the surface represented by the points B' and B" may not be employed to generate the jig's surfaces for matingly contacting the patient's arthroplasty target surfaces. Instead, the slice spacing $D_T$ may be evaluated per block 2516 and reset per block 2518, with the process then started over at block 2502. Alternatively, the points may be subjected to overestimation per block 2510.

Figure 45S:
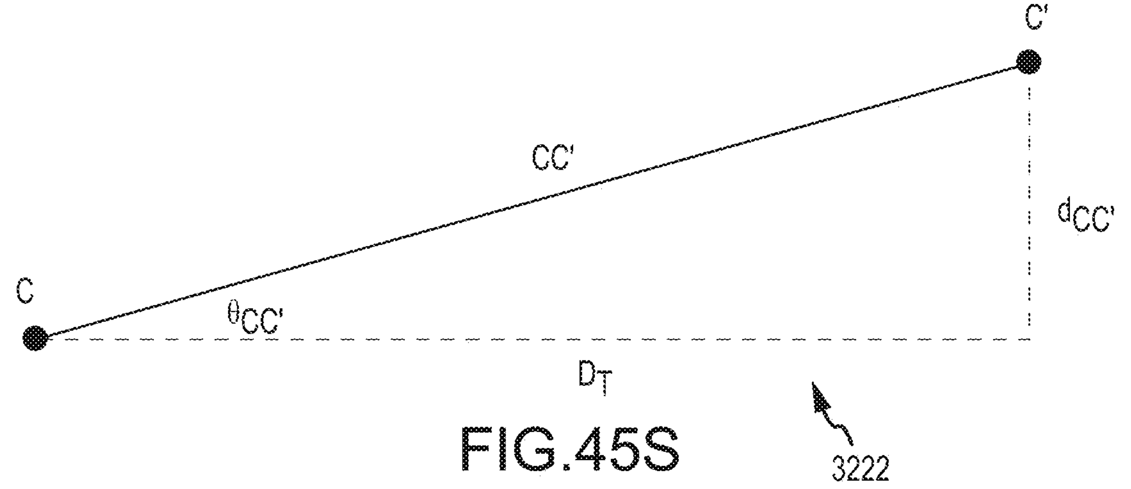
Figure 45T:
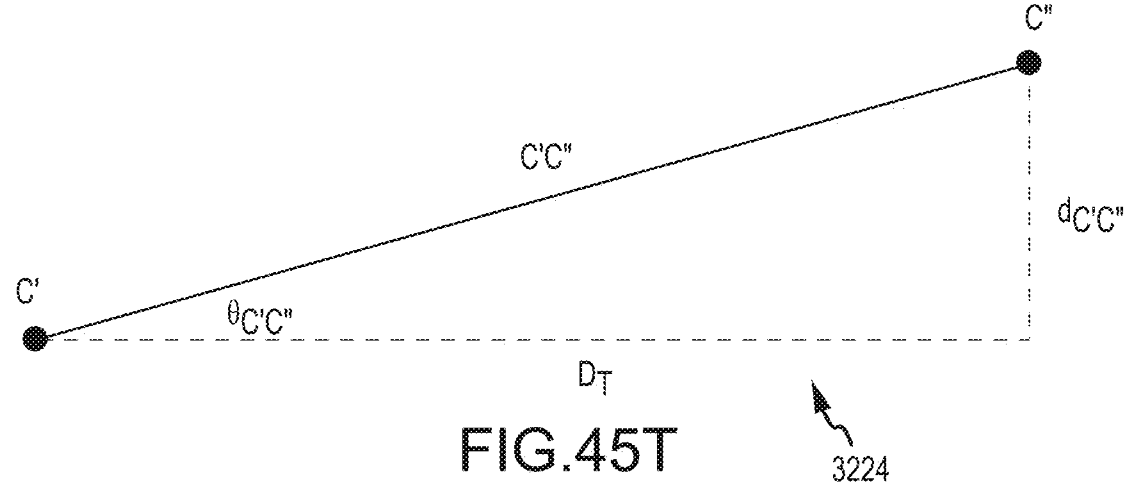

As can be understood from FIGS. 45N and 45S-45T and because of significant rise and fall distances $d_{CC'}$ and $d_{C'C''}$ between the contour lines at points C, C' and C", points C, C' and C" are not in close proximity to each other due to the significant distance between their respective contour line segments. Consequently, line segments CC' and C'C" are relatively long, resulting in angular deviations $\theta_{CC'}$ and $\theta_{C'C''}$ that exceed the angular criterion $\theta_C$ and, therefore, do not satisfy the angular criterion $\theta_C$.

As indicated in FIG. 45N, the angular differences $\varphi_{C-C'}$ and $\varphi_{C-C'}$ between the normal vectors $NV_C$, $NV_{C'}$ and $NV_{C''}$ are small such that they are less than the angular criterion $\varphi_C$ and, therefore, satisfy the angular criterion $\varphi_C$. However, as the points C, C' and C" do not satisfied both of the angular criterion $\theta_C$ and $\varphi_C$, the surfaces represented by the points C, C' and C" may not be employed to generate the jig's surfaces for matingly contacting the patient's arthroplasty target surfaces. Instead, the slice spacing $D_T$ may be evaluated per block 2516 and reset per block 2518, with the process then started over at block 2502. Alternatively, the points may be subjected to overestimation per block 2510.

As can be understood from the preceding discussion, in one embodiment, the analysis of the contour lines may be performed slice-by-slice across the series of contour lines. In other words, a first contour line $m^{th+1}$ is compared at its respective coordinate points to the corresponding coordinate points of the immediate neighbor contour lines (e.g., contour lines $m^{th}$ and $m^{th+2}$) medial and lateral of the first contour line.

While the preceding example process discussed with respect to FIGS. 45N-45T is given in the context of three contour lines $m^{th}$, $m^{th+1}$ and $m^{th+2}$ and nine coordinate points A-C", of course the process can be readily applied to a greater or less number or contour lines and coordinate points. Therefore, the process should not be interpreted as being limited to any number of contour lines or coordinate points.

For another example application of the functions of block 2514, reference is made to FIGS. 46A-46F. FIGS. 46A, 46C and 46E each depict portions of contour lines $n^{th}$, $n^{th+1}$, $n^{th+2}$, $n^{th+3}$ and $n^{th+4}$ in sagittal views similar to that of FIG. 45C. FIGS. 46B, 46D and 46F each represent a bone surface contour line 3300 and a linear interpolation bone surface contour line 3302 as viewed along section lines 46B-46B, 46D-46D and 46F-46F transverse to image slices containing the contour lines $n^{th}$, $n^{th+1}$, $n^{th+2}$, $n^{th+3}$ and $n^{th+4}$ of respective FIGS. 46A, 46C and 46E.

As indicated in FIGS. 46A-F, contour lines $n^{th}$, $n^{th+1}$, $n^{th+2}$, $n^{th+3}$ and $n^{th+4}$ each include a respective coordinate point D, D', D", D'" and D"". In one embodiment, corresponding coordinate points may be identified via the method discussed above with respect to FIG. 45N. Specifically, as can be understood from FIGS. 46A-B, corresponding coordinate points D, D', D", D'" and D"" may be those coordinate points D, D', D", D'" and D"" that each exist in the same medial-lateral plane that is generally perpendicular to the sagittal image slices containing the contour lines and coordinate points. Other groups of corresponding coordinate points may be identified via a similar perpendicular plane methodology.

As can be understood from FIGS. 46C-D, corresponding coordinate points D, D', D", D'" and D"" may be identified via a second method. Specifically, the contour lines $n^{th}$, $n^{th+1}$, $n^{th+2}$, $n^{th+3}$ and $n^{th+4}$ may be superimposed into the same image slice layer as indicated in FIG. 46D by arrow 46D1, resulting in a composite plane 46D2 having a total rise or fall distance $d_{DD''''}$ between coordinate points D and D"". The total rise or fall distance $d_{DD''''}$ may be the sum of the respective rise or fall distances $d_{DD'}$, $d_{D'D''}$, $d_{D''D'''}$, $d_{D'''D''''}$ discussed below with respect to FIGS. 46B, 46C and 46F.

As indicated in FIG. 46C, the normal vector lines $NV_D$, $NV_{D'}$, $NV_{D''}$, $NV_{D'''}$ and $NV_{D''''}$, the determination of which is discussed below with respect to FIGS. 46A, 46C and 46E, are utilized to identify the corresponding coordinate points D, D', D", D'" and D"". For example, the normal vector line $NV_D$ of coordinate point D is extended to contour line $n^{th}$+1, and the intersection between normal vector line $NV_D$ and contour line $n^{th+1}$ identifies the coordinate point corresponding to coordinate point D, namely, coordinate point D'. The normal vector line $NV_{D'}$ of coordinate point D' is extended to contour line $n^{th+2}$, and the intersection between normal vector line $NV_{D'}$ and contour line $n^{th+2}$ identifies the coordinate point corresponding to coordinate point D', namely, coordinate point D". The normal vector line $NV_{D''}$ of coordinate point D" is extended to contour line $n^{th+3}$, and the intersection between normal vector line $NV_{D''}$ and contour line $n^{th+3}$ identifies the coordinate point corresponding to coordinate point D", namely, coordinate point D'". The normal vector line $NV_{D'''}$ of coordinate point D'" is extended to contour line $n^{th+4}$, and the intersection between normal vector line $NV_{D'''}$ and contour line $n^{th+4}$ identifies the coordinate point corresponding to coordinate point D'", namely, coordinate point D"". Other groups of corresponding coordinate points may be identified via a normal vector line methodology.

As can be understood from FIGS. 46F-E, corresponding coordinate points D, D', D", D'" and D"" may be identified via a third method. Specifically, the contour lines $n^{th}$, $n^{th+1}$, $n^{th+2}$, $n^{th+3}$ and $n^{th+4}$ may be superimposed into the same image slice layer as indicated in FIG. 46F by arrow 46D1, resulting in a composite plane 46D2 having a total rise or fall distance $d_{DD''''}$ between coordinate points D and D"". The total rise or fall distance $d_{DD''''}$ may be the sum of the respective rise or fall distances $d_{DD'}$, $d_{D'D''}$, $d_{D''D'''}$, $d_{D'''D''''}$ discussed below with respect to FIGS. 46B, 46C and 46F.

As indicated in FIG. 46E, a center point CP is identified. The center point CP may generally correspond to an axis extending generally perpendicular to the sagittal image slices. The center point CP may be considered to be a center point generally common to the curvature of all of the contour lines $n^{th}$, $n^{th+1}$, $n^{th+2}$, $n^{th+3}$ and $n^{th+4}$ and about which all of the contour lines $n^{th}$, $n^{th+1}$, $n^{th+2}$, $n^{th+3}$ and $n^{th+4}$ arcuately extend.

As shown in FIG. 46E, radius lines R, R', R", etc. may radially extend in a straight line from the center point CP across the contour lines $n^{th}$, $n^{th+1}$, $n^{th+2}$, $n^{th+3}$ and $n^{th+4}$. As can be understood from radius line R, the corresponding coordinate lines D, D', D", D'" and D"" are identified where radius line R intersects each respective contour lines $n^{th}$, $n^{th}$, $n^{th+2}$ $n^{th+3}$ and $n^{th+4}$. Other groups of corresponding coordinate points may be identified with radius lines R', R" and etc.

Once the corresponding coordinate points D, D', D", D'" and D"" are identified via any of the three methods, the extent of the surface variation between the corresponding coordinate points D, D', D", D'" and D"" may be analyzed as follows.

As can be understood from FIGS. 46A-46F, each coordinate point D, D', D", D'" and D"" includes a respective tangent line $t_D$, $t_{D'}$, $t_{D''}$, $t_{D'''}$ and $t_{D''''}$ that is tangent to the corresponding contour line $n^{th}$, $n^{th+1}$, $n^{th+2}$, $n^{th+3}$ and $n^{th+4}$ at the coordinate point D, D', D", D'" and D"", each tangent line $t_D$, $t_{D'}$, $t_{D''}$, $t_{D'''}$ and $t_{D''''}$ being parallel to and contained within the image slice of its contour line. A vector line $NV_D$, $NV_{D'}$ and $NV_{D''}$, $NV_{D'''}$ and $NV_{D''''}$ extends normally from each respective tangent line $t_D$, $t_D'$, $t_{D''}$, $t_{D'''}$ and $t_{D''''}$ at each respective coordinate point D, D', D", D'" and D"". Line segments DD', D'D", D"D'" and D'"D"" extend between their associated coordinate points to create a linear interpolation 3302 of the bone contour line 3300.

In this example, it is assumed the coordinate points D, D', D", D'" and D"" and their respective contour lines portions have already satisfied the tangent angle criterion $w_c$ of block 2508. For example, point D may be point k of potential mating region 2402A of contour line 2400 in FIG. 45D, and coordinate points D'-D"" may be points on contour lines of adjacent image slices, wherein coordinate points D'-D"" are identified as coordinate points corresponding to coordinate point D. Each of the coordinate points D, D', D", D'" and D"" is then evaluated to determine if the criterion of $\theta_c$ and $\varphi_c$ of block 2514 are satisfied too.

As can be understood from FIGS. 46B, 46D and 46F, points D'', D''' and D'''' are in close proximity to each other due to the close proximity of their respective contour line segments. The close proximity of the respective contour lines is a result of the rise or fall distances $d_{D''D'''}$ and $d_{D'''D''''}$ being small at points D'', D''' and D'''', as the contour lines $n^{th}n^{th+1}$, $n^{th+2}$, $n^{th+3}$ and $n^{th+4}$ at all points D, D', D'', D''' and D'''' are evenly spaced medially-laterally due to having equal slice thicknesses $D_T$, which, for example, may be a slice thickness $D_T$ of 2 mm. Due to the close proximity of points D'', D''' and D'''', line segments D''D''' and D'''D'''' range in size from relatively short to nearly zero, resulting in angular deviations $\theta_{D''D'''}$ and $\theta_{D'''D''''}$ that are less than the angular criterion $\theta_C$, which in one embodiment, may be in the range of approximately one to approximately four degrees. As the angular deviations $\theta_{D''D'''}$ and $\theta_{D'''D''''}$ are less than the angular criterion $\theta_C$, the angular criterion $\theta_C$ is satisfied for points D'', D''' and D'''', and these points are potential candidates for the generation of the jig's bone mating surfaces. As can be understood from FIGS. 46B, 46D and 46F, the angular deviations $\theta_{D''D'''}$ and $\theta_{D'''D''''}$ being less than the angular criterion $\theta_C$ results in the corresponding line segments D''D''' and D'''D'''' closely approximating the contour of the bone surface 3300.

As indicated in FIGS. 46A, 46C and 46E, the angular differences $\varphi_{D'''D''''}$ and $\varphi_{D'''-D''''}$ between the normal vectors $NV_{D''}$, $NV_{D'''}$ and $NV_{D''''}$ is small, resulting in angular differences $\varphi_{D'''-D''''}$ and $\varphi_{D'''-D''''}$ that are less than the angular criterion $\varphi_C$, which in one embodiment, may be in the range of approximately two to approximately five degrees. As the angular differences $\varphi_{D'''-D''''}$ and $\varphi_{D'''-D''''}$ are less than the angular criterion $\varphi_C$, the angular criterion $\varphi_C$ is satisfied. As can be understood from the tangent lines $t_{D''}$, $t_{D'''}$ and $t_{D''''}$ depicted in FIGS. 46A, 46C and 46E, the contour line slopes at the respective coordinate points D'', D''' and D'''' are nearly identical, indicating that there is little surface variation between the coordinate points and the coordinate points would be a close approximation of the actual bone surface.

Because the points D'', D''' and D'''' have satisfied both of the angular criterion $\theta_C$ and $\varphi_c$ of block 2514, the surface represented by the points D'', D''' and D'''' may be employed to generate the jig's surfaces that matingly contact the patient's arthroplasty target surfaces per block 2520.

As can be understood from FIGS. 46B, 46D and 46F and because of significant rise and fall distances $d_{DD'}$ and $d_{D'D''}$ between the contour lines at points D, D' and D'', points D, D' and D'' are not in close proximity to each other due to the significant distance between their respective contour line segments. Consequently, line segments DD' and D'D'' are relatively long, resulting in angular deviations $\theta_{DD'}$ and $\theta_{D'D''}$ that exceed the angular criterion $\theta_C$ and, therefore, do not satisfy the angular criterion $\theta_C$. As the angular deviations $\theta_{D''\,D'''}$ and $\theta_{D'''D''''}$ are greater than the angular criterion $\theta_C$, the angular criterion $\theta_C$ is not satisfied for points D, D' and D'', and these points are not potential candidates for the generation of the jig's bone mating surfaces. As can be understood from FIGS. 46B, 46D and 46F, the angular deviations $\theta_{DD'}$ and $\theta_{D'D''}$ being greater than the angular criterion $\theta_C$ results in the corresponding line segments DD' and D'D'' not closely approximating the contour of the bone surface 3300.

As indicated in FIGS. 46A, 46C and 46E, the angular differences pD-D' and pD'-D'' between the normal vectors $NV_D$ and $NV_{D'}$ and $NV_{D'}$ and $NV_{D''}$ are large such that they are greater than the angular criterion $\varphi_C$ and, therefore, do not satisfy the angular criterion $\varphi_c$. Thus, as the points D, D' and D'' do not satisfied both of the angular criterion $\theta_C$ and $\varphi_c$, the surfaces represented by the points D, D' and D'' may not be employed to generate the jig's surfaces for matingly contacting the patient's arthroplasty target surfaces. Instead, the slice spacing $D_T$ may be evaluated per block 2516 and reset per block 2518, with the process then started over at block 2502. Alternatively, the points may be subjected to overestimation per block 2510.

FIG. 46G is a distal view similar to that of FIGS. 42A and 45A depicting contour lines 3400 produced by imaging the right femur at an image spacing $D_T$ of, for example, 2 mm. As shown, the contour lines 3400 may be grouped into multiple regions in the lateral-medial direction 3402-3408 for the sake of discussion. The region 3402 includes the contour lines 3400 of the most lateral half of the femoral lateral condyle and extends medially from the most lateral side of the femoral lateral condyle to the medial-lateral middle of the femoral lateral condyle. The region 3404 includes the contour lines 3400 of the most medial half of the femoral lateral condyle and extends medially from the middle of the femoral lateral condyle to the medial-lateral center of intercondylar notch. The region 3406 includes the contour lines 3400 of the most lateral half of the femoral medial condyle and extends medially from the medial-lateral center of the intercondylar notch to the medial-lateral middle of the femoral medial condyle. The region 3408 includes the contour lines 3400 of the most medial half of the femoral medial condyle and extends medially from the medial-lateral middle of the femoral medial condyle to the most medial side of the femoral medial condyle.

Figure 46H:
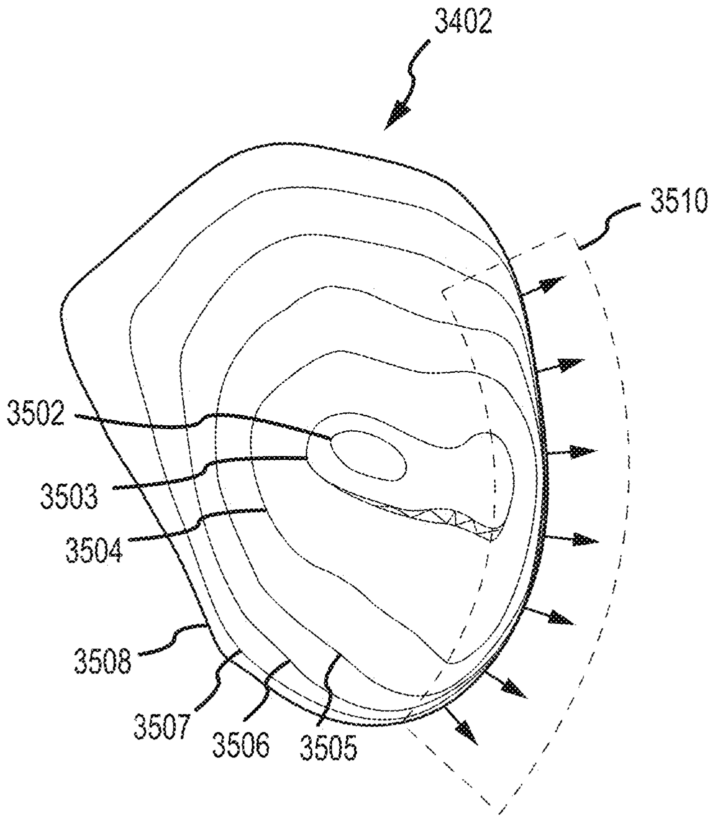

FIG. 46H is a sagittal view of the contour lines 3400 of region 3402 of FIG. 46G. The contour lines 3400 of region 3402 include contour lines 3502, 3503, 3504, 3505, 3506, 3507 and 3508, with the most lateral portion of the femoral lateral condyle being indicated by contour line 3502. The size of each successive contour line 3400 of region 3402 increases moving medially from the most lateral contour line 3502 of region 3402 to the most medial contour line 3508 of region 3402, which is near the medial-lateral middle of the lateral condyle.

As can be understood from FIG. 46H, the contour lines 3502-3504 are spaced apart from their respective adjacent contour lines a substantial amount around their entire boarders. Such wide spacing corresponds to a substantial amount of rise or fall distances between adjacent contour lines, as discussed above with respect to FIG. 46B. Thus, such contour lines would likely fail to meet the angular criterion $\theta_C$ and be subject to the overestimation process such that jig surfaces corresponding to the contour lines 3502-3504 would not contact the corresponding surfaces of the arthroplasty target areas.

As can be understood from FIG. 46H, in the distal portion of the femoral condyle, the contour lines 3505-3508 in the region 3510 converge such that there is little, if any, amount of rise or fall distance between adjacent contour lines. Thus, such contour lines 3505-3508 in the region 3510 would likely meet the first angular criterion $\theta_C$.

As can be understood from the arrows in region 3510, the angular differences between normal vectors for the contour line portions within the region 3510 would be minimal, likely meeting the second angular criterion $\varphi_C$. Thus, as the portions of the contour lines 3505-3508 within region 3510 likely meet both angular criterion $\theta_C$ and $\varphi_C$, the portions of the contour lines 3505-3508 within the region 3510 represent an optimal contact area 3510 for mating contact with the jig's bone mating surface 40. In one embodiment, as can be understood from FIG. 47A discussed below, the optimal contact area 3510 may be the lateral half of the surface of the lateral condyle that displaces against the recess of the lateral tibia plateau.

In one embodiment, the optimal contact area 3510 matingly corresponds to the jig's bone mating surface 40 such that the portions of the contour lines 3402 indicated by region 3510 may be used to generate the jig's bone mating surface 40, per the algorithm 2500 of FIG. 45E. Conversely, per the algorithm 2500, the portions of the contour lines 3402 outside region 3510 may be subjected to the overestimation process discussed above such that the jig's surfaces created from the overestimated contour line portions results in jig surfaces that do not contact the corresponding portions of the patient's arthroplasty target regions.

Figure 46I:
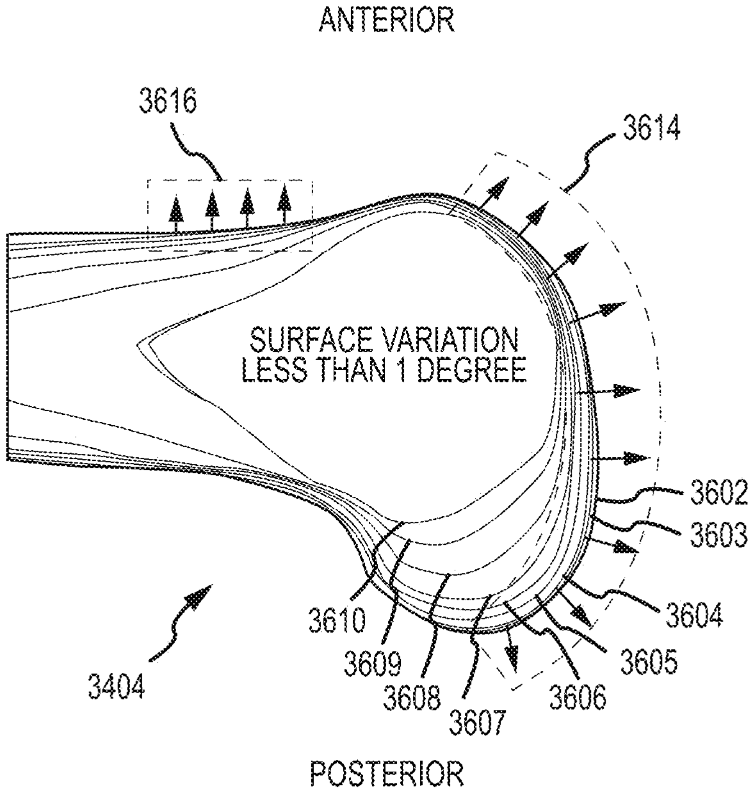

FIG. 46I is a sagittal view of the contour lines 3400 of region 3404 of FIG. 46G. The contour lines 3400 of region 3404 include contour lines 3602, 3603, 3604, 3605, 3606, 3607, 3608, 3609 and 3610 with the most lateral portion of region 3404 being indicated by contour line 3602, which is near the medial-lateral middle of the lateral condyle, and the most medial portion of region 3404 being indicated by contour line 3610, which is near the medial-lateral center of intercondylar notch. The size of each successive contour line 3400 of region 3404 decreases moving medially from the most lateral contour line 3602 to the most medial contour line 3610.

As can be understood from FIG. 46I, the contour lines 3607-3610 are spaced apart from their respective adjacent contour lines a substantial amount in their posterior portions and to a lesser extent in their distal portions, these distal portions corresponding to the intercondylar notch and trochlear groove. Such wide spacing corresponds to a substantial amount of rise or fall distances between adjacent contour lines, as discussed above with respect to FIG. 46B. Thus, such contour lines would likely fail to meet the angular criterion $\theta_C$ and be subject to the overestimation process such that jig surfaces corresponding to the contour lines 3607-3610 would not contact the corresponding surfaces of the arthroplasty target areas.

As can be understood from FIG. 46I, in the distal portion of the femoral condyle, the contour lines 3602-3606 in the region 3614 converge such that there is little, if any, amount of rise or fall distance between adjacent contour lines. Similarly, in the anterior condylar portion of the distal femur, the contour lines 3602-3606 in the region 3616 converge such that there is little, if any, amount of rise or fall distance between adjacent contour lines. Thus, such contour lines 3602-3606 in the regions 3614 and 3616 would likely meet the first angular criterion $\theta_C$.

As can be understood from the arrows in regions 3614 and 3616, the angular differences between normal vectors for the contour line portions within the regions 3614 and 3616 would be minimal, likely meeting the second angular criterion $\varphi_C$. Thus, as the portions of the contour lines 3602-3606 within regions 3614 and 3616 likely meet both angular criterion $\theta_C$ and $\varphi_C$, the portions of the contour lines 3602-3606 within the regions 3614 and 3616 represent optimal contact areas 3614 and 3616 for mating contact with the jig's bone mating surface 40.

In one embodiment, the optimal contact areas 3614 and 3616 matingly correspond to the jig's bone mating surface 40 such that the portions of the contour lines 3404 indicated by regions 3614 and 3616 may be used to generate the jig's bone mating surface 40, per the algorithm 2500 of FIG. 45E. Conversely, per the algorithm 2500, the portions of the contour lines 3404 outside regions 3614 and 3616 may be subjected to the overestimation process discussed above such that the jig's surfaces created from the overestimated contour line portions results in jig surfaces that do not contact the corresponding portions of the patient's arthroplasty target regions.

In one embodiment, as can be understood from FIG. 47A discussed below, the optimal contact area 3614 may be the medial half of the surface of the lateral condyle that displaces against the recess of the lateral tibia plateau. In one embodiment, as can be understood from FIG. 47A discussed below, the optimal contact area 3616 may be the lateral half of a generally flat surface of the anterior condyle, wherein the flat surface is located in an area proximal the concave trochlear groove of the patellar face and extends to a point near the anterior portion of the femoral shaft.

Figure 46J:
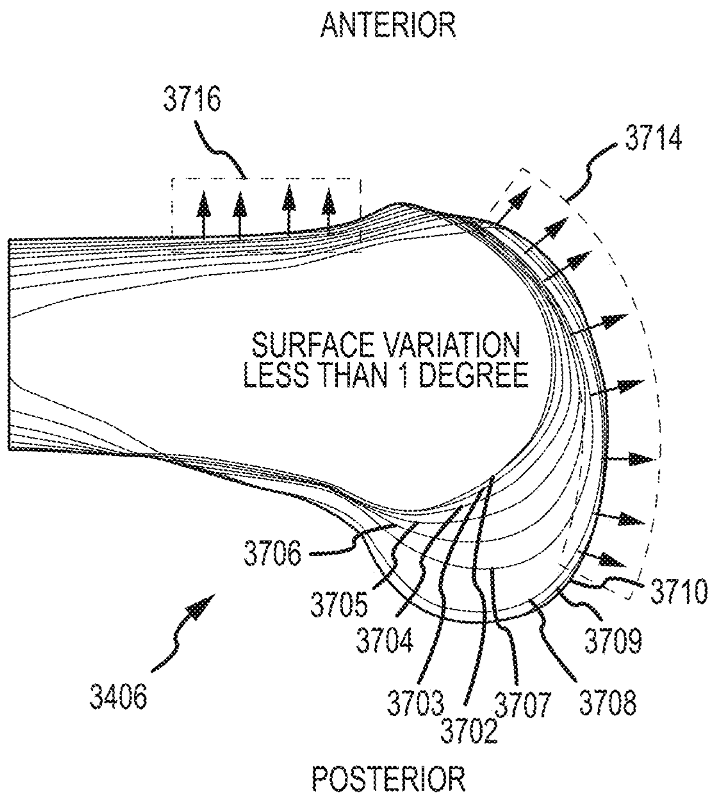

FIG. 46J is a sagittal view of the contour lines 3400 of region 3406 of FIG. 46G. The contour lines 3400 of region 3406 include contour lines 3702, 3703, 3704, 3705, 3706, 3707, 3708, 3709 and 3710 with the most lateral portion of region 3404 being indicated by contour line 3702, which is near the medial-lateral center of intercondylar notch, and the most medial portion of region 3406 being indicated by contour line 3710, which is near the medial-lateral middle of the medial condyle. The size of each successive contour line 3400 of region 3406 increases moving medially from the most lateral contour line 3702 to the most medial contour line 3710.

As can be understood from FIG. 46J, the contour lines 3702-3706 are spaced apart from their respective adjacent contour lines a substantial amount in their posterior portions and to a lesser extent in their distal portions, these distal portions corresponding to the intercondylar notch and trochlear groove. Such wide spacing corresponds to a substantial amount of rise or fall distances between adjacent contour lines, as discussed above with respect to FIG. 46B. Thus, such contour lines would likely fail to meet the angular criterion $\theta_C$ and be subject to the overestimation process such that jig surfaces corresponding to the contour lines 3607-3610 would not contact the corresponding surfaces of the arthroplasty target areas.

As can be understood from FIG. 46J, in the distal portion of the femoral condyle, the contour lines 3707-3710 in the region 3714 converge such that there is little, if any, amount of rise or fall distance between adjacent contour lines. Similarly, in the anterior condylar portion of the distal femur, the contour lines 3707-3710 in the region 3716 converge such that there is little, if any, amount of rise or fall distance between adjacent contour lines. Thus, such contour lines 3707-3710 in the regions 3714 and 3716 would likely meet the first angular criterion $\theta_C$.

As can be understood from the arrows in regions 3714 and 3716, the angular differences between normal vectors for the contour line portions within the regions 3714 and 3716 would be minimal, likely meeting the second angular criterion $\varphi_C$. Thus, as the portions of the contour lines 3707-3710 within regions 3714 and 3716 likely meet both angular criterion $\theta_C$ and $\varphi_C$, the portions of the contour lines 3707-3710 within the regions 3714 and 3716 represent optimal contact areas 3714 and 3716 for mating contact with the jig's bone mating surface 40.

In one embodiment, the optimal contact areas 3714 and 3716 matingly correspond to the jig's bone mating surface 40 such that the portions of the contour lines 3406 indicated by regions 3714 and 3716 may be used to generate the jig's bone mating surface 40, per the algorithm 2500 of FIG. 45E. Conversely, per the algorithm 2500, the portions of the contour lines 3406 outside regions 3714 and 3716 may be subjected to the overestimation process discussed above such that the jig's surfaces created from the overestimated contour line portions results in jig surfaces that do not contact the corresponding portions of the patient's arthroplasty target regions.

In one embodiment, as can be understood from FIG. 47A discussed below, the optimal contact area 3714 may be the lateral half of the surface of the medial condyle that displaces against the recess of the medial tibia plateau. In one embodiment, as can be understood from FIG. 47A discussed below, the optimal contact area 3716 may be the medial half of a generally flat surface of the anterior condyle, wherein the flat surface is located in an area proximal the concave trochlear groove of the patellar face and extends to a point near the anterior portion of the femoral shaft.

Figure 46K:
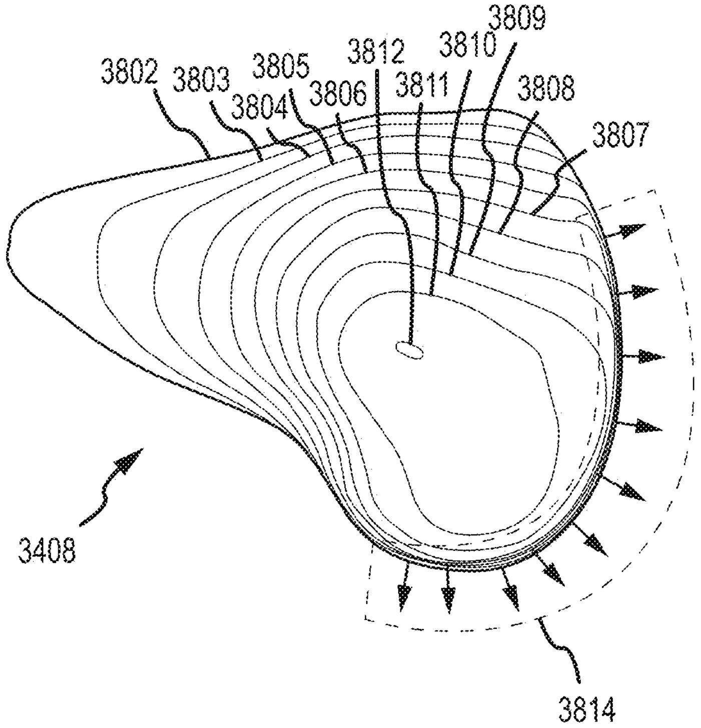

FIG. 46K is a sagittal view of the contour lines 3400 of region 3408 of FIG. 46G. The contour lines 3400 of region 3408 include contour lines 3802, 3803, 3804, 3805, 3806, 3807, 3808, 3809, 3810, 3811 and 3812, with the most medial portion of the femoral lateral condyle being indicated by contour line 3812. The size of each successive contour line 3400 of region 3408 decreases moving medially from the most lateral contour line 3802 of region 3408, which is near the medial-lateral middle of the medial condyle, to the most medial contour line 3812 of region 3408.

As can be understood from FIG. 46K, the contour lines 3810-3812 are spaced apart from their respective adjacent contour lines a substantial amount around their entire boarders. Such wide spacing corresponds to a substantial amount of rise or fall distances between adjacent contour lines, as discussed above with respect to FIG. 46B. Thus, such contour lines would likely fail to meet the angular criterion $\theta_C$ and be subject to the overestimation process such that jig surfaces corresponding to the contour lines 3810-3812 would not contact the corresponding surfaces of the arthroplasty target areas.

As can be understood from FIG. 46K, in the distal portion of the femoral condyle, the contour lines 3802-3809 in the region 3814 converge such that there is little, if any, amount of rise or fall distance between adjacent contour lines. Thus, such contour lines 3802-3809 in the region 3814 would likely meet the first angular criterion $\theta_C$.

As can be understood from the arrows in region 3814, the angular differences between normal vectors for the contour line portions within the region 3814 would be minimal, likely meeting the second angular criterion $\varphi_C$. Thus, as the portions of the contour lines 3802-3809 within region 3814 likely meet both angular criterion $\theta_C$ and $\varphi_C$, the portions of the contour lines 3802-3809 within the region 3814 represent an optimal contact area 3814 for mating contact with the jig's bone mating surface 40. In one embodiment, as can be understood from FIG. 47A discussed below, the optimal contact area 3814 may be the medial half of the surface of the medial condyle that displaces against the recess of the medial tibia plateau.

In one embodiment, the optimal contact area 3814 matingly corresponds to the jig's bone mating surface 40 such that the portions of the contour lines 3408 indicated by region 3814 may be used to generate the jig's bone mating surface 40, per the algorithm 2500 of FIG. 45E. Conversely, per the algorithm 2500, the portions of the contour lines 3408 outside region 3814 may be subjected to the overestimation process discussed above such that the jig's surfaces created from the overestimated contour line portions results in jig surfaces that do not contact the corresponding portions of the patient's arthroplasty target regions.

As can be understood from the preceding discussion, the overestimation process disclosed herein can be used to identifying optimal target areas (e.g., optimal target areas 3510, 3614, 3616, 3714, 3716 and 3814 as discussed with respect to FIGS. 46H-46K). More specifically, the overestimation process disclosed herein can employ these optimal target areas to generate the bone mating surfaces 40 of the jigs 2 while causing the other surface areas of the jigs to be configured such that these other jig surface areas will not contact the surfaces of the arthroplasty target areas when the jig's bone mating surfaces 40 have matingly received and contacted the arthroplasty target areas. The result is a jig that has bone mating surfaces 40 that are based on the regions of the arthroplasty target region that are most accurately represented via 3D computer modeling and most likely to be machinable into the jig. Such a jig provides an increased accuracy of fit between the jig's mating surface 40 and the arthroplasty target areas of the patient's bone.

For most patients, it is common that the overestimation process outlined in FIG. 45E will result in certain areas of the femoral arthroplasty target region being identified as the optimal target areas discussed above with respect to FIGS. 46H-46K. For example, as depicted in FIG. 47A, which is distal-sagittal isometric view of a femoral distal end 3900, a commonly encountered, healthy, non-deformed femoral distal end 3900 may have an arthroplasty target region 3902 with certain optimal target regions 3904, 3906 and 3908. These optimal target regions 3904, 3906 and 3908 commonly identified on most patients via the overestimation process of FIG. 45E are indicated in FIG. 47A by the cross-hatched regions. It has been found that these optimal target regions 3904, 3906 and 3908 are the regions of the arthroplasty target region 3902 that are most likely to satisfy the criterion $w_i$, $\theta_C$ and $\varphi_C$ of blocks 2508 and 2514 of FIG. 45E. Therefore, these target regions 3904, 3906 and 3908 may be used to generate the jig's bone mating surfaces 40.

While, in one embodiment, the overestimation process of FIG. 45E is likely to result in optimal target regions such as those indicated via the cross-hatching 3904, 3906 and 3908, in other embodiments, the optimal target regions may result in target regions in other locations on the femoral distal end 3900 that are in addition to, or in place of, those regions 3904, 3906 and 3908 depicted in FIG. 47A.

One of the benefits of the overestimation process of FIG. 45E is that it identifies two types of contour lines 210*y*, the first type being those contour lines that are most likely to be unacceptable for the generation a jig's bone mating surfaces 40, and the second type being those contour lines that are most likely to be acceptable for the generation of a jig's bone mating surfaces 40. The first type of contour lines are unlikely to be acceptable for the generation of a jig's bone mating surfaces 40 because they pertain to bone surfaces that are too varied to be accurately 3D computer modeled and/or are such that they are not readily machinable into the jig blank. Conversely, the second type of contour lines are likely to be acceptable for the generation of a jig's bone mating surfaces 40 because they pertain to bone surfaces that vary such an insubstantial amount that they can be accurately 3D computer modeled and are such that they are readily machinable into the jig blank. While optimal target regions 3904, 3906 and 3908 represent regions likely corresponding to contour lines of the second type for most commonly encountered patients, the overestimation processes disclosed herein may be adapted to result in other or additional optimal target regions.

In some instances the entirety of the target regions 3904, 3906 and 3908 may correspond to the second type of contour lines, namely those type of contour lines that satisfy the criterion $w_i$, $\theta_C$ and $\varphi_C$ of blocks 2508 and 2514 of FIG. 45E.

In such instances, the entirety of the target regions 3904, 3906 and 3908 are matingly contacted by the jig's bone mating surface 40.

However, in some instances one or more potions of one or more of the target regions 3904, 3906 and 3908 may be subjected to overestimation so that the jig's bone mating surface 40 does not contact such portions of the target regions 3904, 3906 and 3908, although the jig's bone mating surface 40 still matingly contacts the other portions of the target regions 3904, 3906 and 3908 corresponding to the second type of contour lines. Such a situation may arise, for example, where a substantial surface variation (e.g., a hole, deformity or osteophyte) exists on a condyle articular surface 3918, 3919 that meets the criterion $w_i$, $\theta_C$ and $\varphi_C$ of blocks 2508 and 2514 for the rest of its surface.

The overestimation process disclosed herein may result in the identification of target regions 3904, 3906, 3908 that are most likely to result in bone mating surfaces 40 of jigs 2 that are readily machinable into the jigs 2 and most likely to facilitate reliable and accurate mating of the jigs to the arthroplasty target regions. The overestimation process results in such accurate and reliable bone mating surfaces 40 while causing other surfaces of the jigs 2 corresponding to less predictable bone surfaces to not contact the bone surfaces when the bone mating surfaces 40 matingly receive the target regions 3904, 3906, 3908 of the actual arthroplasty target region.

As indicated in FIG. 47A by the cross-hatched regions, optimal target regions 3904, 3906 and 3908 may include three general areas of the femoral condyle 3910. For example, the anterior optimal target region 3904 may include the anterior portion of the femoral distal end 3900 just proximal of the condyle 3910 region, the lateral optimal target region 3906 may include the distal portion of the lateral condyle 3912, and the medial optimal target region 3908 may include the distal portion of the medial condyle 3914.

As indicated in FIG. 47A, the femoral distal end 3900 may include a lateral condyle 3912 and a lateral epicondyle 3913, a medial condyle 3914 and a medial epicondyle 3915, a intercondylar notch 3939 and a trochlear groove 3916 of the patellar surface separating the two condyles 3912 and 3914, and a femoral shaft 3917 extending distally from the condyle region 3910. Each condyle 3912 and 3914 includes an articular surface 3918 and 3919 that articulates against corresponding articular surfaces of the tibia plateau.

As indicated in FIG. 47D, which is a coronal view of the anterior side of the femoral distal end 3900, the articular surfaces of the condyles 3914, 3912 and the trochlear groove 3916 transition into each other to form a patellar facet 39D1 that has an anterior boarder or seam 39D2. Proximal of the patellar facet boarder 39D2 and identified by a dashed line is the capsular line 39$D_3$ extending medial-lateral in an arc. The adductor tubercle is indicated at 39D4, the fibular lateral ligament at 39D5, the popliteus at 39D6, the vastus intermedius at 39D7, and the articular genu at 39D8.

As indicated in FIG. 47A by the cross-hatching, in one embodiment, the lateral optimal target region 3906 may be generally coextensive with the lateral condyle articular surface 3918 that articulates against the respective articulate surface of the tibia plateau. In one embodiment, the lateral optimal target region 3906 may extend: anterior-posterior between the anterior end 3920 and posterior end 3921 of the lateral articular condyle surface 3918; and lateral-medial between the lateral side 3922 and medial side 3923 of the lateral articular condyle surface 3918. In one embodiment, the lateral optimal target region 3906 generally begins near the anterior-distal end 3920 of the lateral condyle 3912 outside the trochlear groove 3916 of the patellar surface and ends near the posterior-distal end 3921 of the lateral condyle 3912. In one embodiment as can be understood from FIG. 47A, the lateral optimal target region 3906 may be the entire cross-hatched region 3906 or any one or more portions of the cross-hatched region 3906.

In one embodiment as indicated in FIG. 47A by the double cross-hatching, an anterior target area 3906A and a distal target area 3906D may be identified within the lateral optimal target region 3906 via the overestimation process disclosed herein. Thus, although the lateral optimal target region 3906 may be generally coextensive with the lateral condyle articular surface 3918, the actual areas within the lateral optimal target region 3906 identified as being reliable surfaces for the generation of the mating surfaces of arthroplasty jigs may be limited to an anterior target area 3906A and a distal target area 3906D, the remainder of the lateral optimal target region 3906 being subjected to the overestimation process. The anterior target area 3906A may be located in the anterior third of the lateral optimal target region 3906, and the distal target area 3906D may be located near a most distal point of the lateral optimal target region 3906.

As indicated in FIG. 47A by the cross-hatching, in one embodiment, the medial optimal target region 3908 may be generally coextensive with the medial condyle articular surface 3919 that articulates against the respective articulate surface of the tibia plateau. Specifically, in one embodiment, the medial optimal target region 3908 may extend: anterior-posterior between the anterior end 3924 and posterior end 3925 of the medial articular condyle surface 3919; and lateral-medial between the lateral side 3926 and medial side 3927 of the medial articular condyle surface 3919. In one embodiment, the medial optimal target region 3908 generally begins near the anterior-distal end 3924 of the medial condyle 3914 outside the trochlear groove 3916 of the patellar surface and ends near the posterior-distal end 3925 of the medial condyle 3914. In one embodiment as can be understood from FIG. 47A, the medial optimal target region 3908 may be the entire cross-hatched region 3908 or any one or more portions of the cross-hatched region 3908.

In one embodiment as indicated in FIG. 47A by the double cross-hatching, an anterior target area 3908A and a distal target area 3908D may be identified within the medial optimal target region 3908 via the overestimation process disclosed herein. Thus, although the medial optimal target region 3908 may be generally coextensive with the medial condyle articular surface 3919, the actual areas within the medial optimal target region 3908 identified as being reliable surfaces for the generation of the mating surfaces of arthroplasty jigs may be limited to an anterior target area 3908A and a distal target area 3908D, the remainder of the medial optimal target region 3908 being subjected to the overestimation process. The anterior target area 3908A may be located in the anterior third of the medial optimal target region 3908, and the distal target area 3908D may be located near a most distal point of the medial optimal target region 3908.

As indicated in FIG. 47A by the cross-hatching, in one embodiment, the anterior optimal target region 3904 may be a generally planar area of the anterior side of the femoral shaft 3917 proximally adjacent the condyle portion 3910 of the femoral distal end 3900. In other words, the anterior optimal target region 3904 may be a generally planar area of the anterior side of the femoral shaft 3917 proximally adjacent the anterior end 3940 of the trochlear groove 3916.

As shown in FIG. 47D by the cross-hatching, in one embodiment, the anterior optimal target region 3904 may be located in a generally planar surface region of the anterior side of the femoral shaft 3917 generally distal of the articularis genu 39D8 and generally proximal of the patellar facet boarder 39D2. In one embodiment, the anterior optimal target region 3904 may be located in a generally planar surface region of the anterior side of the femoral shaft 3917 generally distal of the articularis genu 39D8 and generally proximal of the capsular line 39D3. In either case, the anterior optimal target region 3904 may be generally centered medial-lateral on the anterior side of the femoral shaft 3917.

As can be understood from FIG. 47A, in one embodiment, the anterior target region 3904 may have a lateral-medial dimension of approximately one centimeter to approximately seven centimeters. In one embodiment, the anterior optimal target region 3904 may be approximately centered on a line that: is generally parallel to the femoral anatomical axis; and extends from the center of the trochlear groove 3916. In one embodiment, the medial-lateral width of the anterior optimal target region 3904 may be medially-laterally bounded by lines extending generally parallel to the femoral anatomical axis from the most medial and most lateral boundaries of the trochlear groove 3916. In one embodiment as can be understood from FIG. 47A, the anterior target region 3904 may be the entire cross-hatched region 3904 or any one or more portions of the cross-hatched region 3904.

In one embodiment as indicated in FIGS. 47A and 47D by the double cross-hatching, an anterior target area 3904A may be identified within the anterior optimal target region 3904 via the overestimation process disclosed herein. Thus, although the anterior optimal target region 3904 may be generally coextensive with the generally planar surface area between the articularis genu 39D8 and the capsular line 39D3, the actual areas within the anterior optimal target region 3904 identified as being a reliable surface for the generation of the mating surfaces of arthroplasty jigs may be limited to an anterior target area 3904A, the remainder of the anterior optimal target region 3904 being subjected to the overestimation process. The anterior target area 3904A may be located any where within the anterior optimal target region 3904.

FIG. 47B is bottom perspective view of an example customized arthroplasty femoral jig 2A that has been generated via the overestimation process disclosed herein. Similar to the femoral jig 2A depicted in FIGS. 1G and 1F, the femoral jig 2A of FIG. 47B includes an interior or bone-facing side 100 and an exterior side 102. When the jig 2A is mounted on the arthroplasty target region during a surgical procedure, the bone-facing side 100 faces the surface of the arthroplasty target region while the exterior side 102 faces in the opposite direction.

The interior or bone-facing side 100 of the femur cutting jig 2A includes bone mating surfaces 40-3904, 40-3906 and 40-3908 that: are machined into the jig interior or bone-facing side 100 based on contour lines that met the criterion of blocks 2508 and 2514 of FIG. 45E; and respectively correspond to the optimal target regions 3904, 3906 and 3908 of FIG. 47A. The rest 100' of the interior or bone-facing side 100 (i.e., the regions 100' of the interior or bone facing sides 100 outside the bounds of bone mating surfaces 40-3904, 40-3906 and 40-3908) are the result of the overestimation process wherein the corresponding contour lines failed to meet one or more of the criterion of blocks 2508 and 2514 of FIG. 45E and, consequently, were moved away from the bone surface. As a result, the interior side surface 100' is machined to be spaced away from the bone surfaces of the arthroplasty target region so as to not contact the bone surfaces when the bone mating surfaces 40-3904, 40-3906 and 40-3908 matingly receive and contact the bone surfaces of the arthroplasty target region corresponding to regions 3904, 3906 and 3908.

As can be understood from FIG. 47B, depending on the patient's bone topography, the overestimation process disclosed herein may result in bone mating surfaces 40-3904, 40-3906 and 40-3908 that are actually multiple bone mating surfaces and/or substantially smaller than depicted in FIG. 47B. For example, the lateral condyle bone mating surface 40-3906 may actually be an anterior lateral condyle bone mating surface 40-3906A and a distal lateral condyle bone mating surface 40-3906D, with the areas of the lateral condyle bone mating surface 40-3906 outside the anterior and distal bone mating surfaces 40-3906A and 40-3906D being the result of the overestimation process so as to not contact the corresponding bone surfaces when the anterior and distal mating surfaces 40-3906A and 40-3906D matingly receive and contact their respective corresponding bone surfaces. The anterior and distal bone mating surfaces 40-3906A and 40-3906D may be configured and positioned in the jig inner surface 100 to matingly receive and contact the anterior and distal optimal target areas 3906A and 3906D discussed above with respect to FIG. 47A.

As can be understood from FIG. 47B, the medial condyle bone mating surface 40-3908 may actually be an anterior medial condyle bone mating surface 40-3908A and a distal medial condyle bone mating surface 40-3908D, with the areas of the medial condyle bone mating surface 40-3908 outside the anterior and distal mating surfaces 40-3908A and 40-3908D being the result of the overestimation process so as to not contact the corresponding bone surfaces when the anterior and distal bone mating surfaces 40-3908A and 40-3908D matingly receive and contact their respective corresponding bone surfaces. The anterior and distal bone mating surfaces 40-3908A and 40-3908D may be configured and positioned in the jig inner surface 100 to matingly receive and contact the anterior and distal optimal target areas 3908A and 3908D discussed above with respect to FIG. 47A.

As can be understood from FIG. 47B, the anterior shaft bone mating surface 40-3904 may actually be a smaller anterior shaft bone mating surface 40-3904A, with the area of the anterior shaft bone mating surface 40-3904 outside the smaller anterior mating surface 40-3904A being the result of the overestimation process so as to not contact the corresponding bone surface when the smaller anterior mating surface 40-3904A matingly receives and contacts its corresponding bone surface. The smaller anterior bone mating surface 40-3904A may be configured and positioned in the jig inner surface 100 to matingly receive and contact the anterior optimal target area 3904A discussed above with respect to FIGS. 47A and 47D.

As can be understood from FIG. 47C, which is a anterior-posterior cross-section of the femur jig 2A of FIG. 47B mounted on the femur distal end 3900 of FIG. 47A, the interior or bone-facing side 100 is formed of bone mating surfaces 40-3904, 40-3906 and 40-3908 and spaced-apart surfaces 100' (i.e., bone-facing surfaces 100 that are a product of the overestimation process and are spaced-apart from the corresponding bone surfaces of the arthroplasty target region 3902). As indicated by the plurality of opposed arrows in regions 3984, 3986 and 3988, the bone mating surfaces 40-3904, 40-3906 and 40-3908 matingly receive and contact the corresponding bone surfaces 3904, 3906 and 3908 to form mating surface contact regions 3984, 3986 and 3988. Conversely, the spaced-apart surfaces 100' are spaced apart from the corresponding bone surfaces to form spaced-apart non-contact regions 3999, wherein the spaced-apart surfaces 100' do not contact their corresponding bone surfaces. In addition to having the mating surfaces 40-3904, 40-3906 and 40-3908 and the spaced-apart surfaces 100', the femur jigs 2A may also have a saw cutting guide slot 30 and anterior and posterior drill holes 45N and 32P, as discussed above.

The arrows in FIG. 47C represent a situation where the patient's bone topography and the resulting overestimation process has generated bone mating surfaces 40-3904, 40-3906 and 40-3908 that match the target regions 3904, 3906 and 3908, which are generally coextensive with the entirety of their respective potential regions as discussed above. Of course, where the patient's bone topography and the resulting overestimation process generates bone mating surfaces 40-3904A, 40-3906A, 40-3906D, 40-3908A and 40-3908D that match the target areas 3904A, 3906A, 3906D, 3908A and 3908D, which are substantially smaller than their respective target regions 3904, 3906 and 3908, the mating surface contact regions 3984, 3986 and 3988 may be smaller and/or segmented as compared to what is depicted in FIG. 47C.

FIG. 47E depicts closed-loop contour lines 4002, 4004, and 4006 that are image segmented from image slices, wherein the contour lines outline the cortical bone surface of the lower end of the femur. These contour lines 4002, 4004, and 4006 may be identified via image segmentation techniques from medical imaging slices generated via, e.g., MRI or CT.

As shown in FIG. 47E, there are posterior portions of the contour lines (indicated as 4007) that may be of no interest during overestimation because the contour line region 4007 corresponds to a region of the knee that may be inaccessible during surgery and may not correspond to a jig surface because no part of the jig may access the region 4007 during surgery. An osteophyte in contour line region 4008 may be identified based on the algorithm 2500. The contour lines in region 4008 may be subsequently overestimated (based on the algorithm 2500) such that the resulting jig surface does not come into contact with the osteophyte (i.e., with the osteophyte bone surface represented by contour line region 4008) when the jig's bone mating surface 40 matingly receives and contacts the bone surfaces of the arthroplasty target region. Additionally, optimal contour line regions 4010 and 4012 may be identified during execution of the algorithm 2500 as areas of the patient's bone anatomy that have surface variations within the angular criteria of the algorithm 2500 and, therefore, are used to generate the jig's bone mating surface 40 that matingly receives and contacts the bone surfaces of the arthroplasty target region.

Contour line region 4010 may pertain to region 3904 of FIG. 47A and femur jig region 40-3904 of FIG. 47B. Contour line region 4012 may pertain to either region 3906 or 3908 of FIG. 47A and either femur jig region 40-3906 or 40-3908 of FIG. 47B. Utilizing the optimal areas 4010 and 4012 as jig bone mating surfaces 40 allows irregular areas of the patient's bone anatomy to be accommodated without affecting the fit of the jig 2 to the patient's bone anatomy. In fact, an accurate and custom fit between the jig 2 and the patient's bone anatomy can be made by using only a few of such optimal areas. This allows substantial overestimation of the jig surface in regions corresponding to irregularities, thereby preventing the irregularities from interfering with an accurate and reliable fit between the jig's bone mating surfaces and those bone surfaces of the arthroplasty target region corresponding to those bone mating surfaces. The result of the overestimation process is a jig with bone mating surfaces that offer a reliable and accurate custom fit with the arthroplasty target region. This may result in an increased success rate for TKR or partial knee replacement surgery because the jig may custom fit to the most reliable bone surfaces and be deliberately spaced from the bone surfaces that may be unreliable, for example, because of imaging or tool machinery limitations.

2. Overestimating the 3D Tibia Surface Models

As described above with regard to block 140 of FIG. 1D, the "jig data" 46 is used to produce a jigs having bone mating surfaces customized to matingly receive the target areas 42 of the respective bones of the patent's joint. Data for the target areas 42 may be based, at least in part, on the 3D computer generated surface models 40 of the patient's joint bones. Furthermore, as described above with regard to FIG. 1A and [blocks 100-105] of FIG. 1B, these 3D computer generated surface models 40 may be based on the plurality of 2D scan image slices 16 taken from the imaging machine 8 and, more precisely, from the contour lines derived from those 2D scan image slices via image segmentation processes known in the art or, alternatively, as disclosed in U.S. Provisional Patent Application 61/126,102, which was filed Apr. 30, 2008 and is incorporated by reference herein in its entirety.

Each scan image slice 16 represents a thin slice of the desired bones. FIG. 48A illustrates the proximal axial view of the 3D model of the patient's tibia shown in FIG. 43I with the contour lines 4101 of the image slices shown and spaced apart by the thickness $D_T$ of the slices. FIG. 48B represents a coronal view of a 3D model of the patient's tibia with the contour lines 4101 of the image slices shown and spaced apart by the thickness $D_T$ of the slices.

The slices shown in FIGS. 48A-B have contour lines 4101 similar to the open and closed loop contour line segments 210*y*, 210*y*' depicted in FIGS. 41B and 41E. The contour lines 4101 of each respective image slice 16 are compiled together to form the 3D model of the patient's tibia. The overall resolution or preciseness of the 3D models 40 (shown in FIG. 43C) resulting from compiling together the contour lines of each of these slices (shown in [block 1010]) may be impacted by the thickness $D_T$ of the slices shown in FIGS. 48A-B. Specifically, the greater the thickness $D_T$ of the slices, the lower the resolution/preciseness of the resulting 3D models, and the smaller the thickness $D_T$ of the slices, the higher the resolution/preciseness of the resulting 3D models.

As the resolution/preciseness of the 3D models increases, more accurate customized arthroplasty jigs 2 may be generated. Thus, the general impetus is to have thinner slices rather than thicker slices. However, depending upon the imaging technology used, the feasible thickness $D_T$ of the image slices may vary and may be limited due a variety of reasons. For example, an imaging thickness $D_T$ that is sufficiently precise to provide the desired imaging resolution may also need to be balanced with an imaging duration that is sufficiently brief to allow a patient to remain still for the entire imaging duration.

In embodiments utilizing MRI technology, the range of slice thickness $D_T$ may be from approximately 0.8 mm to approximately 5 mm. MRI slice thicknesses $D_T$ below this range may be unfeasible because they have associated imaging durations that are too long for most patient's to remain still. Also, MRI slice thicknesses $D_T$ below this range may be unfeasible because they may result in higher levels of noise with regard to actual signals present, residuals left between slices, and volume averaging limitations of the MRI machine. MRI slice thicknesses above this range may not provide sufficient image resolution/preciseness. In one embodiment, the MRI slice thicknesses $D_T$ is approximately 2 mm.

While embodiments utilizing CT technology may have a range of slice thicknesses $D_T$ from approximately 0.3 mm to approximately 5 mm, CT imaging may not capture the cartilage present in the patient's joints to generate the arthritic models mentioned above.

Regardless of the imaging technology used and the resulting resolution/preciseness of the 3D models, the CNC machine 10 may be incapable of producing the customized arthroplasty jigs 2 due to mechanical limitations, especially where irregularities in the bone surface are present. This, for example, may result where a milling tool bit has dimensions that exceed those of the feature to be milled.

FIG. 48C illustrates an example sagittal view of compiled contour lines of successive sagittal 2D MRI images based on the slices shown in FIGS. 48A-B with a slice thickness $D_T$ of 2 mm. As can be understood from FIGS. 48A-48C, the contour lines shown begin on the medial side of the knee at the image slice corresponding to contour line 4110 and conclude on the lateral side of the knee at the image slice corresponding to contour line 4130. Thus, in one embodiment, contour lines 4110 and 4130 represent the contour lines of the first and last images slices taken of the tibia, with the other contour lines between contour lines 4110, 4130 representing the contour lines of the intermediate image slices taken of the tibia. Each of the contour lines is unique is size and shape, may be either open-loop or closed-loop, and corresponds to a unique image slice 16.

FIG. 48D illustrates an example contour line 4300 of one of the contour lines depicted in FIGS. 48A-48C, wherein the contour line 4300 is depicted in a sagittal view and is associated with an image slice 16 of the tibia plateau. As shown, the contour line 2400 includes a plurality of surface coordinate points (e.g., i.e., i−n, . . . , i−3, i−2, i−1, i, i+1, i+2, i+3, . . . , i+n; j−n, . . . , j−3, j−2, j−1, j, j+1, j+2, j+3, . . . , j+n; and k−n, . . . , k−3, k−2, k−1, k, k+1, k+2, k+3, . . . , k+n). The contour line and associated points may be generated by imaging technology, for example, via an image segmentation process that may employ, for example, a shape recognition process and/or an pixel intensity recognition process. In one embodiment, the contour line 4300 may represent the boundary line along the cortical-cancellous bone edge. In one embodiment, the boundary line may represent the outer boundary line of the cartilage surface.

Each of the surface contour points in the plurality may be separated by a distance "d". In one embodiment, distance "d" may be a function of the minimum imaging resolution. In some embodiments, distance "d" may be function of, or associated with, the size of the milling tool used to manufacture the jig. For example, the distance "d" may be set to be approximately 10 times smaller than the diameter of the milling tool. In other words, the distance "d" may be set to be approximately $1/10^{th}$ or less of the diameter of the milling tool. In other embodiments, the distance "d" may be in the range of between approximately equal to the diameter of the milling tool to approximately $1/100^{th}$ or less of the diameter of the milling tool.

Depending on the embodiment, the separation distance d may be either uniform along the contour line 4300, or may be non-uniform. For example, in some embodiments, areas of bone irregularities may have points that are closer together than areas where no irregularities are present. In one embodiment, the points shown along the example contour line 4300 may have a separation distance d of approximately 2 mm. In other embodiments, distance d may be in the range of approximately 0.8 mm to approximately 5 mm.

The bone surface of the example contour line 4300 includes a region 4302A on the anterior portion of the tibia plateau, a region 4302B on the tibia plateau that is representative of an irregularity, and a region 4302C on the articular surface of the tibia plateau. The irregularity of region 4302B may be due to a variety of patient specific factors. For example, irregular region 4302B illustrates a type of bone irregularity, referred to as an "osteophyte", where a bony outgrowth has occurred in the tibia plateau. Osteophytes may be present in patients that have undergone trauma to the bone or who have experienced degenerative joint disease.

Irregularities may be due to other factors, such as cartilage damage, which may appear as notches in the contour line 4300. Regardless of the cause of the irregularities, the presence of irregularities in the contour line 4300 may adversely impact the ability to generate a mating surface in the actual arthroplasty jig that accurately and reliably mates with the corresponding bone surface of the patient during the arthroplasty procedure. This may be the result of the imaging impreciseness in the vicinity of the contour irregular region 4302B or because the contour irregular region 4302B represents a surface contour that is too small for the tooling of the CNC machine 10 to generate. To account for contour line regions associated with imaging impreciseness and/or features too small to be milled via the tooling of the CNC machine, in some embodiments, such contour line regions may be identified and corrected or adjusted via the overestimation process prior to being compiled to form the 3D models 40.

As discussed above, FIG. 45E represents an example overestimation algorithm 2500 that may be used to identify and adjust for irregular region 4302B when forming the 3D models 40. In block 2502, medical imaging may be performed on the damaged bone at desired slice thicknesses $D_T$, which in some embodiments may be equal to those slice thicknesses $D_T$ mentioned above with regard to FIGS. 48A-B. For example, MRI and/or CT scans may be performed at predetermined thicknesses $D_T$ as shown in FIGS. 48A-B. In some embodiments, the desired thickness $D_T$ used in block 2502 is set at 2 mm or any other thickness $D_T$ within the range of thicknesses $D_T$ mentioned above.

From this medical imaging, a series of slices 16 may be produced and image segmentation processes can be used to generate the contour lines 210*y*, 210*y*', 4101, 4110, 4130, 4300 discussed with respect to FIGS. 2, 41A-B, 48A-B, and 43 (see block 2504). Also in block 2504, a plurality of surface coordinate points along each contour line segment 4302A-C may be identified as shown in FIG. 48D with respect to contour line 4300. For example, the points in the irregular region corresponding to contour line segment 4302B may be identified and indexed as k−n, . . . , k−3, k−2, k−1, k, k+1, k+2, k+3, . . . , k+n.

With the surface coordinate points along the contour 4300 defined, an analysis may be performed on two or more of the points (e.g., k and k+1) to determine if an irregularity exists in the contour line segment per block 2506.

FIG. 48E depicts implementing an example analysis scheme (according to block 2506) on the irregular contour line region 4302B of FIG. 48D. As shown, the analysis may include constructing one or more tangent lines (labeled as $t_{k-1}$, $t_k$, $t_{k+1}$, $t_{k+2}$, $t_{k+3}$, $t_{k+4}$, etc.), corresponding to the points in the irregular region 4302B. The analysis of block 2506 may further include calculating differences between the angles formed by one or more of the tangent lines. For example, the difference between the angles formed by the tangent lines $t_k$ and $t_{k+1}$ may be defined as $w_k$, where $$w_k = \cos^{-1}\left(\frac{t_{k+1} \cdot t_k}{|t_{k+1}||t_k|}\right).$$

In some embodiments, the operations of block 2506 may be performed repetitively on each point within the contour segment.

The operations of block 2506 may be calculated on subsequent points (e.g., between $t_k$ and $t_{k+1}$) in some embodiments, and on non-subsequent points in other embodiments (e.g., $t_{k+2}$ and $t_{k+4}$).

The angular difference w may indicate whether portions of the contour line segment are too eccentric for use in constructing the 3D models 40. In block 2508, the angular difference w may be compared to a predetermined angular criterion $w_c$. The angular criterion $w_c$ may be determined based on several factors, including the physical dimensions and characteristics of the CNC machine 10. In some embodiments, the predetermined angular criterion $w_c$ is set at approximately 5 degrees. In other embodiments, the predetermined angular criterion $w_c$ is set at between approximately 5 degrees and approximately 20 degrees.

For the sake of discussing the example irregular region 4302B shown in FIG. 48E, the angular criterion $w_c$ is set to 5 degrees in one embodiment. The angular differences between tangent lines associated with adjacent points k−4, k−3, k−2 and k+12, k+13, and k+14 are within the predetermined angular criterion $w_c$ of 5 degrees, but the differences between tangent lines associated with adjacent points k−3, k−2, k−1, ki, k+1, k+2, . . . , k+10 exceeds the predetermined angular criterion $w_c$ of 5 degrees and therefore indicates an irregular region of the contour line. As mentioned above, these irregularities may result from conditions of the patient's bone such as arthritis or osteoarthritis and generally result in a contour line segment being unsuitable for using when forming the 3D models 40. Accordingly, if the comparison from block 2508 indicates that the angular difference w is greater than the predetermined criterion $w_c$, then the data associated with the irregular contour line segment may be modified by overestimating (e.g., adjusting the irregular contour line segment outward or away from the bone portion of the image slice 16) as discussed in greater detail below with respect to FIG. 48F (see block 2510).

FIG. 48F depicts the irregular region 4302B from FIG. 48E including a proposed area of overestimation 4501, wherein an overestimation procedure creates an adjusted contour line 4502 and positionally deviates the adjusted contour line 4502 from the original surface profile contour line 4302B. In the event that the comparison performed in block 2508 indicates that the angular differences between any of the points k−3 through k+10 exceed the predetermined angular criterion $w_c$, then the contour line segment may be overestimated between these points as shown by the dashed line 4502. As can be understood from a comparison of contour line 4302B to the overestimated or adjusted line 4502, the adjusted line 4502 is adjusted or moved outward or away from the location of the contour line 4502B by an offset distance. Depending on the embodiment, the offset distance between the contour line 4302B and the adjusted line 4502 may range between a few millimeters to a few centimeters. This overestimation may be built into the data used to construct 3D surface models 40 and result in a gap between the respective region of the bone mating surface of the jig 2 and the corresponding portion of the patient's bone surface, thereby avoiding contact between these respective areas of the jig and bone surface. The other areas, such as k−6, k−7, k−8, k−9 and k+15, k+16, k+17, and k+18, need not be overestimated, per block 2510, because the differences between their tangent lines fall within the angular difference criterion $w_c$. These areas may be designated as potential target areas that may later be used as the 3D surface models 40 if other angular criteria (described below) are satisfied.

By building overestimation data into the 3D surface models 40, deliberate spaces may be created in regions of the custom arthroplasty jig 2 corresponding to irregularities in the patient's bone, where it is often difficult to predict the size and shape of these irregularities from 2D MRI or where it is difficult to accurately machine the contour line into the jig's bone mating surface because of the largeness of the milling tool relative to the changes in contour. Thus, the jig 2 may include one or more deliberate spaces to accommodate these irregularities or inability to machine. Without these deliberate spaces, the jig 2 may be potentially misaligned during the TKR surgery and may reduce the chances of the surgery's success.

As described above with respect to FIGS. 45H and 45L, the image generation, analysis and overestimation of blocks 2506, 2508 and 2510 may be performed on other irregularities of contour line 4300, if such additional irregularities were present in FIG. 48D.

As shown in FIG. 45, a tool 4504 having diameter $D_2$ may be employed to machine the contour line 4302 into the jig blank. As described above with respect to FIG. 45I, in some embodiments, to allow for an adequate transition from the non-overestimated regions to the overestimated regions 4501 in view of the diameter $D_2$ of the tool 4504 to be used, the overestimation may include additional points to either side of the points falling outside of the predetermined criterion $w_c$ (i.e., points k−3, k−4, and k−5 as well as at points k+12, k+13, and k+14). Thus, the overestimation in region 4302B may extend from k−5 through k+14. Furthermore, since the comparison performed in block 2508 indicates that the angular difference $w_k$ is less than the predetermined criterion $w_c$ at points k−3, k−4, k−5, k−6, k−7, k−8, k−9 and k+12, k+13, k+14, k+15, k+16, k+17, and k+18, these points k−6, k−7, k−8, k−9 and k+15, k+16, k+17, and k+18 (adjusting for the addition of points k−3, k−4, and k−5 as well as at points k+12, k+13 to the overestimation transition regions 4501) may be used in constructing the 3D models 40 as long as other criteria (described below in the context of blocks 2514-2520) are met.

A tool 4504 may be used to form the surface of the jig's bone mating surface from the 3D models 40 formed from the compiled contour lines, some of which may have been modified via the overestimation process. The tool 4504 may be part of the CNC machine 10 or any other type of machining or manufacturing device having any type of tool or device for forming a surface in a jig blank. Regardless of the type of the device used to mill or form the jigs 2, the tool 4504 may have certain attributes associated with jig machining process that are taken into account when performing the overestimating per block 2510. The associated attributes may include the accessible space for the machining tools to reach and machine the jig's bone mating surface. Examples of such attributes may include the collar diameter of the drilling cutter device, the allowable angle the drilling device can make with the surface to be drilled (e.g., 45 degrees±10%), and/or the overall length of the drilling cutter head.

For example, as indicated in FIG. 45, if the minimum diameter of the overestimated region 4501 is larger than the diameter $D_2$ of the tool 4504, then overestimation of block 2510 may not need to account for the dimensions of the tool 4504, except to provide adequate transitions leading to the overestimated region 4501 as illustrated above by the addition of a single or few points (e.g., points k−3, k−4, and k−5 as well as at points k+12, k+13) to either side of the points outside predetermined criterion $w_c$.

If, on the other hand, the tool 4504 has a diameter $D_2$ that is greater than the diameter of the overestimated region, then the overestimated region may be increased in diameter to account for the large tool diameter, as described above with respect to FIGS. 45J-45K. With the curves overestimated to account for factors related to the tool 4504, the resulting overestimated surface profile or contour may be saved for generating the 3D model 40 as long as other criteria (described below in the context of block 2514-2520) are met.

FIGS. 48G-H show similar analyses of the regular regions 4302A and 4302C (from FIG. 43). As was the case with the irregular region 4302B, points i+1, i+2, i+3, . . . , i+n and j+1, j+2, j+3, . . . , j+n along the contour line 4300 may be identified for regions 4302A and 4302C and then tangent lines (labeled as $t_{j+1}$, $t_{j+2}$, $t_{j+3}$, etc. and $t_{i+1}$, $t_{i+2}$, $t_{i+3}$, etc.) may be constructed per block 2506. Per block 2508, comparing the angular differences w between these tangent lines using the formulas $$w_j = \cos^{-1}\left(\frac{t_{j+1} \cdot t_j}{|t_{j+1}||t_j|}\right) \text{ and } w_i = \cos^{-1}\left(\frac{t_{i+1} \cdot t_i}{|t_{i+1}||t_i|}\right)$$

shows that they $w_j$, $w_i$ are within the angular criterion $w_c$, which in this example is 5 degrees. Thus, the points of the regions 4302A and 4302C shown in FIGS. 48G-H may be saved and used as potential surface profiles for the mating surface of the tibial jig if the surface variations between these points and points on contour lines of adjacent slices are not too extreme. That is, if the angular differences associated with a contour line of a particular slice fall within the angular criterion $w_c$, and the points are used as a potential jig surface, then surface variation between contour lines of adjacent slices may be checked in block 2514. This approach may help to identify certain areas where no cartilage damage or osteophyte is observed in the imaging, yet there is a need to overestimate because the surface variation, between the adjacent slices shown in FIGS. 48A-B, may be too great to be used as an accurate representation of the actual bone surface to be a potential tibial jig surface. Example areas falling within this category for the proximal tibia plateau include the areas near the medial and lateral tibial plateaus adjacent to, and including, the spine portion to name a few examples.

Once it is determined that a specific portion of a contour line has satisfied the criterion $w_c$ of block 2508 of FIG. 45E, that contour line portion may be further analyzed to determine if the contour line portion also satisfies both of the criterion $\theta_C$ and $\varphi_C$ of block 2514, as discussed above with respect to FIGS. 45E and 45N-46B. More specifically, corresponding coordinate points are determined via any of the three methods discussed above with respect to FIGS. 46A-46F. The surface variation between the corresponding coordinate points is analyzed as discussed with above with respect to FIGS. 46A-46F with respect to: (1) angular deviation θ between corresponding coordinate points of contour lines of adjacent image slices; and (2) the angular differences φ of normal vectors associated with corresponding coordinate points of contour lines of adjacent image slices. If the contour line portion meets all of the criterion $w_i$, $\theta_c$ and $\varphi_c$ of blocks 2508 and 2514 of FIG. 45E, then, as discussed above and indicated in block 2520 of FIG. 45E, the contour line portion may be recorded and employed in generating the jig's bone mating surfaces. Alternatively, if the contour portion line fails to meet any one or more of the criterion $w_i$, $\theta_c$ and $\varphi_c$ of blocks 2508 and 2514, then as indicated in FIG. 45E and discussed above, the contour line portion may be modified per the overestimation process (block 2510) or, in some instances, the image slice thickness $D_T$ may be reset to a more narrow thickness $D_T$ and the entire process repeated beginning at block 2502 of FIG. 45E.

FIG. 48I is a proximal view of the tibia plateau similar to that of FIG. 43I depicting contour lines 4700 produced by imaging the left tibia at an image spacing $D_T$ of, for example, 2 mm. As shown, the contour lines 4700 may be grouped into multiple regions in the lateral-medial direction 4702-4708 for the sake of discussion. The region 4702 includes the contour lines 4700 of the most medial half of the medial tibial plateau and extends laterally from the most medial side of the medial tibial plateau to the medial-lateral middle of the medial tibial plateau. The region 4704 includes the contour lines 4700 of the most lateral half of the medial tibial plateau and extends laterally from the middle of the medial tibial plateau to the medial-lateral point near the tibial spine. The region 4706 includes the contour lines 4700 of the most medial half of the lateral tibial plateau and extends laterally from the medial-lateral point near the tibial spine to the medial-lateral middle of the lateral tibial plateau. The region 4708 includes the contour lines 4700 of the most lateral half of the lateral tibial plateau and extends laterally from the medial-lateral middle of the lateral tibial plateau to the most lateral side of the lateral tibial plateau.

Figure 48J:
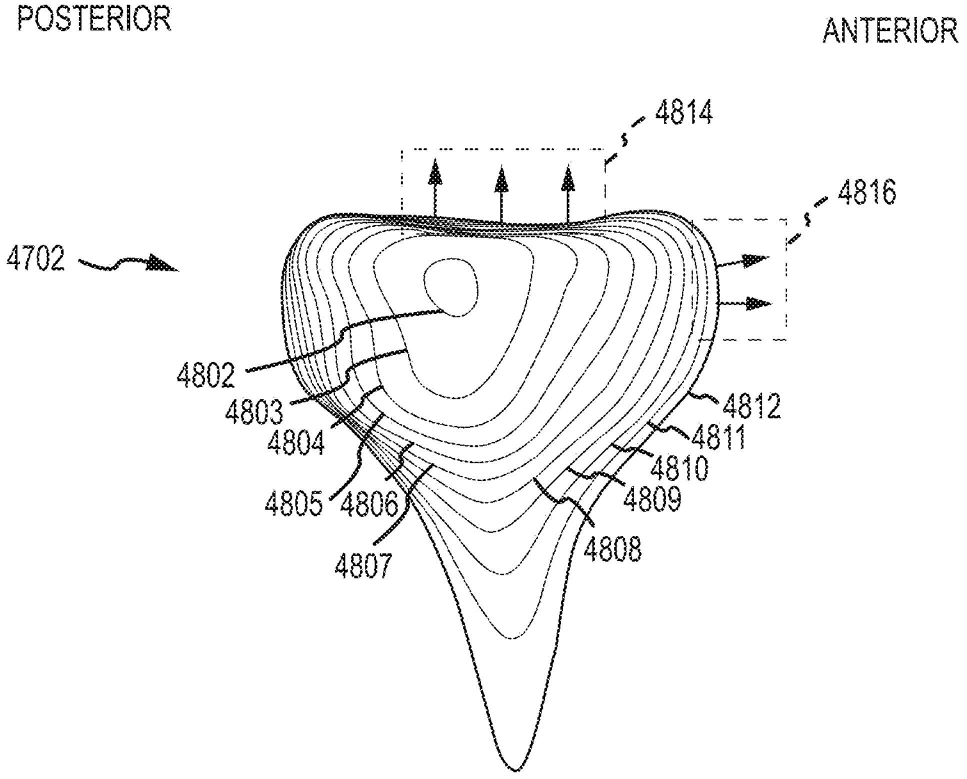

FIG. 48J is a sagittal view of the contour lines 4700 of region 4702 of FIG. 48I. The contour lines 4700 of region 4702 include contour lines 4802-4812, with the most medial portion of the medial tibial plateau being indicated by contour line 4802. The size of each successive contour line 4700 of region 4702 increases moving laterally from the most medial contour line 4802 of region 4702 to the most lateral contour line 4812 of region 4702, which is near the medial-lateral middle of the medial tibial plateau.

As can be understood from FIG. 48J, the contour lines 4802-4803 are spaced apart from their respective adjacent contour lines a substantial amount around their entire boarders. Such wide spacing corresponds to a substantial amount of rise or fall distances between adjacent contour lines, as discussed above with respect to FIG. 46B. Thus, such contour lines would likely fail to meet the angular criterion $\theta_C$ and be subject to the overestimation process such that jig surfaces corresponding to the contour lines 4802-4803 would not contact the corresponding surfaces of the arthroplasty target areas.

As can be understood from FIG. 48J, in the proximal portion of the medial tibial plateau, the contour lines 4804-4812 in the region 4814 converge such that there is little, if any, amount of rise or fall distance between adjacent contour lines. Thus, such contour lines 4804-4812 in the region 4814 would likely meet the first angular criterion $\theta_C$. Similarly, in the anterior tibial plateau portion of the proximal tibia, the contour lines 4811-4812 in region 4816 converge such that there is little, if any, amount of rise or fall distance between adjacent contour lines. Thus, such contour lines 4804-4812 in region 4814 and contour lines 4811-4812 in region 4816 would likely meet the first angular criterion $\theta_C$.

As can be understood from the arrows in regions 4814 and 4816, the angular differences between normal vectors for the contour line portions within regions 4814 and 4816 would be minimal, likely meeting the second angular criterion $\varphi_C$. Thus, as the portions of the contour lines 4804-4812 within region 4814 and the portions of the contour lines 4811-4812 within region 4816 likely meet both angular criterion $\theta_C$ and $\varphi_C$, the portions of the contour lines 4804-4812 within the region 4814 and the portions of the contour lines 4811-4812 within region 4816 represent optimal contact areas 4814 and 4816 for mating contact with the jig's bone mating surface 40.

In one embodiment, as can be understood from FIG. 49A discussed below, the optimal contact area 4814 may be the surface of the medial tibial plateau that displaces against the corresponding articular surface of the medial femoral condyle, and the optimal contact area 4816 may be the medial anterior region of the proximal tibia just distal of the tibial plateau edge and medial of the tuberosity of the tibia.

In one embodiment, the optimal contact areas 4814 and 4816 matingly corresponds to the jig's bone mating surface 40 such that the portions of the contour lines 4702 indicated by regions 4814 and 4816 may be used to generate the jig's bone mating surface 40, per the algorithm 2500 of FIG. 45E. Conversely, per the algorithm 2500, the portions of the contour lines 4702 outside regions 4814 and 4816 may be subjected to the overestimation process discussed above such that the jig's surfaces created from the overestimated contour line portions results in jig surfaces that do not contact the corresponding portions of the patient's arthroplasty target regions.

Figure 48K:
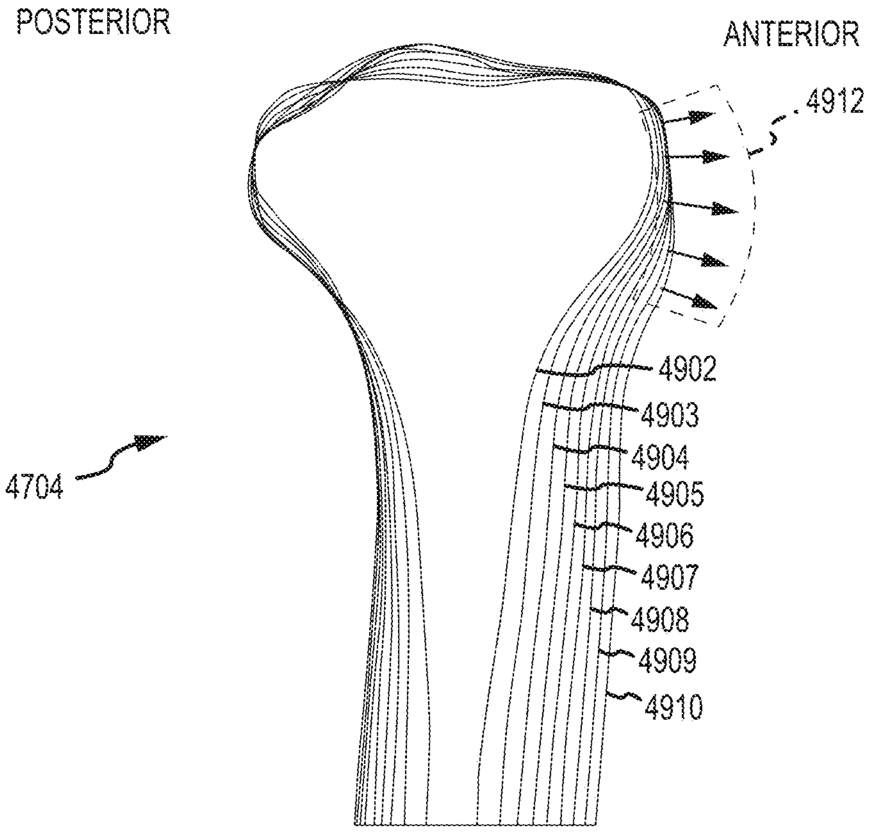

FIG. 48K is a sagittal view of the contour lines 4700 of region 4704 of FIG. 48I. The contour lines 4700 of region 4704 include contour lines 4902, 4903, 4904, 4905, 4906, 4907, 4908, 4909 and 4910 with the most medial portion of region 4704 being indicated by contour line 4802, which is near the medial-lateral middle of the medial tibial plateau, and the most lateral portion of region 4704 being indicated by contour line 4810, which is a medial-lateral point near the tibial spine. The size of each successive contour line 4700 of region 4704 increases moving laterally from the most medial contour line 4902 to the most lateral contour line 4910.

As can be understood from FIG. 48K, the contour lines 4902-4910 are spaced apart from their respective adjacent contour lines a substantial amount in their posterior and anterior portions along the shaft of the tibia, and to a lesser extent in their tibia spine portions. Such wide spacing corresponds to a substantial amount of rise or fall distances between adjacent contour lines, as discussed above with respect to FIG. 46B. Thus, such contour lines would likely fail to meet the angular criterion $\theta_C$ and be subject to the overestimation process such that jig surfaces corresponding to the contour lines 4902-4910 would not contact the corresponding surfaces of the arthroplasty target areas.

As can be understood from FIG. 48K, in the anterior tibial plateau portion of the proximal tibia, the contour lines 4902-4910 in the region 4912 converge such that there is little, if any, amount of rise or fall distance between adjacent contour lines. Thus, such contour lines 4902-4910 in the region 4912 would likely meet the first angular criterion $\theta_C$.

As can be understood from the arrows in region 4912, the angular differences between normal vectors for the contour line portions within the region 4912 would be minimal, likely meeting the second angular criterion $\varphi_C$. Thus, as the portions of the contour lines 4902-4910 within region 4912 likely meet both angular criterion $\theta_C$ and $\varphi_C$, the portions of the contour lines 4902-4910 within the region 4912 represent an optimal contact area 4912 for mating contact with the jig's bone mating surface 40.

In one embodiment, the optimal contact area 4912 matingly corresponds to the jig's bone mating surface 40 such that the portions of the contour lines 4902-4910 indicated by region 4912 may be used to generate the jig's bone mating surface 40, per the algorithm 2500 of FIG. 45E. Conversely, per the algorithm 2500, the portions of the contour lines 4902-4910 outside region 4912 may be subjected to the overestimation process discussed above such that the jig's surfaces created from the overestimated contour line portions results in jig surfaces that do not contact the corresponding portions of the patient's arthroplasty target regions.

In one embodiment, as can be understood from FIG. 49A discussed below, the optimal contact area 4912 may be the anterior region of the proximal tibia just distal of the tibial plateau edge and just distal of the tuberosity of the tibia, extending medial-lateral from just medial of the tuberosity of the tibia to generally centered medial-lateral relative to the tuberosity of the tibia.

Figure 48L:
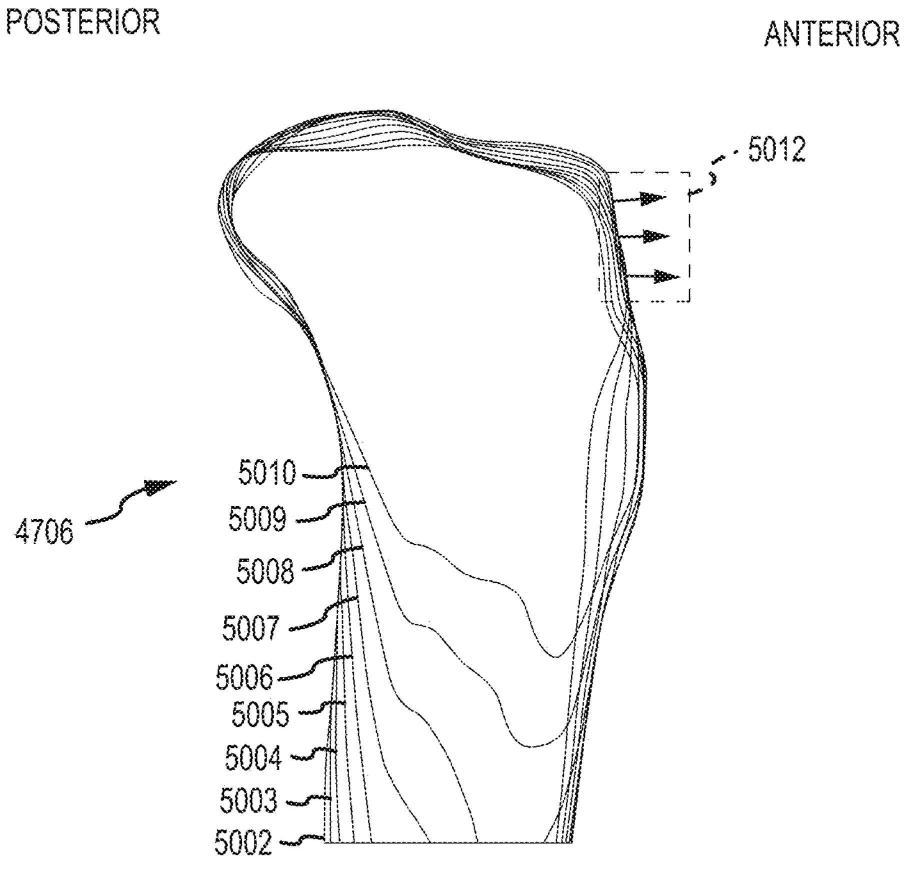

FIG. 48L is a sagittal view of the contour lines 4700 of region 4706 of FIG. 48I. The contour lines 4700 of region 4706 include contour lines 5002, 5003, 5004, 5005, 5006, 5007, 5008, 5009 and 5010 with the most medial portion of region 4706 being indicated by contour line 5002, which is a medial-lateral point near the tibial spine, and the most lateral portion of region 4704 being indicated by contour line 5010, which is near the medial-lateral middle of the lateral tibial plateau. The size of each successive contour line 4700 of region 4704 decreases moving laterally from the most medial contour line 5002 to the most lateral contour line 5010.

As can be understood from FIG. 48L, the contour lines 5002-5010 are spaced apart from their respective adjacent contour lines a substantial amount in their posterior and anterior portions along the shaft of the tibia, and to a lesser extent in their tibia spine and tibia tuberosity portions. Such wide spacing corresponds to a substantial amount of rise or fall distances between adjacent contour lines, as discussed above with respect to FIG. 46B. Thus, such contour lines would likely fail to meet the angular criterion $\theta_C$ and be subject to the overestimation process such that jig surfaces corresponding to the contour lines 5002-5010 would not contact the corresponding surfaces of the arthroplasty target areas.

As can be understood from FIG. 48L, in the anterior tibial plateau portion of the proximal tibia, the contour lines 5002-5010 in the region 5012 converge such that there is little, if any, amount of rise or fall distance between adjacent contour lines. Thus, such contour lines 5002-5010 in the region 5012 would likely meet the first angular criterion $\theta_C$.

As can be understood from the arrows in region 5012, the angular differences between normal vectors for the contour line portions within the region 5012 would be minimal, likely meeting the second angular criterion $\varphi_C$. Thus, as the portions of the contour lines 5002-5010 within region 5012 likely meet both angular criterion $\theta_C$ and $\varphi_C$, the portions of the contour lines 5002-5010 within the region 5012 represent an optimal contact area 5012 for mating contact with the jig's bone mating surface 40.

In one embodiment, the optimal contact area 5012 matingly corresponds to the jig's bone mating surface 40 such that the portions of the contour lines 5002-5010 indicated by region 5012 may be used to generate the jig's bone mating surface 40, per the algorithm 2500 of FIG. 45E. Conversely, per the algorithm 2500, the portions of the contour lines 5002-5010 outside region 5012 may be subjected to the overestimation process discussed above such that the jig's surfaces created from the overestimated contour line portions results in jig surfaces that do not contact the corresponding portions of the patient's arthroplasty target regions.

In one embodiment, as can be understood from FIG. 49A discussed below, the optimal contact area 5012 may be the anterior region of the proximal tibia just distal of the tibial plateau edge and just distal of the tuberosity of the tibia, extending medial-lateral from just lateral of the tuberosity of the tibia to generally centered medial-lateral relative to the tuberosity of the tibia.

Figure 48M:
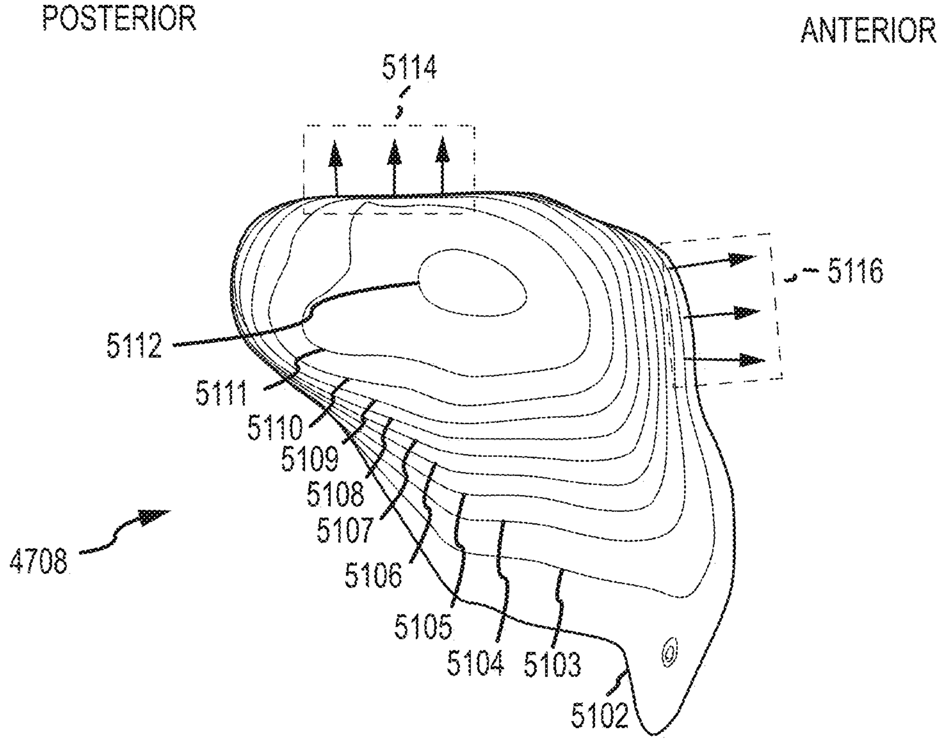

FIG. 48M is a sagittal view of the contour lines 4700 of region 4708 of FIG. 48I. The contour lines 4700 of region 4708 include contour lines 5102-5112, with the most lateral portion of the lateral tibial plateau being indicated by contour line 5102. The size of each successive contour line 4700 of region 4708 increases moving laterally from the most medial contour line 5102 of region 4708, which is near the medial-lateral middle of the medial tibial plateau, to the most lateral contour line 5110 of region 4708, which is the most lateral portion of the lateral tibial plateau.

As can be understood from FIG. 48M, the contour lines 5110-5112 are spaced apart from their respective adjacent contour lines a substantial amount around their entire boarders. Such wide spacing corresponds to a substantial amount of rise or fall distances between adjacent contour lines, as discussed above with respect to FIG. 46B. Thus, such contour lines would likely fail to meet the angular criterion $\theta_C$ and be subject to the overestimation process such that jig surfaces corresponding to the contour lines 5110-5112 would not contact the corresponding surfaces of the arthroplasty target areas.

As can be understood from FIG. 48M, in the proximal portion of the lateral tibial plateau, the contour lines 5102-5109 in the region 5114 converge such that there is little, if any, amount of rise or fall distance between adjacent contour lines. Thus, such contour lines 5102-5109 in the region 5114 would likely meet the first angular criterion $\theta_C$. Similarly, in the anterior tibial plateau portion of the proximal tibia, the contour lines 5102-5105 in region 5116 converge such that there is little, if any, amount of rise or fall distance between adjacent contour lines. Thus, such contour lines 5102-5109 in region 5114 and contour lines 5102-5105 in region 5116 would likely meet the first angular criterion $\theta_C$.

As can be understood from the arrows in regions 5114 and 5116, the angular differences between normal vectors for the contour line portions within regions 5114 and 5116 would be minimal, likely meeting the second angular criterion $\varphi_C$. Thus, as the portions of the contour lines 5102-5109 within region 5114 and the portions of the contour lines 5102-5105 within region 4816 likely meet both angular criterion $\theta_C$ and $\varphi_C$, the portions of the contour lines 5102-5109 within the region 5114 and the portions of the contour lines 5102-5105 within region 5116 represent optimal contact areas 5114 and 5116 for mating contact with the jig's bone mating surface 40.

In one embodiment, as can be understood from FIG. 49A discussed below, the optimal contact area 5114 may be the surface of the lateral tibial plateau that displaces against the corresponding articular surface of the lateral femoral condyle, and the optimal contact area 5116 may be the lateral anterior region of the proximal tibia just distal of the tibial plateau edge and lateral of the tuberosity of the tibia.

In one embodiment, the optimal contact areas 5114 and 5116 matingly corresponds to the jig's bone mating surface 40 such that the portions of the contour lines 4708 indicated by regions 5114 and 5116 may be used to generate the jig's bone mating surface 40, per the algorithm 2500 of FIG. 45E. Conversely, per the algorithm 2500, the portions of the contour lines 4708 outside regions 5114 and 5116 may be subjected to the overestimation process discussed above such that the jig's surfaces created from the overestimated contour line portions results in jig surfaces that do not contact the corresponding portions of the patient's arthroplasty target regions.

As can be understood from the preceding discussion, the overestimation process disclosed herein can be used to identifying optimal target areas (e.g., optimal target areas 4814, 4816, 4912, 5012, 5114, 5116 as discussed with respect to FIGS. 48I-48M). More specifically, the overestimation process disclosed herein can employ these optimal target areas to generate the bone mating surfaces 40 of the jigs 2 while causing the other surface areas of the jigs to be configured such that these other jig surface areas will not contact the surfaces of the arthroplasty target areas when the jig's bone mating surfaces 40 have matingly received and contacted the arthroplasty target areas. The result is a jig that has bone mating surfaces 40 that are based on the regions of the arthroplasty target region that are most accurately represented via 3D computer modeling and most likely to be machinable into the jig. Such a jig provides an increased accuracy of fit between the jig's mating surface 40 and the arthroplasty target areas of the patient's bone.

For most patients, it is common that the overestimation process outlined in FIG. 45E will result in certain areas of the tibial arthroplasty target region being identified as the optimal target areas discussed above with respect to FIGS. 48I-48M. For example, as depicted in FIG. 49A, which is proximal-sagittal isometric view of a tibial proximal end 5200, a commonly encountered, healthy, non-deformed tibial proximal end 5200 may have an arthroplasty target region 5202 with certain optimal target regions 5204, 5206 and 5208. These optimal target regions 5204, 5206 and 5208 commonly identified on most patients via the overestimation process of FIG. 45E are indicated in FIG. 49A by the cross-hatched regions. It has been found that these optimal target regions 5204, 5206 and 5208 are the regions of the arthroplasty target region 5202 that are most likely to satisfy the criterion $w_i$, $\theta_C$ and $\varphi_C$ of blocks 2508 and 2514 of FIG. 45E. Therefore, these target regions 5204, 5206 and 5208 may be used to generate the jig's bone mating surfaces 40.

While, in one embodiment, the overestimation process of FIG. 45E is likely to result in optimal target regions such as those indicated via the cross-hatching regions 5204, 5206 and 5208, in other embodiments, the optimal target regions may result in target regions in other locations on the tibial proximal end 5200 that are in addition to, or in place of, those regions 5204, 5206 and 5208 depicted in FIG. 49A.

One of the benefits of the overestimation process of FIG. 45E is that it identifies two types of contour lines 210*y*, the first type being those contour lines that are most likely to be unacceptable for the generation a jig's bone mating surfaces 40, and the second type being those contour lines that are most likely to be acceptable for the generation of a jig's bone mating surfaces 40. The first type of contour lines are unlikely to be acceptable for the generation of a jig's bone mating surfaces 40 because they pertain to bone surfaces that are too varied to be accurately 3D computer modeled and/or are such that they are not readily machinable into the jig blank. Conversely, the second type of contour lines are likely to be acceptable for the generation of a jig's bone mating surfaces 40 because they pertain to bone surfaces that vary such an insubstantial amount that they can be accurately 3D computer modeled and are such that they are readily machinable into the jig blank. While optimal target regions 5204, 5206 and 5208 represent regions likely corresponding to contour lines of the second type for most commonly encountered patients, the overestimation processes disclosed herein may be adapted to result in other or additional optimal target regions.

In some instances the entirety of the target regions 5204, 5206 and 5208 may correspond to the second type of contour lines, namely those type of contour lines that satisfy the criterion $w_i$, $\theta_C$ and $\varphi_C$ of blocks 2508 and 2514 of FIG. 45E. In such instances, the entirety of the target regions 5204, 5206 and 5208 are matingly contacted by the jig's bone mating surface 40.

However, in some instances one or more potions of one or more of the target regions 5204, 5206 and 5208 may be subjected to overestimation so that the jig's bone mating surface 40 does not contact such portions of the target regions 5204, 5206 and 5208, although the jig's bone mating surface 40 still matingly contacts the other portions of the target regions 5204, 5206 and 5208 corresponding to the second type of contour lines. Such a situation may arise, for example, where a substantial surface variation (e.g., a hole, deformity or osteophyte) exists on a tibial plateau articular surface 5218, 5219 that meets the criterion $w_i$, $\theta_C$ and $\varphi_C$ of blocks 2508 and 2514 for the rest of its surface.

The overestimation process disclosed herein may result in the identification of target regions 5204, 5206 and 5208 that are most likely to result in bone mating surfaces 40 of jigs 2 that are readily machinable into the jigs 2 and most likely to facilitate reliable and accurate mating of the jigs to the arthroplasty target regions. The overestimation process results in such accurate and reliable bone mating surfaces 40 while causing other surfaces of the jigs 2 corresponding to less predictable bone surfaces to not contact the bone surfaces when the bone mating surfaces 40 matingly receive the target regions 5204, 5206 and 5208 of the actual arthroplasty target region.

As indicated in FIG. 49A by the cross-hatched regions, optimal target regions 5204, 5206 and 5208 may include three general areas of the tibial plateau 5210. For example, the anterior optimal target region 5204 may include the anterior portion of the tibial proximal end 5200 just distal of the anterior edge 5212 of the tibia plateau 5210 and just proximal of the tibial tuberosity 5214, the anterior optimal target region 5204 extending both medial and lateral of the tuberosity. Also, for example, the medial optimal target region 5206 may include the articular portion of the medial tibial plateau 5220 (i.e., the portion of the medial tibial plateau 5224 that articulates against the articulate surface of the medial femoral condyle), and the lateral optimal target region 5208 may include the articular portion of the lateral tibial plateau 5222 (i.e., the portion of the lateral tibial plateau 5226 that articulates against the articulate surface of the lateral femoral condyle).

As indicated in FIG. 49A, the tibial proximal end 5200 may include a medial tibial plateau 5224, a lateral tibial plateau 5226, a tibial spine 5228 separating the two plateaus 5224, 5226, a tibial tuberosity 5214, and a tibial shaft 5230 extending distally from the tibial plateau region 5210. Each plateau 5224 and 5226 includes an articular surface 5220 and 5222 that articulates against corresponding articular surfaces of the femoral condyles.

As indicated in FIG. 49E, which is a coronal view of the anterior side of the tibial proximal end 5200, the medial tibial plateau 5224 and lateral tibial plateau 5226 converge to form the tibial spine 5228, which separates the two plateaus 5224, 5226 and forms the intercondyloid eminence 52E1. The tibial shaft 5230 distally extends from the tibial plateau region 5210, and the tibial tuberosity 5214 is located on a proximal region of the shaft 5230. The lateral meniscus is indicated at 52E2, the capsule is indicated at the dashed line at 52E3, the lateral condyle is located at 52E4, the biceps and the anterior tibio-fibular ligament are indicated at 52E5, the fibular lateral ligament is indicated at 52E6, the lateral digitorum longus is indicated at 52E7, the lateral surface of the tibia shaft or tibialis anterior is indicated at 52E17, the semitendinosus is indicated at 52E8, the sartorius is indicated at 52E9, the graoilis is indicated at 52E10, the distal portion of the ligamentum patella is indicated at 52E11, the tibial lateral ligament is indicated at 52E12, the medial condyle is indicated at 52E13, the anterior crucial ligament is indicated at 52E14, the coronary ligament is indicated at 52E15, and the medial meniscus is indicated at 52E16.

As indicated in FIG. 49A by the cross-hatching, in one embodiment, the medial optimal target region 5206 may be generally coextensive with the medial articular surface 5220 that articulates against the respective articulate surface of the medial femoral condyle. In one embodiment, the medial optimal target region 5220 may extend: anterior-posterior between the anterior edge 5240 and posterior edge 5242 of the medial tibial plateau 5224; and lateral-medial between the medial side 5446 of the medial tibial plateau 5224 and the medial base 5248 of the medial tibial spine. In one embodiment as can be understood from FIG. 49A, the medial optimal target region 5206 may be the entire cross-hatched region 5206 or any one or more portions of the cross-hatched region 5206.

In one embodiment as indicated in FIG. 49A by the double cross-hatching, a medial target area 5206A may be identified within the medial optimal target region 5206 via the overestimation process disclosed herein. Thus, although the medial optimal target region 5206 may be generally coextensive with the medial articular surface 5220, the actual area within the medial optimal target region 5206 identified as being a reliable surface for the generation of the mating surfaces of arthroplasty jigs may be limited to a medial target area 5206A, the remainder of the medial optimal target region 5206 being subjected to the overestimation process. The medial target area 5206A may be located near a central portion of the optimal target region 5206.

As indicated in FIG. 49A by the cross-hatching, in one embodiment, the lateral optimal target region 5208 may be generally coextensive with the lateral articular surface 5222 that articulates against the respective articulate surface of the lateral femoral condyle. In one embodiment, the lateral optimal target region 5222 may extend: anterior-posterior between the anterior edge 5250 and posterior edge 5252 of the lateral tibial plateau 5226; and lateral-medial between the lateral side 5256 of the lateral tibial plateau 5226 and the lateral base 5258 of the lateral tibial spine. In one embodiment as can be understood from FIG. 49A, the lateral optimal target region 5208 may be the entire cross-hatched region 5208 or any one or more portions of the cross-hatched region 5208.

In one embodiment as indicated in FIG. 49A by the double cross-hatching, a lateral target area 5208A may be identified within the lateral optimal target region 5208 via the overestimation process disclosed herein. Thus, although the lateral optimal target region 5208 may be generally coextensive with the lateral articular surface 5222, the actual area within the lateral optimal target region 5208 identified as being a reliable surface for the generation of the mating surfaces of arthroplasty jigs may be limited to a lateral target area 5208A, the remainder of the lateral optimal target region 5208 being subjected to the overestimation process. The lateral target area 5208A may be located near a central portion of the optimal target region 5208.

As indicated in FIG. 49A by the cross-hatching, in one embodiment, the anterior optimal target region 5204 may be an anterior surface of the tibia plateau region 5202 distal of the joint line or, more specifically, distal of the anterior tibia plateau edge 5212. The anterior optimal target region 5204 may be the anterior region of the proximal end of the tibia extending between the plateau edge 5212 and the proximal edge 5255 of the tibia tuberosity 5214. The anterior target region 5204 may extend distally along the tibia adjacent to the medial and lateral edges 5256, 5257 of the tibia tuberosity 5214. The anterior target region 5204 may extend medially to the anterior medial edge 5260 of the tibia, and laterally to the anterior lateral edge 5261 of the tibia.

As shown in FIG. 49E by the cross-hatching, the anterior optimal target region 5204 may be divided into three sub-regions 5204-1, 5204-2 and 5204-3. The first or medial sub-region 5204-1 may be a generally planar surface region that extends distally from generally the plateau edge 5212 or capsule line 52E3 to a point generally even with the beginning of the distal half to distal third of the tibial tuberosity 5214. The medial sub-region 5204-1 may extend medial-lateral from the medial edge of the medial tibia condyle to a point generally even with a medial edge of the tibial tuberosity 5214. The medial sub-region 5204-1 may generally taper is the distal direction to be generally triangular.

The second or middle sub-region 5204-2 may be a generally planar surface region that extends distally from generally the plateau edge 5212 or capsule line 52E3 to a point near the proximal boundary of the tibial tuberosity 5214. The middle sub-region 5204-2 may extend medial-lateral from the lateral edge of the medial sub-region 5204-1 to a point generally even with a lateral edge of the tibial tuberosity 5214. The first sub-region 5204-1 may be generally rectangular, with the long length extending medial-lateral.

The third or lateral sub-region 5204-3 may be a generally planar surface region that extends distally from generally the plateau edge 5212 or capsule line 52E3 to a point generally even with the beginning of the distal two-thirds to distal three-quarters of the tibial tuberosity 5214. The lateral sub-region 5204-3 may extend medial-lateral from the lateral edge of the middle sub-region 5204-2 to a lateral edge of the lateral tibia condyle. The lateral sub-region 5204-3 may generally taper is the distal direction to be generally triangular.

In one embodiment as can be understood from FIGS. 49A and 49E, the anterior target region 5204 may be the entire cross-hatched region 5204 or any one or more sub-regions 5204-1, 5204-2, 5204-3 of the cross-hatched region 5204 or any one or more portions of the sub-regions 5204-1, 5204-2, 5204-3. For example, as indicated by the double cross-hatching, each sub-region 5204-1, 5204-2 and 5204-3 may have a respective target area 5204-1A, 5204-2A and 5204-3A therein that may be identified via the overestimation process disclosed herein. Thus, although the anterior optimal target region 5204, or more specifically, its sub-regions 5204-1, 5204-2, 5204-3 may be generally coextensive with the three generally planar surface areas identified above with respect to FIG. 49E, the actual areas within the anterior optimal target region 5204 identified as being a reliable surface for the generation of the mating surfaces of arthroplasty jigs may be limited to an target areas 5204-1A, 5204-2A and 5204-3A, the remainder of the sub-regions 5204-1, 5204-2, 5204-3 being subjected to the overestimation process. The anterior target areas 5204-1A, 5204-2A and 5204-3A may be located any where within the respective sub-regions 5204-1, 5204-2, 5204-3.

FIGS. 49B-C and are, respectively, top and bottom perspective views of an example customized arthroplasty tibial jig 2B that has been generated via the overestimation process disclosed herein. Similar to the femoral jig 2A depicted in FIGS. 1H and 1I, the tibia jig 2B of FIGS. 49B-C includes an interior or bone-facing side 104 and an exterior side 106. When the jig 2B is mounted on the arthroplasty target region during a surgical procedure, the bone-facing side 104 faces the surface of the arthroplasty target region while the exterior side 106 faces in the opposite direction.

The interior or bone-facing side 104 of the tibia cutting jig 2B includes bone mating surfaces 40-5204, 40-5206 and 40-5208 that: are machined into the jig interior or bone-facing side 104 based on contour lines that met the criterion of blocks 2508 and 2514 of FIG. 45E; and respectively correspond to the optimal target regions 5204, 5206 and 5208 of FIG. 49A. The rest 104' of the interior or bone-facing side 104 (i.e., the regions 104' of the interior or bone facing sides 104 outside the bounds of bone mating surfaces 40-5204, 40-5206 and 40-5208) are the result of the overestimation process wherein the corresponding contour lines failed to meet one or more of the criterion of blocks 2508 and 2514 of FIG. 45E and, consequently, were moved away from the bone surface. As a result, the interior side surface 104' is machined to be spaced away from the bone surfaces of the arthroplasty target region so as to not contact the bone surfaces when the bone mating surfaces 40-5204, 40-5206 and 40-5208 matingly receive and contact the bone surfaces of the arthroplasty target region corresponding to regions 5204, 5206 and 5208.

As can be understood from FIG. 49C, the medial bone mating surface 40-5206 may include a smaller sub region bone mating surface 40-5206A, with the area of the medial bone mating surface 40-5206 outside the smaller sub region mating surface 40-5206A being the result of the overestimation process so as to not contact the corresponding bone surface when the smaller sub region mating surface 40-5206A matingly receives and contacts its corresponding bone surface. The smaller sub region bone mating surface 40-5206A may be configured and positioned in the jig inner surface 100 to matingly receive and contact the optimal target area 5206A discussed above with respect to FIGS. 49A and 49E.

As can be understood from FIG. 49C, the lateral bone mating surface 40-5208 may include a smaller sub region bone mating surface 40-5208A, with the area of the lateral bone mating surface 40-5208 outside the smaller sub region mating surface 40-5208A being the result of the overestimation process so as to not contact the corresponding bone surface when the smaller sub region mating surface 40-5208A matingly receives and contacts its corresponding bone surface. The smaller sub region bone mating surface 40-5208A may be configured and positioned in the jig inner surface 100 to matingly receive and contact the optimal target area 5208A discussed above with respect to FIGS. 49A and 49E.

As can be understood from FIG. 49C, depending on the patient's bone topography, the overestimation process disclosed herein may result in an anterior bone mating surface 40-5204 that is actually multiple bone mating surfaces have sub region mating surfaces that may be substantially smaller than surface 5204 depicted in FIGS. 49A and 49E. For example, the anterior bone mating surface 40-5204 may actually be made of an anterior medial bone mating surface 40-5204-1, an anterior middle bone mating surface 40-5204-2 and an anterior lateral bone mating surface 40-5204-3. These mating surfaces 40-5204-1, 40-5204-2, 40-5204-3 may have respective sub region bone mating surfaces 40-5204-1A, 40-5204-2A, 40-5204-3A, with the areas of the mating surfaces 40-5204-1, 40-5204-2, 40-5204-3 outside the respective sub region bone mating surfaces 40-5204-1A, 40-5204-2A, 40-5204-3A being the result of the overestimation process so as to not contact the corresponding bone surfaces when the respective sub region bone mating surfaces 40-5204-1A, 40-5204-2A, 40-5204-3A matingly receive and contact their respective corresponding bone surfaces. The sub region bone mating surfaces 40-5204-1A, 40-5204-2A, 40-5204-3A may be configured and positioned in the jig inner surface 100 to matingly receive and contact the respective optimal target areas 5204-1A, 5204-2A, 5204-3A discussed above with respect to FIGS. 49A and 49E.

As can be understood from FIG. 49D, which is a anterior-posterior cross-section of the tibia jig 2B of FIGS. 49B-C mounted on the tibial proximal end 5200 of FIG. 49A, the interior or bone-facing side 104 is formed of bone mating surfaces 40-5204, 40-5206 and 40-5208 and spaced-apart surfaces 104' (i.e., bone-facing surfaces 104 that are a product of the overestimation process and are spaced-apart from the corresponding bone surfaces of the arthroplasty target region 5202). As indicated by the plurality of opposed arrows in regions 5284, 5286 and 5288, the bone mating surfaces 40-5204, 40-5206 and 40-5208 matingly receive and contact the corresponding bone surfaces 5204, 5206 and 5208 to form mating surface contact regions 5284, 5286 and 5288. Conversely, the spaced-apart surfaces 104' are spaced apart from the corresponding bone surfaces to form spaced-apart non-contact regions 5299, wherein the spaced-apart surfaces 104' do not contact their corresponding bone surfaces. In addition to having the mating surfaces 40-5204, 40-5206 and 40-5208 and the spaced-apart surfaces 104', the tibia jigs 2B may also have a saw cutting guide slot 30 and anterior and posterior drill holes 45N and 32P, as discussed above.

The arrows in FIG. 49D represent a situation where the patient's bone topography and the resulting overestimation process has generated bone mating surfaces 40-5204, 40-5206 and 40-5208 that match the target regions 5204, 5206 and 5208, which are generally coextensive with the entirety of their respective potential regions as discussed above. Of course, where the patient's bone topography and the resulting overestimation process generates bone mating surfaces 40-5204-1A, 40-5204-2A, 40-5204-3A, 40-5206A and 40-5208A that match the target areas 5204-1A, 5204-2A, 5204-3A, 5206A and 5208A, which may be substantially smaller than their respective target regions 5204-1, 5204-2, 5204-3, 5206 and 5208, the mating surface contact regions 5284, 5286 and 5288 may be smaller and/or segmented as compared to what is depicted in FIG. 49D.

FIG. 49F depicts closed-loop contour lines 5302, 5304, and 5306 that are image segmented from image slices, wherein the contour lines outline the cortical bone surface of the upper end of the tibia. These contour lines 5302, 5304, and 5306 may be identified via image segmentation techniques from medical imaging slices generated via, e.g., MRI or CT.

As shown in FIG. 49F, there are posterior portions of the contour lines (indicated as 5307) that may be of no interest during overestimation because the contour line region 5307 corresponds to a region of the knee that may be inaccessible during surgery and may not correspond to a jig surface because no part of the jig may access the region 5307 during surgery. There are also portions of the contour lines (indicated as 5309) which may correspond generally to the plateau edge 5212 and may not correspond to a jig surface because no part of the jig may abut against or matingly engage this contour line region 5309. An osteophyte in contour line region 5308 may be identified based on the algorithm 2500. The contour lines in region 5308 may be subsequently overestimated (based on the algorithm 2500) such that the resulting jig surface does not come into contact with the osteophyte (i.e., with the osteophyte bone surface represented by contour line region 5308) when the jig's bone mating surface 40 matingly receives and contacts the bone surfaces of the arthroplasty target region. Additionally, optimal contour line regions 5310 and 5312 may be identified during execution of the algorithm 2500 as areas of the patient's bone anatomy that have surface variations within the angular criteria of the algorithm 2500 and, therefore, are used to generate the jig's bone mating surface 40 that matingly receives and contacts the bone surfaces of the arthroplasty target region.

Contour line region 5310 may pertain to region 5204 of FIG. 49A and tibia jig region 40-5204 of FIG. 49B. Contour line region 5312 may pertain to either region 5206 or 5208 of FIG. 49A and either tibia jig region 40-5206 or 40-5208 of FIG. 49C.

Utilizing the optimal areas 4310 and 4312 as jig bone mating surfaces 40 allows irregular areas of the patient's bone anatomy to be accommodated without affecting the fit of the jig 2 to the patient's bone anatomy. In fact, an accurate and custom fit between the jig 2 and the patient's bone anatomy can be made by using only a few of such optimal areas. This allows substantial overestimation of the jig surface in regions corresponding to irregularities, thereby preventing the irregularities from interfering with an accurate and reliable fit between the jig's bone mating surfaces and those bone surfaces of the arthroplasty target region corresponding to those bone mating surfaces. The result of the overestimation process is a jig with bone mating surfaces that offer a reliable and accurate custom fit with the arthroplasty target region. This may result in an increased success rate for TKR or partial knee replacement surgery because the jig may custom fit to the most reliable bone surfaces and be deliberately spaced from the bone surfaces that may be unreliable, for example, because of imaging or tool machinery limitations.

As can be understood from FIGS. 49G and 49H, which are respectively anterior isometric views of the femur 3900 and tibia 5200, a patient's bones 3900, 5200 may have regions that are more likely to be accurately computer modeled from two dimensional medical image slices than other regions of the patient's bones. Examples of such regions 3904, 3906, 3908, 5204-1, 5204-2, 5204-3, 5206, and 5208 and how to determine such regions are provided in the preceding discussion and also indicated in FIGS. 49G and 49H.

With respect to the articular regions 3906, 3908, 5206 and 5208 of the femur 3900 and tibia 5200, in one embodiment, where the analysis of blocks 2508 and 2514 of FIG. 45E indicate that there is little, if any contour line variation along a specific contour line or between adjacent contour lines, these regions 3906, 3908, 5206 and 5208 of the femur 3900 and tibia 5200 may be understood to most closely approximate circumferential surfaces 5400, 5500 of cylinders 5402, 5504 each having an axis 5406, 5408, 5506, 5508 extending medial-lateral and having their respective circumferential surfaces 5400, 5500 superimposed onto the articular regions 3906, 3908, 5206, 5208. Accordingly, such regions 3906, 3908, 5206, 5208 may be likely to be readily accurately computer modeled.

In one embodiment, the circumferential surfaces 5400, 5500 may be correspond to an elliptical cylinder having an elliptical cross section transverse to its axis 5406, 5408, 5506, 5508 and having its elliptical major axis extending generally anterior-posterior and is elliptical minor axis extending generally proximal-distal. In one embodiment, the circumferential surfaces 5400, 5500 may be correspond to an circular cylinder having an circular cross section transverse to its axis 5406, 5408, 5506, 5508.

It should be noted that the overestimation process discussed above with respect to FIGS. 45A-49H is useful for the generation of customized arthroplasty jigs, regardless of whether the arthroplasty jigs are configured to produce natural alignment or zero degree or mechanical axis alignment for the patient's knee undergoing the arthroplasty procedure. Also, the overestimation process discussed above may be employed for both the generation of jigs for total knee arthroplasty and partial or uni-compartmental knee arthroplasty. Furthermore, while the overestimation process is discussed in the context of knee arthroplasty, those skilled in the art will readily recognize that the concepts taught herein may be employed for the production of jigs for other types of joint arthroplasty, including, for example, arthroplasty for hip, ankle, elbow, shoulder, wrist, toe joint, finger joint, vertebra-vertebra interfaces, vertebra-pelvis interfaces, vertebra-skull interfaces, etc. Accordingly, the overestimation processes and resulting jigs disclosed herein should be considered as being for all types of arthroplasty procedures.

IV. Overview of Pre-operative Surgical Planning Process

Section II. of the present disclosure describes the acquisition of medical images, the segmentation or auto-segmentation of the medical images, and the generation of a patient bone model from the segmented images that is representative of the bones of the patient in a deteriorated or degenerated state. Section III. of the present disclosure describes an overestimation process where certain areas of the bone in the medical images are identified for generating mating jig surfaces, and certain areas of the bone in the medical images are identified as non-mating areas between a jig and the bone surface. Beginning in Section IV., the present disclosure describes exemplary methods of implant planning (e.g., determining coordinate locations for resections, implant sizes) utilizing the bone models or image data (e.g., 2D image slices, restored 2D image slices) described previously. As described herein, the implant planning may take place utilizing the image data (e.g., 2D image slices) of the bone models representative of the patient's bones in a pre-deteriorated state (described in Section III) or a deteriorated state (described in Section II).

Disclosed herein are customized arthroplasty jigs 2 and systems 4 for, and methods of, producing such jigs 2. The jigs 2 are customized to fit specific bone surfaces of specific patients. Depending on the embodiment, the jigs 2 are automatically planned and generated and may be similar to those disclosed in these three U.S. patent applications: U.S. patent application Ser. No. 11/656,323 to Park et al., titled "Arthroplasty Devices and Related Methods" and filed Jan. 19, 2007, now U.S. Pat. No. 9,017,336; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. patent applications are incorporated by reference in their entireties into this Detailed Description.

A. Overview of System and Method for Manufacturing Customized Arthroplasty Cutting Jigs For an overview discussion of the systems 4 for, and methods of, producing the customized arthroplasty jigs 2, reference is made to FIGS. 1A-1I AND 50A-50E. FIG. 1A is a schematic diagram of a system 4 for employing the automated jig production method disclosed herein. FIGS. 50A-50E are flow chart diagrams outlining the jig production method disclosed herein. The following overview discussion can be broken down into three sections.

The first section, which is discussed with respect to FIG. 1A and [blocks 100-125] of FIGS. 50A, 50B, 50C, and 50E, pertains to an example method of determining, in a two-dimensional ("2D") computer model environment, saw cut and drill hole locations 30, 32 relative to 2D images 16 of a patient's joint 14. The resulting "saw cut and drill hole data" 44 is planned to provide saw cuts 30 and drill holes 32 that will allow arthroplasty implants to restore the patient's joint to its pre-degenerated or natural alignment state.

Figure 50A:
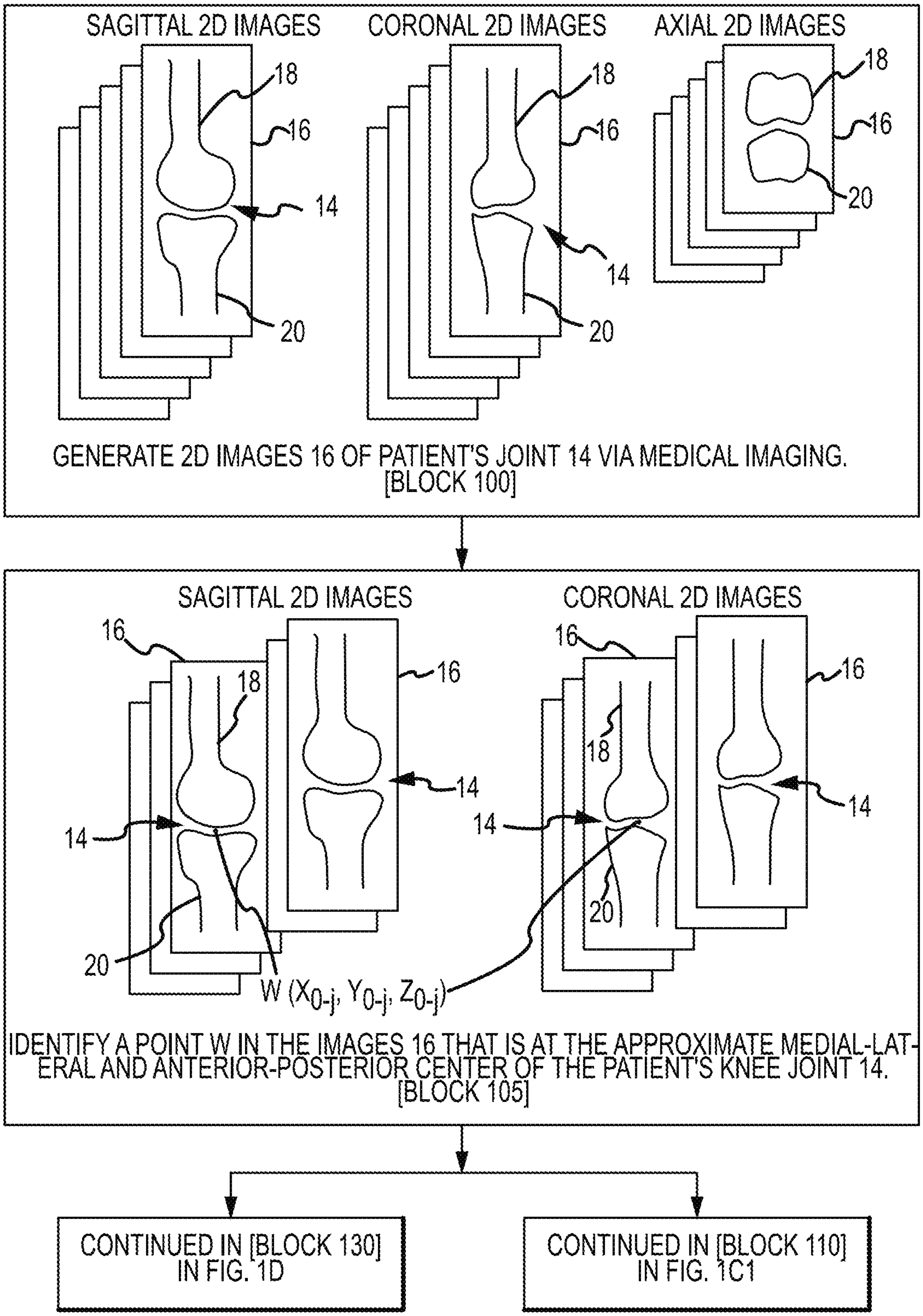
Figure 50D:
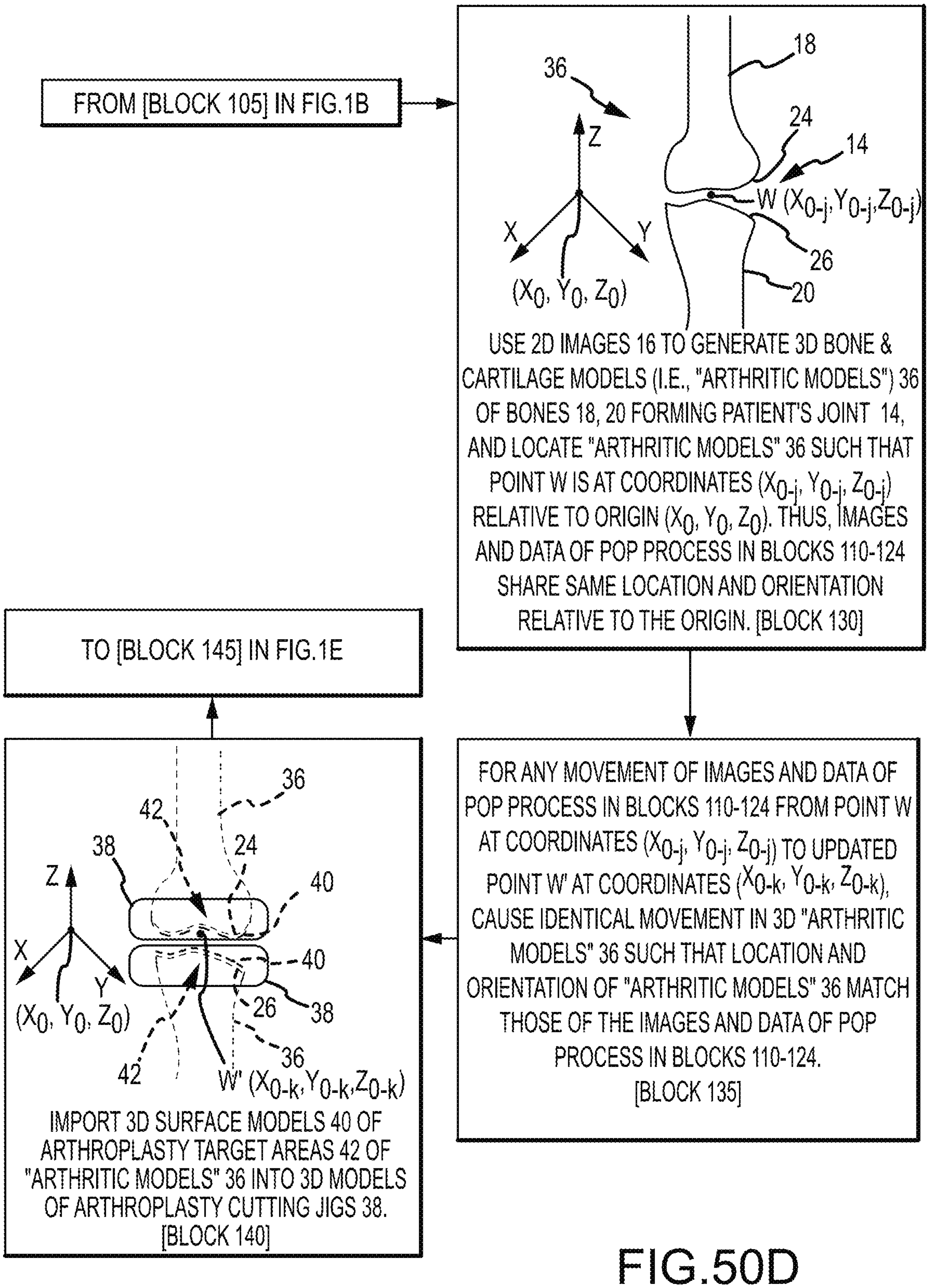
Figure 50E:
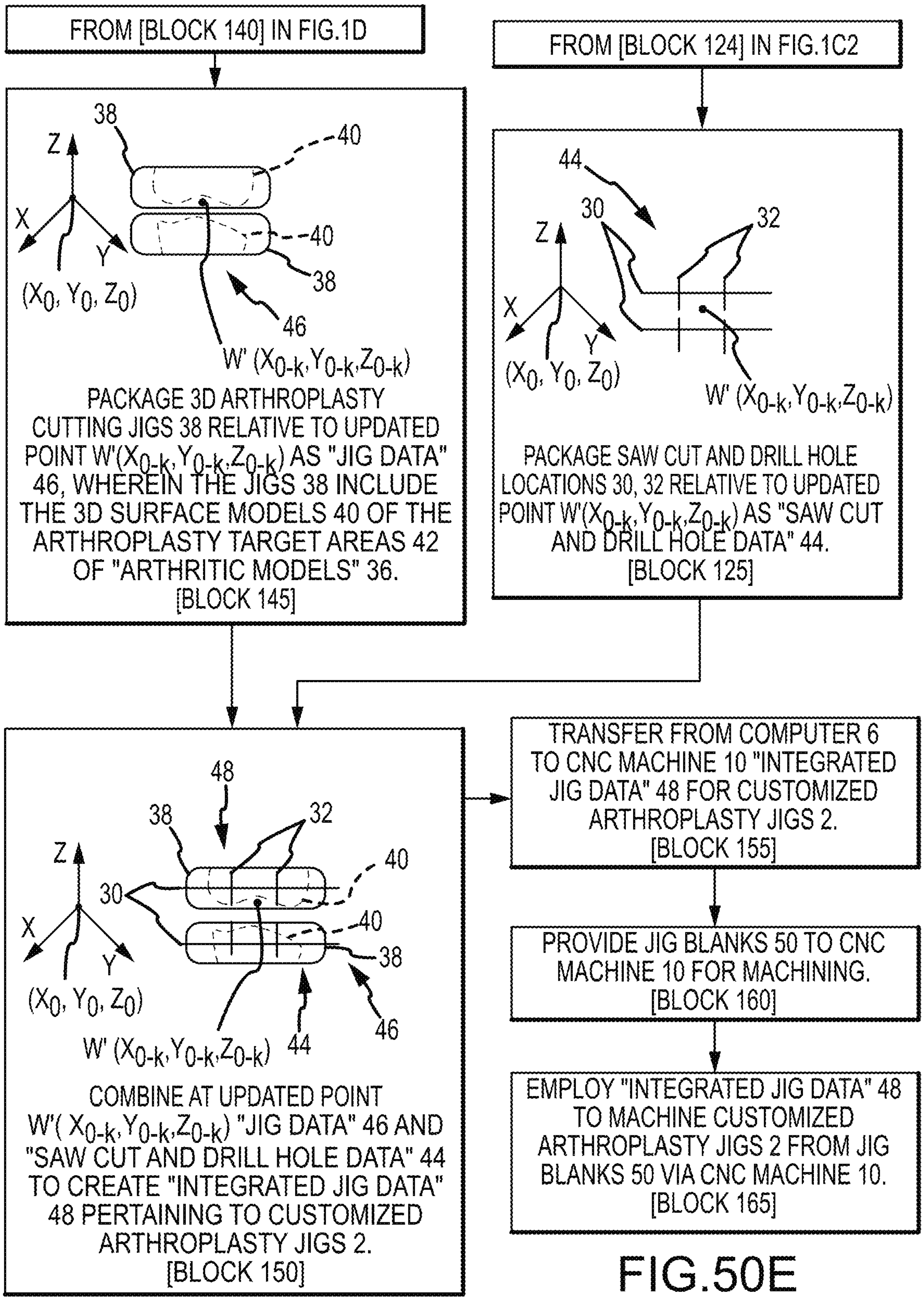

The second section, which is discussed with respect to FIG. 1A and [blocks 100-105 and 130-145] of FIGS. 50A, 50D, and 50E, pertains to an example method of importing into 3D computer generated jig models 38 3D computer generated surface models 40 of arthroplasty target areas 42 of 3D computer generated arthritic models 36 of the patient's joint bones. The resulting "jig data" 46 is used to produce a jig customized to matingly receive the arthroplasty target areas of the respective bones of the patient's joint.

The third section, which is discussed with respect to FIG. 1A and [blocks 150-165] of FIG. 50E, pertains to a method of combining or integrating the "saw cut and drill hole data" 44 with the "jig data" 46 to result in "integrated jig data" 48. The "integrated jig data" 48 is provided to the CNC machine 10 or other rapid production machine (e.g., a stereolithography apparatus ("SLA") machine) for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to generally restore the patient's joint line to its pre-degenerated state or natural alignment state.

As shown in FIG. 1A, the system 4 includes a computer 6 having a CPU 7, a monitor or screen 9 and an operator interface controls 11. The computer 6 is linked to a medical imaging system 8, such as a CT or MRI machine 8, and a computer controlled machining system 10, such as a CNC milling machine 10.

As indicated in FIG. 1A, a patient 12 has a joint 14 (e.g., a knee, elbow, ankle, wrist, hip, shoulder, skull/vertebrae or vertebrae/vertebrae interface, etc.) to be replaced. The patient 12 has the joint 14 scanned in the imaging machine 8. The imaging machine 8 makes a plurality of scans of the joint 14, wherein each scan pertains to a thin slice of the joint 14.

As can be understood from FIG. 50A, the plurality of scans is used to generate a plurality of two-dimensional ("2D") images 16 of the joint 14 [block 100*z*]. Where, for example, the joint 14 is a knee 14, the 2D images will be of the femur 18 and tibia 20. The imaging may be performed via CT or MRI. In one embodiment employing MRI, the imaging process may be as disclosed in U.S. patent application Ser. No. 11/946,002 to Park, which is entitled "Generating MRI Images Usable For The Creation Of 3D Bone Models Employed To Make Customized Arthroplasty Jigs," was filed Nov. 27, 2007 and is incorporated by reference in its entirety into this Detailed Description. The images 16 may be a variety of orientations, including, for example, sagittal 2D images, coronal 2D images and axial 2D images.

As can be understood from FIG. 1A, the 2D images are sent to the computer 6 for analysis and for creating computer generated 2D models and 3D models. In one embodiment, the bone surface contour lines of the bones 18, 20 depicted in the image slices 16 may be auto segmented via an image segmentation process as disclosed in U.S. Patent Application 61/126,102, which was filed Apr. 30, 2008, is entitled System and Method for Image Segmentation in Generating Computer Models of a Joint to Undergo Arthroplasty, and is hereby incorporated by reference into the present application in its entirety.

As indicated in FIG. 50A, in one embodiment, reference point W is identified in the 2D images 16 [block 105]. In one embodiment, as indicated in [block 105] of FIG. 1A, reference point W may be at the approximate medial-lateral and anterior-posterior center of the patient's joint 14. In other embodiments, reference point W may be at any other location in the 2D images 16, including anywhere on, near or away from the bones 18, 20 or the joint 14 formed by the bones 18, 20. Reference point W may be defined at coordinates (X0-j, Y0-j, Z0-j) relative to an origin (X0, Y0, Z0) of an X-Y-Z axis and depicted in FIGS. 50A-50D as W (X0-j, Y0-j, Z0-j). Throughout the processes described herein, to allow for correlation between the different types of images, models or any other data created from the images, movements of such images, models or any other data created form the images may be tracked and correlated relative to the origin.

As described later in this overview, point W may be used to locate the 2D images 16 and computer generated 3D model 36 created from the 2D images 16 respectively with the implant images 34 and jig blank model 38 and to integrate information generated via the POP process. Depending on the embodiment, point W, which serves as a position and/or orientation reference, may be a single point, two points, three points, a point plus a plane, a vector, etc., so long as the reference point W can be used to position and/or orient the 2D images 16, 34 and 3D models 36, 38 relative to each other as needed during the POP process.

As shown in FIG. 50B, the coronal and axial 2D images 16 of the femur 18 forming the patient's joint 14 are analyzed to determine femur reference data [block 110]. For example, the coronal 2D images are analyzed to determine the most distal femur point D1 on a healthy condyle and a joint line perpendicular to a trochlear groove line is used to estimate the location of a hypothetical most distal point D2 on the damaged condyle. Similarly, the axial 2D images are analyzed to determine the most posterior femur point P1 on a healthy condyle and a joint line perpendicular to a trochlear groove line is used to estimate the location of a hypothetical most posterior point P2 on the damaged condyle. The femur reference data points D1, D2, P1, P2 is mapped or otherwise imported to a sagittal or y-z plane in a computer environment and used to determine the sagittal or y-z plane relationship between the femur reference data points D1, D2, P1, P2. The femur reference data D1, D2, P1, P2 is then used to choose candidate femoral implant(s). [Block 112]. The femur reference data points D1, D2, P1, P2 are respectively correlated with similar reference data points D1', D2', P1', P2' of the selected femur implant 34 in a sagittal or y-z plane [block 114]. This correlation determines the locations and orientations of the cut plane 30 and drill holes 32 needed to cause the patient's joint to returned to a natural, pre-deteriorated alignment with the selected implant 34. The cut plane 30 and drill hole 32 locations determined in block 114 are adjusted to account for cartilage thickness [block 118].

As shown in FIG. 50C at block 120, tibia reference data is determined from the images in a manner similar to the process of block 110, except different image planes are employed. Specifically, sagittal and coronal images slices of the tibia are analyzed to identify the lowest (i.e., most distal) and most anterior and posterior points of the tibia recessed condylar surfaces. This tibia reference data is then projected onto an axial view. The tibia reference data is used to select an appropriate tibia implant [Block 121]. The tibia reference data is correlated to similar reference data of the selected tibia implant in a manner similar to that of block 114, except the correlation takes place in an axial view [Block 122]. The cut plane 30 associated with the tibia implant's position determined according to block 122 is adjusted to account for cartilage thickness [Block 123].

Once the saw cut locations 30 and drill hole locations 32 associated with the POP of the femur and tibia implants 34 has been completed with respect to the femur and tibia data 28 (e.g., the 2D femur and tibia images 16 and reference point W), the saw cut locations 30 and drill hole locations 32 are packaged relative to the reference point W(X0-j, Y0-j, Z0-j) [Block 124]. As the images 16 and other data created from the images or by employing the images may have moved during any of the processes discussed in blocks 110-123, the reference point W(X0-j, Y0-j, Z0-j) for the images or associated data may become updated reference point W' at coordinates (X0-k, Y0-k, Z0-k) relative to an origin (X0, Y0, Z0) of an X-Y-Z axis. For example, during the correlation process discussed in blocks 114 and 122, the implant reference data may be moved towards the bone image reference data or, alternatively, the bone image reference data may be moved towards the implant reference data. In the latter case, the location of the bone reference data will move from reference point W(X0-j, Y0-j, Z0-j) to updated reference point W'(X0-k, Y0-k, Z0-k), and this change in location with respect to the origin will need to be matched by the arthritic models 36 to allow for "saw cut and drill hole" data 44 obtained via the POP process of blocks 110-125 to be merged with "jig data" 46 obtained via the jig mating surface defining process of blocks 130-145, as discussed below.

As can be understood from FIG. 50E, the POP process may be completed with the packaging of the saw cut locations 30 and drill hole locations 32 with respect to the updated reference point W'(X0-k, Y0-k, Z0-k) as "saw cut and drill hole data" 44 [Block 125]. The "saw cut and drill hole data" 44 is then used as discussed below with respect to [block 150] in FIG. 50E.

In one embodiment, the POP procedure is a manual process, wherein 2D bone images 28 (e.g., femur and tibia 2D images in the context of the joint being a knee) are manually analyzed to determine reference data to aid in the selection of a respective implant 34 and to determine the proper placement and orientation of saw cuts and drill holes that will allow the selected implant to restore the patient's joint to its natural, pre-deteriorated state. (The reference data for the 2D bone images 28 may be manually calculated or calculated by a computer by a person sitting in front of a computer 6 and visually observing the images 28 on the computer screen 9 and determining the reference data via the computer controls 11. The data may then be stored and utilized to determine the candidate implants and proper location and orientation of the saw cuts and drill holes. In other embodiments, the POP procedure is totally computer automated or a combination of computer automation and manual operation via a person sitting in front of the computer.

In some embodiments, once the selection and placement of the implant has been achieved via the 2D POP processes described in blocks 110-125, the implant selection and placement may be verified in 2D by superimposing the implant models 34 over the bone images data, or vice versa. Alternatively, once the selection and placement of the implant has been achieved via the 2D POP processes described in blocks 110-125, the implant selection and placement may be verified in 3D by superimposing the implant models 34 over 3D bone models generated from the images 16. Such bone models may be representative of how the respective bones may have appeared prior to degeneration. In superimposing the implants and bones, the joint surfaces of the implant models can be aligned or caused to correspond with the joint surfaces of the 3D bone models. This ends the overview of the POP process. A more detailed discussion of various embodiments of the POP process is provided later in this Detailed Description As can be understood from FIG. 50D, the 2D images 16 employed in the 2D POP analysis of blocks 110-124 of FIGS. 50B-50C are also used to create computer generated 3D bone and cartilage models (i.e., "arthritic models") 36 of the bones 18, 20 forming the patient's joint 14 [block 130]. Like the above-discussed 2D images and femur and tibia reference data, the arthritic models 36 are located such that point W is at coordinates (X0-j, Y0-j, Z0-j) relative to the origin (X0, Y0, Z0) of the X-Y-Z axis [block 130]. Thus, the 2D images and femur and tibia data of blocks 110-125 and arthritic models 36 share the same location and orientation relative to the origin (X0, Y0, Z0). This position/orientation relationship is generally maintained throughout the process discussed with respect to FIGS. 50A-50E. Accordingly, movements relative to the origin (X0, Y0, Z0) of the 2D images and femur and tibia data of blocks 110-125 and the various descendants thereof (i.e., bone cut locations 30 and drill hole locations 32) are also applied to the arthritic models 36 and the various descendants thereof (i.e., the jig models 38). Maintaining the position/orientation relationship between the 2D images and femur and tibia data of blocks 110-125 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2, as discussed with respect to block 150 of FIG. 50E.

Computer programs for creating the 3D computer generated arthritic models 36 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

The arthritic models 36 depict the bones 18, 20 in the present deteriorated condition with their respective degenerated joint surfaces 24, 26, which may be a result of osteoarthritis, injury, a combination thereof, etc. The arthritic models 36 also include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 50D and already mentioned above, to coordinate the positions/orientations of the 2D images and femur and tibia data of blocks 110-125 and arthritic models 36 and their respective descendants, any movement of the 2D images and femur and tibia data of blocks 110-125 from point W to point W' is tracked to cause a generally identical displacement for the "arthritic models" 36, and vice versa [block 135].

As depicted in FIG. 50D, computer generated 3D surface models 40 of the arthroplasty target areas 42 of the arthritic models 36 are imported into computer generated 3D arthroplasty jig models 38 [block 140]. Thus, the jig models 38 are configured or indexed to matingly receive the arthroplasty target areas 42 of the arthritic models 36. Jigs 2 manufactured to match such jig models 38 will then matingly receive the arthroplasty target areas of the actual joint bones during the arthroplasty surgical procedure.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly receive the arthroplasty target areas 42 of the arthritic models 36. Point W' (X0-k, Y0-k, Z0-k) can also be imported into the jig models 38, resulting in jig models 38 positioned and oriented relative to point W' (X0-k, Y0-k, Z0-k) to allow their integration with the bone cut and drill hole data 44 of [block 125].

In one embodiment, the procedure for indexing the jig models 38 to the arthroplasty target areas 42 is generally or completely automated, as disclosed in U.S. patent application Ser. No. 11/959,344 to Park, which is entitled System and Method for Manufacturing Arthroplasty Jigs, was filed Dec. 18, 2007, now U.S. Pat. No. 8,221,430 and is incorporated by reference in its entirety into this Detailed Description. For example, a computer program may create 3D computer generated surface models 40 of the arthroplasty target areas 42 of the arthritic models 36. The computer program may then import the surface models 40 and point W' (X0-k, Y0-k, Z0-k) into the jig models 38, resulting in the jig models 38 being indexed to matingly receive the arthroplasty target areas 42 of the arthritic models 36. The resulting jig models 38 are also positioned and oriented relative to point W' (X0-k, Y0-k, Z0-k) to allow their integration with the bone cut and drill hole data 44 of [block 125].

In one embodiment, the arthritic models 36 may be 3D volumetric models as generated from the closed-loop process discussed in U.S. patent application Ser. No. 11/959,344 filed by Park. In other embodiments, the arthritic models 36 may be 3D surface models as generated from the open-loop process discussed in U.S. patent application Ser. No. 11/959,344 filed by Park.

In one embodiment, the models 40 of the arthroplasty target areas 42 of the arthritic models 36 may be generated via an overestimation process as disclosed in U.S. Provisional Patent Application 61/083,053, which is entitled System and Method for Manufacturing Arthroplasty Jigs Having Improved Mating Accuracy, was filed by Park Jul. 23, 2008, and is hereby incorporated by reference in its entirety into this Detailed Description.

As indicated in FIG. 50E, in one embodiment, the data regarding the jig models 38 and surface models 40 relative to point W' (X0-k, Y0-k, Z0-k) is packaged or consolidated as the "jig data" 46 [block 145]. The "jig data" 46 is then used as discussed below with respect to [block 150] in FIG. 50E.

As can be understood from FIG. 50E, the "saw cut and drill hole data" 44 is integrated with the "jig data" 46 to result in the "integrated jig data" 48 [block 150]. As explained above, since the "saw cut and drill hole data" 44, "jig data" 46 and their various ancestors (e.g., 2D images and femur and tibia data of blocks 110-125 and models 36, 38) are matched to each other for position and orientation relative to point W and W', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated state or natural alignment state.

As can be understood from FIGS. 1A and 50E, the "integrated jig data" 44 is transferred from the computer 6 to the CNC machine 10 [block 155]. Jig blanks 50 are provided to the CNC machine 10 [block 160], and the CNC machine 10 employs the "integrated jig data" to machine the arthroplasty jigs 2 from the jig blanks 50 [block 165].

For a discussion of example customized arthroplasty cutting jigs 2 capable of being manufactured via the above-discussed process, reference is made to FIGS. 51A-51D. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 51A-51D are for total knee replacement ("TKR") or partial knee ("uni-knee") replacement procedures. Thus, FIGS. 51A and 51B are, respectively, bottom and top perspective views of an example customized arthroplasty femur jig 2A, and FIGS. 51C and 51D are, respectively, bottom and top perspective views of an example customized arthroplasty tibia jig 2B.

As indicated in FIGS. 51A and 51B, a femur arthroplasty jig 2A may include an interior side or portion 98 and an exterior side or portion 102. When the femur cutting jig 2A is used in a TKR procedure, the interior side or portion 98 faces and matingly receives the arthroplasty target area 42 of the femur lower end, and the exterior side or portion 102 is on the opposite side of the femur cutting jig 2A from the interior portion 98.

The interior portion 98 of the femur jig 2A is configured to match the surface features of the damaged lower end (i.e., the arthroplasty target area 42) of the patient's femur 18. Thus, when the target area 42 is received in the interior portion 98 of the femur jig 2A during the TKR surgery, the surfaces of the target area 42 and the interior portion 98 match. The cutting jig 2A may include one or more saw guiding slots 123 and one or more drill holes 124.

The surface of the interior portion 98 of the femur cutting jig 2A is machined or otherwise formed into a selected femur jig blank 50A and is based or defined off of a 3D surface model 40 of a target area 42 of the damaged lower end or target area 42 of the patient's femur 18.

As indicated in FIGS. 51C and 51D, a tibia arthroplasty jig 2B may include an interior side or portion 104 and an exterior side or portion 106. When the tibia cutting jig 2B is used in a TKR procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR surgery, the surfaces of the target area 42 and the interior portion 104 match.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient's tibia 20. The cutting jig 2B may include one or more saw guiding slots 123 and one or more drill holes 124.

While the discussion provided herein is given in the context of TKR and TKR jigs and the generation thereof, the disclosure provided herein is readily applicable to uni-compartmental or partial arthroplasty procedures in the knee or other joint contexts. Thus, the disclosure provided herein should be considered as encompassing jigs and the generation thereof for both total and uni-compartmental arthroplasty procedures.

The remainder of this Detailed Discussion will now focus on various embodiments for performing POP.

B. Overview of Preoperative Planning ("POP") Procedure

In one embodiment, as can be understood from [blocks 100-110] of FIGS. 50A-50C, medical images 16 of the femur and tibia 18, 20 are generated [blocks 100 and 105] and coronal, axial and sagittal image slices are analyzed to determine reference data 28, 100*z*, 900*z*. [Block 115]. The sizes of the implant models 34 are selected relative to the femur and tibia reference data. [Block 112, 114 and 121, 122]. The reference data 28, 100*z*, 900*z* is utilized with the data associated with implant models 34 to determine the cut plane location. The joint spacing between the femur and the tibia is determined. An adjustment value tr is determined to account for cartilage thickness or joint gap of a restored joint. The implant models 34 are shifted or adjusted according to the adjustment value tr [blocks 118 and 123]. Two dimensional computer implant models 34 are rendered into the two dimensional imaging slice(s) of the bones 28 such that the 2D implant models 34 appear alongside the 2D imaging slices of the bones 28. In one embodiment, ITK software, manufactured by Kitware, Inc. of Clifton Park, N.Y. is used to perform this rendering. Once the 2D implant models 34 are rendered into the MRI/CT image, the proper selection, orientation and position of the implant models can be verified. An additional verification process may be used wherein 3D models of the bones and implants are created and proper positioning of the implant may be verified. Two dimensional computer models 34 and three dimensional computer models 1004*z*, 1006*z* of the femur and tibia implants are generated from engineering drawings of the implants and may be generated via any of the above-referenced 2D and 3D modeling programs to confirm planning. If the implant sizing is not correct, then the planning will be amended by further analysis of the 2D images. If the implant sizing is accurate, then planning is complete. The process then continues as indicated in [block 125] of FIG. 50E.

This ends the overview of the POP process. The following discussions will address each of the aspects of the POP process in detail.

C. Femur and Tibia Images

FIG. 52A depicts 3D bone models or images 28', 28" of the femur and tibia 18, 20 from medical imaging scans 16. While FIG. 52A represents the patient's femur 18 and tibia 20 prior to injury or degeneration (such as, for example, in the case of the femur and tibia restored bone models 28A, 28B of FIGS. 42D and 42E), it can be understood that, in other embodiments, the images 28', 28" may also represent the patient's femur 18 and tibia 20 after injury or degeneration (such as, for example, the femur bone model 22A in FIG. 44A and the tibia bone model 22B in FIG. 44B). More specifically, FIG. 52A is a 3D bone model 28' of a femur lower end 200*z* and an 3D bone model 28" of a tibia upper end 205*z* representative of the corresponding patient bones 18, 20 in a non-deteriorated state and in position relative to each to form a knee joint 14. The femur lower end 200*z* includes condyles 215*z*, and the tibia upper end 205*z* includes a plateau 220*z*. The images or bone models 28', 28" are positioned relative to each other such that the curved articular surfaces of the condyles 215*z*, which would normally mate with complementary articular surfaces of the plateau 220*z*, are instead not mating, but roughly positioned relative to each other to generally approximate the knee joint 14.

As generally discussed above with respect to FIGS. 50A-50C, the POP begins by using a medical imaging process, such as magnetic resonance imaging (MRI), computed tomography (CT), and/or another other medical imaging process, to generate imaging data of the patient's knee. For example, current commercially available MRI machines use 8 bit (255 grayscale) to show the human anatomy. Therefore, certain components of the knee, such as the cartilage, cortical bone, cancellous bone, meniscus, etc., can be uniquely viewed and recognized with 255 grayscale. The generated imaging data is sent to a preoperative planning computer program. Upon receipt of the data, a user or the computer program may analyze the data (e.g., two-dimensional MRI images 16, and more specifically, the 2D femur image(s) 28' or 2D tibia image(s) 28") to determine various reference points, reference lines and reference planes. In one embodiment, the MRI imaging scans 16 may be analyzed and the reference data for POP may be generated by a proprietary software program called PerForm.

For greater detail regarding the methods and systems for computer modeling joint bones, such as the femur and tibia bones forming the knee, please see the following U.S. patent applications, which are all incorporated herein in their entireties: U.S. patent application Ser. No. 11/656,323 to Park et al., titled "Arthroplasty Devices and Related Methods" and filed Jan. 19, 2007, now U.S. Pat. No. 9,017,336; U.S. patent application Ser. No. 10/146,862 to Park et al., titled "Improved Total Joint Arthroplasty System" and filed May 15, 2002; U.S. patent Ser. No. 11/642,385 to Park et al., titled "Arthroplasty Devices and Related Methods" and filed Dec. 19, 2006.

FIG. 52B is an isometric view of a computer model of a femur implant 34' and a computer model of a tibia implant 34" in position relative to each to form an artificial knee joint 14. The computer models 34', 34" may be formed, for example, via computer aided drafting or 3D modeling programs. As will be discussed later in this detailed description, the implant computer models may be in 2D or in 3D as necessary for the particular planning step.

The femur implant model 34' will have a joint side 240*z* and a bone engaging side 245*z*. The joint side 240*z* will have a condyle-like surface for engaging a complementary surface of the tibia implant model 34". The bone engaging side 245*z* will have surfaces and engagement features 250*z* for engaging the prepared (i.e., sawed to shape) lower end of the femur 18.

The tibia implant model 34" will have a joint side 255*z* and a bone engaging side 260*z*. The joint side 255*z* will have a plateau-like surface configured to engage the condyle-like surface of the femur implant model 34'. The bone engaging side 260*z* will have an engagement feature 265*z* for engaging the prepared (i.e., sawed to shape) upper end of the tibia 20.

As discussed in the next subsections of this Detailed Description, the reference data of the femur and tibia bone models or images 28', 28" may be used in conjunction with the implant models 34', 34" to select the appropriate sizing for the implants actually to be used for the patient. The resulting selections can then be used for planning purposes, as described later in this Detailed Description.

D. Femur Planning Process

For a discussion of the femur planning process, reference is now made to FIGS. 53-58. FIGS. 53-58 illustrate a process in the POP wherein the system 4 utilizes 2D imaging slices (e.g., MRI slices, CT slices, etc.) to determine femur reference data, such as reference points, lines and planes via their relationship to the trochlear groove plane-GHO of the femur. The resulting femur reference data 100*z* is then mapped or projected to a y-z coordinate system (sagittal plane). The femur reference data is then applied to a candidate femur implant model, resulting in femoral implant reference data 100*z'*. The data 100*z*, 100*z'* is utilized to select an appropriate set of candidate implants, from which a single candidate implant will be chosen, which selection will be discussed in more detail below with reference to FIGS. 59-71.

1. Determining Femur Reference Data

For a discussion of a process used to determine the femur reference data, reference is now made to FIGS. 53-56C. FIG. 53 is a perspective view of the distal end of a 3D model 1000*z* of the femur image of FIG. 52A wherein the femur reference data 100*z* is shown. As will be explained in more detail below, the femur reference data is generated by an analysis of the 2D image scans and FIG. 53 depicts the relative positioning of the reference data on a 3D model. As shown in FIG. 53, the femur reference data 100*z* may include reference points (e.g. D1, D2), reference lines (e.g. GO, EF) and reference planes (e.g. P, S). The femur reference data 100*z* may be determined by a process illustrated in FIGS. 54A-56D and described in the next sections.

As shown in FIG. 54A, which is a sagittal view of a femur 18 illustrating the orders and orientations of imaging slices 16 that are utilized in the femur POP, a multitude of image slices may be compiled. In some embodiments, the image slices may be analyzed to determine, for example, distal contact points prior to or instead of being compiled into a bone model. Image slices may extend medial-lateral in planes that would be normal to the longitudinal axis of the femur, such as image slices 1-5 of FIGS. 54A and 55D. Image slices may extend medial-lateral in planes that would be parallel to the longitudinal axis of the femur, such as image slices 6-9 of FIGS. 54A and 56B. The number of image slices may vary from 1-50 and may be spaced apart in a 2 mm spacing or other spacing.

a. Determining Reference Points P1P2

In some embodiments, the planning process begins with the analysis of the femur slices in a 2D axial view. As can be understood from FIG. 54B, which depicts axial imaging slices of FIG. 54A, the series of 2D axial femur slices are aligned to find the most posterior point of each condyle. For example, the most posterior points of slice 5, P1A, P2A, are compared to the most posterior points of slice 4, P1B, P2B. The most posterior points of slice 4 are more posterior than those of slice 5. Therefore, the points of slice 4 will be compared to slice 3. The most posterior points of slice 3, P1C, P2C, are more posterior than the posterior points P1B, P2B of slice 4. Therefore, the points of slice 3 will be compared to slice 2. The most posterior points of slice 2, P1D, P2D, are more posterior than the posterior points P1C, P2C of slice 3. Therefore, the points of slice 2 will be compared to slice 1. The most posterior points of slice 1, P1E, P2E, are more posterior than the posterior points P1D, P2D of slice 2. In some embodiments, the points of slice 1 may be compared to slice 0 (not shown). The most posterior points of slice 0, P1F, P2F, are less posterior than the posterior points P1E, P2E of slice 1. Therefore, the points of slice 1 are determined to be the most posterior points P1P2 of the femur. In some embodiments, points P1 and P2 may be found on different axial slices. That is, the most posterior point on the medial side and most posterior point on the lateral side may lie in different axial slices. For example, slice 2 may include the most posterior point on the lateral side, while slice 1 may include the most posterior point on the medial side. It can be appreciated that the number of slices that are analyzed as described above may be greater than five slices or less than five slices. The points P1, P2 are stored for later analysis.

b. Determining Reference Points D1, D2

The planning process continues with the analysis of the femur slices in a 2D coronal view. As can be understood from FIG. 54C, which depicts coronal imaging slices of FIG. 54A, the series of 2D coronal femur slices are aligned to find the most distal point of each condyle. For example, the most distal points of slice 6, D1A, D2A, are compared to the most distal points of slice 7, D1B, D2B. The most distal points of slice 7 are more distal than those of slice 6. Therefore, the points of slice 7 will be compared to slice 8. The most distal points of slice 8, D1C, D2C, are more distal than the distal points D1B, D2B of slice 7. Therefore, the points of slice 8 will be compared to slice 9. The most distal points of slice 9, D1D, D2D, are more distal than the distal points D1C, D2C of slice 8. In some embodiments, the points of slice 9 may be compared to slice 10 (not shown). The most distal points of slice 10, D1E, D2E, are less distal than the distal points D1D, D2D of slice 9. Therefore, the points of slice 9 are determined to be the most distal points D1, D2 of the femur. In some embodiments, points D1 and D2 may be found on different coronal slices. That is, the most distal point on the medial side and most distal point on the lateral side may lie in different coronal slices. For example, slice 9 may include the most distal point on the lateral side, while slice 8 may include the most distal point on the medial side. It can be appreciated that the number of slices that are analyzed as described above may be greater than four slices or less than four slices. The points D1, D2 are stored for future analysis.

c. Determining Reference Lines CD and GO

Analysis of the 2D slices in the axial view aid in the determination of internal/external rotation adjustment. The points D1, D2 represent the lowest contact points of each of the femoral lateral and medial condyles 302*z*, 303*z*. Thus, to establish an axial-distal reference line, line CD, in 2D image slice(s), the analysis utilizes the most distal point, either D1 or D2, from the undamaged femoral condyle. For example, as shown in FIG. 55A, which is an axial imaging slice of the femur of FIG. 54A, when the lateral condyle 302*z* is undamaged but the medial condyle 303*z* is damaged, the most distal point D1 will be chosen as the reference point in establishing the axial-distal reference line, line CD. The line CD is extended from the lateral edge of the lateral condyle, through point D1, to the medial edge of the medial condyle. If the medial condyle was undamaged, then the distal point D2 would be used as the reference point through which line CD would be extended. The distal points D1, D2 and line CD are stored for later analysis.

A line CD is verified. A most distal slice of the series of axial views is chosen to verify the position of an axial-distal reference line, line CD. As shown in FIG. 55A, the most distal slice 300*z* of the femur (e.g., slice 5 in FIGS. 54A and 55D) is chosen to position line CD such that line CD is generally anteriorly-posteriorly centered in the lateral and medial condyles 302*z*, 303*z*. Line CD is generally aligned with the cortical bone of the undamaged posterior condyle. For example, if the medial condyle 303*z* is damaged, the line CD will be aligned with the undamaged lateral condyle, and vice versa. To verify the location of line CD and as can be understood from FIGS. 53 and 55C, the line CD will also connect the most distal points D1, D2. The geography information of line CD will be stored for future analysis.

Line GO is determined. The “trochlear groove axis” or the “trochlear groove reference plane” is found. In the knee flexion/extension motion movement, the patella 304*z* generally moves up and down in the femoral trochlear groove along the vertical ridge and generates quadriceps forces on the tibia. The patellofemoral joint and the movement of the femoral condyles play a major role in the primary structure and mechanics across the joint. In a normal knee model or properly aligned knee, the vertical ridge of the posterior patella is generally straight (vertical) in the sliding motion. For the OA patients’ knees, there is rarely bone damage in the trochlear groove; there is typically only cartilage damage. Therefore, the trochlear groove of the distal femur can serve as a reliable bone axis reference. In relation to the joint line assessment, as discussed with reference to FIGS. 63A-63J, the trochlear groove axis of the distal femur is perpendicular or nearly perpendicular to the joint line of the knee. A detailed discussion of the trochlear groove axis or the trochlear groove reference plane may be found in co-owned U.S. patent application Ser. No. 12/111,924, now U.S. Pat. No. 8,480,679, which is incorporated by reference in its entirety.

To perform the trochlear groove analysis, the MRI slice in the axial view with the most distinct femoral condyles (e.g., the slice with the largest condyles such as slice 400z of FIG. 55B) will be chosen to position the trochlear groove bisector line, line TGB. As shown in FIG. 55B, which is an axial imaging slice of the femur of FIG. 54A, the most distinct femoral condyles 302z, 303z are identified. The trochlear groove 405z is identified from image slice 400z. The lowest extremity 406z of the trochlear groove 405z is then identified. Line TGB is then generally aligned with the trochlear groove 405z across the lowest extremity 406z. In addition, and as shown in FIG. 55D, which is the axial imaging slices 1-5 taken along section lines 1-5 of the femur in FIG. 54A, each of the slices 1-5 can be aligned vertically along the trochlear groove 405z, wherein points G1, G2, G3, G4, G5 respectively represent the lowest extremity 406z of trochlear groove 405z for each slice 1-5. By connecting the various points G1, G2, G3, G4, G5, a point O can be obtained. As can be understood from FIGS. 53 and 55C, resulting line GO is perpendicular or nearly perpendicular to line D1 D2. In a 90° knee extension, line GO is perpendicular or nearly perpendicular to the joint line of the knee and line P1P2. Line GO is stored for later analysis.

d. Determining Reference Lines EF and HO

Analysis of the 2D slices in the coronal view aid in the determination of femoral varus/valgus adjustment. The points P1, P2 determined above represent the most posterior contact points of each of the femoral lateral and medial condyles 302z, 303z. Thus, to establish a coronal posterior reference line, line EF, in 2D image slice(s), the analysis utilizes the most posterior point, either P1 or P2, from the undamaged femoral condyle. For example, as shown in FIG. 56A, when the lateral condyle 302z is undamaged but the medial condyle 303z is damaged, the most posterior point P1 will be chosen as the reference point in establishing the coronal posterior reference line, line EF. The line EF is extended from the lateral edge of the lateral condyle, through point P1, to the medial edge of the medial condyle. If the medial condyle was undamaged, then the posterior point P2 would be used as the reference point through which line EF would be extended. The posterior points P1, P2 and line EF are stored for later analysis.

The points, P1P2 were determined as described above with reference to FIG. 54B. Line EF is then verified. A most posterior slice of the series of coronal views is chosen to verify the position of a coronal posterior reference line, line EF. As shown in FIG. 56A, which is a coronal imaging slice of FIG. 54A, the most posterior slice 401 of the femur (e.g., slice 6 in FIGS. 54A and 56B) is chosen to position line EF such that line EF is generally positioned in the center of the lateral and medial condyles 302z, 303z. Line EF is generally aligned with the cortical bone of the undamaged posterior condyle. For example, if the medial condyle 303z is damaged, the line EF will be aligned with the undamaged lateral condyle, and vice versa. To verify the location of line EF and as can be understood from FIG. 53, the line EF will also connect the most posterior points P1, P2. The geography information of line EF will be stored for future analysis.

In some embodiments, line HO may be determined. As shown in FIG. 56B, which are coronal imaging slices 6-9 taken along section lines 6-9 of the femur in FIG. 54A, each of the image slices 6-9 taken from FIG. 54A can be aligned along the trochlear groove. The points H6, H7, H8, H9 respectively represent the lowest extremity of the trochlear groove for each of the image slices 6-8 from FIG. 54A. By connecting the various points H6, H7, H8, the point O can again be obtained. The resulting line HO is established as the shaft reference line-line SHR. The coronal-posterior reference line, line EF and coronal-distal reference line, line AB may be adjusted to be perpendicular or nearly perpendicular to the shaft reference line-line SHR (line HO). Thus, the shaft reference line, line SHR (line HO) is perpendicular or nearly perpendicular to the coronal-posterior reference line, line EF and to the coronal-distal reference line, line AB throughout the coronal image slices.

As can be understood from FIGS. 53 and 56B, the trochlear groove plane-GHO, as the reference across the most distal extremity of the trochlear groove of the femur and in a 90° knee extension, should be perpendicular to line AB. The line-HO, as the reference across the most posterior extremity of trochlear groove of the femur and in a 0° knee extension, should be perpendicular to line AB.

e. Determining Reference Line AB and Reference Planes P and S

As can be understood from FIG. 53, a posterior plane S may be constructed such that the plane S is normal to line GO and includes posterior reference points P1, P2. A distal plane P may be constructed such that it is perpendicular to posterior plane S and may include distal reference points D1, D2 (line CD). Plane P is perpendicular to plane S and forms line AB therewith. Line HO and line GO are perpendicular or nearly perpendicular to each other. Lines CD, AB and EF are parallel or nearly parallel to each other. Lines CD, AB and EF are perpendicular or nearly perpendicular to lines HO and GO and the trochlear plane GHO.

f. Verification of the Femoral Reference Data

As shown in FIG. 56C, which is an imaging slice of the femur of FIG. 54A in the sagittal view, after the establishment of the reference lines from the axial and coronal views, the axial-distal reference line CD and coronal-posterior reference line EF and planes P, S are verified in the 2D sagittal view. The sagittal views provide the extension/flexion adjustment. Thus, as shown in FIG. 56C, slice 800z shows a sagittal view of the femoral medial condyle 303z. Line-bf and line-bd intersect at point-b. As can be understood from FIGS. 53 and 56C, line-bf falls on the coronal plane-S, and line-bd falls on the axial plane-P. Thus, in one embodiment of POP planning, axial and coronal views are used to generate axial-distal and coronal-posterior reference lines CD, EF. These two reference lines CD, EF can be adjusted (via manipulation of the reference data once it has been imported and opened on the computer) to touch in the black cortical rim of the femur. The adjustment of the two reference lines on the femur can also be viewed simultaneously in the sagittal view of the MRI slice, as displayed in FIG. 56C. Thus, the sagittal view in FIG. 56C provides one approach to verify if the two reference lines do touch or approximately touch with the femur cortical bone. In some embodiments, line-bf is perpendicular or nearly perpendicular to line-bd. In other embodiments, line bf may not be perpendicular to bd. This angle depends at least partially on the rotation of femoral bone within MRI.

With reference to FIGS. 53-56C, in one embodiment, lines HO and GO may be within approximately six degrees of being perpendicular with lines P1P2, D1D2 and A1A2 or the preoperative planning for the distal femur will be rejected and the above-described processes to establish the femoral reference data 100z (e.g. reference lines CD, EF, AB, reference points P1P2, D1D2) will be repeated until the femoral reference data meets the stated tolerances, or a manual segmentation for setting up the reference lines will be performed. In other embodiments, if there are multiple failed attempts to provide the reference lines, then the reference data may be obtained from another similar joint that is sufficiently free of deterioration. For example, in the context of knees, if repeated attempts have been made without success to determined reference data in a right knee medial femur condyle based on data obtained from the right knee lateral side, then reference data could be obtained from the left knee lateral or medial sides for use in the determination of the femoral reference data.

g. Mapping the Femoral Reference Data to a Y-Z Plane

As can be understood from FIGS. 56D-58, the femoral reference data 100_z_ will be mapped to a y-z coordinate system to aid in the selection of an appropriate implant. As shown in FIGS. 56D-56E, which are axial and coronal slices, respectively, of the femur, the points D1D2 of the distal reference line D1D2 or CD were determined from both a 2D axial view and a 2D coronal view and therefore are completely defined in 3D. Similarly, the points P1P2 of the posterior reference line P1P2 or EF were determined from both a 2D axial view and a 2D coronal view and therefore are completely defined in 3D.

As shown in FIG. 57, which is a posterior view of a femur 3D model 1000_z_, the reference data 100_z_ determined by an analysis of 2D images may be imported onto a 3D model of the femur for verification purposes. The distance L between line EF and line CD can be determined and stored for later analysis during the selection of an appropriate implant size.

As indicated in FIG. 58, which depicts a y-z coordinate system, the posterior points P1P2 and distal points D1D2 of the 2D images 28' may also be projected onto a y-z plane and this information is stored for later analysis.

2. Determining Femoral Implant Reference Data

There are 6 degrees of freedom for a femoral implant to be moved and rotated for placement on the femoral bone. The femur reference data 100_z_ (e.g. points P1P2, D1D2, reference lines EF, CD, reference planes P, S) is utilized in the selection and placement of the femoral implant. For a discussion of a process used to determine the implant reference data, reference is now made to FIGS. 59-71.

a. Map Femur Reference Data to Implant Model to Establish Femoral Implant Reference Data As shown in FIGS. 59 and 60, which are perspective views of a femoral implant model 34', the femur reference data 100_z_ may be mapped to a 3D model of the femur implant model 34' in a process of POP. The femur reference data 100_z_ and the femur implant model 34' are opened together. The femur implant model 34' is placed on a 3D coordinate system and the data 100_z_ is also transferred to that coordinate system thereby mapping the data 100_z_ to the model 34' to create femoral implant data 100_z'_. The femoral implant data 100_z'_ includes an axial-distal reference line (line-C'D') and a coronal-posterior reference line (line-E'F').

As can be understood from FIGS. 59 and 60, distal line-D1'D2' represents the distance between the two most distal points D1', D2'. Posterior line-P1'P2' represents the distance between the two most posterior points P1', P2'. The lines—D1'D2' P1'P2' of the implant model 34' can be determined and stored for further analysis.

As shown in FIG. 61, which shows a coordinate system wherein some of the femoral implant reference data 100_z'_ is shown, the endpoints D1'D2' and P1'P2' may also be projected onto a y-z plane and this information is stored for later analysis. As shown in FIG. 62, the implant reference data 100_z'_ may also be projected onto the coordinate system. The distance L' between line E'F' and line C'D', and more specifically between lines D1'D2', P1'P2' can be determined and stored for later use during the selection of an implant.

3. Determining Joint Line and Adjustment to Implant That Allows Condylar Surfaces of Implant Model to Restore Joint to Natural Configuration In order to allow an actual physical arthroplasty implant to restore the patient's knee to the knee's pre-degenerated or natural configuration with the natural alignment and natural tensioning in the ligaments, the condylar surfaces of the actual physical implant generally replicate the condylar surfaces of the pre-degenerated joint bone. In one embodiment of the systems and methods disclosed herein, condylar surfaces of the 2D implant model 34' are matched to the condylar surfaces of the 2D bone model or image 28'. However, because the bone model 28' may be bone only and not reflect the presence of the cartilage that actually extends over the pre-degenerated condylar surfaces, the alignment of the implant 34' may be adjusted to account for cartilage or proper spacing between the condylar surfaces of the cooperating actual physical implants (e.g., an actual physical femoral implant and an actual physical tibia implant) used to restore the joint such that the actual physical condylar surfaces of the actual physical cooperating implants will generally contact and interact in a manner substantially similar to the way the cartilage covered condylar surfaces of the pre-degenerated femur and tibia contacted and interacted. Thus, in one embodiment, the implant models are modified or positionally adjusted to achieve the proper spacing between the femur and tibia implants.

a. Determine Adjustment Value tr

To achieve the correct adjustment, an adjustment value tr may be determined. In one embodiment, the adjustment value tr may be determined in 2D by a calipers measuring tool (a tool available as part of the software). The calipers tool is used to measure joint spacing between the femur and the tibia by selection of two points in any of the 2D MRI views and measuring the actual distance between the points. In another embodiment, the adjustment value tr that is used to adjust the implant during planning may be based off of an analysis associated with cartilage thickness. In another embodiment, the adjustment value tr used to adjust the implant during planning may be based off of an analysis of proper joint gap spacing. Both the cartilage thickness and joint gap spacing methods are discussed below in turn.

i. Determining Cartilage Thickness and Joint Line

FIG. 63A shows the femoral condyle 310_z_ and the proximal tibia of the knee in a sagittal MRI image slice. The distal femur 28' is surrounded by the thin black rim of cortical bone. Due to the nature of irregular bone and cartilage loss in OA patients, it can be difficult to find the proper joint line reference for the models used during the POP.

The space between the elliptical outlining 325_z'_, 325_z"_ along the cortical bone represents the cartilage thickness of the femoral condyle 310_z_. The ellipse contour of the femoral condyle 310_z_ can be seen on the MRI slice shown in FIG. 63A and obtained by a three-point tangent contact spot (i.e., point t1, t2, t3) method. In a normal, healthy knee, the bone joint surface is surrounded by a layer of cartilage. Because the cartilage is generally worn-out in OA and the level of cartilage loss varies from patient to patient, it may be difficult to accurately account for the cartilage loss in OA patients when trying to restore the joint via TKA surgery. Therefore, in one embodiment of the methodology and system disclosed herein, a minimum thickness of cartilage is obtained based on medical imaging scans (e.g., MRI, etc.) of the undamaged condyle. Based on the cartilage information, the joint line reference can be restored. For example, the joint line may be line 630*z* in FIG. 63B.

The system and method disclosed herein provides a POP method to substantially restore the joint line back to a "normal or natural knee" status (i.e., the joint line of the knee before OA occurred) and preserves ligaments in TKA surgery (e.g., for a total knee arthroplasty implant) or partial knee arthroplasty surgery (e.g., for a uni-knee implant).

FIG. 63B is a coronal view of a knee model in extension. As depicted in FIG. 63B, there are essentially four separate ligaments that stabilize the knee joint, which are the medial collateral ligament (MCL), anterior cruciate ligament (ACL), lateral collateral ligament (LCL), and posterior cruciate ligament (PCL). The MCL and LCL lie on the sides of the joint line and serve as stabilizers for the side-to-side stability of the knee joint. The MCL is a broader ligament, whereas the LCL is a distinct cord-like structure.

The ACL is located in the front part of the center of the joint. The ACL is a very important stabilizer of the femur on the tibia and serves to prevent the tibia from rotating and sliding forward during agility, jumping, and deceleration activities. The PCL is located directly behind the ACL and serves to prevent the tibia from sliding to the rear. The system and method disclosed herein provides POP that allows the preservation of the existing ligaments without ligament release during TKA surgery. Also, the POP method provides ligament balance, simplifying TKA surgery procedures and reducing pain and trauma for OA patients.

As indicated in FIG. 63B, the joint line reference 630*z* is defined between the two femoral condyles 302*z*, 303*z* and their corresponding tibia plateau regions 404*z*, 406*z*. Area A illustrates a portion of the lateral femoral condyle 302*z* and a portion of the corresponding lateral plateau 404*z* of tibia 205*z*. Area B illustrates the area of interest showing a portion of the medial femoral condyle 303*z* and a portion of the corresponding medial plateau 406*z* of tibia 205*z*.

FIGS. 63C, 63D and 63F illustrate MRI segmentation slices for joint line assessment. FIG. 63E is a flow chart illustrating the method for determining cartilage thickness used to determine proper joint line. The distal femur 200*z* is surrounded by the thin black rim of cortical bone 645*z*. The cancellous bone (also called trabecular bone) 650*z* is an inner spongy structure. An area of cartilage loss 655*z* can be seen at the posterior distal femur. For OA patients, the degenerative cartilage process typically leads to an asymmetric wear pattern that results in one femoral condyle with significantly less articulating cartilage than the other femoral condyle. This occurs when one femoral condyle is overloaded as compared to the other femoral condyle.

As can be understood from FIGS. 63C, 63E and 63F, the minimum cartilage thickness is observed and measured for the undamaged and damaged femoral condyle 302*z*, 303*z* [block 1170]. If the greatest cartilage loss is identified on the surface of medial condyle 303*z*, for example, then the lateral condyle 302*z* can be used as the cartilage thickness reference for purposes of POP. Similarly, if the greatest cartilage loss is identified on the lateral condyle 302*z*, then the medial condyle 303*z* can be used as the cartilage thickness reference for purposes of POP. In other words, use the cartilage thickness measured for the least damaged condyle cartilage as the cartilage thickness reference for POP [block 1175].

As indicated in FIG. 63D, the thickness of cartilage can be analyzed in order to restore the damaged knee compartment back to its pre-OA status. In each of the MRI slices taken in regions A and B in FIG. 63B, the reference lines as well as the major and minor axes 485*z*, 490*z* of ellipse contours 480*z*', 480*z*" in one femoral condyle 303*z* can be obtained.

As shown in FIG. 63F, for the three-point method, the tangents are drawn on the condylar curve at zero degrees and 90 degrees articular contact points. The corresponding tangent contact spots t1 and t2 are obtained from the tangents. The line 1450*z* perpendicular to the line 1455*z* determines the center of the ellipse curve, giving the origin of (0, 0). A third tangent contact spot t3 can be obtained at any point along the ellipse contour between the zero degree, t1 point and the 90 degree, t2 point. This third spot t3 can be defined as k, where k=1 to n points.

The three-point tangent contact spot analysis may be employed to configure the size and radius of the condyle 303*z* of the femur bone model 28'. This provides the "x" coordinate and "y" coordinate, as the (x, y) origin (0, 0) shown in FIG. 63D. The inner ellipse model 480*z*' of the femoral condyle shows the femoral condyle surrounded by cortical bone without the cartilage attached. The minimum cartilage thickness tmmin outside the inner ellipse contour 480*z*' is measured. Based on the analysis of the inner ellipse contour 480*z*' (i.e., the bone surface) and outer ellipse contour 480*z*" (i.e., the cartilage surface) of the one non-damaged condyle of the femur bone model 28', the inner ellipse contour 480*z*' (i.e., the bone surface) and the outer ellipse contour 480*z*" (i.e., the cartilage surface) of the other condyle (i.e., the damage or deteriorated condyle) may be determined.

As can be understood from FIGS. 63B and 63D, ellipse contours 480*z*', 480*z*" are determined in areas A and B for the condyles 302*z*, 303*z* of the femur bone model 28'. The inner ellipse contour 480*z*', representing the bone-only surface, and the outer ellipse contour 480*z*", representing the bone-and-cartilage surface, can be obtained. The minimum cartilage thickness tmmin is measured based on the cartilage thickness tr between the inner ellipse 480*z*' and outer ellipse 480*z*". MRI slices of the two condyles 302*z*, 303*z* of the femur bone model 28' in areas A and B are taken to compare the respective ellipse contours in areas A and B. If the cartilage loss is greatest at the medial condyle 303*z* in the MRI slices, the minimum thickness tmmin for the cartilage can be obtained from the lateral condyle 302*z*. Similarly, if the lateral condyle 302*z* has the greatest cartilage loss, the cartilage thickness tmmin can be obtained from undamaged medial condyle 303*z* of the femur restored bone model 28'. The minimum cartilage can be illustrated in the formula, tmmin=MIN ($t_i$), where i=1 to k.

ii. Determining Joint Gap

As mentioned above, in one embodiment, the adjustment value tr may be determined via a joint line gap assessment. The gap assessment may serve as a primary estimation of the gap between the distal femur and proximal tibia of the bone images. The gap assessment may help achieve proper ligament balancing.

In one embodiment, an appropriate ligament length and joint gap may not be known from the 2D bone models or images 28', 28" (see, e.g. FIG. 52B) as the bone models or images may be oriented relative to each other in a fashion that reflects their deteriorated state. For example, as depicted in FIG. 63J, which is a coronal view of bone models 28', 28" oriented (e.g., tilted) relative to each other in a deteriorated state orientation, the lateral side 1487*z* was the side of the deterioration and, as a result, has a greater joint gap between the distal femur and the proximal tibia than the medial side 1485*z*, which was the non-deteriorated side of the joint in this example.

In one embodiment, ligament balancing may also be considered as a factor for selecting the appropriate implant size. As can be understood from FIG. 63J, because of the big joint gap in the lateral side 1487*z*, the presumed lateral ligament length (L1+L2+L3) may not be reliable to determine proper ligament balancing. However, the undamaged side, which in FIG. 63J is the medial side 1485*z*, may be used in some embodiments as the data reference for a ligament balancing approach. For example, the medial ligament length (M1+M2+M3) of the undamaged medial side 1485*z* may be the reference ligament length used for the ligament balancing approach for implant size selection.

In one embodiment of the implant size selection process, it may be assumed that the non-deteriorated side (i.e., the medial side 1485*z* in FIG. 63J in this example) may have the correct ligament length for proper ligament balancing, which may be the ligament length of (M1+M2+M3). When the associated ligament length ("ALL") associated with a selected implant size equals the correct ligament length of (M1+M2+M3), then the correct ligament balance is achieved, and the appropriate implant size has been selected. However, when the ALL ends up being greater than the correct ligament length (M1+M2+M3), the implant size associated with the ALL may be incorrect and the next larger implant size may need to be selected for the design of the arthroplasty jig 2.

For a discussion regarding the gap assessment, which may also be based on ligament balance off of a non-deteriorated side of the joint, reference is made to FIGS. 63G and 63H. FIGS. 63G and 63H illustrate coronal views of the bone models 28', 28" in their post-degeneration alignment relative to each as a result of OA or injury. As shown in FIG. 63G, the tibia model 28" is tilted away from the lateral side 1487*z* of the knee 1486*z* such that the joint gap between the femoral condylar surfaces 1490*z* and the tibia condylar surfaces 1491*z* on the lateral side 1487*z* is greater than the joint gap on the medial side 1485*z*.

As indicated in FIG. 63H, which illustrates the tibia in a coronal cross section, the line 1495*z* may be employed to restore the joint line of the knee 1486*z*. The line 1495*z* may be caused to extend across each of lowest extremity points 1496*z*, 1497*z* of the respective femoral lateral and medial condyles 1498*z*, 1499*z*. In this femur bone model 28', line 1495*z* may be presumed to be parallel or nearly parallel to the joint line of the knee 1486*z*.

As illustrated in FIG. 63H, the medial gap Gp2 represents the distance between the distal femoral medial condyle 1499*z* and the proximal tibia medial plateau 1477*z*. The lateral gap Gp1 represents the distance between the distal femoral lateral condyle 1498*z* and the proximal tibia lateral plateau 1478*z*. In this example illustrated in FIG. 63H, the lateral gap Gp1 is significantly larger than the medial gap Gp2 due to degeneration caused by injury, OA, or etc., that occurred in the lateral side 1487*z* of the knee 1486*z*. It should be noted that the alignment of the bone models 28', 28" relative to each other for the example illustrated in FIGS. 63G and 63H depict the alignment the actual bones have relative to each other in a deteriorated state. To restore the joint line reference and maintain ligament balancing for the medial collateral ligament (MCL) and lateral collateral ligament (LCL), the joint line gap Gp3 that is depicted in FIG. 63I, which is the same view as FIG. 63G, except with the joint line gap Gp3 in a restored state, may be used for the joint spacing compensation adjustment as described below. As illustrated in FIG. 63I, the lines 1495*z* and 1476*z* respectively extend across the most distal contact points 1496*z*, 1497*z* of the femur condyles 1498*z*, 1499*z* and the most proximal contact points 1466*z*, 1467*z* of the tibia plateau condyles 1477*z*, 1478*z*.

For calculation purposes, the restored joint line gap Gp3 may be whichever of Gp1 and Gp2 has the minimum value. In other words, the restored joint line gap Gp3 may be as follows: Gp3=MIN (Gp1, Gp2). For purposes of the adjustment for joint spacing compensation, the adjustment value tr may be calculated as being half of the value for Gp3, or in other words, tr=Gp3/2. As can be understood from FIGS. 63G-63H and 14J, in this example, the non-deteriorated side 1485*z* has Gp2, which is the smallest joint line gap and, therefore, Gp3=Gp2 in the example depicted in FIG. 63G-14J, and tr=Gp2/2.

In one embodiment, the joint line gap assessment may be at least a part of a primary assessment of the geometry relationship between the distal femur and proximal tibia. In such an embodiment, the joint gap assessment step may occur prior to the femur planning steps of the POP process. However, in other embodiments, the joint line gap assessment may occur at other points along the overall POP process.

b. Determine Compensation for Joint Spacing

Once the adjustment value tr is determined based off of cartilage thickness or joint line gap Gp3, the planning for the femoral implant model 34' can be modified or adjusted to compensate for the joint spacing in order to restore the joint line. As shown in FIG. 64, which is a 3D coordinate system wherein the femur reference data 100*z* is shown, the compensation for the joint spacing is performed both in distal and posterior approaches. Thus, the joint compensation points relative to the femur reference data are determined. As will be discussed later in this Detailed Description, the joint compensation points relative to the femur reference data will be used to determine the joint compensation relative to the femur implant.

As can be understood from FIG. 65, which is a y-z plane wherein the joint compensation points are shown, the posterior plane S and the distal plane P are moved away in the direction of normal of plane S and P respectively by the adjustment value tr. In one embodiment, the adjustment value tr is equal to the cartilage thickness. That is, the joint compensation points will be determined relative to the posterior plane S and the distal plane P which are moved away in the direction of normal of plane S and P, respectively, by an amount equal to the cartilage thickness. In some embodiments, the adjustment value tr is equal to one-half of the joint spacing. That is, the joint compensation points will be determined relative to the posterior plane S and the distal plane P which are moved away in the direction of normal of plane S and P, respectively, by an amount equal one-half the joint spacing. In other words, the femoral implant accounts for half of the joint spacing compensation, while the tibia implant will account for the other half of the joint spacing compensation.

As can be understood from FIG. 64, the femur reference data 100*z* was uploaded onto a coordinate system, as described above. To compensate for the joint spacing, the distal line-D1D2 is moved closer to the distal plane-P by an amount equal to the adjustment value tr, thereby resulting in joint spacing compensation points D1J, D2J and line D1J D2J. The distal plane P was previously moved by adjustment value tr. Similarly, posterior reference line P1P2 is moved closer to the posterior plane-S by an amount equal to the adjustment value tr, thereby resulting in joint spacing compensation points P1J, P2J and line P1J P2J. The trochlear groove reference line-line GO does not move and remains as the reference line for the joint spacing compensation. Lines D1J D2J and P1J P2J will be stored and utilized later for an analysis related to the femoral implant silhouette curve.

4. Selecting the Sizes for the Femoral Implants

The next steps are designed to select an appropriate implant size such that the implant will be positioned within the available degrees of freedom and may be optimized by 2D optimization. There are 6 degrees of freedom for a femoral implant to be moved and rotated for placement on the femur. For example, the translation in the x direction is fixed based on the reference planes-S and P and sagittal slices of femur as shown in FIGS. 53 and 63C. Rotation around the y axis, which corresponds to the varus/valgus adjustment is fixed based on the reference lines determined by analysis of the coronal slices, namely, lines EF and AB, and coronal plane-S as shown in FIGS. 53 and 56B. Rotation around the z axis, which corresponds to internal/external rotation, is fixed by the trochlear groove reference line, line GO or TGB, axial-distal reference line, line CD, and axial-posterior reference line, line AB, as shown in the axial views in FIGS. 53 and 55A-55E. By fixing these three degrees of freedom, the position of the implant can be determined so that the outer silhouette line of the implant passes through both the distal reference line and posterior reference line. Optimization will search for a sub-optimal placement of the implant such that an additional angle of flange contact is greater than but relatively close to 7 degrees. Thus, by constraining the 3 degrees of freedom, the appropriate implant can be determined.

a. Overview of Selection of Femoral Implant

Based on previously determined femoral implant data 100*z*', as shown in FIGS. 60-62, a set of 3 possible sizes of implants are chosen. For each implant, the outer 2D silhouette curve of the articular surface of the candidate implant model is computed and projected onto a y-z plane, as shown in FIGS. 69A-69C. The calculated points of the silhouette curve are stored. Then, the sagittal slice corresponding to the inflection point 500*z* (see FIG. 70A) is found and the corresponding segmentation spline is considered and the information is stored. Then an iterative closest point alignment is devised to find the transform to match the implant to the femur.

The next sections of this Detailed Description will now discuss the process for determining the appropriate implant candidate, with reference to FIGS. 66-71.

i. Implant Selection

In one embodiment, there is a limited number of sizes of a candidate femoral implant. For example, one manufacturer may supply six sizes of femoral implants and another manufacturer may supply eight or another number of femoral implants. A first implant candidate 700*z* (see FIG. 66) may be chosen based on the distance L' between the posterior and distal reference lines P1'P2' and D1'D2' determined above in FIG. 62, with reference to the femoral implant reference data 100*z*'. The distance L' of the candidate implants may be stored in a database and can be retrieved from the implant catalogue. In some embodiments, a second and third implant candidate 702, 704 (not shown) may be chosen based on the distance L between the posterior and distal reference lines P1P2 and D1D2 of the femur 28' determined above in FIG. 57, with reference to the femoral reference data 100*z* and distance L'. First implant candidate 700*z* has the same distance L as the patient femur. Second implant candidate 702 is one size smaller than the first implant candidate 700*z*. Third implant candidate 704 is one size larger than the first implant candidate 700*z*. In some embodiments, more than 3 implant candidates may be chosen.

The following steps 2-6 are performed for each of the implant candidates 700*z*, 702, 704 in order to select the appropriate femoral implant 34'.

ii. Gross Alignment of Implant onto Femur

In some embodiments, the gross alignment of the implant 34' onto the femur 28' may be by comparison of the implant reference data 100*z*' and the femur reference data 100*z*. In some embodiments, gross alignment may be via comparison of the medial-lateral extents of both the implant and the femur. In some embodiments, both gross alignment techniques may be used.

In some embodiments, as shown in FIG. 66, which shows the implant 34' placed onto the same coordinate plane with the femur reference data 100*z*, the implant candidate may be aligned with the femur. Alignment with the femur may be based on the previously determined implant reference lines D1'D2' and P1'P2' and femur reference lines D1D2 and P1P2.

In some embodiments, and as can be understood from FIGS. 67A-67C and 68A-68C, the medial lateral extent of the femur and the implant can be determined and compared to ensure the proper initial alignment. FIG. 67A is a plan view of the joint side 240*z* of the femur implant model 34' depicted in FIG. 52B. FIG. 67B is an axial end view of the femur lower end 200*z* of the femur bone model 28' depicted in FIG. 52A. The views depicted in FIGS. 67A and 67B are used to select the proper size for the femoral implant model 34'.

As can be understood from FIG. 67A, each femoral implant available via the various implant manufacturers may be represented by a specific femoral implant 3D computer model 34' having a size and dimensions specific to the actual femoral implant. Thus, the representative implant model 34' of FIG. 67A may have an associated size and associated dimensions in the form of, for example, an anterior-posterior extent iAP and medial-lateral extent iML, which data can be computed and stored in a database. These implant extents iAP, iML may be compared to the dimensions of the femur slices from the patient's actual femur 18. For example, the femur bone 18 may have dimensions such as, for example, an anterior-proximal extent bAP and a medial-lateral extent bML, as shown in FIG. 67B. In FIG. 67A, the anterior-posterior extent iAP of the femoral implant model 34' is measured from the anterior edge 270*z* to the posterior edge 275*z* of the femoral implant model 34', and the medial-lateral extent iML is measured from the medial edge 280*z* to the lateral edge 285*z* of the femoral implant model 34'.

Each patient has femurs that are unique in size and configuration from the femurs of other patients. Accordingly, each femur slice will be unique in size and configuration to match the size and configuration of the femur medically imaged. As can be understood from FIG. 67B, the femoral anterior-posterior length bAP is measured from the anterior edge 290*z* of the patellofemoral groove to the posterior edge 295 of the femoral condyle, and the femoral medial-lateral length bML is measured from the medial edge 301*z* of the medial condyle to the lateral edge 305*z* of the lateral condyle. The implant extents iAP and iML and the femur extents bAP, bML may be aligned for proper implant placement as shown in FIG. 67C and along the direction of axial-distal reference line-CD.

As can be understood from FIGS. 68A-68C, these medial-lateral extents of the implant iML and femur bML can be measured from the 2D slices of the femur of FIG. 54A. For example, FIG. 68A, which shows the most medial edge of the femur in a 2D sagittal slice and FIG. 68B, which shows the most lateral edge of the femur in a 2D sagittal slice, can be used to calculate the bML of the femur 28'. The implant 34' will be centered between the medial and lateral edges, as shown in FIG. 68C, which is a 2D slice in coronal view showing the medial and lateral edges, thereby grossly aligning the implant with the femur.

iii. Determine Outer Silhouette Curve of Implant in Y-Z Plane

The silhouette of the femoral implant is the curve formed by farthest points from center in y-z plane projection of the femoral implant geometry. The points of the silhouette curve may be utilized to confirm placement of the implant onto the femur based on the femur reference lines that have been altered to account for the joint compensation.

For a discussion of the process for determining the points of the silhouette curve of the femoral implant, reference is now made to FIGS. 69A-69C. As can be understood from FIG. 69A, which is an implant 34' mapped onto a y-z plane, the points of a candidate implant are retrieved from the implant database. The points are then imported onto a y-z plane and the silhouette curve can be determined. The silhouette curve 34" is determined by finding the points that are the farthest from the center along an outer circumference 35 of the articular surface of the implant 34'. FIG. 69B, which is the silhouette curve 34'" of the implant 34', shows the result of the silhouette curve calculations. The silhouette curve data is then imported into a y-z plane that includes the joint spacing compensation data, as shown in FIG. 69C, which is the silhouette curve 34'" aligned with the joint spacing compensation points D1J D2J and P1J P2J. The resulting joint spacing compensation and silhouette curve data 800*z* (e.g. D1'"D2'"P1'"P2'") is stored for later analysis.

iv. Determination of Inflection Point, Flange Point, Femur Spline and Anterior Femur Cut Plane The flange point is determined and stored. As can be understood from FIG. 70A, which shows a distal femur 28' with an implant 34', the distal femur is analyzed and the flange point 500*z* of the implant 34' is determined relative to the anterior surface 502*z* of the distal end of a femur condyle 28'. FIG. 70B, which depicts a femur implant 34', illustrates the location of the flange point 500*z* on the implant 34' as determined by an analysis such as one illustrated in FIG. 70A.

The anterior cut plane 504*z* is determined and stored. The range of the anterior cut plane of the implant is determined such that the cut plane (and therefore the implant) is within certain tolerances. As shown in FIG. 70A, a cut plane 504*z* is determined based on the location of the implant 34' on the femur 28'. An angle A between the cut plane 504*z* and the flange point 500*z* is between approximately 7 and approximately 15 degrees. In some embodiments, the angle A is approximately 7 degrees. In some embodiments, the distal cut plane may be found as described below with respect to the final verification step. For each respective implant, the anterior cut plane and the distal cut plane are at a fixed angle for the implant. That is, once the anterior cut plane is found, the distal cut plane can be determined relative to the fixed angle and the anterior cut plane. Alternatively, once the distal cut plane is found, the anterior cut plane can be determined relative to the fixed angle and the distal cut plane.

The inflection point 506*z* is determined and stored. As shown in FIG. 70C, which shows a slice of the distal femur 28' in the sagittal view, the inflection point 506*z* is located on the anterior shaft of the spline 508 of femur 28' where the flange point 500*z* of the implant 34' is in contact with the femur 28'. An implant matching algorithm will match the flange point 500*z* of implant 34' to the spline 508 of the femur at approximately the inflection point 506*z* of the femur 28'. As can be understood from FIG. 70D, which shows the implant 34' positioned on the femur 28', the implant 34' should be aligned to touch the distal and posterior reference planes P, S respectively to reach proper alignment. In one embodiment, the implant matching algorithm is a customized extension of an algorithm known as iterative closest point matching.

The next section of the Detailed Description now discusses how the data and data points determined above and stored for future analysis will be used in the selection of an appropriate implant.

v. Determine Points of Set A and Set B

Determination of the data sets contained in Set A and Set B aid in determining the appropriate implant and ensuring that the chosen implant mates with the femur within certain tolerances.

The joint spacing compensation points D1J D2J and P1JP2J were determined as described with reference to FIG. 65 and are added to Set A. Next, the joint spacing compensation points D1J D2J and P1J P2J are matched to the closest respective points on the silhouette curve, as shown in FIG. 69C, thereby resulting in points D1'"D2'" and P1'"P2'" or the joint spacing compensation and silhouette curve data 800*z*. Points D1'"D2'" and P1'"P2'" will be added to Set B.

The inflection point and flange point data are analyzed. An inflection point 506*z'* is found to represent the inflection point 506*z* that is closest in proximity to the flange point 500*z*, which were both discussed with reference to FIGS. 70A-70D. The point 506*z'* is added to Set A. The flange point 500*z* is then projected to a y-z plane. The resulting flange point 500*z'* is added to Set B.

Thus, Set A contains the following points: the joint spacing compensation points D1J D2J and P1J P2J and the inflection point 506*z'*. Set B contains the following points: Points D1'"D2'" and P1'"P2'" (the joint spacing compensation and silhouette curve data 800*z*) and the flange point 500*z'*.

vi. Utilize the Data of Sets A and B

Find a rigid body transform. The data points of Set A and Set B are compared and a rigid body transform that most closely matches Set A to Set B is chosen. The rigid body transform will transform an object without scaling or deforming. That is, the rigid body transform will show a change of position and orientation of the object. The chosen transform will have rotation about the x-axis and translation in the y-z plane.

Find the inverse of the rigid body transform. The inverse of this rigid body transform is then imported into the y-z plane that also contains the femur reference lines D1D2 and P1P2 and the femur spline 508 that corresponds to the flange point 500*z* of the implant 34'.

The steps described in this Detailed Description are repeated until the relative motion is within a small tolerance. In one embodiment, the steps are repeated fifty times. In some embodiments, the steps are repeated more than fifty times or less than fifty times.

Figure 71A:
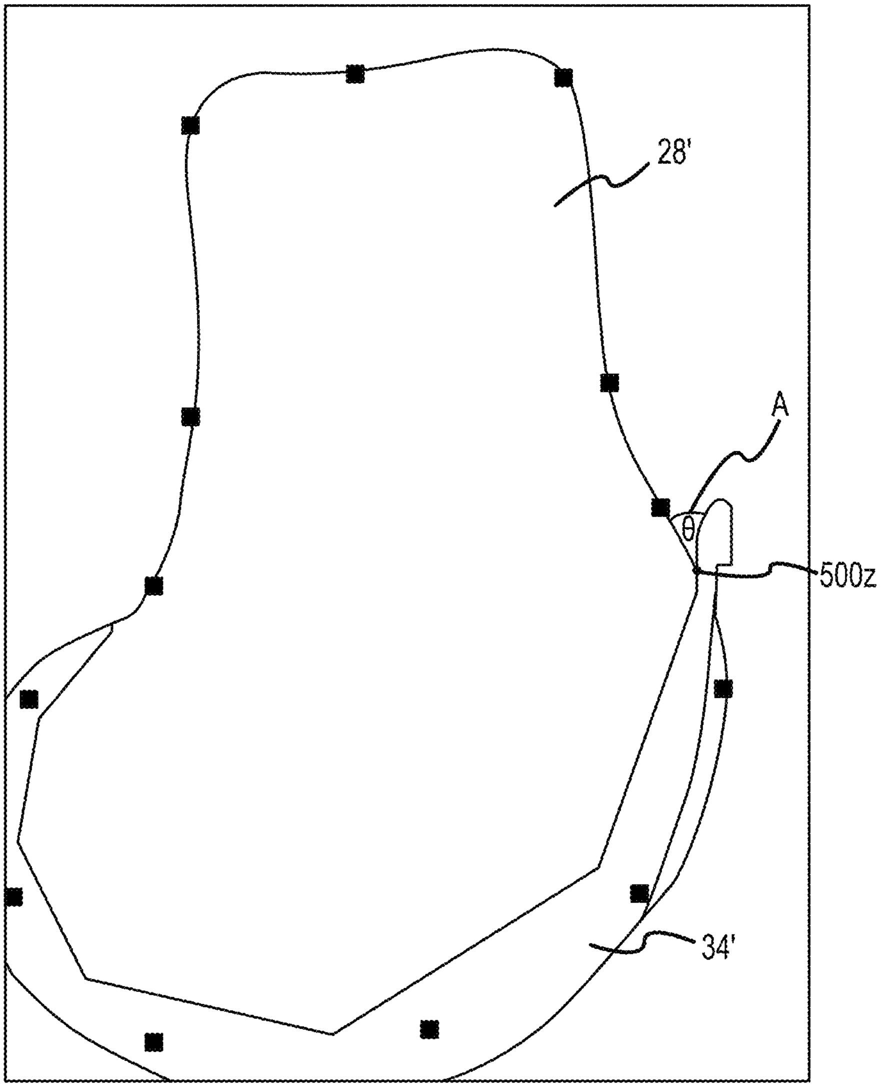
Figure 71B:
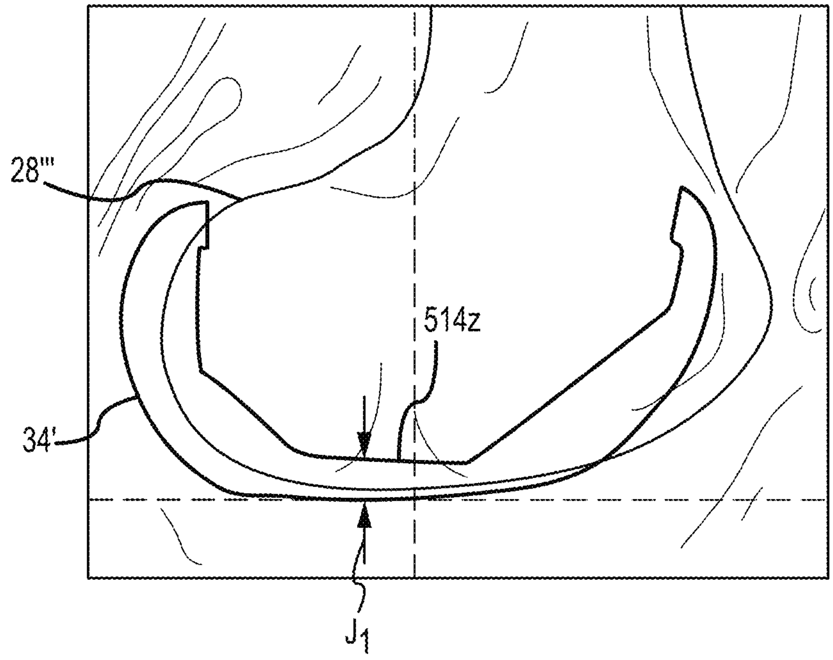

In some embodiments, and as shown in FIG. 71A, an acceptable translation in y-z plane may be determined. FIG. 71A depicts an implant that is improperly aligned on a femur, but shows the range of the search for an acceptable angle A. Within this range for angle A, the translation in y-z leads to finding the rigid body transform as described above. In some embodiments, the process may optimize y-z translation and rotation around the x-axis in one step. This can be done by rotating the implant silhouette curve by several half degree increments and then, for each increment, performing the steps described in this Detailed Description. Translation in the y-z axis only occurs during the analysis utilizing the inverse of the rigid body transform.

vii. Additional Verification and Confirmation of Femur Cut Plane

By using the above outlined procedure, an appropriate implant is found by choosing the implant and transform combination that provides an inflection angle that is greater than 7 degrees but closest to 7 degrees, as explained with reference to FIG. 70A.

In some embodiments, an additional verification step is performed by placing the implant 34' in the MRI with the transform 28''' that is found by the above described method. As can be understood from FIG. 7IB, which illustrates the implant positioned on the femur transform wherein a femur cut plane is shown, during the verification step, a user may determine the amount of bone that is cut J1 on the medial and lateral condyles by looking at the distal cut plane 514*z* of the implant 34'. J1 is determined such that the thickness of the bone cut on both the medial and lateral sides is such that the bone is flat after the cut. Multiple slices in both the distal and medial areas of the bone can be viewed to verify J1 is of proper thickness.

Once an appropriate femur implant is chosen, the preoperative planning process turns to the selection of an appropriate tibia implant. The tibia planning process includes a determination of the tibia reference lines to help determine the proper placement of the tibia implant. The candidate tibia implant is placed relative to the tibia reference lines and placement is confirmed based on comparison with several 2D segmentation splines.

E. Tibia Planning Process

For a discussion of the tibia planning process, reference is now made to FIGS. 72-81D. FIGS. 72-75B illustrate a process in the POP wherein the system 10 utilizes 2D imaging slices (e.g., MRI slices, CT slices, etc.) to determine tibia reference data, such as reference points and reference lines, relative to the undamaged side of the tibia plateau. The resulting tibia reference data 900*z* is then mapped or projected to an x-y plane (axial plane). A candidate tibia implant is chosen, which selection will be discussed with reference to FIGS. 76A-76C. The tibia implant placement is adjusted and confirmed relative to the tibia, as discussed in more detail below with reference to FIGS. 77-81D.

1. Determining Tibia Reference Data

For a discussion of a process used to determine the tibia reference data 900*z*, reference is now made to FIGS. 72-76B. As can be understood from FIG. 72, which is a top view of the tibia plateaus 404*z*, 406*z* of a tibia bone image or model 28'', the tibia reference data 900*z* may include reference points (e.g. Q1, Q1'), reference lines (e.g. T1T2, $V_1$) and a reference plane (e.g. S') (see FIGS. 75A-75B). In some embodiments, the tibia reference data 900*z* may also include the anterior-posterior extant (tAP) and the medial-lateral extant (tML) of the tibia 28'' (see FIGS. 76A-76B). As shown in FIG. 72, each tibia plateau 404*z*, 406*z* includes a curved recessed condyle contacting surface 421*z*, 422*z* that is generally concave extending anterior/posterior and medial/lateral. Each curved recessed surface 421*z*, 422*z* is generally oval in shape and includes an anterior curved edge 423*z*, 424*z* and a posterior curved edge 425*z*, 426*z* that respectively generally define the anterior and posterior boundaries of the condyle contacting surfaces 421*z*, 422*z* of the tibia plateaus 404*z*, 406*z*. Depending on the patient, the medial tibia plateau 406*z* may have curved edges 424*z*, 426*z* that are slightly more defined than the curved edges 423*z*, 425*z* of the lateral tibia plateau 404*z*.

a. Identify Points Q1, Q2 and Q1', Q2'

2D slices in the sagittal view are analyzed to determine the tibia flexion/extension adjustment. Anterior tangent lines TQ1, TQ2 can be extended tangentially to the most anterior location on each anterior curved edge 423*z*, 424*z* to identify the most anterior points Q1, Q2 of the anterior curved edges 423*z*, 424*z*. Posterior tangent lines TQ1', TQ2' can be extended tangentially to the most posterior location on each posterior curved edge 425*z*, 426*z* to identify the most posterior points Q1', Q2' of the posterior curved edges 425*z*, 426*z*. Thus, in one embodiment, the lateral side tibia plateau 404*z* can be analyzed via tangent lines to identify the highest points Q1, Q1'. For example, tangent line TQ1 can be used to identify the anterior highest point Q1, and tangent line TQ1' can be used to identify the posterior highest point Q1'. In some embodiments, a vector $V_1$ extending between the highest points Q1, Q1' may be generally perpendicular to the tangent lines TQ1, TQ1'. Similarly, the medial side tibia plateau 406*z* can be analyzed via tangent lines to identify the highest points Q2, Q2'. For example, tangent line TQ2 can be used to identify the anterior highest point Q2, and tangent line TQ2' can be used to identify the posterior highest point Q2'. In some embodiments, a vector $V_2$ extending between the highest points Q2, Q2' may be generally perpendicular to the tangent lines TQ2, TQ2'.

i. Confirm points Q1, Q2 and Q1', Q2'

As can be understood from FIGS. 73A-73D, the location of Q1, Q1', Q2 and Q2' may also be confirmed by an analysis of the appropriate sagittal slice. As shown in FIG. 73A, which is a sagittal cross section through a lateral tibia plateau 404*z* of the tibia model or image 28', points Q1 and Q1' can be identified as the most anterior and posterior points, respectively, of the curved recessed condyle contacting surface 421*z* of the lateral tibia plateau 404*z*. As shown in FIG. 73B, which is a sagittal cross section through a medial tibia plateau 406*z* of the tibia model 28'', points Q2 and Q2' can be identified as the most anterior and posterior points, respectively, of the curved recessed condyle contacting surface 422*z* of the medial tibia plateau 406*z*. Such anterior and posterior points may correspond to the highest points of the anterior and posterior portions of the respective tibia plateaus.

b. Determine lines V1 and V2

As can be understood from FIGS. 72-73B, line V1 extends through anterior and posterior points Q1, Q1', and line V2 extends through anterior and posterior points Q2, Q2'. Line V1 is a lateral anterior-posterior reference line. Line V2 is a medial posterior-anterior reference line. Each line V1, V2 may align with the lowest point of the anterior-posterior extending groove/valley that is the elliptical recessed tibia plateau surface 421*z*, 422*z*. The lowest point of the anterior-posterior extending groove/valley of the elliptical recessed tibia plateau surface 421*z*, 422*z* may be determined via ellipsoid calculus. Each line V1, V2 will be generally parallel to the anterior-posterior extending valleys of its respective elliptical recessed tibia plateau surface 421*z*, 422*z* and will be generally perpendicular to its respective tangent lines TQ1, TQ1', TQ2, TQ2'. The anterior-posterior extending valleys of the elliptical recessed tibia plateau surfaces 421*z*, 422*z* and the lines V1, V2 aligned therewith may be generally parallel. The planes associated with lines V1 and V2 are generally parallel or nearly parallel to the joint line of the knee joint, as determined above.

Depending on the patient, the medial tibia plateau 406*z* may be undamaged or less damaged than the lateral tibia plateau 404*z*. In such a case, the reference points Q2, Q2' and reference line V2 of the medial plateau 406*z* may be used to establish one or more reference points and the reference line of the damaged lateral tibia plateau. FIG. 73C depicts a sagittal cross section through an undamaged or little damaged medial tibia plateau 406z of the tibia model 28", wherein osteophytes 432z are also shown. As indicated in FIG. 73C, the points Q2, Q2' can be located on the undamaged medial plateau and set as reference points. The anterior-posterior reference line, line V2, can be constructed by connecting the anterior and posterior reference points Q2, Q2'. The reference line V2 from the undamaged or little damaged medial side is saved for use in determining the reference line of the lateral tibia plateau in the case where the lateral tibia plateau is damaged. For example, as shown in FIG. 73D, which is a sagittal cross section through a damaged lateral tibia plateau 404z of the tibia model 28", the anterior point Q1 is found to be undamaged. In this case, the established reference line V2 from the medial plateau can be applied to the damaged lateral plateau by aligning the reference line V2 with point Q1. By doing so, the reference line V1 of the lateral plateau can be established such that line V1 touches the reference point Q1 and extends through the damaged area 403z. Thus, the reference line V1 in the lateral plateau is aligned to be parallel or nearly parallel to the reference line V2 in the medial plateau. While the above described process is described in terms of extrapolating one or more reference lines of a damaged lateral plateau from an analysis of the undamaged medial tibia plateau, it is understood that the same process can be undertaken where the lateral tibia plateau is undamaged and one or more reference lines of a damaged medial plateau can be extrapolated from the lateral tibia plateau.

In other embodiments, as can be understood from FIG. 73D and assuming the damage to the lateral tibia plateau 404z is not so extensive that at least one of the highest anterior or posterior points Q1, Q1' still exists, the damaged tibia plateau 404z can be analyzed via tangent lines to identify the surviving high point Q1, Q1'. For example, if the damage to the lateral tibia plateau 404z was concentrated in the posterior region such that the posterior highest point Q1' no longer existed, the tangent line TQ1 could be used to identify the anterior highest point Q1. Similarly, if the damage to the medial tibia plateau 406z was concentrated in the anterior region such that the anterior highest point Q1' no longer existed, the tangent line TQ1' could be used to identify the posterior highest point Q1'. In some embodiments, a vector extending between the highest points Q1, Q1' may be generally perpendicular to the tangent lines TQ1, TQ1'.

c. Determine Reference Points T1 and T2 and Reference Line T1T2

2D slices in both the axial and coronal views are analyzed to determine the varus/valgus adjustment by finding the reference points T1 and T2. As shown in FIGS. 74A-74B, which are coronal and axial 2D slices of the tibia, reference points T1 and T2 are determined by an analysis of the most proximal coronal slice (FIG. 74A) and the most proximal axial slice (FIG. 74B). As indicated in FIG. 74A, in which the tibia is shown in a 0° knee extension, reference points T1 and T2 are determined. The points T1 and T2 represent the lowest extremity of tangent contact points on each of the lateral and medial tibia plateaus, respectively. In one embodiment, tangent points T1 and T2 are located within the region between the tibia spine and the medial and lateral epicondyle edges of the tibia plateau, where the slopes of tangent lines in this region are steady and constant. For example, and as shown in FIG. 74A, the tangent point T1 is in the lateral plateau in Area I between the lateral side of the lateral intercondylar tubercle to the attachment of the lateral collateral ligament. For the medial portion, the tangent point T2 is in Area II between the medial side of the medial intercondylar tubercle to the medial condyle of the tibia.

As shown in FIG. 74B, the most proximal slice of the tibia in the axial view is analyzed to find reference points T1 and T2. As above, reference points T1 and T2 represent the lowest extremity of tangent contact points on each of the lateral and medial tibia plateaus. Once the reference points T1 and T2 are found in both the coronal and axial views, a line T1T2 is found.

A line T1T2 is created by extending a line between reference points T1 and T2. In some embodiments, the coronal and axial slices are viewed simultaneously in order to align the lateral and medial anterior-posterior reference lines V1 and V2. As shown in FIG. 72, the lateral and medial anterior-posterior reference lines V1 and V2 are generally perpendicular or nearly perpendicular to line T1T2.

d. Determine the Approximate ACL Attachment Point (AE) and the Approximate PCL Attachment Point (PE) of the Tibia and Reference Line AEPE As can be understood from FIGS. 72 and 74B, the reference points representing the approximate anterior cruciate ligament (ACL) attachment point of the tibia AE and the approximate posterior cruciate ligament (PCL) attachment point of the tibia PE are determined. The reference point AE can be determined by finding the approximate tibia attachment point for the ACL. The reference point PE can be determined by finding the approximate tibia attachment point for the PCL. The line AEPE connects through reference points AE and PE and may also be referred to as an ACL/PCL bisector line.

e. Confirm Location of Tibia Reference Data

As can be understood from FIG. 72, the tibia reference data 900z includes reference points and reference lines that help to define flexion/extension adjustment, varus/valgus adjustment and internal/external rotation. For example, the tibia flexion/extension adjustment is determined by an analysis of the sagittal images as shown in FIGS. 73A-D, which determine reference points Q1, Q1', Q2, Q2'. The tibia varus/valgus adjustment may be found by an analysis of FIG. 74A and finding reference points T1, T2 and reference line T1T2. As can be understood from FIG. 72, the proximal reference line, line T1T2, defines the internal/external rotation as shown in an axial view (line T1T2 in FIG. 74B) and the varus/valgus angle as shown in a coronal view (line T1T2 in FIG. 74A).

The location of the reference points and reference lines may also be confirmed based on their spatial relationship to each other. For example, as shown in FIGS. 72-73B, the anterior-posterior reference lines V1, V2 of the tibia plateau are generally parallel to the ACL/PCL bisector reference line, line AEPE. As indicated in FIGS. 72 and 74B, the axial-proximal reference line, line T1T2 is perpendicular or nearly perpendicular to anterior-posterior reference lines V1, V2. As shown in FIG. 72, the tangent lines TQ1, TQ2, TQ1', TQ2' are perpendicular or nearly perpendicular to the ACL/PCL bisector reference line, line AEPE.

f. Mapping the Tibia Reference Data to an x-y Plane

As can be understood from FIGS. 75A-75B, which depict the tibia reference data 900z on a coordinate system (FIG. 75A) and on a proximal end of the tibia (FIG. 75B), the tibia reference data 900z is mapped to an x-y coordinate system to aid in the selection of an appropriate tibia implant. As shown in FIG. 75A, the endpoints Q1, Q1', Q2, 02' and their respective anterior posterior reference lines V1 and V2 and the endpoints T1, T2 and the proximal reference line T1T2 are each mapped to the reference plane. In addition, and as shown in FIG. 75B, the reference data 900*z* may be imported onto a 3D model of the tibia 28" for verification purposes. The tibia reference data 900*z* is stored for later analysis.

2. Selecting Tibia Implant Candidate

There are six degrees of freedom for placing the tibial implant onto the tibia. The reference points and reference lines determined above will constrain all but 2 degrees of freedom which are translated in the x-y plane. The sizing and positioning of the tibia implant (and the femoral component) will be verified with a 2D view of the knee and components.

As briefly discussed above with reference to FIGS. 1A and 50B-50C, when selecting the tibia implant model 34" corresponding to the appropriate tibia implant size to be used in the actual arthroplasty procedure, the system 4 may use one of at least two approaches to select the appropriate size for a tibia implant [block 115]. In one embodiment, the tibia implant is chosen based on the size of the femoral implant that was determined above. In some embodiments, as discussed with reference to FIGS. 76A-76C, the system 4 determines the tibial anterior-posterior length tAP and the tibial medial-lateral length tML and the tibia implant 34" can be selected based on the anterior-posterior extent tAP of the proximal tibia. In some embodiments, the tibia implant may be selected based on both the tibial anterior-posterior length tAP and the tibial medial-lateral length tML.

In one embodiment, there is a limited number of sizes of a candidate tibia implant. For example, one manufacturer may supply six sizes of tibia implants and another manufacturer may supply eight or another number of tibia implants. The anterior-posterior length jAP and medial-lateral length jML dimensions of these candidate implants may be stored in a database. The tAP and tML are compared to the jAP and jML of candidate tibia implants stored in the database.

FIG. 76A is a 2D sagittal image slice of the tibia wherein a segmentation spline with an AP extant is shown. FIG. 76B is an axial end view of the tibia upper end of the tibia bone image or model 28" depicted in FIG. 52A. FIG. 76C is a plan view of the joint side 255*z* of the tibia implant model 34" depicted in FIG. 52B. The views depicted in FIGS. 76A-76C are used to select the proper size for the tibial implant model 34". The tibia implant may be chosen based on the maximum tAP extent as measured in an analysis of the segmentation spine as shown in FIG. 76A.

Each patient has tibias that are unique in size and configuration from the tibias of other patients. Accordingly, each tibia bone model 28" will be unique in size and configuration to match the size and configuration of the tibia medically imaged. As can be understood from FIG. 76B, the tibial anterior-posterior length tAP is measured from the anterior edge 335*z* of the tibial bone model 28" to the posterior edge 330*z* of the tibial bone model 28", and the tibial medial-lateral length tML is measured from the medial edge 340*z* of the medial plateau of the tibia bone model 28" to the lateral edge 345*z* of the lateral plateau of the tibia bone model 28".

As can be understood from FIG. 76C, each tibial implant available via the various implant manufacturers may be represented by a specific tibia implant 3D computer model 34" having a size and dimensions specific to the actual tibia implant. Thus, the representative implant model 34" of FIG. 3D may have an associated size and associated dimensions in the form of, for example, anterior-proximal extent tAP and the medial-lateral extent tML of the tibia model 34", as shown in FIG. 76B. In FIG. 76C, the anterior-posterior extent jAP of the tibia implant model 34" is measured from the anterior edge 315*z* to the posterior edge 310*z* of the tibial implant model 34", and the medial-lateral extent jML is measured from the medial edge 320*z* to the lateral edge 325*z* of the tibial implant model 34". Once the tibia implant candidate 34" is chosen, the reference lines jML, jAP of the implant candidate 34" are stored by the system 4 for later analysis.

3. Determine Tibia Implant Reference Data

As can be understood from FIG. 77, which is a top view of the tibia plateaus 404*z*', 406*z*' of a tibia implant model 34", wherein the tibia implant reference data 900*z*' is shown, the tibia reference data 900*z*' may include tangent points q1, q1', q2, q2' and corresponding anterior-posterior reference lines V3, V4 and intersection points t1, t2 and its corresponding proximal reference line t1t2.

In order to define the implant reference data 900*z*' relative to the tibia model 28", the implant reference lines jML, jAP are imported into the same x-y plane with the tibia reference data 900*z* that was previously mapped to the x-y plane. For gross alignment purposes, the medial-lateral extent jML of the tibia implant 34" is aligned with the proximal reference line T1T2 of the tibia model 28". Then, the tibia reference data 900*z*' is determined. The implant 34" and the bone model 28" may then undergo additional alignment processes.

a. Determine Tangent Points q1, q1', q2, q2'

As shown in FIG. 77, each tibia plateau 404*z*', 406*z*' includes a curved recessed condyle contacting surface 421*z*', 422*z*' that is generally concave extending anterior/posterior and medial/lateral. Each curved recessed surface 421*z*', 422*z*' is generally oval in shape and includes an anterior curved edge 423*z*', 424*z*' and a posterior curved edge 425*z*', 426*z*' that respectively generally define the anterior and posterior boundaries of the condyle contacting surfaces 421*z*', 422*z*' of the tibia plateaus 404*z*', 406*z*'. Thus, the lateral tangent points q1, q1' can be identified as the most anterior and posterior points, respectively, of the curved recessed condyle contacting surface 421*z*' of the lateral tibia plateau 404*z*'. The medial tangent points q2, q2' can be identified as the most anterior and posterior points, respectively, of the curved recessed condyle contacting surface 422*z*' of the medial tibia plateau 406*z*'.

b. Determine Reference Lines V3 and V4

As can be understood from FIG. 77, line V3 extends through anterior and posterior points q1, q1', and line V4 extends through anterior and posterior points q2, q2'. Line V3 is a lateral anterior-posterior reference line. Line V4 is a medial posterior-anterior reference line. Each line V3, V4 may align with the lowest point of the anterior-posterior extending groove/valley that is the elliptical recessed tibia plateau surface 421*z*', 422*z*'. The lowest point of the anterior-posterior extending groove/valley of the elliptical recessed tibia plateau surface 421*z*', 422*z*' may be determined via ellipsoid calculus. Each line V3, V4 will be generally parallel to the anterior-posterior extending valleys of its respective elliptical recessed tibia plateau surface 421*z*', 422*z*'. The length of the reference lines V3, V4 can be determined and stored for later analysis.

c. Determine Intersection Points t1, t2 and Implant Proximal Reference Line t1t2

As shown in FIG. 77, the intersection or reference points t1, t2 represent the midpoints of the respective surfaces of the lateral tibia plateau 404*z*' and the medial tibia plateau 406*z*'. Also, each intersection point t1, t2 may represent the most distally recessed point in the respective tibia plateau 404*z*', 406*z*'. An implant proximal reference line t1t2 is created by extending a line between the lateral and medial lowest reference points t1, t2. The length of the reference line t1t2 can be determined and stored for later analysis. This line t1t2 is parallel or generally parallel to the joint line of the knee. Also, as indicated in FIG. 77, the tibia implant 34" includes a base member 780*z* for being secured to the proximal tibia 28".

d. Align Implant Reference Data 900*z*' with Tibia Reference Data 900*z*

As can be understood from FIGS. 77 and 75A, the implant reference data 900*z*' specifies the position and orientation of the tibia implant 34" and generally aligns with similar data 900*z* from the tibia bone model 28". Thus, the lateral tangent points q1, q1' and medial tangent points q2, q2' of the implant 34" generally align with the lateral tangent points Q1, Q1' and medial tangent points Q2, Q2' of the tibia 28". The anterior posterior reference lines V3, V4 of the implant 34" generally align with the anterior posterior reference lines V1, V2 of the tibia model 28". The intersection points t1, t2 of the implant 34" generally align with the reference points T1, T2 of the tibia 28". The proximal reference line t1t2 of the implant 34" generally aligns with the proximal reference line T1T2 of the tibia 28". Reference line t1t2 is approximately perpendicular to the anterior-posterior reference lines V3, V4.

The implant reference data 900*z*' lies on a coordinate frame, plane r'. The tibia reference data 900*z* lies on a coordinate frame, plane s'. Thus, the alignment of the implant 34" with the tibia 28" is the transformation between the two coordinate frames plane r', plane s'. Thus, the gross alignment includes aligning the proximal line t1t2 of the implant 34" to the proximal line T1T2 of the tibia 28". Then, in a further alignment process, the reference points t1, t2 of the implant and the reference points T1, T2 of the tibia 28" are aligned. The implant 34" is rotated such that the sagittal lines of the implant 34" (e.g. V3, V4) are parallel or generally parallel to the sagittal lines of the tibia 28" (e.g. V1, V2). Once the tibia 28" and the implant 34" are in alignment (via the reference data 900*z*, 900*z*'), the tibial cut plane can be determined.

4. Determine Surgical Cut Plane for Tibia a. Determine Cut Plane of the Tibia Implant The cut plane of the tibia implant is determined. The user may determine this cut plane by a method such as one described with respect to FIGS. 78A-78C. FIG. 78A is an isometric view of the 3D tibia bone model 1002*z* showing the surgical cut plane SCP design. FIGS. 78B and 78C are sagittal MRI views of the surgical tibia cut plane SCP design with the posterior cruciate ligament PCL.

During the TKA surgery, the damaged bone surface portions of the proximal tibia will be resected from the cut plane level 850*z* and be removed by the surgeon. As shown in FIGS. 78B and 78C, the surgical tibial cut plane 850*z* may be positioned above the surface where the PCL is attached, thereby providing for the maintenance of the PCL during TKA surgery.

FIG. 79A is an isometric view of the tibia implant 34" wherein a cut plane r1 is shown. As can be understood from FIG. 79A, the cut plane r1 of the implant 34" is the surgical tibial cut plane 850*z* and is a data point or set of data points that may be stored in the implant database. In order to determine whether an adjustment to the cut plane r1 must be made, the cut plane r1 of the tibia implant 34" is aligned with the tibia 28".

b. Determine Initial Cut Plane of the Tibia

As shown in FIG. 79B, which is a top axial view of the implant 34" superimposed on the tibia reference data 900*z*, the implant 34" is opened with the tibia reference data 900*z* and is generally aligned with the tibia reference data 900*z* at the level of the cut plane r1 by the system 4. However, the implant 34" is not centered relative to the tibia reference data 900*z*. The anterior/posterior extent tAP" and medial/lateral extent tML" of the tibia 28" at the cut level are found.

The implant 34" may be centered by the system (or manually by a user of the system). As indicated in FIG. 79C, which is an axial view of the tibial implant aligned with the tibia reference data 900*z*, the tibia implant 34" is then centered relative to the anterior posterior extent tAP" and the medial lateral extents tML" of the tibia 28".

c. Determine Joint Line and Adjustment

In order to allow an actual physical arthroplasty implant to restore the patient's knee to the knee's pre-degenerated or natural configuration with the its natural alignment and natural tensioning in the ligaments, the condylar surfaces of the actual physical implant generally replicate the condylar surfaces of the pre-degenerated joint bone. In one embodiment of the systems and methods disclosed herein, condylar surfaces of the bone model 28" are surface matched to the condylar surfaces of the implant model 34". However, because the bone model 28" may be bone only and not reflect the presence of the cartilage that actually extends over the pre-degenerated condylar surfaces, the surface matching of the modeled condylar surfaces may be adjusted to account for cartilage or proper spacing between the condylar surfaces of the cooperating actual physical implants (e.g., an actual physical femoral implant and an actual physical tibia implant) used to restore the joint such that the actual physical condylar surfaces of the actual physical cooperating implants will generally contact and interact in a manner substantially similar to the way the cartilage covered condylar surfaces of the pre-degenerated femur and tibia contacted and interacted.

i. Determine Adjustment Value tr

Thus, in one embodiment, the implant model is modified or positionally adjusted (via e.g. the tibia cut plane) to achieve the proper spacing between the femur and tibia implants. To achieve the correct adjustment or joint spacing compensation, an adjustment value tr may be determined. In one embodiment, the adjustment value tr that is used to adjust the implant location may be based off of an analysis associated with cartilage thickness. In another embodiment, the adjustment value tr used to adjust the implant location may be based off of an analysis of proper joint gap spacing, as described above with respect to FIGS. 63G and 63H. Both of the methods are discussed below in turn.

1. Determining Cartilage Thickness

FIG. 79D is a MRI image slice of the medial portion of the proximal tibia and indicates the establishment of landmarks for the tibia POP design. FIG. 79E is a MRI image slice of the lateral portion of the proximal tibia. The wm in FIG. 79D represents the cartilage thickness of the medial tibia meniscus, and the wl in FIG. 79E represents the cartilage thickness of the lateral tibia meniscus. In one embodiment, the cartilage thicknesses wl and wm are measured for the tibia meniscus for both the lateral and medial plateaus 760*z*, 765*z* via the MRI slices depicted in FIGS. 79D and 79E. The measured thicknesses may be compared. If the cartilage loss is observed for the medial plateau 765*z*, then the wlmin of lateral plateau 760*z* is selected as the minimum cartilage thickness. Similarly, if the lateral plateau 760*z* is damaged due to cartilage loss, then the wmmin of medial plateau 765*z* is selected as the minimum cartilage thickness. The minimum cartilage wr may be illustrated in the formula, wr=min (wm, wl). In one embodiment, for purposes of the adjustment to the tibia, the adjustment value tr may be may be equal to the minimum cartilage value wr.

2. Determining Joint Gap

In one embodiment, the joint gap is analyzed as discussed above with respect to FIGS. 63G and 63H to determine the restored joint line gap Gp3. In one embodiment, for purposes of the adjustment to the tibia shape matching, the adjustment value tr may be calculated as being half of the value for Gp3, or in other words, tr=Gp3/2.

d. Determine Compensation for Joint Spacing

After centering the implant 34" within the cut plane, joint spacing compensation is taken into account. As shown in FIG. 79F, which is an isometric view of the tibia implant and the cut plane, the implant 34" and cut plane-r1 are moved in a direction that is generally perpendicular to both the proximal and sagittal reference lines by an amount equal to adjustment value tr, thereby creating an adjusted cut plane r1'. In one embodiment, the adjustment value tr is equal to approximately one-half of the joint spacing. In other embodiments, the adjustment value tr is equal to the cartilage thickness.

Thus, the implant candidate may be selected relative to the joint spacing compensation that was determined previously with reference to FIGS. 63G, 63H, 79D and 79E. As discussed above, in one embodiment, once the joint spacing compensation is determined, one-half of the joint spacing compensation will be factored in to the femur planning process and one-half of the joint spacing compensation will be factored in to the tibia planning process. That is, the femur implant is adjusted by an amount equal to one-half of the joint spacing compensation. Thus, the candidate femur implant will be chosen such that when it is positioned on the femur relative to the joint spacing compensation, the candidate implant will approximate the pre-degenerated joint line. Similarly, the tibia implant is adjusted by an amount equal to one-half of the joint spacing compensation. Thus, the candidate tibia implant will be chosen such that when it is positioned on the tibia relative to the joint spacing compensation, the candidate implant will approximate the pre-degenerated joint line. Also, the tibia implant mounting post 780*z* (see FIG. 80B) and the femur implant mounting post 781*z* (see FIG. 31A) will be oriented at approximately the center of the tibia and femur.

F. Verification of Implant Planning Models and Generation of Surgical Jigs Based on Planning Model Information FIGS. 80A-81 illustrate one embodiment of a verification process that may be utilized for the preoperative planning process disclosed herein. FIGS. 80A-80C are sagittal views of a 2D image slice of the femur 28' (FIGS. 80A and 80B) and the tibia 28" (FIG. 80B) wherein the 2D computer generated implant models 34 are also shown. As can be understood from FIGS. 80A-80C, verification for both the distal femur and proximal tibia is performed by checking the reference lines/planes in 2D sagittal views. The reference lines/planes may also be checked in other views (e.g. coronal or axial). For example, and as can be understood from FIGS. 80A and 80B, for the femur planning model, the flexion-extension rotation is verified by checking whether the inflection point 506*z* of the anterior cortex of the femur 28' sufficiently contacts the interior surface 510*z* of the anterior flange 512*z* of implant 34'. That is, as can be understood from FIG. 80A2, when the implant 34' is properly aligned with the femur 28', the flange point 500*z* of the implant should touch the inflection point of the segmentation spline or femur 28'.

As can be understood with reference to FIG. 80B, the tibia planning may be verified by looking at a 2D sagittal slice. Depending on the initial planning choice made above, one of the following can be verified: 1) whether the size of the tibial implant 34" matches or corresponds with the size of the femoral implant 34', or 2) whether the tibial implant 34" is one size larger or one size smaller than the femoral implant 34' size (e.g., a size 2 femur, and a size 1 tibia; or a size 2 femur, and a size 2 tibia; or a size 2 femur, and a size 3 tibia). In other embodiments, the size of tibial implant may be chosen without taking into account the size of the femoral implant. One of skill in the art will recognize that different implant manufacturers may utilize a different naming convention to describe different sizes of implants. The examples provided herein are provided for illustrative purposes and are not intended to be limiting.

As indicated in FIG. 80B, the placement of the tibial implant can be verified by viewing the anterior and posterior positions of the implant 34" relative to the tibial bone 28". If the implant is properly positioned, the implant should not extend beyond the posterior or anterior edge of the tibia bone. The flexion-extension of the tibia 28" can be verified by checking that the tibial implant reference line 906*z*, which is a line segment approximating the normal direction of the implant's proximal surface, is at least parallel with the posterior surface 904*z* of the tibia 28" or converging with the posterior tibial surface 906*z* around the distal terminus of the tibial shaft.

In other embodiments, as shown in FIGS. 81A-81G and FIGS. 82A-82C, the planning can also be confirmed from generated 3D bone models 1000*z*, 1002*z* and 3D implant models 1004*z*, 1006*z*. If the planning is done incorrectly, the reference lines 100*z*, 100*z*', 900*z*, 900*z*' will be corrected in the 2D MRI views to amend the planning. FIGS. 81A-81C and FIGS. 81E-81G are various views of the implant 3D models 1004*z*, 1006*z* superimposed on the 3D bone models 1000*z*, 1002*z*. FIG. 81D is a coronal view of the bone models 1000*z*, 1002*z*.

FIGS. 81A-81G show an embodiment of the POP system disclosed herein. The alignment of the implant models 1004*z*, 1006*z* with the bone models 1000*z*, 1002*z* is checked in the anterior view (FIG. 81A), the posterior view (FIG. 81E), the lateral view (FIG. 81B), the medial view (FIG. 81C), the top view (FIG. 81F) and the bottom view (FIG. 81G).

The flexion/extension between the femur and tibia implant models 1004*z*, 1006*z* and the femur and tibia bone models 1000*z*, 1002*z* is examined in both the medial view and the lateral view. For example, FIG. 81B shows the lateral view wherein the knee is shown in full extension or 0 degree flexion and in its natural alignment similar to its pre-arthritis status (e.g., neutral, varus or valgus), and FIG. 81C shows the medial view of the knee in full extension or 0 degree flexion and in its natural alignment (e.g., neutral, varus or valgus).

FIG. 81D shows the varus/valgus alignment of the knee model 28 m', 28 m" with the absence of the implants 34 m', 34 m". The gaps Gp4, Gp5 between the lowermost portions of distal femoral condyles 302*z*, 303*z* and the lowermost portions of the tibia plateau 404*z*, 406*z* will be measured in the femoral and tibia bone models 28 m', 28 m". Gap Gp4 represents the distance between the distal lateral femoral condyle 302*z* and the lateral tibial plateau 404*z*. Gap Gp5 represents the distance between the distal medial femoral condyle 303*z* and the medial tibial plateau 406*z*. In the varus/valgus rotation and alignment, Gp4 is substantially equal to Gp5, or |Gp4-Gp5|1 mm. FIG. 81D shows the knee model 28 m', 28 m" that is intended to restore the patient's knee back to his pre-OA stage.

The IR/ER rotation between the femur and tibia implant models 1004z, 1006z and the femur and tibia bone models 1000z, 1002z is examined in both the top and bottom views. For example, FIG. 81F shows the top view of the tibia showing the IR/ER rotation between no flexion and high flexion, and FIG. 81G shows the bottom view of the femur showing the IR/ER rotation between no flexion and high flexion. The stem of the tibia implant model 1006z and the surgical cut plane of the tibia implant model 1006z provide the information for the IR/ER rotation.

FIGS. 82A-82C show another embodiment of the POP system disclosed herein. FIG. 82A is an medial view of the 3D bone models. FIG. 82B is an medial view of the 3D implant models. FIG. 82C is an medial view of the 3D implant models superimposed on the 3D bone models.

As shown in FIG. 82A, a 3D model of the femur bone 1000z and a 3D model of the tibia bone 1002z may be generated from the 2D segmentation splines of image slices and the reference data 100z, 900z determined above for verification of the POP. As shown in FIG. 82B, a 3D model of the femur implant 1004z and a 3D model of the tibia implant 1006z may be generated based on the reference lines 100z', 900z' determined above for verification of the POP. The implant models 1004z, 1006z and the bone models 1000z, 1002z are aligned based on the reference lines in a 3D computer modeling environment and the alignment is checked in the sagittal view as shown in FIG. 82C. If the alignment of the bone models 1000z, 1002z and the implant models 1004z, 1006z is not correct, the reference lines 100z, 100z', 900z, 900z' will be corrected in the 2D views to amend the planning.

The knee model 28', 28", 1000z, 1002z and associated implant models 34', 34", 1004z, 1006z developed through the above-discussed processes include dimensions, features and orientations that the system 10 depicted in FIG. 1A can be utilized to generate 3D models of femur and tibia cutting jigs 2. The 3D model information regarding the cutting jigs can then be provided to a CNC machine 10 to machine the jigs 2 from a polymer or other material.

G. Mechanical Axis Alignment

While much of the preceding disclosure is provided in the context of achieving natural alignment for the patient's knee post implantation of the actual physical femur and tibia implants, it should be noted that the systems and methods disclosed herein can be readily modified to produce an arthroplasty jig 2 that would achieve a zero degree mechanical axis alignment for the patient's knee post implantation.

For example, in one embodiment, the surgeon utilizes a natural alignment femoral arthroplasty jig 2A as depicted in FIGS. 51A and 51B to complete the first distal resection in the patient's femoral condylar region. Instead of utilizing a natural alignment tibia arthroplasty jig 2B as depicted in FIGS. 51C and 51D, the surgeon instead completes the first proximal resection in the patient's tibia plateau region via free hand or a mechanical axis guide to cause the patient's tibia implant to result in a mechanical axis alignment or an alignment based off of the mechanical axis (e.g., an alignment that is approximately one to approximately three degrees varus or valgus relative to zero degree mechanical axis).

In one embodiment of the POP systems and methods disclosed herein, instead of superposing the 3D bone models 1000z, 1002z to the 3D implant models 1004z, 1006z in a manner that results in the saw cut and drill hole data 44 that leads to the production of natural alignment arthroplasty jigs 2A, 2B, the superposing of the bone and implant models 1000z, 1002z, 1004z, 1006z may be conducted such that the resulting saw cut and drill hole data 44 leads to the production of zero degree mechanical axis alignment arthroplasty jigs or some other type of arthroplasty jig deviating in a desired manner from zero degree mechanical axis.

Thus, depending on the type of arthroplasty jig desired, the systems and methods disclosed herein may be applied to both the production of natural alignment arthroplasty jigs, zero degree mechanical axis alignment jigs, or arthroplasty jigs configured to provide a result that is somewhere between natural alignment and zero degree mechanical axis alignment.

Although the present invention has been described with respect to particular embodiments, it should be understood that changes to the described embodiments and/or methods may be made yet still embraced by alternative embodiments of the invention. For example, certain embodiments may operate in conjunction with a MRI or a CT medical imaging system. Yet other embodiments may omit or add operations to the methods and processes disclosed herein. Accordingly, the proper scope of the present invention is defined by the claims herein.

What is claimed is:

1. A natural alignment knee replacement analysis computing device comprising memory comprising programmed instructions and one or more processors coupled to the memory and configured to be capable of executing the programmed instructions stored in the memory to:

obtain implant data for a selected implant;

generate bone data for a patient femur, wherein the bone data comprises:

data pertaining to a healthy region of the patient femur and an arthritic region of the patient femur; and an angle defined in a coronal view of the patient femur between a knee joint line and an axis extending along a femoral shaft of the patient femur;

generate resection data based at least in part on the implant data and the bone data; and output a recommended three-dimensional knee replacement surgery plan for the patient femur comprising the resection data for facilitating implantation of the selected implant on the patient femur.

2. The computing device of claim 1, wherein the knee joint line intersects a most distal point on a medial condylar surface of the patient femur and a most distal point on a lateral condylar surface of the patient femur.

3. The computing device of claim 2, wherein the axis extending along the femoral shaft of the patient femur comprises a trochlear groove line.

4. The computing device of claim 2, wherein the axis extending along the femoral shaft of the patient femur comprises a femoral mechanical axis.

5. The computing device of claim 1, wherein, when the angle is less than or equal to three degrees of being zero degree mechanical axis, the knee joint line is considered to be aligned in an acceptable natural alignment.

6. The computing device of claim 1, wherein the angle is 90 degrees or nearly 90 degrees.

7. The computing device of claim 1, wherein the bone data further comprises a line intersecting a most posterior point on a medial condylar surface of the patient femur and a most posterior point on a lateral condylar surface of the patient femur.

8. The computing device of claim 1, wherein the resection data comprises at least one adjustment for internal/external rotation or cartilage thickness.

9. The computing device of claim 1, wherein the one or more processors are further configured to be capable of executing the programmed instructions stored in the memory to:

employ patient attribute data retrieved from a database in the process of generating the resection data, the patient attribute data comprising demographic information for a plurality of other patients.

10. The computing device of claim 9, wherein the demographic information comprises at least one of weight, height, race, gender, age or diagnosed disease condition.

11. The computing device of claim 1, wherein the one or more processors are further configured to be capable of executing the programmed instructions stored in the memory to select the selected implant from a database of candidate implants according to at least one of an implant manufacturer, an implant type or an implant size.

12. The computing device of claim 1, wherein the one or more processors are further configured to be capable of executing the programmed instructions stored in the memory to select the selected implant by comparison of a characteristic of the patient femur to characteristics of candidate implants.

13. The computing device of claim 12, wherein the characteristic of the patient femur is a size of the patient femur and the characteristics of the candidate implants is sizes of the candidate implants.

14. The computing device of claim 1, wherein the one or more processors are further configured to be capable of executing the programmed instructions stored in the memory to facilitate the generation of one or more individualized knee replacement guides according to the recommended three-dimensional knee replacement surgery plan.

15. The computing device of claim 1, wherein bone data is generated at least in part from medical imaging of the patient femur.

16. The computing device of claim 15, wherein the medical imaging includes at least one of MRI or CT.

17. The computing device of claim 1, wherein the implant data comprises a computer model of the selected implant, and the bone data includes a computer model of the patient femur.

18. The computing device of claim 17, wherein generating the resection data comprises overlaying the computer model of the selected implant and the computer model of the patient femur with each other in a computer coordinate system.

19. The computing device of claim 1, wherein the one or more processors are further configured to be capable of executing the programmed instructions stored in the memory to identify a registration surface on the patient femur and correlate the registration surface with the resection data so as to result in a desired and planned resection of the patient femur.

20. The computing device of claim 19, wherein the one or more processors are further configured to be capable of executing the programmed instructions stored in the memory to generate a mating surface in an individualized knee replacement guide such that when the individualized knee replacement guide is applied to the patient femur during an arthroplasty surgery, a resection guide surface is aligned with the patient femur according to the recommended three-dimensional knee replacement surgery plan.

* * * * *